US012441704B2

(12) United States Patent
Schrøder Glad et al.

(10) Patent No.: US 12,441,704 B2
(45) Date of Patent: Oct. 14, 2025

(54) COMPOUNDS ACTIVE TOWARDS NUCLEAR RECEPTORS

(71) Applicant: NUEVOLUTION A/S, Copenhagen (DK)

(72) Inventors: Sanne Schrøder Glad, Copenhagen (DK); Ian Sarvary, Copenhagen (DK); Alex Haahr Gouliaev, Copenhagen (DK); Thomas Franch, Copenhagen (DK); Søren Jensby Nielsen, Copenhagen (DK); Luigi Piero Stasi, Copenhagen (DK); Montserrat Erra Solà, Sant Feliu de Llobregat (ES); Lorena Taboada Martínez, Sant Feliu de Llobregat (ES); Joan Taltavull Moll, Sant Feliu de Llobregat (ES); Juan Francisco Caturla Javaloyes, Sant Feliu de Llobregat (ES); Lluís Miquel Pagès Santacana, Sant Feliu de Llobregat (ES)

(73) Assignee: NUEVOLUTION A/S, Copenhagen (DK)

( * ) Notice: Subject to any disclaimer, the term of this patent is extended or adjusted under 35 U.S.C. 154(b) by 0 days.

(21) Appl. No.: 18/143,975

(22) Filed: May 5, 2023

(65) Prior Publication Data

US 2023/0271937 A1 Aug. 31, 2023

Related U.S. Application Data

(62) Division of application No. 17/126,182, filed on Dec. 18, 2020, now Pat. No. 11,685,727.

(60) Provisional application No. 63/064,502, filed on Aug. 12, 2020, provisional application No. 62/951,221, filed on Dec. 20, 2019.

(51) Int. Cl.

| | |
|---|---|
| ***A61K 31/506*** | (2006.01) |
| ***A61P 19/02*** | (2006.01) |
| ***A61P 21/00*** | (2006.01) |
| ***C07D 401/12*** | (2006.01) |
| ***C07D 401/14*** | (2006.01) |
| ***C07D 413/14*** | (2006.01) |

(52) U.S. Cl.
CPC ............ *C07D 401/12* (2013.01); *A61P 19/02* (2018.01); *A61P 21/00* (2018.01); *C07D 401/14* (2013.01); *C07D 413/14* (2013.01)

(58) Field of Classification Search
CPC .................................................... A61K 31/506
See application file for complete search history.

(56) References Cited

U.S. PATENT DOCUMENTS

| | | | |
|---|---|---|---|
| 4,298,602 | A | 11/1981 | Pawloski |
| 5,463,071 | A | 10/1995 | Himmelsbach et al. |
| 5,530,129 | A | 6/1996 | Gallenkamp et al. |
| 7,931,909 | B2 | 4/2011 | Hughes et al. |
| 8,338,439 | B2 | 12/2012 | Singh et al. |
| 10,683,293 | B2 | 6/2020 | Glad et al. |
| 10,683,393 | B2 | 6/2020 | Boydston et al. |
| 10,689,383 | B2 | 6/2020 | Glad et al. |
| 11,543,310 | B2 | 1/2023 | Liu et al. |
| 2003/0191121 | A1 | 10/2003 | Miller et al. |
| 2004/0054173 | A1 | 3/2004 | Kimura et al. |
| 2004/0087577 | A1 | 5/2004 | Pratt et al. |
| 2004/0097492 | A1 | 5/2004 | Pratt et al. |
| 2004/0180906 | A1 | 9/2004 | Flynn et al. |
| 2005/0124623 | A1 | 6/2005 | Bender et al. |
| 2005/0153989 | A1 | 7/2005 | Grotzfeld et al. |
| 2005/0182045 | A1 | 8/2005 | Nagase et al. |
| 2005/0245536 | A1 | 11/2005 | Hao et al. |
| 2005/0288286 | A1 | 12/2005 | Flynn et al. |
| 2006/0004018 | A1 | 1/2006 | Xue et al. |
| 2006/0052374 | A1 | 3/2006 | Carroll et al. |
| 2006/0069093 | A1 | 3/2006 | Scarborough et al. |
| 2006/0199821 | A1 | 9/2006 | Tester et al. |
| 2006/0235017 | A1 | 10/2006 | Cirillo et al. |
| 2006/0241104 | A1 | 10/2006 | Borzilleri et al. |
| 2006/0281712 | A1 | 12/2006 | Yen et al. |
| 2008/0021063 | A1 | 1/2008 | Kazantsev |
| 2008/0070319 | A1 | 3/2008 | Makino |
| 2009/0018112 | A1 | 1/2009 | Chapdelaine et al. |
| 2009/0018116 | A1 | 1/2009 | Jin et al. |
| 2009/0018134 | A1 | 1/2009 | Pike et al. |
| 2009/0018166 | A1 | 1/2009 | Amin et al. |
| 2009/0029994 | A1 | 1/2009 | Nakamura et al. |
| 2009/0036434 | A1 | 2/2009 | Jones et al. |
| 2009/0069559 | A1 | 3/2009 | Kazantsev |
| 2009/0143302 | A1 | 6/2009 | Yen et al. |
| 2009/0163545 | A1 | 6/2009 | Goldfarb |
| 2010/0152445 | A1 | 6/2010 | Bolin et al. |
| 2010/0249153 | A1 | 9/2010 | Tandon et al. |

(Continued)

FOREIGN PATENT DOCUMENTS

| | | |
|---|---|---|
| CL | 201700271 | 10/2017 |
| CL | 201700287 | 11/2017 |

(Continued)

OTHER PUBLICATIONS

Database Registry Chemical Abstracts Service, Columbus, Ohio, XP002802066, Database accession No. 1932820-62-6 (2016).

(Continued)

*Primary Examiner* — Brian E Mcdowell
(74) *Attorney, Agent, or Firm* — MARSHALL, GERSTEIN & BORUN LLP

(57) ABSTRACT

Disclosed are compounds active towards nuclear receptors, pharmaceutical compositions containing the compounds and use of the compounds in therapy.

18 Claims, No Drawings

(56) References Cited

U.S. PATENT DOCUMENTS

| | | | |
|---|---|---|---|
| 2011/0135604 A1 | 6/2011 | Casarez et al. |
| 2011/0281842 A1 | 11/2011 | Michaelides et al. |
| 2012/0142714 A1 | 6/2012 | Yasuma et al. |
| 2012/0214762 A1 | 8/2012 | Staben et al. |
| 2012/0264798 A1 | 10/2012 | Sinha et al. |
| 2013/0040855 A1 | 2/2013 | Takayama et al. |
| 2013/0158031 A1 | 6/2013 | Cai et al. |
| 2013/0190249 A1 | 7/2013 | Lemieux et al. |
| 2013/0231519 A1 | 9/2013 | Heinrich et al. |
| 2014/0018361 A1 | 1/2014 | Harriman et al. |
| 2020/0392140 A1 | 12/2020 | Schrøder Glad et al. |
| 2021/0188807 A1 | 6/2021 | Schrøder Glad et al. |
| 2021/0188828 A1 | 6/2021 | Schrøder Glad et al. |

FOREIGN PATENT DOCUMENTS

| | | | |
|---|---|---|---|
| CL | 201701288 | | 12/2017 |
| CL | 201701289 | | 3/2018 |
| CL | 202201641 | | 6/2022 |
| CL | 202201594 | | 1/2023 |
| CL | 202201353 | | 2/2023 |
| CL | 202201456 | | 2/2023 |
| CL | 202201671 | | 2/2023 |
| CL | 202201612 | | 3/2023 |
| CL | 202201625 | | 3/2023 |
| CL | 202201646 | | 3/2023 |
| CL | 202201675 | | 3/2023 |
| CN | 102786512 | A | 11/2012 |
| CN | 103588795 | A | 2/2014 |
| DE | 3737748 | A1 | 5/1989 |
| DE | 4124942 | A1 | 1/1993 |
| DE | 10108480 | A1 | 9/2002 |
| EP | 0384244 | A1 | 8/1990 |
| EP | 0419831 | A2 | 4/1991 |
| EP | 0434341 | A1 | 6/1991 |
| EP | 1396489 | A1 | 3/2004 |
| EP | 3177612 | B1 | 2/2022 |
| FR | 2870541 | A1 | 11/2005 |
| FR | 2926556 | A1 | 7/2009 |
| JP | 04-348326 | A | 12/1992 |
| JP | 06-220059 | A | 8/1994 |
| JP | 10-251255 | A | 9/1998 |
| JP | 2000-086663 | A | 3/2000 |
| JP | 2002-284779 | A | 10/2002 |
| JP | 2007-507529 | A | 3/2007 |
| JP | 2007-119450 | A | 5/2007 |
| JP | 2007-126551 | A | 5/2007 |
| JP | 2007-186580 | A | 7/2007 |
| JP | 2008-501698 | A | 1/2008 |
| JP | 2008-051696 | A | 3/2008 |
| JP | 2012-519005 | A | 8/2012 |
| JP | 2013-517809 | A | 5/2013 |
| JP | 7106623 | B2 | 7/2022 |
| WO | 93/14082 | A1 | 7/1993 |
| WO | 93/22311 | A1 | 11/1993 |
| WO | 96/40142 | A1 | 12/1996 |
| WO | 97/12878 | A1 | 4/1997 |
| WO | 97/44038 | A1 | 11/1997 |
| WO | 98/23613 | A1 | 6/1998 |
| WO | 01/12601 | A1 | 2/2001 |
| WO | 2001/030778 | A1 | 5/2001 |
| WO | 2001/047921 | A1 | 7/2001 |
| WO | 01/57038 | A1 | 8/2001 |
| WO | 02/22584 | A1 | 3/2002 |
| WO | 03/11836 | A1 | 2/2003 |
| WO | 03/45941 | A1 | 6/2003 |
| WO | 03/66604 | A2 | 8/2003 |
| WO | 03/75828 | A2 | 9/2003 |
| WO | 03/94918 | A1 | 11/2003 |
| WO | 2003/101959 | A1 | 12/2003 |
| WO | 2004/000843 | A1 | 12/2003 |
| WO | 2004/014384 | A2 | 2/2004 |
| WO | 2004/039785 | A1 | 5/2004 |
| WO | 2004/039786 | A1 | 5/2004 |
| WO | 2004/039788 | A1 | 5/2004 |
| WO | 2004/054987 | A1 | 7/2004 |
| WO | 2004/060305 | A2 | 7/2004 |
| WO | 2004/060306 | A2 | 7/2004 |
| WO | 2004/083174 | A2 | 9/2004 |
| WO | 2004/083185 | A2 | 9/2004 |
| WO | 2004/101557 | A1 | 11/2004 |
| WO | 2004/110350 | A2 | 12/2004 |
| WO | 2005/033072 | A2 | 4/2005 |
| WO | 2005/040119 | A1 | 5/2005 |
| WO | 2005/067546 | A2 | 7/2005 |
| WO | 2005/068457 | A1 | 7/2005 |
| WO | 2005/084667 | A1 | 9/2005 |
| WO | 2005/111003 | A1 | 11/2005 |
| WO | 2005/117909 | A2 | 12/2005 |
| WO | 2005/121121 | A2 | 12/2005 |
| WO | 2005/123731 | A2 | 12/2005 |
| WO | 2006/004741 | A2 | 1/2006 |
| WO | 2006/022773 | A1 | 3/2006 |
| WO | 2006/045828 | A1 | 5/2006 |
| WO | 2006/074057 | A2 | 7/2006 |
| WO | 2006/076706 | A1 | 7/2006 |
| WO | 2006/091963 | A1 | 8/2006 |
| WO | 2006/122773 | A1 | 11/2006 |
| WO | 2007/012661 | A1 | 2/2007 |
| WO | 2007/021941 | A2 | 2/2007 |
| WO | 2007/030574 | A2 | 3/2007 |
| WO | 2007/068418 | A1 | 6/2007 |
| WO | 2007/072163 | A2 | 6/2007 |
| WO | 2007/072201 | A2 | 6/2007 |
| WO | 2007/080382 | A1 | 7/2007 |
| WO | 2007/088277 | A1 | 8/2007 |
| WO | 2007/107545 | A1 | 9/2007 |
| WO | 2007/121280 | A1 | 10/2007 |
| WO | 2008/005368 | A2 | 1/2008 |
| WO | 2008/005538 | A2 | 1/2008 |
| WO | 2008/011476 | A2 | 1/2008 |
| WO | 2008/023159 | A1 | 2/2008 |
| WO | 2008/023180 | A1 | 2/2008 |
| WO | 2008/074982 | A1 | 6/2008 |
| WO | 2008/104077 | A1 | 9/2008 |
| WO | 2008/115973 | A2 | 9/2008 |
| WO | 2008/152093 | A2 | 12/2008 |
| WO | 2009/007749 | A2 | 1/2009 |
| WO | 2009/007750 | A1 | 1/2009 |
| WO | 2009/007751 | A2 | 1/2009 |
| WO | 2009/017664 | A1 | 2/2009 |
| WO | 2009/055331 | A2 | 4/2009 |
| WO | 2009/079683 | A1 | 7/2009 |
| WO | 2009/099193 | A1 | 8/2009 |
| WO | 2009/102736 | A1 | 8/2009 |
| WO | 2009/103432 | A2 | 8/2009 |
| WO | 2009/123221 | A1 | 10/2009 |
| WO | 2009/128661 | A2 | 10/2009 |
| WO | 2009/134384 | A1 | 11/2009 |
| WO | 2009/149188 | A1 | 12/2009 |
| WO | 2009/156484 | A2 | 12/2009 |
| WO | 2010/012442 | A2 | 2/2010 |
| WO | 2010/020432 | A2 | 2/2010 |
| WO | 2010/022121 | A1 | 2/2010 |
| WO | 2010/022125 | A1 | 2/2010 |
| WO | 2010/022128 | A1 | 2/2010 |
| WO | 2010/036316 | A1 | 4/2010 |
| WO | 2010/048207 | A2 | 4/2010 |
| WO | 2010/052569 | A2 | 5/2010 |
| WO | 2010/080996 | A1 | 7/2010 |
| WO | 2010/100127 | A1 | 9/2010 |
| WO | WO-2010/106097 | A1 | 9/2010 |
| WO | 2010/114957 | A1 | 10/2010 |
| WO | 2010/120994 | A2 | 10/2010 |
| WO | 2010/129053 | A2 | 11/2010 |
| WO | 2010/129242 | A2 | 11/2010 |
| WO | 2010/135470 | A1 | 11/2010 |
| WO | 2011/017513 | A1 | 2/2011 |
| WO | 2011/022440 | A2 | 2/2011 |
| WO | 2011/029043 | A1 | 3/2011 |
| WO | 2011/029046 | A1 | 3/2011 |
| WO | 2011/049946 | A1 | 4/2011 |
| WO | 2011/055911 | A1 | 5/2011 |
| WO | 2011/075684 | A1 | 6/2011 |

(56) References Cited

FOREIGN PATENT DOCUMENTS

| | | | |
|---|---|---|---|
| WO | 2011/078143 | A1 | 6/2011 |
| WO | 2011/105572 | A1 | 9/2011 |
| WO | 2011/115940 | A1 | 9/2011 |
| WO | 2011/143129 | A1 | 11/2011 |
| WO | 2011/153553 | A2 | 12/2011 |
| WO | 2012/037226 | A1 | 3/2012 |
| WO | 2012/041872 | A1 | 4/2012 |
| WO | 2012/041873 | A1 | 4/2012 |
| WO | 2012/046869 | A1 | 4/2012 |
| WO | 2012/074022 | A1 | 6/2012 |
| WO | 2012/103295 | A2 | 8/2012 |
| WO | 2012/147516 | A1 | 11/2012 |
| WO | 2012/147890 | A1 | 11/2012 |
| WO | 2012/163773 | A1 | 12/2012 |
| WO | 2012/166716 | A2 | 12/2012 |
| WO | 2013/011033 | A1 | 1/2013 |
| WO | 2013/017461 | A1 | 2/2013 |
| WO | 2013/019824 | A2 | 2/2013 |
| WO | 2013/022766 | A1 | 2/2013 |
| WO | 2013/036912 | A2 | 3/2013 |
| WO | 2013/052526 | A1 | 4/2013 |
| WO | 2013/068306 | A1 | 5/2013 |
| WO | 2013/090912 | A1 | 6/2013 |
| WO | 2013/117649 | A1 | 8/2013 |
| WO | 2013/134467 | A1 | 9/2013 |
| WO | 2013/157022 | A1 | 10/2013 |
| WO | 2013/178075 | A1 | 12/2013 |
| WO | 2013/183673 | A1 | 12/2013 |
| WO | 2014/005129 | A1 | 1/2014 |
| WO | 2014/015523 | A1 | 1/2014 |
| WO | 2014/015675 | A1 | 1/2014 |
| WO | 2014/015830 | A1 | 1/2014 |
| WO | 2014/015936 | A1 | 1/2014 |
| WO | 2014/017513 | A1 | 1/2014 |
| WO | 2014/019908 | A2 | 2/2014 |
| WO | 2014/185358 | A1 | 11/2014 |
| WO | 2015/033558 | A1 | 3/2015 |
| WO | 2015/129263 | A1 | 9/2015 |
| WO | 2016/020288 | A1 | 2/2016 |
| WO | 2016/020295 | A1 | 2/2016 |
| WO | 2016/020320 | A1 | 2/2016 |
| WO | 2016/081670 | A2 | 5/2016 |
| WO | 2016/081918 | A1 | 5/2016 |
| WO | 2017/024018 | A1 | 2/2017 |
| WO | WO-2017/181177 | A1 | 10/2017 |
| WO | 2021/124279 | A1 | 6/2021 |
| WO | 2021/127561 | | 6/2021 |
| WO | WO-2021/120890 | A1 | 6/2021 |
| WO | WO-2021/122975 | A1 | 6/2021 |
| WO | WO-2021/122976 | A1 | 6/2021 |
| WO | WO-2021/122986 | A1 | 6/2021 |
| WO | WO-2021/123051 | A1 | 6/2021 |
| WO | WO-2021/123084 | A1 | 6/2021 |
| WO | WO-2021/127429 | A1 | 6/2021 |

OTHER PUBLICATIONS

International Application No. PCT/IB2020/062227, International Preliminary Report on Patentability, mailed Jun. 30, 2022.
International Application No. PCT/IB2020/062227, International Search Report and Written Opinion, mailed Feb. 22, 2021.
33 Substances CAS Registry Nos. 1515972-57-2; 357614-47-2; 1537342-62-3; 357614-41-6; 1509319-43-0; 357614-39-2; 1508163-79-8; 1543241-09-3; 1507549-73-6; 1539058-95-1; 1504736-18-8; 1538881-49-0; 1502546-73-7; 537342-62-3; 1502393-44-3; 1536916-94-5; 1501684-14-5; 1536417-79-4; 1500313-42-7; 1529040-93-4; 1499708-15-4; 1526739-06-9; 1020711-29-8; 1526652-58-3; 1020711-25-4; 1522387-54-7; 403668-62-2; 1522083-19-7; 357614-51-8; 1521680-88-5; 357614-49-4; 1519623-48-3; 357614-48-3 (2014).
Alm et al., Effects of topically applied PGF2 alpha and its isopropylester on normal and glaucomatous human eyes, Prog. Clin. Biol. Res., 312:447-458 (1989).
Aloisi et al., Lymphoid neogenesis in chronic inflammatory diseases, Nat. Rev. Immunol., 6(3):205-217 (2006).
Barnes et al., Immunology of asthma and chronic obstructive pulmonary disease, Nat. Rev. Immunol., 8(3):183-192 (2008).
Bronner et al., ROR (gamma) antagonists and inverse agonists: a patent review, Expert Opinion on Therapeutics Patents, 27(1):101-112 (2017).
Caira, Crystalline Polymorphism of Organic Compounds, Topics in Current Chemistry, 198:163-208 (1998).
Cas Reg No. 929970-65-0, STN Entry Date: Apr. 13, 2007; 7H-Pyrrolo[2,3-d]pyrimidin-4-amine,5,6-dimethyl-7-(phenylmethyl)-N-(4-pyridinylmethyl)- [2].
Cas Reg. No. 1539496-16-6, STN Entry Date: Feb. 9, 2014; 4,6-Pyrimidinediamine, N6-ethyl-N4-methyl-5-(1-methylethyl)-N4-[(1-methyl-1 H-pyrazol-4-yl)methyl- ]-.
Cas Reg. No. 1540192-80-0, STN Entry Date: Feb. 10, 2014; 4,6-Pyrimidinediamine, N4,N6-diethyl-2,5-dimethyl-N4-(2-thienylmethyl)-.
CAS Reg. No. 1542543-24-7, STN Entry Date: Feb. 14, 2014; 4,6-Pyrimidinediamine, N4-[(4-chlorophenyl)methyl]-N4,5-dimethyl-N6-propyl-.
Cas Reg. No. 1543250-40-3, STN Entry Date: Feb. 14, 2014; 4,6-Pyrimidinediamine, 5- methoxy-N4-methyl-N6-propyl-N4-[(tetrahydro-2H-pyran-3-yl)methyl]-.
Cas Reg. No. 1544786-92-6, STN Entry Date: Feb. 16, 2014; 4,6-Pyrimidinediamine, N6- ethyl-N4,2-dimethyl-N4-[(5-methyl-2-furanyl)methyl]-.
Cas Reg.No. 1101785-73-2, STN Entry Date: Feb. 6, 2009; L-Alanine, N-[7-(2-furanylmethyl)-5,6-dimethyl-7H-pyrrolo[2,3-d]pyrimidin-4-yl]- [2].
Castro et al., ROR?t and RORa signature genes in human Th17 cells, 12(8):e0181868 (2017).
Chang et al., Pharmacologic Repression of Retinoic Acid Receptor-Related Orphan Nuclear Receptor ? is Therapeutic in the Collagen-Induced Arthritis Experimental Model, Arthritis & Rheumatism, 66(3):579-588 (2014).
Chang et al., RORs in autoimmune disease, sphingosine-1-phosphate signaling in immunology and infectious diseases, Curr. Topics in Microb. Immun., 378:171-182 (2014).
Cook et al., "Retinoic Acid-Related Orphan Receptors (RORs): Regulatory Functions in Immunity, Development, Circadian Rhythm, and Metabolism", Nuclear Receptor Research, 2, Article ID 101185:1-24 (2015).
Current topics in microbiology and immunology, 378:171-182 (2014).
Cyr et al., Recent progress on nuclear receptor ROR.gamma. modulators, Bioorganic & Medicinal Chemistry Letters 26(18):4387-4393 (2016).
Database Registry,2013, RN 1445611 - 7, 1424439 [03, 2006.01, 01, 1, 1423758-[35, 2006.01, 74] 3, 13118835, 1281111-22-5, 1281111-13-4; Retrieved from STN international [online] ;retrieved on Apr. 12, 2019.
Fa et al., Synthesis, structure, and fullerene-complexing property of azacalix[6]aromatics, J. Org. Chem. v., 79:3559-3571 (2014).
Fan et al., "Retinoic Acid Receptor-Related Orphan Receptors: Critical Roles in Tumorigenesis", Frontiers in Immunology. vol. 9. Article 1187:1-10 (2018).
Fauber et al., Modulators of the nuclear receptor retinoic acid receptor-related orphan receptor -? (ROR? or RORc), J. Med. Chem., 57(14):5871-92 (2014).
Fauber et al., Modulators of the Nuclear Receptor Retinoic Acid Receptor-Related Orphan Receptor-y (ROR? or RORc), J. Med. Chem. 2014, 57(14):5871-5892 (2014).
Fingl et al., The pharmacological basis of therapeutics, Ch. 1 (1975).
Gaffen et al., The IL-23-IL-17 immune axis: from mechanisms to therapeutic testing, Nat. Rev. Immunol., 14(9):585-600 (2014).
Google patents translation, WO 2011105572, downloaded Sep. 22, 2017.
Han et al., Efficient and library-friendly synthesis of furo- and thienol[2,3-d] pyrimidin-4-amine derivatives by microwave irradiation, Tetrahedron Letters, v. 51: 629-632 (2010).
Huang et al., Acyclic nucleic acid analogs: synthesis and oligomerization of .gamma.,4-diamino-2-oxo-1(2H)-pyrimidinepentanoic acid and .delta.,4-diamino-2-oxo-1(2H)-pyrimidinehexanoic acid, Journal of Organic Chemistry, 56(21):6007-6018 (1991).

(56) References Cited

OTHER PUBLICATIONS

Huh et al., Small molecule inhibitors of RORyt: Targeting Th17 cells and other applications, NIH public access author manuscript, Eur. J. Immunol., 42(9):2232-2237 (2012).
International Application No. PCT/EP2015/067692, International Search Report and Written Opinion, mailed Sep. 21, 2015.
International Application No. PCT/EP2015/067713, International Preliminary Report on Patentability, mailed Feb. 16, 2017.
International Application No. PCT/EP2015/067713, International Search Report and Written Opinion, mailed Sep. 22, 2015.
International Application No. PCT/IB2021/052701, International Search Report and Written Opinion, mailed Jun. 17, 2021.
International Application No. PCT/IB2021/052702, International Search Report and Written Opinion, mailed Jun. 17, 2021.
International Preliminary Report on Patentability for corresponding International Application No. PCT/EP2015/067692, dated Feb. 16, 2017.
Isono et al., Inhibiting ROR ?t/Th17 axis for autoimmune disorders, Drug Disc. Today, 18:1205-11 (2014).
IUPAC-IUB [International Union of Pure and Applied Chemistry-International Union of Biochemistry] Commission of Biochemical Nomenclature. Abbreviated nomenclature of synthetic polypeptides (polymerized amino acids). Revised recommendations (1971), Biochem., 11(5):942-944 (1972).
Jager et al., Th1, Th17, and Th9 effector cells induce experimental autoimmune encephalomyelitis with different pathological phenotypes, J. Immunol., 183(11):7169-7177 (2009).
Jetten, Retinoid-related orphan receptors (RORs): critical roles in development, immunity, circadian rhythm, and cellular metabolism, Nuclear Receptor Signaling, 7:e003 (2009).
Joshi, Microparticulates for ophthalmic drug delivery, J. Ocul. Pharmacol., 10(1):29-45 (1994).
Kamenecka et al., Synthetic modulators of the retinoic acid receptor-related orphan receptors, Med. Chem. Commun., 4:764-776 (2013).
Kim et al., Substituted pyrimidines as cannabinoid CB1 receptor ligands, Bioorganic & Medicinal Chemistry Letters, 19:4692-4697 (2009).
Klecka et al., Direct C—H borylation and C—H arylation of pyrrolo[2,3d]pyrimidines: synthesis of 6,8-disubstituted7-deazapurines, Org. Biomol. Chem., 7:866-868 (2009).
Kojetin et al., REV-ERB and ROR nuclear receptors as drug targets, Nature Rev. Drug Disc., 13:197-216 (2014).
Kosary et al., Preparation of pyrimidine derivatives with potential cardiotonic activity, Acta Pharmacetical Hungarica., 56(6):7147-7156 (2003).
Kosary et al., Preparation of pyrimidine derivatives with potential cardiotonic activity, Acta. Pharmacetical Hungarica., 56(6):241-247 (abstract CA 112:216531), Retrieved from Chemical Abstracts (1989).
Krueger et al., Interleukin-17 alters the biology of many cell types involved in the genesis of psoriasis, systemic inflammation and associated comorbidities, Exp. Dermatol., 27(2):115-123 (2018).
Lai et al., Mesenchymal stem cell exosomes, 40:82-8 (2015).
Ma et al., Combinatorial synthesis of substituted biaryls and heterocyclic arylamines, J. Comb. Chem., 6(3):426-430 (2004).
Magliozzi et al., Meningeal B-cell follicles in secondary progressive multiple sclerosis associate with early onset of disease and severe cortical pathology, Brain, 130(4):1089-1104 (2007).
Marquet et al., New series of purine analogs with antimitotic action. Structure activity relations, Chimica. Therapeutica., 6(6):427-38 (1971).
Marquet et al., Sur une nouvelle serie d'analogues puriques a action antimitotique: relations structure-activite, European Journal of medicinal chemistry—Chimie Therapeutique, 6:427-438 (1971).
Mashkovskiy, Lekarstvennie sredstva, Moscow. Medicina. part 1:8 (1993) with partial English translation.
Mayer et al., Efficacy of a novel hydrogel formulation in human volunteers, Ophthalmologica, 210(2):101-103 (1996).
Meier et al., Ectopic lymphoid-organ development occurs through interleukin 7-mediated enhanced survival of lymphoid-tissue-inducer cells, Immunity, 26(5):643-654 (2007).
Miossec et al., Targeting IL-17 and TH17 cells in chronic inflammation, Nature Rev. Drug Disc., 11(10):763-776 (2012).
Montebugnoli et al., Traceless solid-phase synthesis of 2,4,6-chlorodiamino and triaminopyrimidines, Tetrahedron, 59:7147-7156 (2003).
Mordenti et al., Intraocular pharmacokinetics and safety of a humanized monoclonal antibody in rabbits after intravitreal administration of a solution or a PLGA microsphere formulation, Toxicol. Sci., 52(1):101-106 (1999).
Muller et al., Chiral Pyrrolo[2,3d]pyrimidine and pyrimido[4,5-b]indole derivatives: structure-activity relationships of potent, highly stereoselective A.sub.1-adenosine receptor antagonists, J. Med. Chem., 39:2482-2491 (1996).
Nogrady, Medicinal chemistry a biochemical approach, Oxford university press, New York, 388-392 (1985).
Pandya et al., Combating Autoimmune Diseases With Retinoic Acid Receptor-Related Orphan Receptor-? (ROR? or RORc) Inhibitors: Hits and Misses, J. Med. Chem., 61(24):10976-10995 (2018).
Pryde et al., The discovery of a novel prototype small molecule TLR7 agonist for the treatment of hepatitis C virus infection, Med. Chem. Commun., 2:185-189(2011).
PUBCHEM (National Center for Biotechnology Information. PUBCHEM Compound Database; CID=3236972, https://pubchem.ncbi.nlm.nih.gov/compound/3236972 (accessed Sep. 15, 2018), created Aug. 16, 2005, pp. 1-13).
Search Report for Swedish Patent Application No. 1450920-2, dated Feb. 17, 2015.
Search Report for Swedish Patent Application No. 1451406-1, mailed May 29, 2015.
Serafini et al., Detection of ectopic b-cell follicles with germinal centers in the meninges of patients with secondary progressive multiple sclerosis, Brain Pathol., 14(2):164-174 (2004).
Shedden et al., Efficacy and tolerability of timolol maleate ophthalmic gel-forming solution versus timolol ophthalmic solution in adults with open-angle glaucoma or ocular hypertension: a six-month, double-masked, multicenter study, Clin. Ther., 23(3):440-450 (2001).
Solt et al., Action of RORs and their ligands in (patho) physiology, Trends in Endocrinology and Metabolism, 23(12):619-627 (2012).
Traverso et al., The syntheses and pharmacological activities of amide, sulfamide, and urea derivatives of 4,6-diaminopyrimidines, J. Med. Pharm. Chem., 91:808-15 (1962).
Tyukavkina et al., Bioorganicheskaya himiya, moskva, Drofa., 83-85 (2005) with partial English translation.
Upadhyaya et al., Identification of adducts formed in the reactions of 5'-acetoxy-N'-nitrosonornicotine with ZXCITY,.\deoxyadenosine, thymidine, and DNA, Chem. Res. Toxicol., 21:2164-2171 (2008).
Wu et al., Discovery of aminoheterocycles as potent and brain penetrant prolylcarboxypeptidase inhibitors, Bioorganic & Medicinal Chemistry Letters, 22:1727-1730 (2012).
Yang et al., Discovery of Tertiary Amine and Indole Derivatives as Potent ROR.gamma.t Inverse Agonists, ACS Medical Chemistry Letters, 5:65-68 (2014).
Yang et al., Targeting Th17 cells in autoimmune diseases, Trends Pharmacol Sci., 35(10):493-500 (2014).
Yoo et al., Synthesis of mono-, Di-, and triaminosubstituted-Pyrimidine derivatives, Korean J. Med. Chem., 9:83-86 (1999).
Burris et al., Nuclear Receptors and Their Selective Pharmacologic Modulators, Pharmacological Reviews, 65:710-778 (Apr. 2013).
Zhang et al., ROR nuclear receptors: structures, related diseases, and drug discovery, Acta Pharmacologieca Sinica, 36:71-87 (2015).
Goel et al., Recent advancement of piperidine moiety in treatment of cancer—A review, European Journal of Medicinal Chemistry, 157:480-502 (Sep. 2018).
Search Report for Brunei Patent Application No. BN/N/2022/0046, mailed Feb. 24, 2025.

COMPOUNDS ACTIVE TOWARDS NUCLEAR RECEPTORS

CROSS REFERENCE TO RELATED APPLICATIONS

This application is a divisional of U.S. patent application Ser. No. 17/126,182 filed Dec. 18, 2020, which claims the priority benefit under 35 U.S.C. § 119 (e) of U.S. Provisional Patent Application No. 62/951,221, filed Dec. 20, 2019 and U.S. Provisional Patent Application No. 63/064,502, filed Aug. 12, 2020 the disclosures of which is incorporated herein by reference in their entirety.

FIELD

Aspects and embodiments described herein relate to compounds active towards nuclear receptors, pharmaceutical compositions comprising the compounds, and methods of treating inflammatory, metabolic, oncologic and autoimmune diseases or disorders using the compounds.

BACKGROUND

Nuclear receptors are a family of transcription factors involved in the regulation of physiological functions, such as cell differentiation, embryonic development, and organ physiology. Nuclear receptors have also been identified as important pathological regulators in diseases such as cancer, diabetes, and autoimmune disorders.

Examples of nuclear receptors include the nuclear retinoic acid receptor-related orphan receptors (RORs). RORs contain four principal domains: an N-terminal A/B domain, a DNA-binding domain, a hinge domain and a ligand binding domain. Binding of ligands to the ligand-binding domain is believed to cause conformational changes in the domain resulting in downstream actions. Different isoforms exist and these isoforms differ in their N-terminal A/B domain only (Jetten, 2009, Nuclear Receptor Signaling).

RORs consist of three members, namely ROR alpha (RORα or RORa), ROR beta (RORβ or RORb) and ROR gamma (RORγ or RORc).

RORα is expressed in many tissues such as cerebellar Purkinje cells, the liver, thymus, skeletal muscle, skin, lung, adipose tissue and kidney. RORα regulates neuronal cell development, bone metabolism, and arteriosclerosis (Jetten, 2009, Nuclear Receptor Signaling). Additionally, RORα plays a role in the immune responses, such as in the regulation interleukin (IL) 17A expression in T helper (Th) 17 cells and the function of T regulatory (Treg) cells (Castro PLOS 2017; Malhotra 2018).

RORβ exhibits a restriction pattern of expression limited to certain regions of brain (cerebral cortex, thalamus, hypothalamus and pineal gland) as well as retina (Jetten, 2009, Nuclear Receptor Signaling). RORβ has been related to epilepsy and together with RORα also to bipolar disease (Rudolf 2016; Lai 2015).

RORγ shows a broad expression pattern and was the most recently discovered of the three members. To date two different protein isoforms have been recorded: RORγ1 and RORγ2 (RORγ2 is also known as RORγt). Generally RORγ is used to describe RORγ1 and/or RORγt. RORγ1 is expressed in many tissues and is predominantly expressed in the kidneys, liver, and skeletal muscle. In contrast, expression of RORγt is restricted to some cell types of the immune system and to lymphoid organs such as the thymus and secondary lymphoid tissues (Hirose 1994; Jetten, 2009, Nuclear Receptor Signaling).

RORγt has been identified as a key regulator of Th17 cell differentiation and IL-17 production by γδ T cells, Th17 cells, T cytotoxic (Tc) 17 cells and innate lymphoid cells type 3 (ILC3) cells (Gaffen 2014). Th17 cells are a subset of T helper cells which preferentially produce the cytokines IL-17A, IL-17F, IL-21 and IL-22 (Castro PLOS 2017). T cells lacking RORγt failed to differentiate into Th17 cells even under Th17-polarizing culture conditions, while overexpression of RORγt in naïve CD4+ T cells was sufficient to accelerate the expression of Th17-related cytokines and chemokines (Gaffen 2014, Nat Rev Immunol; Yang 2014, Trend Pharmacol Sci). IL-23 is a vital checkpoint in the generation, maintenance and activation of pathogenic Th17 cells. In response to IL-23 signals, RORγt cooperates with a network of transcription factors (STAT3, IRF4 and BATF) to initiate the complete differentiation program of Th17 cells (Gaffen 2014, Nat Rev Immunol).

Th17 cells and IL-17 immune response have been shown to be associated with the pathology of many human inflammatory and autoimmune disorders. Therapeutic strategies targeting the IL-23-IL-17 axis are being developed in many autoimmune diseases, and some of them have already demonstrated to provide clinical efficacy some diseases (Patel 2015; Krueger 2018 Exp Dermatol).

There is thus evidence that RORα, RORβ and RORγ play a role in the pathogenesis of many diseases.

It would be desirable to provide compounds that modulate the activity of RORα and/or RORγ for use in treating inflammatory, metabolic and autoimmune diseases.

WO2016020288 and WO2016020295 describe compounds that modulate the activity or RORgamma receptors. However, a need still exists for potent RORgamma modulators having improved physicho-chemical properties.

SUMMARY

In one aspect provided herein are compounds of Formula (I)

(I)

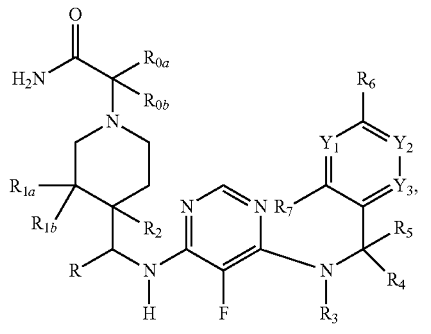

a stereoisomer thereof, or a pharmaceutically acceptable salt of the compound or stereoisomer, wherein:

$Y_1$, $Y_2$ and $Y_3$ are independently N or $CR_8$;

R is selected from the group consisting of hydrogen, $C_{1-6}$ alkyl, and $C_{1-4}$ hydroxyalkyl;

$R_{0a}$ and $R_{0b}$ independently are selected from the group consisting of hydrogen, $C_{1-4}$ alkyl, $C_{1-4}$ hydroxyalkyl, $C_{1-4}$ haloalkyl, CN, substituted or unsubstituted heteroalicyclyl and substituted or unsubstituted heteroaryl;

$R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;

$R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, C(═O)OH, C(═O)$NH_2$, C(═O)O—$C_{1-4}$ alkyl, and substituted or unsubstituted heteroaryl;

$R_3$ is selected from the group consisting of $C_{1-4}$ alkyl, $C_{2-4}$ alkenyl, $C_{1-4}$ haloalkyl, $C_{1-4}$ hydroxyalkyl, $C_{1-6}$ hydroxyhaloalkyl, $C_{1-4}$ alkylene-$C_{1-4}$ alkoxy, substituted or unsubstituted $C_{3-7}$ cycloalkyl, and substituted or unsubstituted $C_{3-7}$ cycloalkenyl;

$R_4$ and $R_5$ are each independently hydrogen or $C_{1-4}$ alkyl, or $R_4$ and $R_5$ are taken together with the carbon atom to which they are attached to form a $C_{3-4}$ cycloalkyl;

$R_6$ is selected from the group consisting of hydrogen, CN, halogen, $C_{1-4}$ alkyl, $C_{1-4}$ hydroxyalkyl, $C_{1-6}$ hydroxyhaloalkyl, $C_{1-4}$ haloalkyl, $C_{1-4}$ alkoxy, $C_{1-4}$ haloalkoxy, and substituted or unsubstituted heteroaryl;

$R_7$ is selected from the group consisting of hydrogen, hydroxyl, CN, halogen, $C_{1-4}$ alkyl, $C_{1-4}$ haloalkyl, $C_{1-4}$ hydroxyalkyl, $C_{1-4}$ alkoxy, $C_{1-4}$ haloalkoxy, and substituted or unsubstituted heteroaryl;

each $R_8$ independently is selected from the group consisting of hydrogen, hydroxyl, CN, halogen, $C_{1-4}$ alkyl, $C_{1-4}$haloalkyl, $C_{1-4}$ alkoxy, $C_{1-4}$ haloalkoxy, and substituted or unsubstituted heteroaryl; and whenever $R_7$ is hydrogen and each $R_8$ present is hydrogen, then $R_6$ is selected from the group consisting of CN, halogen, $C_{1-4}$ alkyl, $C_{1-4}$ haloalkyl, $C_{1-4}$ hydroxyalkyl, $C_{1-6}$ hydroxyhaloalkyl, $C_{1-4}$ alkoxy, $C_{1-4}$ haloalkoxy, and substituted or unsubstituted heteroaryl; and when substituted, a heteroalicyclyl is substituted with 1 to 3 substituents independently selected from the group consisting of $C_{1-4}$ alkyl, $C_{1-4}$ haloalkyl, $C_{1-4}$ hydroxyalkyl, $C_{1-6}$ hydroxyhaloalkyl, hydroxy, $C_{1-4}$ alkoxy, and halogen; and when substituted, a heteroaryl is substituted with 1 to 3 substitutents independently selected from the group consisting of $C_{1-4}$ alkyl, $C_{1-4}$ hydroxyalkyl, $C_{2-4}$ alkenyl, $C_{2-4}$ alkynyl, hydroxy, $C_{1-4}$ alkoxy, cyano, halogen, $C_{1-4}$ haloalkyl, $C_{1-4}$ haloalkoxy and $C_{1-6}$ hydroxyhaloalkyl; and when substituted, a cycloalkyl or cycloalkenyl is substituted with 1 to 3 substituents independently selected from the group consisting of $C_{1-4}$ alkyl and halogen.

In one aspect provided herein are pharmaceutical compositions comprising a compound of Formula (I) or a stereoisomer thereof, or a pharmaceutically acceptable salt of the compound or stereoisomer of Formula (I) and at least one pharmaceutical acceptable excipient.

In one aspect provided herein are compounds of Formula (I) or a stereoisomer thereof, or a pharmaceutically acceptable salt of the compound or stereoisomer of Formula (I), or pharmaceutical compositions thereof for use in treatment and/or prevention of a disease or disorder or a symptom thereof selected from the group consisting of asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ankylosing spondylitis, psoriasis, psoriatic arthritis, ichthyoses, bullous diseases, hidradenitis suppurativa, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myastehnia Gravis, Guillain-Barre syndrome, Graves' disease, scleritis, obesity, obesity-induced insulin resistance, type II diabetes, and cancer.

Further, advantageous features of various embodiments are defined in the dependent claims and within the detailed description below.

DETAILED DESCRIPTION OF PREFERRED EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

As used herein, any "R" group(s) such as, without limitation, R, $R_{0a}$, $R_{0b}$, $R_{1a}$, $R_{1b}$, $R_2$, $R_3$, $R_4$, $R_5$, $R_6$, $R_7$, $R_8$, $R_9$, and $R_{10}$, represent substituents that can be attached to the indicated atom. Examples of R groups includes but is not limited to hydrogen, hydroxy, alkyl, alkenyl, alkynyl, alkoxy, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined" as defined herein to form a cycloalkyl, aryl, heteroaryl or heteroalicyclyl group. For example, without limitation, if $R_a$ and $R_b$ of an $NR_aR_b$ group are indicated to be "taken together" or "combined", it means that they are covalently bonded to one another at their terminal atoms to form a ring that includes the nitrogen:

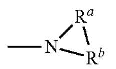

As readily recognized by the skilled person, any given group disclosed herein may comprise further hydrogen(s) than the one(s) provided by a R-group, being hydrogen, attached to the group.

Whenever a group is described as being "unsubstituted or substituted," if substituted, the substituent(s) (which may be present one or more times, such as 1, 2, 3 or 4 times) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof. When a substituent on a group is deemed to be "substituted," the substitutent itself is substituted with one or more of the indicated substitutents. When the referenced substituent is substituted, it is meant that one or more hydrogen atoms on the referenced substituent may be replaced with a group(s)

individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, $3^{rd}$ Ed., John Wiley & Sons, New York, NY, 1999, which is hereby incorporated by reference in its entirety.

As used herein, "$C_m$ to $C_n$," "$C_m$-$C_n$" or "$C_{m-n}$" in which "m" and "n" are integers refers to the number of carbon atoms in the relevant group. That is, the group can contain from "m" to "n", inclusive, carbon atoms. Thus, for example, a "$C_1$ to $C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH)_3CH_2$—, $CH_3CH(CH)_3CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms, such as "$C_{1-6}$". The alkyl group could also be a lower alkyl having 1 to 4 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When substituted, the substituent group(s) is(are) one or more group(s) individually and independently selected from alkenyl, alkynyl, cycloalkyl including but not limited to cyclopropyl, cycloalkenyl, cycloalkynyl, aryl, heteroaryl, heteroalicyclyl, aralkyl, heteroaralkyl, (heteroalicyclyl)alkyl, hydroxy, oxo, alkoxy including but not limited to methoxy, aryloxy, acyl, ester, O-carboxy, mercapto, alkylthio, arylthio, cyano, halogen including but not limited to fluoro, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof.

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atoms, 3 carbon atoms, 4 carbon atoms, etc., up to and including 20 carbon atoms, although the present definition also covers the occurrence of the term "alkenyl" where no numerical range is designated). When substituted, the substituent group(s) is(are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, mercapto, alkylthio, cyano, halogen, nitro, haloalkyl, hydroxyalkyl, haloalkoxy, and amino, including mono- and di-substituted amino groups, and the protected derivatives thereof.

As used herein, "alkynyl" refers to an alkyl group that contains in the straight or branched hydrocarbon chain one or more triple bonds. The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atoms, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" may be attached to a group and refers to one or more carbon atom(s) and the associated hydrogen atom(s) in the attached group have been independently replaced with the same or different heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replaced may be in the middle or at the end of the alkyl group. Examples of heteroalkyl include $C_{1-6}$ heteroalkyl wherein one or more of the carbon atom(s) has been replaced by a heteroatom selected from the group consisting of nitrogen, oxygen and sulfur, examples are, —S-alkyl, —O-alkyl, —NH-alkyl, -alkylene-O-alkyl, etc. A heteroalkyl may be substituted.

As used herein, "aryl" refers to a carbocyclic (all carbon) ring or two or more fused rings (rings that share two adjacent carbon atoms) that have a fully delocalized pi-electron system. In some embodiments described herein the aryl group is a $C_{1-10}$ aryl, which may be substituted or unsubstituted. Examples of aryl groups include, but are not limited to, benzene, naphthalene and azulene. An aryl group may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. In some embodiments described herein the heteroaryl includes, but is not limited to, $C_{6-10}$ heteroaryl, wherein one to four carbon atoms is/are replaced by one to four heteroatoms independently selected from the group consisting of nitrogen, oxygen and sulfur. Examples of monocyclic "heteroaryl" include, but are not limited to, furan, thiophene, phthalazine, pyrrole, oxazole, oxadiazole including but not limited to 1, 2, 4-oxadiazole and 1, 3, 4-oxadiazole, thiazole, imidazole, pyrazole, isoxazole, isothiazole, triazole including but not limited to 1, 2,4-triazole and 1, 2,3-triazole, thiadiazole, pyridine, pyridazine, pyrimidine, pyrazine, tetrazole, and triazine. Examples of multicyclic "heteroaryl" include, but are not limited to, quinoline, isoquinoline, quinazoline, quinoxaline, indole, purines, benzofuran, benzothiophene, benzopyranones (e.g. coumarin, chromone, and isocoumarin). A heteroaryl may be substituted. When substituted, hydrogen atoms are replaced by substituent group(s) that is(are) one or more group(s) independently selected from alkyl including but not limited to methyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl including but not limited to 2-hydroxyethyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a medium size alkylene having 1 to 10 carbon atoms, such as "$C_{1-6}$" The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene ($-CH_2-$), ethylene ($-CH_2CH_2-$), propylene ($-CH_2CH_2CH_2-$), and butylene ($-(CH_2)_4-$) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to $-CH_2-O-$, $-CH_2-CH_2-O-$, $-CH_2-CH_2-CH_2-O-$, $-CH_2-NH-$, $-CH_2-CH_2-NH-$, $-CH_2-CH_2-CH_2-NH-$, $-CH_2-CH_2-NH-CH_2-$, $-O-CH_2-CH_2-O-CH_2-CH_2-O-$, $-O-CH_2-CH_2-O-CH_2-CH_2-$, and the like.

As used herein, "alkylidene" refers to a divalent group, such as $=CR'R''$, which is attached to one carbon of another group, forming a double bond. Alkylidene groups include, but are not limited to, methylidene ($=CH_2$) and ethylidene ($=CHCH_3$). As used herein, "arylalkylidene" refers to an alkylidene group in which either R' or R'' is an aryl group. An alkylidene group may be substituted.

As used herein, "alkoxy" refers to the group $-OR$ wherein R is an alkyl, e.g. methoxy, ethoxy, n-propoxy, cyclopropoxy, 1-methylethoxy (isopropoxy), n-butoxy, iso-butoxy, sec-butoxy, tert-butoxy, amoxy, tert-amoxy and the like. An alkoxy may be substituted.

As used herein, "alkylthio" refers to the formula $-SR$ wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO— and RS—, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula $-OR$ wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, such as from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be independently selected from an alkyl, including but not limited to methyl, or a halogen, including but not limited to fluoro, or may be selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. Cycloalkenyl groups may range from $C_3$ to $C_{10}$, such as from $C_3$ to $C_8$ or from $C_5$ to $C_{10}$. For example, $C_{3-8}$ cycloalkenyl includes $C_{4-8}$ cycloalkenyl, $C_{5-8}$ cycloalkenyl or $C_{6-8}$ cycloalkenyl. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered ring which consists of carbon atoms and from one to five heteroatoms selected from the group consisting of nitrogen, oxygen and sulfur. The heteroalicyclic or heteroalicyclyl groups may range from $C_2$ to $C_{10}$, in some embodiments it may range from $C_2$ to $C_9$, and in other embodiments it may range from $C_2$ to $C_8$. In some embodiments The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings, examples are 2H-benzo[b][1,4]oxazin-3(4H)-one, 3,4-dihydroquinolin-2(1H)-one, 1,2,3,4-tetrahydroquinoline, 3,4-dihydro-2H-benzo[b][1,4]oxazine, 2,3-dihydrobenzo[d]oxazole, 2,3-dihydro-1H-benzo[d]imidazole, indoline, and 1,3-dihydro-2H-benzo[d]imidazol-2-one, and benzo[d]oxazol-2(3H)-one. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, hydroxyalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, dioxolanyl, imidazolinyl, morpholinyl, oxetanyl, oxiranyl, piperidinyl N-Oxide, piperidinyl, piperazinyl, pyrrolidinyl, pyranyl, 4-piperidonyl, pyrazolidinyl, 2-oxopyrrolidinyl, tetrahydrofuranyl, tetrahydropyranyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "(cycloalkyl)alkyl" is a cycloalkyl group connected, as a substituent, via an alkylene group. The alkylene and cycloalkyl of a (cycloalkyl)alkyl may be substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), $C_1$ (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl, 1,1-difluoroethyl, 2-fluoroethyl, 1-chloro-2-fluoromethyl and 2-fluoroisobutyl. A haloalkyl may be substituted or unsubstituted, and some embodiments relate to a medium size haloalkyl having 1 to 10 carbon atoms, such as $C_{1-6}$ haloalkyl.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutyoxy. A haloalkoxy may be substituted.

As used herein, the term "hydroxyalkyl" refers to an alkyl group in which one of more of the hydrogen atoms are replaced by a hydroxyl group. Such groups include but are not limited to hydroxymethyl, hydroxyethyl, including but not limited to 2-hydroxyethyl, hydroxypropyl, hydroxybutyl, hydroxypentyl and hydroxyhexyl. A hydroxyalkyl group may be substituted or unsubstituted, and some embodiments relate to a medium size hydroxyalkyl having 1 to 10 carbon atoms, such as $C_{1-6}$ hydroxyalkyl; when substituted the substituents may be one or more groups independently selected from the group consisting of halogen, including but not limited to fluoro, and haloalkyl, including but not limited to trifluoromethyl; such substituted "hydroxyalkyl" groups include but are not limited to 1,1,1,3,3,3-hexafluoro-2-hydroxypropan-2-yl and 1,1-difluoro-2-hydroxyethyl.

An "O-carboxy" group refers to a "RC(═O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(═O)OR" group in which R can be the same as defined with respect to O-carboxy. A C-carboxy may be substituted.

A "trihalomethanesulfonyl" group refers to an "$X_3CSO_2$—" group" wherein X is a halogen.

A dashed bond, - - - -, represents an optional unsaturation between the atoms forming the bond. This bond may be unsaturated (e.g. C═C, C═N, C═O) or saturated (e.g.

C—C, C—N, C—O). When a dashed bond is present in a ring system it may form part of an aromatic ring system.

As used herein, a straight (unwedged) bolded or hashed bond, ━ or ''''', refers to relative stereochemistry inclusive of all possible stereoisomers at that position.

As used herein, and unless otherwise indicated, a wedged-bond (bolded, hashed, or otherwise), ◀, ◁, or ·''''', refers to absolute stereochemistry referring to the particular stereoisomer as depicted at that position.

A "nitro" group refers to a "—$NO_2$" group.

A "cyano" group refers to a "—CN" group.

A "cyanato" group refers to an "—OCN" group.

An "isocyanato" group refers to a "—NCO" group.

A "thiocyanato" group refers to a "—SCN" group.

A "carbonyl" group refers to a "—C(═O)—" group.

A "thiocarbonyl" group refers to a "—C(═S)—" group.

An "oxo" group refers to a "═O" group.

A "hydroxy" group or "hydroxyl" group refers to an "—OH" group.

An "isothiocyanato" group refers to an "—NCS" group.

A "sulfinyl" group refers to an "—S(═O)—R" group in which R can be the same as defined with respect to O-carboxy. A sulfinyl may be substituted.

A "sulfonyl" group refers to an "$SO_2R$" group in which R can be the same as defined with respect to O-carboxy. A sulfonyl may be substituted.

An "S-sulfonamido" group refers to a "—$SO_2NR_AR_B$" group in which $R_A$ and $R_B$ indendently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl substituted or unsubstituted heteroalicyclyl, substituted or unsubstituted aryl, and substituted or unsubstituted heteroaryl. A S-sulfonamido may be substituted.

An "N-sulfonamido" group refers to a "$RSO_2N(R_A)$—" group in which R and $R_A$ indendently of each other can be the same as defined with respect to the R group as defined for O-carboxy. An N-sulfonamido may be substituted.

A "trihalomethanesulfonamido" group refers to an "$X_3CSO_2N(R)$—" group with X as halogen and R can be the same as defined with respect to O-carboxy. A trihalomethanesulfonamido may be substituted.

A "C-amido" group refers to a "—C(═O)$NR_AR_B$" group in which $R_A$ and $R_B$ indendently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl substituted or unsubstituted heteroalicyclyl, substituted or unsubstituted aryl, and substituted or unsubstituted heteroaryl. A C-amido may be substituted.

An "N-amido" group refers to a "RC(═O)$NR_A$—" group in which R and $R_A$ independently of each other can be the same as defined with respect to the R group as defined for O-carboxy. An N-amido may be substituted.

An "ester" refers to a "—C(═O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amine" or "amino" refers to "$RNH_2$" (a primary amine), "$R_2NH$" (a secondary amine), "$R_3N$" (a tertiary amine). An amino group may be substituted.

A lower aminoalkyl refers to an amino group connected via a lower alkylene group. A lower aminoalkyl may be substituted.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, $3^{rd}$ Ed., John Wiley & Sons, New York, NY, 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

List of Abbreviations

DMF dimethylformamide
DMSO dimethylsulfoxide
MeOH methanol
EtOH ethanol
THF tetrahydrofurane
DCM dichloromethane, methylene chloride
DCE 1,2-dichloroethane
LRMS low resolution mass spectrometry
HPLC high pressure liquid chromatography
Prep-HPLC preparative high pressure liquid chromatography
h hour
min minutes
EA ethyl acetate
EDC-HCl 3-((ethylimino)methyleneamino)-N,N-dimethylpropan-1-aminium chloride
DIEA diisopropylethyamine
TEA triethylamine
TFA trifluoroacetic acid
HCl hydrochloric acid, hydrogen chloride
HOBt 1-hydroxybenzotriazole hydrate
HOAt 1-hydroxy-7-azabenzotriazole
HATU 1-[bis(dimethylamino)methylene]-1H-1,2,3-triazolo[4,5-b]pyridinium 3-oxid hexafluorophosphate
DMAP 4-(dimethylamino)pyridine
DAST (diethylamino)sulfur trifluoride
DIAD Diisopropyl azodicarboxilate
DMP Dess-Martin Periodinane, 1,1,1-tris(acetyloxy)-1,1-dihydro-1,2-benziodoxol-3-(1H)-one
TBAF tetrabutylammonium fluoride trihydrate
TBDMSCl tert-butyldimethylsilyl chloride
MsCl methanesulfonyl chloride
NAS nucleophilic aromatic substitution
nBuLi n-Butyllithium
iPr isopropyl
Boc tert-Butyloxycarbonyl
Flash CC Flash Column Chromatography
on overnight
rt room temperature
aq aqueous
ND Not Determined
Cbz Carboxybenzyl
Hex hexane
Hept heptane DEA diethylamine
PE petroleum ether
DAD Diode Array Detector
TOF Time of Flight
IPA isopropanol
Pg Protective group
" Enantiomerically enriched It is understood that, in any compound disclosed herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. Further, compounds provided herein may be scalemic mixtures. In addition, it is understood that in any compound having one or more double bond(s) generating geometrical isomers that can be defined as E or Z each double bond may independently be E or Z or a mixture thereof. Likewise, all tautomeric forms are also intended to be included.

As used herein, the term "rac" refers to "racemic", "racemate", etc., as is understood by one of ordinary skill in the art. For example, a racemate comprises a mixture of enantiomers of a chiral molecule in equivalent amounts. Typically, a racemate does not exhibit optical activity.

As used herein, the term "rel" refers to the relative, but not absolute, configuration of a stereogenic center with respect to any other stereogenic center within the same compound, as is understood by one of ordinary skill in the art.

As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

It is understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, reference to an element, whether by description or chemical structure, encompasses all isotopes of that element unless otherwise described. By way of example, the term "hydrogen" or "H" in a chemical structure as used herein is understood to encompass, for example, not only $^1H$, but also deuterium ($^2H$), tritium ($^3H$), and mixtures thereof unless otherwise denoted by use of a specific isotope. Other specific non-limiting examples of elements for which isotopes are encompassed include carbon, phosphorous, idodine, and fluorine.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, a "prodrug" refers to a compound that may not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a carboxylic acid (the active entity) once inside the cell where water-solubility is beneficial. A further example of a prodrug might be a short peptide (polyaminoacid) bonded to an acid group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985) Medicinal Chemistry A Biochemical Approach, Oxford University Press, New York, pages 388-392).

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any intracellular molecule that in response to ligation generates a signal. A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

"Selective" or "selectivity" is defined as a compound's ability to generate a desired response from a particular receptor type, subtype, class or subclass while generating less or little response from other receptor types. "Selective" or "selectivity" of one or more particular subtypes of a compound means a compound's ability to increase the activity of the subtypes while causing less, little or no increase in the activity of other subtypes.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Compounds

In one embodiment the present disclosure relates to a compound of Formula (I)

(I)

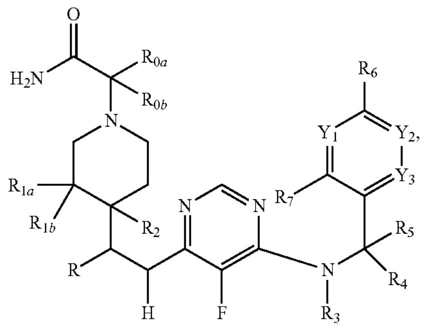

a stereoisomer thereof, or a pharmaceutically acceptable salt of the compound or stereoisomer, wherein

- $Y_1$, $Y_2$ and $Y_3$ are independently N or $CR_8$;
- R is selected from the group consisting of hydrogen, $C_{1-6}$ alkyl, and $C_{1-4}$ hydroxyalkyl;
- $R_{0a}$ and $R_{0b}$ independently are selected from the group consisting of hydrogen, $C_{1-4}$ alkyl, $C_{1-4}$ hydroxyalkyl, $C_{1-4}$ haloalkyl, CN, substituted or unsubstituted heteroalicyclyl and substituted or unsubstituted heteroaryl;
- $R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;
- $R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, C(═O)OH, C(═O)$NH_2$, C(═O)O—$C_{1-4}$ alkyl, and substituted or unsubstituted heteroaryl;
- $R_3$ is selected from the group consisting of $C_{1-4}$ alkyl, $C_{2-4}$ alkenyl, $C_{1-4}$ haloalkyl, $C_{1-4}$ hydroxyalkyl, $C_{1-6}$ hydroxyhaloalkyl, $C_{1-4}$ alkylene-$C_{1-4}$ alkoxy, substituted or unsubstituted $C_{3-7}$ cycloalkyl, and substituted or unsubstituted $C_{3-7}$ cycloalkenyl;

$R_4$ and $R_5$ are each independently hydrogen or $C_{1-4}$ alkyl, or $R_4$ and $R_5$ are taken together with the carbon atom to which they are attached to form a $C_{3-4}$ cycloalkyl;

$R_6$ is selected from the group consisting of hydrogen, CN, halogen, $C_{1-4}$ alkyl, $C_{1-4}$ hydroxyalkyl, $C_{1-6}$ hydroxyhaloalkyl, $C_{1-4}$ haloalkyl, $C_{1-4}$ alkoxy, $C_{1-4}$ haloalkoxy, and substituted or unsubstituted heteroaryl;

$R_7$ is selected from the group consisting of hydrogen, hydroxyl, CN, halogen, $C_{1-4}$ alkyl, $C_{1-4}$ haloalkyl, $C_{1-4}$ hydroxyalkyl, $C_{1-4}$ alkoxy, $C_{1-4}$ haloalkoxy, and substituted or unsubstituted heteroaryl;

each $R_8$ independently is selected from the group consisting of hydrogen, hydroxyl, CN, halogen, $C_{1-4}$ alkyl, $C_{1-4}$haloalkyl, $C_{1-4}$ alkoxy, $C_{1-4}$ haloalkoxy, and substituted or unsubstituted heteroaryl; and whenever $R_7$ is hydrogen and each $R_8$ present is hydrogen, then $R_6$ is selected from the group consisting of CN, halogen, $C_{1-4}$ alkyl, $C_{1-4}$ haloalkyl, $C_{1-4}$ hydroxyalkyl, $C_{1-6}$ hydroxyhaloalkyl, $C_{1-4}$ alkoxy, $C_{1-4}$ haloalkoxy, and substituted or unsubstituted heteroaryl; and when substituted, a heteroalicyclyl is substituted with 1 to 3 substituents independently selected from the group consisting of $C_{1-4}$ alkyl, $C_{1-4}$ haloalkyl, $C_{1-4}$ hydroxyalkyl, $C_{1-6}$ hydroxyhaloalkyl, hydroxy, $C_{1-4}$ alkoxy, and halogen; and when substituted, a heteroaryl is substituted with 1 to 3 substitutents independently selected from the group consisting of $C_{1-4}$ alkyl, $C_{1-4}$ hydroxyalkyl, $C_{2-4}$ alkenyl, $C_{2-4}$ alkynyl, hydroxy, $C_{1-4}$ alkoxy, cyano, halogen, $C_{1-4}$ haloalkyl, $C_{1-4}$ haloalkoxy and $C_{1-6}$ hydroxyhaloalkyl; and when substituted, a cycloalkyl or cycloalkenyl is substituted with 1 to 3 substituents independently selected from the group consisting of $C_{1-4}$ alkyl and halogen.

In some embodiments disclosed herein, R is hydrogen.

In some embodiments disclosed herein, $R_6$ is selected from the group consisting of hydrogen, CN, halogen, $C_{1-4}$haloalkyl, $C_{1-4}$haloalkoxy, $C_{1-4}$ hydroxyalkyl, $C_{1-6}$ hydroxyhaloalkyl; 5 membered heteroaryl, and 5-membered heteroaryl substituted with 1 or 2 substituents independently selected from methyl or hydroxyethyl, and whenever $R_7$ is hydrogen and each $R_8$ present is hydrogen, then $R_6$ cannot be hydrogen. In other embodiments, $R_6$ is selected from the group consisting of hydrogen, CN, chloro, $CF_3$, $CHF_2$, $CCH_3F_2$, $OCF_3$, and $OCHF_2$, $OCH_2F$, $C(CF_3)_2OH$, $CF_2CH_2OH$, pyrazolyl, and pyrazolyl substituted with 1 substituent selected from methyl or 2-hydroxyethyl, and whenever $R_7$ is hydrogen and each $R_8$ present is hydrogen, then $R_6$ cannot be hydrogen. In other embodiments, $R_6$ is selected from the group consisting of hydrogen, $CF_3$, $CCH_3F_2$, $OCHF_2$, $C(CF_3)_2OH$, pyrazolyl, and methyl-pyrazolyl, and whenever $R_7$ is hydrogen and each $R_8$ present is hydrogen, then $R_6$ cannot be hydrogen. In other embodiments, $R_6$ is selected from the group consisting of $CF_3$, $C(CF_3)_2OH$, 1-methyl-1H-pyrazol-4-yl, and 1H-pyrazol-1-yl. In other embodiments, $R_6$ is $CF_3$.

In some embodiments disclosed herein, $R_7$ is selected from the group consisting of hydrogen, halogen, hydroxyl, cyano, $CH_3$, $OCH_3$, $CF_3$, $CHF_2$, $OCF_3$ and $OCHF_2$. In other embodiments, $R_7$ is hydrogen or fluoro.

In some embodiments disclosed herein, $Y_1$, $Y_2$ and $Y_3$ are each CH. In some embodiments, $Y_1$ is N and $Y_2$ and $Y_3$ are each CH. In some embodiments, $Y_2$ is N and $Y_1$ and $Y_3$ are each CH. In some embodiments, $Y_3$ is N and $Y_1$ and $Y_2$ are each CH. In some embodiments; $Y_3$ is CH— and $Y_1$ and $Y_2$ are each N.

In some embodiments disclosed herein, $Y_1$ and $Y_2$ are each CH—, and $Y_3$ is $CR_8$ wherein $R_8$ is selected from the group consisting of hydrogen, hydroxyl, methyl, $OCH_3$, fluoro, chloro, and $CF_3$.

In some embodiments disclosed herein, $R_8$ is hydrogen or fluoro.

In some embodiments disclosed herein $Y_2$ is N and $Y_1$ and $Y_3$ independently are CH. In some embodiments, $Y_3$ is N and $Y_1$ and $Y_2$ independently are each CH.

In some embodiments disclosed herein, $R_6$ is hydrogen, at least one of $Y_2$ or $Y_3$ is $CR_8$, and $R_8$ is selected from the group consisting of CN, halogen, $C_{1-4}$ alkyl, $C_{1-4}$ haloalkyl, $C_{1-4}$ alkoxy, and $C_{1-4}$ haloalkoxy. In some embodiments, $R_6$ is hydrogen, and $Y_2$ is $C(OCF_3)$.

In some embodiments disclosed herein, $R_4$ and $R_5$ independently are hydrogen or methyl. In some embodiments, $R_4$ and $R_5$ are taken together with the carbon atom to which they are attached to form a cyclopropyl.

In some embodiments disclosed herein, $R_4$ is hydrogen or methyl, and $R_5$ is hydrogen.

In some embodiments disclosed herein, $R_4$ and $R_5$ are each hydrogen.

In some embodiments disclosed herein, $R_3$ is selected from the group consisting of methyl, ethyl, n-propyl, isopropyl, n-butyl, iso-butyl, tert-butyl, $CH_2CH_2F$, $CH_2CH_2OCH_3$, cyclopropyl-$CH_2$—, cyclopropyl, methylcyclopropyl, cyclobutyl, and fluorocyclobutyl. In some embodiments, $R_3$ is selected from the group consisting of methyl, ethyl, n-propyl, isopropyl, n-butyl, iso-butyl, tert-butyl, cyclopropyl, 1-methylcyclopropyl, cyclobutyl, and 3-fluorocyclobutyl. In some embodiments, $R_3$ is selected from the group consisting of methyl, ethyl, isopropyl, cyclopropyl, 1-methylcyclopropyl, cyclobutyl, (1r,3S)-3-fluorocyclobutyl, and (1s,3R)-3-fluorocyclobutyl. In some embodiments, $R_3$ is selected from the group consisting of methyl, ethyl, and cyclopropyl. In some embodiments, $R_3$ is ethyl. In some embodiments, $R_3$ is cyclopropyl.

In some embodiments disclosed herein, $R_2$ is selected from the group consisting of hydrogen, hydroxyl, amino, CN, halogen, methyl, ethyl, $CH_2OH$, $CH_2CH_2OH$, $C(=O)OC_{1-2}$ alkyl, $C(=O)NH_2$, and unsubstituted or substituted 5 membered heteroaryl. In some embodiments, $R_2$ is selected from the group consisting of hydrogen, hydroxyl, CN, fluoro, methyl, $CH_2OH$, $C(=O)OCH_3$, $C(=O)NH_2$, oxadiazolyl, and triazolyl. In some embodiments, $R_2$ is selected from the group consisting of hydrogen, hydroxyl, CN, methyl, $CH_2OH$, $C(=O)OCH_3$, $C(=O)NH_2$, 1,2,4-oxadiazol-3-yl, 1,3,4-oxadiazol-2-yl, 1H-1,2,4-triazol-3-yl, and 1H-1,2,3-triazol-5-yl. In some embodiments, $R_2$ is selected from the group consisting of hydrogen, CN, methyl, $CH_2OH$, and hydroxyl. In some embodiments, $R_2$ is hydrogen or hydroxyl. In some embodiments, $R_2$ is hydrogen. In some embodiments, $R_2$ is hydroxyl.

In some embodiments disclosed herein, $R_{1a}$ is selected from the group consisting of hydrogen, hydroxyl, fluoro, and $CF_3$, and $R_{1b}$ is selected from the group consisting of hydrogen, fluoro, and methyl.

In some embodiments disclosed herein, $R_{1a}$ is selected from the group consisting of hydroxyl, fluoro, and $CF_3$, and $R_{1b}$ is selected from the group consisting of hydrogen, fluoro, and methyl.

In some embodiments disclosed herein, $R_{1a}$ is hydroxyl or fluoro. In some embodiments, $R_{1a}$ is hydroxyl.

In some embodiments disclosed herein, $R_{1b}$ is hydrogen. In some embodiments, $R_{1b}$ is methyl.

In some embodiments disclosed herein, at least one of $R_{1a}$, $R_{1b}$, and $R_2$ is not hydrogen.

In some embodiments disclosed herein, $R_{1a}$ is selected from the group consisting of hydrogen, hydroxyl, and fluoro; $R_{1b}$ is selected from the group consisting of hydrogen, fluoro, and methyl; and $R_2$ is selected from the group consisting of hydrogen, hydroxyl, methyl, CN, $CH_2OH$, and $CH_2CH_2OH$. In some embodiments, $R_{1a}$ is selected from the group consisting of hydroxyl and hydrogen. In some embodiments, $R_{1b}$ is hydrogen and $R_2$ is selected from the group consisting of hydrogen, hydroxyl, $CH_2OH$, and $CH_2CH_2OH$, provided either $R_{1a}$ is hydroxyl or $R_2$ is selected from the group consisting of hydroxyl, $CH_2OH$, and $CH_2CH_2OH$.

In some embodiments disclosed herein, $R_{0a}$ is selected from the group consisting of hydrogen, methyl, $CH_2OH$, $CH_2CH_2OH$, $CH_2F$, and $CHF_2$; and $R_{0b}$ is selected from the group consisting of hydrogen, $C_{1-4}$ alkyl, $C_{1-4}$ hydroxyalkyl, and $C_{1-4}$ haloalkyl.

In some embodiments disclosed herein, $R_{0a}$ is selected from the group consisting of hydrogen, methyl, $CH_2OH$, and $CH_2CH_2OH$. In some embodiments, $R_{0a}$ is hydrogen. In some embodiments, $R_{0b}$ is hydrogen.

In some embodiments, provided herein is a compound having a structure of Formula (II) or Formula (III):

(II)

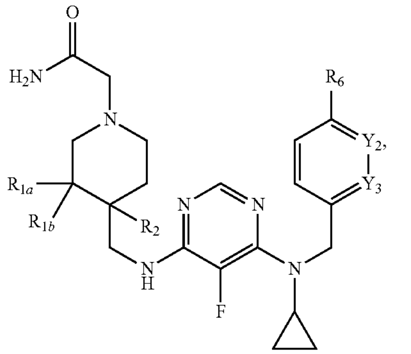

or (III)

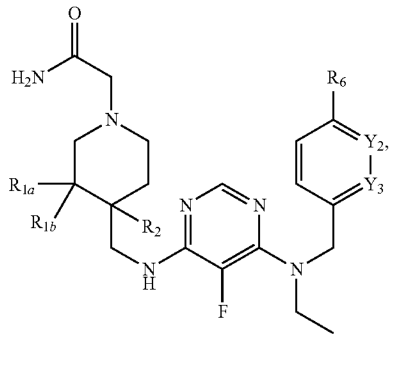

a stereoisomer thereof, or a pharmaceutically acceptable salt of the compound or stereoisomer, wherein $R_{1a}$ is fluoro or hydroxyl, $R_{1b}$ is hydrogen or fluoro, $R_2$ is hydrogen or hydroxyl, $R_6$ is $CF_3$, $Y_2$ and $Y_3$ are independently N or $CR_8$, and $R_8$ is hydrogen or fluoro. In some embodiments $Y_2$ and $Y_3$ are each CH, or $Y_2$ is CH and $Y_3$ is CF. In some embodiments, $R_{1a}$ is hydroxyl and $R_{1b}$ is hydrogen. In some embodiments, $R_2$ is hydrogen. In some embodiments $R_2$ is hydroxyl.

In some embodiments disclosed herein, $R_{0a}$ is selected from the group consisting of hydrogen, methyl, $CH_2OH$, and $CH_2CH_2OH$; $R_{0b}$ is selected from the group consisting of hydrogen and methyl; $R_{1a}$ is selected from the group consisting of hydrogen, hydroxyl, fluoro, and $CF_3$; $R_{1b}$ is selected from the group consisting of hydrogen, fluoro, and methyl; $R_2$ is selected form the group consisting of hydrogen, hydroxyl, amino, CN, fluoro, methyl, $CH_2$—OH, C(═O)—$NH_2$, C(═O)O—$CH_3$, 1,2,4-oxadiazol-3-yl, 1,3,4-oxadiazol-2-yl, 1H-imidazol-2-yl, 1H-1,2,3-triazol-5-yl, 1H-1,2,4-triazol-3-yl, and 4-methyl-4H-1,2,4-triazol-3-yl; R is selected from the group consisting of hydrogen and $CH_2OH$; $R_3$ is selected from the group consisting of methyl, ethyl, isopropyl, isobutyl, $CH_2CH_2F$, $CH_2CH_2OCH_3$, cyclopropyl-$CH_2$—, cyclopropyl, 1-methylcyclopropyl, cyclobutyl, and 3-fluorocyclobutyl; $R_4$ is hydrogen or methyl; $R_5$ is hydrogen; $R_6$ is selected from the group consisting of hydrogen, chloro, CN, $CF_3$, $CHF_2$, $CCH_3F_2$, $OCH_3$, $OCF_3$, $OCH_2F$, $OCHF_2$, $C(CF_3)_2OH$, $CF_2CH_2OH$, 1H-pyrazol-1-yl, 1-methyl-1H-pyrazol-4-yl, and 1-(2-hydroxyethyl)-1H-pyrazol-4-yl; $R_7$ is hydrogen or chloro; $Y_1$, $Y_2$ and $Y_3$ are each CH; or $Y_1$ is CH, $Y_2$ is CH, and $Y_3$ is selected from the group consisting of N, C(F), $C(OCH_3)$, $C(CH_3)$, $C(C_1)$, and $C(CF_3)$; or $Y_1$ is CH, $Y_2$ is selected from the group consisting of N, C(CN), C(1H-1,2,4-triazol-1-yl), $C(OCF_3)$, $C(OCH_3)$, C(F), $C(OCHF_2)$, and $C(C_1)$, and $Y_3$ is CH; or $Y_1$ is CH, $Y_2$ is $C(C_1)$ and $Y_3$ is $C(C_1)$; or $Y_1$ is $C(CH_3)$, $Y_2$ is CH and $Y_3$ is $C(CH_3)$; or $Y_1$ is $C(CH_3)$, $Y_2$ is $C(CH_3)$ and $Y_3$ is CH; or $Y_1$ is $C(CF_3)$, $Y_2$ is $C(CF_3)$ and $Y_3$ is CH; or $Y_1$ is $C(C_1)$, $Y_2$ is $C(C_1)$ and $Y_3$ is CH; or $Y_1$ is N, $Y_2$ is N and $Y_3$ is CH. In some cases; when $R_7$ is H and $Y_1$, $Y_2$ and $Y_3$ are CH, $R_6$ is selected from the group consisting of chloro, CN, $CF_3$, $C(CH_3)F_2$, $OCF_3$, $OCH_2F$, $OCHF_2$, $C(CF_3)_2OH$, $CF_2CH_2OH$, 1H-pyrazol-1-yl, 1-methyl-1H-pyrazol-4-yl, and 1-(2-hydroxyethyl)-1H-pyrazol-4-yl.

In some embodiments disclosed herein, $R_{0a}$ is selected from the group consisting of hydrogen, methyl, $CH_2OH$, and $CH_2CH_2OH$; $R_{0b}$ is hydrogen or methyl; $R_{1a}$ is selected from the group consisting of hydrogen, hydroxyl, $CF_3$, and fluoro; $R_{1b}$ is selected from the group consisting of hydrogen, fluoro, and methyl; $R_2$ is selected from the group consisting of hydrogen, hydroxyl, CN, $CH_2OH$, methyl, $CO_2Me$, $CONH_2$, 1,2,4-oxadiazol-3-yl, 1,3,4-oxadiazol-2-yl, 1H-1,2,3-triazol-5-yl, and 1H-1,2,4-triazol-3-yl; R is hydrogen; $R_3$ is selected from the group consisting of methyl, ethyl, isopropyl, cyclopropyl-$CH_2$—, cyclopropyl, 1-methylcyclopropyl, cyclobutyl, (1r,3S)-3-fluorocyclobutyl, and (1s,3R)-3-fluorocyclobutyl; $R_4$ is hydrogen; $R_5$ is hydrogen; $R_6$ is selected from the group consisting of hydrogen, $CF_3$, $CF_2CH_3$, $OCHF_2$, $C(CF_3)_2OH$, 1H-pyrazol-1-yl, and 1-methyl-1H-pyrazol-4-yl; $R_7$ is hydrogen; $Y_1$, $Y_2$ and $Y_3$ are each CH; or $Y_1$ is CH, $Y_2$ is CH and $Y_3$ is C(F); or $Y_1$ is CH, $Y_2$ is $C(OCF_3)$ or $C(OCH_3)$, and $Y_3$ is CH; or $Y_1$ is CH, $Y_2$ is CH, and $Y_3$ is N; or $Y_1$ is CH, $Y_2$ is N, and $Y_3$ is CH; or $Y_1$ is N, $Y_2$ is N, and $Y_3$ is CH. In some cases, when $R_7$ is H and $Y_1$, $Y_2$ and $Y_3$ are each CH, $R_6$ is selected from the group consisting of $CF_3$, $CF_2CH_3$, $OCHF_2$, $C(CF_3)_2OH$, 1H-pyrazol-1-yl, and 1-methyl-1H-pyrazol-4-yl.

In some embodiments, $R_{0a}$ is selected from the group consisting of hydrogen, methyl, and $CH_2OH$; $R_{0b}$ is hydrogen or methyl; $R_{1a}$ is selected from the group consisting of hydrogen, hydroxyl, and fluoro; $R_{1b}$ is selected from the group consisting of hydrogen, fluoro, and methyl; $R_2$ is selected from the group consisting of hydrogen, hydroxyl, CN, $CH_2OH$, methyl, 1,2,4-oxadiazol-3-yl, 1,3,4-oxadiazol-2-yl, and 1H-1,2,3-triazol-5-yl; R is hydrogen; $R_3$ is ethyl or cyclopropyl; $R_4$ is hydrogen; $R_5$ is hydrogen; $R_6$ is selected from the group consisting of hydrogen, $CF_3$, $CF_2CH_3$, $OCHF_2$, $C(CF_3)_2OH$, 1H-pyrazol-1-yl, and 1-methyl-1H-pyrazol-4-yl; $R_7$ is hydrogen; $Y_1$, $Y_2$ and $Y_3$ are each CH; or $Y_1$ is CH, $Y_2$ is CH, and $Y_3$ is C(F); or $Y_1$ is CH, $Y_2$ is $C(OCF_3)$, and $Y_3$ is CH. In some cases; when $R_7$ is H and $Y_1$, $Y_2$ and $Y_3$ are each CH, $R_6$ is selected from the group consisting of $CF_3$, $CF_2CH_3$, $OCHF_2$, $C(CF_3)_2OH$, 1H-pyrazol-1-yl, and 1-methyl-1H-pyrazol-4-yl.

In some embodiments disclosed herein, $R_{0a}$ is selected from the group consisting of CN, substituted or unsubstituted heteroalicyclyl, and substituted or unsubstituted heteroaryl; and $R_{0b}$ is hydrogen or $C_{1-4}$ alkyl. In some embodiments, $R_{0a}$ is unsubstituted or substituted heteroaryl. In some embodiments, $R_{0a}$ is substituted or unsubstituted pyridinyl.

In some embodiments disclosed herein, $R_{0b}$ is hydrogen.

In one embodiment disclosed herein, the compound, stereoisomer, or salt of Formula (I) is selected from the group consisting of:

A7-1
rac-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, A7-1-1
rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, 1st eluting isomer, A7-1-2
rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, 2nd eluting isomer, A7-2
2-(4-(((6-(cyclopropyl(2-methyl-4-(trifluoromethyl)benzyl)amino)-5-fluoropyrimidin-4-yl)amino)methyl)piperidin-1-yl)acetamide, A7-3-1
rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide, 1st eluting isomer, A7-3-2
rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide, 2nd eluting isomer, A7-4-1
rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide, 1st eluting isomer, A7-4-2
rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide 2nd eluting isomer, A7-5-1
rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide, 1st eluting isomer, A7-5-2
rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide, 2nd eluting isomer, A7-6-1
rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide, 1st eluting isomer, A7-6-2
rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide, 2nd eluting isomer, A7-7-1
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 1st eluting isomer, A7-7-2
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 2nd eluting isomer, A7-7-3
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 3rd eluting isomer, A7-7-4
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 4th eluting isomer, A7-8
methyl 1-(2-amino-2-oxoethyl)-4-(((6-(cyclopropyl(4-(trifluoromethyl)benzyl)amino)-5-fluoropyrimidin-4-yl)amino)methyl)piperidine-4-carboxylate, A7-9
2-(4-(((6-(cyclopropyl((5-(trifluoromethyl)pyridin-2-yl)methyl)amino)-5-fluoropyrimidin-4-yl)amino)methyl)-4-hydroxypiperidin-1-yl)acetamide, A7-10
2-(4-(((6-(cyclopropyl(4-(trifluoromethyl)benzyl)amino)-5-fluoropyrimidin-4-yl)amino)methyl)-4-hydroxypiperidin-1-yl)acetamide, A7-11
2-(4-(((6-(cyclopropyl((6-(trifluoromethyl)pyridin-3-yl)methyl)amino)-5-fluoropyrimidin-4-yl)amino)methyl)-4-hydroxypiperidin-1-yl)acetamide, A7-14
rac-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide, A7-14-1
rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide, 1st eluting isomer, A7-14-2
rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide, 2nd eluting isomer, A7-15
rac-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide, A7-15-1
rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide, 1st eluting isomer, A7-15-2
rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide, 2nd eluting isomer, A7-16
rac-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide, A7-16-1
rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide, 1$^{st}$ eluting isomer,
A7-16-2
rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide, 2$^{nd}$ eluting isomer,
A7-17
rac-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide,
A7-17-1
rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide, 1$^{st}$ eluting isomer,
A7-17-2
rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide, 2$^{nd}$ eluting isomer,
A7-18
rac-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide,
A7-18-1
rel-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide, 1$^{st}$ eluting isomer,
A7-18-2
rel-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide, 2$^{nd}$ eluting isomer,
A7-19
rac-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide,
A7-19-1
rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide, 1$^{st}$ eluting isomer,
A7-19-2
rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide, 2$^{nd}$ eluting isomer,
rac-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide,
A7-20-1
rel-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide, 1$^{st}$ eluting isomer,
A7-20-2
rel-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide, 2$^{nd}$ eluting isomer,
A7-21
rac-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide,
A7-21-1
rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide, 1$^{st}$ eluting isomer,
A7-21-2
rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide, 2$^{nd}$ eluting isomer,
A7-22
rac-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide,
A7-22-1
rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide, 2$^{nd}$ eluting isomer,
A7-22-2
rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide 1$^{st}$ eluting isomer,
A7-23
rac-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide,
A7-23-1
rel-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide, 1$^{st}$ eluting isomer,
A7-23-2
rel-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide, 2$^{nd}$ eluting isomer,
A7-24
rac-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide,
A7-24-1
rel-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide, 1$^{st}$ eluting isomer,
A7-24-2
rel-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide, 2$^{nd}$ eluting isomer,
A7-25
rac-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide,
A7-25-1
rel-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide, 1$^{st}$ eluting isomer,
A7-26
rac-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide,
A7-26-1
rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide, 2$^{nd}$ eluting isomer,
A7-26-2
rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide, 1$^{st}$ eluting isomer, A7-27
rac-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide,
A7-27-1
rel-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide, $1^{st}$ eluting isomer,
A7-27-2
rel-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide, $2^{nd}$ eluting isomer.
A7-28
rac-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide,
A7-28-1
rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide, $1^{st}$ eluting isomer,
A7-28-2
rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide, $2^{nd}$ eluting isomer,
A7-29
rac-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide.
A7-29-1
rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide, $1^{st}$ eluting isomer,
A7-29-2
rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide, $2^{nd}$ eluting isomer,
A7-30
rac-2-((3R,4R)-4-(((5-fluoro-6-((2-fluoroethyl)(4-(trifluoromethyl)benzyl)amino)pyrimidin-4-yl)amino)methyl)-3-hydroxypiperidin-1-yl)acetamide,
A7-31
rac-2-((3R,4R)-4-(((5-fluoro-6-(((1r,3S)-3-fluorocyclobutyl)(4-(trifluoromethyl)benzyl)amino)pyrimidin-4-yl)amino)methyl)-3-hydroxypiperidin-1-yl)acetamide,
A7-32
rac-2-((3R,4R)-4-(((5-fluoro-6-(((1s,3R)-3-fluorocyclobutyl)(4-(trifluoromethyl)benzyl)amino)pyrimidin-4-yl)amino)methyl)-3-hydroxypiperidin-1-yl)acetamide,
A7-33
2-(4-(((6-(cyclopropyl(1-(5-(trifluoromethyl)pyridin-2-yl)ethyl)amino)-5-fluoropyrimidin-4-yl)amino)methyl)piperidin-1-yl)acetamide,
A7-34
2-(4-(((6-(cyclopropyl(1-(4-(trifluoromethyl)phenyl)ethyl)amino)-5-fluoropyrimidin-4-yl)amino)methyl)piperidin-1-yl)acetamide,
A7-35
2-(4-(((6-(cyclopropyl((5-(trifluoromethyl)pyridin-2-yl)methyl)amino)-5-fluoropyrimidin-4-yl)amino)methyl)piperidin-1-yl)acetamide,
A7-36
2-(4-(((6-((3-cyanobenzyl)(cyclopropyl)amino)-5-fluoropyrimidin-4-yl)amino)methyl)piperidin-1-yl)acetamide,
A7-38
2-(4-(((6-((3-(1H-1,2,4-triazol-1-yl)benzyl)(cyclopropyl)amino)-5-fluoropyrimidin-4-yl)amino)methyl)piperidin-1-yl)acetamide,
A7-39
2-(4-(((6-(cyclopropyl(4-(trifluoromethyl)benzyl)amino)-5-fluoropyrimidin-4-yl)amino)methyl)piperidin-1-yl)acetamide,
A7-40
rac-2-((3R,4R)-4-(((6-(cyclopropyl(4-(1,1-difluoroethyl)benzyl)amino)-5-fluoropyrimidin-4-yl)amino)methyl)-3-hydroxypiperidin-1-yl)acetamide,
A7-41
rac-2-((3R,4R)-4-(((5-fluoro-6-((1-methylcyclopropyl)(4-(trifluoromethyl)benzyl)amino)pyrimidin-4-yl)amino)methyl)-3-hydroxypiperidin-1-yl)acetamide,
A7-42
rac-2-((3R,4R)-4-(((6-(cyclopropyl(4-(difluoromethoxy)-2-fluorobenzyl)amino)-5-fluoropyrimidin-4-yl)amino)methyl)-3-hydroxypiperidin-1-yl)acetamide,
A7-43
rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide,
A7-44
1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide,
A7-45
2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide,
A7-46
2-(4-(((6-((4-chloro-2,5-dimethylbenzyl)(cyclopropyl)amino)-5-fluoropyrimidin-4-yl)amino)methyl)piperidin-1-yl)acetamide,
A7-47
2-(4-(((6-(cyclopropyl(2,5-dimethylbenzyl)amino)-5-fluoropyrimidin-4-yl)amino)methyl)piperidin-1-yl)acetamide,
A7-49
rac-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide,
A7-50
2-(4-cyano-4-(((6-(cyclopropyl(4-(trifluoromethyl)benzyl)amino)-5-fluoropyrimidin-4-yl)amino)methyl)piperidin-1-yl)acetamide,
A7-51
2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide,
A7-52
2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide,
A7-53
2-(4-(((6-((4-chloro-3,5-dimethylbenzyl)(cyclopropyl)amino)-5-fluoropyrimidin-4-yl)amino)methyl)piperidin-1-yl)acetamide,
A7-54
rac-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, A7-54-1
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, 1st eluting isomer,
A7-54-2
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, 2nd eluting isomer,
A7-55"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide, enantiomerically enriched,
A7-56
rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide,
A7-57"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide, enantiomerichally enriched,
A7-58
rac-2-((3R,4R)-4-(((6-(cyclopropyl(3-methoxy-4-(trifluoromethyl)benzyl)amino)-5-fluoropyrimidin-4-yl)amino)methyl)-3-hydroxypiperidin-1-yl)acetamide,
A7-60
rac-2-((3R,4R)-4-(((5-fluoro-6-((methyl-$d_3$)(4-(trifluoromethyl)benzyl)amino)pyrimidin-4-yl)amino)methyl)-3-hydroxypiperidin-1-yl)acetamide,
A7-61
rac-2-((3R,4R)-4-(((6-(cyclopropyl(2-methoxy-4-(trifluoromethyl)benzyl)amino)-5-fluoropyrimidin-4-yl)amino)methyl)-3-hydroxypiperidin-1-yl)acetamide,
A7-64
2-(4-(((6-(cyclopropyl(4-(trifluoromethyl)benzyl)amino)-5-fluoropyrimidin-4-yl)amino)methyl)piperidin-1-yl)-3-hydroxypropanamide,
A7-65
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide,
A7-66-1
rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide or rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide, 1st eluting major isomer,
A7-66-2
rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide or
rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide, 2nd eluting major isomer,
A7-67"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-4-hydroxybutanamide, enantiomerichally enriched,
A7-68
2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide,
A7-69"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$, enantiomerichally enriched,
A7-70
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide,
A7-72
rac-2-((3R,4R)-4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide,
A7-73
rac-2-((3R,4R)-4-(((6-(ethyl(4-(1-(2-hydroxyethyl)-1H-pyrazol-4-yl)benzyl)amino)-5-fluoropyrimidin-4-yl)amino)methyl)-3-hydroxypiperidin-1-yl)acetamide,
A7-74
rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide,
A7-75
rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide,
A7-76
rac-2-((3R,4R)-4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide,
A7-77
rac-2-((3R,4R)-4-(((6-((4-(1H-Pyrazol-1-yl)benzyl)(ethyl)amino)-5-fluoropyrimidin-4-yl)amino)methyl)-3-hydroxypiperidin-1-yl)acetamide,
A7-78
rac-2-((3R,4R)-4-(((6-((4-cyanobenzyl)(ethyl)amino)-5-fluoropyrimidin-4-yl)amino)methyl)-3-hydroxypiperidin-1-yl)acetamide,
A7-79
rac-2-((3R,4R)-4-(((6-((4-(1,1-difluoro-2-hydroxyethyl)benzyl)(ethyl)amino)-5-fluoropyrimidin-4-yl)amino)methyl)-3-hydroxypiperidin-1-yl)acetamide,
A7-80
2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide,
A7-81
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide,
A7-82
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide,
A7-83
2-(4-(((6-(Cyclopropyl(4-(trifluoromethyl)benzyl)amino)-5-fluoropyrimidin-4-yl)amino)methyl)-4-(4-methyl-4H-1,2,4-triazol-3-yl)piperidin-1-yl)acetamide,
A7-84
2-(4-(((6-(Cyclopropyl(4-(trifluoromethyl)benzyl)amino)-5-fluoropyrimidin-4-yl)amino)methyl)-4-(1H-imidazol-2-yl)piperidin-1-yl)acetamide, A7-85
2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide,
A7-86
rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide,
A7-87
2-(4-(1-((6-(cyclopropyl(4-(trifluoromethyl)benzyl)amino)-5-fluoropyrimidin-4-yl)amino)-2-hydroxyethyl)piperidin-1-yl)acetamide,
B4-1-1-1
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, $1^{st}$ eluting isomer,
B4-1-1-2
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, $2^{nd}$ eluting isomer,
B4-1-2-1
rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, $1^{st}$ eluting isomer,
B4-1-2-2
rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, $2^{nd}$ eluting isomer,
B4-2-1-1
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, $1^{st}$ eluting isomer
B4-2-1-2
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, $2^{nd}$ eluting isomer,
C4-1-1
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, $1^{st}$ eluting isomer,
C4-1-2
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, $2^{nd}$ eluting isomer,
C4-2-1
2-(4-(((6-((3,5-bis(trifluoromethyl)benzyl)(ethyl)amino)-5-fluoropyrimidin-4-yl)amino)methyl)-3-hydroxy-4-(hydroxymethyl)piperidin-1-yl)acetamide, st eluting isomer,
D5-1-1-1
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide, 1st eluting isomer,
D5-1-1-2
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-1-2-1
rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-1-2-2
rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-2-1-1
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide, 1st eluting isomer,
D5-2-1-2
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-2-2-1
rel-2-((3R,4S)-4-(((6-(cyclopropyl(4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-2-2-2
rel-2-((3R,4S)-4-(((6-(cyclopropyl(4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-3-1-1
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-3-1-2
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-3-2-1
rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-3-2-2
rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide $2^{nd}$ eluting isomer,
D5-4"
rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, enantiomerichally enriched,
D5-5-1
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, major isomer,
D5-5-2
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, minor isomer,
D5-6"
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, enantiomerically enriched,
D5-9"
rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, enantiomerichally enriched,
D5-10"
rel-2-((3R,4R)-4-(((6-(cyclopropyl(2-fluorobenzyl)amino)-5-fluoropyrimidin-4-yl)amino)methyl)-3,4-dihydroxypiperidin-1-yl)acetamide, enantiomerically enriched, E6-1
2-(4-Amino-4-(((6-(cyclopropyl(4-(trifluoromethyl)benzyl)amino)-5-fluoropyrimidin-4-yl)amino)methyl)piperidin-1-yl)acetamide,
F2-1
rac-2-((3R,4R)-4-(((5-fluoro-6-(methyl(2-methylbenzyl)amino)pyrimidin-4-yl)amino)methyl)-3-hydroxypiperidin-1-yl)acetamide,
F2-2
rac-2-((3R,4R)-4-(((6-((2,6-dichlorobenzyl)(methyl)amino)-5-fluoropyrimidin-4-yl)amino)methyl)-3-hydroxypiperidin-1-yl)acetamide,
F2-3
rac-2-((3R,4R)-4-(((6-((2,3-dichlorobenzyl)(methyl)amino)-5-fluoropyrimidin-4-yl)amino)methyl)-3-hydroxypiperidin-1-yl)acetamide,
F2-4
rac-2-((3R,4R)-4-(((6-((2,6-dichlorobenzyl)(ethyl)amino)-5-fluoropyrimidin-4-yl)amino)methyl)-3-hydroxypiperidin-1-yl)acetamide,
F2-5
rac-2-((3R,4R)-4-(((5-fluoro-6-(methyl(1-(o-tolyl)ethyl)amino)pyrimidin-4-yl)amino)methyl)-3-hydroxypiperidin-1-yl)acetamide,
F2-6
rac-2-((3R,4R)-4-(((6-((1-(2-chlorophenyl)ethyl)(methyl)amino)-5-fluoropyrimidin-4-yl)amino)methyl)-3-hydroxypiperidin-1-yl)acetamide,
F2-7
rac-2-((3R,4R)-4-(((5-fluoro-6-(methyl(3-(trifluoromethoxy)benzyl)amino)pyrimidin-4-yl)amino)methyl)-3-hydroxypiperidin-1-yl)acetamide,
F2-8
rac-2-((3R,4R)-4-(((6-((3-cyanobenzyl)(methyl)amino)-5-fluoropyrimidin-4-yl)amino)methyl)-3-hydroxypiperidin-1-yl)acetamide,
F2-9
rac-2-((3R,4R)-4-(((5-fluoro-6-(isobutyl(4-(trifluoromethyl)benzyl)amino)pyrimidin-4-yl)amino)methyl)-3-hydroxypiperidin-1-yl)acetamide,
F2-10
rac-2-((3R,4R)-4-(((6-((cyclopropylmethyl)(2-(trifluoromethyl)benzyl)amino)-5-fluoropyrimidin-4-yl)amino)methyl)-3-hydroxypiperidin-1-yl)acetamide,
F2-11
rac-2-((3R,4R)-4-(((6-((4-cyanobenzyl)(isobutyl)amino)-5-fluoropyrimidin-4-yl)amino)methyl)-3-hydroxypiperidin-1-yl)acetamide,
F2-12
rac-2-((3R,4R)-4-(((6-((4-chloro-3-fluorobenzyl)(methyl)amino)-5-fluoropyrimidin-4-yl)amino)methyl)-3-hydroxypiperidin-1-yl)acetamide,
F2-13
rac-2-((3R,4R)-4-(((6-((4-(difluoromethoxy)benzyl)(methyl)amino)-5-fluoropyrimidin-4-yl)amino)methyl)-3-hydroxypiperidin-1-yl)acetamide,
F2-14
rac-2-((3R,4R)-4-(((6-((4-(difluoromethoxy)-3-methoxybenzyl)(methyl)amino)-5-fluoropyrimidin-4-yl)amino)methyl)-3-hydroxypiperidin-1-yl)acetamide,
F2-15
rac-2-((3R,4R)-4-(((6-((4-chlorobenzyl)(isopropyl)amino)-5-fluoropyrimidin-4-yl)amino)methyl)-3-hydroxypiperidin-1-yl)acetamide,
F2-16
rac-2-((3R,4R)-4-(((5-fluoro-6-((2-methoxyethyl)(4-(trifluoromethyl)benzyl)amino)pyrimidin-4-yl)amino)methyl)-3-hydroxypiperidin-1-yl)acetamide,
F2-17
rac-2-((3R,4R)-4-(((6-((2,4-dichlorobenzyl)(isobutyl)amino)-5-fluoropyrimidin-4-yl)amino)methyl)-3-hydroxypiperidin-1-yl)acetamide,
F2-18
rac-2-((3R,4R)-4-(((6-((4-cyanobenzyl)(methyl)amino)-5-fluoropyrimidin-4-yl)amino)methyl)-3-hydroxypiperidin-1-yl)acetamide,
F2-19
rac-2-((3R,4R)-4-(((5-fluoro-6-(((6-methoxypyridin-3-yl)methyl)(methyl)amino)pyrimidin-4-yl)amino)methyl)-3-hydroxypiperidin-1-yl)acetamide,
F2-20
rac-2-((3R,4R)-4-(((6-((3-(difluoromethoxy)benzyl)(methyl)amino)-5-fluoropyrimidin-4-yl)amino)methyl)-3-hydroxypiperidin-1-yl)acetamide,
F2-21
rac-2-((3R,4R)-4-(((6-((3,5-dichlorobenzyl)(methyl)amino)-5-fluoropyrimidin-4-yl)amino)methyl)-3-hydroxypiperidin-1-yl)acetamide,
F2-22
rac-2-((3R,4R)-4-(((5-fluoro-6-(methyl(4-(trifluoromethoxy)benzyl)amino)pyrimidin-4-yl)amino)methyl)-3-hydroxypiperidin-1-yl)acetamide,
F2-23
rac-2-((3R,4R)-4-(((6-((3-chlorobenzyl)(isopropyl)amino)-5-fluoropyrimidin-4-yl)amino)methyl)-3-hydroxypiperidin-1-yl)acetamide.

In some cases, the compound, stereoisomer, or salt has a structure of Formula (I) is selected from the group consisting of:

2-(4-(((6-(cyclopropyl(4-(trifluoromethyl)benzyl)amino)-5-fluoropyrimidin-4-yl)amino)methyl)-3-hydroxypiperidin-1-yl)acetamide,
2-(4-(((6-(cyclopropyl(2-methyl-4-(trifluoromethyl)benzyl)amino)-5-fluoropyrimidin-4-yl)amino)methyl)piperidin-1-yl)acetamide,
2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide,
2-(4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide,
2-(4-(((6-(cyclopropyl(4-(trifluoromethyl)benzyl)amino)-5-fluoropyrimidin-4-yl)amino)methyl)-3-fluoropiperidin-1-yl)acetamide,
2-(4-(((6-(cyclopropyl(4-(trifluoromethyl)benzyl)amino)-5-fluoropyrimidin-4-yl)amino)methyl)-3,3-difluoropiperidin-1-yl)acetamide,
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide,
methyl1-(2-amino-2-oxoethyl)-4-(((6-(cyclopropyl(4-(trifluoromethyl)benzyl)amino)-5-fluoropyrimidin-4-yl)amino)methyl)piperidine-4-carboxylate,
2-(4-(((6-(cyclopropyl((5-(trifluoromethyl)pyridin-2-yl)methyl)amino)-5-fluoropyrimidin-4-yl)amino)methyl)-4-hydroxypiperidin-1-yl)acetamide,
2-(4-(((6-(cyclopropyl(4-(trifluoromethyl)benzyl)amino)-5-fluoropyrimidin-4-yl)amino)methyl)-4-hydroxypiperidin-1-yl)acetamide,
2-(4-(((6-(cyclopropyl((6-(trifluoromethyl)pyridin-3-yl)methyl)amino)-5-fluoropyrimidin-4-yl)amino)methyl)-4-hydroxypiperidin-1-yl)acetamide, 2-(4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide, 2-(4-(((6-(cyclobutyl(4-(difluoromethoxy)-2-fluorobenzyl)amino)-5-fluoropyrimidin-4-yl)amino)methyl)-3-hydroxypiperidin-1-yl)acetamide, 2-(4-(((6-(cyclobutyl(4-(trifluoromethyl)benzyl)amino)-5-fluoropyrimidin-4-yl)amino)methyl)-3-hydroxypiperidin-1-yl)acetamide, 2-(4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide, 2-(4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide, 2-(4-(((5-fluoro-6-(isopropyl(4-(trifluoromethyl)benzyl)amino)pyrimidin-4-yl)amino)methyl)-3-hydroxypiperidin-1-yl)acetamide, 2-(4-(((5-fluoro-6-(methyl(4-(trifluoromethyl)benzyl)amino)pyrimidin-4-yl)amino)methyl)-3-hydroxypiperidin-1-yl)acetamide, 2-(4-(((6-(ethyl(4-(trifluoromethyl)benzyl)amino)-5-fluoropyrimidin-4-yl)amino)methyl)-3-hydroxypiperidin-1-yl)acetamide, 2-(4-(((6-(cyclopropyl(2-fluoro-4-(trifluoromethyl)benzyl)amino)-5-fluoropyrimidin-4-yl)amino)methyl)-3-hydroxypiperidin-1-yl)acetamide, 2-(4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide, 2-(4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide, 2-(4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide, 2-(4-(((6-(ethyl(2-fluoro-4-(trifluoromethyl)benzyl)amino)-5-fluoropyrimidin-4-yl)amino)methyl)-3-hydroxypiperidin-1-yl)acetamide, 2-(4-(((6-(ethyl((5-(trifluoromethyl)pyridin-2-yl)methyl)amino)-5-fluoropyrimidin-4-yl)amino)methyl)-3-hydroxypiperidin-1-yl)acetamide, 2-(4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide, 2-(4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide, 2-((((5-fluoro-6-((2-fluoroethyl)(4-(trifluoromethyl)benzyl)amino)pyrimidin-4-yl)amino)methyl)-3-hydroxypiperidin-1-yl)acetamide, 2-(4-(((5-fluoro-6-((3-fluorocyclobutyl)(4-(trifluoromethyl)benzyl)amino)pyrimidin-4-yl)amino)methyl)-3-hydroxypiperidin-1-yl)acetamide, 2-(4-(((6-(cyclopropyl(1-(5-(trifluoromethyl)pyridin-2-yl)ethyl)amino)-5-fluoropyrimidin-4-yl)amino)methyl)piperidin-1-yl)acetamide, 2-(4-(((6-(cyclopropyl(1-(4-(trifluoromethyl)phenyl)ethyl)amino)-5-fluoropyrimidin-4-yl)amino)methyl)piperidin-1-yl)acetamide, 2-(4-(((6-(cyclopropyl((5-(trifluoromethyl)pyridin-2-yl)methyl)amino)-5-fluoropyrimidin-4-yl)amino)methyl)piperidin-1-yl)acetamide, 2-(4-(((6-((3-cyanobenzyl)(cyclopropyl)amino)-5-fluoropyrimidin-4-yl)amino)methyl)piperidin-1-yl)acetamide, 2-(4-(((6-((3-(1H-1,2,4-triazol-1-yl)benzyl)(cyclopropyl)amino)-5-fluoropyrimidin-4-yl)amino)methyl)piperidin-1-yl)acetamide, 2-(4-(((6-(cyclopropyl(4-(trifluoromethyl)benzyl)amino)-5-fluoropyrimidin-4-yl)amino)methyl)piperidin-1-yl)acetamide, 2-(4-(((6-(cyclopropyl(4-(1,1-difluoroethyl)benzyl)amino)-5-fluoropyrimidin-4-yl)amino)methyl)-3-hydroxypiperidin-1-yl)acetamide, 2-(4-(((5-fluoro-6-((1-methylcyclopropyl)(4-(trifluoromethyl)benzyl)amino)pyrimidin-4-yl)amino)methyl)-3-hydroxypiperidin-1-yl)acetamide, 2-(4-(((6-(cyclopropyl(4-(difluoromethoxy)-2-fluorobenzyl)amino)-5-fluoropyrimidin-4-yl)amino)methyl)-3-hydroxypiperidin-1-yl)acetamide, 2-(4-(((6-(cyclopropyl(4-(difluoromethoxy)benzyl)amino)-5-fluoropyrimidin-4-yl)amino)methyl)-3-hydroxypiperidin-1-yl)acetamide, 1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide, 2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide, 2-(4-(((6-((4-chloro-2,5-dimethylbenzyl)(cyclopropyl)amino)-5-fluoropyrimidin-4-yl)amino)methyl)piperidin-1-yl)acetamide, 2-(4-(((6-(cyclopropyl(2,5-dimethylbenzyl)amino)-5-fluoropyrimidin-4-yl)amino)methyl)piperidin-1-yl)acetamide, 2-(4-(((6-(cyclopropyl(4-(trifluoromethyl)benzyl)amino)-5-fluoropyrimidin-4-yl)amino)methyl)-3-hydroxypiperidin-1-yl)acetamide, 2-(4-cyano-4-(((6-(cyclopropyl(4-(trifluoromethyl)benzyl)amino)-5-fluoropyrimidin-4-yl)amino)methyl)piperidin-1-yl)acetamide, 2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide, 2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide, 2-(4-(((6-((4-chloro-3,5-dimethylbenzyl)(cyclopropyl)amino)-5-fluoropyrimidin-4-yl)amino)methyl)piperidin-1-yl)acetamide, 2-(4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, 2-(4-(((6-(cyclopropyl(4-(trifluoromethyl)benzyl)amino)-5-fluoropyrimidin-4-yl)amino)methyl)-3-hydroxypiperidin-1-yl)-2-methylpropanamide, 2-(4-(((6-(cyclopropyl(3-(trifluoromethoxy)benzyl)amino)-5-fluoropyrimidin-4-yl)amino)methyl)-3-hydroxypiperidin-1-yl)acetamide, 2-(4-(((6-(ethyl(4-(trifluoromethyl)benzyl)amino)-5-fluoropyrimidin-4-yl)amino)methyl)-3-hydroxypiperidin-1-yl)-2-methylpropanamide, 2-(4-(((6-(cyclopropyl(3-methoxy-4-(trifluoromethyl)benzyl)amino)-5-fluoropyrimidin-4-yl)amino)methyl)-3-hydroxypiperidin-1-yl)acetamide, 2-(4-(((5-fluoro-6-((methyl-$d_3$)(4-(trifluoromethyl)benzyl)amino)pyrimidin-4-yl)amino)methyl)-3-hydroxypiperidin-1-yl)acetamide, 2-(4-(((6-(cyclopropyl(2-methoxy-4-(trifluoromethyl)benzyl)amino)-5-fluoropyrimidin-4-yl)amino)methyl)-3-hydroxypiperidin-1-yl)acetamide, 2-(4-(((6-(cyclopropyl(4-(trifluoromethyl)benzyl)amino)-5-fluoropyrimidin-4-yl)amino)methyl)piperidin-1-yl)-3-hydroxypropanamide,
2-(4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide,
2-(4-(((6-(ethyl(4-(trifluoromethyl)benzyl)amino)-5-fluoropyrimidin-4-yl)amino)methyl)-3-hydroxypiperidin-1-yl)-3-hydroxypropanamide,
2-(4-(((6-(ethyl(4-(trifluoromethyl)benzyl)amino)-5-fluoropyrimidin-4-yl)amino)methyl)-3-hydroxypiperidin-1-yl)-4-hydroxybutanamide,
2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide,
2-(4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$,
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide,
2-(4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide,
2-(4-(((6-(ethyl(4-(1-(2-hydroxyethyl)-1H-pyrazol-4-yl)benzyl)amino)-5-fluoropyrimidin-4-yl)amino)methyl)-3-hydroxypiperidin-1-yl)acetamide,
2-(4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide,
2-(4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide,
2-(4-(((6-(cyclopropyl(2-fluoro-4-(1H-pyrazol-1-yl)benzyl)amino)-5-fluoro pyrimidin-4-yl)amino)methyl)-3-hydroxypiperidin-1-yl)acetamide,
2-(4-(((6-((4-(1H-pyrazol-1-yl)benzyl)(ethyl)amino)-5-fluoropyrimidin-4-yl)amino)methyl)-3-hydroxypiperidin-1-yl)acetamide,
2-(4-(((6-((4-cyanobenzyl)(ethyl)amino)-5-fluoropyrimidin-4-yl)amino)methyl)-3-hydroxypiperidin-1-yl)acetamide,
2-(4-(((6-((4-(1,1-difluoro-2-hydroxyethyl)benzyl)(ethyl)amino)-5-fluoropyrimidin-4-yl)amino)methyl)-3-hydroxypiperidin-1-yl)acetamide,
2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide,
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide,
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide,
2-(4-(((6-(Cyclopropyl(4-(trifluoromethyl)benzyl)amino)-5-fluoropyrimidin-4-yl)amino)methyl)-4-(4-methyl-4H-1,2,4-triazol-3-yl)piperidin-1-yl)acetamide,
2-(4-(((6-(Cyclopropyl(4-(trifluoromethyl)benzyl)amino)-5-fluoropyrimidin-4-yl)amino)methyl)-4-(1H-imidazol-2-yl)piperidin-1-yl)acetamide,
2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide,
2-(4-(((6-((4-(1H-pyrazol-1-yl)benzyl)(cyclopropyl)amino)-5-fluoropyrimidin-4-yl)amino)methyl)-3-hydroxypiperidin-1-yl)acetamide,
2-(4-(1-((6-(cyclopropyl(4-(trifluoromethyl)benzyl)amino)-5-fluoropyrimidin-4-yl)amino)-2-hydroxyethyl)piperidin-1-yl)acetamide,
2-(4-(((6-(cyclopropyl(4-(trifluoromethyl)benzyl)amino)-5-fluoropyrimidin-4-yl)amino)methyl)-3-hydroxy-3-methylpiperidin-1-yl)acetamide,
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide,
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide,
2-(4-(((6-((3,5-bis(trifluoromethyl)benzyl)(ethyl)amino)-5-fluoropyrimidin-4-yl)amino)methyl)-3-hydroxy-4-(hydroxymethyl)piperidin-1-yl)acetamide,
2-(4-(((6-(ethyl(4-(trifluoromethyl)benzyl)amino)-5-fluoropyrimidin-4-yl)amino)methyl)-3,4-dihydroxypiperidin-1-yl)acetamide,
2-(4-(((6-(cyclopropyl(4-(trifluoromethyl)benzyl)amino)-5-fluoropyrimidin-4-yl)amino)methyl)-3,4-dihydroxypiperidin-1-yl)acetamide,
2-(4-(((6-(ethyl(2-fluoro-4-(trifluoromethyl)benzyl)amino)-5-fluoropyrimidin-4-yl)amino)methyl)-3,4-dihydroxypiperidin-1-yl)acetamide,
2-(4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,
2-(4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide,
2-(4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,
2-(4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide,
2-((3R,4R)-4-(((6-(cyclopropyl(2-fluorobenzyl)amino)-5-fluoropyrimidin-4-yl)amino)methyl)-3,4-dihydroxypiperidin-1-yl)acetamide,
2-(4-Amino-4-(((6-(cyclopropyl(4-(trifluoromethyl)benzyl)amino)-5-fluoropyrimidin-4-yl)amino)methyl)piperidin-1-yl)acetamide,
2-(4-(((5-fluoro-6-(methyl(2-methylbenzyl)amino)pyrimidin-4-yl)amino)methyl)-3-hydroxypiperidin-1-yl)acetamide,
2-(4-(((6-((2,6-dichlorobenzyl)(methyl)amino)-5-fluoropyrimidin-4-yl)amino)methyl)-3-hydroxypiperidin-1-yl)acetamide,
2-(4-(((6-((2,3-dichlorobenzyl)(methyl)amino)-5-fluoropyrimidin-4-yl)amino)methyl)-3-hydroxypiperidin-1-yl)acetamide,
2-(4-(((6-((2,6-dichlorobenzyl)(ethyl)amino)-5-fluoropyrimidin-4-yl)amino)methyl)-3-hydroxypiperidin-1-yl)acetamide,
2-(4-(((5-fluoro-6-(methyl(1-(o-tolyl)ethyl)amino)pyrimidin-4-yl)amino)methyl)-3-hydroxypiperidin-1-yl)acetamide,
2-(4-(((6-((1-(2-chlorophenyl)ethyl)(methyl)amino)-5-fluoropyrimidin-4-yl)amino)methyl)-3-hydroxypiperidin-1-yl)acetamide,
2-(4-(((5-fluoro-6-(methyl(3-(trifluoromethoxy)benzyl)amino)pyrimidin-4-yl)amino)methyl)-3-hydroxypiperidin-1-yl)acetamide,
2-(4-(((6-((3-cyanobenzyl)(methyl)amino)-5-fluoropyrimidin-4-yl)amino)methyl)-3-hydroxypiperidin-1-yl)acetamide, 2-(4-(((5-fluoro-6-(isobutyl(4-(trifluoromethyl)benzyl) amino)pyrimidin-4-yl)amino)methyl)-3-hydroxypiperidin-1-yl)acetamide,
2-(4-(((6-((cyclopropylmethyl)(2-(trifluoromethyl)benzyl) amino)-5-fluoropyrimidin-4-yl)amino)methyl)-3-hydroxypiperidin-1-yl)acetamide,
2-(4-(((6-((4-cyanobenzyl)(isobutyl)amino)-5-fluoropyrimidin-4-yl)amino)methyl)-3-hydroxypiperidin-1-yl)acetamide,
2-(4-(((6-((4-chloro-3-fluorobenzyl)(methyl)amino)-5-fluoropyrimidin-4-yl)amino)methyl)-3-hydroxypiperidin-1-yl)acetamide,
2-(4-(((6-((4-(difluoromethoxy)benzyl)(methyl)amino)-5-fluoropyrimidin-4-yl)amino)methyl)-3-hydroxypiperidin-1-yl)acetamide,
2-(4-(((6-((4-(difluoromethoxy)-3-methoxybenzyl)(methyl) amino)-5-fluoropyrimidin-4-yl)amino)methyl)-3-hydroxypiperidin-1-yl)acetamide,
2-(4-(((6-((4-chlorobenzyl)(isopropyl)amino)-5-fluoropyrimidin-4-yl)amino)methyl)-3-hydroxypiperidin-1-yl)acetamide,
2-(4-(((5-fluoro-6-((2-methoxyethyl)(4-(trifluoromethyl) benzyl)amino)pyrimidin-4-yl)amino)methyl)-3-hydroxypiperidin-1-yl)acetamide,
2-(4-(((6-((2,4-dichlorobenzyl)(isobutyl)amino)-5-fluoropyrimidin-4-yl)amino)methyl)-3-hydroxypiperidin-1-yl) acetamide,
2-(4-(((6-((4-cyanobenzyl)(methyl)amino)-5-fluoropyrimidin-4-yl)amino)methyl)-3-hydroxypiperidin-1-yl)acetamide,
2-(4-(((5-fluoro-6-(((6-methoxypyridin-3-yl)methyl) (methyl)amino)pyrimidin-4-yl)amino)methyl)-3-hydroxypiperidin-1-yl)acetamide,
2-(4-(((6-((3-(difluoromethoxy)benzyl)(methyl)amino)-5-fluoropyrimidin-4-yl)amino)methyl)-3-hydroxypiperidin-1-yl)acetamide,
2-(4-(((6-((3,5-dichlorobenzyl)(methyl)amino)-5-fluoropyrimidin-4-yl)amino)methyl)-3-hydroxypiperidin-1-yl)acetamide,
2-(4-(((5-fluoro-6-(methyl(4-(trifluoromethoxy)benzyl) amino)pyrimidin-4-yl)amino)methyl)-3-hydroxypiperidin-1-yl)acetamide, and
2-(4-(((6-((3-chlorobenzyl)(isopropyl)amino)-5-fluoropyrimidin-4-yl)amino)methyl)-3-hydroxypiperidin-1-yl)acetamide.

In some cases, the compound, salt, stereoisomer, or salt of a stereoisomer according to Formula (I) is selected from the group consisting of:

A7-1
rac-2-((3R,4R)-4-(((6-(Cyclopropyl(4-(trifluoromethyl) benzyl)amino)-5-fluoropyrimidin-4-yl)amino)methyl)-3-hydroxypiperidin-1-yl)acetamide,
A7-1-1
rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide,
A7-2
2-(4-(((6-(cyclopropyl(2-methyl-4-(trifluoromethyl)benzyl) amino)-5-fluoropyrimidin-4-yl)amino)methyl)piperidin-1-yl)acetamide,
A7-3-1
rel-(R)-2-(4-(((6-(cyclopropyl((5-(trifluoromethyl)pyridin-2-yl)methyl)amino)-5-fluoropyrimidin-4-yl)amino) methyl)-3,3-difluoropiperidin-1-yl)acetamide,
A7-4-1
rel-2-((3R,4R)-4-(((6-(cyclopropyl((5-(trifluoromethyl) pyridin-2-yl)methyl)amino)-5-fluoropyrimidin-4-yl) amino)methyl)-3-fluoropiperidin-1-yl)acetamide,
A7-5-1
rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide,
A7-6-1
rel-(R)-2-(4-(((6-(cyclopropyl(4-(trifluoromethyl)benzyl) amino)-5-fluoropyrimidin-4-yl)amino)methyl)-3,3-difluoropiperidin-1-yl)acetamide,
A7-7-1
2-(4-(((6-(cyclopropyl(4-(trifluoromethyl)benzyl)amino)-5-fluoropyrimidin-4-yl)amino)methyl)-3-(trifluoromethyl) piperidin-1-yl)acetamide,
A7-8
methyl 1-(2-amino-2-oxoethyl)-4-(((6-(cyclopropyl(4-(trifluoromethyl)benzyl)amino)-5-fluoropyrimidin-4-yl) amino)methyl)piperidine-4-carboxylate,
A7-9
2-(4-(((6-(cyclopropyl((5-(trifluoromethyl)pyridin-2-yl) methyl)amino)-5-fluoropyrimidin-4-yl)amino)methyl)-4-hydroxypiperidin-1-yl)acetamide,
A7-10
2-(4-(((6-(cyclopropyl(4-(trifluoromethyl)benzyl)amino)-5-fluoropyrimidin-4-yl)amino)methyl)-4-hydroxypiperidin-1-yl)acetamide,
A7-11
2-(4-(((6-(cyclopropyl((6-(trifluoromethyl)pyridin-3-yl) methyl)amino)-5-fluoropyrimidin-4-yl)amino)methyl)-4-hydroxypiperidin-1-yl)acetamide,
A7-14
rac-2-((3R,4R)-4-(((6-(cyclopropyl((5-(trifluoromethyl) pyridin-2-yl)methyl)amino)-5-fluoropyrimidin-4-yl) amino)methyl)-3-hydroxypiperidin-1-yl)acetamide,
A7-14-1
rel-2-((3R,4R)-4-(((6-(cyclopropyl((5-(trifluoromethyl) pyridin-2-yl)methyl)amino)-5-fluoropyrimidin-4-yl) amino)methyl)-3-hydroxypiperidin-1-yl)acetamide,
A7-15
rac-2-((3R,4R)-4-(((6-(cyclobutyl(4-(difluoromethoxy)-2-fluorobenzyl)amino)-5-fluoropyrimidin-4-yl)amino) methyl)-3-hydroxypiperidin-1-yl)acetamide,
A7-15-1
rel-2-((3R,4R)-4-(((6-(cyclobutyl(4-(difluoromethoxy)-2-fluorobenzyl)amino)-5-fluoropyrimidin-4-yl)amino) methyl)-3-hydroxypiperidin-1-yl)acetamide,
A7-16
rac-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide,
A7-16-1
rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide,
rac-2-((3R,4R)-4-(((6-(cyclopropyl((2-(trifluoromethyl)pyrimidin-5-yl)methyl)amino)-5-fluoropyrimidin-4-yl) amino)methyl)-3-hydroxypiperidin-1-yl)acetamide,
A7-17-1
rel-2-((3R,4R)-4-(((6-(cyclopropyl((2-(trifluoromethyl)pyrimidin-5-yl)methyl)amino)-5-fluoropyrimidin-4-yl) amino)methyl)-3-hydroxypiperidin-1-yl)acetamide,
A7-18
rac-2-((3R,4R)-4-(((6-(cyclobutyl((2-(trifluoromethyl)pyrimidin-5-yl)methyl)amino)-5-fluoropyrimidin-4-yl) amino)methyl)-3-hydroxypiperidin-1-yl)acetamide, A7-18-1
rel-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide,
A7-19
rac-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide,
A7-19-1
rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide,
A7-20
rac-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide,
A7-20-1
rel-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide,
A7-21
rac-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide,
A7-21-1
rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide,
A7-22
rac-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide,
A7-22-1
rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide,
A7-23
rac-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide,
A7-23-1
rel-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide,
A7-24
rac-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide,
A7-24-1
rel-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide,
A7-25
rac-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide,
A7-25-1
rel-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide,
A7-26
rac-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide,
A7-26-1
rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide,
A7-27
rac-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide,
A7-27-1
rel-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide,
rac-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide,
A7-28-1
rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide,
A7-29
rac-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide,
A7-29-1
rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide,
A7-30
rac-2-((3R,4R)-4-(((5-fluoro-6-((2-fluoroethyl)(4-(trifluoromethyl)benzyl)amino)pyrimidin-4-yl)amino)methyl)-3-hydroxypiperidin-1-yl)acetamide,
A7-31
rac-2-((3R,4R)-4-(((5-fluoro-6-(((1r,3S)-3-fluorocyclobutyl)(4-(trifluoromethyl)benzyl)amino)pyrimidin-4-yl)amino)methyl)-3-hydroxypiperidin-1-yl)acetamide,
A7-32
rac-2-((3R,4R)-4-(((5-fluoro-6-(((1s,3R)-3-fluorocyclobutyl)(4-(trifluoromethyl)benzyl)amino)pyrimidin-4-yl)amino)methyl)-3-hydroxypiperidin-1-yl)acetamide,
A7-33
2-(4-(((6-(cyclopropyl(1-(5-(trifluoromethyl)pyridin-2-yl)ethyl)amino)-5-fluoropyrimidin-4-yl)amino)methyl)piperidin-1-yl)acetamide,
A7-34
2-(4-(((6-(cyclopropyl(1-(4-(trifluoromethyl)phenyl)ethyl)amino)-5-fluoropyrimidin-4-yl)amino)methyl)piperidin-1-yl)acetamide,
A7-35
2-(4-(((6-(cyclopropyl((5-(trifluoromethyl)pyridin-2-yl)methyl)amino)-5-fluoropyrimidin-4-yl)amino)methyl)piperidin-1-yl)acetamide,
A7-36
2-(4-(((6-((3-cyanobenzyl)(cyclopropyl)amino)-5-fluoropyrimidin-4-yl)amino)methyl)piperidin-1-yl)acetamide,
A7-38
2-(4-(((6-((3-(1H-1,2,4-triazol-1-yl)benzyl)(cyclopropyl)amino)-5-fluoropyrimidin-4-yl)amino)methyl)piperidin-1-yl)acetamide,
A7-39
2-(4-(((6-(cyclopropyl(4-(trifluoromethyl)benzyl)amino)-5-fluoropyrimidin-4-yl)amino)methyl)piperidin-1-yl)acetamide,
A7-40
rac-2-((3R,4R)-4-(((6-(cyclopropyl(4-(1,1-difluoroethyl)benzyl)amino)-5-fluoropyrimidin-4-yl)amino)methyl)-3-hydroxypiperidin-1-yl)acetamide, A7-41
rac-2-((3R,4R)-4-(((5-fluoro-6-((1-methylcyclopropyl)(4-(trifluoromethyl)benzyl)amino)pyrimidin-4-yl)amino)methyl)-3-hydroxypiperidin-1-yl)acetamide,
A7-42
rac-2-((3R,4R)-4-(((6-(cyclopropyl(4-(difluoromethoxy)-2-fluorobenzyl)amino)-5-fluoropyrimidin-4-yl)amino)methyl)-3-hydroxypiperidin-1-yl)acetamide,
A7-43
rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide,
A7-44
1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide,
A7-45
2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide,
A7-46
2-(4-(((6-((4-chloro-2,5-dimethylbenzyl)(cyclopropyl)amino)-5-fluoropyrimidin-4-yl)amino)methyl)piperidin-1-yl)acetamide,
A7-47
2-(4-(((6-(cyclopropyl(2,5-dimethylbenzyl)amino)-5-fluoropyrimidin-4-yl)amino)methyl)piperidin-1-yl)acetamide,
A7-49
rac-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide,
A7-50
2-(4-cyano-4-(((6-(cyclopropyl(4-(trifluoromethyl)benzyl)amino)-5-fluoropyrimidin-4-yl)amino)methyl)piperidin-1-yl)acetamide,
A7-51
2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide,
A7-52
2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide,
A7-53
2-(4-(((6-((4-chloro-3,5-dimethylbenzyl)(cyclopropyl)amino)-5-fluoropyrimidin-4-yl)amino)methyl)piperidin-1-yl)acetamide,
A7-54
rac-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide,
A7-54-1
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide,
A7-55"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide,
A7-56
rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide,
A7-57"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide,
A7-58
rac-2-((3R,4R)-4-(((6-(cyclopropyl(3-methoxy-4-(trifluoromethyl)benzyl)amino)-5-fluoropyrimidin-4-yl)amino)methyl)-3-hydroxypiperidin-1-yl)acetamide,
A7-60
rac-2-((3R,4R)-4-(((5-fluoro-6-((methyl-$d_3$)(4-(trifluoromethyl)benzyl)amino)pyrimidin-4-yl)amino)methyl)-3-hydroxypiperidin-1-yl)acetamide,
rac-2-((3R,4R)-4-(((6-(cyclopropyl(2-methoxy-4-(trifluoromethyl)benzyl)amino)-5-fluoropyrimidin-4-yl)amino)methyl)-3-hydroxypiperidin-1-yl)acetamide,
A7-64
2-(4-(((6-(cyclopropyl(4-(trifluoromethyl)benzyl)amino)-5-fluoropyrimidin-4-yl)amino)methyl)piperidin-1-yl)-3-hydroxypropanamide,
A7-65
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide,
A7-66-1
rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide, or
rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide,
A7-67"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-4-hydroxybutanamide,
A7-68
2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide,
A7-69"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-d2,
A7-70
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide,
A7-72
rac-2-((3R,4R)-4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide,
A7-73
rac-2-((3R,4R)-4-(((6-(ethyl(4-(1-(2-hydroxyethyl)-1H-pyrazol-4-yl)benzyl)amino)-5-fluoropyrimidin-4-yl)amino)methyl)-3-hydroxypiperidin-1-yl)acetamide,
A7-74
rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide,
A7-75
rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide,
A7-76
rac-2-((3R,4R)-4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide, A7-77
rac-2-((3R,4R)-4-(((6-((4-(1H-Pyrazol-1-yl)benzyl)(ethyl)amino)-5-fluoropyrimidin-4-yl)amino)methyl)-3-hydroxypiperidin-1-yl)acetamide,
A7-78
rac-2-((3R,4R)-4-(((6-((4-cyanobenzyl)(ethyl)amino)-5-fluoropyrimidin-4-yl)amino)methyl)-3-hydroxypiperidin-1-yl)acetamide,
A7-79
rac-2-((3R,4R)-4-(((6-((4-(1,1-difluoro-2-hydroxyethyl)benzyl)(ethyl)amino)-5-fluoropyrimidin-4-yl)amino)methyl)-3-hydroxypiperidin-1-yl)acetamide,
A7-80
2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide,
A7-81
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide,
A7-82
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide,
A7-83
2-(4-(((6-(Cyclopropyl(4-(trifluoromethyl)benzyl)amino)-5-fluoropyrimidin-4-yl)amino)methyl)-4-(4-methyl-4H-1,2,4-triazol-3-yl)piperidin-1-yl)acetamide,
A7-84
2-(4-(((6-(Cyclopropyl(4-(trifluoromethyl)benzyl)amino)-5-fluoropyrimidin-4-yl)amino)methyl)-4-(1H-imidazol-2-yl)piperidin-1-yl)acetamide,
A7-85
2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide,
rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide,
A7-87
2-(4-(1-((6-(cyclopropyl(4-(trifluoromethyl)benzyl)amino)-5-fluoropyrimidin-4-yl)amino)-2-hydroxyethyl)piperidin-1-yl)acetamide,
B4-1-1-1
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide,
B4-1-2-1
rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide,
B4-2-1-1
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide,
C4-1-1
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide,
C4-2-1
2-(4-(((6-((3,5-bis(trifluoromethyl)benzyl)(ethyl)amino)-5-fluoropyrimidin-4-yl)amino)methyl)-3-hydroxy-4-(hydroxymethyl)piperidin-1-yl)acetamide,
D5-1-1-1
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide,
D5-1-2-1
rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide,
D5-2-1-1
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide,
D5-2-2-1
rel-2-((3R,4S)-4-(((6-(cyclopropyl(4-(trifluoromethyl)benzyl)amino)-5-fluoropyrimidin-4-yl)amino)methyl)-3,4-dihydroxypiperidin-1-yl)acetamide,
D5-3-1-1
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide,
D5-3-2-1
rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide,
D5-4"
rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,
D5-5-1
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide,
D5-6"
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,
D5-9"
rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide,
D5-10"
rel-2-((3R,4R)-4-(((6-(cyclopropyl(2-fluorobenzyl)amino)-5-fluoropyrimidin-4-yl)amino)methyl)-3,4-dihydroxypiperidin-1-yl)acetamide,
E6-1
2-(4-Amino-4-(((6-(cyclopropyl(4-(trifluoromethyl)benzyl)amino)-5-fluoropyrimidin-4-yl)amino)methyl)piperidin-1-yl)acetamide,
F2-1
rac-2-((3R,4R)-4-(((5-fluoro-6-(methyl(2-methylbenzyl)amino)pyrimidin-4-yl)amino)methyl)-3-hydroxypiperidin-1-yl)acetamide,
F2-2
rac-2-((3R,4R)-4-(((6-((2,6-dichlorobenzyl)(methyl)amino)-5-fluoropyrimidin-4-yl)amino)methyl)-3-hydroxypiperidin-1-yl)acetamide,
F2-3
rac-2-((3R,4R)-4-(((6-((2,3-dichlorobenzyl)(methyl)amino)-5-fluoropyrimidin-4-yl)amino)methyl)-3-hydroxypiperidin-1-yl)acetamide,
F2-4
rac-2-((3R,4R)-4-(((6-((2,6-dichlorobenzyl)(ethyl)amino)-5-fluoropyrimidin-4-yl)amino)methyl)-3-hydroxypiperidin-1-yl)acetamide,
F2-5
rac-2-((3R,4R)-4-(((5-fluoro-6-(methyl(1-(o-tolyl)ethyl)amino)pyrimidin-4-yl)amino)methyl)-3-hydroxypiperidin-1-yl)acetamide, F2-6
rac-2-((3R,4R)-4-(((6-((1-(2-chlorophenyl)ethyl)(methyl)amino)-5-fluoropyrimidin-4-yl)amino)methyl)-3-hydroxypiperidin-1-yl)acetamide,
F2-7
rac-2-((3R,4R)-4-(((5-fluoro-6-(methyl(3-(trifluoromethoxy)benzyl)amino)pyrimidin-4-yl)amino)methyl)-3-hydroxypiperidin-1-yl)acetamide,
F2-8
rac-2-((3R,4R)-4-(((6-((3-cyanobenzyl)(methyl)amino)-5-fluoropyrimidin-4-yl)amino)methyl)-3-hydroxypiperidin-1-yl)acetamide,
F2-9
rac-2-((3R,4R)-4-(((5-fluoro-6-(isobutyl(4-(trifluoromethyl)benzyl)amino)pyrimidin-4-yl)amino)methyl)-3-hydroxypiperidin-1-yl)acetamide,
F2-10
rac-2-((3R,4R)-4-(((6-((cyclopropylmethyl)(2-(trifluoromethyl)benzyl)amino)-5-fluoropyrimidin-4-yl)amino)methyl)-3-hydroxypiperidin-1-yl)acetamide,
F2-11
rac-2-((3R,4R)-4-(((6-((4-cyanobenzyl)(isobutyl)amino)-5-fluoropyrimidin-4-yl)amino)methyl)-3-hydroxypiperidin-1-yl)acetamide,
F2-12
rac-2-((3R,4R)-4-(((6-((4-chloro-3-fluorobenzyl)(methyl)amino)-5-fluoropyrimidin-4-yl)amino)methyl)-3-hydroxypiperidin-1-yl)acetamide,
F2-13
rac-2-((3R,4R)-4-(((6-((4-(difluoromethoxy)benzyl)(methyl)amino)-5-fluoropyrimidin-4-yl)amino)methyl)-3-hydroxypiperidin-1-yl)acetamide,
F2-14
rac-2-((3R,4R)-4-(((6-((4-(difluoromethoxy)-3-methoxybenzyl)(methyl)amino)-5-fluoropyrimidin-4-yl)amino)methyl)-3-hydroxypiperidin-1-yl)acetamide,
F2-15
rac-2-((3R,4R)-4-(((6-((4-chlorobenzyl)(isopropyl)amino)-5-fluoropyrimidin-4-yl)amino)methyl)-3-hydroxypiperidin-1-yl)acetamide,
F2-16
rac-2-((3R,4R)-4-(((5-fluoro-6-((2-methoxyethyl)(4-(trifluoromethyl)benzyl)amino)pyrimidin-4-yl)amino)methyl)-3-hydroxypiperidin-1-yl)acetamide,
F2-17
rac-2-((3R,4R)-4-(((6-((2,4-dichlorobenzyl)(isobutyl)amino)-5-fluoropyrimidin-4-yl)amino)methyl)-3-hydroxypiperidin-1-yl)acetamide,
F2-18
rac-2-((3R,4R)-4-(((6-((4-cyanobenzyl)(methyl)amino)-5-fluoropyrimidin-4-yl)amino)methyl)-3-hydroxypiperidin-1-yl)acetamide,
F2-19
rac-2-((3R,4R)-4-(((5-fluoro-6-(((6-methoxypyridin-3-yl)methyl)(methyl)amino)pyrimidin-4-yl)amino)methyl)-3-hydroxypiperidin-1-yl)acetamide,
F2-20
rac-2-((3R,4R)-4-(((6-((3-(difluoromethoxy)benzyl)(methyl)amino)-5-fluoropyrimidin-4-yl)amino)methyl)-3-hydroxypiperidin-1-yl)acetamide,
F2-21
rac-2-((3R,4R)-4-(((6-((3,5-dichlorobenzyl)(methyl)amino)-5-fluoropyrimidin-4-yl)amino)methyl)-3-hydroxypiperidin-1-yl)acetamide,
F2-22
rac-2-((3R,4R)-4-(((5-fluoro-6-(methyl(4-(trifluoromethoxy)benzyl)amino)pyrimidin-4-yl)amino)methyl)-3-hydroxypiperidin-1-yl)acetamide,
F2-23
rac-2-((3R,4R)-4-(((6-((3-chlorobenzyl)(isopropyl)amino)-5-fluoropyrimidin-4-yl)amino)methyl)-3-hydroxypiperidin-1-yl)acetamide.

In other preferred embodiment disclosed herein, the compound, salt, stereoisomer, or salt of a stereoisomer according to Formula (I) is selected from the group consisting of:
A7-1-1
rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, 1$^{st}$ eluting isomer,
A7-1-2
rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, 2$^{nd}$ eluting isomer,
A7-3-1
rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide, 1$^{st}$ eluting isomer,
A7-3-2
rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide, 2$^{nd}$ eluting isomer,
A7-4-1
rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide, 1$^{st}$ eluting isomer,
A7-4-2
rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide, 2$^{nd}$ eluting isomer,
A7-5-1
rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide, 1$^{st}$ eluting isomer,
A7-5-2
rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide, 2$^{nd}$ eluting isomer,
A7-6-1
rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide, 1$^{st}$ eluting isomer,
A7-6-2
rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide, 2$^{nd}$ eluting isomer,
A7-7-1
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 1$^{st}$ eluting isomer,
A7-7-2
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 2$^{nd}$ eluting isomer,
A7-7-3
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 3$^{rd}$ eluting isomer, A7-7-4
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, 4$^{th}$ eluting isomer,
A7-8
methyl 1-(2-amino-2-oxoethyl)-4-(((6-(cyclopropyl(4-(trifluoromethyl)benzyl)amino)-5-fluoropyrimidin-4-yl)amino)methyl)piperidine-4-carboxylate,
A7-9
2-(4-(((6-(cyclopropyl((5-(trifluoromethyl)pyridin-2-yl)methyl)amino)-5-fluoropyrimidin-4-yl)amino)methyl)-4-hydroxypiperidin-1-yl)acetamide,
A7-10
2-(4-(((6-(cyclopropyl(4-(trifluoromethyl)benzyl)amino)-5-fluoropyrimidin-4-yl)amino)methyl)-4-hydroxypiperidin-1-yl)acetamide,
A7-14-1
rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide, 1$^{st}$ eluting isomer,
A7-14-2
rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide, 2$^{nd}$ eluting isomer
A7-15-1
rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide, 1$^{st}$ eluting isomer,
A7-15-2
rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide 2$^{nd}$ eluting isomer,
A7-16-1
rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide, 1$^{st}$ eluting isomer,
A7-16-2
rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide, 2$^{nd}$ eluting isomer,
A7-17-1
rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide, 1$^{st}$ eluting isomer,
A7-17-2
rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide, 2$^{nd}$ eluting isomer,
A7-19-1
rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide, 1$^{st}$ eluting isomer,
A7-19-2
rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide, 2$^{nd}$ eluting isomer,
A7-20-1
rel-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide, 1$^{st}$ eluting isomer,
A7-20-2
rel-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide, 2$^{nd}$ eluting isomer,
A7-21-1
rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide, 1$^{st}$ eluting isomer,
A7-21-2
rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide, 2$^{nd}$ eluting isomer,
A7-22-1
rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide, 2$^{nd}$ eluting isomer,
A7-22-2
rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide, st eluting isomer,
A7-26-1
rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide, 2$^{nd}$ eluting isomer,
A7-26-2
rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide, 1$^{st}$ eluting isomer,
A7-28-1
rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide, st eluting isomer,
A7-28-2
rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide, 2$^{nd}$ eluting isomer,
A7-29-1
rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide, 1$^{st}$ eluting isomer,
A7-29-2
rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide, 2$^{nd}$ eluting isomer,
A7-31
rac-2-((3R,4R)-4-(((5-fluoro-6-(((1r,3S)-3-fluorocyclobutyl)(4-(trifluoromethyl)benzyl)amino)pyrimidin-4-yl)amino)methyl)-3-hydroxypiperidin-1-yl)acetamide,
A7-32
rac-2-((3R,4R)-4-(((5-fluoro-6-(((1s,3R)-3-fluorocyclobutyl)(4-(trifluoromethyl)benzyl)amino)pyrimidin-4-yl)amino)methyl)-3-hydroxypiperidin-1-yl)acetamide,
A7-39
2-(4-(((6-(cyclopropyl(4-(trifluoromethyl)benzyl)amino)-5-fluoropyrimidin-4-yl)amino)methyl)piperidin-1-yl)acetamide,
A7-40
rac-2-((3R,4R)-4-(((6-(cyclopropyl(4-(1,1-difluoroethyl)benzyl)amino)-5-fluoropyrimidin-4-yl)amino)methyl)-3-hydroxypiperidin-1-yl)acetamide, A7-41
rac-2-((3R,4R)-4-(((5-fluoro-6-((1-methylcyclopropyl)(4-(trifluoromethyl)benzyl)amino)pyrimidin-4-yl)amino)methyl)-3-hydroxypiperidin-1-yl)acetamide,
A7-42
rac-2-((3R,4R)-4-(((6-(cyclopropyl(4-(difluoromethoxy)-2-fluorobenzyl)amino)-5-fluoropyrimidin-4-yl)amino)methyl)-3-hydroxypiperidin-1-yl)acetamide,
A7-43
rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide,
A7-44
1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide,
A7-45
2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide,
A7-50
2-(4-cyano-4-(((6-(cyclopropyl(4-(trifluoromethyl)benzyl)amino)-5-fluoropyrimidin-4-yl)amino)methyl)piperidin-1-yl)acetamide,
A7-51
2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide,
A7-52
2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide,
A7-54-1
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, $1^{st}$ eluting isomer,
A7-54-2
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, $2^{nd}$ eluting isomer,
A7-55"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide, enantiomerically enriched,
A7-56
rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide,
A7-57"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide, enantiomerically enriched,
A7-58
rac-2-((3R,4R)-4-(((6-(cyclopropyl(3-methoxy-4-(trifluoromethyl)benzyl)amino)-5-fluoropyrimidin-4-yl)amino)methyl)-3-hydroxypiperidin-1-yl)acetamide,
A7-60
rac-2-((3R,4R)-4-(((5-fluoro-6-((methyl-$d_3$)(4-(trifluoromethyl)benzyl)amino)pyrimidin-4-yl)amino)methyl)-3-hydroxypiperidin-1-yl)acetamide,
A7-65
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide,
A7-66-1
rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide or rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide, $1^{st}$ eluting major isomer,
A7-66-2
rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide
OR
rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide, $2^{nd}$ eluting major isomer,
A7-67"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-4-hydroxybutanamide, enantiomerically enriched,
A7-68
2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide,
A7-69"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$, enantiomerically enriched,
A7-70
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide,
A7-72
rac-2-((3R,4R)-4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide,
A7-74
rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide,
A7-75
rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide,
A7-76
rac-2-((3R,4R)-4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide,
A7-80
2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide,
A7-81
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide,
A7-82
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide, A7-85
2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide,
A7-86
rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide,
B4-1-1-1
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, st eluting isomer,
B4-1-1-2
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, $2^{nd}$ eluting isomer,
B4-1-2-1
rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, $1^{st}$ eluting isomer,
B4-1-2-2
rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, $2^{nd}$ eluting isomer,
B4-2-1-1
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, $1^{st}$ eluting isomer,
B4-2-1-2
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, $2^{nd}$ eluting isomer,
C4-1-1
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, 1st eluting isomer,
C4-1-2
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, $2^{nd}$ eluting isomer,
D5-1-1-1
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-1-1-2
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-1-2-1
rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-1-2-2
rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-2-1-1
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-2-1-2
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-2-2-1
rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide, $1^{st}$ eluting isomer,
D5-2-2-2
rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide, $2^{nd}$ eluting isomer,
D5-3-1-1
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, 1st eluting isomer,
D5-3-1-2
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-3-2-1
rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, $1^{st}$ eluting isomer,
D5-3-2-2
rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, $2^{nd}$ eluting isomer,
D5-4"
rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, enantiomerically enriched,
D5-5-1
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, major isomer,
D5-5-2
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, minor isomer,
D5-6"
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, enantiomerically enriched,
D5-9"
rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, enantiomerically enriched,
F2-7
rac-2-((3R,4R)-4-(((5-fluoro-6-(methyl(3-(trifluoromethoxy)benzyl)amino)pyrimidin-4-yl)amino)methyl)-3-hydroxypiperidin-1-yl)acetamide.

In some cases, the compound, salt, stereoisomer, or salt of a stereoisomer according to Formula (I) is selected from the group consisting of:
A7-1-1
rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide,
A7-3-1
rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide, A7-4-1
rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide,
A7-5-1
rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide,
A7-6-1
rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide,
A7-7-1
2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide,
A7-8
methyl1-(2-amino-2-oxoethyl)-4-(((6-(cyclopropyl(4-(trifluoromethyl)benzyl)amino)-5-fluoropyrimidin-4-yl)amino)methyl)piperidine-4-carboxylate,
A7-9
2-(4-(((6-(cyclopropyl((5-(trifluoromethyl)pyridin-2-yl)methyl)amino)-5-fluoropyrimidin-4-yl)amino)methyl)-4-hydroxypiperidin-1-yl)acetamide,
A7-10
2-(4-(((6-(cyclopropyl(4-(trifluoromethyl)benzyl)amino)-5-fluoropyrimidin-4-yl)amino)methyl)-4-hydroxypiperidin-1-yl)acetamide,
A7-14-1
rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide,
A7-15-1
rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide,
A7-16-1
rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide,
A7-17-1
rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide,
A7-19-1
rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide,
A7-20-1
rel-2-((3R,4R)-4-(((5-fluoro-6-(methyl(4-(trifluoromethyl)benzyl)amino)pyrimidin-4-yl)amino)methyl)-3-hydroxypiperidin-1-yl)acetamide,
A7-21-1
rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide,
A7-22-1
rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide,
A7-26-1
rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide,
A7-28-1
rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide,
A7-29-1
rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide,
A7-31
rac-2-((3R,4R)-4-(((5-fluoro-6-(((1r,3S)-3-fluorocyclobutyl)(4-(trifluoromethyl)benzyl)amino)pyrimidin-4-yl)amino)methyl)-3-hydroxypiperidin-1-yl)acetamide,
A7-32
rac-2-((3R,4R)-4-(((5-fluoro-6-(((1s,3R)-3-fluorocyclobutyl)(4-(trifluoromethyl)benzyl)amino)pyrimidin-4-yl)amino)methyl)-3-hydroxypiperidin-1-yl)acetamide,
A7-39
2-(4-(((6-(cyclopropyl(4-(trifluoromethyl)benzyl)amino)-5-fluoropyrimidin-4-yl)amino)methyl)piperidin-1-yl)acetamide,
A7-40
rac-2-((3R,4R)-4-(((6-(cyclopropyl(4-(1,1-difluoroethyl)benzyl)amino)-5-fluoropyrimidin-4-yl)amino)methyl)-3-hydroxypiperidin-1-yl)acetamide,
A7-41
rac-2-((3R,4R)-4-(((5-fluoro-6-((1-methylcyclopropyl)(4-(trifluoromethyl)benzyl)amino)pyrimidin-4-yl)amino)methyl)-3-hydroxypiperidin-1-yl)acetamide,
A7-42
rac-2-((3R,4R)-4-(((6-(cyclopropyl(4-(difluoromethoxy)-2-fluorobenzyl)amino)-5-fluoropyrimidin-4-yl)amino)methyl)-3-hydroxypiperidin-1-yl)acetamide,
A7-43
rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide,
A7-44
1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide,
A7-45
2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide,
A7-50
2-(4-cyano-4-(((6-(cyclopropyl(4-(trifluoromethyl)benzyl)amino)-5-fluoropyrimidin-4-yl)amino)methyl)piperidin-1-yl)acetamide,
A7-51
2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide,
A7-52
2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide,
A7-54-1
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide,
A7-55"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide, A7-56
rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide,
A7-57"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide,
A7-58
rac-2-((3R,4R)-4-(((6-(cyclopropyl(3-methoxy-4-(trifluoromethyl)benzyl)amino)-5-fluoropyrimidin-4-yl)amino)methyl)-3-hydroxypiperidin-1-yl)acetamide,
A7-60
rac-2-((3R,4R)-4-(((5-fluoro-6-((methyl-$d_3$)(4-(trifluoromethyl)benzyl)amino)pyrimidin-4-yl)amino)methyl)-3-hydroxypiperidin-1-yl)acetamide,
A7-65
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide,
A7-66-1
rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide, or
rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide,
A7-67"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-4-hydroxybutanamide,
A7-68
2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide,
A7-69"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-d2,
A7-70
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide,
A7-72
rac-2-((3R,4R)-4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide,
A7-74
rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide,
A7-75
rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide,
A7-76
rac-2-((3R,4R)-4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide,
A7-80
2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide,
A7-81
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide,
A7-82
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide,
A7-85
2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide,
A7-86
rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide,
B4-1-1-1
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide,
B4-1-2-1
rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide,
B4-2-1-1
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide,
C4-1-1
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide,
D5-1-1-1
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide,
D5-1-2-1
rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide,
D5-2-1-1
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide,
D5-2-2-1
rel-2-((3R,4S)-4-(((6-(cyclopropyl(4-(trifluoromethyl)benzyl)amino)-5-fluoropyrimidin-4-yl)amino)methyl)-3,4-dihydroxypiperidin-1-yl)acetamide,
D5-3-1-1
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide,
D5-3-2-1
rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide,
D5-4"
rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,
D5-5-1
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide,
D5-6"
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,

D5-9"

rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide,

F2-7 rac-2-((3R,4R)-4-(((5-fluoro-6-(methyl(3-(trifluoromethoxy)benzyl)amino)pyrimidin-4-yl)amino)methyl)-3-hydroxypiperidin-1-yl)acetamide.

In some cases, the compound, salt, or salt of a stereoisomer is selected from the group consisting of 2-(4-(((6-(Cyclopropyl(4-(trifluoromethyl)benzyl)amino)-5-fluoropyrimidin-4-yl)amino)methyl)-3-hydroxypiperidin-1-yl)acetamide, 2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide, 2-(4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide, 2-(4-(((6-(cyclopropyl(4-(trifluoromethyl)benzyl)amino)-5-fluoropyrimidin-4-yl)amino)methyl)-3-fluoropiperidin-1-yl)acetamide, 2-(4-(((6-(cyclopropyl(4-(trifluoromethyl)benzyl)amino)-5-fluoropyrimidin-4-yl)amino)methyl)-3,3-difluoropiperidin-1-yl)acetamide, 2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide, methyl 1-(2-amino-2-oxoethyl)-4-(((6-(cyclopropyl(4-(trifluoromethyl)benzyl)amino)-5-fluoropyrimidin-4-yl)amino)methyl)piperidine-4-carboxylate, 2-(4-(((6-(cyclopropyl((5-(trifluoromethyl)pyridin-2-yl)methyl)amino)-5-fluoropyrimidin-4-yl)amino)methyl)-4-hydroxypiperidin-1-yl)acetamide, 2-(4-(((6-(cyclopropyl(4-(trifluoromethyl)benzyl)amino)-5-fluoropyrimidin-4-yl)amino)methyl)-4-hydroxypiperidin-1-yl)acetamide, 2-(4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide, 2-(4-(((6-(cyclobutyl(4-(difluoromethoxy)-2-fluorobenzyl)amino)-5-fluoropyrimidin-4-yl)amino)methyl)-3-hydroxypiperidin-1-yl)acetamide, 2-(4-(((6-(cyclobutyl(4-(trifluoromethyl)benzyl)amino)-5-fluoropyrimidin-4-yl)amino)methyl)-3-hydroxypiperidin-1-yl)acetamide, 2-(4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide, 2-(4-(((5-fluoro-6-(isopropyl(4-(trifluoromethyl)benzyl)amino)pyrimidin-4-yl)amino)methyl)-3-hydroxypiperidin-1-yl)acetamide, 2-(4-(((5-fluoro-6-(methyl(4-(trifluoromethyl)benzyl)amino)pyrimidin-4-yl)amino)methyl)-3-hydroxypiperidin-1-yl)acetamide, 2-(4-(((6-(ethyl(4-(trifluoromethyl)benzyl)amino)-5-fluoropyrimidin-4-yl)amino)methyl)-3-hydroxypiperidin-1-yl)acetamide, 2-(4-(((6-(cyclopropyl(2-fluoro-4-(trifluoromethyl)benzyl)amino)-5-fluoropyrimidin-4-yl)amino)methyl)-3-hydroxypiperidin-1-yl)acetamide, 2-(4-(((6-(ethyl(2-fluoro-4-(trifluoromethyl)benzyl)amino)-5-fluoropyrimidin-4-yl)amino)methyl)-3-hydroxypiperidin-1-yl)acetamide, 2-(4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide, 2-(4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide, 2-(4-(((5-fluoro-6-(3-fluorocyclobutyl)(4-(trifluoromethyl)benzyl)amino)pyrimidin-4-yl)amino)methyl)-3-hydroxypiperidin-1-yl)acetamide, 2-(4-(((6-(cyclopropyl(4-(trifluoromethyl)benzyl)amino)-5-fluoropyrimidin-4-yl)amino)methyl)piperidin-1-yl)acetamide, 2-(4-(((6-(cyclopropyl(4-(1,1-difluoroethyl)benzyl)amino)-5-fluoropyrimidin-4-yl)amino)methyl)-3-hydroxypiperidin-1-yl)acetamide, 2-(4-(((5-fluoro-6-((1-methylcyclopropyl)(4-(trifluoromethyl)benzyl)amino)pyrimidin-4-yl)amino)methyl)-3-hydroxypiperidin-1-yl)acetamide, 2-(4-(((6-(cyclopropyl(4-(difluoromethoxy)-2-fluorobenzyl)amino)-5-fluoropyrimidin-4-yl)amino)methyl)-3-hydroxypiperidin-1-yl)acetamide, 2-(4-(((6-(cyclopropyl(4-(difluoromethoxy)benzyl)amino)-5-fluoropyrimidin-4-yl)amino)methyl)-3-hydroxypiperidin-1-yl)acetamide, 1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide, 2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide, 2-(4-cyano-4-(((6-(cyclopropyl(4-(trifluoromethyl)benzyl)amino)-5-fluoropyrimidin-4-yl)amino)methyl)piperidin-1-yl)acetamide, 2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide, 2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide, 2-(4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, 2-(4-(((6-(cyclopropyl(4-(trifluoromethyl)benzyl)amino)-5-fluoropyrimidin-4-yl)amino)methyl)-3-hydroxypiperidin-1-yl)-2-methylpropanamide, 2-(4-(((6-(cyclopropyl(3-(trifluoromethoxy)benzyl)amino)-5-fluoropyrimidin-4-yl)amino)methyl)-3-hydroxypiperidin-1-yl)acetamide, 2-(4-(((6-(ethyl(4-(trifluoromethyl)benzyl)amino)-5-fluoropyrimidin-4-yl)amino)methyl)-3-hydroxypiperidin-1-yl)-2-methylpropanamide, 2-(4-(((6-(cyclopropyl(3-methoxy-4-(trifluoromethyl)benzyl)amino)-5-fluoropyrimidin-4-yl)amino)methyl)-3-hydroxypiperidin-1-yl)acetamide, 2-(4-(((5-fluoro-6-((methyl-$d_3$)(4-(trifluoromethyl)benzyl)amino)pyrimidin-4-yl)amino)methyl)-3-hydroxypiperidin-1-yl)acetamide, 2-(4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide, 2-(4-(((6-(ethyl(4-(trifluoromethyl)benzyl)amino)-5-fluoropyrimidin-4-yl)amino)methyl)-3-hydroxypiperidin-1-yl)-3-hydroxypropanamide, 2-(4-(((6-(ethyl(4-(trifluoromethyl)benzyl)amino)-5-fluoropyrimidin-4-yl)amino)methyl)-3-hydroxypiperidin-1-yl)-4-hydroxybutanamide, 2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide, 2-(4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$, 2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide, 2-(4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide, 2-(4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide, 2-(4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide, 2-(4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide, 2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide, 2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide, 2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide, 2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide, 2-(4-(((6-((4-(1H-pyrazol-1-yl)benzyl)(cyclopropyl)amino)-5-fluoropyrimidin-4-yl)amino)methyl)-3-hydroxypiperidin-1-yl)acetamide, 2-(4-(((6-(cyclopropyl(4-(trifluoromethyl)benzyl)amino)-5-fluoropyrimidin-4-yl)amino)methyl)-3-hydroxy-3-methylpiperidin-1-yl)acetamide, 2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, 2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, 2-(4-(((6-(ethyl(4-(trifluoromethyl)benzyl)amino)-5-fluoropyrimidin-4-yl)amino)methyl)-3,4-dihydroxypiperidin-1-yl)acetamide, 2-(4-(((6-(cyclopropyl(4-(trifluoromethyl)benzyl)amino)-5-fluoropyrimidin-4-yl)amino)methyl)-3,4-dihydroxypiperidin-1-yl)acetamide, 2-(4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, 2-(4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, 2-(4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, 2-(4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, 2-(4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, and 2-(4-(((5-fluoro-6-(methyl(3-(trifluoromethoxy)benzyl)amino)pyrimidin-4-yl)amino)methyl)-3-hydroxypiperidin-1-yl)acetamide.

In some cases, the compound, salt, stereoisomer, or salt of a stereoisomer according to Formula (I) is selected from the group consisting of:

A7-1-1 rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, $1^{st}$ eluting isomer,

A7-1-2 rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, $2^{nd}$ eluting isomer,

A7-5-1 rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide, $1^{st}$ eluting isomer,

A7-5-2 rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide, $2^{nd}$ eluting isomer,

A7-6-1 rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide, $1^{st}$ eluting isomer,

A7-6-2 rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide, $2^{nd}$ eluting isomer,

A7-10

2-(4-(((6-(cyclopropyl(4-(trifluoromethyl)benzyl)amino)-5-fluoropyrimidin-4-yl)amino)methyl)-4-hydroxypiperidin-1-yl)acetamide,

A7-21-1 rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide, $1^{st}$ eluting isomer,

A7-21-2 rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide, $2^{nd}$ eluting isomer,

A7-22-1 rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide, $2^{nd}$ eluting isomer,

A7-22-2 rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide, $1^{st}$ eluting isomer,

A7-26-1 rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide, $2^{nd}$ eluting isomer,

A7-26-2 rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide, $1^{st}$ eluting isomer,

A7-40 rac-2-((3R,4R)-4-(((6-(cyclopropyl(4-(1,1-difluoroethyl)benzyl)amino)-5-fluoropyrimidin-4-yl)amino)methyl)-3-hydroxypiperidin-1-yl)acetamide,

A7-43 rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide, A7-50
2-(4-cyano-4-(((6-(cyclopropyl(4-(trifluoromethyl)benzyl)amino)-5-fluoropyrimidin-4-yl)amino)methyl)piperidin-1-yl)acetamide, A7-51
2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide, A7-54-1
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, 1st eluting isomer, A7-54-2
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide, 2nd eluting isomer, A7-55"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide, enantiomerically enriched, A7-56
rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide, A7-57"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide, enantiomerically enriched, A7-65
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide, A7-69"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$, enantiomerically enriched, A7-70
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide, A7-74
rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide, A7-75
rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide, A7-76
rac-2-((3R,4R)-4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide, A7-81
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide, A7-82
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide, A7-85
2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide, A7-86
rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide, B4-1-1-1
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, st eluting isomer, B4-1-1-2
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide, 2nd eluting isomer, B4-2-1-1
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, 1st eluting isomer, B4-2-1-2
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, 2nd eluting isomer, C4-1-1
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, st eluting isomer, C4-1-2
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, 2nd eluting isomer, D5-1-1-1
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide, 1st eluting isomer, D5-1-1-2
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide, 2nd eluting isomer, D5-2-1-1
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide, 1st eluting isomer, D5-2-1-2
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide, 2nd eluting isomer, D5-2-2-1
rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide, 1st eluting isomer, D5-2-2-2
rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide, 2nd eluting isomer, D5-3-1-1
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, 1st eluting isomer, D5-3-1-2
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, 2nd eluting isomer, D5-4"
rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, enantiomerically enriched
D5-5-1
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, major isomer,
D5-5-2
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, minor isomer,
D5-6"
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, enantiomerically enriched,
D5-9"
rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, enantiomerically enriched.

In some cases, the compound, salt, stereoisomer, or salt of a stereoisomer according to Formula (I) is selected from the group consisting of:
A7-1-1
rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide,
A7-5-1
rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide,
A7-6-1
rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide,
A7-10
2-(4-(((6-(cyclopropyl(4-(trifluoromethyl)benzyl)amino)-5-fluoropyrimidin-4-yl)amino)methyl)-4-hydroxypiperidin-1-yl)acetamide,
A7-21-1
rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide,
A7-22-1
rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide,
A7-26-1
rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide,
A7-40
rac-2-((3R,4R)-4-(((6-(cyclopropyl(4-(1,1-difluoroethyl)benzyl)amino)-5-fluoropyrimidin-4-yl)amino)methyl)-3-hydroxypiperidin-1-yl)acetamide,
A7-43
rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide,
A7-50
2-(4-cyano-4-(((6-(cyclopropyl(4-(trifluoromethyl)benzyl)amino)-5-fluoropyrimidin-4-yl)amino)methyl)piperidin-1-yl)acetamide,
A7-51
2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide,
A7-54-1
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide,
A7-55"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide,
A7-56
rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide,
A7-57"
rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide,
A7-65
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide,
A7-69"
rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$,
A7-70
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide,
A7-74
rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide,
A7-75
rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide,
A7-76
rac-2-((3R,4R)-4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide,
A7-81
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide,
A7-82
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide,
A7-85
2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide,
A7-86
rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide, B4-1-1-1
rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide,
B4-1-2-1
rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide,
B4-2-1-1
2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide,
C4-1-1
2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide,
D5-1-1-1
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide,
D5-1-2-1
rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide
D5-2-1-1
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide,
D5-2-2-1
rel-2-((3R,4S)-4-(((6-(cyclopropyl(4-(trifluoromethyl)benzyl)amino)-5-fluoropyrimidin-4-yl)amino)methyl)-3,4-dihydroxypiperidin-1-yl)acetamide,
D5-3-1-1
rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide,
D5-3-2-1
rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide,
D5-4"
rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,
D5-5-1
rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide,
D5-6"
rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide,
D5-9"
rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, and.
F2-7
rac-2-((3R,4R)-4-(((5-fluoro-6-(methyl(3-(trifluoromethoxy)benzyl)amino)pyrimidin-4-yl)amino)methyl)-3-hydroxypiperidin-1-yl)acetamide.

In some cases, the compound, stereoisomer, or salt of the disclosure is selected from the group consisting of 2-(4-(((6-(Cyclopropyl(4-(trifluoromethyl)benzyl)amino)-5-fluoropyrimidin-4-yl)amino)methyl)-3-hydroxypiperidin-1-yl)acetamide,
2-(4-(((6-(cyclopropyl(4-(trifluoromethyl)benzyl)amino)-5-fluoropyrimidin-4-yl)amino)methyl)-3-fluoropiperidin-1-yl)acetamide,
2-(4-(((6-(cyclopropyl(4-(trifluoromethyl)benzyl)amino)-5-fluoropyrimidin-4-yl)amino)methyl)-3,3-difluoropiperidin-1-yl)acetamide,
2-(4-(((6-(cyclopropyl(4-(trifluoromethyl)benzyl)amino)-5-fluoropyrimidin-4-yl)amino)methyl)-4-hydroxypiperidin-1-yl)acetamide,
2-(4-(((6-(ethyl(4-(trifluoromethyl)benzyl)amino)-5-fluoropyrimidin-4-yl)amino)methyl)-3-hydroxypiperidin-1-yl)acetamide,
2-(4-(((6-(cyclopropyl(2-fluoro-4-(trifluoromethyl)benzyl)amino)-5-fluoropyrimidin-4-yl)amino)methyl)-3-hydroxypiperidin-1-yl)acetamide,
2-(4-(((6-(ethyl(2-fluoro-4-(trifluoromethyl)benzyl)amino)-5-fluoropyrimidin-4-yl)amino)methyl)-3-hydroxypiperidin-1-yl)acetamide,
2-(4-(((6-(cyclopropyl(4-(1,1-difluoroethyl)benzyl)amino)-5-fluoropyrimidin-4-yl)amino)methyl)-3-hydroxypiperidin-1-yl)acetamide,
2-(4-(((6-(cyclopropyl(4-(difluoromethoxy)benzyl)amino)-5-fluoropyrimidin-4-yl)amino)methyl)-3-hydroxypiperidin-1-yl)acetamide,
2-(4-cyano-4-(((6-(cyclopropyl(4-(trifluoromethyl)benzyl)amino)-5-fluoropyrimidin-4-yl)amino)methyl)piperidin-1-yl)acetamide,
2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide,
2-(4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide,
2-(4-(((6-(cyclopropyl(4-(trifluoromethyl)benzyl)amino)-5-fluoropyrimidin-4-yl)amino)methyl)-3-hydroxypiperidin-1-yl)-2-methylpropanamide,
2-(4-(((6-(cyclopropyl(3-(trifluoromethoxy)benzyl)amino)-5-fluoropyrimidin-4-yl)amino)methyl)-3-hydroxypiperidin-1-yl)acetamide,
2-(4-(((6-(ethyl(4-(trifluoromethyl)benzyl)amino)-5-fluoropyrimidin-4-yl)amino)methyl)-3-hydroxypiperidin-1-yl)-2-methylpropanamide,
2-(4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide,
2-(4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$,
2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide,
2-(4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide,
2-(4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide,
2-(4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide,
2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide,
2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide, 2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide, 2-(4-(((6-((4-(1H-pyrazol-1-yl)benzyl)(cyclopropyl)amino)-5-fluoropyrimidin-4-yl)amino)methyl)-3-hydroxypiperidin-1-yl)acetamide, 2-(4-(((6-(cyclopropyl(4-(trifluoromethyl)benzyl)amino)-5-fluoropyrimidin-4-yl)amino)methyl)-3-hydroxy-3-methylpiperidin-1-yl)acetamide, 2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide, 2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide, 2-(4-(((6-(ethyl(4-(trifluoromethyl)benzyl)amino)-5-fluoropyrimidin-4-yl)amino)methyl)-3,4-dihydroxypiperidin-1-yl)acetamide, 2-(4-(((6-(cyclopropyl(4-(trifluoromethyl)benzyl)amino)-5-fluoropyrimidin-4-yl)amino)methyl)-3,4-dihydroxypiperidin-1-yl)acetamide, 2-(4-(((6-(ethyl(2-fluoro-4-(trifluoromethyl)benzyl)amino)-5-fluoropyrimidin-4-yl)amino)methyl)-3,4-dihydroxypiperidin-1-yl)acetamide, 2-(4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, 2-(4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide, 2-(4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide, 2-(4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, and 2-(4-(((5-fluoro-6-(methyl(3-(trifluoromethoxy)benzyl)amino)pyrimidin-4-yl)amino)methyl)-3-hydroxypiperidin-1-yl)acetamide.

In an embodiment, the compound has a structure selected from the group consisting of:

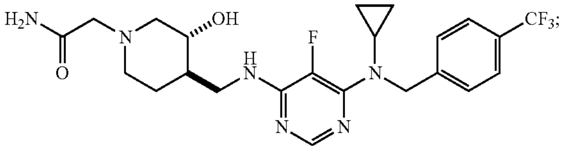

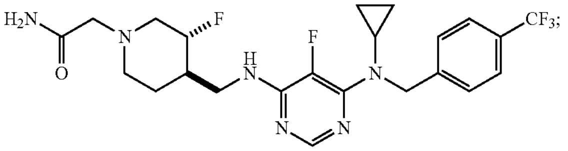

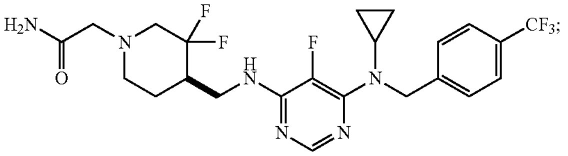

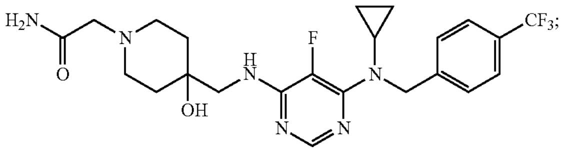

-continued

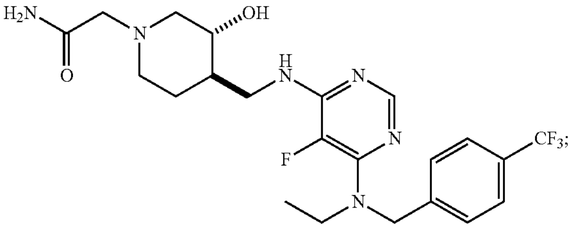

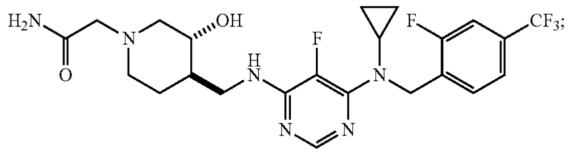

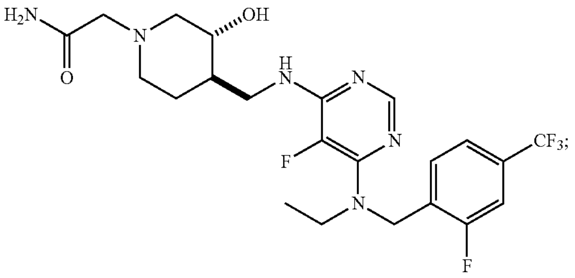

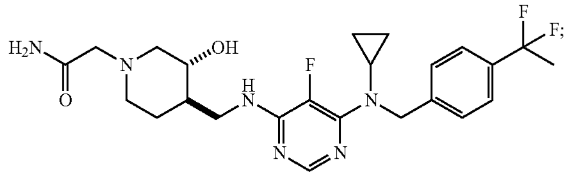

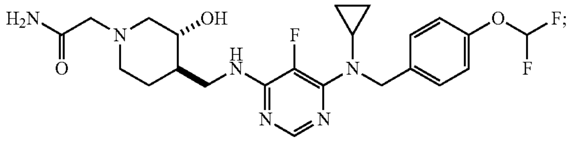

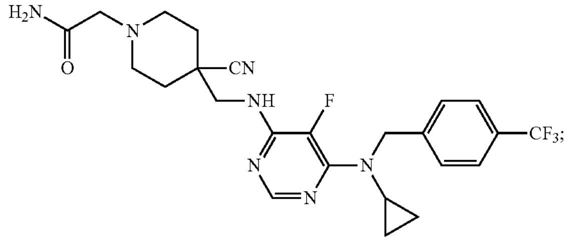

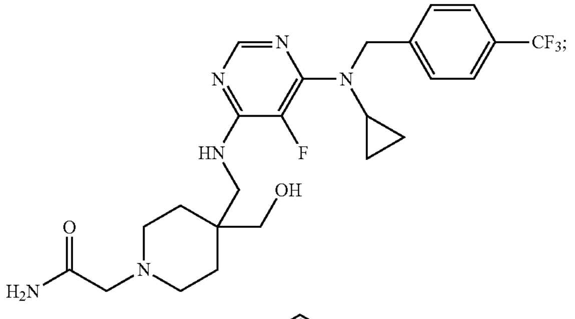

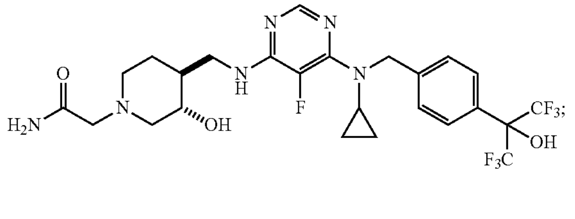

-continued
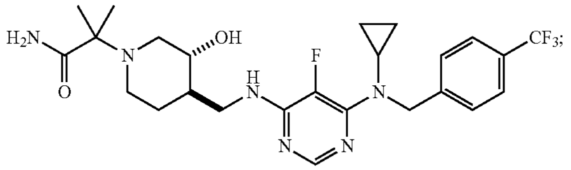
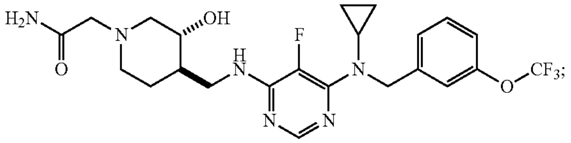
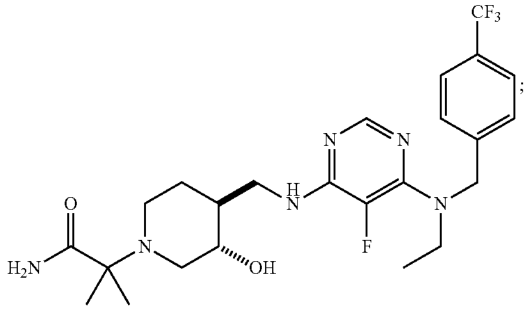
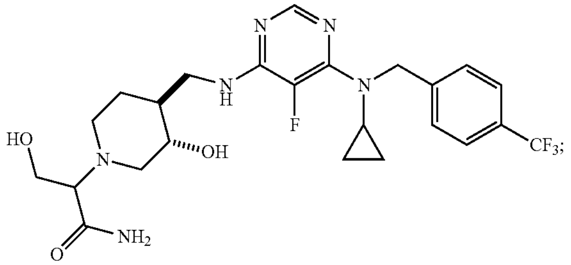
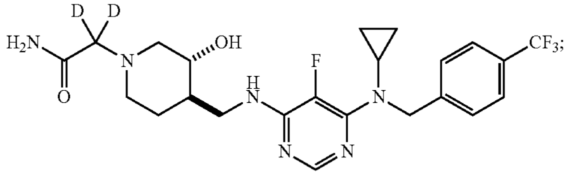
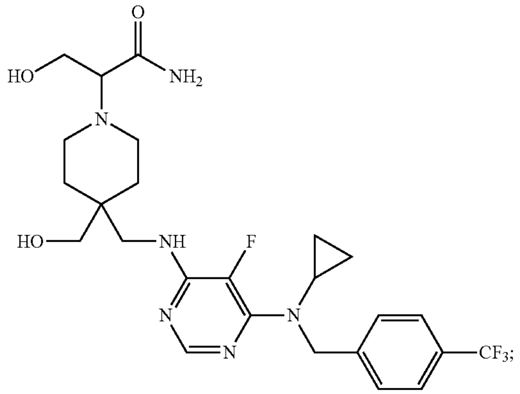
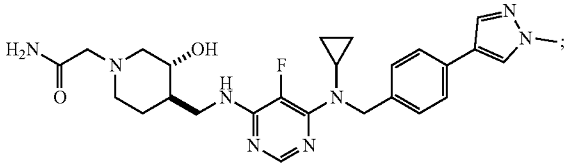
-continued
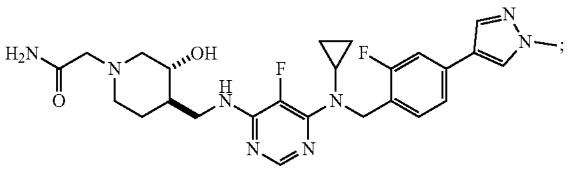
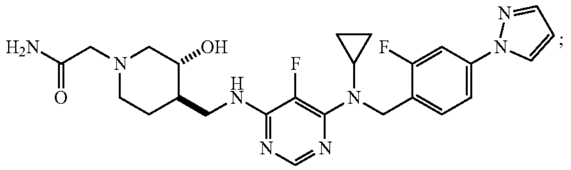
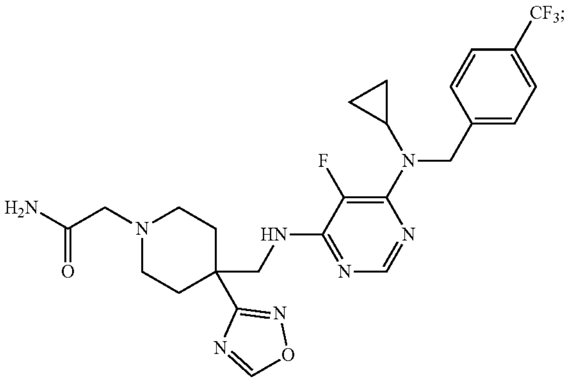
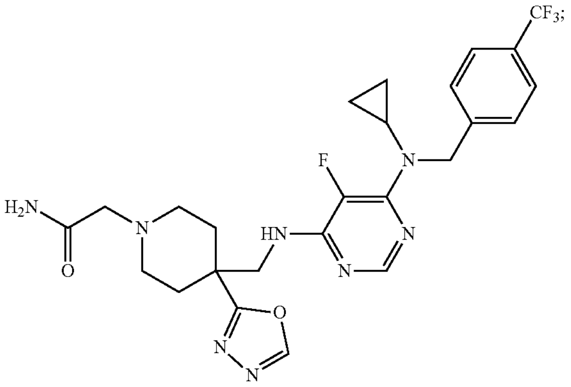
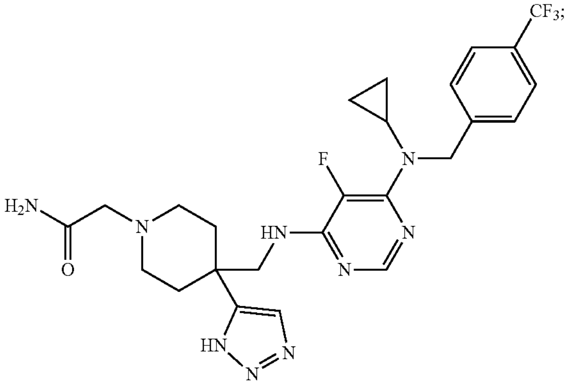
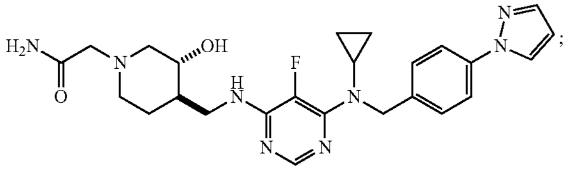

-continued
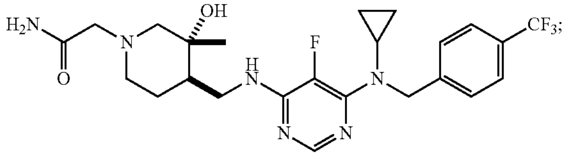
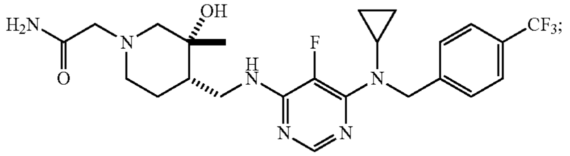
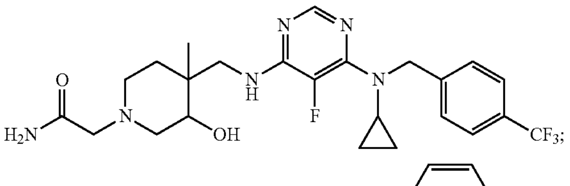
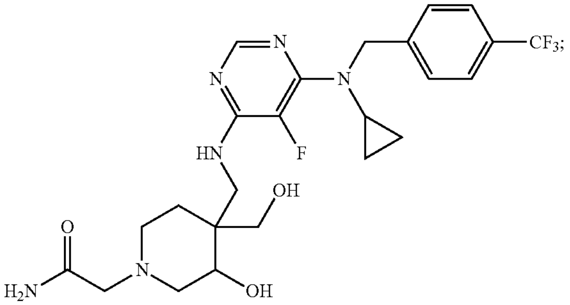
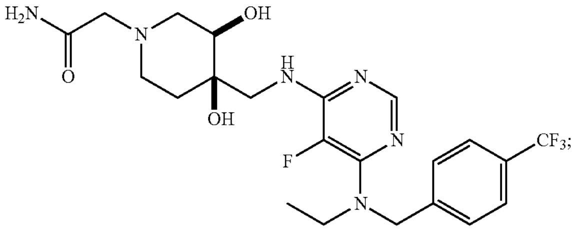
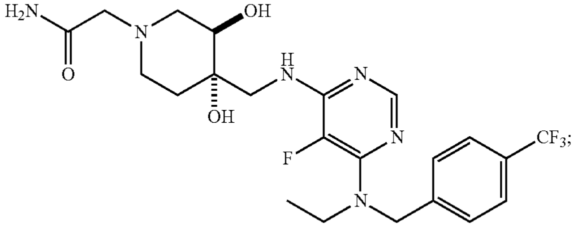
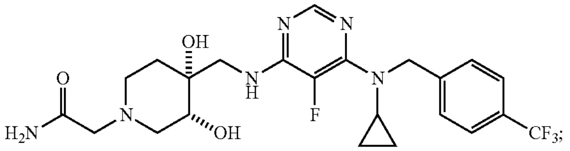
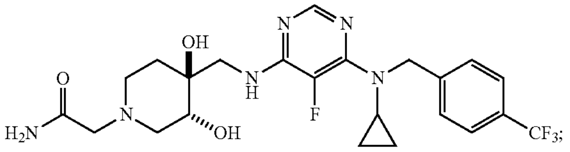
-continued
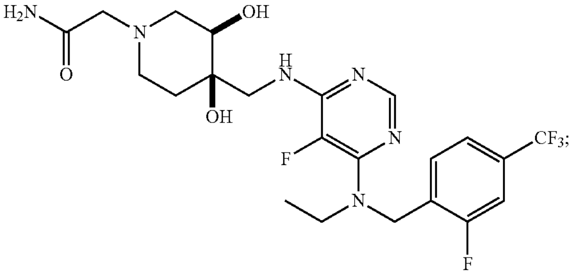
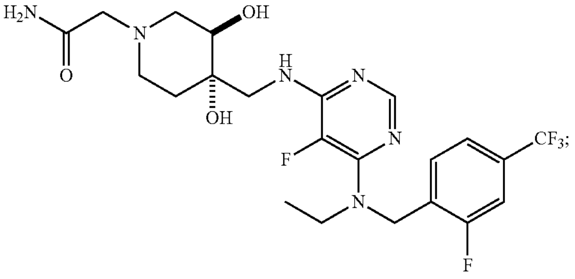
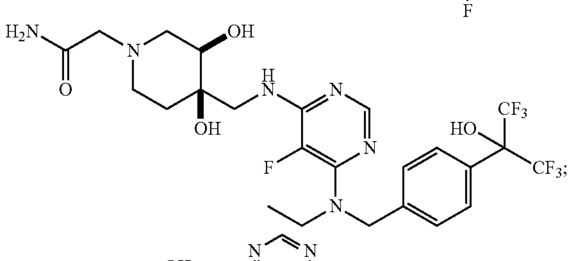
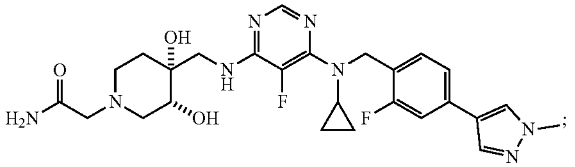
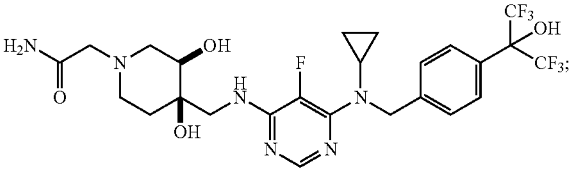
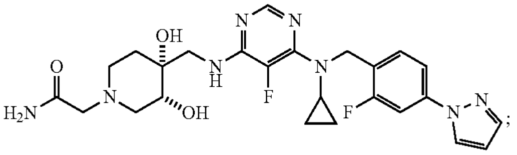
and
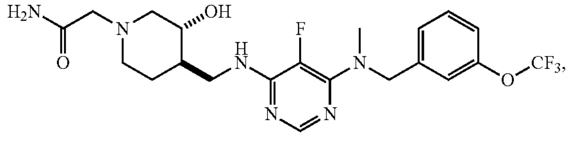
or a stereoisomer or salt or salt of a stereoisomer thereof.
In an embodiment, the compound has a structure selected from the group consisting of:
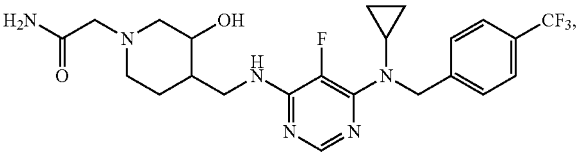

-continued
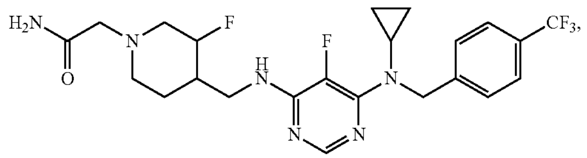
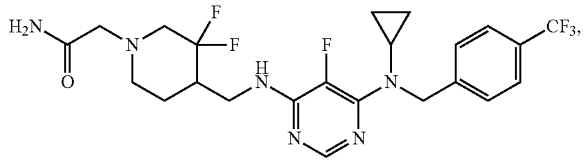
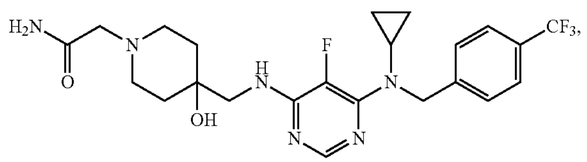
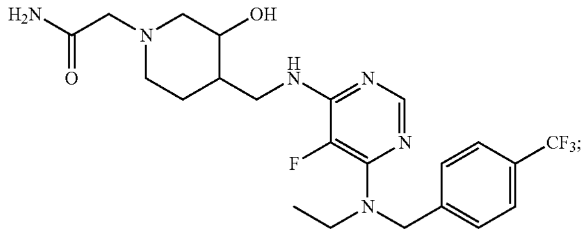
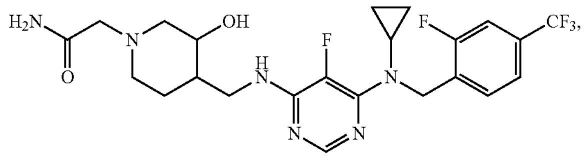
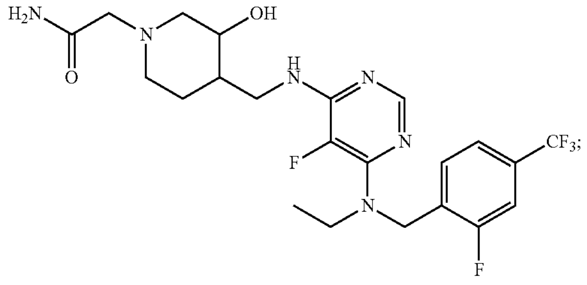
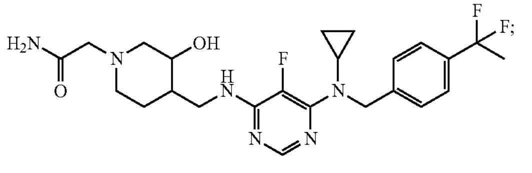
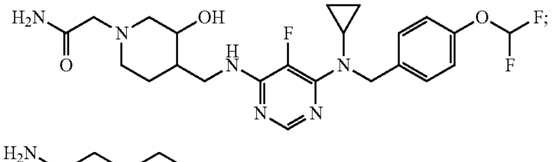
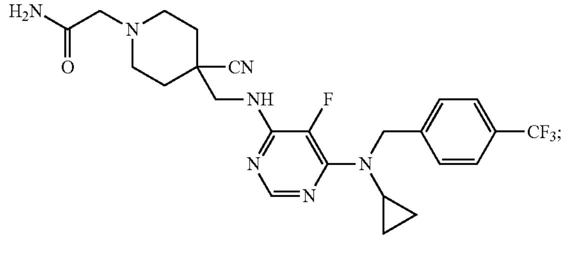
-continued
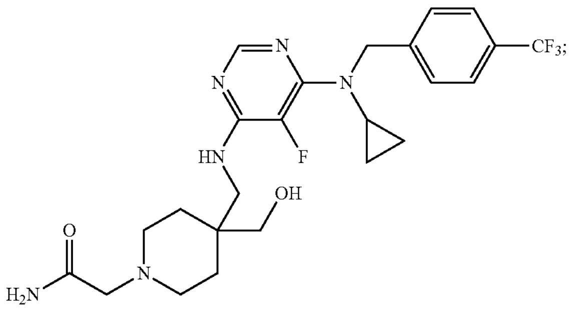
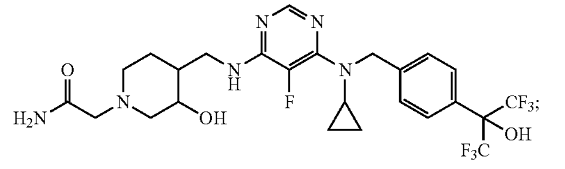
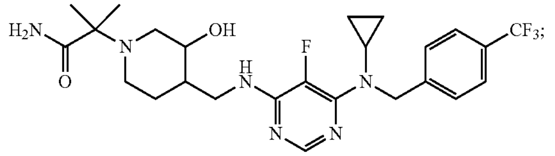
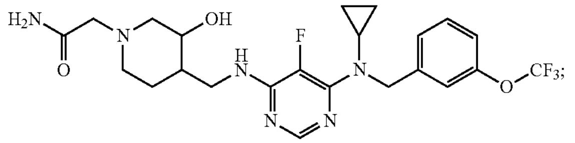
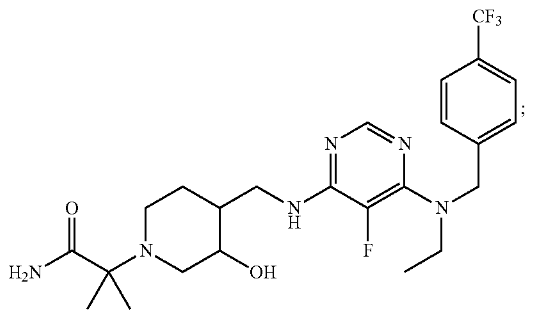
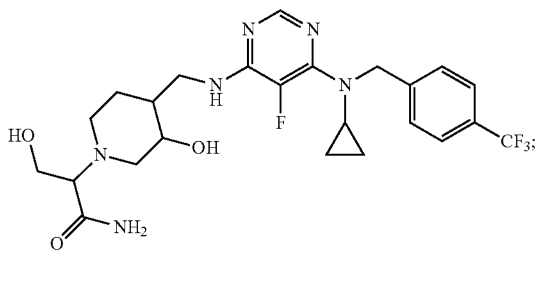
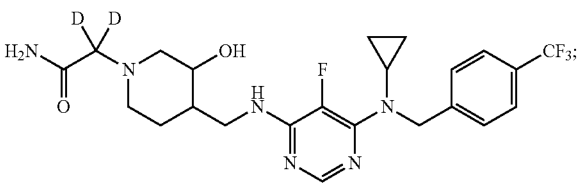

-continued
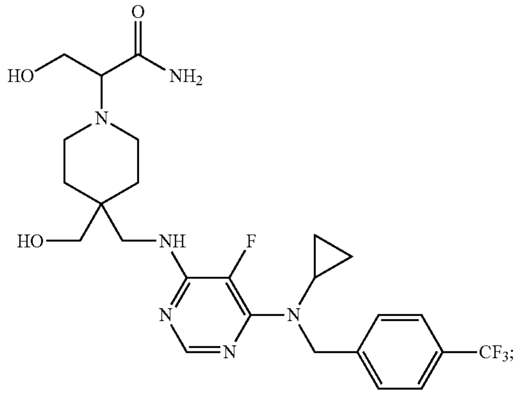
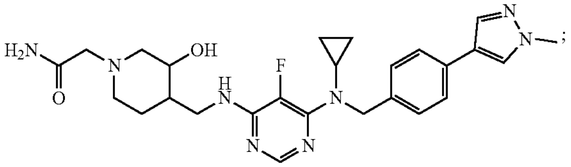
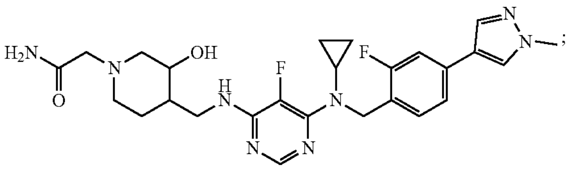
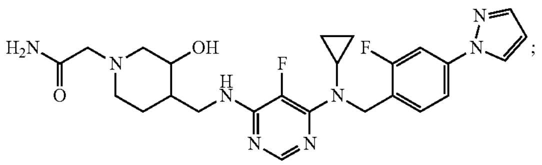
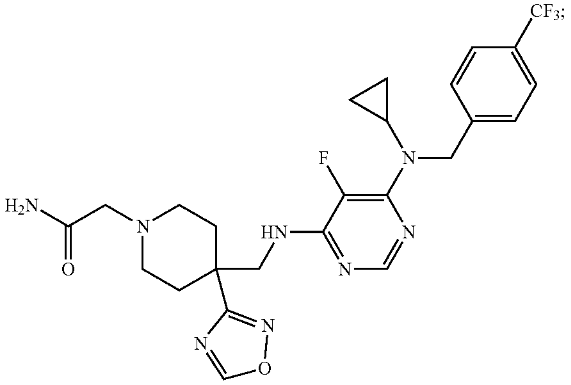
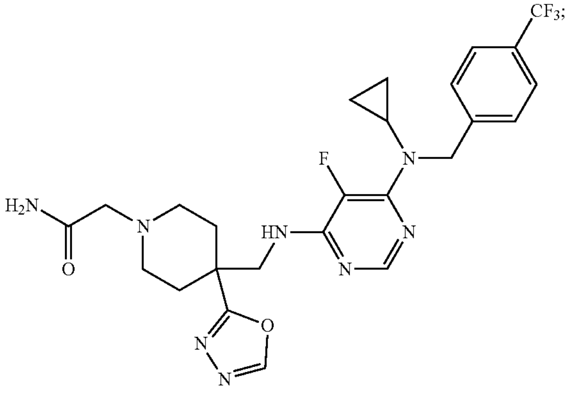
-continued
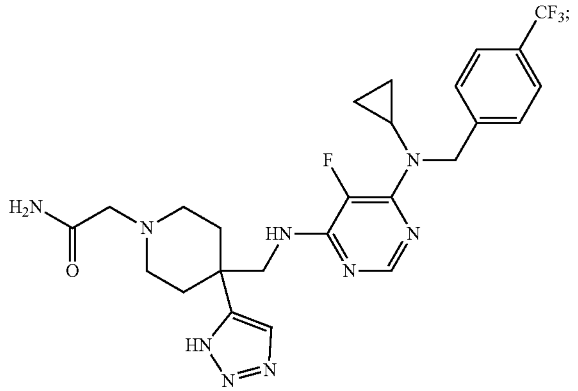
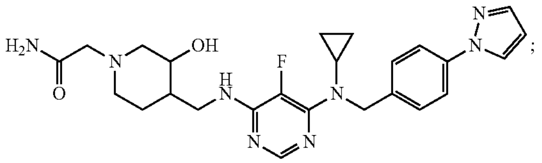
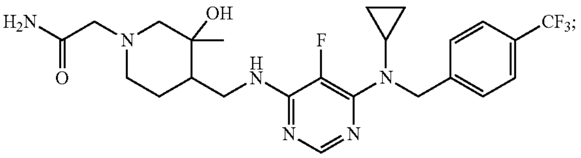
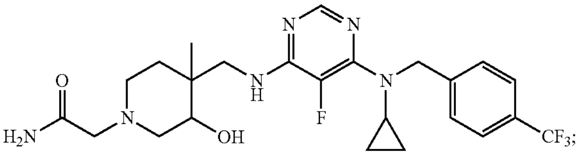
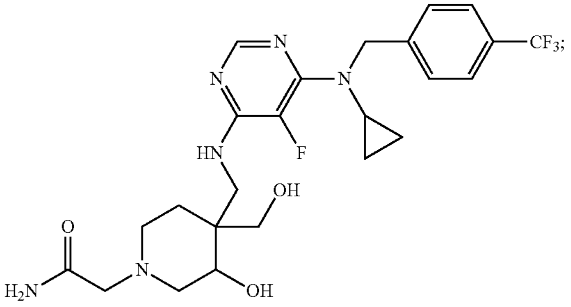
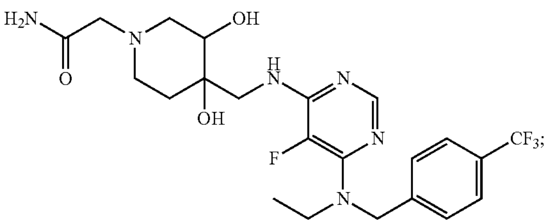
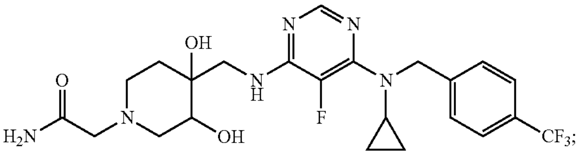

-continued

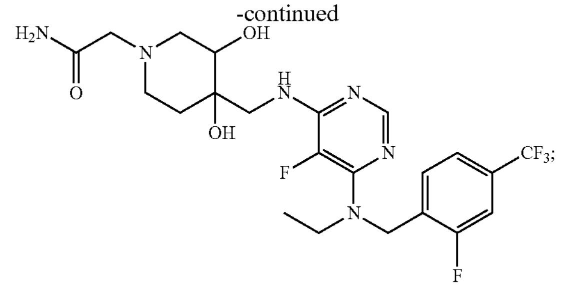

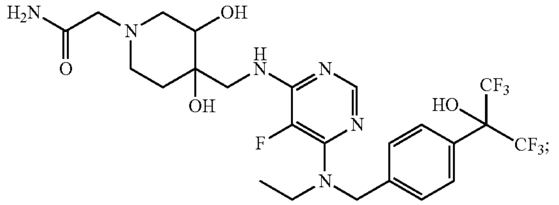

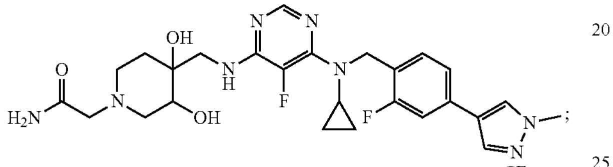

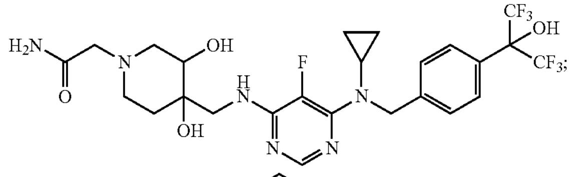

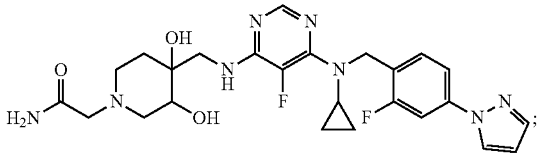

and

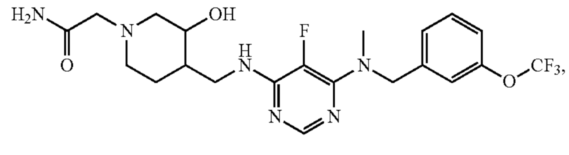 [SMILES: CN(Cc1cccc(OC(F)(F)F)c1)c1ncnc(NCC2CCN(CC(N)=O)CC2O)c1F]

or a stereoisomer or salt or salt of a stereoisomer thereof.

In a preferred embodiment, the compound of the invention is: 2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide.

In a preferred embodiment, the compound of the invention is: 2-((3S,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide.

In a preferred embodiment, the compound of the invention is: 2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide.

In a preferred embodiment, the compound of the invention is: 2-((3S,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide.

In a preferred embodiment, the compound of the invention is: 2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide.

In a preferred embodiment, the compound of the invention is: 2-((3S,4S)-4-(((6-(ethyl(4-(trifluoromethyl)benzyl)amino)-5-fluoropyrimidin-4-yl)amino)methyl)-3,4-dihydroxypiperidin-1-yl)acetamide.

In a preferred embodiment, the compound of the invention is: 2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide.

In a preferred embodiment, the compound of the invention is: 2-((3S,4R)-4-(((6-(ethyl(4-(trifluoromethyl)benzyl)amino)-5-fluoropyrimidin-4-yl)amino)methyl)-3,4-dihydroxypiperidin-1-yl)acetamide.

In a preferred embodiment, the compound of the invention is: 2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide.

In a preferred embodiment, the compound of the invention is: 2-((3S,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide.

In a preferred embodiment, the compound of the invention is: 2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide.

In a preferred embodiment, the compound of the invention is: 2-((3S,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide.

In other particular embodiment, the present disclosure relates to compounds of formula (I) or salt, stereoisomer, or salt of a stereoisomer thereof, wherein $R_{0a}$ is selected from the group consisting of —CN, substituted or unsubstituted heteroalicyclyl and substituted or unsubstituted heteroaryl; and $R_{0b}$ is hydrogen or $C_{1-4}$ alkyl. In some preferred embodiments $R_{0a}$ is substituted or unsubstituted heteroaryl. In other more preferred embodiments $R_{0a}$ is substituted or unsubstituted pyridinyl. In still more preferred embodiments $R_{0b}$ is hydrogen.

In some embodiments disclosed herein, the compound, stereoisomer, or salt has a structure of Formula (IV):

(IV)

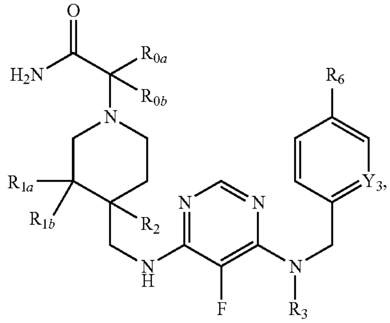

wherein:

$R_{0a}$ is a substituted or unsubstituted pyridinyl; $R_{0b}$ is hydrogen; $R_{1a}$ is hydroxyl;

$R_{1b}$ is hydrogen; $R_2$ is hydrogen or hydroxyl; $R_3$ is ethyl or cyclopropyl;

$R_6$ is $CF_3$; and $Y_3$ is $CR_8$, wherein $R_8$ is hydrogen or fluoro.

In some embodiments disclosed herein, $R_{0a}$ is selected from the group consisting of CN, pyridinyl, and tetrahydropyranyl; $R_{0b}$ is hydrogen; $R_{1a}$ is hydroxyl; $R_{1b}$ is hydrogen; $R_2$ is hydrogen or hydroxyl; R is hydrogen; $R_3$ is ethyl or cyclopropyl; $R_4$ is hydrogen; $R_5$ is hydrogen; $R_6$ is $CF_3$; $R_7$ is hydrogen; and $Y_1$, $Y_2$ and $Y_3$ are each CH.

In some embodiments disclosed herein, $R_{0a}$ is pyridinyl; $R_{0b}$ is hydrogen; $R_{1a}$ is hydroxyl; $R_{1b}$ is hydrogen; $R_2$ is hydrogen or hydroxyl; R is hydrogen; $R_3$ is ethyl or cyclopropyl; $R_4$ is hydrogen; $R_5$ is hydrogen; $R_6$ is $CF_3$; $R_7$ is hydrogen; and $Y_1$, $Y_2$ and $Y_3$ are each CH.

In other embodiment the present disclosure relates to a compound of Formula (I) or a salt, stereoisomer, or salt of a stereoisomer thereof, wherein: $R_{0a}$ is selected from the group consisting of —CN, pyridinyl and tetrahydropyranyl; $R_{0b}$ is hydrogen; $R_{1a}$ is hydroxyl; $R_{1b}$ is hydrogen; $R_2$ is hydrogen or hydroxyl; R is hydrogen; $R_3$ is ethyl or cyclopropyl; $R_4$ is hydrogen; $R_5$ is hydrogen; $R_6$ is —$CF_3$; $R_7$ is hydrogen; and $Y_1$, $Y_2$ and $Y_3$ are each —CH—.

In other more preferred embodiment, the present disclosure relates to a compound of Formula (I) or a salt, stereoisomer, or salt of a stereoisomer thereof, wherein: $R_{0a}$ is pyridinyl; $R_{0b}$ is hydrogen; $R_{1a}$ is hydroxyl; $R_{1b}$ is hydrogen; $R_2$ is hydrogen or hydroxyl; R is hydrogen; $R_3$ is ethyl or cyclopropyl; $R_4$ is hydrogen; $R_5$ is hydrogen; $R_6$ is —$CF_3$; $R_7$ is hydrogen; and $Y_1$, $Y_2$ and $Y_3$ are each —CH—.

In other embodiment disclosed herein, the compound, salt, stereoisomer, or salt of a stereoisomer according to Formula (I) is selected from the group consisting of:

A7-59 rac-2-cyano-2-((3R,4R)-4-(((6-(ethyl(4-(trifluoromethyl) benzyl)amino)-5-fluoropyrimidin-4-yl)amino)methyl)-3-hydroxypiperidin-1-yl)acetamide,

A7-62 rac-2-((3R,4R)-4-(((6-(ethyl(4-(trifluoromethyl)benzyl) amino)-5-fluoropyrimidin-4-yl)amino)methyl)-3-hydroxypiperidin-1-yl)-2-(pyridin-4-yl)acetamide,

A7-63 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(pyridin-4-yl)acetamide,

A7-71 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetamide,

D5-7"

rel-2-((3R,4R)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide, enantiomerically enriched,

D5-7-1 rel-(R)-2-((3R,4R)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide or rel-(R)-2-((3S,4S)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide, 1st eluting major isomer,

D5-7-2 rel-(R)-2-((3R,4R)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide orrel-(R)-2-((3S,4S)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide, 2nd eluting major isomer, and

D5-8"

rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)-2-(pyridin-4-yl)acetamide, enantiomerically enriched.

In some cases, the compound, salt, stereoisomer, or salt of a stereoisomer according to Formula (I) is selected from the group consisting of:

A7-59 rac-2-cyano-2-((3R,4R)-4-(((6-(ethyl(4-(trifluoromethyl) benzyl)amino)-5-fluoropyrimidin-4-yl)amino)methyl)-3-hydroxypiperidin-1-yl)acetamide,

A7-62 rac-2-((3R,4R)-4-(((6-(ethyl(4-(trifluoromethyl)benzyl) amino)-5-fluoropyrimidin-4-yl)amino)methyl)-3-hydroxypiperidin-1-yl)-2-(pyridin-4-yl)acetamide,

A7-63 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(pyridin-4-yl)acetamide,

A7-71 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetamide,

D5-7"

rel-2-((3R,4R)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide,

D5-7-1 rel-(R)-2-((3R,4R)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide, rel-(R)-2-((3S,4S)-4-(((6-(ethyl(4-(trifluoromethyl)benzyl) amino)-5-fluoropyrimidin-4-yl)amino)methyl)-3,4-dihydroxypiperidin-1-yl)-2-(pyridin-4-yl)acetamide, and

D5-8"

rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)-2-(pyridin-4-yl)acetamide.

In some cases, the compound, salt, stereoisomer, or salt of a stereoisomer according to Formula (I) is selected from the group consisting of:

2-cyano-2-(4-(((6-(ethyl(4-(trifluoromethyl)benzyl)amino)-5-fluoropyrimidin-4-yl)amino)methyl)-3-hydroxypiperidin-1-yl)acetamide, 2-(4-(((6-(ethyl(4-(trifluoromethyl)benzyl)amino)-5-fluoropyrimidin-4-yl)amino)methyl)-3-hydroxypiperidin-1-yl)-2-(pyridin-4-yl)acetamide, 2-(4-(((6-(cyclopropyl(4-(trifluoromethyl)benzyl)amino)-5-fluoropyrimidin-4-yl)amino)methyl)-3-hydroxypiperidin-1-yl)-2-(pyridin-4-yl)acetamide, 2-(4-(((6-(cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetamide, 2-(4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide, and 2-(4-(((6-(cyclopropyl (4-(trifluoromethyl)benzyl)amino)-5-fluoropyrimidin-4-yl)amino)methyl)-3,4-dihydroxypiperidin-1-yl)-2-(pyridin-4-yl)acetamide.

In some cases, the compound, salt, stereoisomer, or salt of a stereoisomer according to Formula (I) is selected from the group consisting of:

A7-62 rac-2-((3R,4R)-4-(((6-(ethyl(4-(trifluoromethyl)benzyl) amino)-5-fluoropyrimidin-4-yl)amino)methyl)-3-hydroxypiperidin-1-yl)-2-(pyridin-4-yl)acetamide, A7-63
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(pyridin-4-yl)acetamide,
D5-7"
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide, enantiomerically enriched,
D5-7-1
rel-(R)-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide or rel-(R)-2-((3S,4S)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide, 1 eluting major isomer,
D5-7-2
rel-(R)-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide or rel-(R)-2-((3S,4S)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide, 2nd eluting major isomer, and
D5-8"
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)-2-(pyridin-4-yl)acetamide, enantiomerically enriched.

In some cases, the compound, salt, stereoisomer, or salt of a stereoisomer according to Formula (I) is selected from the group consisting of:

A7-62
rac-2-((3R,4R)-4-(((6-(ethyl(4-(trifluoromethyl)benzyl)amino)-5-fluoropyrimidin-4-yl)amino)methyl)-3-hydroxypiperidin-1-yl)-2-(pyridin-4-yl)acetamide,
A7-63
rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(pyridin-4-yl)acetamide,
D5-7"
rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide,
D5-7-1
rel-(R)-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide, rel-(R)-2-((3S,4S)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide, and
D5-8"
rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)-2-(pyridin-4-yl)acetamide.

In some embodiments whenever a halogen is specified as a substituent the halogen is selected from fluoro or chloro.

Embodiments and particular disclosures used herein are to illustrate different alternatives of the disclosure and embodiments may be combined with other applicable embodiments.

Specific examples of compounds are disclosed in Table 1 below. Table 1. Example compounds by Structure and Name.

TABLE 1

Example compounds by Structure and Name.

| Ex. No | Structure | Name |
|---|---|---|
| A7-1 | 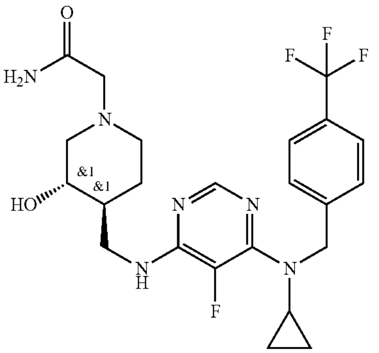 [SMILES: NC(=O)CN1CC[C@@H](CNc2ncnc(N(Cc3ccc(C(F)(F)F)cc3)C3CC3)c2F)[C@H](O)C1] | A7-1 rac-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide |
| A7-1-1 | 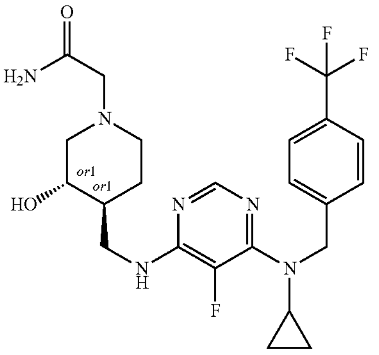 [SMILES: NC(=O)CN1CC[C@@H](CNc2ncnc(N(Cc3ccc(C(F)(F)F)cc3)C3CC3)c2F)[C@H](O)C1] | A7-1-1 rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide 1st eluting isomer |

TABLE 1-continued

| Ex. No | Structure | Name |
| --- | --- | --- |
| | Example compounds by Structure and Name. | |
| A7-1-2 | | A7-1-2<br>rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide<br>2nd eluting isomer |
| A7-2 | 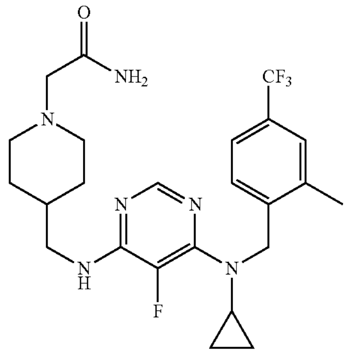 [SMILES: Cc1cc(C(F)(F)F)ccc1CN(c1ncnc(NCC2CCN(CC(N)=O)CC2)c1F)C1CC1] | A7-2<br>2-(4-(((6-(cyclopropyl(2-methyl-4-(trifluoromethyl)benzyl)amino)-5-fluoropyrimidin-4-yl)amino)methyl)piperidin-1-yl)acetamide |
| A7-3-1 | 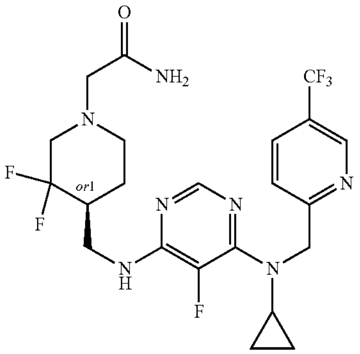 [SMILES: NC(=O)CN1CC[C@@H](CNc2ncnc(N(Cc3ccc(C(F)(F)F)cn3)C3CC3)c2F)C(F)(F)C1] | A7-3-1<br>rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide<br>1st eluting isomer |
| A7-3-2 | | A7-3-2<br>rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide<br>2nd eluting isomer |
| A7-4-1 | 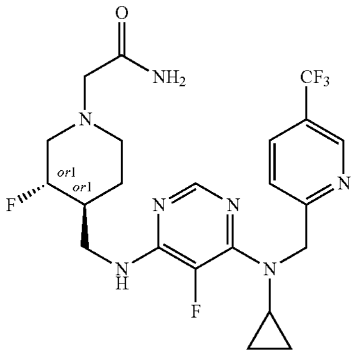 [SMILES: NC(=O)CN1CC[C@@H](CNc2ncnc(N(Cc3ccc(C(F)(F)F)cn3)C3CC3)c2F)[C@H](F)C1] | A7-4-1<br>rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide<br>1st eluting isomer |
| A7-4-2 | | A7-4-2<br>rel-2-((3R,4R)-4-(((6-(cyclopropyl((5-(trifluoromethyl)pyridin-2-yl)methyl)amino)-5- |

TABLE 1-continued

| Example compounds by Structure and Name. | | |
|---|---|---|
| Ex. No | Structure | Name |
| | | fluoropyrimidin-4-yl)amino)methyl)-3-fluoropiperidin-1-yl)acetamide 2$^{nd}$ eluting isomer |
| A7-5-1 | 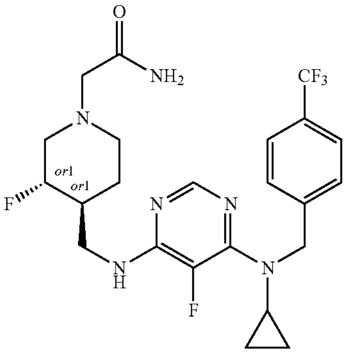 [SMILES: NC(=O)CN1CC[C@@H](CNc2ncnc(N(Cc3ccc(C(F)(F)F)cc3)C3CC3)c2F)[C@H](F)C1] | A7-5-1 rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide 1$^{st}$ eluting isomer |
| A7-5-2 | | A7-5-2 rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide 2$^{nd}$ eluting isomer |
| A7-6-1 | 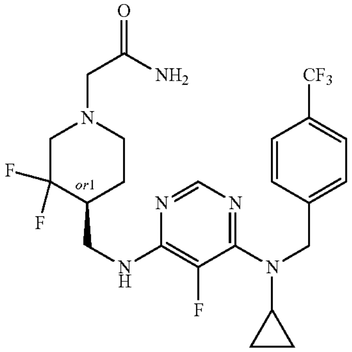 [SMILES: NC(=O)CN1CC[C@@H](CNc2ncnc(N(Cc3ccc(C(F)(F)F)cc3)C3CC3)c2F)C(F)(F)C1] | A7-6-1 rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide 1$^{st}$ eluting isomer |
| A7-6-2 | | A7-6-2 rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide 2$^{nd}$ eluting isomer |
| A7-7-1 | 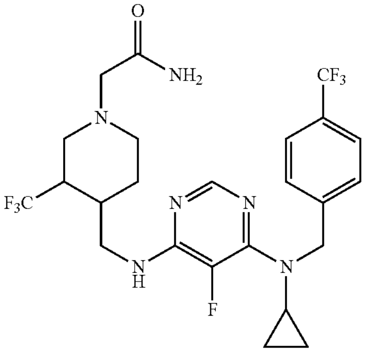 [SMILES: NC(=O)CN1CCC(CNc2ncnc(N(Cc3ccc(C(F)(F)F)cc3)C3CC3)c2F)C(C(F)(F)F)C1] | A7-7-1 2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide |

TABLE 1-continued

| Example compounds by Structure and Name. | | |
|---|---|---|
| Ex. No | Structure | Name |
| A7-7-2 | | A7-7-2<br>2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide<br>2$^{nd}$ eluting isomer |
| A7-7-3 | | A7-7-3<br>2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide<br>3$^{rd}$ eluting isomer |
| A7-7-4 | | A7-7-4<br>2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide<br>4$^{th}$ eluting isomer |
| A7-8 | 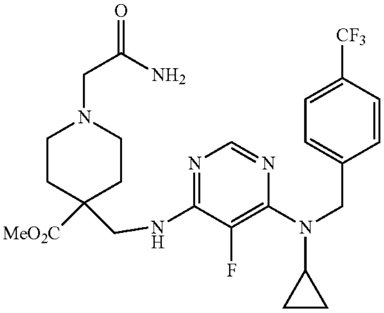 [SMILES: COC(=O)C1(CNc2ncnc(N(Cc3ccc(C(F)(F)F)cc3)C3CC3)c2F)CCN(CC(N)=O)CC1] | A7-8<br>methyl 1-(2-amino-2-oxoethyl)-4-(((6-(cyclopropyl(4-(trifluoromethyl)benzyl)amino)-5-fluoropyrimidin-4-yl)amino)methyl)piperidine-4-carboxylate |
| A7-9 | 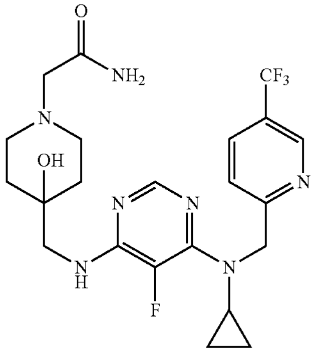 | A7-9<br>2-(4-(((6-(cyclopropyl((5-(trifluoromethyl)pyridin-2-yl)methyl)amino)-5-fluoropyrimidin-4-yl)amino)methyl)-4-hydroxypiperidin-1-yl)acetamide |
| A7-10 | 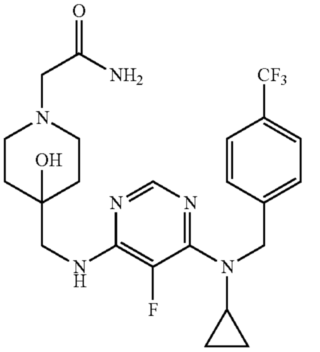 | A7-10<br>2-(4-(((6-(cyclopropyl(4-(trifluoromethyl)benzyl)amino)-5-fluoropyrimidin-4-yl)amino)methyl)-4-hydroxypiperidin-1-yl)acetamide |

TABLE 1-continued

| Example compounds by Structure and Name. | | |
|---|---|---|
| Ex. No | Structure | Name |
| A7-11 | 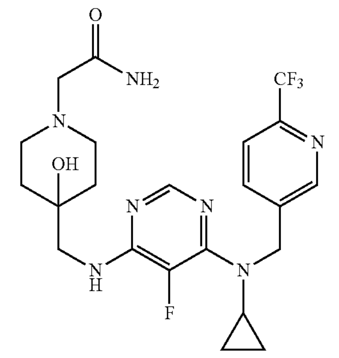 | A7-11<br>2-(4-(((6-(cyclopropyl((6-(trifluoromethyl)pyridin-3-yl)methyl)amino)-5-fluoropyrimidin-4-yl)amino)methyl)-4-hydroxypiperidin-1-yl)acetamide |
| A7-14 | 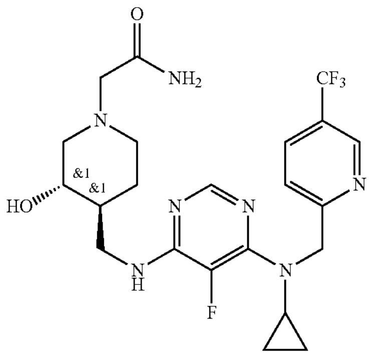 [SMILES: NC(=O)CN1CC[C@@H](CNc2ncnc(N(Cc3ccc(C(F)(F)F)cn3)C3CC3)c2F)[C@H](O)C1] | A7-14<br>rac-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide |
| A7-14-1 | 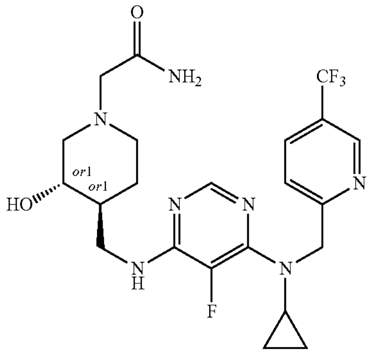 [SMILES: NC(=O)CN1CC[C@@H](CNc2ncnc(N(Cc3ccc(C(F)(F)F)cn3)C3CC3)c2F)[C@H](O)C1] | A7-14-1<br>rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide<br>1st eluting isomer |
| A7-14-2 | | A7-14-2<br>rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide<br>2nd eluting isomer |

TABLE 1-continued

Example compounds by Structure and Name.

| Ex. No | Structure | Name |
| --- | --- | --- |
| A7-15 | 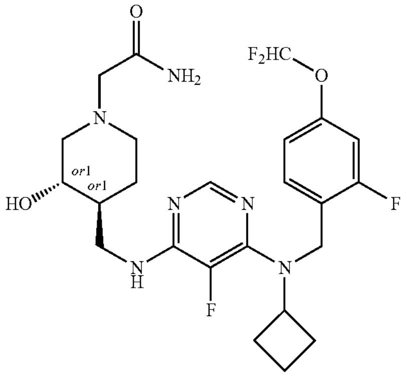 [SMILES: NC(=O)CN1CC[C@@H](CNc2ncnc(N(Cc3ccc(OC(F)F)cc3F)C3CCC3)c2F)[C@H](O)C1] | A7-15 rac-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide |
| A7-15-1 | 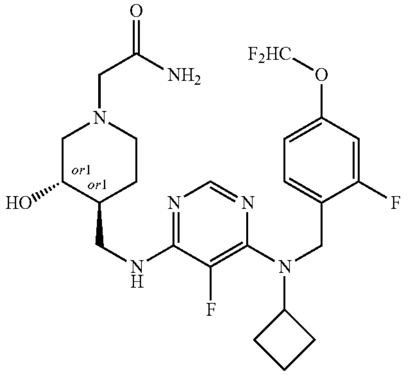 [SMILES: NC(=O)CN1CC[C@@H](CNc2ncnc(N(Cc3ccc(OC(F)F)cc3F)C3CCC3)c2F)[C@H](O)C1] | A7-15-1 rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide |
| A7-15-2 | | A7-15-2 rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide $2^{nd}$ eluting isomer |
| A7-16 | 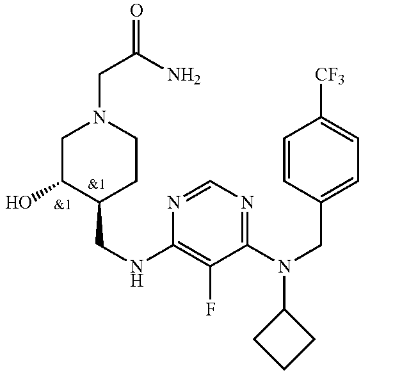 [SMILES: NC(=O)CN1CC[C@@H](CNc2ncnc(N(Cc3ccc(C(F)(F)F)cc3)C3CCC3)c2F)[C@H](O)C1] | A7-16 rac-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| A7-16-1 | 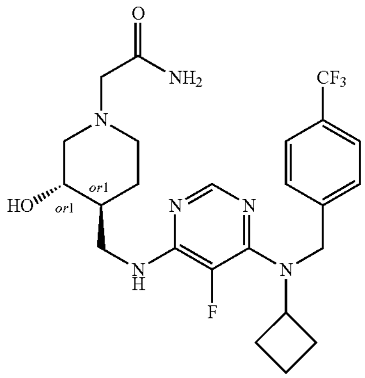 [SMILES: NC(=O)CN1CC[C@@H](CNc2ncnc(N(Cc3ccc(C(F)(F)F)cc3)C3CCC3)c2F)[C@H](O)C1] | A7-16-1 rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide |
| A7-16-2 | | A7-16-2 rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide $2^{nd}$ eluting isomer |
| A7-17 | 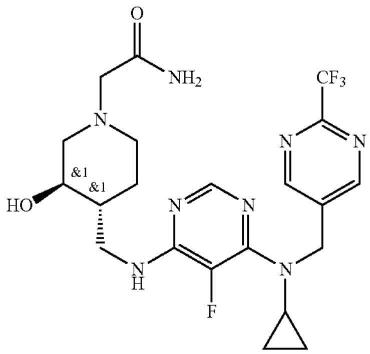 [SMILES: NC(=O)CN1CC[C@H](CNc2ncnc(N(Cc3cnc(C(F)(F)F)nc3)C3CC3)c2F)[C@@H](O)C1] | A7-17 rac-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide |
| A7-17-1 | 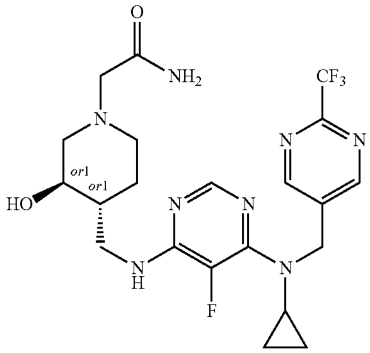 [SMILES: NC(=O)CN1CC[C@H](CNc2ncnc(N(Cc3cnc(C(F)(F)F)nc3)C3CC3)c2F)[C@@H](O)C1] | A7-17-1 rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide $1^{st}$ eluting isomer |
| A7-17-2 | | A7-17-2 rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide $2^{nd}$ eluting isomer |

TABLE 1-continued

Example compounds by Structure and Name.

| Ex. No | Structure | Name |
|---|---|---|
| A7-18 | 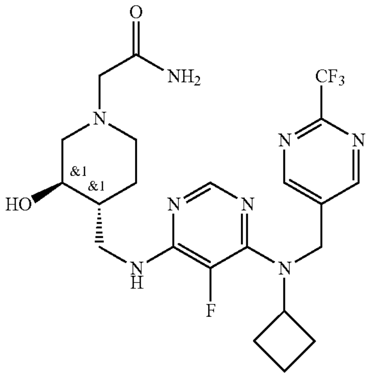 [SMILES: NC(=O)CN1CC[C@H](CNc2ncnc(N(Cc3cnc(C(F)(F)F)nc3)C3CCC3)c2F)[C@@H](O)C1] | A7-18 rac-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide |
| A7-18-1 | 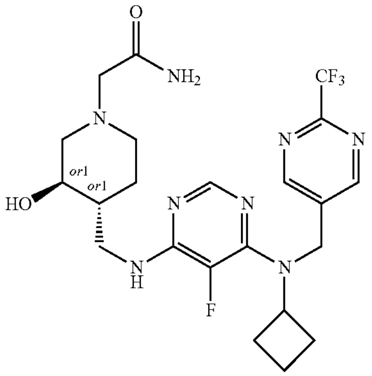 [SMILES: NC(=O)CN1CC[C@H](CNc2ncnc(N(Cc3cnc(C(F)(F)F)nc3)C3CCC3)c2F)[C@@H](O)C1] | A7-18-1 rel-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide 1$^{st}$ eluting isomer |
| A7-18-2 | | A7-18-2 rel-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide 2$^{nd}$ eluting isomer |
| A7-19 | 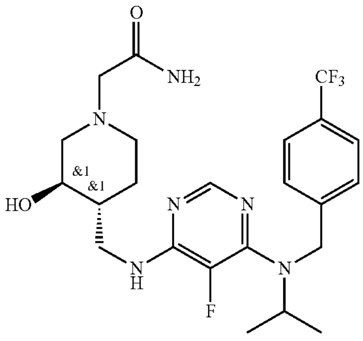 | A7-19 rac-2-((3R,4R)-4-(((5-fluoro-6-(isopropyl(4-(trifluoromethyl)benzyl)amino) pyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| A7-19-1 | 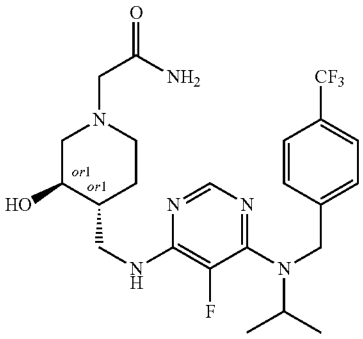 [SMILES: CC(C)N(Cc1ccc(C(F)(F)F)cc1)c1ncnc(NC[C@H]2CCN(CC(N)=O)C[C@@H]2O)c1F] | A7-19-1 rel-2-((3R,4R)-4-(((5-fluoro-6-(isopropyl(4-(trifluoromethyl)benzyl)amino) pyrimidin-4-yl)amino)methyl)-3-hydroxypiperidin-1-yl)acetamide 1st eluting isomer |
| A7-19-2 | | A7-19-2 rel-2-((3R,4R)-4-(((5-fluoro-6-(isopropyl(4-(trifluoromethyl)benzyl)amino) pyrimidin-4-yl)amino)methyl)-3-hydroxypiperidin-1-yl)acetamide 2nd eluting isomer |
| A7-20 | 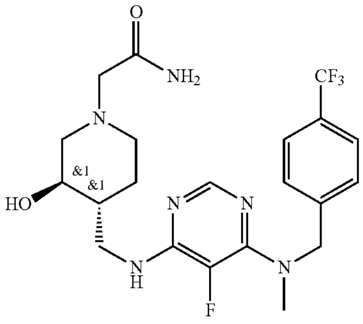 [SMILES: CN(Cc1ccc(C(F)(F)F)cc1)c1ncnc(NC[C@H]2CCN(CC(N)=O)C[C@@H]2O)c1F] | A7-20 rac-2-((3R,4R)-4-(((5-fluoro-6-(methyl(4-(trifluoromethyl)benzyl)amino) pyrimidin-4-yl)amino)methyl)-3-hydroxypiperidin-1-yl)acetamide |
| A7-20-1 | 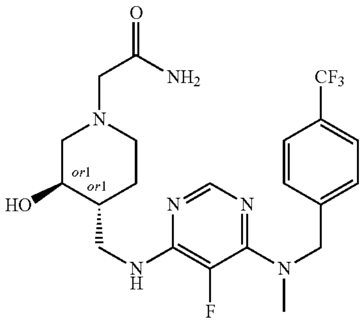 [SMILES: CN(Cc1ccc(C(F)(F)F)cc1)c1ncnc(NC[C@H]2CCN(CC(N)=O)C[C@@H]2O)c1F] | A7-20-1 rel-2-((3R,4R)-4-(((5-fluoro-6-(methyl(4-(trifluoromethyl)benzyl)amino) pyrimidin-4-yl)amino)methyl)-3-hydroxypiperidin-1-yl)acetamide 1st eluting isomer |
| A7-20-2 | | A7-20-2 rel-2-((3R,4R)-4-(((5-fluoro-6-(methyl(4-(trifluoromethyl)benzyl)amino) pyrimidin-4-yl)amino)methyl)-3-hydroxypiperidin-1-yl)acetamide 2nd eluting isomer |

TABLE 1-continued

| Ex. No | Structure | Name |
|---|---|---|
| A7-21 | 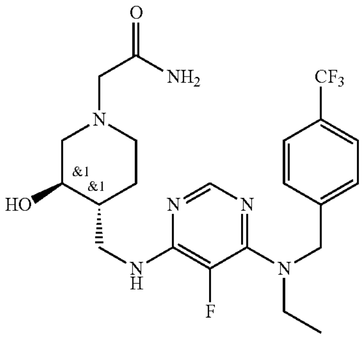 [SMILES: CCN(Cc1ccc(C(F)(F)F)cc1)c1ncnc(NC[C@H]2CCN(CC(N)=O)C[C@@H]2O)c1F] | A7-21 rac-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide |
| A7-21-1 | 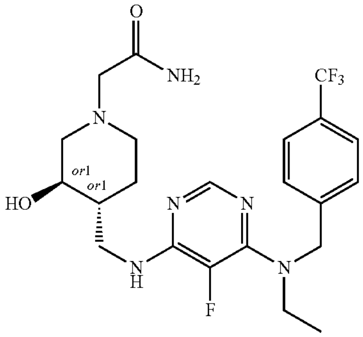 [SMILES: CCN(Cc1ccc(C(F)(F)F)cc1)c1ncnc(NC[C@H]2CCN(CC(N)=O)C[C@@H]2O)c1F] | A7-21-1 rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide 1st eluting isomer |
| A7-21-2 | | A7-21-2 rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide 2nd eluting isomer |
| A7-22 | 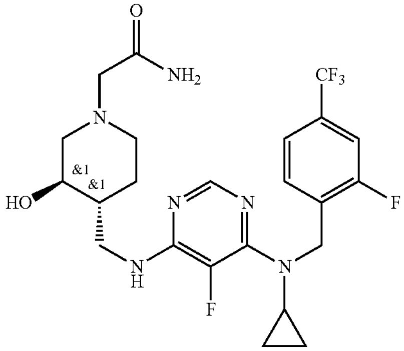 [SMILES: NC(=O)CN1CC[C@H](CNc2ncnc(N(Cc3ccc(C(F)(F)F)cc3F)C3CC3)c2F)[C@@H](O)C1] | A7-22 rac-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide |
| A7-22-1 | 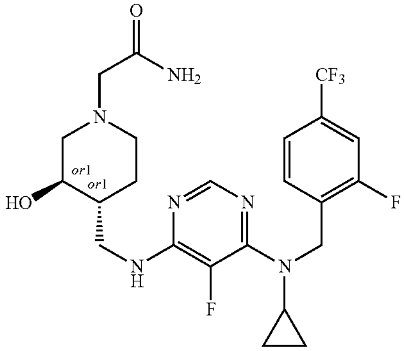 [SMILES: NC(=O)CN1CC[C@H](CNc2ncnc(N(Cc3ccc(C(F)(F)F)cc3F)C3CC3)c2F)[C@@H](O)C1] | A7-22-1 rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide 2nd eluting isomer |

Example compounds by Structure and Name.

TABLE 1-continued

| Example compounds by Structure and Name. | | |
|---|---|---|
| Ex. No | Structure | Name |
| A7-22-2 | | A7-22-2 rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide 1st eluting isomer |
| A7-23 | 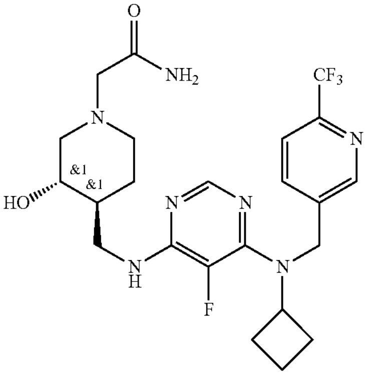 [SMILES: NC(=O)CN1CC[C@@H](CNc2ncnc(N(Cc3ccc(C(F)(F)F)nc3)C3CCC3)c2F)[C@H](O)C1] | A7-23 rac-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide |
| A7-23-1 | 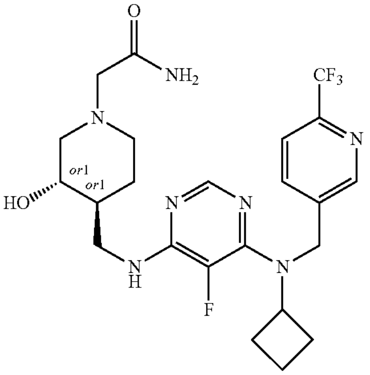 [SMILES: NC(=O)CN1CC[C@@H](CNc2ncnc(N(Cc3ccc(C(F)(F)F)nc3)C3CCC3)c2F)[C@H](O)C1] | A7-23-1 rel-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide 1st eluting isomer |
| A7-23-2 | | A7-23-2 rel-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide 2nd eluting isomer |
| A7-24 | 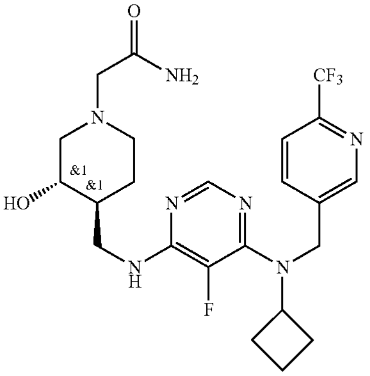 [SMILES: NC(=O)CN1CC[C@@H](CNc2ncnc(N(Cc3ccc(C(F)(F)F)nc3)C3CCC3)c2F)[C@H](O)C1] | A7-24 rac-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| A7-24-1 | 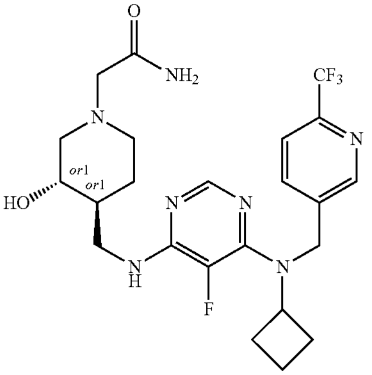 [SMILES: NC(=O)CN1CC[C@@H](CNc2ncnc(N(Cc3ccc(C(F)(F)F)nc3)C3CCC3)c2F)[C@H](O)C1] | A7-24-1 rel-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide 1st eluting isomer |
| A7-24-2 | | A7-24-2 rel-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide 2nd eluting isomer |
| A7-25 | 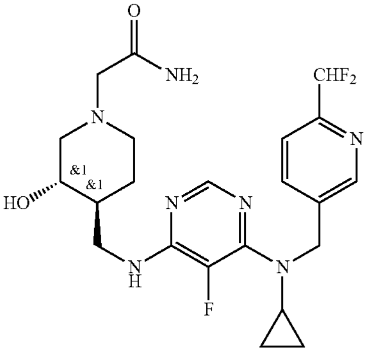 [SMILES: NC(=O)CN1CC[C@@H](CNc2ncnc(N(Cc3ccc(C(F)F)nc3)C3CC3)c2F)[C@H](O)C1] | A7-25 rac-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide |
| A7-25-1 | 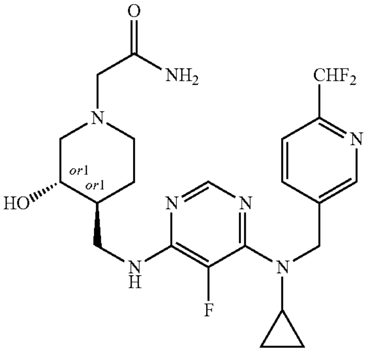 [SMILES: NC(=O)CN1CC[C@@H](CNc2ncnc(N(Cc3ccc(C(F)F)nc3)C3CC3)c2F)[C@H](O)C1] | A7-25-1 rel-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide 1st eluting isomer |
| A7-25-2 | | A7-25-2 rel-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide 2nd eluting isomer |

TABLE 1-continued

| Ex. No | Structure | Name |
|---|---|---|
| A7-26 | 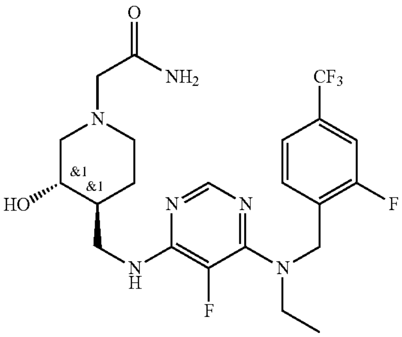 [SMILES: CCN(Cc1ccc(C(F)(F)F)cc1F)c1ncnc(NC[C@@H]2CCN(CC(N)=O)C[C@H]2O)c1F] | A7-26<br>rac-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide |
| A7-26-1 | 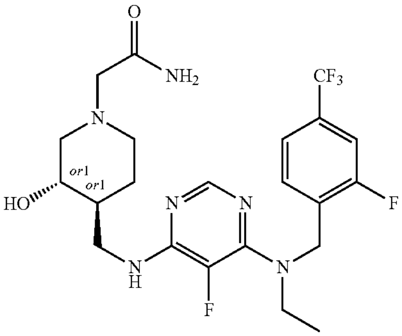 [SMILES: CCN(Cc1ccc(C(F)(F)F)cc1F)c1ncnc(NC[C@@H]2CCN(CC(N)=O)C[C@H]2O)c1F] | A7-26-1<br>rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide<br>2nd eluting isomer |
| A7-26-2 | | A7-26-2<br>rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide<br>1st eluting isomer |
| A7-27 | 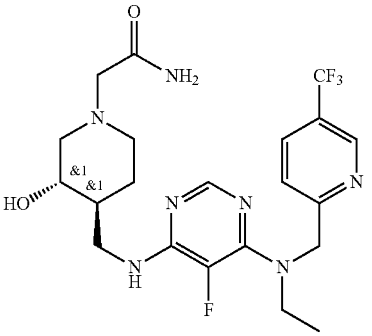 [SMILES: CCN(Cc1ccc(C(F)(F)F)cn1)c1ncnc(NC[C@@H]2CCN(CC(N)=O)C[C@H]2O)c1F] | A7-27<br>rac-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide |
| A7-27-1 | 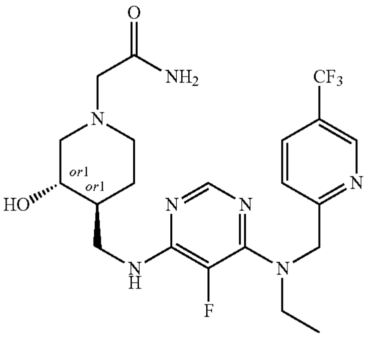 [SMILES: CCN(Cc1ccc(C(F)(F)F)cn1)c1ncnc(NC[C@@H]2CCN(CC(N)=O)C[C@H]2O)c1F] | A7-27-1<br>rel-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide<br>1st eluting isomer |

TABLE 1-continued

| Example compounds by Structure and Name. | | |
|---|---|---|
| Ex. No | Structure | Name |
| A7-27-2 | | A7-27-2<br>rel-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide<br>2nd eluting isomer |
| A7-28 | 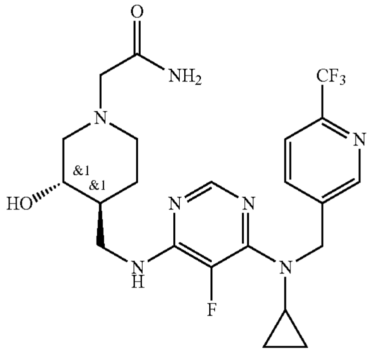 [SMILES: NC(=O)CN1CC[C@@H](CNc2ncnc(N(Cc3ccc(C(F)(F)F)nc3)C3CC3)c2F)[C@H](O)C1] | A7-28<br>rac-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide |
| A7-28-1 | 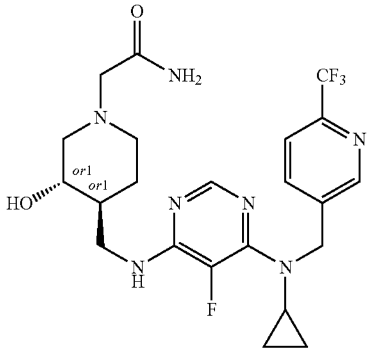 [SMILES: NC(=O)CN1CC[C@@H](CNc2ncnc(N(Cc3ccc(C(F)(F)F)nc3)C3CC3)c2F)[C@H](O)C1] | A7-28-1<br>rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide<br>1st eluting isomer |
| A7-28-2 | | A7-28-2<br>rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide<br>2nd eluting isomer |
| A7-29 | 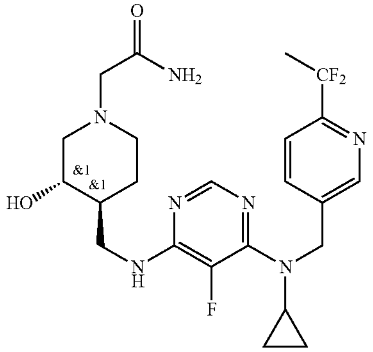 [SMILES: CC(F)(F)c1ccc(CN(c2ncnc(NC[C@@H]3CCN(CC(N)=O)C[C@H]3O)c2F)C2CC2)cn1] | A7-29<br>rac-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide |

TABLE 1-continued

Example compounds by Structure and Name.

| Ex. No | Structure | Name |
| --- | --- | --- |
| A7-29-1 | 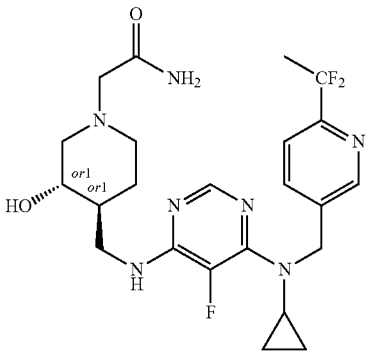 [SMILES: CC(F)(F)c1ccc(CN(c2ncnc(NC[C@@H]3CCN(CC(N)=O)C[C@H]3O)c2F)C2CC2)cn1] | A7-29-1 rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide 1st eluting isomer |
| A7-29-2 | | A7-29-2 rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide 2nd eluting isomer |
| A7-30 | 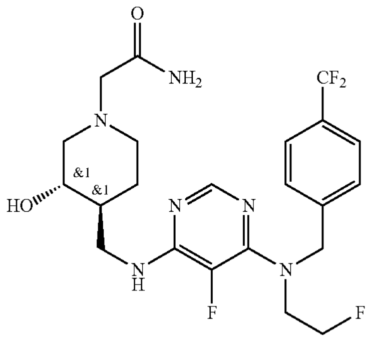 | A7-30 rac-2-((3R,4R)-4-(((5-fluoro-6-((2-fluoroethyl)(4-(trifluoromethyl)benzyl)amino)pyrimidin-4-yl)amino)methyl)-3-hydroxypiperidin-1-yl)acetamide |
| A7-31 | 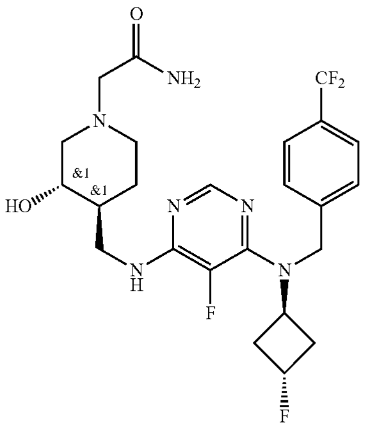 | A7-31 rac-2-((3R,4R)-4-(((5-fluoro-6-(((1r,3S)-3-fluorocyclobutyl)(4-(trifluoromethyl)benzyl)amino)pyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| A7-32 | 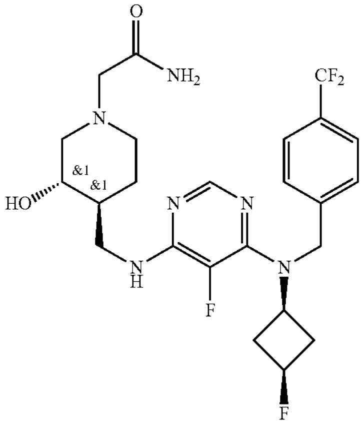 | A7-32<br>rac-2-((3R,4R)-4-(((5-fluoro-6-(((1s,3R)-3-fluorocyclobutyl)(4-(trifluoromethyl)benzyl)amino) pyrimidin-4-yl)amino)methyl)-3-hydroxypiperidin-1-yl)acetamide |
| A7-33 | 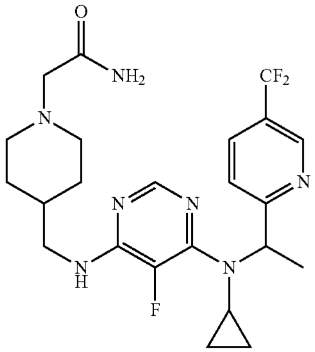 | A7-33<br>2-(4-(((6-(cyclopropyl(1-(5-(trifluoromethyl)pyridin-2-yl)ethyl)amino)-5-fluoropyrimidin-4-yl)amino)methyl)piperidin-1-yl)acetamide |
| A7-34 | 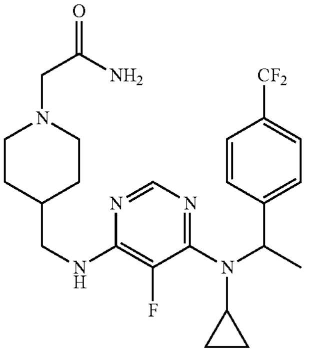 | A7-34<br>2-(4-(((6-(cyclopropyl(1-(4-(trifluoromethyl)phenyl)ethyl) amino)-5-fluoropyrimidin-4-yl)amino)methyl)piperidin-1-yl)acetamide |
| A7-35 | 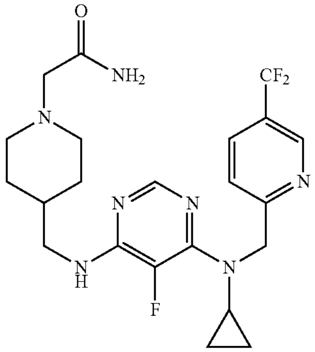 | A7-35<br>2-(4-(((6-(cyclopropyl((5-(trifluoromethyl)pyridin-2-yl)methyl)amino)-5-fluoropyrimidin-4-yl)amino)methyl)piperidin-1-yl)acetamide |

TABLE 1-continued

| Example compounds by Structure and Name. | | |
|---|---|---|
| Ex. No | Structure | Name |
| A7-36 | 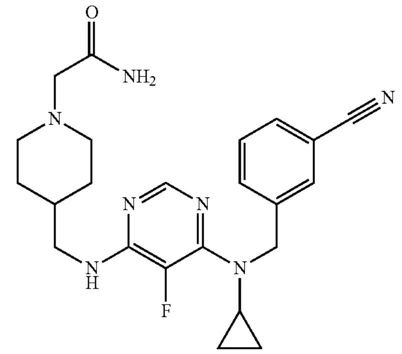 [SMILES: N#Cc1cccc(CN(c2ncnc(NCC3CCN(CC(N)=O)CC3)c2F)C2CC2)c1] | A7-36 2-(4-(((6-((3-cyanobenzyl)(cyclopropyl)amino)-5-fluoropyrimidin-4-yl)amino)methyl)piperidin-1-yl)acetamide |
| A7-38 | 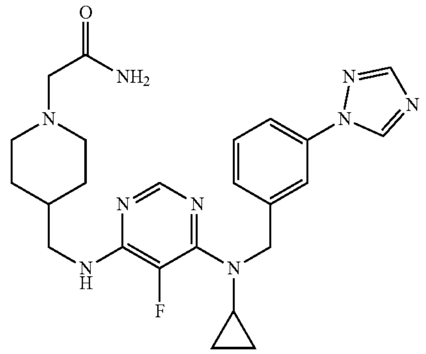 [SMILES: NC(=O)CN1CCC(CNc2ncnc(N(Cc3cccc(-n4cncn4)c3)C3CC3)c2F)CC1] | A7-38 2-(4-(((6-((3-(1H-1,2,4-triazol-1-yl)benzyl)(cyclopropyl)amino)-5-fluoropyrimidin-4-yl)amino)methyl)piperidin-1-yl)acetamide |
| A7-39 | 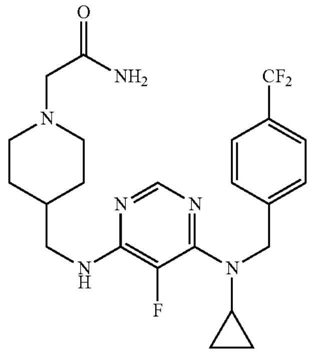 | A7-39 2-(4-(((6-(cyclopropyl(4-(trifluoromethyl)benzyl)amino)-5-fluoropyrimidin-4-yl)amino)methyl)piperidin-1-yl)acetamide |
| A7-40 | 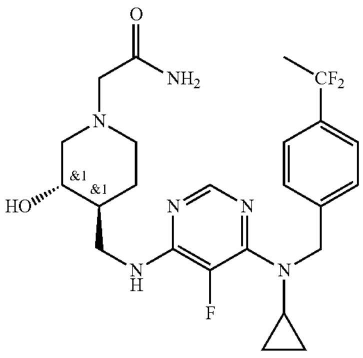 | A7-40 rac-2-((3R,4R)-4-(((6-(cyclopropyl(4-(1,1-difluoroethyl)benzyl)amino)-5-fluoropyrimidin-4-yl)amino)methyl)-3-hydroxypiperidin-1-yl)acetamide |

TABLE 1-continued

| Ex. No | Structure | Name |
| --- | --- | --- |
| A7-41 | 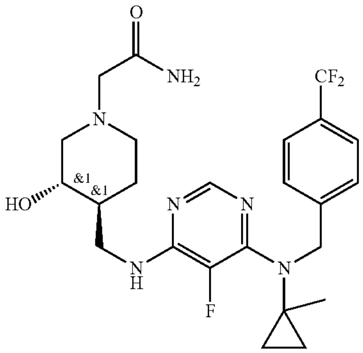 | A7-41 rac-2-((3R,4R)-4-(((5-fluoro-6-((1-methylcyclopropyl)(4-(trifluoromethyl)benzyl)amino) pyrimidin-4-yl)amino)methyl)-3-hydroxypiperidin-1-yl)acetamide |
| A7-42 | 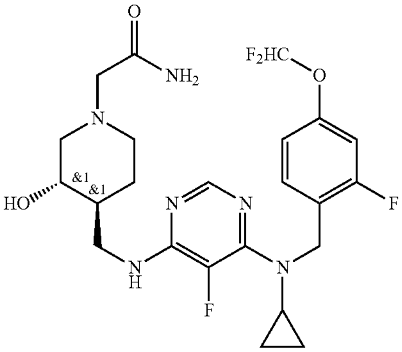 [SMILES: NC(=O)CN1CC[C@@H](CNc2ncnc(N(Cc3ccc(OC(F)F)cc3F)C3CC3)c2F)[C@H](O)C1] | A7-42 rac-2-((3R,4R)-4-(((6-(cyclopropyl(4-(difluoromethoxy)-2-fluorobenzyl)amino)-5-fluoropyrimidin-4-yl)amino)methyl)-3-hydroxypiperidin-1-yl)acetamide |
| A7-43 | 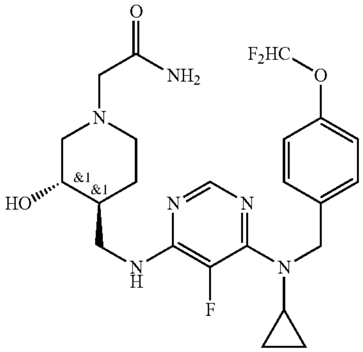 [SMILES: NC(=O)CN1CC[C@@H](CNc2ncnc(N(Cc3ccc(OC(F)F)cc3)C3CC3)c2F)[C@H](O)C1] | A7-43 rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide |
| A7-44 | 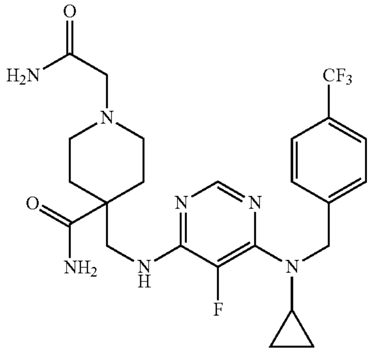 [SMILES: NC(=O)CN1CCC(CNc2ncnc(N(Cc3ccc(C(F)(F)F)cc3)C3CC3)c2F)(C(N)=O)CC1] | A7-44 1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide |

Example compounds by Structure and Name.

TABLE 1-continued

| Example compounds by Structure and Name. | | |
|---|---|---|
| Ex. No | Structure | Name |
| A7-45 | 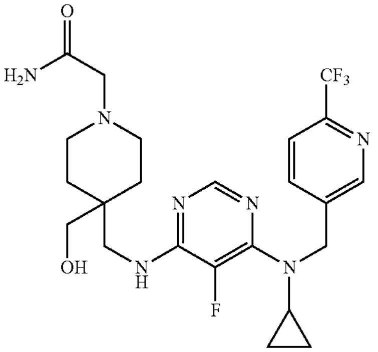 [SMILES: NC(=O)CN1CCC(CO)(CNc2ncnc(N(Cc3ccc(C(F)(F)F)nc3)C3CC3)c2F)CC1] | A7-45 2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide |
| A7-46 | 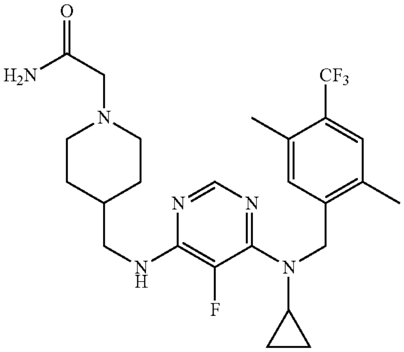 [SMILES: Cc1cc(C(F)(F)F)c(C)cc1CN(c1ncnc(NCC2CCN(CC(N)=O)CC2)c1F)C1CC1] | A7-46 2-(4-(((6-((4-chloro-2,5-dimethylbenzyl)(cyclopropyl)amino)-5-fluoropyrimidin-4-yl)amino)methyl)piperidin-1-yl)acetamide |
| A7-47 | 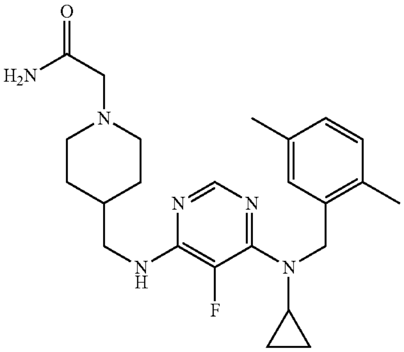 [SMILES: Cc1ccc(C)c(CN(c2ncnc(NCC3CCN(CC(N)=O)CC3)c2F)C2CC2)c1] | A7-47 2-(4-(((6-(cyclopropyl(2,5-dimethylbenzyl)amino)-5-fluoropyrimidin-4-yl)amino)methyl)piperidin-1-yl)acetamide |
| A7-49 | 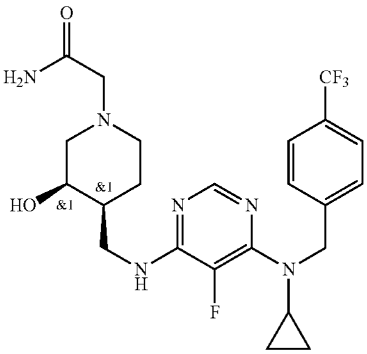 [SMILES: NC(=O)CN1CC[C@@H](CNc2ncnc(N(Cc3ccc(C(F)(F)F)cc3)C3CC3)c2F)[C@@H](O)C1] | A7-49 rac-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide |

TABLE 1-continued

Example compounds by Structure and Name.

| Ex. No | Structure | Name |
|---|---|---|
| A7-50 | 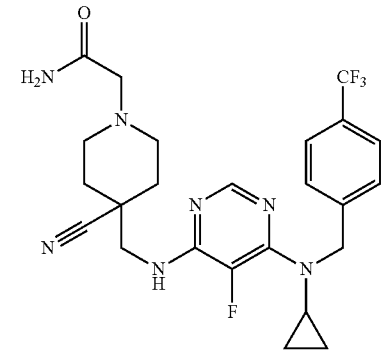 [SMILES: N#CC1(CNc2ncnc(N(Cc3ccc(C(F)(F)F)cc3)C3CC3)c2F)CCN(CC(N)=O)CC1] | A7-50<br>2-(4-cyano-4-(((6-(cyclopropyl(4-(trifluoromethyl)benzyl)amino)-5-fluoropyrimidin-4-yl)amino)methyl)piperidin-1-yl)acetamide |
| A7-51 | 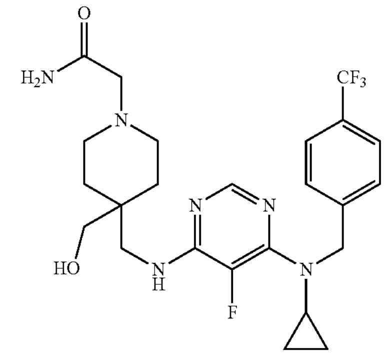 [SMILES: NC(=O)CN1CCC(CO)(CNc2ncnc(N(Cc3ccc(C(F)(F)F)cc3)C3CC3)c2F)CC1] | A7-51<br>2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide |
| A7-52 | 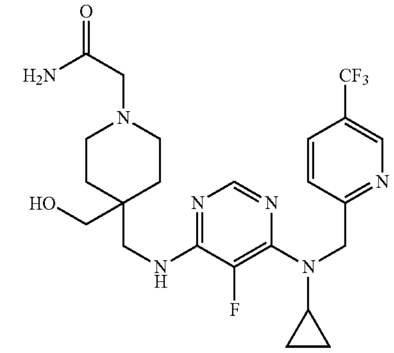 [SMILES: NC(=O)CN1CCC(CO)(CNc2ncnc(N(Cc3ccc(C(F)(F)F)cn3)C3CC3)c2F)CC1] | A7-52<br>2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide |
| A7-53 | 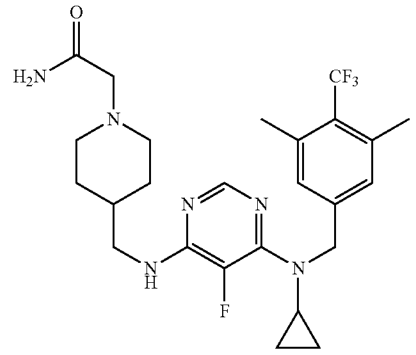 [SMILES: Cc1cc(CN(c2ncnc(NCC3CCN(CC(N)=O)CC3)c2F)C2CC2)cc(C)c1C(F)(F)F] | A7-53<br>2-(4-(((6-((4-chloro-3,5-dimethylbenzyl)(cyclopropyl)amino)-5-fluoropyrimidin-4-yl)amino)methyl)piperidin-1-yl)acetamide |

TABLE 1-continued

| Ex. No | Structure | Name |
| --- | --- | --- |
| A7-54 | 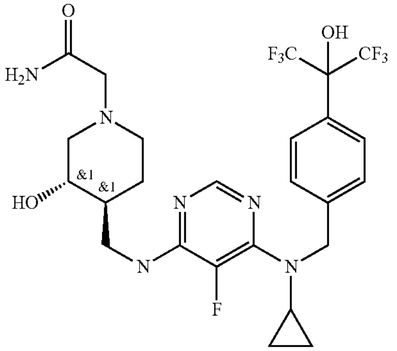 [SMILES: NC(=O)CN1CC[C@@H](CNc2ncnc(N(Cc3ccc(C(O)(C(F)(F)F)C(F)(F)F)cc3)C3CC3)c2F)[C@H](O)C1] | A7-54 rac-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide |
| A7-54-1 | 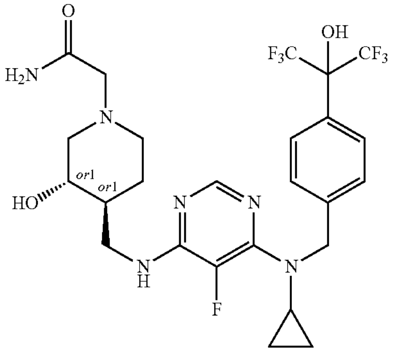 [SMILES: NC(=O)CN1CC[C@@H](CNc2ncnc(N(Cc3ccc(C(O)(C(F)(F)F)C(F)(F)F)cc3)C3CC3)c2F)[C@H](O)C1] | A7-54-1 rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide 1st eluting isomer |
| A7-54-2 | | A7-54-2 rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide 2nd eluting isomer |
| A7-55" Enantiomerically enriched | 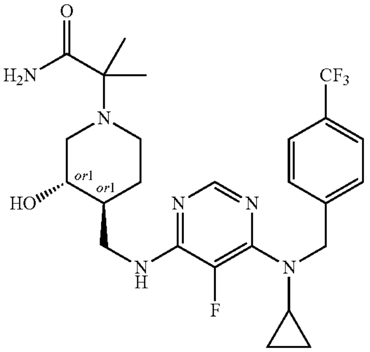 [SMILES: CC(C)(C(N)=O)N1CC[C@@H](CNc2ncnc(N(Cc3ccc(C(F)(F)F)cc3)C3CC3)c2F)[C@H](O)C1] | A7-55" rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide Enantiomerically enriched |

Example compounds by Structure and Name.

TABLE 1-continued

| Example compounds by Structure and Name. | | |
|---|---|---|
| Ex. No | Structure | Name |
| A7-56 | 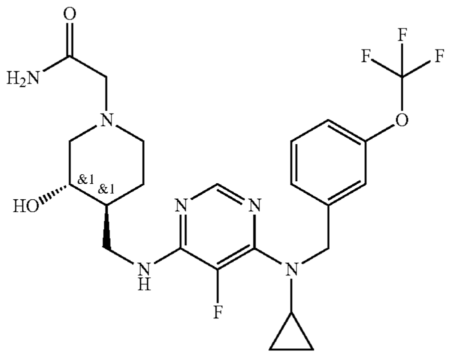 [SMILES: NC(=O)CN1CC[C@@H](CNc2ncnc(N(Cc3cccc(OC(F)(F)F)c3)C3CC3)c2F)[C@H](O)C1] | A7-56<br>rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide |
| A7-57"<br>Enantiomerically enriched | 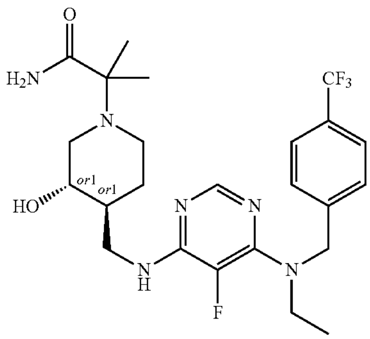 [SMILES: CCN(Cc1ccc(C(F)(F)F)cc1)c1ncnc(NC[C@@H]2CCN(C(C)(C)C(N)=O)C[C@H]2O)c1F] | A7-57"<br>rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide<br>Enantiomerically enriched |
| A7-58 | 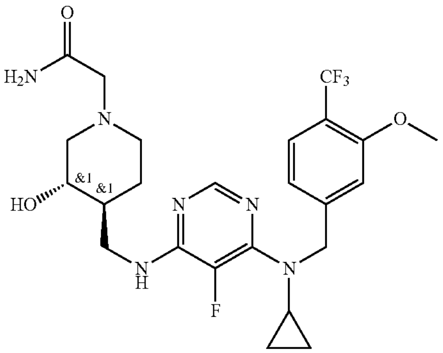 [SMILES: COc1cc(CN(c2ncnc(NC[C@@H]3CCN(CC(N)=O)C[C@H]3O)c2F)C2CC2)ccc1C(F)(F)F] | A7-58<br>rac-2-((3R,4R)-4-(((6-(cyclopropyl(3-methoxy-4-(trifluoromethyl)benzyl)amino)-5-fluoropyrimidin-4-yl)amino)methyl)-3-hydroxypiperidin-1-yl)acetamide |
| A7-59 | 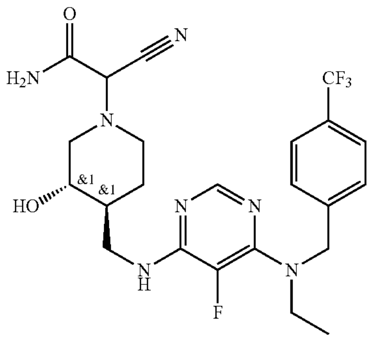 [SMILES: CCN(Cc1ccc(C(F)(F)F)cc1)c1ncnc(NC[C@@H]2CCN(C(C#N)C(N)=O)C[C@H]2O)c1F] | A7-59<br>rac-2-cyano-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| A7-60 | 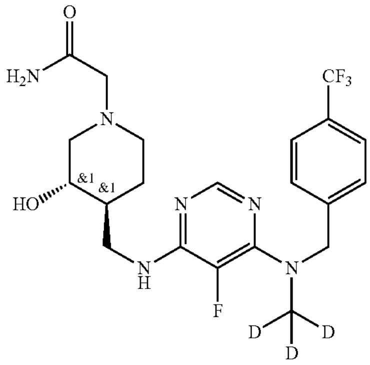 [SMILES: [2H]C([2H])([2H])N(Cc1ccc(C(F)(F)F)cc1)c1ncnc(NC[C@@H]2CCN(CC(N)=O)C[C@H]2O)c1F] | A7-60 rac-2-((3R,4R)-4-(((5-fluoro-6-((methyl-d3)(4-(trifluoromethyl)benzyl)amino) pyrimidin-4-yl)amino)methyl)-3-hydroxypiperidin-1-yl)acetamide |
| A7-61 | 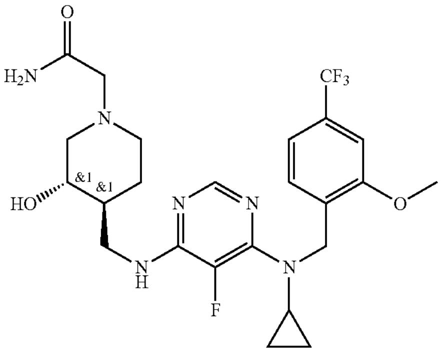 [SMILES: COc1cc(C(F)(F)F)ccc1CN(c1ncnc(NC[C@@H]2CCN(CC(N)=O)C[C@H]2O)c1F)C1CC1] | A7-61 rac-2-((3R,4R)-4-(((6-(cyclopropyl(2-methoxy-4-(trifluoromethyl)benzyl)amino)-5-fluoropyrimidin-4-yl)amino)methyl)-3-hydroxypiperidin-1-yl)acetamide |
| A7-62 | 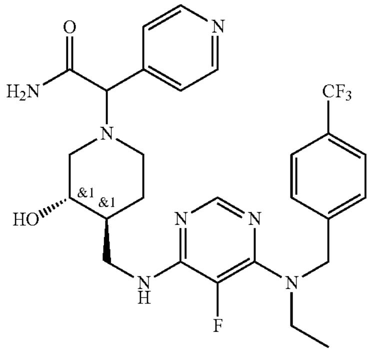 [SMILES: CCN(Cc1ccc(C(F)(F)F)cc1)c1ncnc(NC[C@@H]2CCN(C(C(N)=O)c3ccncc3)C[C@H]2O)c1F] | A7-62 rac-2-((3R,4R)-4-(((6-(ethyl(4-(trifluoromethyl)benzyl)amino)-5-fluoropyrimidin-4-yl)amino)methyl)-3-hydroxypiperidin-1-yl)-2-(pyridin-4-yl)acetamide |
| A7-63 | 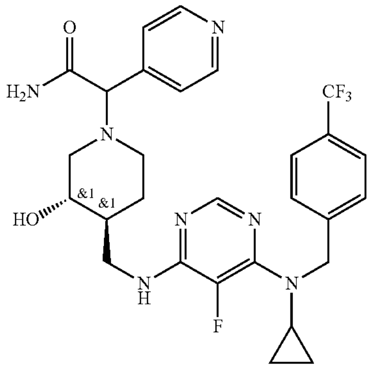 [SMILES: NC(=O)C(c1ccncc1)N1CC[C@@H](CNc2ncnc(N(Cc3ccc(C(F)(F)F)cc3)C3CC3)c2F)[C@H](O)C1] | A7-63 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(pyridin-4-yl)acetamide |

TABLE 1-continued

| Example compounds by Structure and Name. | | |
|---|---|---|
| Ex. No | Structure | Name |
| A7-64 | 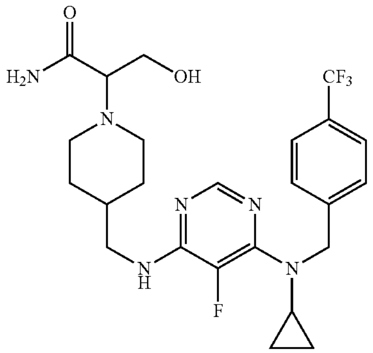 [SMILES: NC(=O)C(CO)N1CCC(CNc2ncnc(N(Cc3ccc(C(F)(F)F)cc3)C3CC3)c2F)CC1] | A7-64<br>2-(4-(((6-(cyclopropyl(4-(trifluoromethyl)benzyl)amino)-5-fluoropyrimidin-4-yl)amino)methyl)piperidin-1-yl)-3-hydroxypropanamide |
| A7-65 | 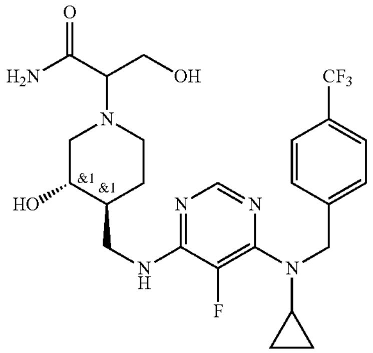 [SMILES: NC(=O)C(CO)N1CC[C@@H](CNc2ncnc(N(Cc3ccc(C(F)(F)F)cc3)C3CC3)c2F)[C@H](O)C1] | A7-65<br>rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide |
| A7-66-1 | 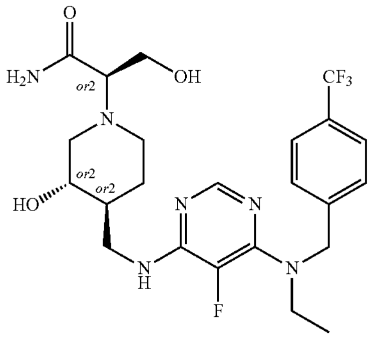 [SMILES: CCN(Cc1ccc(C(F)(F)F)cc1)c1ncnc(NC[C@@H]2CCN([C@H](CO)C(N)=O)C[C@H]2O)c1F] | A7-66-1<br>rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>OR<br>rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>1st eluting major isomer |
| A7-66-2 | | A7-66-2<br>rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>OR<br>rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>2nd eluting major isomer. |

TABLE 1-continued

| Example compounds by Structure and Name. | | |
|---|---|---|
| Ex. No | Structure | Name |
| A7-67"<br>Enantiomerically enriched | 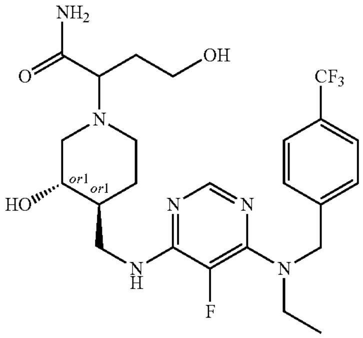 [SMILES: CCN(Cc1ccc(C(F)(F)F)cc1)c1ncnc(NC[C@@H]2CCN(C(CCO)C(N)=O)C[C@H]2O)c1F] | A7-67"<br>rel-2-((3R,4R)-4-(((6-(ethyl(4-(trifluoromethyl)benzyl)amino)-5-fluoropyrimidin-4-yl)amino)methyl)-3-hydroxypiperidin-1-yl)-4-hydroxybutanamide<br>Enantiomerically enriched |
| A7-68 | 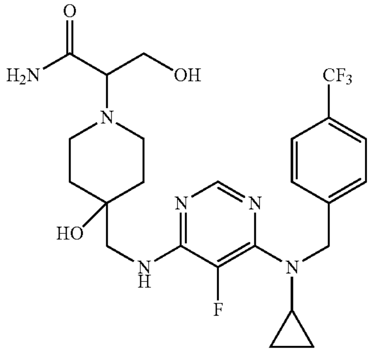 [SMILES: NC(=O)C(CO)N1CCC(O)(CNc2ncnc(N(Cc3ccc(C(F)(F)F)cc3)C3CC3)c2F)CC1] | A7-68<br>2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide |
| A7-69"<br>Enantiomerically enriched | 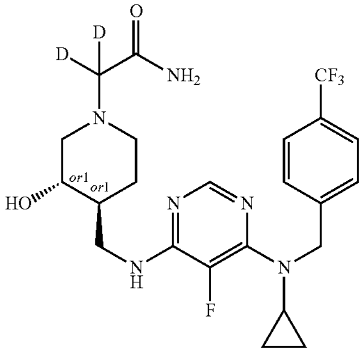 [SMILES: [2H]C([2H])(C(N)=O)N1CC[C@@H](CNc2ncnc(N(Cc3ccc(C(F)(F)F)cc3)C3CC3)c2F)[C@H](O)C1] | A7-69"<br>rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$<br>Enantiomerically enriched |
| A7-70 | 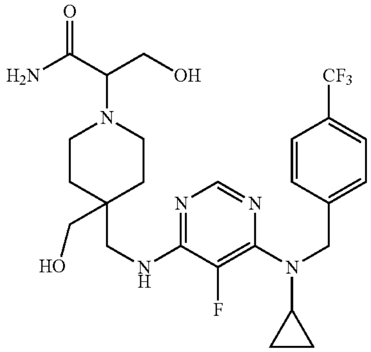 [SMILES: NC(=O)C(CO)N1CCC(CO)(CNc2ncnc(N(Cc3ccc(C(F)(F)F)cc3)C3CC3)c2F)CC1] | A7-70<br>2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide |

TABLE 1-continued

| Example compounds by Structure and Name. | | |
|---|---|---|
| Ex. No | Structure | Name |
| A7-71 | 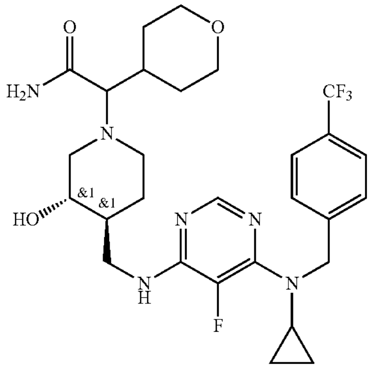 [SMILES: NC(=O)C(C1CCOCC1)N1CC[C@@H](CNc2ncnc(N(Cc3ccc(C(F)(F)F)cc3)C3CC3)c2F)[C@H](O)C1] | A7-71 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetamide |
| A7-72 | 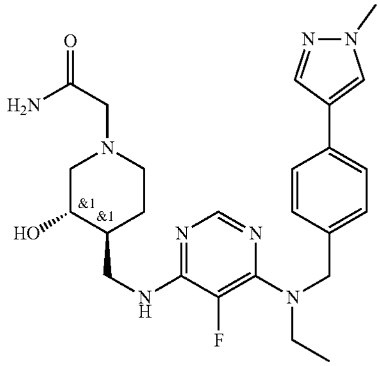 [SMILES: CCN(Cc1ccc(-c2cnn(C)c2)cc1)c1ncnc(NC[C@@H]2CCN(CC(N)=O)C[C@H]2O)c1F] | A7-72 rac-2-((3R,4R)-4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide |
| A7-73 | 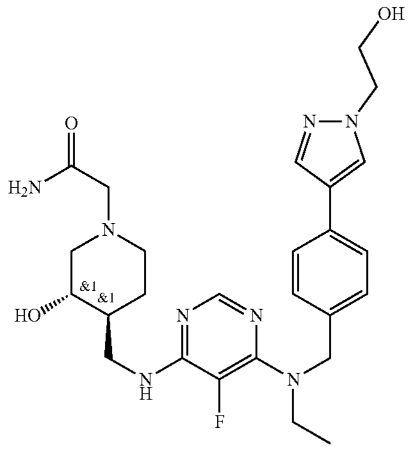 [SMILES: CCN(Cc1ccc(-c2cnn(CCO)c2)cc1)c1ncnc(NC[C@@H]2CCN(CC(N)=O)C[C@H]2O)c1F] | A7-73 rac-2-((3R,4R)-4-(((6-(ethyl(4-(1-(2-hydroxyethyl)-1H-pyrazol-4-yl)benzyl)amino)-5-fluoropyrimidin-4-yl)amino)methyl)-3-hydroxypiperidin-1-yl)acetamide |
| A7-74 | 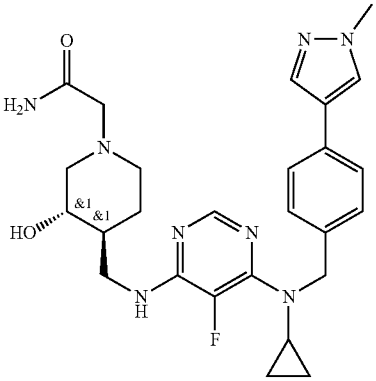 [SMILES: Cn1cc(-c2ccc(CN(c3ncnc(NC[C@@H]4CCN(CC(N)=O)C[C@H]4O)c3F)C3CC3)cc2)cn1] | A7-74 rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide |

TABLE 1-continued

| Ex. No | Structure | Name |
|---|---|---|
| A7-75 | 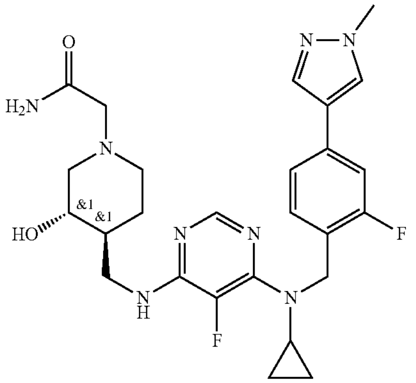 [SMILES: Cn1cc(-c2ccc(CN(c3ncnc(NC[C@@H]4CCN(CC(N)=O)C[C@H]4O)c3F)C3CC3)c(F)c2)cn1] | A7-75 rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide |
| A7-76 | 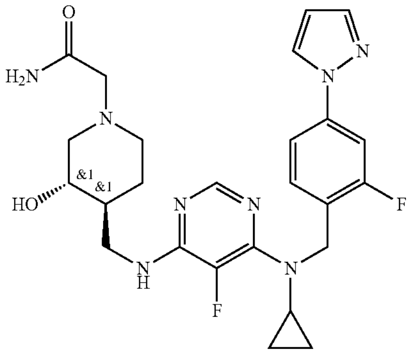 [SMILES: NC(=O)CN1CC[C@@H](CNc2ncnc(N(Cc3ccc(-n4cccn4)cc3F)C3CC3)c2F)[C@H](O)C1] | A7-76 rac-2-((3R,4R)-4-(((6-(Cyclopropyl(2-fluoro-4-(1H-pyrazol-1-yl)benzyl)amino)-5-fluoro pyrimidin-4-yl)amino)methyl)-3-hydroxypiperidin-1-yl)acetamide |
| A7-77 | 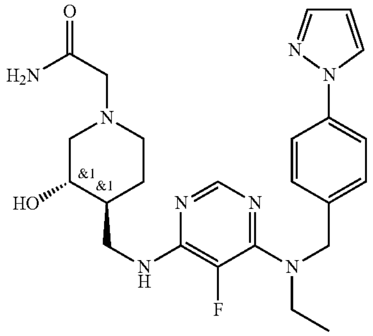 [SMILES: CCN(Cc1ccc(-n2cccn2)cc1)c1ncnc(NC[C@@H]2CCN(CC(N)=O)C[C@H]2O)c1F] | A7-77 rac-2-((3R,4R)-4-(((6-((4-(1H-Pyrazol-1-yl)benzyl)(ethyl)amino)-5-fluoropyrimidin-4-yl)amino)methyl)-3-hydroxypiperidin-1-yl)acetamide |
| A7-78 | 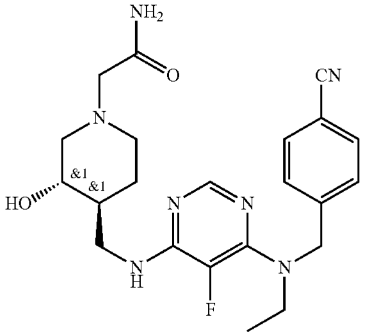 [SMILES: CCN(Cc1ccc(C#N)cc1)c1ncnc(NC[C@@H]2CCN(CC(N)=O)C[C@H]2O)c1F] | A7-78 rac-2-((3R,4R)-4-(((6-((4-cyanobenzyl)(ethyl)amino)-5-fluoropyrimidin-4-yl)amino)methyl)-3-hydroxypiperidin-1-yl)acetamide |

Example compounds by Structure and Name.

TABLE 1-continued

| Example compounds by Structure and Name. | | |
|---|---|---|
| Ex. No | Structure | Name |
| A7-79 | 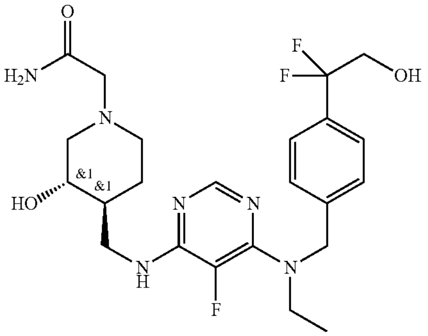 [SMILES: CCN(Cc1ccc(C(F)(F)CO)cc1)c1ncnc(NC[C@@H]2CCN(CC(N)=O)C[C@H]2O)c1F] | A7-79 rac-2-((3R,4R)-4-(((6-((4-(1,1-difluoro-2-hydroxyethyl)benzyl)(ethyl)amino)-5-fluoropyrimidin-4-yl)amino)methyl)-3-hydroxypiperidin-1-yl)acetamide |
| A7-80 | 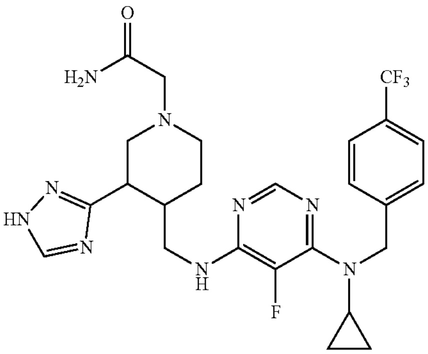 [SMILES: NC(=O)CN1CCC(CNc2ncnc(N(Cc3ccc(C(F)(F)F)cc3)C3CC3)c2F)C(c2nc[nH]n2)C1] | A7-80 2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide |
| A7-81 | 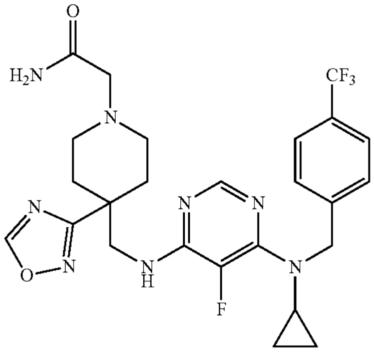 [SMILES: NC(=O)CN1CCC(CNc2ncnc(N(Cc3ccc(C(F)(F)F)cc3)C3CC3)c2F)(c2ncon2)CC1] | A7-81 2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide |
| A7-82 | 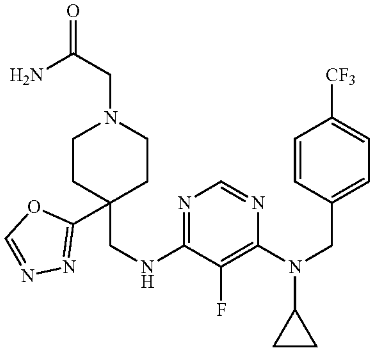 [SMILES: NC(=O)CN1CCC(CNc2ncnc(N(Cc3ccc(C(F)(F)F)cc3)C3CC3)c2F)(c2nnco2)CC1] | A7-82 2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide |

TABLE 1-continued

Example compounds by Structure and Name.

| Ex. No | Structure | Name |
| --- | --- | --- |
| A7-83 | 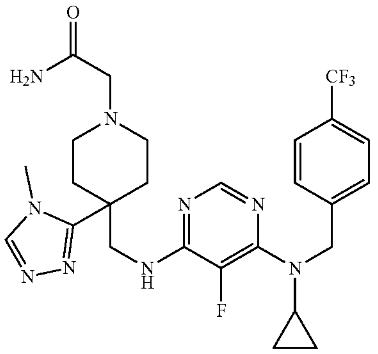 [SMILES: Cn1cnnc1C1(CNc2ncnc(N(Cc3ccc(C(F)(F)F)cc3)C3CC3)c2F)CCN(CC(N)=O)CC1] | A7-83 2-(4-(((6-(Cyclopropyl(4-(trifluoromethyl)benzyl)amino)-5-fluoropyrimidin-4-yl)amino)methyl)-4-(4-methyl-4H-1,2,4-triazol-3-yl)piperidin-1-yl)acetamide |
| A7-84 | 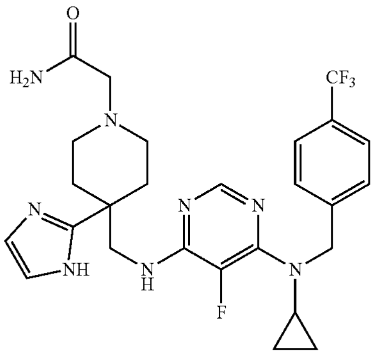 [SMILES: NC(=O)CN1CCC(CNc2ncnc(N(Cc3ccc(C(F)(F)F)cc3)C3CC3)c2F)(c2ncc[nH]2)CC1] | A7-84 2-(4-(((6-(Cyclopropyl(4-(trifluoromethyl)benzyl)amino)-5-fluoropyrimidin-4-yl)amino)methyl)-4-(1H-imidazol-2-yl)piperidin-1-yl)acetamide |
| A7-85 | 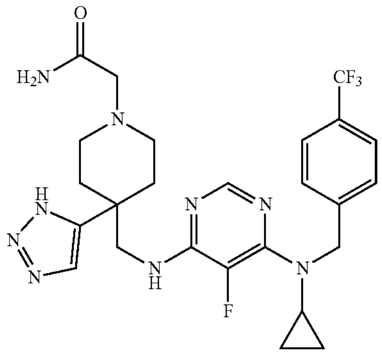 [SMILES: NC(=O)CN1CCC(CNc2ncnc(N(Cc3ccc(C(F)(F)F)cc3)C3CC3)c2F)(c2cnn[nH]2)CC1] | A7-85 2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide |
| A7-86 | 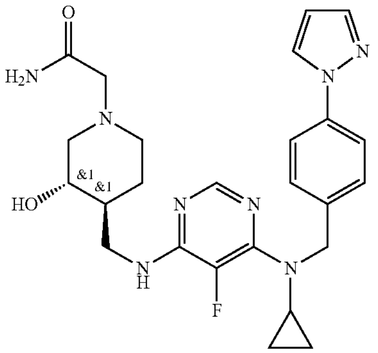 [SMILES: NC(=O)CN1CC[C@@H](CNc2ncnc(N(Cc3ccc(-n4cccn4)cc3)C3CC3)c2F)[C@H](O)C1] | A7-86 rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide |

TABLE 1-continued

Example compounds by Structure and Name.

| Ex. No | Structure | Name |
| --- | --- | --- |
| A7-87 | 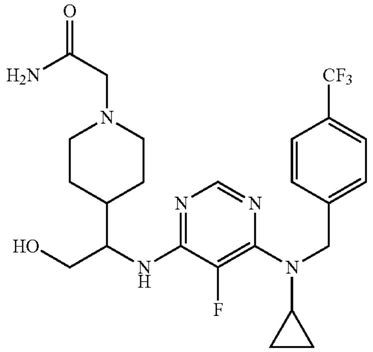 [SMILES: NC(=O)CN1CCC(C(CO)Nc2ncnc(N(Cc3ccc(C(F)(F)F)cc3)C3CC3)c2F)CC1] | A7-87 2-(4-(1-((6-(cyclopropyl(4-(trifluoromethyl)benzyl)amino)-5-fluoropyrimidin-4-yl)amino)-2-hydroxyethyl)piperidin-1-yl)acetamide |
| B4-1-1-1 | 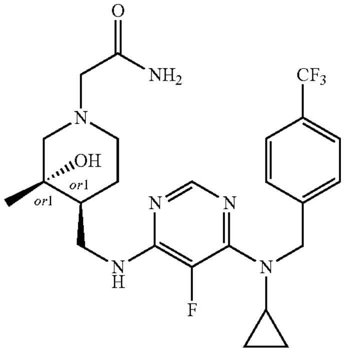 | B4-1-1-1 rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide 1st eluting isomer |
| B4-1-1-2 | | B4-1-1-2 rel-2-((3R,4R)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide 2nd eluting isomer |
| B4-1-2-1 | 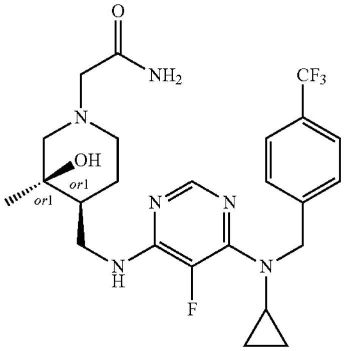 | B4-1-2-1 rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide 1st eluting isomer |
| B4-1-2-2 | | B4-1-2-2 rel-2-((3R,4S)-4-(((6-(cyclopropyl(4-(trifluoromethyl)benzyl)amino)-5-fluoropyrimidin-4-yl)amino)methyl)-3-hydroxy-3-methylpiperidin-1-yl)acetamide 2nd eluting isomer |

TABLE 1-continued

| Example compounds by Structure and Name. | | |
|---|---|---|
| Ex. No | Structure | Name |
| B4-2-1-1 | 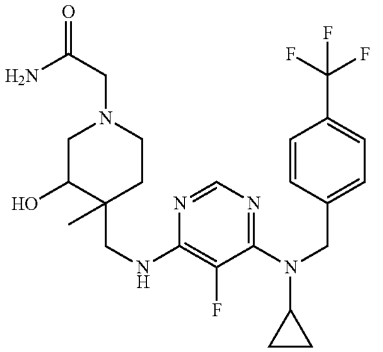 [SMILES: CC1(CNc2ncnc(N(Cc3ccc(C(F)(F)F)cc3)C3CC3)c2F)CCN(CC(N)=O)CC1O] | B4-2-1-1 2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide 1$^{st}$ eluting isomer |
| B4-2-1-2 | | B4-2-1-2 2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide 2$^{nd}$ eluting isomer |
| C4-1-1 | 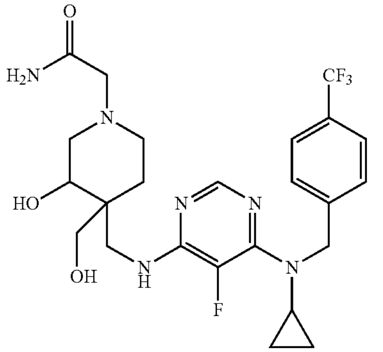 [SMILES: NC(=O)CN1CCC(CO)(CNc2ncnc(N(Cc3ccc(C(F)(F)F)cc3)C3CC3)c2F)C(O)C1] | C4-1-1 2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide 1$^{st}$ eluting isomer |
| C4-1-2 | | C4-1-2 2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide 2$^{nd}$ eluting isomer |
| C4-2-1 | 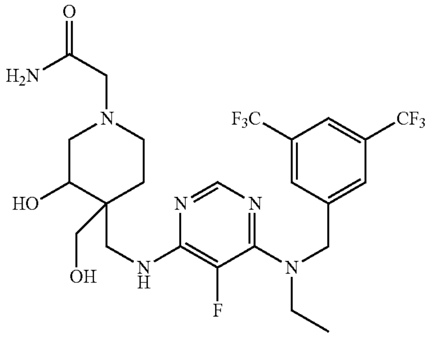 [SMILES: CCN(Cc1cc(C(F)(F)F)cc(C(F)(F)F)c1)c1ncnc(NCC2(CO)CCN(CC(N)=O)CC2O)c1F] | C4-2-1 2-(4-(((6-((3,5-bis(trifluoromethyl)benzyl)(ethyl)amino)-5-fluoropyrimidin-4-yl)amino)methyl)-3-hydroxy-4-(hydroxymethyl)piperidin-1-yl)acetamide 1$^{st}$ eluting isomer |

TABLE 1-continued

| Example compounds by Structure and Name. | | |
|---|---|---|
| Ex. No | Structure | Name |
| C4-2-2 | | C4-2-2 2-(4-(((6-((3,5-bis(trifluoromethyl)benzyl)(ethyl) amino)-5-fluoropyrimidin-4-yl)amino)methyl)-3-hydroxy-4-(hydroxymethyl)piperidin-1-yl)acetamide 2nd eluting isomer |
| D5-1-1-1 | 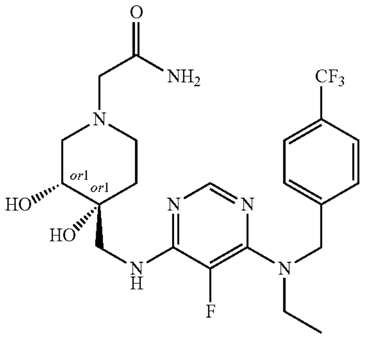 [SMILES: CCN(Cc1ccc(C(F)(F)F)cc1)c1ncnc(NC[C@]2(O)CCN(CC(N)=O)C[C@H]2O)c1F] | D5-1-1-1 rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide 1st eluting isomer |
| D5-1-1-2 | | D5-1-1-2 rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide 2nd eluting isomer |
| D5-1-2-1 | 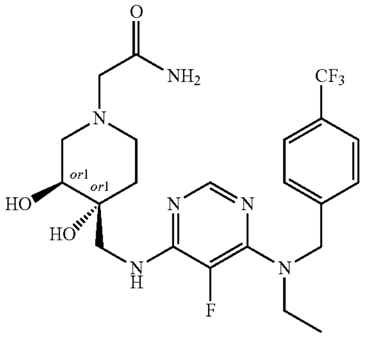 [SMILES: CCN(Cc1ccc(C(F)(F)F)cc1)c1ncnc(NC[C@]2(O)CCN(CC(N)=O)C[C@@H]2O)c1F] | D5-1-2-1 rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide 1st eluting isomer |
| D5-1-2-2 | | D5-1-2-2 rel-2-((3R,4S)-4-(((6-(ethyl(4-(trifluoromethyl)benzyl)amino)-5-fluoropyrimidin-4-yl)amino)methyl)-3,4-dihydroxypiperidin-1-yl)acetamide 2nd eluting isomer |

TABLE 1-continued

| Example compounds by Structure and Name. | | |
|---|---|---|
| Ex. No | Structure | Name |
| D5-2-1-1 | 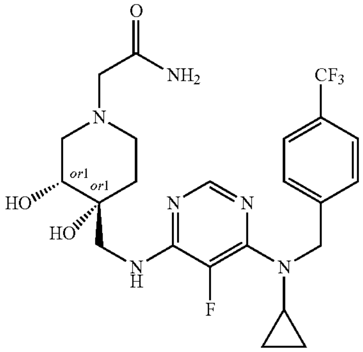 [SMILES: NC(=O)CN1CC[C@@](O)(CNc2ncnc(N(Cc3ccc(C(F)(F)F)cc3)C3CC3)c2F)[C@H](O)C1] | D5-2-1-1 rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide 1st eluting isomer |
| D5-2-1-2 | | D5-2-1-2 rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide 2nd eluting isomer |
| D5-2-2-1 | 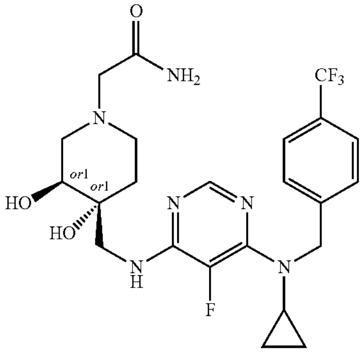 [SMILES: NC(=O)CN1CC[C@@](O)(CNc2ncnc(N(Cc3ccc(C(F)(F)F)cc3)C3CC3)c2F)[C@@H](O)C1] | D5-2-2-1 rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide 1st eluting isomer |
| D5-2-2-2 | | D5-2-2-2 rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide 2nd eluting isomer |
| D5-3-1-1 | 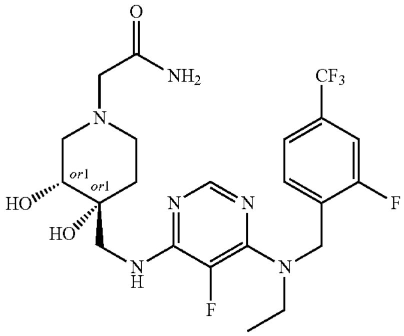 [SMILES: CCN(Cc1ccc(C(F)(F)F)cc1F)c1ncnc(NC[C@]2(O)CCN(CC(N)=O)C[C@H]2O)c1F] | D5-3-1-1 rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide 1st eluting isomer |
| D5-3-1-2 | | D5-3-1-2 rel-2-((3R,4R)-4-(((6-(ethyl(2-fluoro-4-(trifluoromethyl)benzyl)amino)-5-fluoropyrimidin-4- |

TABLE 1-continued

| Example compounds by Structure and Name. | | |
|---|---|---|
| Ex. No | Structure | Name |
| | | yl)amino)methyl)-3,4-dihydroxypiperidin-1-yl)acetamide 2nd eluting isomer |
| D5-3-2-1 | 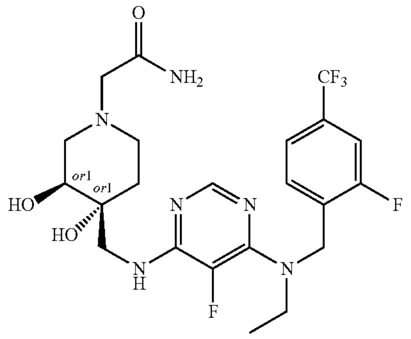 [SMILES: CCN(Cc1ccc(C(F)(F)F)cc1F)c1ncnc(NC[C@]2(O)CCN(CC(N)=O)C[C@@H]2O)c1F] | D5-3-2-1 rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide 1st eluting isomer |
| D5-3-2-2 | | D5-3-2-2 rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide 2nd eluting isomer |
| D5-4" Enantiomerically enriched | 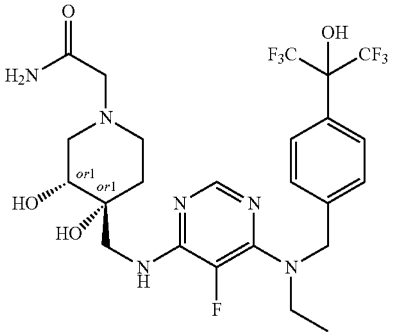 [SMILES: CCN(Cc1ccc(C(O)(C(F)(F)F)C(F)(F)F)cc1)c1ncnc(NC[C@]2(O)CCN(CC(N)=O)C[C@H]2O)c1F] | D5-4" rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide Enantiomerically enriched |
| D5-5-1 | 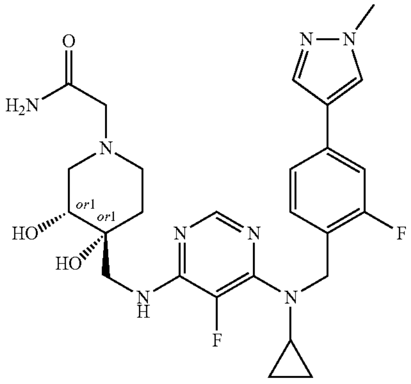 [SMILES: Cn1cc(-c2ccc(CN(c3ncnc(NC[C@]4(O)CCN(CC(N)=O)C[C@H]4O)c3F)C3CC3)c(F)c2)cn1] | D5-5-1 rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide Major isomer |

TABLE 1-continued

| Example compounds by Structure and Name. | | |
|---|---|---|
| Ex. No | Structure | Name |
| D5-5-2 | | D5-5-2<br>rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide<br>Minor isomer |
| D5-6''<br>Enantiomerically enriched | 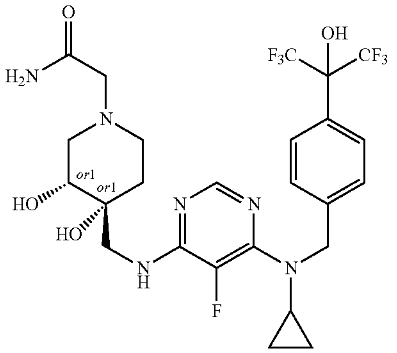 [SMILES: NC(=O)CN1CC[C@@](O)(CNc2ncnc(N(Cc3ccc(C(O)(C(F)(F)F)C(F)(F)F)cc3)C3CC3)c2F)[C@H](O)C1] | D5-6''<br>rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide<br>Enantiomerically enriched |
| D5-7''<br>Enantiomerically enriched | 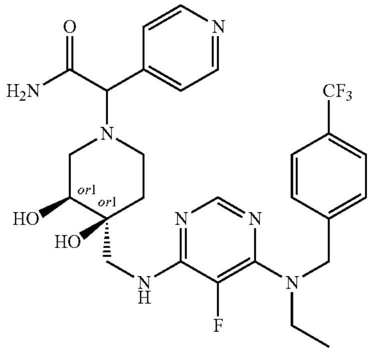 [SMILES: CCN(Cc1ccc(C(F)(F)F)cc1)c1ncnc(NC[C@@]2(O)CCN(C(C(N)=O)c3ccncc3)C[C@@H]2O)c1F] | D5-7''<br>rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>Enantiomerically enriched |
| D5-7-1 | 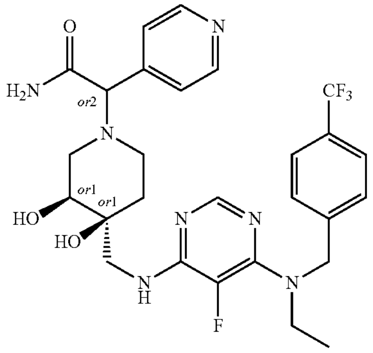 [SMILES: CCN(Cc1ccc(C(F)(F)F)cc1)c1ncnc(NC[C@@]2(O)CCN(C(C(N)=O)c3ccncc3)C[C@@H]2O)c1F] | D5-7-1<br>rel-(R)-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>OR<br>rel-(R)-2-((3S,4S)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>$1^{st}$ eluting major isomer |
| D5-7-2 | | D5-7-2<br>rel-(R)-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>OR<br>rel-(R)-2-((3S,4S)-4-(((6-(ethyl(4-(trifluoromethyl)benzyl)amino)-5-fluoropyrimidin-4-yl)amino)methyl)-3,4- |

TABLE 1-continued

| Example compounds by Structure and Name. | | |
|---|---|---|
| Ex. No | Structure | Name |
| | | dihydroxypiperidin-1-yl)-2-(pyridin-4-yl)acetamide 2$^{nd}$ eluting major isomer |
| D5-8" Enantiomerically enriched | 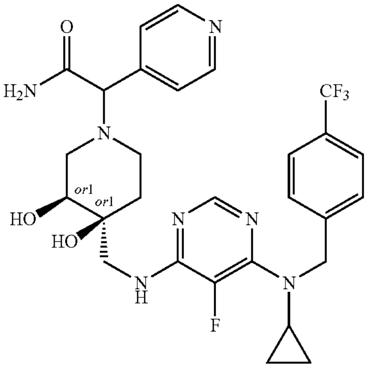 [SMILES: NC(=O)C(c1ccncc1)N1CC[C@](O)(CNc2ncnc(N(Cc3ccc(C(F)(F)F)cc3)C3CC3)c2F)[C@@H](O)C1] | D5-8" rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)-2-(pyridin-4-yl)acetamide Enantiomerically enriched |
| D5-9" Enantiomerically enriched | 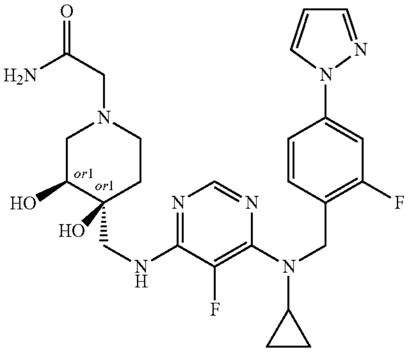 [SMILES: NC(=O)CN1CC[C@](O)(CNc2ncnc(N(Cc3ccc(-n4cccn4)cc3F)C3CC3)c2F)[C@@H](O)C1] | D5-9" rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, Enantiomerically enriched |
| D5-10" Enantiomerically enriched | 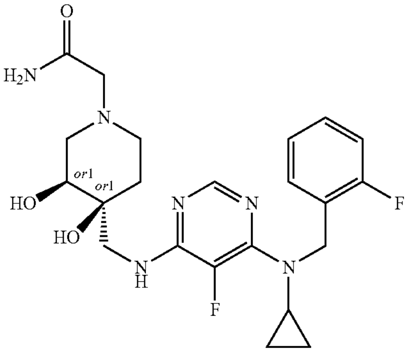 [SMILES: NC(=O)CN1CC[C@](O)(CNc2ncnc(N(Cc3ccccc3F)C3CC3)c2F)[C@@H](O)C1] | D5-10" rel-2-((3R,4R)-4-(((6-(cyclopropyl(2-fluorobenzyl)amino)-5-fluoropyrimidin-4-yl)amino)methyl)-3,4-dihydroxypiperidin-1-yl)acetamide, Enantiomerically enriched |
| E6-1 | 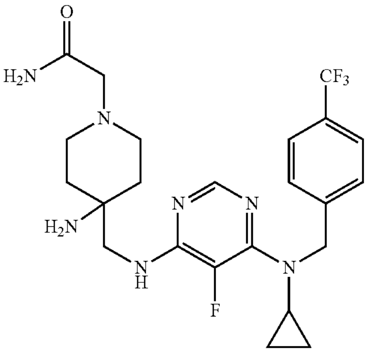 [SMILES: NC(=O)CN1CCC(N)(CNc2ncnc(N(Cc3ccc(C(F)(F)F)cc3)C3CC3)c2F)CC1] | E6-1 2-(4-Amino-4-(((6-(cyclopropyl(4-(trifluoromethyl)benzyl)amino)-5-fluoropyrimidin-4-yl)amino)methyl)piperidin-1-yl)acetamide |

TABLE 1-continued

Example compounds by Structure and Name.

| Ex. No | Structure | Name |
| --- | --- | --- |
| F2-1 | 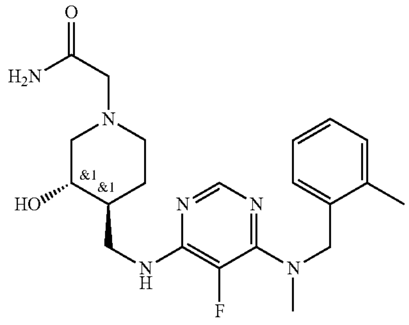 [SMILES: Cc1ccccc1CN(C)c1ncnc(NC[C@@H]2CCN(CC(N)=O)C[C@H]2O)c1F] | F2-1 rac-2-((3R,4R)-4-(((5-fluoro-6-(methyl(2-methylbenzyl)amino)pyrimidin-4-yl)amino)methyl)-3-hydroxypiperidin-1-yl)acetamide |
| F2-2 | 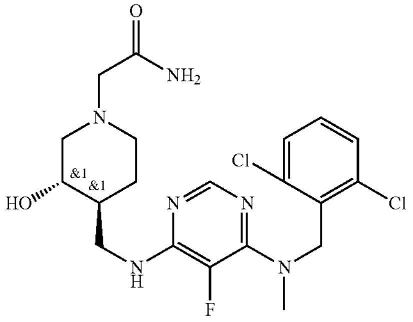 [SMILES: CN(Cc1c(Cl)cccc1Cl)c1ncnc(NC[C@@H]2CCN(CC(N)=O)C[C@H]2O)c1F] | F2-2 rac-2-((3R,4R)-4-(((6-((2,6-dichlorobenzyl)(methyl)amino)-5-fluoropyrimidin-4-yl)amino)methyl)-3-hydroxypiperidin-1-yl)acetamide |
| F2-3 | 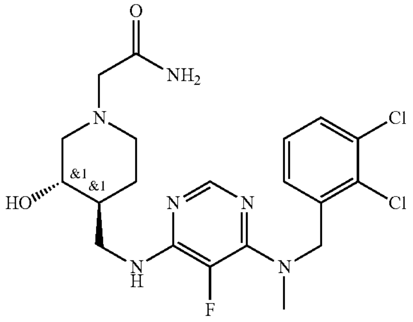 [SMILES: CN(Cc1cccc(Cl)c1Cl)c1ncnc(NC[C@@H]2CCN(CC(N)=O)C[C@H]2O)c1F] | F2-3 rac-2-((3R,4R)-4-(((6-((2,3-dichlorobenzyl)(methyl)amino)-5-fluoropyrimidin-4-yl)amino)methyl)-3-hydroxypiperidin-1-yl)acetamide |
| F2-4 | 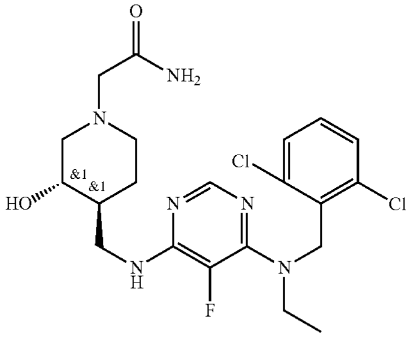 [SMILES: CCN(Cc1c(Cl)cccc1Cl)c1ncnc(NC[C@@H]2CCN(CC(N)=O)C[C@H]2O)c1F] | F2-4 rac-2-((3R,4R)-4-(((6-((2,6-dichlorobenzyl)(ethyl)amino)-5-fluoropyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| F2-5 | 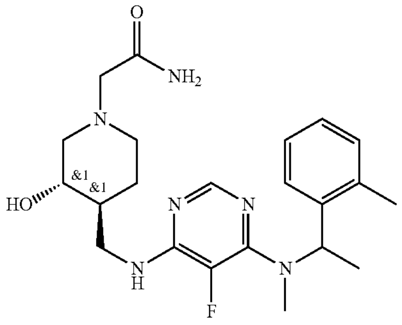 [SMILES: Cc1ccccc1C(C)N(C)c1ncnc(NC[C@@H]2CCN(CC(N)=O)C[C@H]2O)c1F] | F2-5 rac-2-((3R,4R)-4-(((5-fluoro-6-(methyl(1-(o-tolyl)ethyl)amino)pyrimidin-4-yl)amino)methyl)-3-hydroxypiperidin-1-yl)acetamide |
| F2-6 | 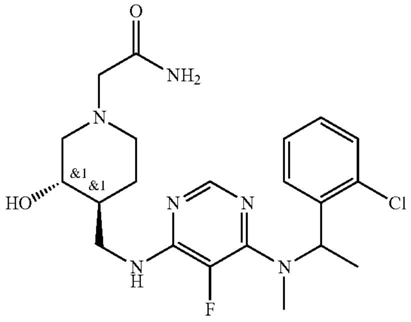 [SMILES: CC(c1ccccc1Cl)N(C)c1ncnc(NC[C@@H]2CCN(CC(N)=O)C[C@H]2O)c1F] | F2-6 rac-2-((3R,4R)-4-(((6-((1-(2-chlorophenyl)ethyl)(methyl)amino)-5-fluoropyrimidin-4-yl)amino)methyl)-3-hydroxypiperidin-1-yl)acetamide |
| F2-7 | 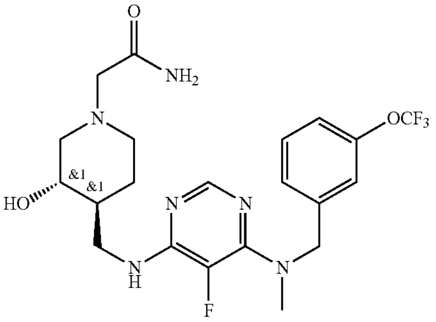 [SMILES: CN(Cc1cccc(OC(F)(F)F)c1)c1ncnc(NC[C@@H]2CCN(CC(N)=O)C[C@H]2O)c1F] | F2-7 rac-2-((3R,4R)-4-(((5-fluoro-6-(methyl(3-(trifluoromethoxy)benzyl)amino)pyrimidin-4-yl)amino)methyl)-3-hydroxypiperidin-1-yl)acetamide |
| F2-8 | 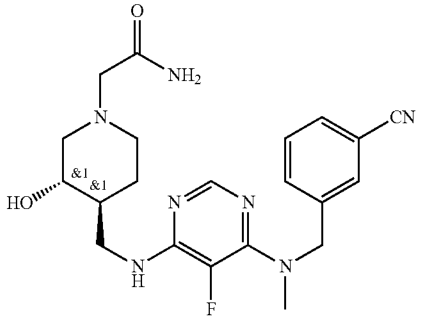 [SMILES: CN(Cc1cccc(C#N)c1)c1ncnc(NC[C@@H]2CCN(CC(N)=O)C[C@H]2O)c1F] | F2-8 rac-2-((3R,4R)-4-(((6-((3-cyanobenzyl)(methyl)amino)-5-fluoropyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| F2-9 | 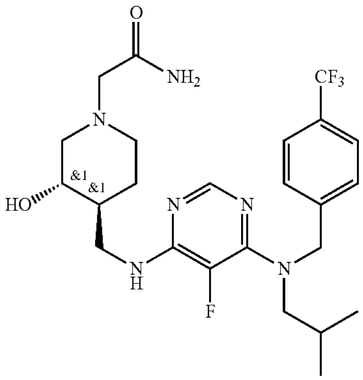 | F2-9 rac-2-((3R,4R)-4-(((5-fluoro-6-(isobutyl(4-(trifluoromethyl)benzyl)amino) pyrimidin-4-yl)amino)methyl)-3-hydroxypiperidin-1-yl)acetamide |
| F2-10 | 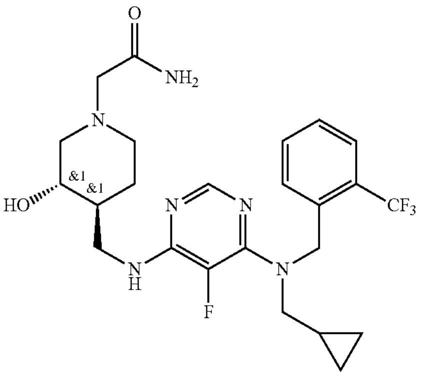 [SMILES: NC(=O)CN1CC[C@@H](CNc2ncnc(N(Cc3ccccc3C(F)(F)F)CC3CC3)c2F)[C@H](O)C1] | F2-10 rac-2-((3R,4R)-4-(((6-((cyclopropylmethyl)(2-(trifluoromethyl)benzyl)amino)-5-fluoropyrimidin-4-yl)amino)methyl)-3-hydroxypiperidin-1-yl)acetamide |
| F2-11 | 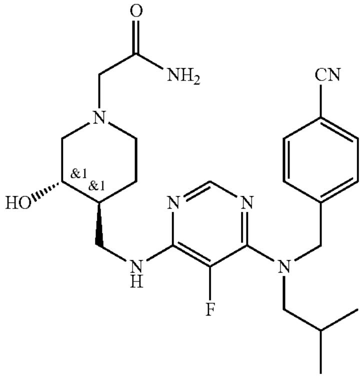 [SMILES: CC(C)CN(Cc1ccc(C#N)cc1)c1ncnc(NC[C@@H]2CCN(CC(N)=O)C[C@H]2O)c1F] | F2-11 rac-2-((3R,4R)-4-(((6-((4-cyanobenzyl)(isobutyl)amino)-5-fluoropyrimidin-4-yl)amino)methyl)-3-hydroxypiperidin-1-yl)acetamide |
| F2-12 | 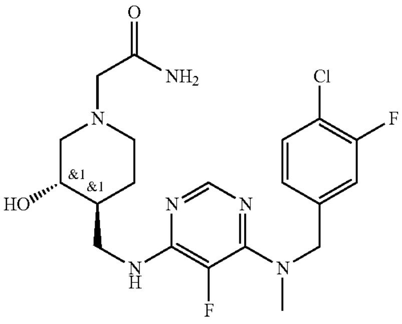 [SMILES: CN(Cc1ccc(Cl)c(F)c1)c1ncnc(NC[C@@H]2CCN(CC(N)=O)C[C@H]2O)c1F] | F2-12 rac-2-((3R,4R)-4-(((6-((4-chloro-3-fluorobenzyl)(methyl)amino)-5-fluoropyrimidin-4-yl)amino)methyl)-3-hydroxypiperidin-1-yl)acetamide |

TABLE 1-continued

| Ex. No | Structure | Name |
| --- | --- | --- |
| F2-13 | 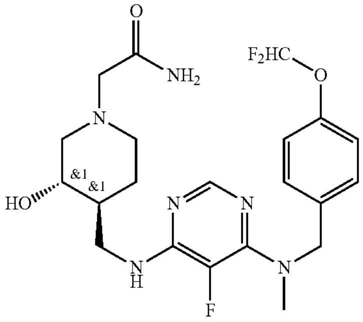 [SMILES: CN(Cc1ccc(OC(F)F)cc1)c1ncnc(NC[C@@H]2CCN(CC(N)=O)C[C@H]2O)c1F] | F2-13 rac-2-((3R,4R)-4-(((6-((4-(difluoromethoxy)benzyl)(methyl) amino)-5-fluoropyrimidin-4-yl)amino)methyl)-3-hydroxypiperidin-1-yl)acetamide |
| F2-14 | 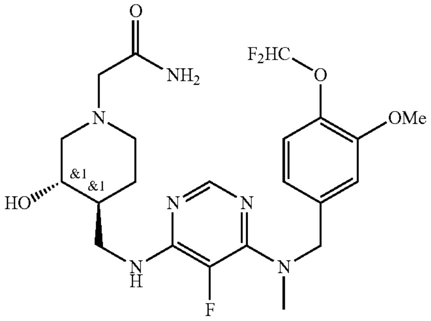 [SMILES: COc1cc(CN(C)c2ncnc(NC[C@@H]3CCN(CC(N)=O)C[C@H]3O)c2F)ccc1OC(F)F] | F2-14 rac-2-((3R,4R)-4-(((6-((4-(difluoromethoxy)-3-methoxybenzyl)(methyl)amino)-5-fluoropyrimidin-4-yl)amino)methyl)-3-hydroxypiperidin-1-yl)acetamide |
| F2-15 | 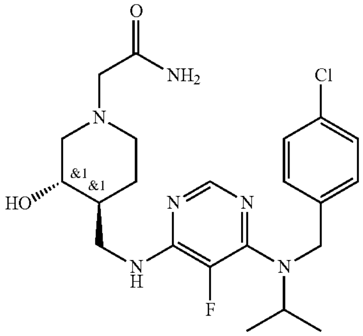 [SMILES: CC(C)N(Cc1ccc(Cl)cc1)c1ncnc(NC[C@@H]2CCN(CC(N)=O)C[C@H]2O)c1F] | F2-15 rac-2-((3R,4R)-4-(((6-((4-chlorobenzyl)(isopropyl)amino)-5-fluoropyrimidin-4-yl)amino)methyl)-3-hydroxypiperidin-1-yl)acetamide |
| F2-16 | 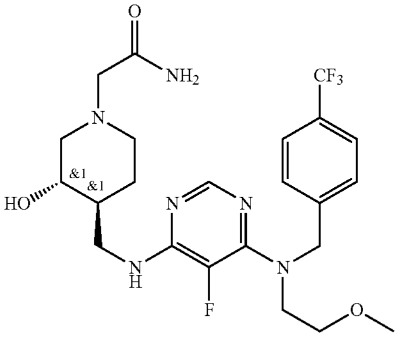 [SMILES: COCCN(Cc1ccc(C(F)(F)F)cc1)c1ncnc(NC[C@@H]2CCN(CC(N)=O)C[C@H]2O)c1F] | F2-16 rac-2-((3R,4R)-4-(((5-fluoro-6-((2-methoxyethyl)(4-(trifluoromethyl)benzyl)amino) pyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| F2-17 | 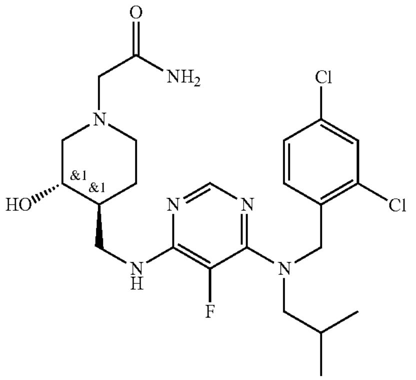 [SMILES: CC(C)CN(Cc1ccc(Cl)cc1Cl)c1ncnc(NC[C@@H]2CCN(CC(N)=O)C[C@H]2O)c1F] | F2-17 rac-2-((3R,4R)-4-(((6-((2,4-dichlorobenzyl)(isobutyl)amino)-5-fluoropyrimidin-4-yl)amino)methyl)-3-hydroxypiperidin-1-yl)acetamide |
| F2-18 | 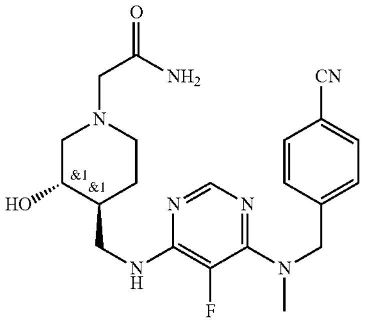 [SMILES: CN(Cc1ccc(C#N)cc1)c1ncnc(NC[C@@H]2CCN(CC(N)=O)C[C@H]2O)c1F] | F2-18 rac-2-((3R,4R)-4-(((6-((4-cyanobenzyl)(methyl)amino)-5-fluoropyrimidin-4-yl)amino)methyl)-3-hydroxypiperidin-1-yl)acetamide |
| F2-19 | 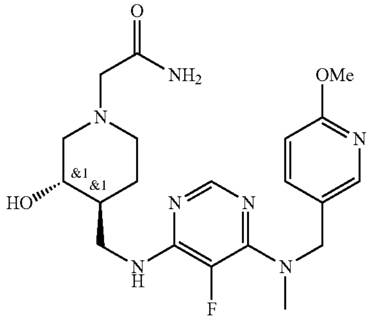 [SMILES: COc1ccc(CN(C)c2ncnc(NC[C@@H]3CCN(CC(N)=O)C[C@H]3O)c2F)cn1] | F2-19 rac-2-((3R,4R)-4-(((5-fluoro-6-(((6-methoxypyridin-3-yl)methyl)(methyl)amino)pyrimidin-4-yl)amino)methyl)-3-hydroxypiperidin-1-yl)acetamide |
| F2-20 | 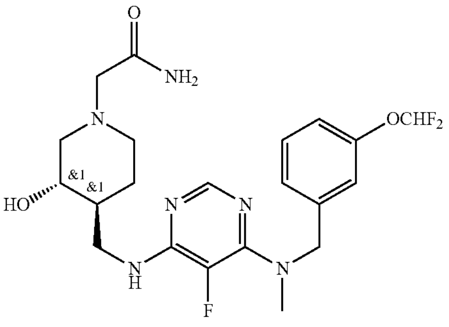 [SMILES: CN(Cc1cccc(OC(F)F)c1)c1ncnc(NC[C@@H]2CCN(CC(N)=O)C[C@H]2O)c1F] | F2-20 rac-2-((3R,4R)-4-(((6-((3-(difluoromethoxy)benzyl)(methyl)amino)-5-fluoropyrimidin-4-yl)amino)methyl)-3-hydroxypiperidin-1-yl)acetamide |

TABLE 1-continued

| Example compounds by Structure and Name. | | |
|---|---|---|
| Ex. No | Structure | Name |
| F2-21 | 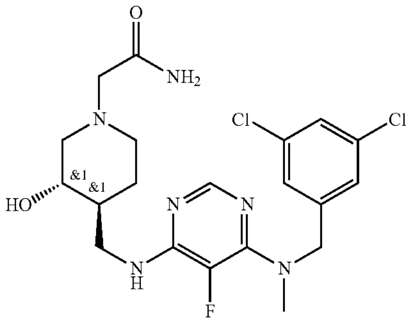 [SMILES: CN(Cc1cc(Cl)cc(Cl)c1)c1ncnc(NC[C@@H]2CCN(CC(N)=O)C[C@H]2O)c1F] | F2-21<br>rac-2-((3R,4R)-4-(((6-((3,5-dichlorobenzyl)(methyl)amino)-5-fluoropyrimidin-4-yl)amino)methyl)-3-hydroxypiperidin-1-yl)acetamide |
| F2-22 | 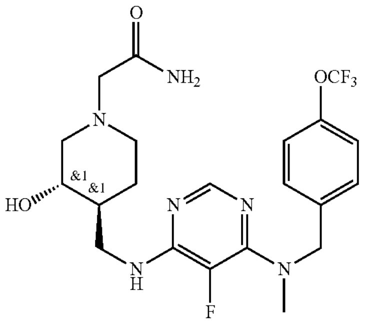 [SMILES: CN(Cc1ccc(OC(F)(F)F)cc1)c1ncnc(NC[C@@H]2CCN(CC(N)=O)C[C@H]2O)c1F] | F2-22<br>rac-2-((3R,4R)-4-(((5-fluoro-6-(methyl(4-(trifluoromethoxy)benzyl)amino)pyrimidin-4-yl)amino)methyl)-3-hydroxypiperidin-1-yl)acetamide |
| F2-23 | 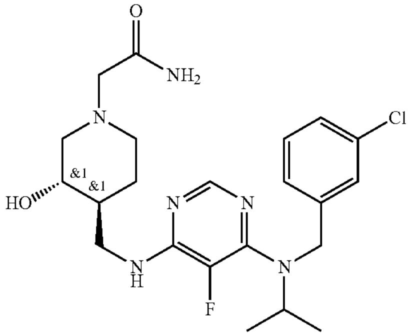 [SMILES: CC(C)N(Cc1cccc(Cl)c1)c1ncnc(NC[C@@H]2CCN(CC(N)=O)C[C@H]2O)c1F] | F2-23<br>rac-2-((3R,4R)-4-(((6-((3-chlorobenzyl)(isopropyl)amino)-5-fluoropyrimidin-4-yl)amino)methyl)-3-hydroxypiperidin-1-yl)acetamide |

In a related aspect there is provided a prodrug of a compound of Formula (I) as described herein.

The compounds of the present disclosure are active, e.g. having a RORγ Gal4<1000 nM, such as <500 nM, such as <100 nM, and have a log P substantially lower (e.g. a decreased log P of 1.5, such as 2.0, such as 2.5 log units) than compounds disclosed in WO2016020288 and WO2016020295. In certain embodiments Log D and Log P are substantially lower than compounds in WO2016020288 and WO2016020295. The compounds disclosed herein thus have an improved lipophilicity at similar potency. The compounds disclosed herein may thus be improved modulators of RORγ, e.g. having an attractive interaction (e.g. higher binding ability) to the hydrophobic binding sites of the ligand binding domain (LBD) of the RORγ and a low log P and/or low log D.

Pharmaceutical Compositions

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound as disclosed herein, e.g., a compound of Formulae (I), (II), (III) and (IV) as disclosed herein, or a salt, stereoisomer, or salt of a stereoisomer thereof. The compound of Formulae (I), (II), (III) and (IV) included in the pharmaceutical composition may also be any compound of the preferred embodiments described above. In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound of any one of Formulae I, II or III as disclosed herein. Acceptable carriers or diluents, as well as other additives to be combined with one or more compound(s) of Formula (I), (II), (III) and (IV) as disclosed herein to provide a pharmaceutical composition, for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, taste masking agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Similar, pharmaceutical compositions can also be obtained by reacting compounds with inorganic or organic bases, such as ammonia, sodium carbonate, sodium hydrogen carbonate, sodium hydroxide, and the like.

The term "carrier" defines a chemical compound that facilitates the incorporation of a compound into cells or tissues. For example, and without limitation dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, PA, 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use as described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Topical ophthalmic compositions may be formulated as a solution in water buffered at a pH of 5.0 to 8.0. Other ingredients that may be desirable to use in the ophthalmic preparations include preservatives (such as benzalkonium chloride, stabilized oxychloro complex, which is sold as Purite™, or stabilized chlorine dioxide), cosolvents (such as polysorbate 20, 60 and 80, Pluronic® F-68, F-84 and P-103, cyclodextrin, or Solutol) and viscosity-building agents (such as polyvinyl alcohol, polyvinyl pyrrolidone, methyl cellulose, hydroxypropyl methyl cellulose, hydroxyethyl cellulose, carboxymethyl cellulose, or hydroxypropyl cellulose). The compounds disclosed herein may also be used in an intraocular implant as described in U.S. Pat. No. 7,931,909 which is hereby incorporated by reference. Pharmaceutical compositions for intraocular delivery include aqueous ophthalmic solutions of the active compounds in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references, are incorporated herein by reference in their entireties. Such suitable pharmaceutical formulations for intraocular delivery are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, PA (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds disclosed herein may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Combinations

The compounds disclosed herein may also be combined with other active compounds in the treatment and/or prevention of inflammatory, metabolic, oncologic and autoimmune diseases or disorders or a symptom thereof.

The combinations provided herein comprise the compounds disclosed herein and one or more additional active substances, such as:

a) Corticosteroids, such as prednisone, methylprednisolone or beta-methasone;
b) Immunosuppressants, such as cyclosporine, tacrolimus methotrexate, hydroxyurea, mycophenolate mofetil, mycophenolic acid, sulfasalazine, 6-thioguanine or azathioprine;
c) Fumaric acid esters, such as dimethyl fumarate;
d) Dihydroorotate dehydrogenase (DHODH) inhibitors such as leflunomide;
e) Retinoids, such as acitretin or isotretinoin;
f) Anti-inflammatories such as apremilast, crisaborole, celecoxib, diclofenac, aceclofenac, aspirin or naproxen;
g) JAK inhibitors such as tofacitinib, baricitinib, upadacitinib, ruxolitinib or delgocitinib;
h) Antibiotics such as gentamicin;
i) Anti-cancer agents such as lenalidomide, pomalidomide, pembrolizumab, nivolumab, daratumumab, bortezomib, carfilzomib, ixazomib, bendamustine or ventoclast;
j) T-cell blockers such as alefacept or efalizumab;
k) Tumor necrosis factor-alpha (TNF-alpha) blockers such as etanercept, adalimumab, infliximab, golimumab, certolizumab pegol;
l) interleukin 12/23 blockers such as ustekinumab;
m) IL-23 blockers such as risankizumab, guselkumab or tildrakizumab;
n) anti-IL4/IL13 antagonist such as dupilumab, lebrikizumab or tralokinumab;
o) IL-1β blockers such as canakinumab;
p) IL-alpha blockers such as bermekimab;
q) CD6 blockers such as itolizumab;
r) IL-36R blockers such as BI-655130 or bimekizumab;
s) IL-6 antagonist such as tocilizumab;
t) Calcineurin inhibitors such as pimecrolimus, tacrolimus or cyclosporine;
u) Phototherapy agents commonly employed in phototherapy such as psoralen, methoxypsoralen or 5-methoxypsoralen+UVA (PUVA) or treatment with UVB (with or without tar);
v) Fixed combinations of corticosteroids and vitamin D derivatives;
w) Fixed combinations of corticosteroids and retinoids;
x) Corticosteroid tapes; and
y) one or more agents selected from the group consisting of BMS986165, PF-06700841, PF-06826647, piclidenoson, tepilamide fumarate, LYC-30937, LEO-32731, BI-730357, PRCL-02, LNP-1955, GSK-2982772, CBP-307, KD-025, MP-1032, petesicatib, JTE-451, Hemay-005, SM-04755, EDP-1815, BI-730460, SFA-002 ER, JNJ-3534, SAR-441169, BOS-172767, SCD-044, ABBV-157, BAY-1834845, AUR-101, R-835, PBF-1650, RTA-1701, AZD-0284, mirikizumab, CD20 antagonist, salicylic acid, coal tar, Mical-1, DUR-928, AM-001, BMX-010, TA-102, SNA-125, brepocitinib tosylate, pegcantratinib, ESR-114, NP-000888, SM-04755, BOS-475, SB-414, LEO-134310, CBS-3595, PF-06763809, XCUR-17 and BTX-1308.

The active compounds in the combination, i.e the compounds disclosed herein, and the other optional active compounds may be administered together in the same pharmaceutical composition or in different compositions intended for separate, simultaneous, concomitant or sequential administration by the same or a different route.

Uses

The compounds or pharmaceutical compositions disclosed herein as described above may be used to modulate the activity of a retinoic acid receptor-related orphan receptor (ROR), such as a RORα, RORβ and/or RORγ receptor. Modulators of RORγ have been reviewed by B. Fauber and S. Magnuson in J. Med. Chem., Feb. 6, 2014, and Pandya et al in J. Med. Chem. 2018, 61, 24, 10976-10995 which hereby are incorporated by reference in its entirety. Examples of RORγ receptors are RORγ1 and RORγt receptors. The compounds or pharmaceutical compositions as described above may also display selective modulation of a particular ROR receptor relative to a different ROR receptor. For example, according to some embodiments disclosed herein some compounds or pharmaceutical compositions modulate the activity of an RORγ receptor to a larger extent than they modulate the activity of RORα and/or RORβ receptors.

The compounds or pharmaceutical compositions disclosed herein may also be used to modulate the activity of cells producing IL-17A in a RORγt dependent manner, for example, γδT cells, Th17 cells, Tc17 cells and ILC3 cells. The compounds or pharmaceutical compositions disclosed herein may also be used to inhibit RORγt function upon IL-23 stimulation, which in turn negatively impacts on the differentiation and expansion of pathogenic Tc17 and Th17.

Publications providing useful background information are Arthritis & Rheumatism, 2014, 66, 579-588; Curr Top Microbial Immun, 2014, 378, 171-182; Drug Disc. Today, 2014, May; Nature Rev. Drug Disc. 2012, 11, 763-776, and Nature Rev. Drug Disc., 2014, 13, 197-216, all of which are hereby incorporated by reference in their entirety.

The compounds or pharmaceutical compositions as described herein and above may also be used in therapy or may be used to treat inflammatory, metabolic, oncologic and autoimmune diseases or disorders or a symptom thereof. Examples of such diseases or disorders are inflammatory, metabolic, oncologic and autoimmune diseases or disorders mediated or affected by IL-17A and/or RORγ. The role of RORγ in the pathogenesis of autoimmune or inflammatory diseases has been disclosed in Immunity 2007, 26(5), 643-654; Nat. Rev. Immunol. 2006, 6, 205-217; J. Immunol. 2009, 183, 7169-7177; Brain Pathol. 2004, 14, 164-174; Brain 2007, 130, 1089-1104; and Nat Rev. Immunol. 2008, 8, 183-192 all of which are hereby incorporated by reference in their entirety.

More specific examples of diseases or disorders, or a symptom thereof include asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ankylosing spondylitis, psoriasis, psoriatic arthritis, ichtyoses, bullous diseases, hidradenitis suppurativa, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance, type II diabetes and cancer.

More preferably, the diseases or disorders, or a symptom thereof include acne, atopic dermatitis, lichen planus, multiple sclerosis, rheumatoid arthritis, juvenile idiopathic arthritis, osteoarthritis, ankylosing spondylitis, psoriasis, psoriatic arthritis, ichthyoses, bullous diseases, hidradenitis suppurativa, ulcerative colitis, colitis, Crohn's disease, inflammatory bowel disease (IBD) and lupus erythematosus.

An example of a symptom is a physical or mental feature which is regarded as indicating a condition of disease, particularly such a feature that is apparent to the patient, e.g. treating o preventing a symptom is not considered disease-modifying but preventing or alleviating one or more symptoms commonly experience in connection with such a disease.

More specifically, compounds or pharmaceutical compositions having an antagonistic or inverse agonistic effect on RORγ may be used to reduce levels of IL-17A and/or other gene products, such as interleukins, and cytokines, regulated RORγ. This may for example be in subjects suffering from for example, asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ichthyoses, bullous diseases, hidradenitis suppurativa, ankylosing spondylitis, psoriasis, psoriatic arthritis, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance and type II diabetes.

Conversely, compounds or pharmaceutical compositions having an agonistic effect on RORγ may be used to increase IL-17A levels. Increasing IL-17A levels may be particularly useful in immune compromised conditions or boosting the immune system response for example during infections and in cancer.

The compounds described herein may be used in the manufacture of a medicament for the treatment and/or prevention of inflammatory, metabolic, oncologic and autoimmune diseases or disorders or a symptom thereof.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation, by intratumoral injection, or by intra-lymph node injection; (e) administration topically; as well as as well as (f) administration to cells ex vivo followed by insertion of said cells into the patient; as deemed appropriate by those of skill in the art for bringing the compound disclosed herein into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including mammal, e.g. human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication.

Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps the dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. An ocular eye drop may range in concentration between 0.005 and 5 percent. In one embodiment, an eye drop may range between 0.01 and 1 percent, or between 0.01 and 0.3 percent in another embodiment. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range or frequency in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local or ex vivo administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

GENERAL REMARKS

As described above with reference to specific illustrative embodiments, it is not intended to be limited to the specific form set forth herein. Any combination of the above mentioned embodiments should be appreciated as being within the scope of the disclosure. Rather, the disclosure is limited only by the accompanying claims and other embodiments than the specific above are equally possible within the scope of these appended claims.

In the claims, the term “comprises/comprising” does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms “a”, “an”, “first”, “second” etc. do not preclude a plurality. The phrases “at least one” or “one or more” refer to 1 or a number greater than 1, such as to 1, 2, 3, 4, 5, 6, 7, 8, 9, or 10.

Whenever a chemical name or structure has been given it has been generated by conventional means or by means of a suitable software. Names for the compounds were generated with ChemDraw Professional, version 17.1.0.105 (19).

In the present disclosure, in the drawings of the structures, the labels “or1”, “or2”, “& 1”, or “&2” at each stereogenic center specify the “stereochemical group” to which the center belongs.

In the case of the “or” groups, the meaning is a structure that represents one stereoisomer that has either the “stereochemical group” as drawn ((R, S), for instance) or the stereoisomer in which the stereogenic centers of the group have the opposite configuration (S, R).

In the case of the “&” groups, & in combination with the number given (e.g. &1) indicate a mixture of the marked asymmetrically substituted atoms. When the numbering pools several asymmetrically substituted atoms together this displays their configuration relative to each other. If they are displayed as (R,S) the opposite configuration (S,R) is also present for the specified pooled group.

In the present disclosure, the symbol " specifies enantiomerically enriched. Any compound or intermediate synthesized in a enantiomerically enriched manner and where no chiral separation has been performed is identified with ".

EXPERIMENTAL

The following examples are mere examples and should by no mean be interpreted to limit the scope of the disclosure. Rather, the disclosure is limited only by the accompanying claims.

General Chemical Procedures

General

Unless otherwise stated, starting materials were obtained from commercial suppliers, such as (but not limited to); AbBchem, ABCR, Alfa Aesar, Anaspec, Anichem, Apollo Scientific, ASDI-Inter, Asiba Pharmatech, Astatech, ArkPharm, Bachem, Chem-Impex, ChemCollect, Chembridge, Combi-Blocks, Enamine, FCH, Fluka, Fluorochem, Frontier Scientific, HDH Pharma, InFarmatik, InterBioScreen, Life Chemicals, Manchester organics, Matrix, MercaChem, NetChem, Oakwood Chemical, PepTech, Pharmcore, PrincetonBio, Sigma-Aldrich, TRC, Tyger Scientific and Ukrorgsyn, and were used without further purification. Solvents such as DMF, DMSO and DCM, etc were used directly or dried over molecular sieves.

Equipment

NMR $^1$H NMR spectra were recorded on the following; Bruker Avance 300 spectrometer (at 300 MHz), Bruker Avance III 400 spectrometer (at 400 MHz), Bruker Avance Neo (400 MHz), Bruker Avance III 600 (at 600 MHz), Varian VNMR spectrometer (at 400 MHz) using $CD_3OD$, $CDCl_3$ or DMSO-$d_6$ solvents. Chemical shifts are reported in ppm (δ) using residual solvent as an internal standard; $CDCl_3$: 7.26 ppm; $CD_3OD$: 3.31 ppm; DMSO-$d_6$: 2.50 ppm. Coupling constants (J) are given in Hz.

Analytical U/HPLC

The following equipment was used for analytical U/HPLC:

Waters Acquity system equipped with an Acquity BEH C18 (1.7 μm, 2.1×50 mm) with a linear gradient of a binary solvent system using a flow rate of 0.5 mL/min and DAD at ambient temperature, combined with MS detection SQD I.

Agilent Infinity I/II-TOF6230B/CLND Antek 8060 equipped with Acquity BEH C18 (1.7 μm, 2.1×50 mm) with a linear gradient of a binary solvent system using a flow rate of 0.75 mL/min combined with DAD.

Agilent 1200series-1260 Infinity equipped with a Waters XBridge C18 (5 μm, 4.6×50 mm) with a linear gradient of a binary solvent system using a flow rate of 1.5 mL/min and UV detection at 214 nm or 254 nm, combined with MS detection (Agilent).

Shimadzu Nexera equipped with a Waters XBridge C18 (5 μm, 4.6×50 mm) with a linear gradient of a binary solvent system using a flow rate of 1.5 mL/min and UV detection at 214 nm or 254 nm, combined with MS detection (Shimadzu).

Waters Acquity system equipped with an Acquity BEH C18 (1.7 μm, 2.1×50 mm) with a linear gradient of a binary solvent system using a flow rate of 0.65 mL/min and DAD at ambient temperature, combined with MS detection Waters spectrometer.

Preparative HPLC

The following equipment was used for Prep-HPLC:

Waters Acquity system equipped with a Supelco DISCOVERY C18 (5 μm, 25 cm×21.2 mm), with a linear gradient of a binary solvent system using a flow rate of 45 mL/min and UV detection at 254 nm, combined with MS detection on a Waters Micromass ZQ Quadrupole MS.

Shimadzu Nexera X2 equipped with a Merck Chromolith SpeedROD RP-18E (5 μm, 10×100 mm) with a linear gradient of a binary solvent system using a flow rate between 4 and 7 mL/min and UV detection at 254 nm, combined with MS detecting on a Shimadzu LCMS-2020.

Waters Masslynx system equipped with a Waters XBridge C18 column (5 μm, 19×150 mm) with a linear gradient of a binary solvent system using a flow rate of 15 mL/min and UV detection at 214 nm or 254 nm, combined with MS detection (Waters).

Gilson GX-281 TRILUTION equipped with a Phenomenex Gemini NX-C18 column (5 μm, 21.2×150 mm) with a linear gradient of a binary solvent system using a flow rate of 15 mL/min and UV detection at 214 nm or 254 nm, combined with MS detection (Waters).

The following linear gradients have been used:

$HCO_2H$—($H_2O/CH_3CN/HCO_2H$ (100/0/0.1% to 0/100/0.1%))

$NH_4OAc$—($H_2O/CH_3CN/NH_4OAc$ (100/0/0.02% to 0/100/0.02%))

TFA—($H_2O/CH_3CN$/TFA (100/0/0.1% to 0/100/0.1%))

$NH_4HCO_3$— ($H_2O/CH_3CN/NH_4HCO_3$ (100/0/0.1% to 0/100/0.1%))

$NH_4OH$—($H_2O/CH_3CN/NH_4OH$ (100/0/0.1% to 0/100/0.1%))

$HCO_2$ $NH_4$—($H_2O$/50% MeOH+50% $CH_3CN/HCO_2H/NH_3$ (95/5/0.05%/0.01% to 5/95/0.05%/0.01%))

Flash CC was most often performed on a Isolera® automated systems. Flash CC and Prep TLC were performed employing $SiO_2$, if not otherwise mentioned. However, C18 columns have also been employed (using a gradient of water-acetonitrile/MeOH (1:1), with or without 0.1% v/v ammonium formate in both phases, from 0% to 100% acetonitrile/MeOH (1:1)).

Analytical Chiral Chromatography

Was performed on a Waters UPC2 system coupled to a DAD detector and a Waters QDa MS detector, equipped with a chiral column with gradient elution using a flow rate of 1 mL/min. The available chiral columns were CHIRALPAK (3 μm, 4.6×100 mm) IA, IB, IC and ID and Trefoil AMY1 (2.5 μm, 2.1×150 mm).

The following linear gradients have been used for analytical UPC2:

$CO_2$/MeOH/DEA (99/1/0.2% to 60/40/0.2%))

$CO_2$/EtOH/DEA (99/1/0.2% to 60/40/0.2%)

$CO_2$/IPA/DEA (99/1/0.2% to 60/40/0.2%)

Preparative Chiral Chromatography

Before chiral separation, compounds were purified by the standards methods previously described using the appropriate solvents.

Preparative chiral separations were performed either on a Gilson (306, GX-281 trilution, 156-UV/Vis, Waters 3100 MSD), or a Waters SFC-80, equipped with a chiral column with the solvents specified using flow rates between 10-50 mL/min (only 50 g/min for SCF) and detection at either 214 or 230 nm; The available chiral columns were Reprosil AMS (5 μm, 20 mm×250 mm), Lux C2 (5 μm, 21.2 mm×250 mm), Lux C4 (5 μm, 21.2 mm×250 mm), Chiralpak® column IA, IB, IC, ID, IF or IG (5 μm, 20 mm×250 mm) or Chiralcel® OJ-H or OD-H. Exact column and elution conditions used for each compound are described in the experimental part.

Synthetic Methods

The compounds disclosed herein may be synthesized by one of the following general methods: General Method A, General Method 2A, General Method 3A, General Method 4A, General Method 5A, General Method 6A, General Method B, General Method C, General Method 1D, General Method 2D, General Method 2D', General Method 3D, General Method E and General Method F.

General Method A—Synthesis from Boc-Protected Piperidines.

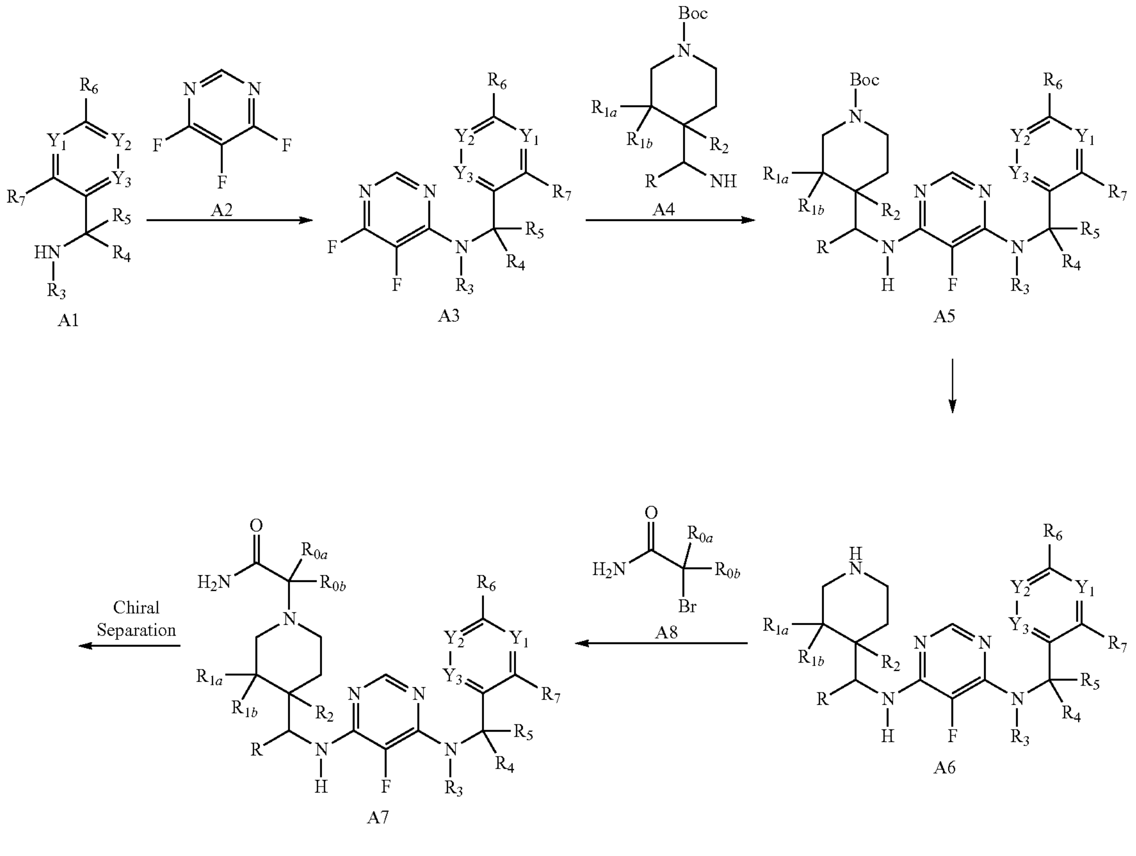

The secondary amine A1 was reacted with A2 (at ambient temperature or slightly above, 30° C.) together with a suitable base (such as; DIEA, TEA or $K_2CO_3$) at rt. After the reaction was deemed complete the intermediate A3 was worked up and purified by chromatography (Flash CC or HPLC) or used as the crude. Intermediate A3, a base (such as; DIEA, TEA or $Cs_2CO_3$) and the primary amine A4 were thereafter dissolved in a solvent (such as DMSO or DMSO-$H_2O$, $H_2O$, $H_2O$-EtOH mixtures) and the temperature was increased to 70-100° C. on, or until the reaction was considered complete. Workup and purification then gave Intermediate A5, which was subjected to de-protection. The intermediate formed following boc-deprotection A6 was most often used directly, as the corresponding piperidinium salt (HCl or TFA), in the alkylation with 2-bromoacetamides A8 and a suitable base, such as DIEA, $Na_2CO_3$ or $K_2CO_3$ at rt or heating up to 100° C. The products A7 were first purified by standard chromatographic methods.

In the cases when the A7 products were mixture of stereoisomers they were often (but not always) subjected to chiral resolution (chromatography) to obtain single stereoisomers as end products.

All the compounds in Table A were synthesized employing this methodology, in ranges from 2 μmol up to ca 1 mol scale.

Example A7-1

Synthesis of rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide A7-1 and chiral separation to A7-1-1 and A7-1-2

Scheme A7-1

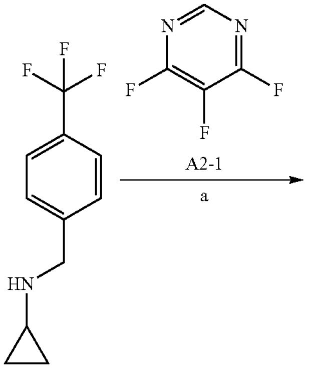

A1-1

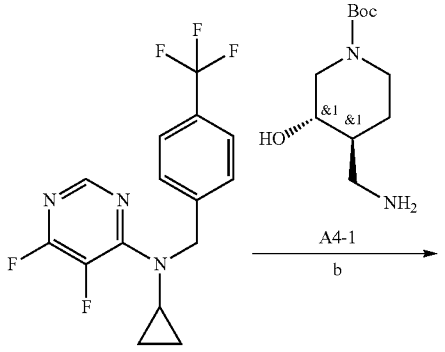

A3-1

-continued

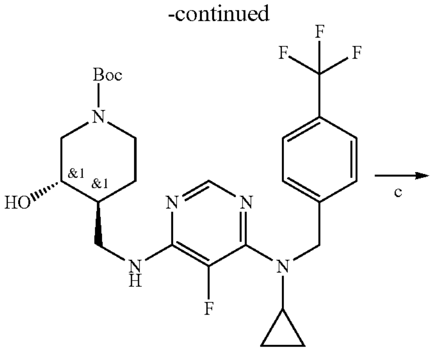

A5-1

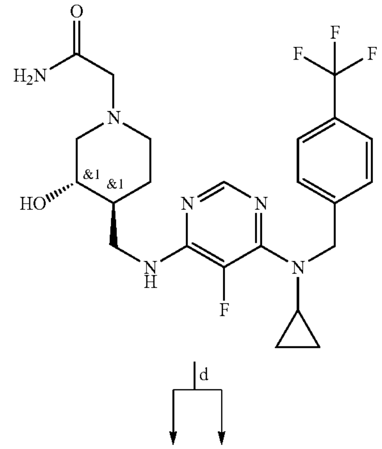

A7-1-1 A7-1-2 a) DIEA, DMSO, rt, on. b) DMSO, 80° C., on. c) i) HCl, dioxane, 60 min. ii) DIEA, 2-bromoacetamide. d) Chiral chromatography.

Synthesis of rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide, A7-1

N-Cyclopropyl-5,6-difluoro-N-(4-(trifluoromethyl)benzyl)pyrimidin-4-amine, A3-1

A3-1

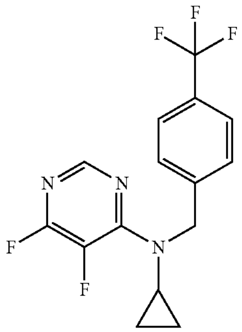

To dry DMSO (7 mL) A2-1 (375 mg, 2.8 mmol), A1-1 (737 mg, 3.1 mmol) and DIEA (1.5 mL) were added and the reaction was stirred on. The reaction mixture was then poured onto aq LiCl (40 mL, 5%) extracted three times with EA. The combined EA phase was then washed twice with aq LiCl (5%), once with brine, and subsequently dried ($Na_2SO_4$). Filtration, followed by concentration under reduced pressure gave a crude that was thereafter purified by Flash CC (EA:Hept) to yield A3-1 (832 mg).

LCMS: MS Calcd.: 329; MS Found: 330 ($[M+1]^+$).

rac-tert-Butyl (3R,4R)-4-(((6-(cyclopropyl(4-(trifluoromethyl)benzyl)amino)-5-fluoropyrimidin-4-yl)amino)methyl)-3-hydroxypiperidine-1-carboxylate, A5-1

A5-1

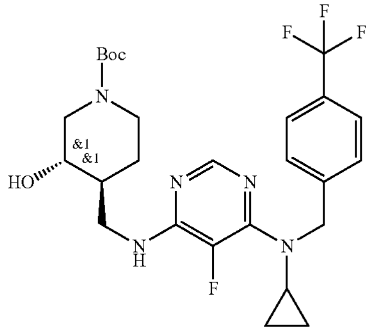

Compound A3-1 (828 mg, 2.5 mmol) was dissolved in dry DMSO (8 mL) followed by A4-1 (750 mg, 3.26 mmol) and DIEA (2.2 mL). The reaction mixture was heated to 80° C. on. The reaction mixture was cooled and then poured onto aq LiCl (40 mL, 5%) and extracted three times with EA. The combined EA phase was then washed twice with aq LiCl (5%), brine and then dried ($Na_2SO_4$). Filtration followed by concentration under reduced pressure gave a crude that was then purified by Flash CC (EA:Hept) to yield A5-1 (1.28 g).

LCMS: MS Calcd.: 539; MS Found: 540 ($[M+1]^+$).

rac-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, A7-1

A7-1

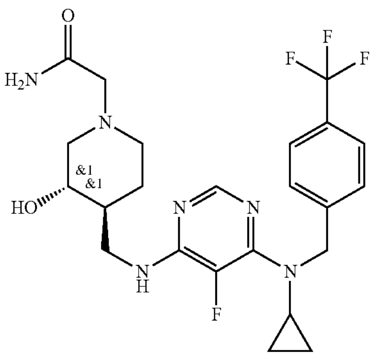

Compound A5-1 (1.27 g, 2.35 mmol) was added to HCl in dioxane (2M, 10 mL), stirred at ambient temperature for 60 min and thereafter concentrated under reduced pressure. The resulting residue was dissolved in a solution of DIEA (3.3 mL) in DCM (30 mL) on an ice bath. Thereafter, 2-bromoacetamide (0.39 g, 2.8 mmol) was added and reaction was allowed to reach rt and was then stirred on. The reaction was concentrated under reduced pressure. Thereafter, aq $NaHCO_3$ (sat) was added to the resulting slurry the resulting mixture was then extracted three times with EA. The combined EA phase were washed with brine, dried ($Na_2SO_4$), filtered, concentrated and purified, Flash CC (MeOH:DCM), to yield A7-1 (1.0 g, 2.0 mmol, 71% over 4 steps).

rel-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)acetamide, A7-1-1 and A7-1-2

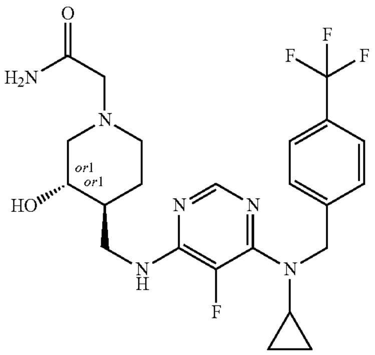

A7-1-1
A7-1-2

Compound A7-1 (0.95 g) was then subjected to chiral chromatography, to yield the optically pure compounds: A7-1-1 (380 mg) as the $1^{st}$ eluting isomer and A7-1-2 (365 mg) as the $2^{nd}$ eluting isomer.

General method A was used to prepare the following example numbers using the shown starting materials (Table A).

TABLE A

| A1 | A4 | A7 |
|---|---|---|
| A1-2 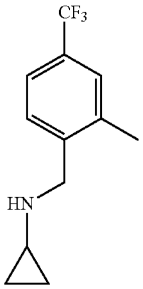 N-(2-methyl-4-(trifluoromethyl)benzyl) cyclopropanamine | A4-2 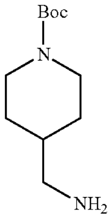 tert-butyl 4-(aminomethyl)piperidine-1-carboxylate | A7-2 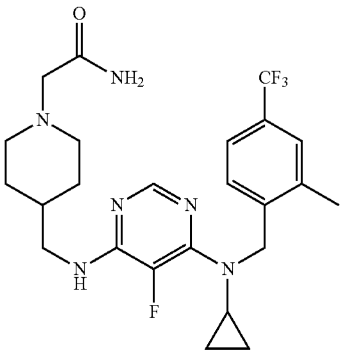 2-(4-(((6-(cyclopropyl(2-methyl-4-(trifluoromethyl)benzyl)amino)-5-fluoropyrimidin-4-yl)amino)methyl)piperidin-1-yl)acetamide |
| A1-3 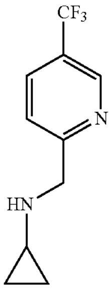 N-((5-(trifluoromethyl)pyridin-2-yl)methyl)cyclopropanamine | A4-3 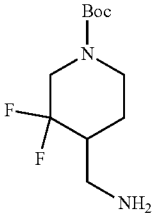 tert-butyl 4-(aminomethyl)-3,3-difluoro-piperidine-1-carboxylate | A7-3-1 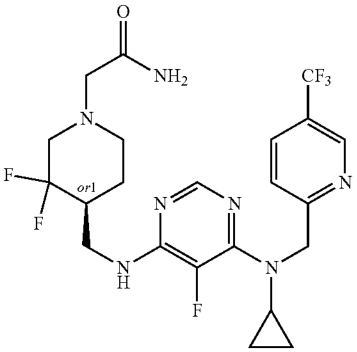 rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide 1$^{st}$ eluting isomer |
| A1-3 | A4-3 | A7-3-2 rel-(R)-2-(4-(((6-(cyclopropyl((5-(trifluoromethyl)pyridin-2-yl)methyl)amino)-5-fluoropyrimidin-4-yl)amino)methyl)-3,3-difluoropiperidin-1-yl)acetamide 2$^{nd}$ eluting isomer |

TABLE A-continued

| A1 | A4 | A7 |
|---|---|---|
| A1-3 | A4-4<br>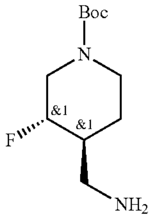<br>rac-tert-butyl (3R,4R)-4-(aminomethyl)-3-fluoropiperidine-1-carboxylate | A7-4-1<br>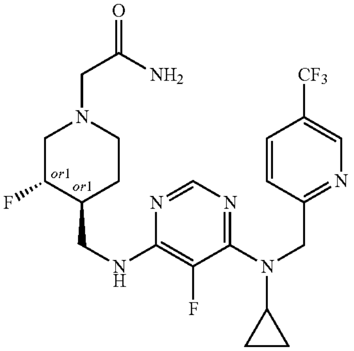<br>rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide<br>1st eluting isomer |
| A1-3 | A4-4 | A7-4-2<br>rel-2-((3R,4R)-4-(((6-(cyclopropyl((5-(trifluoromethyl)pyridin-2-yl)methyl)amino)-5-fluoropyrimidin-4-yl)amino)methyl)-3-fluoropiperidin-1-yl)acetamide<br>2nd eluting isomer |
| A1-1<br>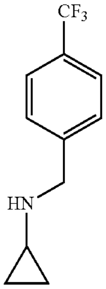<br>N-(4-(trifluoromethyl)benzyl) cyclopropanamine | A4-4 | A7-5-1<br>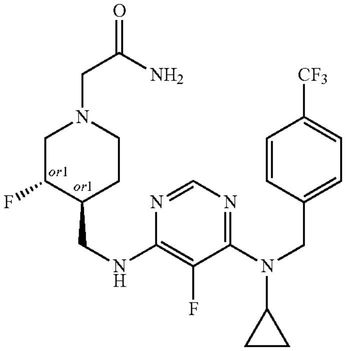<br>rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide<br>1st eluting isomer |
| A1-1 | A4-4 | A7-5-2<br>rel-2-((3R,4R)-4-(((6-(cyclopropyl(4-(trifluoromethyl)benzyl)amino)-5-fluoropyrimidin-4-yl)amino)methyl)-3-fluoropiperidin-1-yl)acetamide<br>2nd eluting isomer |

TABLE A-continued

| A1 | A4 | A7 |
|---|---|---|
| A1-1 | A4-3 | A7-6-1<br>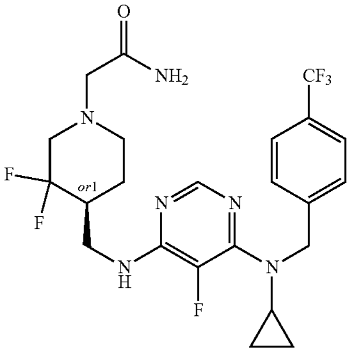<br>rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide<br>1st eluting isomer |
| A1-1 | A4-3 | A7-6-2<br>rel-(R)-2-(4-(((6-(cyclopropyl(4-(trifluoromethyl)benzyl)amino)-5-fluoropyrimidin-4-yl)amino)methyl)-3,3-difluoropiperidin-1-yl)acetamide<br>2nd Eluting isomer |
| A1-1 | A4-5<br>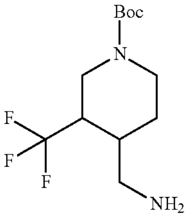<br>tert-butyl 4-(aminomethyl)-3-(trifluoromethyl)piperidine-1-carboxylate | A7-7-1<br>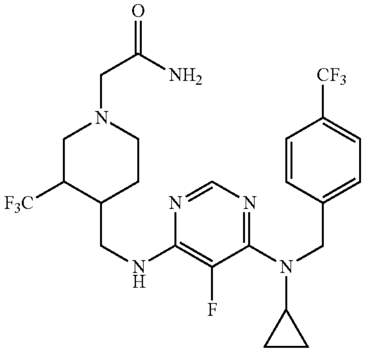<br>2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide<br>1st eluting isomer |
| A1-1 | A4-5 | A7-7-2<br>2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide<br>2nd eluting isomer |
| A1-1 | A4-5 | A7-7-3<br>2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide<br>3rd eluting isomer |

TABLE A-continued

| A1 | A4 | A7 |
|---|---|---|
| A1-1 | A4-5 | A7-7-4<br>2-(4-(((6-(cyclopropyl(4-(trifluoromethyl)benzyl)amino)-5-fluoropyrimidin-4-yl)amino)methyl)-3-(trifluoromethyl)piperidin-1-yl)acetamide<br>$4^{th}$ eluting isomer |
| A1-1 | A4-6<br>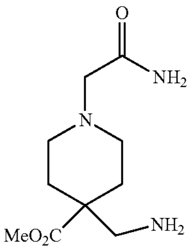<br>methyl 1-(2-amino-2-oxomethyl)-4-(aminomethyl)piperidine-4-carboxylate | A7-8<br>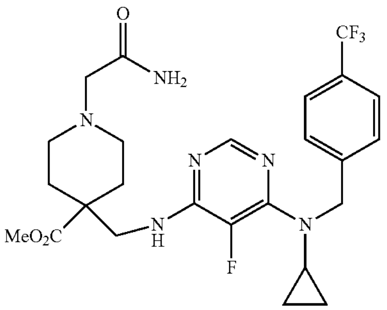<br>methyl 1-(2-amino-2-oxoethyl)-4-(((6-(cyclopropyl(4-(trifluoromethyl)benzyl)amino)-5-fluoropyrimidin-4-yl)amino)methyl)piperidine-4-carboxylate |
| A1-3<br>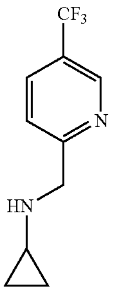<br>N-((5-(trifluoromethyl)pyridin-2-yl)methyl)cyclopropanamine | A4-7<br>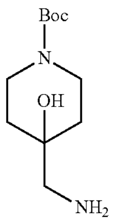<br>tert-butyl 4-(aminomethyl)-4-hydroxypiperidine-1-carboxylate | A7-9<br>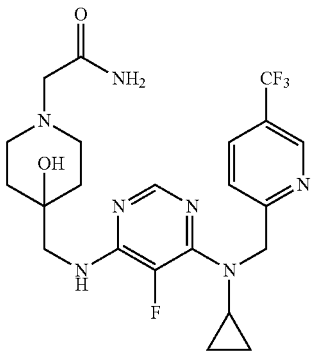<br>2-(4-(((6-(cyclopropyl((5-(trifluoromethyl)pyridin-2-yl)methyl)amino)-5-fluoropyrimidin-4-yl)amino)methyl)-4-hydroxypiperidin-1-yl)acetamide |

TABLE A-continued

| A1 | A4 | A7 |
|---|---|---|
| A1-1 | A4-7 | A7-10<br>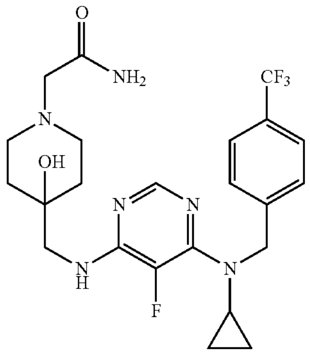<br>2-(4-(((6-(cyclopropyl(4-(trifluoromethyl)benzyl)amino)-5-fluoropyrimidin-4-yl)amino)methyl)-4-hydroxypiperidin-1-yl)acetamide |
| A1-4<br>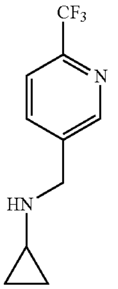<br>N-((6-(trifluoromethyl)pyridin-3-yl)methyl)cyclopropanamine | A4-7 | A7-11<br>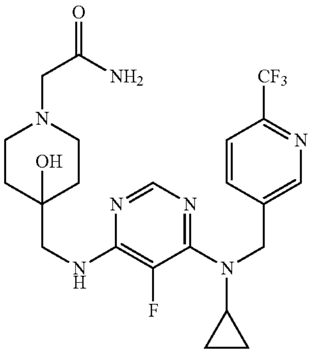<br>2-(4-(((6-(cyclopropyl((6-(trifluoromethyl)pyridin-3-yl)methyl)amino)-5-fluoropyrimidin-4-yl)amino)methyl)-4-hydroxypiperidin-1-yl)acetamide |
| A1-5<br>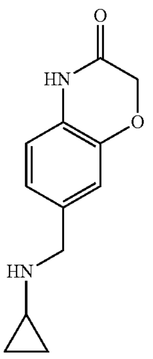<br>7-((cyclopropylamino)methyl)-2H-benzo[b][1,4]oxazin-3(4H)-one | A4-8<br>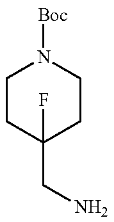<br>tert-butyl 4-(aminomethyl)-4-fluoropiperidine-1-carboxylate | A7-12<br>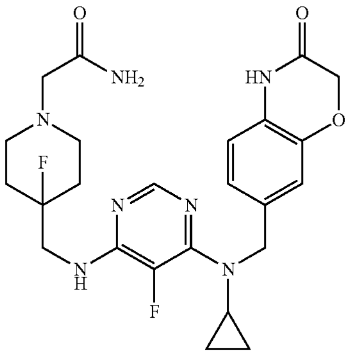<br>2-(4-(((6-(cyclopropyl((3-oxo-3,4-dihydro-2H-benzo[b][1,4]oxazin-7-yl)methyl)amino)-5-fluoropyrimidin-4-yl)amino)methyl)-4-fluoropiperidin-1-yl)acetamide |

TABLE A-continued

| A1 | A4 | A7 |
|---|---|---|
| A1-6<br>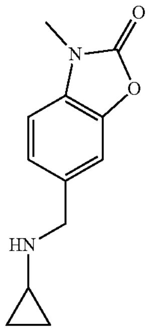<br>6-((cyclopropylamino) methyl)-3-methylbenzo[d]oxazol-2(3H)-one | A4-8 | A7-13<br>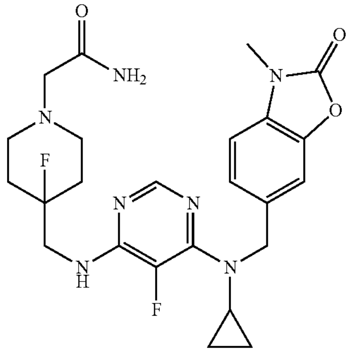<br>2-(4-(((6-(cyclopropyl((3-methyl-2-oxo-2,3-dihydrobenzo[d]oxazol-6-yl)methyl)amino)-5-fluoropyrimidin-4-yl)amino)methyl)-4-fluoropiperidin-1-yl)acetamide |
| A1-3 | A4-1<br>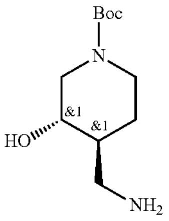<br>rac-tert-butyl (3R,4R)-4-(aminomethyl)-3-hydroxypiperidine-1-carboxylate | A7-14<br>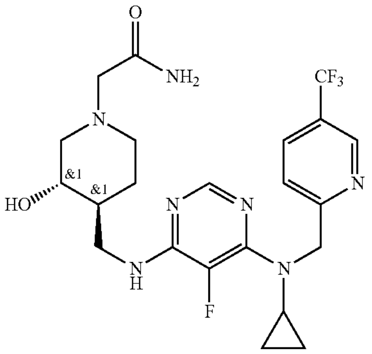<br>rac-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide |
| A1-3 | A4-1 | A7-14-1<br>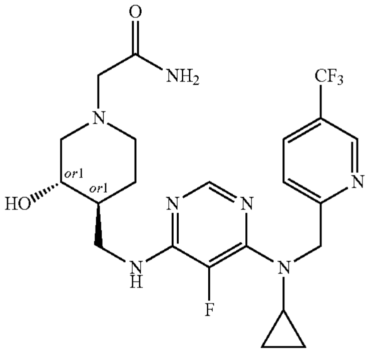<br>rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide<br>1st eluting isomer |

TABLE A-continued

| A1 | A4 | A7 |
|---|---|---|
| A1-3 | A4-1 | A7-14-2<br>rel-2-((3R,4R)-4-(((6-(cyclopropyl((5-(trifluoromethyl)pyridin-2-yl)methyl)amino)-5-fluoropyrimidin-4-yl)amino)methyl)-3-hydroxypiperidin-1-yl)acetamide<br>2nd eluting isomer |
| A1-7<br>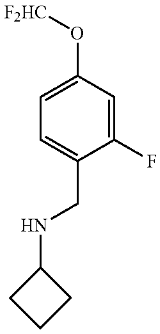<br>N-(4-(difluoromethoxy)-2-fluorobenzyl) cyclobutanamine | A4-1 | A7-15<br>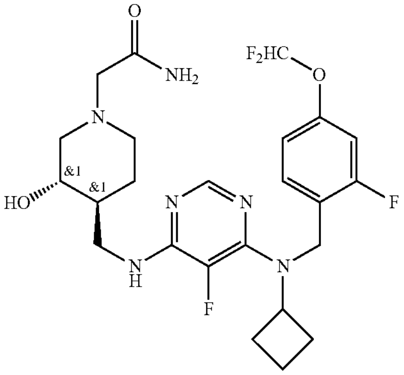<br>rac-2-((3R,4R)-4-(((6-cyclobutyl(4-(difluoromethoxy)-2-fluorobenzyl)amino)-5-fluoropyrimidin-4-yl)amino)methyl)-3-hydroxypiperidin-1-yl)acetamide |
| A1-7 | A4-1 | A7-15-1<br>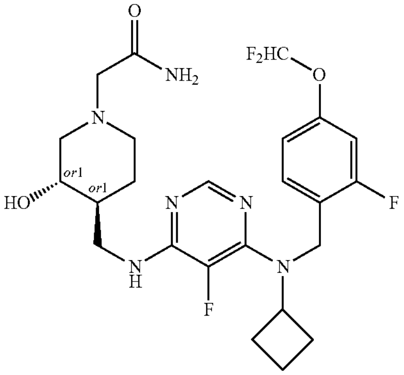<br>rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide<br>1st eluting isomer |
| A1-7 | A4-1 | A7-15-2<br>rel-2-((3R,4R)-4-(((6-(cyclobutyl(4-(difluoromethoxy)-2-fluorobenzyl)amino)-5-fluoropyrimidin-4-yl)amino)methyl)-3-hydroxypiperidin-1-yl)acetamide<br>2nd eluting isomer |

TABLE A-continued

| A1 | A4 | A7 |
| --- | --- | --- |
| A1-8 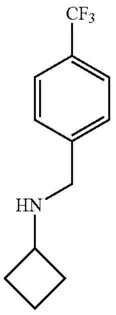 N-(4-(trifluoromethyl)benzyl) cyclobutanamine | A4-1 | A7-16 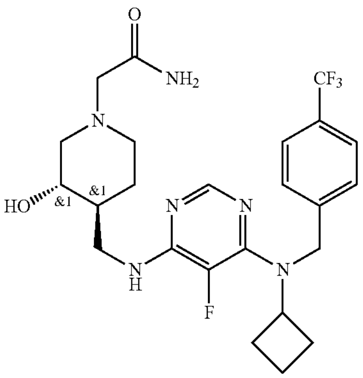 rac-2-((3R,4R)-4-(((6-cyclobutyl(4-(trifluoromethyl)benzyl)amino)-5-fluoropyrimidin-4-yl)amino)methyl)-3-hydroxypiperidin-1-yl)acetamide |
| A1-8 | A4-1 | A7-16-1 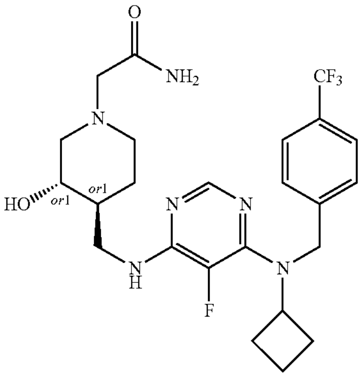 rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide 1st eluting isomer |
| A1-8 | A4-1 | A7-16-2 rel-2-((3R,4R)-4-(((6-(cyclobutyl(4-(trifluoromethyl)benzyl)amino)-5-fluoropyrimidin-4-yl)amino)methyl)-3-hydroxypiperidin-1-yl)acetamide 2nd eluting isomer |

TABLE A-continued

| A1 | A4 | A7 |
|---|---|---|
| A1-9<br>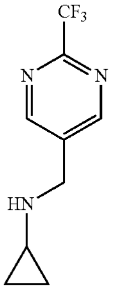<br>N-((2-(trifluoromethyl)pyrimidin-5-yl)methyl)cyclopropanamine | A4-1 | A7-17<br>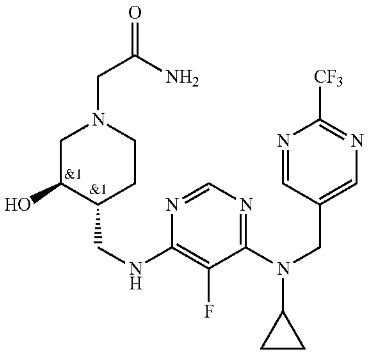<br>rac-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide |
| A1-9 | A4-1 | A7-17-1<br>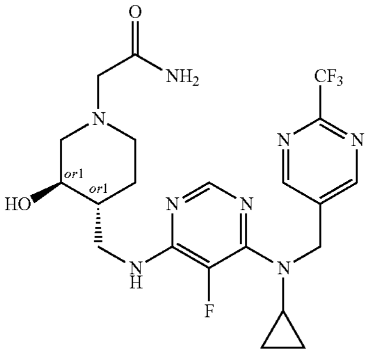<br>rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide 1st eluting isomer |
| A1-9 | A4-1 | A7-17-2<br>rel-2-((3R,4R)-4-(((6-(cyclopropyl((2-(trifluoromethyl)pyrimidin-5-yl)methyl)amino)-5-fluoropyrimidin-4-yl)amino)methyl)-3-hydroxypiperidin-1-yl)acetamide 2nd eluting isomer |

TABLE A-continued

| A1 | A4 | A7 |
| --- | --- | --- |
| A1-10<br>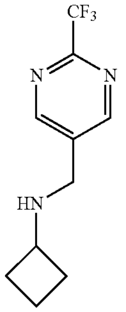<br>N-((2-(trifluoromethyl) pyrimidin-5-yl) methyl)cyclobutanamine | A4-1 | A7-18<br>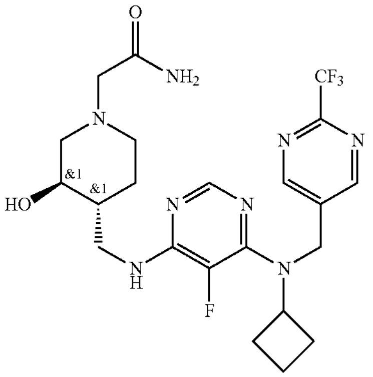<br>rac-2-((3R,4R)-4-(((6-cyclobutyl((2-(trifluoromethyl)pyrimidin-5-yl)methyl)amino)-5-fluoropyrimidin-4-yl)amino)methyl)-3-hydroxypiperidin-1-yl)acetamide |
| A1-10 | A4-1 | A7-18-1<br>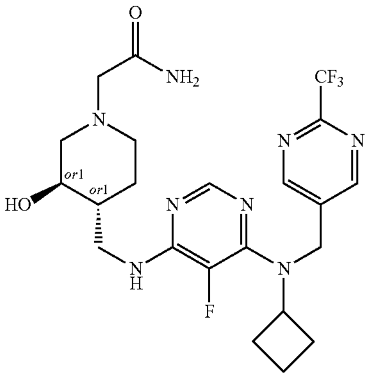<br>rel-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide<br>1st eluting isomer |
| A1-10 | A4-1 | A7-18-2<br>rel-2-((3R,4R)-4-(((6-(cyclobutyl((2-(trifluoromethyl)pyrimidin-5-yl)methyl)amino)-5-fluoropyrimidin-4-yl)amino)methyl)-3-hydroxypiperidin-1-yl)acetamide<br>2nd eluting isomer |

TABLE A-continued

| A1 | A4 | A7 |
| --- | --- | --- |
| A1-11<br>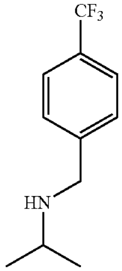<br>N-(4-(trifluoromethyl)benzyl)propan-2-amine | A4-1 | A7-19<br>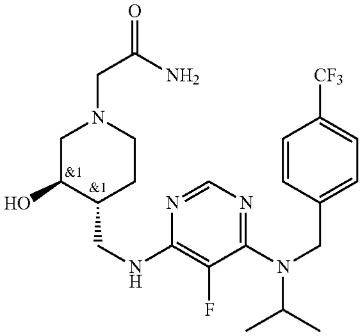<br>rac-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide |
| A1-11 | A4-1 | A7-19-1<br>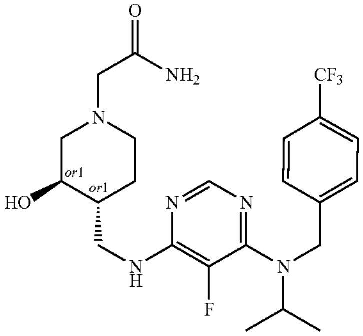<br>rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide<br>1st eluting isomer |
| A1-11 | A4-1 | A7-19-2<br>rel-2-((3R,4R)-4-(((5-fluoro-6-(isopropyl(4-(trifluoromethyl)benzyl)amino)pyrimidin-4-yl)amino)methyl)-3-hydroxypiperidin-1-yl)acetamide<br>2nd eluting isomer |

TABLE A-continued

| A1 | A4 | A7 |
|---|---|---|
| A1-12 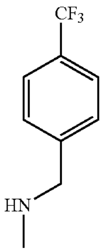 N-methyl-1-(4-(trifluoromethyl)phenyl) methanamine | A4-1 | A7-20 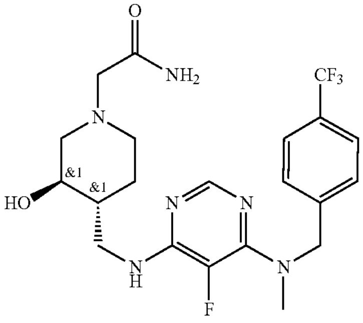 rac-2-((3R,4R)-4-(((5-fluoro-6-(methyl(4-(trifluoromethyl)benzyl)amino) pyrimidin-4-yl)amino)methyl)-3-hydroxypiperidin-1-yl)acetamide |
| A1-12 | A4-1 | A7-20-1 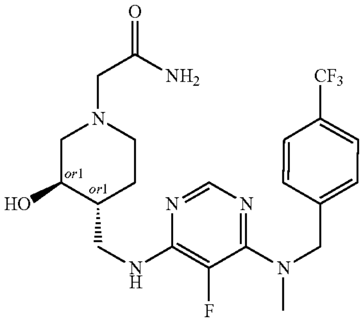 rel-2-((3R,4R)-4-(((5-fluoro-6-(methyl(4-(trifluoromethyl)benzyl)amino) pyrimidin-4-yl)amino)methyl)-3-hydroxypiperidin-1-yl)acetamide 1st eluting isomer |
| A1-12 | A4-1 | A7-20-2 rel-2-((3R,4R)-4-(((5-fluoro-6-(methyl(4-(trifluoromethyl)benzyl)amino) pyrimidin-4-yl)amino)methyl)-3-hydroxypiperidin-1-yl)acetamide 2nd eluting isomer |

TABLE A-continued

| A1 | A4 | A7 |
|---|---|---|
| A1-13<br>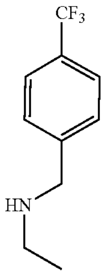<br>N-(4-(trifluoromethyl)benzyl) ethanamine | A4-1 | A7-21<br>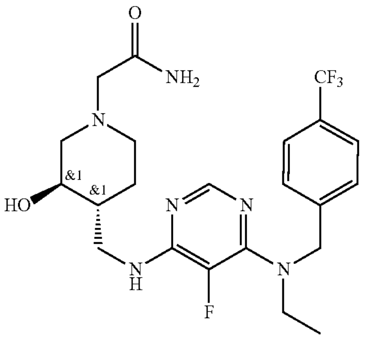<br>rac-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide |
| A1-13 | A4-1 | A7-21-1<br>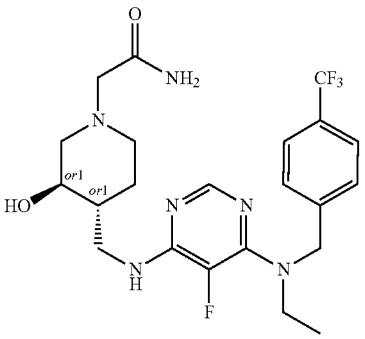<br>rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide<br>1st eluting isomer |
| A1-13 | A4-1 | A7-21-2<br>rel-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide<br>2nd eluting isomer |

TABLE A-continued

| A1 | A4 | A7 |
|---|---|---|
| A1-14<br>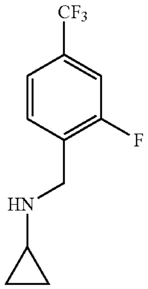<br>N-(2-fluoro-4-(trifluoromethyl)benzyl) cyclopropanamine | A4-1 | A7-22<br>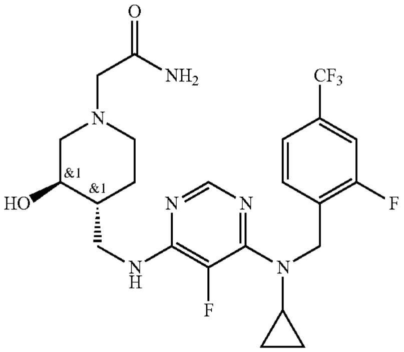<br>rac-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide |
| A1-14 | A4-1 | A7-22-1<br>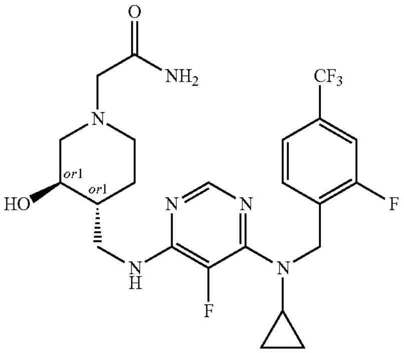<br>rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide<br>2nd eluting isomer |
| A1-14 | A4-1 | A7-22-2<br>rel-2-((3R,4R)-4-(((6-(cyclopropyl(2-fluoro-4-(trifluoromethyl)benzyl)amino)-5-fluoropyrimidin-4-yl)amino)methyl)-3-hydroxypiperidin-1-yl)acetamide<br>1st eluting isomer |

TABLE A-continued

| A1 | A4 | A7 |
| --- | --- | --- |
| A1-15 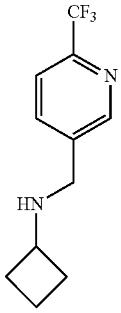 N-((6-(trifluoromethyl)pyridin-3-yl)methyl)cyclobutanamine | A4-1 | A7-23 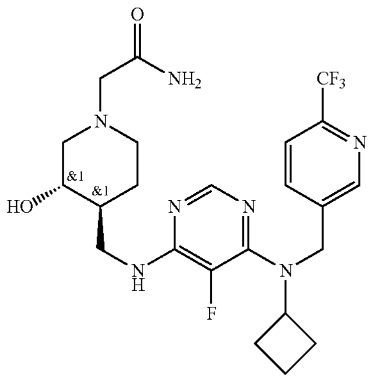 rac-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide |
| A1-15 | A4-1 | A7-23-1 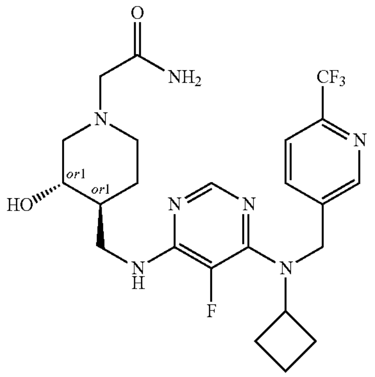 rel-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide 1st eluting isomer |
| A1-15 | A4-1 | A7-23-2 rel-2-((3R,4R)-4-(((6-(cyclobutyl((6-(trifluoromethyl)pyridin-3-yl)methyl)amino)-5-fluoropyrimidin-4-yl)amino)methyl)-3-hydroxypiperidin-1-yl)acetamide 2nd eluting isomer |

TABLE A-continued

| A1 | A4 | A7 |
|---|---|---|
| A1-16<br>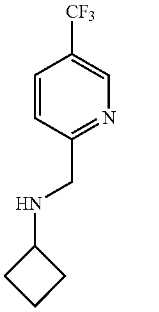<br>N-((5-(trifluoromethyl)pyridin-2-yl)methyl) cyclobutanamine | A4-1 | A7-24<br>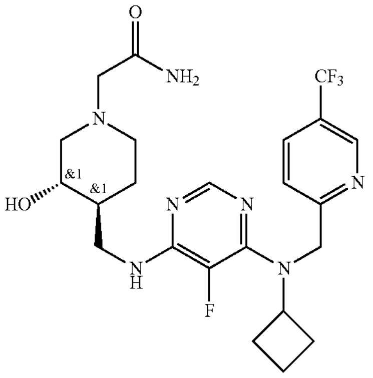<br>rac-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide |
| A1-16 | A4-1 | A7-24-1<br>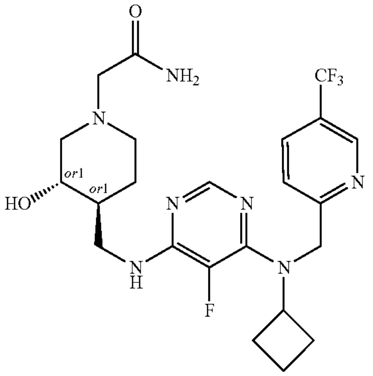<br>rel-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide<br>1$^{st}$ eluting isomer |
| A1-16 | A4-1 | A7-24-2<br>rel-2-((3R,4R)-4-(((6-(cyclobutyl((5-(trifluoromethyl)pyridin-2-yl)methyl)amino)-5-fluoropyrimidin-4-yl)amino)methyl)-3-hydroxypiperidin-1-yl)acetamide<br>2$^{nd}$ eluting isomer |

TABLE A-continued

| A1 | A4 | A7 |
|---|---|---|
| A1-17<br>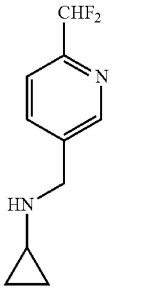<br>N-((6-(difluoromethyl)pyridin-3-yl)methyl)cyclopropanamine | A4-1 | A7-25<br>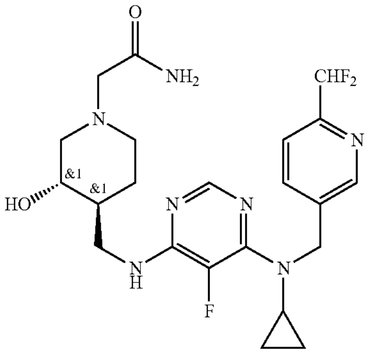<br>rac-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide |
| A1-17 | A4-1 | A7-25-1<br>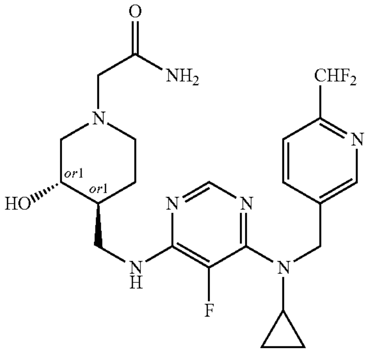<br>rel-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide<br>1st eluting isomer |
| A1-17 | A4-1 | A7-25-2<br>rel-2-((3R,4R)-4-(((6-(cyclopropyl((6-(difluoromethyl)pyridin-3-yl)methyl)amino)-5-fluoropyrimidin-4-yl)amino)methyl)-3-hydroxypiperidin-1-yl)acetamide<br>2nd eluting isomer |

TABLE A-continued

| A1 | A4 | A7 |
|---|---|---|
| A1-18<br>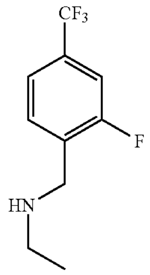<br>N-(2-fluoro-4-(trifluoromethyl)benzyl) ethanamine | A4-1 | A7-26<br>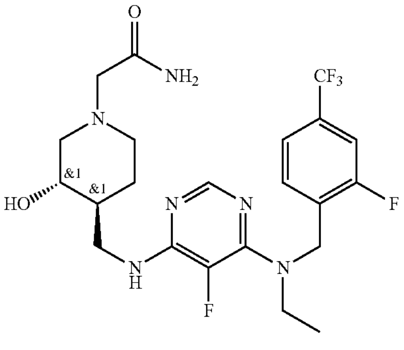<br>rac-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide |
| A1-18 | A4-1 | A7-26-1<br>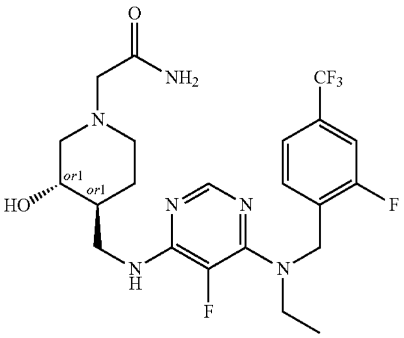<br>rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide<br>2nd eluting isomer |
| A1-18 | A4-1 | A7-26-2<br>rel-2-((3R,4R)-4-(((6-(ethyl(2-fluoro-4-(trifluoromethyl)benzyl)amino)-5-fluoropyrimidin-4-yl)amino)methyl)-3-hydroxypiperidin-1-yl)acetamide<br>1st eluting isomer |

TABLE A-continued

| A1 | A4 | A7 |
|---|---|---|
| A1-19<br>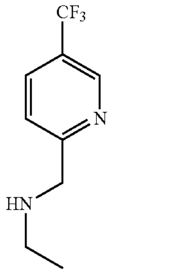<br>N-((5-(trifluoromethyl)pyridin-2-yl)methyl)ethanamine | A4-1 | A7-27<br>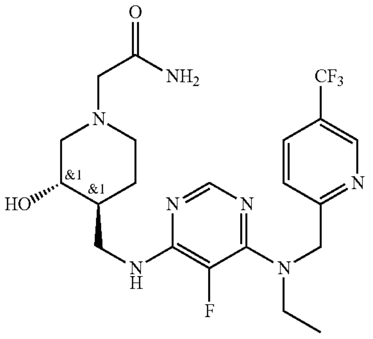<br>rac-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide |
| A1-19 | A4-1 | A7-27-1<br>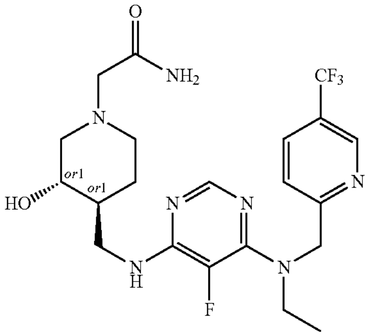<br>rel-2-((3R,4R)-4-(((6-ethyl((5-(trifluoromethyl)pyridin-2-yl)methyl)amino)-5-fluoropyrimidin-4-yl)amino)methyl)-3-hydroxypiperidin-1-yl)acetamide<br>1$^{st}$ eluting isomer |
| A1-19 | A4-1 | A7-27-2<br>rel-2-((3R,4R)-4-(((6-(ethyl((5-(trifluoromethyl)pyridin-2-yl)methyl)amino)-5-fluoropyrimidin-4-yl)amino)methyl)-3-hydroxypiperidin-1-yl)acetamide<br>2$^{nd}$ eluting isomer |

TABLE A-continued

| A1 | A4 | A7 |
|---|---|---|
| A1-4<br>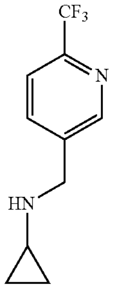<br>N-((6-(trifluoromethyl)pyridin-3-yl)methyl)cyclopropanamine | A4-1 | A7-28<br>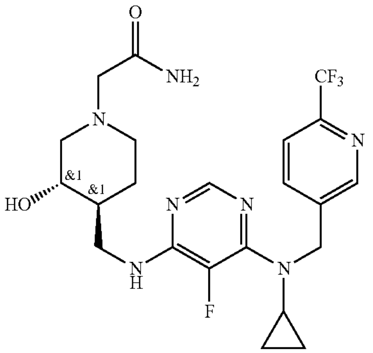<br>rac-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide |
| A1-4 | A4-1 | A7-28-1<br>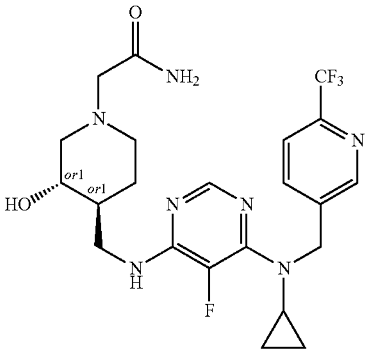<br>rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide<br>1st eluting isomer |
| A1-4 | A4-1 | A7-28-2<br>rel-2-((3R,4R)-4-(((6-(cyclopropyl((6-(trifluoromethyl)pyridin-3-yl)methyl)amino)-5-fluoropyrimidin-4-yl)amino)methyl)-3-hydroxypiperidin-1-yl)acetamide<br>2nd eluting isomer |

TABLE A-continued

| A1 | A4 | A7 |
| --- | --- | --- |
| A1-20<br>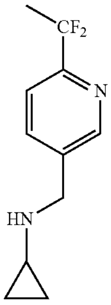<br>N-((6-1,1-difluoroethyl)pyridin-3-yl)methyl)cyclopropanamine | A4-1 | A7-29<br>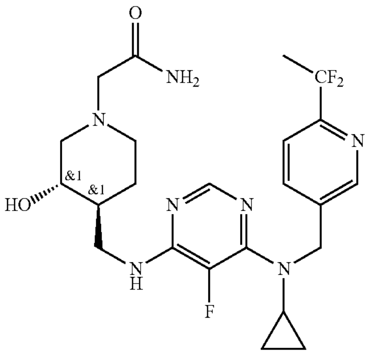<br>rac-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide |
| A1-20 | A4-1 | A7-29-1<br>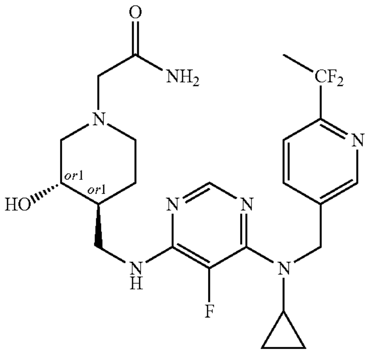<br>rel-2-((3R,4R)-4-(((6-cyclopropyl((6-(1,1-difluoroethyl)pyridin-3-yl)methyl)amino)-5-fluoropyrimidin-4-yl)amino)methyl)-3-hydroxypiperidin-1-yl)acetamide<br>$1^{st}$ eluting isomer |
| A1-20 | A4-1 | A7-29-2<br>rel-2-((3R,4R)-4-(((6-(cyclopropyl((6-(1,1-difluoroethyl)pyridin-3-yl)methyl)amino)-5-fluoropyrimidin-4-yl)amino)methyl)-3-hydroxypiperidin-1-yl)acetamide<br>$2^{nd}$ eluting isomer |

TABLE A-continued
| A1 | A4 | A7 |
|---|---|---|
| A1-21<br>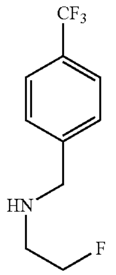 | A4-1 | A7-30<br>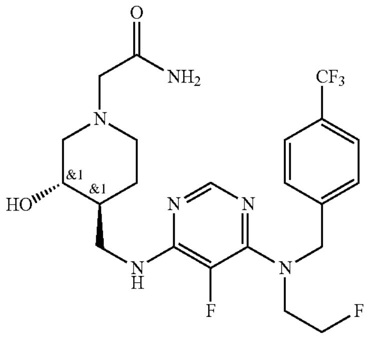<br>rac-2-((3R,4R)-4-(((5-fluoro-6-((2-fluoroethyl)(4-trifluoromethyl)benzyl)amino)pyrimidin-4-yl)amino)methyl)-3-hydroxypiperidin-1-yl)acetamide |
| A1-22a<br>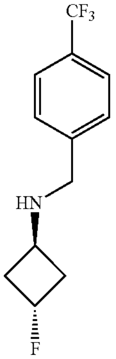<br>(1r,3r)-3-fluoro-N-(4-(trifluoromethyl)benzyl) cyclobutan-1-amine | A4-1 | A7-31<br>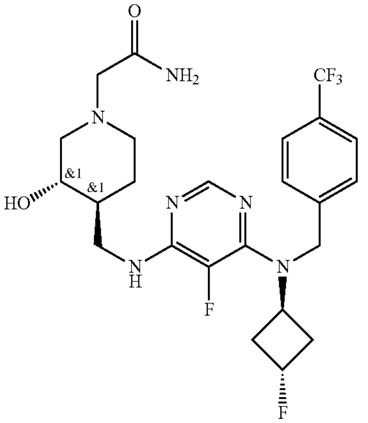<br>rac-2-((3R,4R)-4-(((5-fluoro-6-(((1r,3S)-3-fluorocyclobutyl)(4-(trifluoromethyl)benzyl)amino)pyrimidin-4-yl)amino)methyl)-3-hydroxypiperidin-1-yl)acetamide |

TABLE A-continued

| A1 | A4 | A7 |
|---|---|---|
| A1-22b 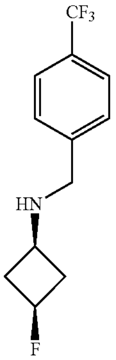 (1s,3s)-3-fluoro-N-(4-(trifluoromethyl)benzyl) cyclobutan-1-amine | A4-1 | A7-32 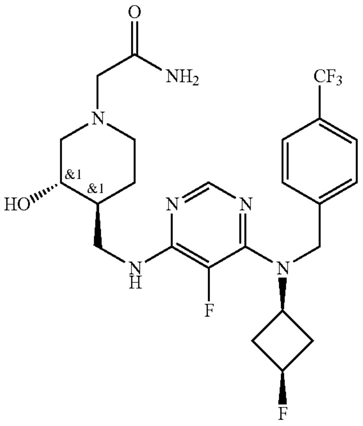 rac-2-((3R,4R)-4-(((5-fluoro-6-(((1s,3R)-3-fluorocyclobutyl)(4-(trifluoromethyl)benzyl)amino)pyrimidin-4-yl)amino)methyl)-3-hydroxypiperidin-1-yl)acetamide |
| A1-23 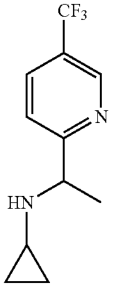 N-(1-(5-(trifluoromethyl)pyridin-2-yl)ethyl)cyclopropanamine | A4-2 | A7-33 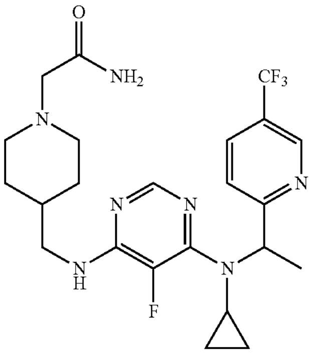 2-(4-(((6-cyclopropyl(1-(5-(trifluoromethyl)pyridin-2-yl)ethyl)amino)-5-fluoropyrimidin-4-yl)amino)methyl)piperidin-1-yl)acetamide |
| A1-24 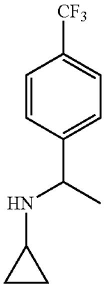 N-(1-(4-(trifluoromethyl)phenyl) ethyl)cyclopropanamine | A4-2 | A7-34 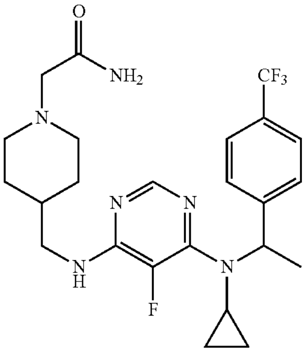 2-(4-(((6-cyclopropyl(1-(4-(trifluoromethyl)phenyl)ethyl)amino)-5-fluoropyrimidin-4-yl)amino)methyl)piperidin-1-yl)acetamide |

TABLE A-continued

| A1 | A4 | A7 |
|---|---|---|
| A1-3<br>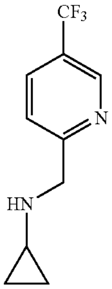<br>N-((5-(trifluoromethyl)pyridin-2-yl)methyl)cyclopropanamine | A4-2 | A7-35<br>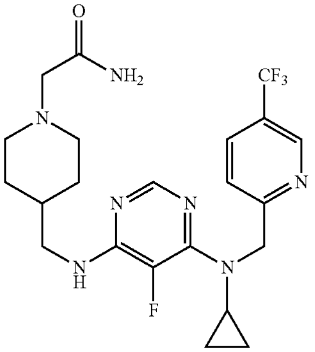<br>2-(4-(((6-cyclopropyl((5-(trifluoromethyl)pyridin-2-yl)methyl)amino)-5-fluoropyrimidin-4-yl)amino)methyl)piperidin-1-yl)acetamide |
| A1-25<br>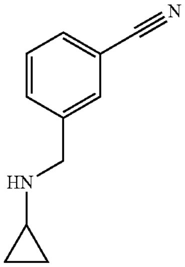<br>3-((cyclopropylamino)methyl)benzonitrile | A4-2 | A7-36<br>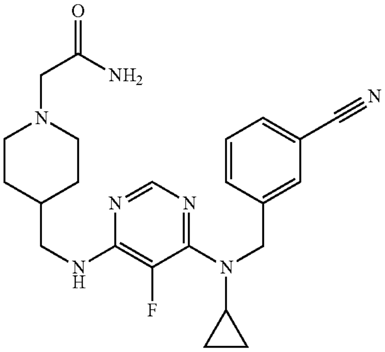<br>2-(4-(((6-((3-cyanobenzyl)(cyclopropyl)amino)-5-fluoropyrimidin-4-yl)amino)methyl)piperidin-1-yl)acetamide |
| A1-5<br>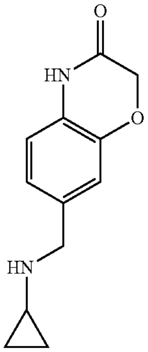<br>7-((cyclopropylamino)methyl)-2H-benzo[b][1,4]oxazin-3(4H)-one | A4-2 | A7-37<br>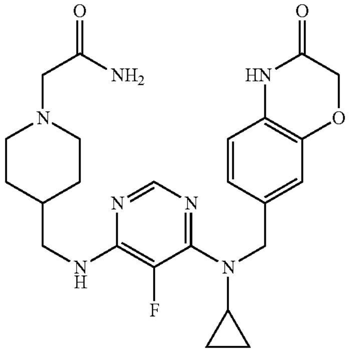<br>2-(4-(((6-(cyclopropyl((3-oxo-3,4-dihydro-2H-benzo[b][1,4]oxazin-7-yl)methyl)amino)-5-fluoropyrimidin-4-yl)amino)methyl)piperidin-1-yl)acetamide |

TABLE A-continued

| A1 | A4 | A7 |
|---|---|---|
| A1-26 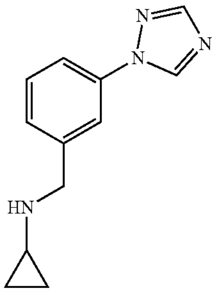 N-(3-(1H-1,2,4-triazol-1-yl)benzyl) cyclopropanamine | A4-2 | A7-38 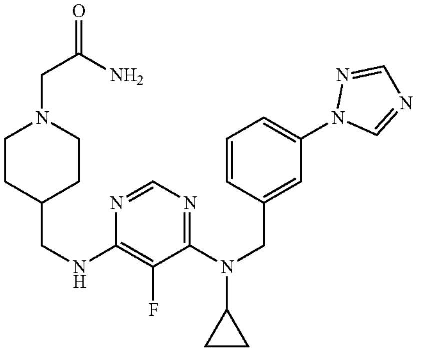 2-(4-(((6-((3-(1H-1,2,4-triazol-1-yl)benzyl)(cyclopropyl)amino)-5-fluoropyrimidin-4-yl)amino)methyl)piperidin-1-yl)acetamide |
| A1-1 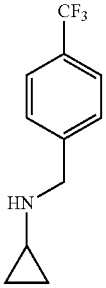 N-(4-(trifluoromethyl)benzyl) cyclopropanamine | A4-2 | A7-39 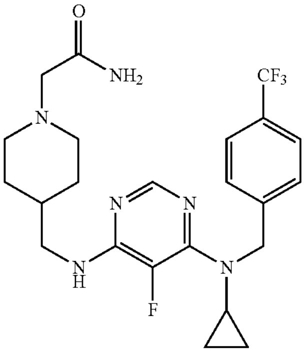 2-(4-(((6-(cyclopropyl(4-(trifluoromethyl)benzyl)amino)-5-fluoropyrimidin-4-yl)amino)methyl)piperidin-1-yl)acetamide |
| A1-27 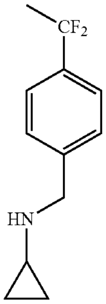 N-(4-(1,1-difluoromethyl)benzyl) cyclopropanamine | A4-1 | A7-40 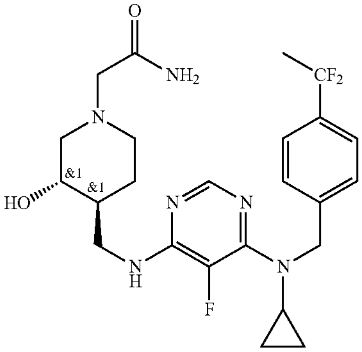 rac-2-((3R,4R)-4-(((6-cyclopropyl(4-(1,1-difluoroethyl)benzyl)amino)-5-fluoropyrimidin-4-yl)amino)methyl)-3-hydroxypiperidin-1-yl)acetamide |

TABLE A-continued

| A1 | A4 | A7 |
|---|---|---|
| A1-28 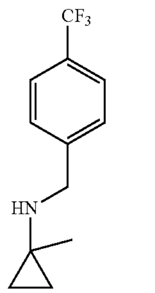 1-methyl-N-(4-(trifluoromethyl)benzyl)cyclopropan-1-amine | A4-1 | A7-41 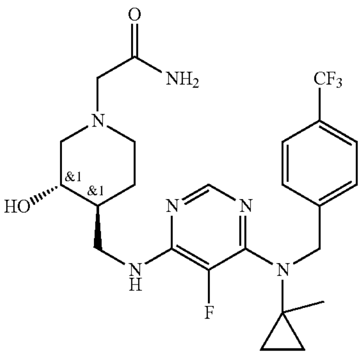 rac-2-((3R,4R)-4-(((5-fluoro-6-((1-methylcyclopropyl)(4-(trifluoromethyl)benzyl)amino)pyrimidin-4-yl)amino)methyl)-3-hydroxypiperidin-1-yl)acetamide |
| A1-29 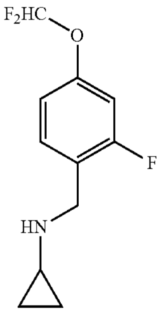 N-(4-(difluoromethoxy)-2-fluorobenzyl)cyclopropanamine | A4-1 | A7-42 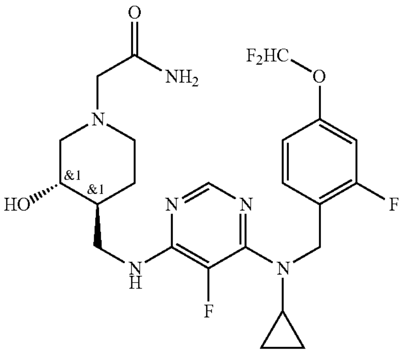 rac-2-((3R,4R)-4-(((6-(cyclopropyl(4-(difluoromethoxy)-2-fluorobenzyl)amino)-5-fluoropyrimidin-4-yl)amino)methyl)-3-hydroxypiperidin-1-yl)acetamide |
| A1-30 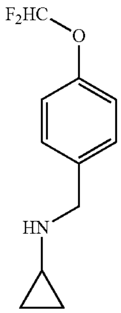 N-(4-(difluoromethoxy)benzyl)cyclopropanamine | A4-1 | A7-43 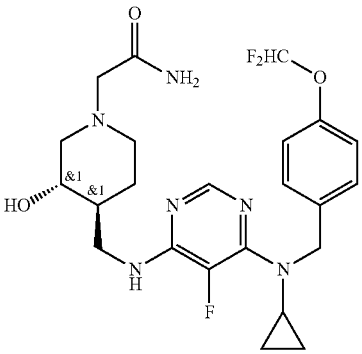 rac-2-((3R,4R)-4-(((6-(cyclopropyl(4-(difluoromethoxy)benzyl)amino)-5-fluoropyrimidin-4-yl)amino)methyl)-3-hydroxypiperidin-1-yl)acetamide |

TABLE A-continued

| A1 | A4 | A7 |
|---|---|---|
| A1-1 | A4-9<br>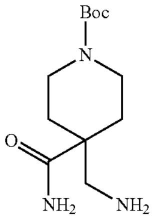<br>tert-butyl 4-(aminomethyl)-4-carbamoylpiperidine-1-carboxylate | A7-44<br>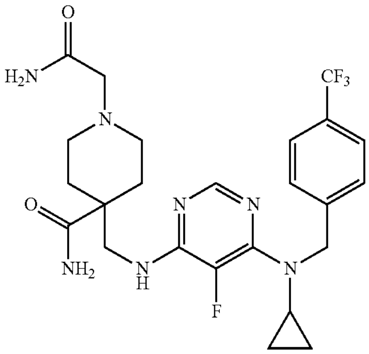<br>1-(2-amino-2-oxoethyl)-4-(((6-(cyclopropyl(4-(trifluoromethyl)benzyl)amino)-5-fluoropyrimidin-4-yl)amino)methyl)piperidine-4-carboxamide |
| A1-4 | A4-10<br>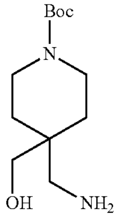<br>tert-butyl 4-(aminomethyl)-4-(hydroxymethyl)piperidine-1-carboxylate | A7-45<br>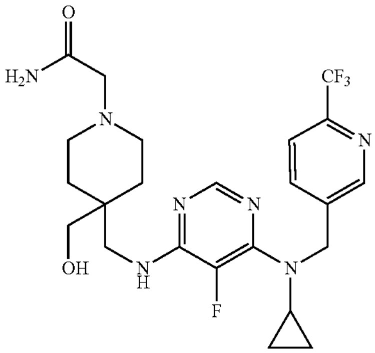<br>2-(4-(((6-(cyclopropyl((6-(trifluoromethyl)pyridin-3-yl)methyl)amino)-5-fluoropyrimidin-4-yl)amino)methyl)-4-(hydroxymethyl)piperidin-1-yl)acetamide |
| A1-31<br>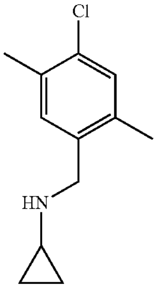<br>N-(4-chloro-2,5-dimethylbenzyl)cyclopropanamine | A4-2 | A7-46<br>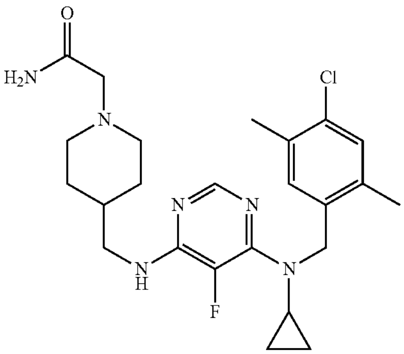<br>2-(4-(((6-((4-chloro-2,5-dimethylbenzyl)(cyclopropyl)amino)-5-fluoropyrimidin-4-yl)amino)methyl)piperidin-1-yl)acetamide |

TABLE A-continued

| A1 | A4 | A7 |
|---|---|---|
| A1-32<br>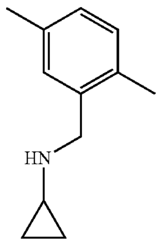<br>N-(2,5-dimethylbenzyl)cyclopropanamine | A4-2 | A7-47<br>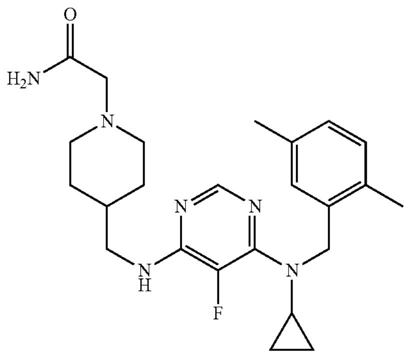<br>2-(4-(((6-(cyclopropyl(2,5-dimethylbenzyl))amino)-5-fluoropyrimidin-4-yl)amino)methyl)piperidin-1-yl)acetamide |
| A1-1 | A4-11<br>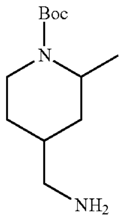<br>tert-butyl 4-(aminomethyl)-2-methylpiperidine-1-carboxylate | A7-48<br>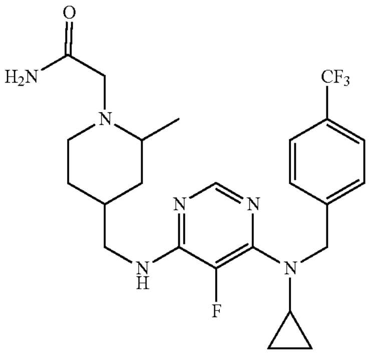<br>2-(4-(((6-(cyclopropyl(4-(trifluoromethyl)benzyl)amino)-5-fluoropyrimidin-4-yl)amino)methyl)-2-methylpiperidin-1-yl)acetamide |
| A1-1 | A4-12<br>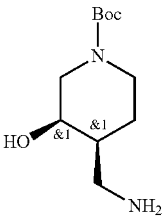<br>rac-tert-butyl (3R,4S)-4-(aminomethyl)-3-hydroxypiperidine-1-carboxylate | A7-49<br>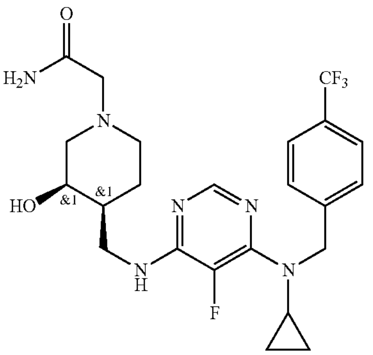<br>rac-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide |

TABLE A-continued

| A1 | A4 | A7 |
|---|---|---|
| A1-1 | A4-13<br>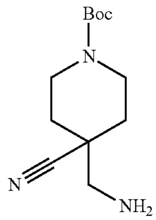<br>tert-butyl 4-(aminomethyl)-4-cyanopiperidine-1-carboxylate | A7-50<br>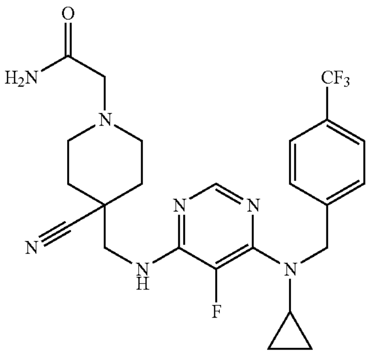<br>2-(4-cyano-4-(((6-(cyclopropyl(4-(trifluoromethyl)benzyl)amino)-5-fluoropyrimidin-4-yl)amino)methyl)piperidin-1-yl)acetamide |
| A1-1 | A4-10 | A7-51<br>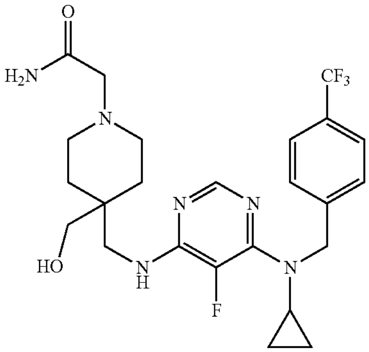<br>2-(4-(((6-(cyclopropyl(4-(trifluoromethyl)benzyl)amino)-5-fluoropyrimidin-4-yl)amino)methyl)-4-(hydroxymethyl)piperidin-1-yl)acetamide |
| A1-3 | A4-10 | A7-52<br>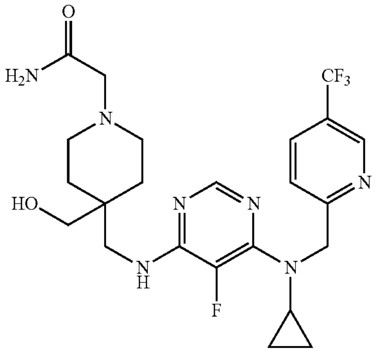<br>2-(4-(((6-(cyclopropyl((5-(trifluoromethyl)pyridin-2-yl)methyl)amino)-5-fluoropyrimidin-4-yl)amino)methyl)-4-(hydroxymethyl)piperidin-1-yl)acetamide |

TABLE A-continued

| A1 | A4 | A7 |
|---|---|---|
| A1-33<br>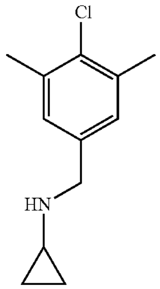<br>N-(4-chloro-3,5-dimethylbenzyl) cyclopropanamine | A4-2 | A7-53<br>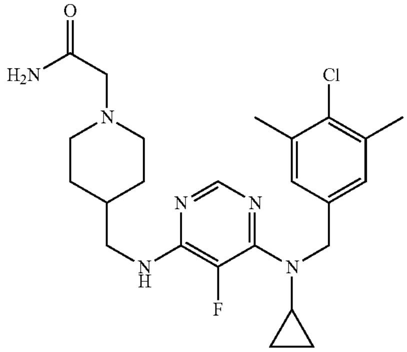<br>2-(4-(((6-((4-chloro-3,5-dimethylbenzyl)(cyclopropyl)amino)-5-fluoropyrimidin-4-yl)amino)methyl)piperidin-1-yl)acetamide |
| A1-34<br>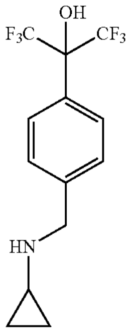<br>2-(4-((cyclopropylamino) methyl)phenyl)-1,1,1,3,3,3-hexafluoropropan-2-ol | A4-1 | A7-54<br>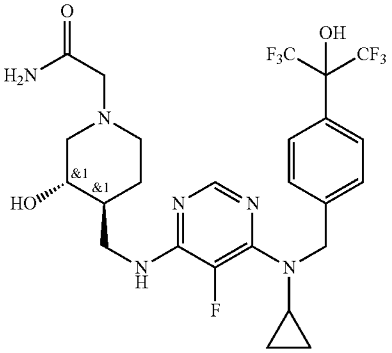<br>rac-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide |
| A1-34 | A4-1 | A7-54-1<br>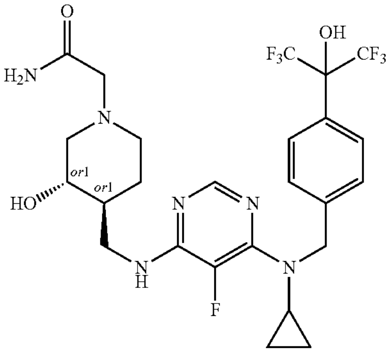<br>rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide 1st eluting isomer |

TABLE A-continued

| A1 | A4 | A7 |
|---|---|---|
| A1-34 | A4-1 | A7-54-2<br>rel-2-((3R,4R)-4-(((6-(cyclopropyl(4-(1,1,1,3,3,3-hexafluoro-2-hydroxypropan-2-yl)benzyl)amino)-5-fluoropyrimidin-4-yl)amino)methyl)-3-hydroxypiperidin-1-yl)acetamide<br>2nd eluting isomer |
| A1-1 | A4-1″<br>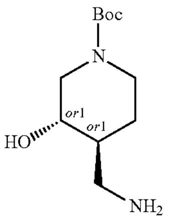<br>rel-tert-butyl (3R,4R)-4-(aminomethyl)-3-hydroxypiperidine-1-carboxylate<br>Enantiomerically enriched | A7-55″<br>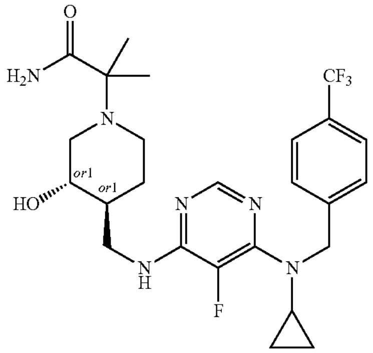<br>rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-methylpropanamide<br>Enantiomerically enriched |
| A1-35<br>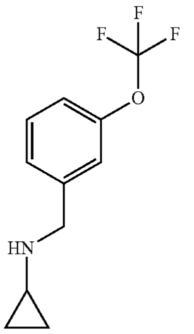<br>N-(3-(trifluoromethoxy)benzyl)cyclopropanamine | A4-1 | A7-56<br>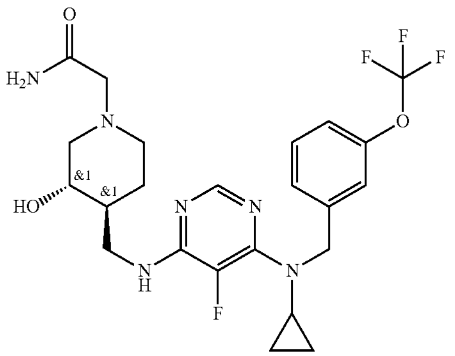<br>rac-2-((3R,4R)-4-(((6-(cyclopropyl(3-(trifluoromethoxy)benzyl)amino)-5-fluoropyrimidin-4-yl)amino)methyl)-3-hydroxypiperidin-1-yl)acetamide |

TABLE A-continued

| A1 | A4 | A7 |
|---|---|---|
| A1-13 | A4-1" Enantiomerically enriched | A7-57" 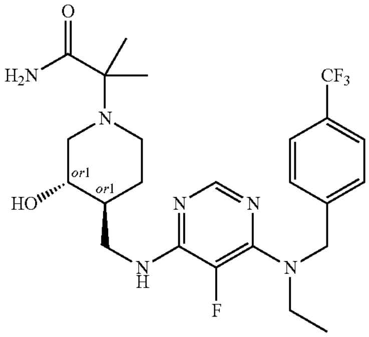 rel-2-((3R,4R)-4-(((6-(ethyl(4-(trifluoromethyl)benzyl)amino)-5-fluoropyrimidin-4-yl)amino)methyl)-3-hydroxypiperidin-1-yl)-2-methylpropanamide Enantiomerically enriched |
| A1-36 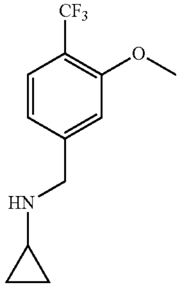 N-(3-methoxy-4-(trifluoromethyl)benzyl) cyclopropanamine | A4-1 | A7-58 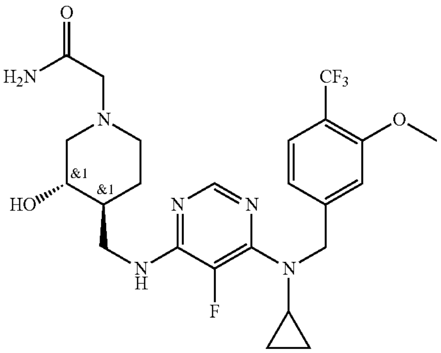 rac-2-((3R,4R)-4-(((6-(cyclopropyl(3-methoxy-4-(trifluoromethyl)benzyl)amino)-5-fluoropyrimidin-4-yl)amino)methyl)-3-hydroxypiperidin-1-yl)acetamide |
| A1-13 | A4-1 | A7-59 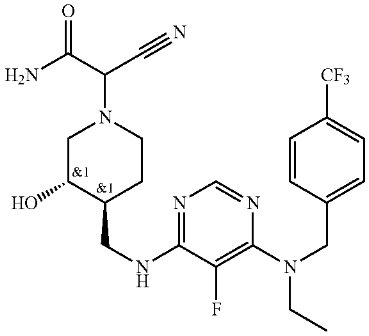 rac-2-cyano-2-((3R,4R)-4-(((6-(ethyl(4-(trifluoromethyl)benzyl)amino)-5-fluoropyrimidin-4-yl)amino)methyl)-3-hydroxypiperidin-1-yl)acetamide |

TABLE A-continued

| A1 | A4 | A7 |
|---|---|---|
| A1-37<br>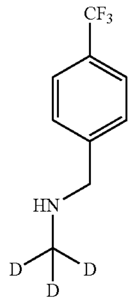<br>N-(4-(trifluoromethyl)benzyl) methan-d3-amine | A4-1 | A7-60<br>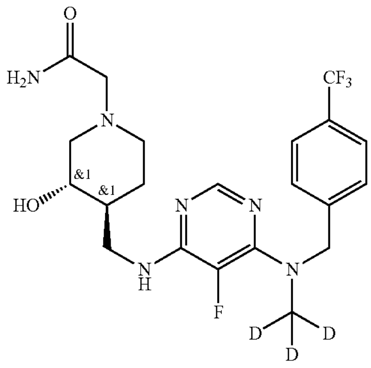<br>rac-2-((3R,4R)-4-(((5-fluoro-6-((methyl-d3)(4-(trifluoromethyl)benzyl)amino)pyrimidin-4-yl)amino)methyl)-3-hydroxypiperidin-1-yl)acetamide |
| A1-40<br>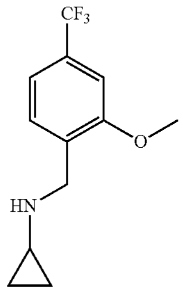<br>N-(2-methoxy-4-(trifluoromethyl)benzyl) cyclopropanamine | A4-1 | A7-61<br>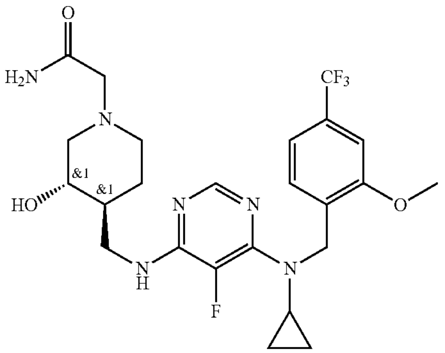<br>rac-2-((3R,4R)-4-(((6-(cyclopropyl(2-methoxy-4-(trifluoromethyl)benzyl)amino)-5-fluoropyrimidin-4-yl)amino)methyl)-3-hydroxypiperidin-1-yl)acetamide |
| A1-66<br>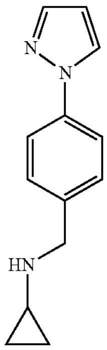<br>N-(4-(1H-pyrazol-1-yl)benzyl) cyclopropanamine | A4-1 | A7-86<br>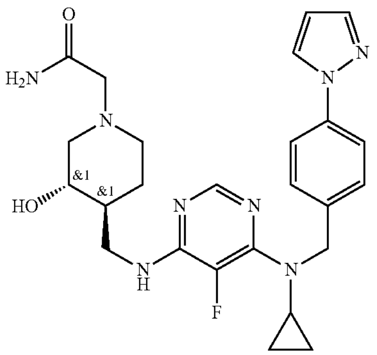<br>rac-2-((3R,4R)-4-(((6-((4-(1H-pyrazol-1-yl)benzyl)(cyclopropyl)amino)-5-fluoropyrimidin-4-yl)amino)methyl)-3-hydroxypiperidin-1-yl)acetamide |

TABLE A-continued

| A1 | A4 | A7 |
|---|---|---|
| A1-1 | A4-14 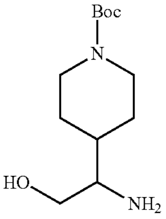 tert-butyl 4-(1-amino-2-hydroxyethyl)piperidine-1-carboxylate | A7-87 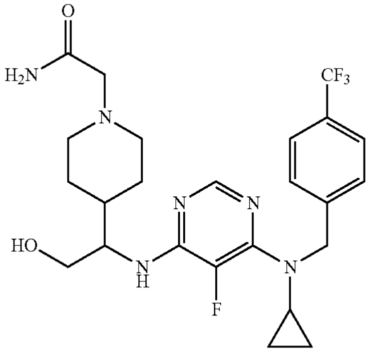 2-(4-(1-((6-(cyclopropyl(4-(trifluoromethyl)benzyl)amino)-5-fluoropyrimidin-4-yl)amino)-2-hydroxyethyl)piperidin-1-yl)acetamide |

General Method 2A—Synthesis with Substituted Bromoacetamides

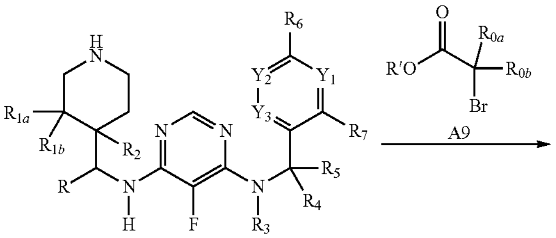

A6

-continued

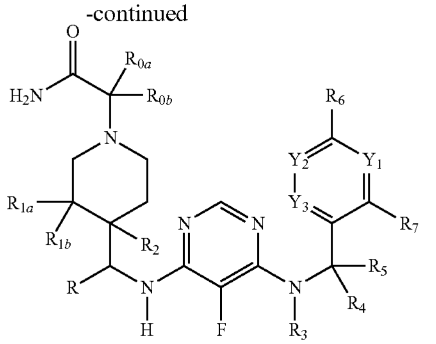

A7

A7 has also been obtained by alkylation of A6 with A9, to give A10, followed by subsequent aminolysis ($NH_3$ in MeOH) to yield A7. However, in addition to the alkylating procedure described above, the alkylation may require an elevated temperature (up to 100° C.).

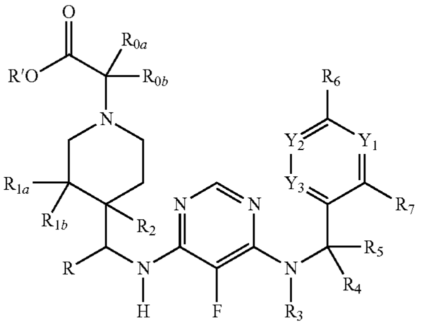

A10

When A7 was a mixture of stereoisomers they were often (but not always) subjected to chiral resolution (chromatography) to obtain the single stereoisomers as end products.

Example A7-62

Synthesis of rac-2-((3R,4R)-4-(((6-(ethyl(4-(trifluoromethyl)benzyl)amino)-5-fluoropyrimidin-4-yl)amino)methyl)-3-hydroxypiperidin-1-yl)-2-(pyridin-4-yl)acetamide, A7-62

Scheme A7-62

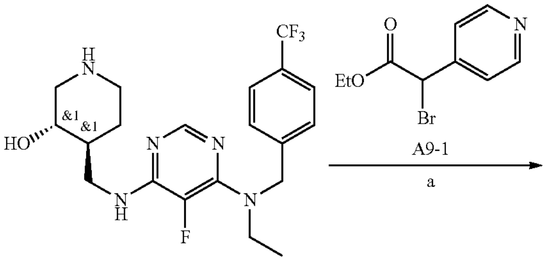

A6-1

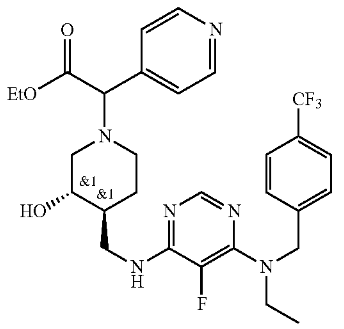

A10-1

-continued

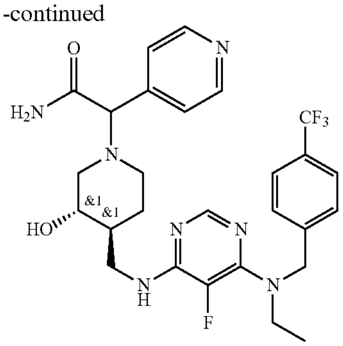

A7-62 a) DIEA, DMF. b) $NH_3$, MeOH.

rac-Ethyl 2-((3R,4R)-4-(((6-(ethyl(4-(trifluoromethyl)benzyl)amino)-5-fluoropyrimidin-4-yl)amino)methyl)-3-hydroxypiperidin-1-yl)-2-(pyridin-4-yl)acetate, A10-1

A10-1

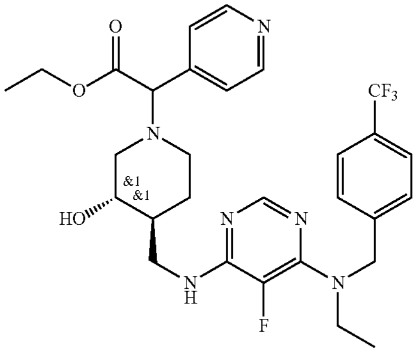

DIEA (0.89 ml, 5.1 mmol) and ethyl 2-bromo-2-(4-pyridyl)acetate (229 mg, 0.94 mmol) were in turn added to a solution of A6-1 (425 mg, 0.85 mmol) in DMF (11 mL) and the reaction was stirred on at rt. The reaction was quenched with $H_2O$ (60 mL) and then extracted with EA (3×30 mL). The combined organic layers were washed with brine (3×15 mL), dried ($Na_2SO_4$), filtered and concentrated in vacuo. The residue was then purified by Flash CC (DCM:MeOH=100:0 to 93:7) to afford A10-1 (218 mg, 0.37 mmol).

rac-2-((3R,4R)-4-(((6-(Ethyl(4-(trifluoromethyl)benzyl)amino)-5-fluoropyrimidin-4-yl)amino)methyl)-3-hydroxypiperidin-1-yl)-2-(pyridin-4-yl)acetamide, A7-62

A7-62

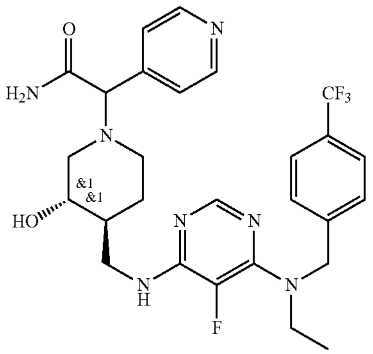

A10-1 (218 mg, 0.37 mmol) was dissolved in 7N ammonia in MeOH (10 mL) and the resulting solution was stirred at 80° C. for 45 h in a closed flask. The solution was concentrated in vacuo and the residue purified by chromatography; first C18 column ($H_2O$:MeOH=100:0 to 0:100) and thereafter the purified material was subjected to Flash CC (DCM:MeOH=10:0 to 9:1) to afford A7-62 (18 mg, 32 μmol).

The following examples were synthesized according to General Method 2A.

TABLE 2A

| A6 | A9 | A7 |
|---|---|---|
| A6-2 | A9-1 | A7-63 |
| 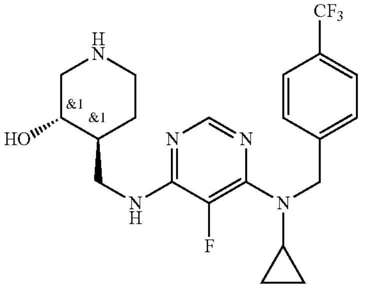 rac-(3R,4R)-4-(((6-(cyclopropyl(4-(trifluoromethyl)benzyl)amino)-5-fluoropyrimidin-4-yl)amino)methyl)piperidin-3-ol | 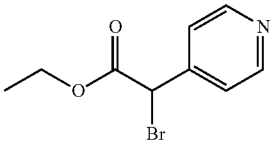 ethyl 2-bromo-2-(pyridin-4-yl)acetate | 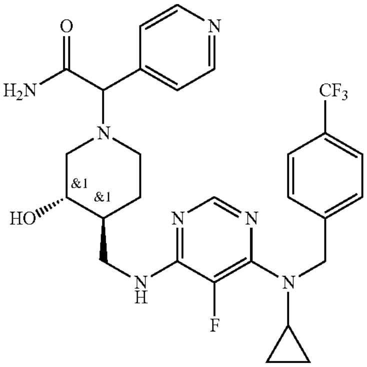 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(pyridin-4-yl)acetamide |

TABLE 2A-continued

| A6 | A9 | A7 |
|---|---|---|
| A6-5 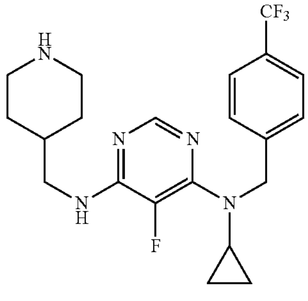 N4-cyclopropyl-5-fluoro-N6-(piperidin-4-ylmethyl)-N4-(4-(trifluoromethyl)benzyl) pyrimidine-4,6-diamine | A9-2 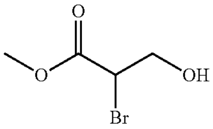 methyl 2-bromo-3-hydroxypropanoate | A7-64 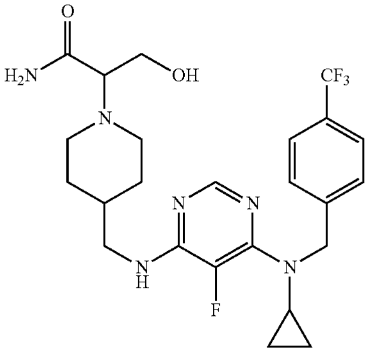 2-(4-(((6-(cyclopropyl(4-(trifluoromethyl)benzyl)amino)-5-fluoropyrimidin-4-yl)amino)methyl)piperidin-1-yl)-3-hydroxypropanamide |
| A6-2 | A9-2 | A7-65 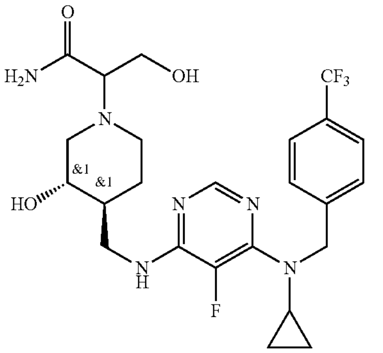 rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-3-hydroxypropanamide |

TABLE 2A-continued

| A6 | A9 | A7 |
|---|---|---|
| A6-1''<br>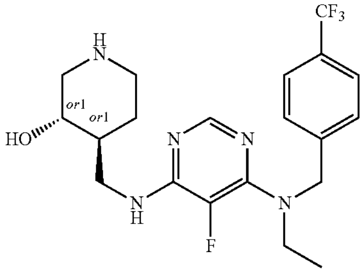<br>rel-(3R,4R)-4-(((6-(ethyl(4-(trifluoromethyl)benzyl)amino)-5-fluoropyrimidin-4-yl)amino)methyl)piperidin-3-ol<br>Enantiomerically enriched | A9-2 | A7-66-1<br>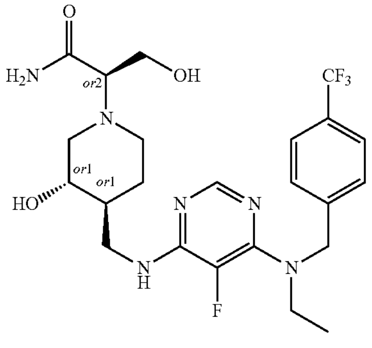<br>rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>OR<br>rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>1st eluting major isomer |
| A6-1'' | A9-2 | A7-66-2<br>rel-(R)-2-((3R,4R)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>OR<br>rel-(R)-2-((3S,4S)-4-(((6-(ethyl(4-(trifluoromethyl)benzyl)amino)-5-fluoropyrimidin-4-yl)amino)methyl)-3-hydroxypiperidin-1-yl)-3-hydroxypropanamide<br>2nd eluting major isomer |

TABLE 2A-continued

| A6 | A9 | A7 |
|---|---|---|
| A6-1" | A9-3<br>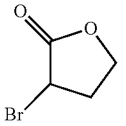<br>3-bromodihydrofuran-2(3H)-one | A7-67"<br>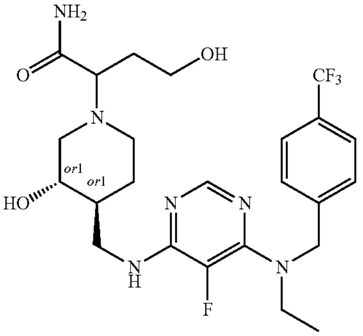<br>rel-2-((3R,4R)-4-(((6-(ethyl(4-(trifluoromethyl)benzyl)amino)-5-fluoropyrimidin-4-yl)amino)methyl)-3-hydroxypiperidin-1-yl)-4-hydroxybutanamide Enantiomerically enriched |
| A6-6<br>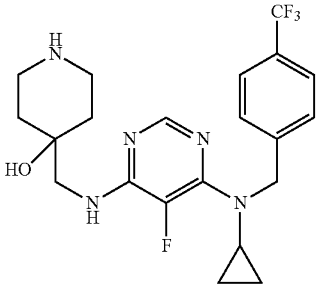<br>4-(((6-(cyclopropyl(4-(trifluoromethyl)benzyl)amino)-5-fluoropyrimidin-4-yl)amino)methyl)piperidin-4-ol | A9-2 | A7-68<br>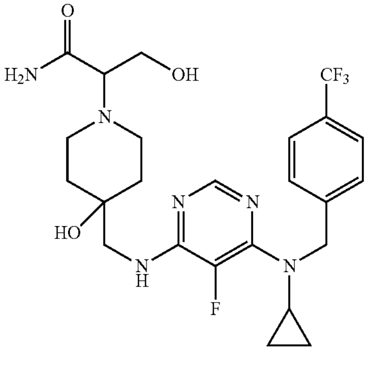<br>2-(4-(((6-(cyclopropyl(4-(trifluoromethyl)benzyl)amino)-5-fluoropyrimidin-4-yl)amino)methyl)-4-hydroxypiperidin-1-yl)-3-hydroxypropanamide |

TABLE 2A-continued

| A6 | A9 | A7 |
| --- | --- | --- |
| A6-2" 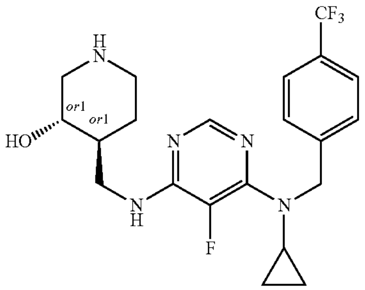 rel-(3R,4R)-4-(((6-(cyclopropyl(4-(trifluoromethyl)benzyl)amino)-5-fluoropyrimidin-4-yl)amino)methyl)piperidin-3-ol Enantiomerically enriched | A9-4 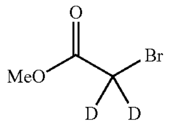 | A7-69" 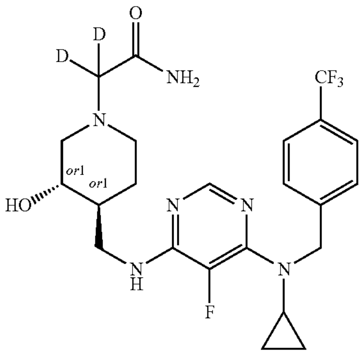 rel-2-((3R,4R)-4-(((6-(cyclopropyl(4-(trifluoromethyl)benzyl)amino)-5-fluoropyrimidin-4-yl)amino)methyl)-3-hydroxypiperidin-1-yl)acetamide-2,2-$d_2$ Enantiomerically enriched |
| A6-7 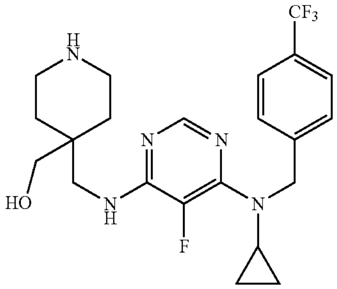 (4-(((6-(cyclopropyl(4-(trifluoromethyl)benzyl)amino)-5-fluoropyrimidin-4-yl)amino)methyl)piperidin-4-yl)MeOH | A9-2 | A7-70 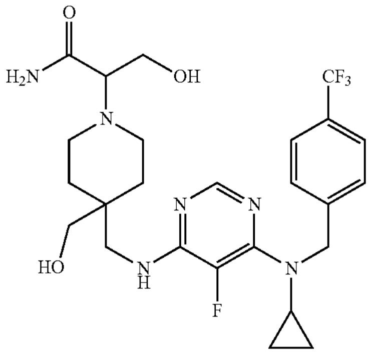 2-(4-(((6-(cyclopropyl(4-(trifluoromethyl)benzyl)amino)-5-fluoropyrimidin-4-yl)amino)methyl)-4-(hydroxymethyl)piperidin-1-yl)-3-hydroxypropanamide |

For the A7-66-1 and A7-66-2 compounds only the 2 major isomers were isolated.

General Method 3A—Synthesis with Substituted Bromoacetamides

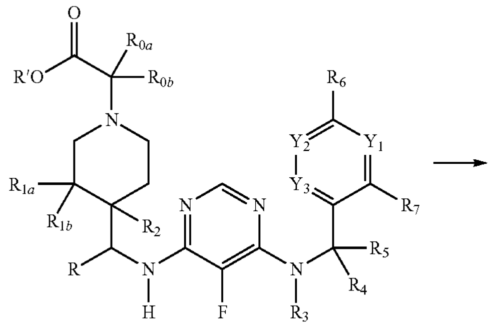

A10

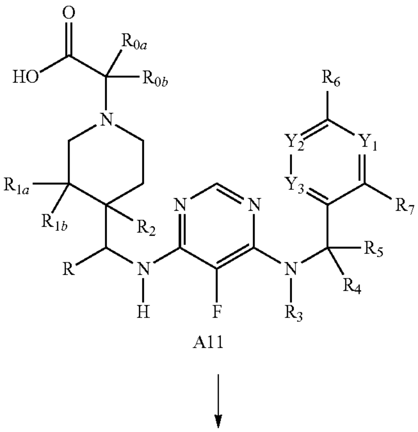

A11

-continued

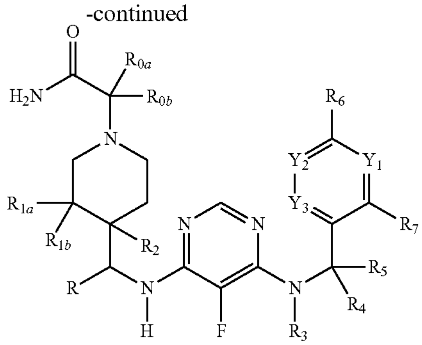

A7

A7 has also been synthesized from A10 by hydrolysis of the ester (with a suitable base such as LiOH or NaOH) to yield A11 (or the corresponding metal salt) followed by a coupling reaction with $NH_3$ (employing standard coupling reagents such as HATU).

Example A7-71

Synthesis of rac-2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetamide, A7-71

Scheme A7-71

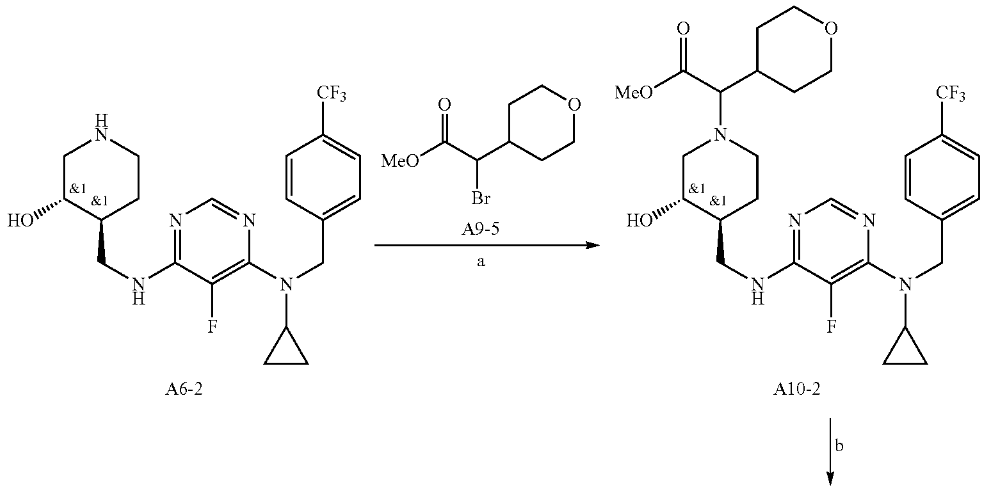

A6-2

A10-2

-continued

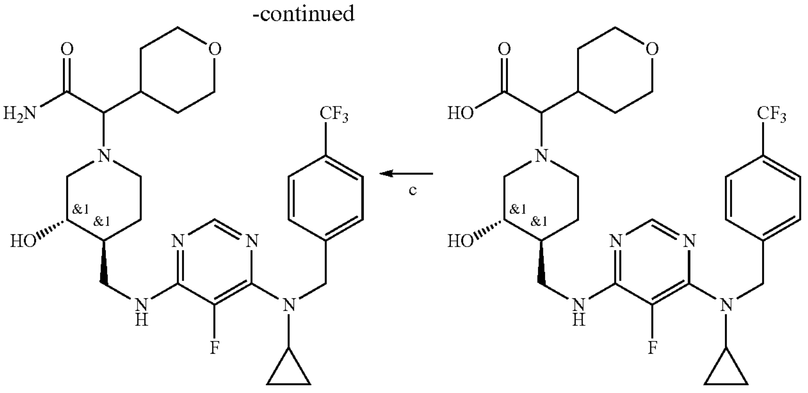

A7-71 A11-1 a) DIEA, DMF. b) LiOH, THF/MeOH (1/1). c) $NH_3$, TEA, HATU, THF.

rac-Methyl 2-((3R,4R)-4-(((6-(cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetate, A10-2

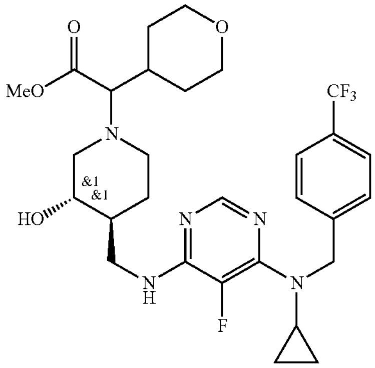 [SMILES: COC(=O)C(C1CCOCC1)N1CC[C@@H](CNc2ncnc(N(Cc3ccc(C(F)(F)F)cc3)C3CC3)c2F)[C@H](O)C1]

DIEA (0.82 ml, 4.7 mmol) and methyl 2-bromo-2-tetrahydropyran-4-yl-acetate (383 mg, 1.61 mmol) were in turn added to a solution of intermediate A6-2 (400 mg, 0.78 mmol) in DMF (8.5 mL) and the reaction was stirred 24 h at 60° C. The reaction was quenched with $H_2O$ (60 mL) and then extracted with EA (3×30 mL). The combined organic layers were washed with brine (3×15 mL), dried ($Na_2SO_4$), filtered and concentrated in vacuo. The residue was then purified by Flash CC (DCM:MeOH=100:0 to 95:5) to afford A10-2 (131 mg, 0.22 mmol).

rac-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetic acid, A11-1

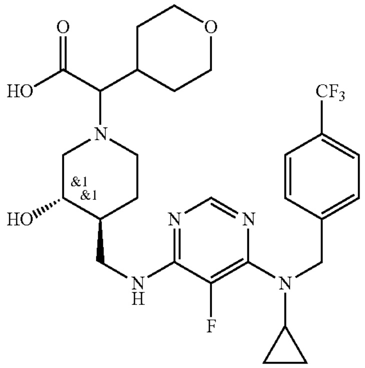 [SMILES: O=C(O)C(C1CCOCC1)N1CC[C@@H](CNc2ncnc(N(Cc3ccc(C(F)(F)F)cc3)C3CC3)c2F)[C@H](O)C1]

A10-2 (131 mg, 0.22 mmol) was dissolved in THE (1 mL) and MeOH (1 mL) and a solution of LiOH monohydrate (33 mg, 079 mmol) was added and the mixture was stirred on at 60° C. Solvent was evaporated, obtaining 125 mg of crude. This crude was purified using a C18 column ($H_2O$: MeOH=100:0 to 0:100) to afford A11-1 (34 mg, 0.058 mmol).

rac-2-((3R,4R)-4-(((6-(Cyclopropyl(4-(trifluoromethyl)benzyl)amino)-5-fluoropyrimidin-4-yl)amino)methyl)-3-hydroxypiperidin-1-yl)-2-(tetrahydro-2H-pyran-4-yl)acetamide, A7-71

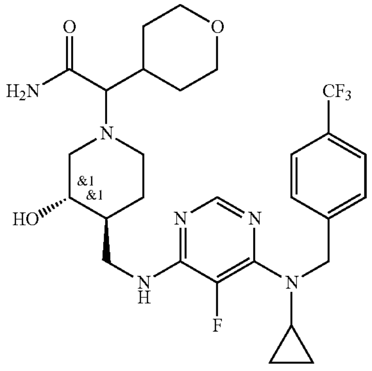 [SMILES: NC(=O)C(C1CCOCC1)N1CC[C@@H](CNc2ncnc(N(Cc3ccc(C(F)(F)F)cc3)C3CC3)c2F)[C@H](O)C1]

A11-1 (34 mg, 0.058 mmol) was dissolved in DMF (0.5 mL) and 0.4 M ammonia solution in THF (22 μL, 0.18 mmol), HATU (33 mg, 0.09 mmol) and triethylamine (40 μL, 0.29 mmol) were added and the mixture was stirred on at rt. Work-up was done by adding $H_2O$ and extracting with EA (3x20 mL). Organic phase was washed with 1N NaOH aq. and brine, affording 7 mg of crude. The crude was purified by Flash CC (DCM:MeOH=100:0 to 90:10) to afford A7-71 (2.8 mg, 0.005 mmol).

General Method 4A

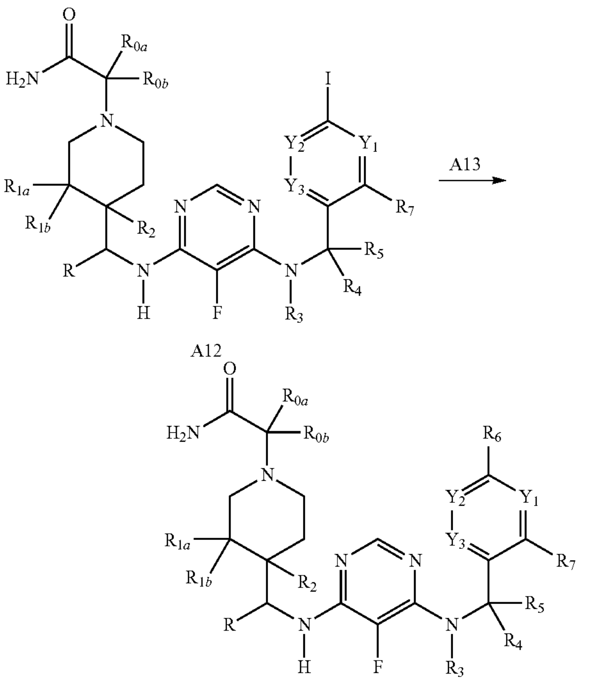

A12

A7

When R6 was a heterocyclic ring the iodo-intermediate A12, synthesized as outlined in General Method A from the corresponding iodo-benzylamine, underwent either Suzuki coupling (together with Pd and boronic acid, or esters) or a standard Buchwald coupling (together with Cu and a nitrogen containing heterocyclic ring) to give A7.

Example A7-72

Synthesis of rac-2-((3R,4R)-4-(((6-(ethyl(4-(1-methyl-1H-pyrazol-4-yl)benzyl)amino)-5-fluoropyrimidin-4-yl)amino)methyl)-3-hydroxypiperidin-1-yl)acetamide, A7-72

Sheme A7-72

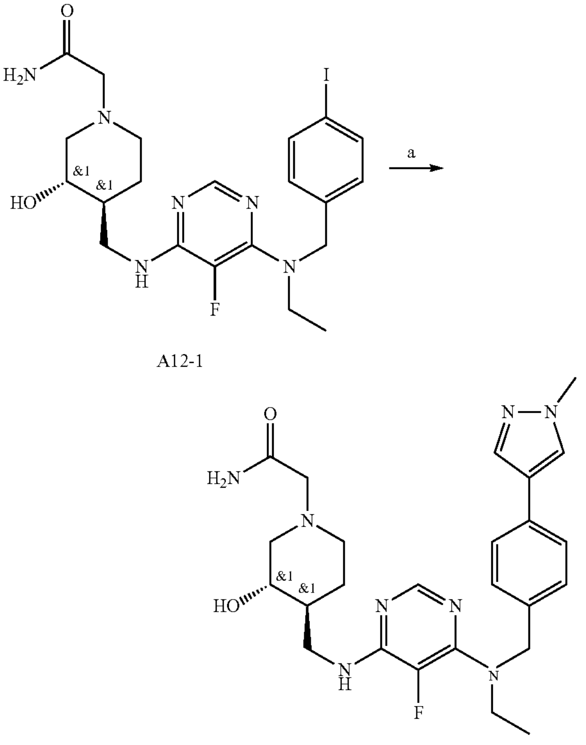

A12-1

A7-72 a) Standard Suzuki coupling

Under $N_2$ atmosphere, 1-methyl-4-(4,4,5,5-tetramethyl-1,3,2-dioxaborolan-2-yl)-1H-pyrazole A13-1 (17 mg, 82 μmol), 2M $Cs_2CO_3$ (111 μL, 0.22 mmol) and [1,1'-bis(diphenylphosphino) ferrocene]dichloropalladium(II), complex with DCM (6 mg, 7 μmol) were added to a solution of A12-1 (40 mg, 74 μmol) in dioxane (1 mL). The reaction mixture was stirred at 100° C. for 4h. $H_2O$ was added, and the product was extracted with EA (x3). The combined organic layer was washed with $H_2O$, brine, dried ($MgSO_4$), filtered and concentrated in vacuo. The residue was first purified by flash CC (MeOH:DCM=1:9) and then by C18 column ($H_2O$:MeOH=100:0 to 0:100) to yield A7-72 (8 mg, 16 μmol) as a white solid.

LCMS: MS Calcd.: 496.6; MS Found: 497 ($[M+H]^+$).

The following compounds were synthesized according to Method 4A, like example A7-72, using the shown starting materials (Table 4A).

TABLE 4A

| A13 | A12 | A7 |
|---|---|---|
| A13-2 | A12-1 | A7-73 |
| 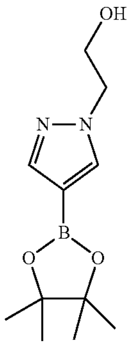<br>2-(4-(4,4,5,5-tetramethyl-1,3,2-dioxaborolan-2-yl)-1H-pyrazol-1-yl)ethan-1-ol | | 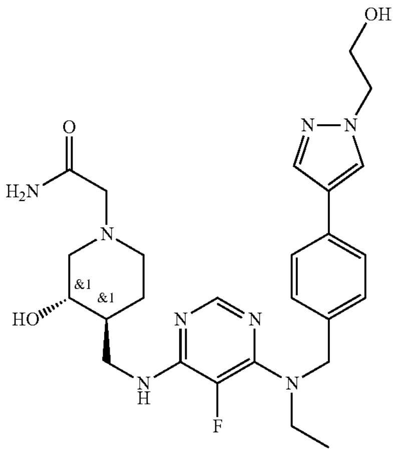<br>rac-2-((3R,4R)-4-(((6-(ethyl(4-(1-(2-hydroxyethyl)-1H-pyrazol-4-yl)benzyl)amino)-5-fluoropyrimidin-4-yl)amino)methyl)-3-hydroxypiperidin-1-yl)acetamide |
| A13-1 | A12-2 | A7-74 |
| | 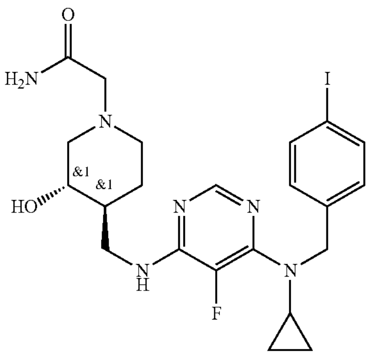<br>rac-2-((3R,4R)-4-(((6-(ethyl(4-iodobenzyl)amino)-5-fluoropyrimidin-4-yl)amino)methyl)-3-hydroxypiperidin-1-yl)acetamide | 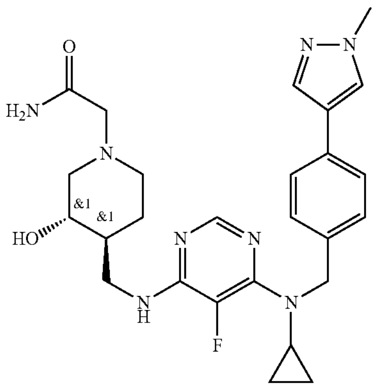<br>rac-2-((3R,4R)-4-(((6-(cyclopropyl(4-(1-methyl-1H-pyrazol-4-yl)benzyl)amino)-5-fluoropyrimidin-4-yl)amino)methyl)-3-hydroxypiperidin-1-yl)acetamide |

TABLE 4A-continued

| A13 | A12 | A7 |
|---|---|---|
| A13-1 | A12-3 | A7-75 |
| | 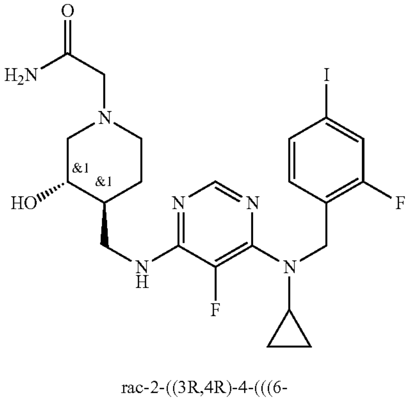 rac-2-((3R,4R)-4-(((6-(cyclopropyl(2-fluoro-4-iodobenzyl)amino)-5-fluoropyrimidin-4-yl)amino)methyl)-3-hydroxypiperidin-1-yl)acetamide | 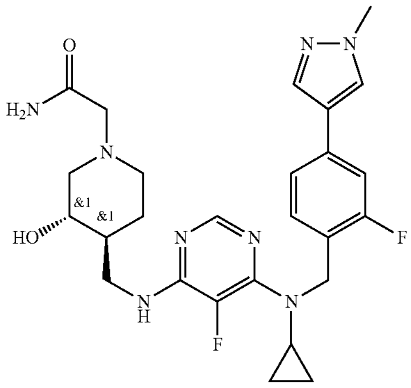 rac-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3-hydroxypiperidin-1-yl)acetamide |

Example A7-76

Synthesis of rac-2-((3R,4R)-4-(((6-(cyclopropyl(2-fluoro-4-(1H-pyrazol-1-yl)benzyl)amino)-5-fluoro pyrimidin-4-yl)amino)methyl)-3-hydroxypiperidin-1-yl)acetamide, A7-76

Scheme A7-76

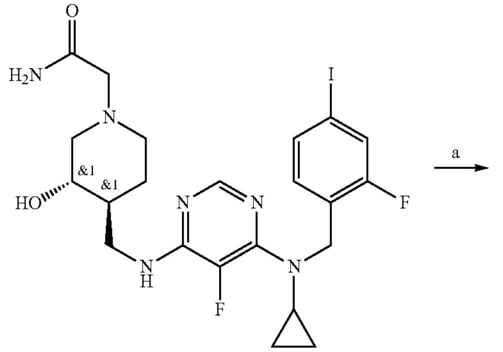

A12-3

-continued

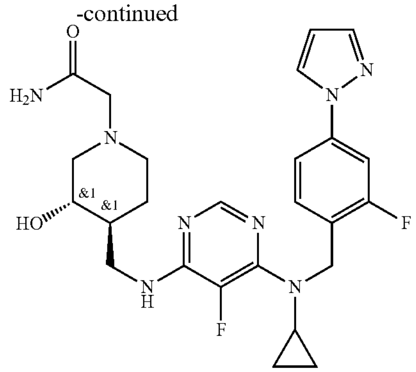

A7-76 a) Standard Buchwald coupling

Under $N_2$ atmosphere, 1H-pyrazole (30 mg, 0.44 mmol), $K_2CO_3$ (38 mg, 0.27 mmol), trans-1,2-cyclohexane-1,2-diamine (6.6 μL, 55 μmol) and CuI (2.6 mg, 14 μmol) were added to a solution of A12-3 in NMP (2 mL). The reaction mixture was stirred to reflux on. Additional amount of all the reagents was added and the mixture was heated to reflux for one more day. $H_2O$ was added and the product was extracted with EA (×3). The combined organic layer was washed with $H_2O$, brine, dried ($MgSO_4$), filtered and concentrated in vacuo. The residue was then purified by Flash CC (MeOH:DCM=15:85) and then by C18 column ($H_2O$:MeOH=100:0 to 0:100) to afford A7-76 (35 mg, 68 μmol) as a white solid.

LCMS: MS Calcd.: 512.6; MS Found: 513 ($[M+H]^+$).

General Method 5a: From Left to Right

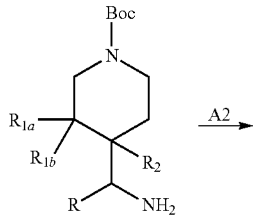

A4

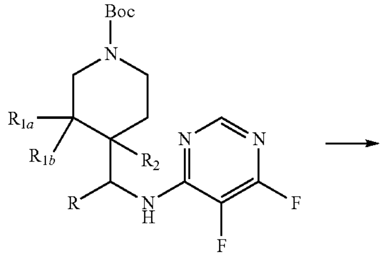

A14

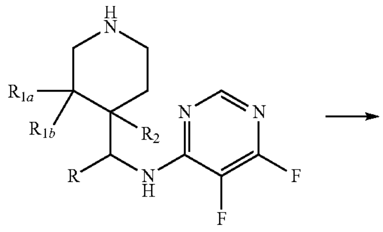

A15

-continued

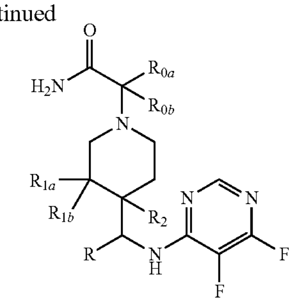

A16

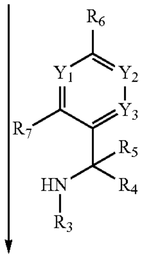

A1

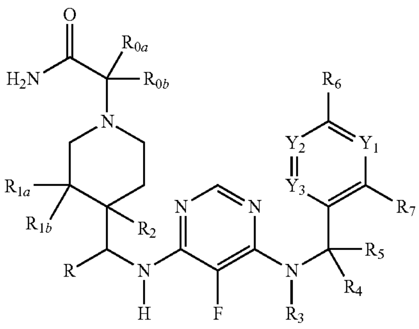

A7

The primary amine A4 was reacted with A2 (at ambient temperature or slightly above, ie 30° C.) together with a suitable base (such as; DIEA, TEA or $K_2CO_3$). After the reaction was deemed complete the intermediate A14 was worked up and purified by chromatography (Flash CC or HPLC) or used as the crude. Deprotection of intermediate A14 in acidic media (TFA or HCl) at rt gave intermediate A15, which was used directly in the next alkylation step with 2-bromoacetamide and a suitable base (such as; DIEA, TEA or $Cs_2CO_3$). Intermediate A16 obtained was then stirred with the secondary amine A1 in a solvent (such as DMSO or DMSO-$H_2O$, $H_2O$, $H_2O$-ethanol mixtures) and at a temperature of 70-150° C. on, or until the reaction was considered complete. Workup and purification then gave the desired final compounds A7.

Example A7-77

Synthesis of rac-2-((3R,4R)-4-(((6-((4-(1H-pyrazol-1-yl)benzyl)(ethyl)amino)-5-fluoropyrimidin-4-yl)amino)methyl)-3-hydroxypiperidin-1-yl)acetamide Scheme A7-77

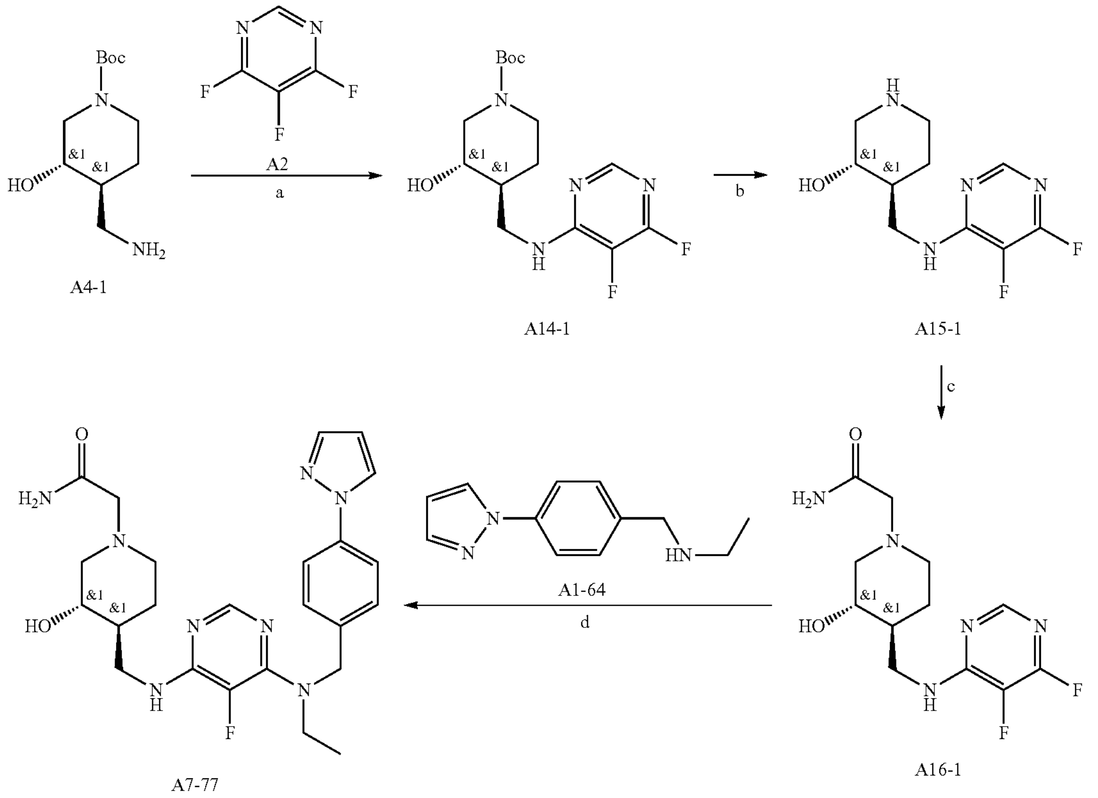

a)DIEA, DMSO. b)TFA, DCM. c) DIEA, DMF, 2-bromoacetamide. d) DIEA, DMSO rac-tert-Butyl (3R,4R)-4-(((5,6-difluoropyrimidin-4-yl)amino)methyl)-3-hydroxypiperidine-1-carboxylate, A14-1

A14-1

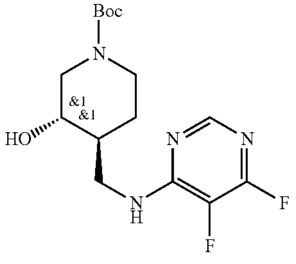

A2 (367 μL, 4.0 mmol) was dissolved in DMSO (17 mL) and DIEA (2.09 mL, 12.0 mmol) and A4-1 (970 mg, 4.0 mmol) were added. The reaction mixture was stirred at rt on. The crude was poured into $H_2O$ and extracted with EA (2×). The organic phase was washed with $H_2O$ (2×) and brine. Then, the organic phase was dried over $MgSO_4$, filtered and concentrated to afford A14-1 (1.38 g, 4.0 mmol).

LCMS: MS Calcd.: 344; MS Found: 345 ($[M+H]^+$).

rac-(3R,4R)-4-(((5,6-Difluoropyrimidin-4-yl)amino)methyl)piperidin-3-ol, A15-1

A15-1

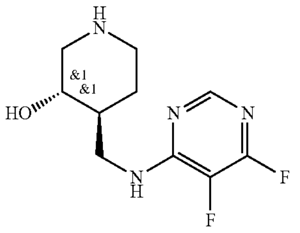

A14-1 (1.47 g, 4.27 mmol) was dissolved in DCM (8.5 mL) and TFA (3.3 mL, 43.1 mmol) was added. This mixture was stirred at rt for 3h. The solvents were evaporated under reduced pressure. Cyclohexane was twice added and evaporated. A15-1 (1.04 g, 4.27 mmol) was used without further purification.

LCMS: MS Calcd.: 244; MS Found: 245 ($[M+H]^+$).

rac-2-((3R,4R)-4-(((5,6-Difluoropyrimidin-4-yl) amino)methyl)-3-hydroxypiperidin-1-yl)acetamide, A16-1

A16-1

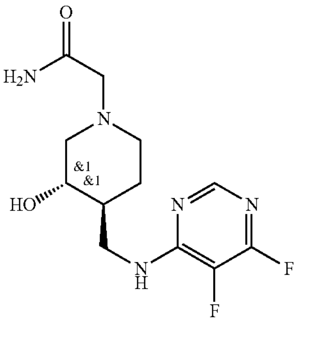

A15-1 (1.04 g, 4.27 mmol) was dissolved in DMF (56 mL), DIEA (4.5 mL, 25.77 mmol) was added and the mixture was stirred at rt for 30 min. Then 2-bromoacetamide (650 mg, 4.71 mmol) was added and the mixture was stirred on at rt. The solvent was evaporated under reduced pressure and the residue was dissolved in MeOH (10 mL) and passed through a 15 g ionic-exchange SCX column. Additional 50 mL of MeOH were passed through the column, followed by 40 mL of a 3.5M solution of $NH_3$ in MeOH in order to release the product from the column. After evaporation of the solvents A16-1 (981 mg, 3.2 mmol) was obtained.

LCMS: MS Calcd.: 301; MS Found: 302 ($[M+H]^+$).

rac-2-((3R,4R)-4-(((6-((4-(1H-Pyrazol-1-yl)benzyl) (ethyl)amino)-5-fluoropyrimidin-4-yl)amino) methyl)-3-hydroxypiperidin-1-yl)acetamide, A7-77

A7-77

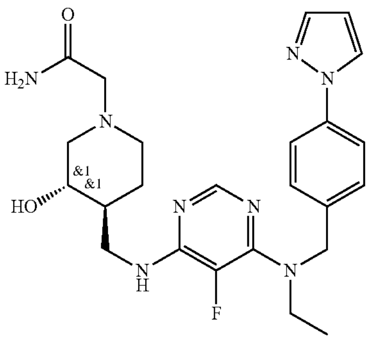

A16-1 (90 mg, 0.30 mmol) was dissolved in DMSO (0.8 mL) and DIEA (160 μL, 0.92 mmol) and N-[(4-pyrazol-1-ylphenyl)methyl]ethanamine A1-64 (63 mg, 0.31 mmol) were added. The reaction mixture was heated at 140° C. for 3h. The crude was poured into $H_2O$ and extracted with EA (2×). The organic phase was washed with $H_2O$ (2×) and brine, dried and concentrated in vacuo to afford 115 mg of crude material. The crude residue was purified by flash CC (DCM:MeOH=100:0 to 90:10) to afford A7-77 (53 mg, 0.11 mmol).

LCMS: MS Calcd.: 482; MS Found: 483 ($[M+H]^+$).

The following cmpds were synthesized according to General Method 5A using the shown starting materials (Table 5A).

TABLE 5A

| A4 | A1 | A7 |
|---|---|---|
| A4-1 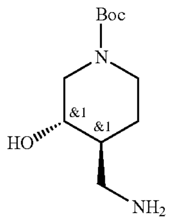 rac- tert-butyl (3R,4R)-4-(aminomethyl)-3-hydroxypiperidine-1-carboxylate | A1-38 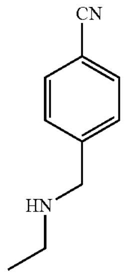 4-((ethylamino) methyl) benzonitrile | A7-78 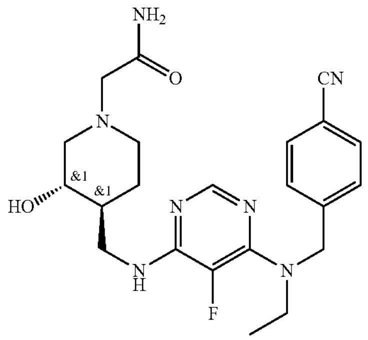 rac-2-((3R,4R)-4-(((6-((4-cyanobenzyl)(ethyl)amino)-5-fluoropyrimidin-4-yl)amino)methyl)-3-hydroxypiperidin-1-yl)acetamide |

TABLE 5A-continued

| A4 | A1 | A7 |
|---|---|---|
| A4-1 | A1-39 | A7-79 |
| | 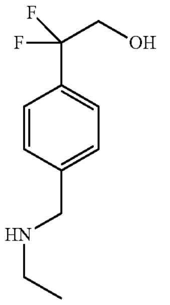 2-(4-((ethylamino)methyl)phenyl)-2,2-difluoroethan-1-ol | 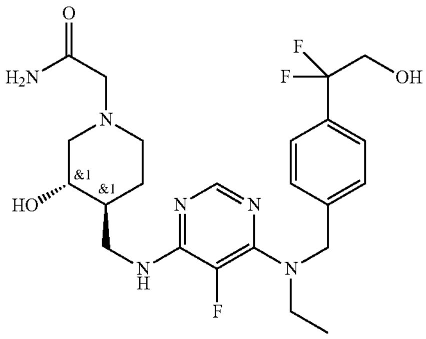 rac-2-((3R,4R)-4-(((6-((4-(1,1-difluoro-2-hydroxyethyl)benzyl)(ethyl)amino)-5-fluoropyrimidin-4-yl)amino)methyl)-3-hydroxypiperidin-1-yl)acetamide |

General Method 6A—Transformation of $R_2$ into a 5-Membered Heterocyclic Ring

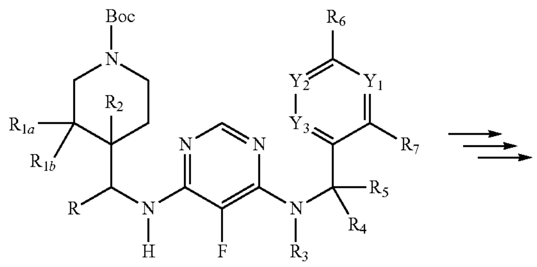

A5

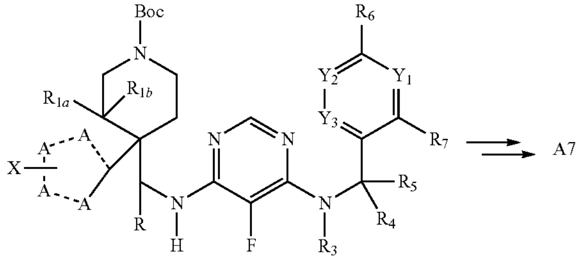

A5'

When the R2 group in A5 was either a carboxamide, cyano or ester the R2 group has, in the examples described below, been transformed into a 5-membered heterocyclic ring. The compounds were thereafter transformed from A5' to the A7 end products, employing the deprotection-alkylation procedure, as described in General Method A.

Example A7-80

Synthesis of 2-(4-(((6-(cyclopropyl(4-(trifluoromethyl)benzyl)amino)-5-fluoropyrimidin-4-yl)amino)methyl)-4-(1H-1,2,4-triazol-3-yl)piperidin-1-yl)acetamide, A7-80

Scheme A7-80

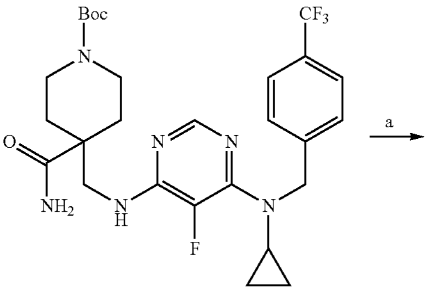

A5-2

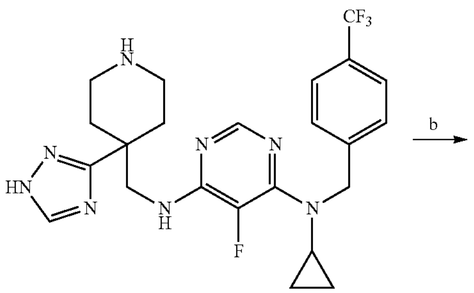

A6-8

-continued

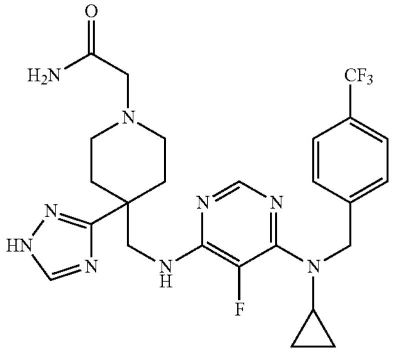

A7-80 a) i) DMF-DMA ii) $NH_2NH_2$•2HCl, NaOH, Dioxane iii) AcOH.
b) i) HCl, dioxane. ii) 2-Bromoacetamide, DIEA.

$N^4$-((4-(1H-1,2,4-Triazol-3-yl)piperidin-4-yl)methyl)-$N^6$-cyclopropyl-5-fluoro-$N^6$-(4-(trifluoromethyl)benzyl)pyrimidine-4,6-diamine, A6-8

A6-8

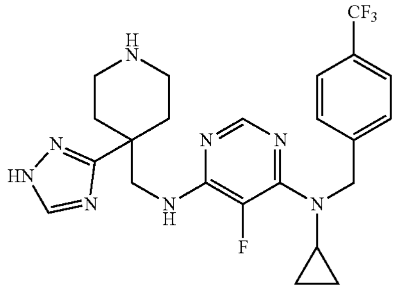

DMF-DMA (0.35 mL, 2.5 mmol) was added to the tert-butyl 4-carbamoyl-4-(((6-(cyclopropyl(4-(trifluoromethyl)benzyl)amino)-5-fluoropyrimidin-4-yl)amino)methyl)piperidine-1-carboxylate A5-2 (61 mg, 0.11 mmol) and the mixture was refluxed at 110° C. for about 2 h. The volatiles were evaporated under reduced pressure to obtain the corresponding amidine intermediate. Hydrazine dihydrochloride (57 mg, 0.54 mmol) in 5 M NaOH aq solution (0.15 ml, 0.75 mmol) was added to a solution of this amidine intermediate in 1,4-dioxane (0.3 mL). Glacial AcOH (1.6 mL) was added and the reaction mixture was stirred for about 30 min at rt and then at 90° C. for 5 h. Then, 0.8 ml of 4M HCl in dioxane were added to fully deprotect the Boc-group and the mixture was stirred for 1 h at rt. The work-up was done adding $H_2O$ (20 mL) and washing with EA (20 mL). The aq phase was basified with 2N NaOH and extracted with DCM (2×20 mL). This organic phase was washed with brine (20 mL), dried ($Na_2SO_4$) and concentrated to afford A6-8 (36 mg, 0.07 mmol).

LCMS: MS Calcd.: 490.5; MS Found: 491 ($[M+H]^+$).

2-(4-(((6-(Cyclopropyl(4-(trifluoromethyl)benzyl)amino)-5-fluoropyrimidin-4-yl)amino)methyl)-4-(1H-1,2,4-triazol-3-yl)piperidin-1-yl)acetamide, A7-80

A7-80

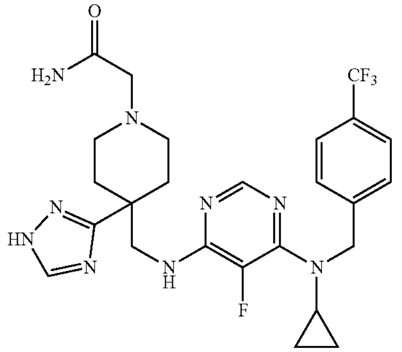

This compound was prepared by alkylation of A6-8 with 2-bromoacetamide following the procedure described previously for the synthesis of example A7-1.

LCMS: MS Calcd.: 547.6; MS Found: 548 ($[M+H]^+$).

Example A7-81

Synthesis of 2-(4-(((6-(cyclopropyl(4-(trifluoromethyl)benzyl)amino)-5-fluoropyrimidin-4-yl)amino)methyl)-4-(1,2,4-oxadiazol-3-yl)piperidin-1-yl)acetamide Scheme A7-81

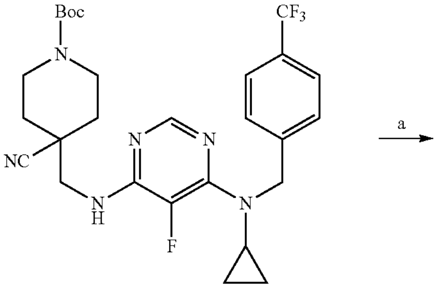

A5-3

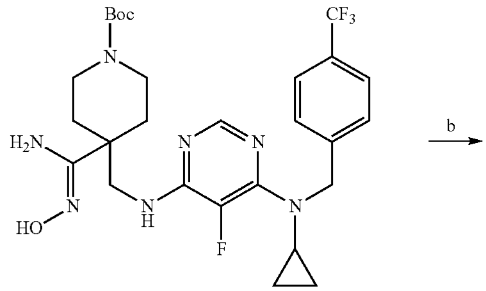

A5-4

-continued

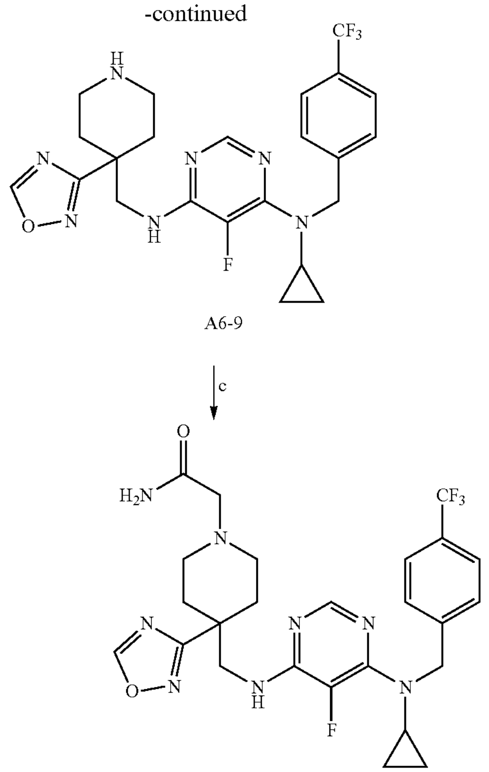

A6-9

A7-81 a) Hydroxylamine hydrochloride, $NaHCO_3$, MeOH. b) i) $CH(OEt)_3$, $BF_3$•$Et_2O$, ii) HCl/dioxane. c) 2-bromoacetamide, DIEA.

tert-Butyl (Z)-4-(((6-(cyclopropyl(4-(trifluoromethyl)benzyl)amino)-5-fluoropyrimidin-4-yl)amino)methyl)-4-(N'-hydroxycarbamimidoyl)piperidine-1-carboxylate, A5-4

A5-4

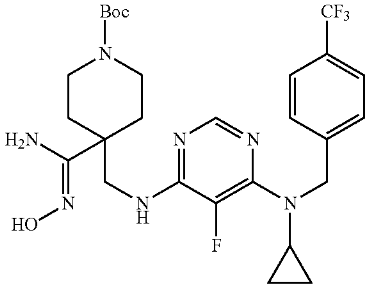

A suspension of tert-butyl 4-cyano-4-(((6-(cyclopropyl(4-(trifluoromethyl)benzyl)amino)-5-fluoropyrimidin-4-yl)amino)methyl)piperidine-1-carboxylate A5-3 (50 mg, 0.09 mmol), hydroxylamine hydrochloride (26 mg, 0.37 mmol) and $NaHCO_3$ (38 mg, 0.45 mmol) in MeOH (0.5 mL) was heated to 75° C. on to form the corresponding amidoxime intermediate. The work-up was done filtering the reaction with DCM and then the filtrated was washed with $H_2O$ (20 mL) and brine (20 mL). The organic phase was dried ($Na_2SO_4$) and concentrated to afford A5-4 (37 mg, 0.06 mmol).

LCMS: MS Calcd.: 581.6; MS Found: 582 ($[M+H]^+$).

$N^4$-((4-(1,2,4-Oxadiazol-3-yl)piperidin-4-yl)methyl)-$N^6$-cyclopropyl-5-fluoro $N^6$-(4-(trifluoromethyl)benzyl)pyrimidine-4,6-diamine, A6-9

A6-9

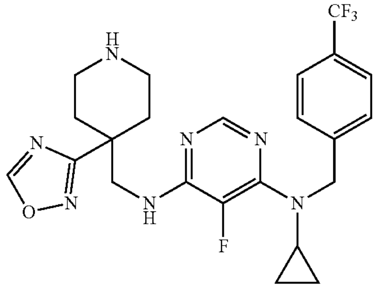

To a solution of A5-4 (37 mg, 0.06 mmol) in triethylorthoformate (100 μL, 0.6 mmol) was added $BF_3 \cdot Et_2O$ (5 μL, 0.04 mmol) under $N_2$ and the mixture was heated to 100° C. for 90 min. Then, the reaction was concentrated to dryness and it was added 4N HCl in dioxane (0.5 ml) and the mixture was stirred for 1 hour at rt. After this period, the reaction was concentrated again and the corresponding oxadiazole intermediate was used directly in the next synthesis step.

LCMS: MS Calcd.: 491.5; MS Found: 492 ($[M+H]^+$).

2-(4-(((6-(Cyclopropyl(4-(trifluoromethyl)benzyl)amino)-5-fluoropyrimidin-4-yl)amino)methyl)-4-(1,2,4-oxadiazol-3-yl)piperidin-1-yl)acetamide, A7-81

A7-81

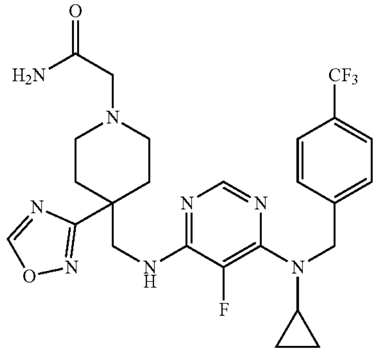

This compound was prepared by alkylation of A6-9 with 2-bromoacetamide following the procedure described previously for the synthesis of example A7-1.

LCMS: MS Calcd.: 548.5; MS Found: 549 ($[M+H]^+$).

Example A7-82
Synthesis of 2-(4-(((6-(cyclopropyl(4-(trifluoromethyl)benzyl)amino)-5-fluoropyrimidin-4-yl)amino)methyl)-4-(1,3,4-oxadiazol-2-yl)piperidin-1-yl)acetamide, A7-82
Scheme A7-82
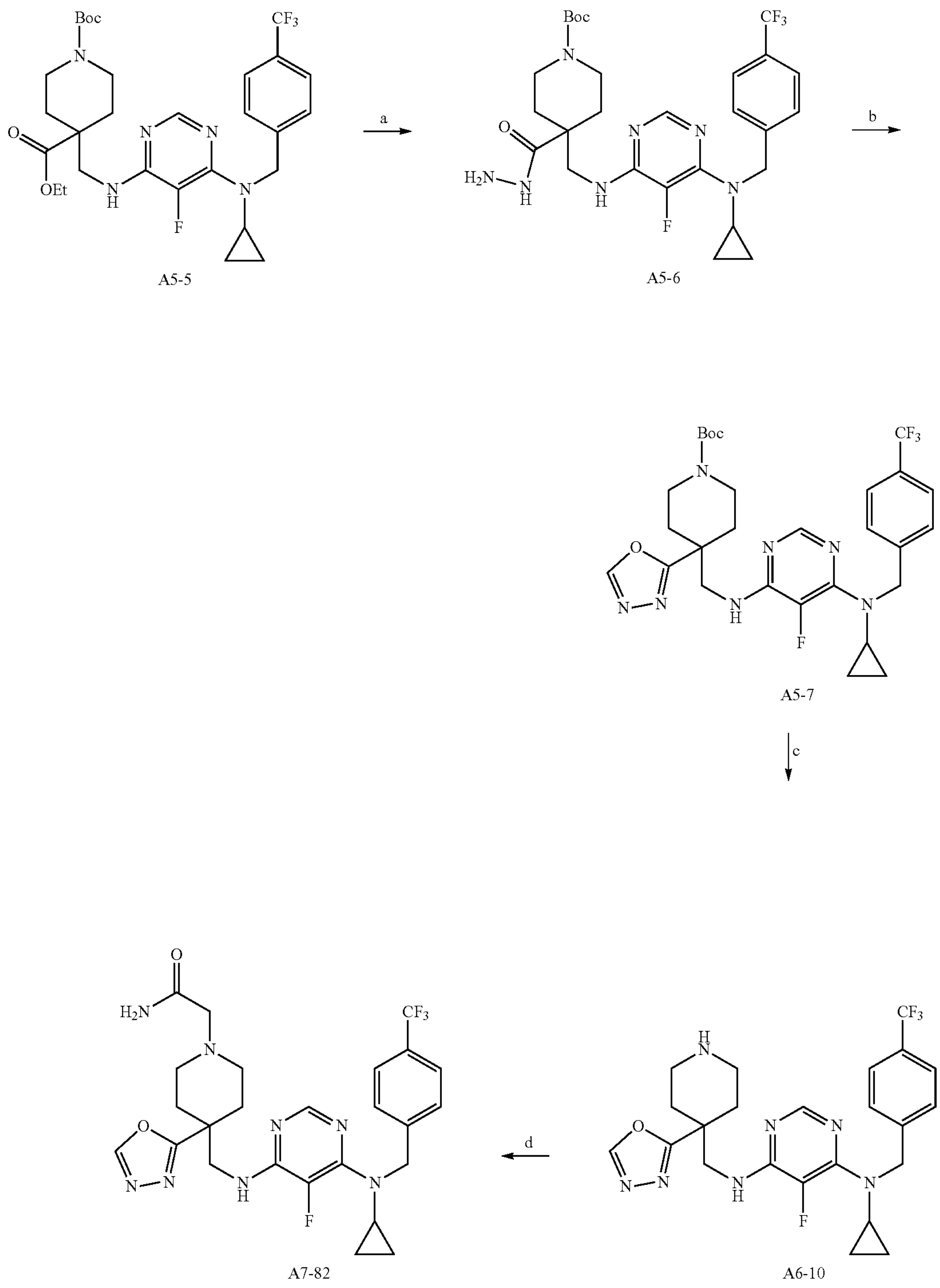
a) Hydrazine hydrate, EtOH. b) $CH(OMe)_3$. c) TFA, DCM. d) DIEA, 2-bromoacetamide.

tert-Butyl 4-(((6-(cyclopropyl(4-(trifluoromethyl)benzyl)amino)-5-fluoropyrimidin-4-yl)amino)methyl)-4-(hydrazinecarbonyl)piperidine-1-carboxylate, A5-6

A5-6

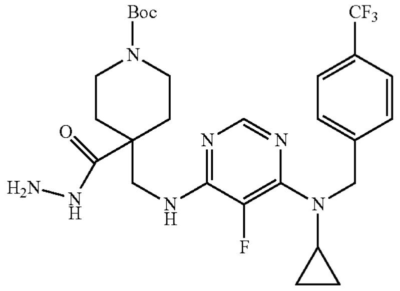

The mixture of 1-(tert-butyl) 4-ethyl 4-(((6-(cyclopropyl(4-(trifluoromethyl)benzyl)amino)-5-fluoropyrimidin-4-yl)amino)methyl)piperidine-1,4-dicarboxylate A5-5 (356 mg, 0.60 mmol) and hydrazine hydrate (0.6 ml, 10 mmol) in EtOH (1 mL) was heated to 120° C. for 18 h in the microwave. The solvent was evaporated and $Et_2O$ (30 mL) was added, washing with aq 2N NaOH (30 mL) and brine (30 mL). The organic phase was dried ($Na_2SO_4$) and concentrated to afford A5-6 (258 mg, 0.11 mmol).

LCMS: MS Calcd.: 581.6; MS Found: 582 ($[M+H]^+$).

tert-Butyl 4-(((6-(cyclopropyl(4-(trifluoromethyl)benzyl)amino)-5-fluoropyrimidin-4-yl)amino)methyl)-4-(1,3,4-oxadiazol-2-yl)piperidine-1-carboxylate, A5-7

A5-7

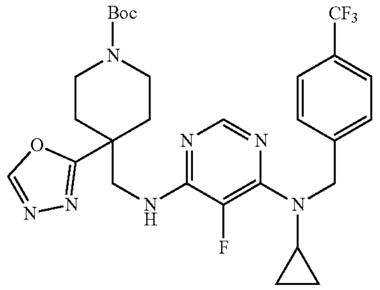

The mixture of A5-6 (258 mg, 0.11 mmol) and $CH(OMe)_3$ (0.24 mL, 2.2 mmol) was heated to 125° C. in a sealed tube on. Then, EA (30 mL) was added and the organic phase was washed with aq sat. $NaHCO_3$ (30 mL), $H_2O$ (30 mL) and brine (30 mL). After drying ($Na_2SO_4$) and evaporation, a crude of 217 mg was obtained. This crude was purified by flash CC (Hex:EA=100:0 to 50:50). Collection of the fractions containing the product yielded A5-7 (9 mg, 0.015 mmol).

LCMS: MS Calcd.: 591.6; MS Found: 592 ($[M+H]^+$).

$N^4$-((4-(1,3,4-oxadiazol-2-yl)piperidin-4-yl)methyl)-$N^6$-cyclopropyl-5-fluoro-$N^6$-(4-(trifluoromethyl)benzyl)pyrimidine-4,6-diamine, A6-10

A6-10

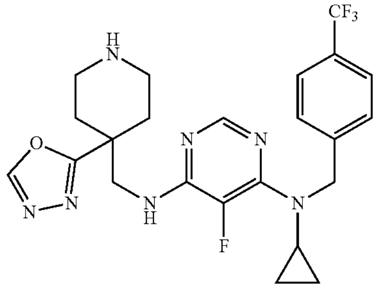

A5-7 (9 mg, 0.015 mmol) was dissolved in DCM (50 μL) and TFA (12 μL) was added and the mixture was stirred at rt for 3 h. Then, the reaction was concentrated to dryness to afford A6-10.

LCMS: MS Calcd.: 491.5; MS Found: 492 ($[M+H]^+$).

2-(4-(((6-(Cyclopropyl(4-(trifluoromethyl)benzyl)amino)-5-fluoropyrimidin-4-yl)amino)methyl)-4-(1,3,4-oxadiazol-2-yl)piperidin-1-yl)acetamide, A7-82

A7-82

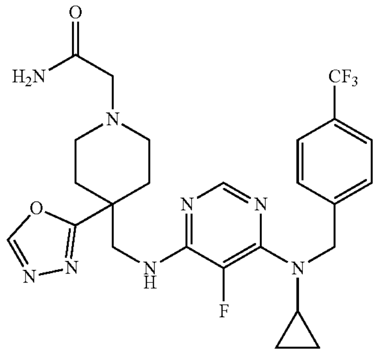

This compound was prepared by alkylation of the above intermediate with 2-bromoacetamide following the procedure described previously for the synthesis of example A7-1.

LCMS: MS Calcd.: 548.5; MS Found: 549 ($[M+H]^+$).

Example A7-83

Synthesis of 2-(4-(((6-(cyclopropyl(4-(trifluoromethyl)benzyl)amino)-5-fluoropyrimidin-4-yl)amino)methyl)-4-(4-methyl-4H-1,2,4-triazol-3-yl)piperidin-1-yl)acetamide, A7-83

Scheme A7-83

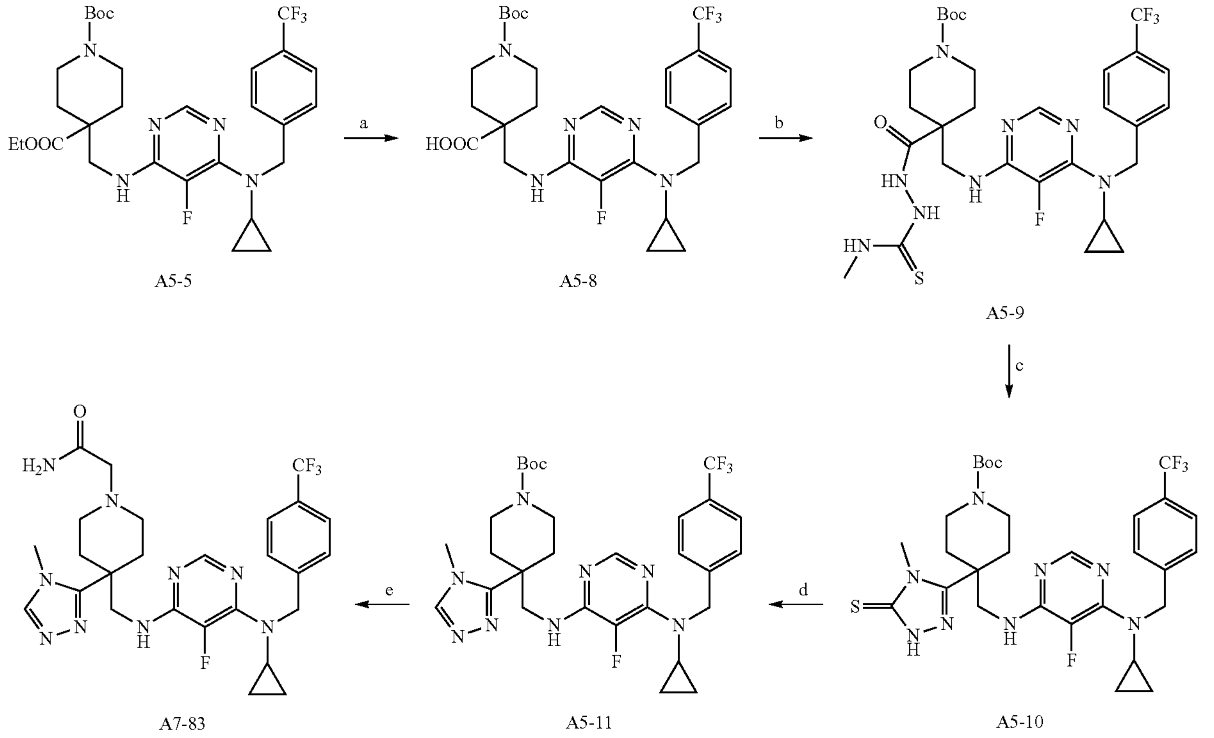

a) i) NaOH, EtOH. ii) EDC•HCl, HOBt, N-methylhydrazinecarbothioamide, DCM. iii) NaOH, EtOH. iv) $H_2O_2$, DCM.
b) i) TFA, DCM, ii) DIEA, 2-bromoacetamide.

1-(tert-Butoxycarbonyl)-4-(((6-(cyclopropyl(4-(trifluoromethyl)benzyl)amino)-5-fluoropyrimidin-4-yl)amino)methyl)piperidine-4-carboxylic acid, A5-8

A5-8

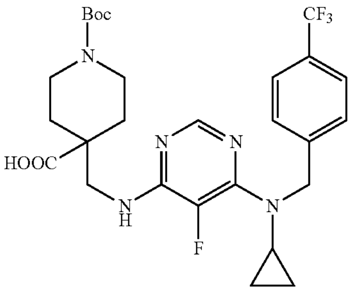

2N NaOH (1.6 mL, 3.2 mmol) was added to a solution of A5-5 (181 mg, 0.30 mmol) in EtOH (3 mL). The reaction mixture was stirred at rt for 3 h. The organic solvent was removed, $H_2O$ was added and the solution was acidified with 2N HCl until pH 3. The product was extracted with DCM (×3). The combined organic layer was washed with $H_2O$, dried (phase separator cartridge) and concentrated in vacuo. A5-8 was obtained (168 mg, 0.29 mmol) as a white solid. LCMS: MS Calcd.: 567.6; MS Found: 568 ($[M+H]^+$).

tert-Butyl 4-(((6-(cyclopropyl(4-(trifluoromethyl)benzyl)amino)-5-fluoropyrimidin-4-yl)amino)methyl)-4-(2-(methylcarbamothioyl)hydrazine-1-carbonyl)piperidine-1-carboxylate, A5-9

A5-9

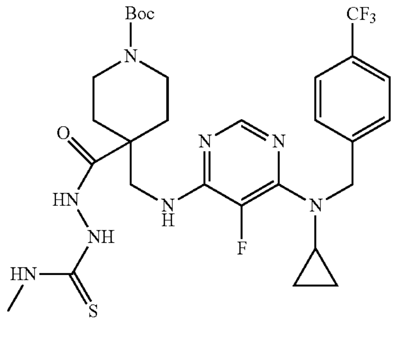

EDC·HCl (85 mg, 0.44 mmol), HOBt (60 mg, 0.44 mmol) and N-methylhydrazinecarbothioamide (47 mg, 0.45 mmol) were added to a solution of A5-8 (168 mg, 0.29 mmol) in DCM (5 mL) and the reaction mixture was stirred at rt for 4 h. Additional N-methylhydrazinecarbothioamide (47 mg, 0.45 mmol) was added and the reaction mixture was stirred at rt for 2 days. The mixture was diluted with DCM and the organic layer was washed with $H_2O$, dried (phase separator cartridge) and the solvent was removed in vacuo. The residue was then purified by flash CC (MeOH:DCM=1:9) to yield A5-9 (121 mg, 0.18 mmol) as a solid.

LCMS: MS Calcd.: 654.7; MS Found: 655 ($[M+H]^+$).

tert-Butyl 4-(((6-(cyclopropyl(4-(trifluoromethyl) benzyl)amino)-5-fluoropyrimidin-4-yl)amino) methyl)-4-(4-methyl-5-thioxo-4,5-dihydro-1H-1,2,4-triazol-3-yl)piperidine-1-carboxylate, A5-10

A5-10

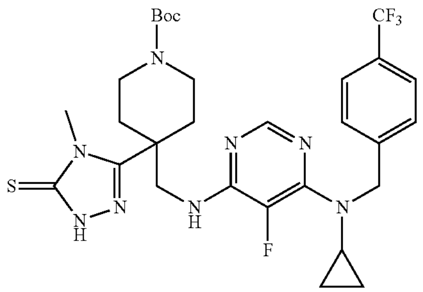

A5-9 (114 mg, 0.17 mmol) was dissolved in EtOH (1.8 mL) and 8N NaOH (0.55 mL, 4.4 mmol) was added. The reaction mixture was stirred on at 80° C. $H_2O$ was added to the reaction mixture and 2N HCl was added until pH was 4. The product was extracted with DCM (×3), the combined organic layer was washed with $H_2O$ and brine, dried (phase separator cartridge) and the solvent was removed in vacuo. The product A5-10 (98 mg, 0.15 mmol) was used for next reaction without further purification.

LCMS: MS Calcd.: 636.7; MS Found: 637 ($[M+H]^+$).

tert-Butyl 4-(((6-(cyclopropyl(4-(trifluoromethyl) benzyl)amino)-5-fluoropyrimidin-4-yl)amino) methyl)-4-(4-methyl-4H-1,2,4-triazol-3-yl)piperidine-1-carboxylate, A5-11

A5-11

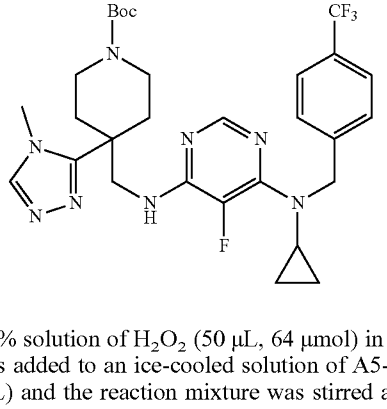

A 35% solution of $H_2O_2$ (50 μL, 64 μmol) in AcOH (280 μL) was added to an ice-cooled solution of A5-10 in DCM (1.5 mL) and the reaction mixture was stirred at rt for 1 h. The solvent was removed in vacuo, the crude was diluted with $H_2O$ and 2N NaOH was added until pH 12. The product was extracted with DCM (×3), the combined organic layer was washed with $H_2O$, dried (phase separator cartridge) and the solvent was removed in vacuo. The residue was then purified by flash CC (MeOH:DCM=1:9) to yield A5-11 (39 mg, 64 μmol) as a solid.

LCMS: MS Calcd.: 604.6; MS Found: 605 ($[M+H]^+$).

2-(4-(((6-(Cyclopropyl(4-(trifluoromethyl)benzyl) amino)-5-fluoropyrimidin-4-yl)amino)methyl)-4-(4-methyl-4H-1,2,4-triazol-3-yl)piperidin-1-yl)acetamide, A7-83

A7-83

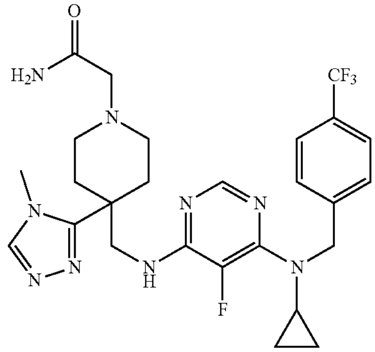

This compound was prepared first by Boc-deprotection and then by alkylation with 2-bromoacetamide following the procedure described previously for the synthesis of example A7-1.

LCMS: MS Calcd.: 561.6; MS Found: 562 ($[M+H]^+$).

Example A7-84

Synthesis of 2-(4-(((6-(cyclopropyl(4-(trifluoromethyl)benzyl)amino)-5-fluoropyrimidin-4-yl)amino) methyl)-4-(1H-imidazol-2-yl)piperidin-1-yl)acetamide, A7-84

Scheme A7-84

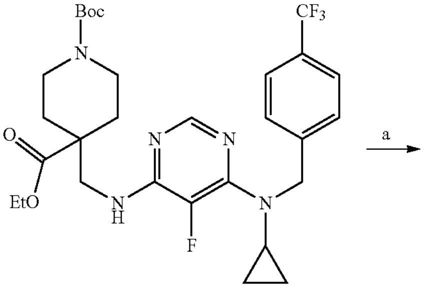

A5-5

-continued

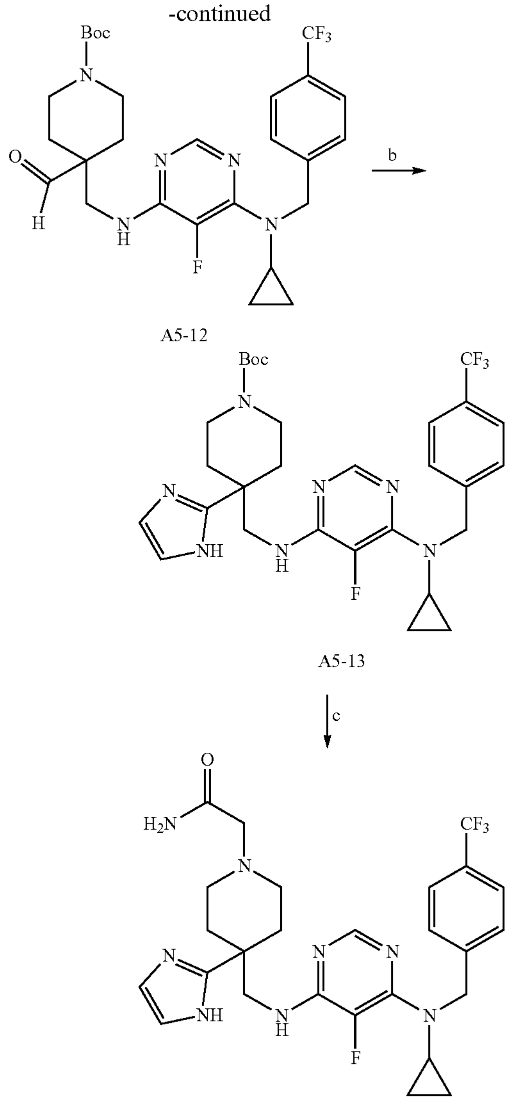

A5-12

A5-13

A7-84 a) $LiAlH_4$, THF. b) Glyoxal, $NH_4OH$, MeOH. c) i) TFA, DCM, ii) DIEA, 2-bromoacetamide tert-Butyl 4-(((6-(cyclopropyl(4-(trifluoromethyl)benzyl)amino)-5-fluoropyrimidin-4-yl)amino)methyl)-4-formylpiperidine-1-carboxylate, A5-12

A5-12

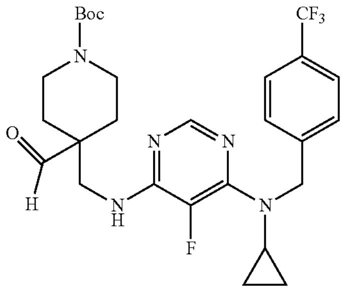

1M $LiAlH_4$ in THF (1.1 mL, 1.1 mmol) was added dropwise to a suspension of A5-5 (520 mg, 0.87 mmol) in THF (8 mL) at −78° C. The reaction mixture was stirred at this temperature for 2 h and then it was quenched by the addition of $H_2O$ (0.15 mL), 2N NaOH (0.75 mL) and $H_2O$ (2.25 mL). The suspension was filtered through Celite® and the solvent was removed in vacuo. The residue was purified by flash CC (Hex:EA=100:0 to 0:100) to yield A5-12 (340 mg, 0.61 mmol) as a solid.

LCMS: MS Calcd.: 551.6; MS Found: 552 ($[M+H]^+$).

tert-Butyl 4-(((6-(cyclopropyl(4-(trifluoromethyl)benzyl)amino)-5-fluoropyrimidin-4-yl)amino)methyl)-4-(1H-imidazol-2-yl)piperidine-1-carboxylate, A5-13

A5-13

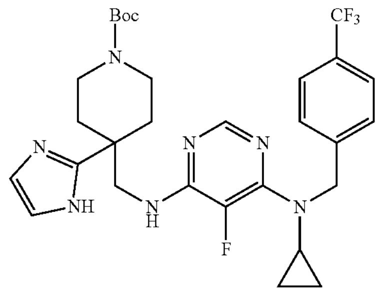

Glyoxal monohydrate (213 mg, 2.79 mmol) was added to a solution of A5-12 (141 mg, 0.26 mmol) in MeOH (7.5 mL) and 32% w/w $NH_4OH$ (3.75 mL, 63 mmol). The reaction mixture was stirred at rt for 3 h. Additional amount of 32% w/w $NH_4OH$ (2 mL, 34 mmol) and glyoxal monohydrate (150 mg, 2 mmol) were added and the mixture was stirred at rt for 2 days. The solvent was removed in vacuo, $H_2O$ was added and the product was extracted with EA (x3), the combined organic layer was washed with brine, dried ($MgSO_4$), filtered and concentrated. The residue was purified by flash CC (Hex:EA=100:0 to 0:100) to yield A5-13 (25 mg, 0.04 mmol) as a solid.

LCMS: MS Calcd.: 589.6; MS Found: 590 ($[M+H]^+$).

2-(4-(((6-(Cyclopropyl(4-(trifluoromethyl)benzyl)amino)-5-fluoropyrimidin-4-yl)amino)methyl)-4-(1H-imidazol-2-yl)piperidin-1-yl)acetamide, A7-84

A7-84

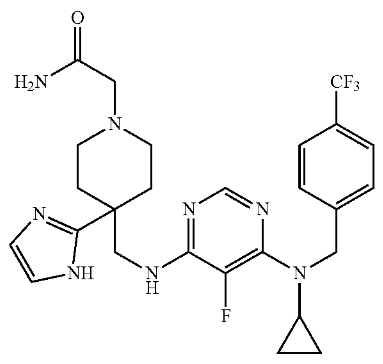

This compound was prepared first by Boc-deprotection and then by alkylation with 2-bromoacetamide following the procedure described previously for the synthesis of example A7-1.

LCMS: MS Calcd.: 546.6; MS Found: 547 ([M+H]$^+$).

Example A7-85

Synthesis of 2-(4-(((6-(cyclopropyl(4-(trifluoromethyl)benzyl)amino)-5-fluoropyrimidin-4-yl)amino)methyl)-4-(1H-1,2,3-triazol-5-yl)piperidin-1-yl)acetamide, A7-85

Scheme A7-85

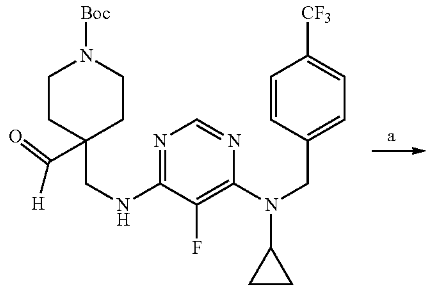

A5-12

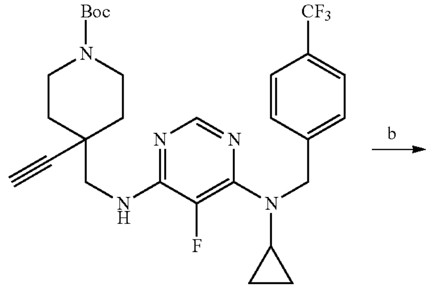

A5-14

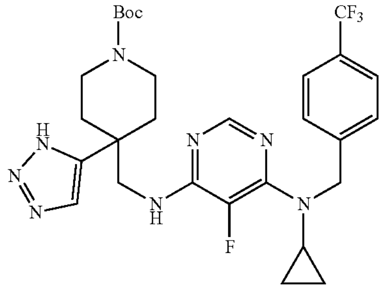

A5-15 c

-continued

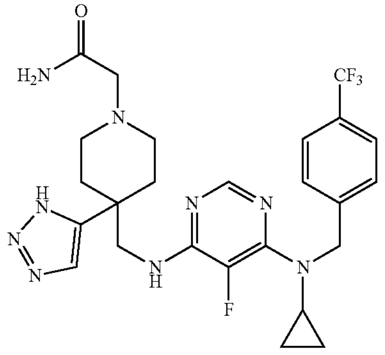

A7-85 a) Dimethyl (1-diazo-2-oxopropyl)phosphonate, $K_2CO_3$, MeOH. b) CuI, azidotrimethylsilane, DMF. c) i)TFA, DCM, ii) DIEA, 2-bromoacetamide tert-Butyl 4-(((6-(cyclopropyl(4-(trifluoromethyl)benzyl)amino)-5-fluoropyrimidin-4-yl)amino)methyl)-4-ethynylpiperidine-1-carboxylate, A5-14

A5-14

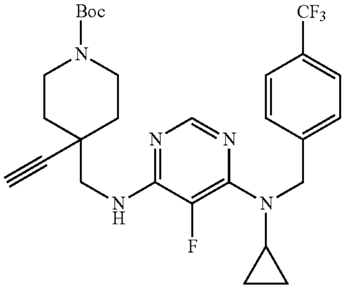

$K_2CO_3$ (66 mg, 0.48 mmol) was added to an ice-cooled solution of A5-12 (100 mg, 0.18 mmol) and dimethyl (1-diazo-2-oxopropyl)phosphonate (36 μL, 0.239 mmol) in MeOH (2 mL) and the reaction mixture was stirred on at rt. The mixture was diluted with $H_2O$ and the product was extracted with EA (x3), the combined organic layer was washed with brine, dried ($MgSO_4$), filtered and concentrated. The residue was purified by flash CC (Hex:EA=100:0 to 0:100) to yield A5-14 (78 mg, 0.14 mmol) as a solid.

LCMS: MS Calcd.: 547.6; MS Found: 548 ([M+H]$^+$).

tert-Butyl 4-(((6-(cyclopropyl(4-(trifluoromethyl)benzyl)amino)-5-fluoropyrimidin-4-yl)amino)methyl)-4-(1H-1,2,3-triazol-5-yl)piperidine-1-carboxylate, A5-15

A5-15

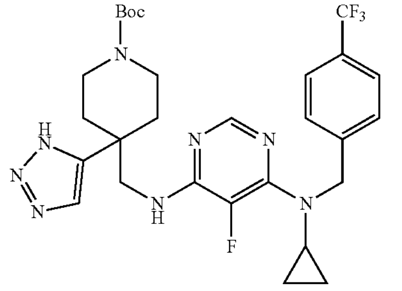

Under an $N_2$ atmosphere CuI (1.1 mg, 5.8 μmol) was added to a solution of A5-14 (75 mg, 0.14 mmol) in DMF (1 mL) and MeOH (0.11 mL). Then azidotrimethylsilane (28 μL, 0.21 mmol) was added and the reaction mixture was stirred on at 100° C. Additional azidotrimethylsilane (15 μL, 0.11 mmol) was added and the reaction mixture was heated on at 100° C. The mixture was diluted with EA and the organic layer was washed with $H_2O$ and brine, dried ($MgSO_4$), filtered and concentrated. The residue was purified by flash CC (MeOH:DCM=1:9) to yield A5-15 (18 mg, 0.03 mmol) as a white solid.

LCMS: MS Calcd.: 590.6; MS Found: 591 ($[M+H]^+$).

2-(4-(((6-(Cyclopropyl(4-(trifluoromethyl)benzyl)amino)-5-fluoropyrimidin-4-yl)amino)methyl)-4-(1H-1,2,3-triazol-5-yl)piperidin-1-yl)acetamide, A7-85

A7-85

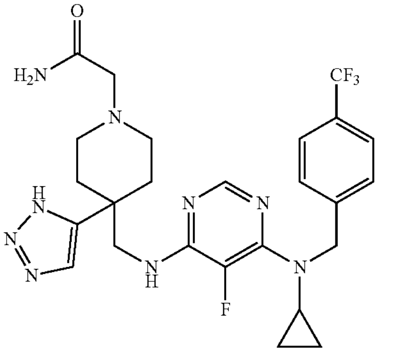

This compound was prepared first by Boc-deprotection and then by alkylation with 2-bromoacetamide following the procedure described previously for the synthesis of example A7-1.

LCMS: MS Calcd.: 547.6; MS Found: 548 ($[M+H]^+$).

Synthesis of benzylic amines A1

The A1 building blocks were either commercially available or were synthesized by reductive amination in as outlined below.

Synthesis of N-(2-fluoro-4-(trifluoromethyl)benzyl)ethanamine, A1-18

Scheme A1-18

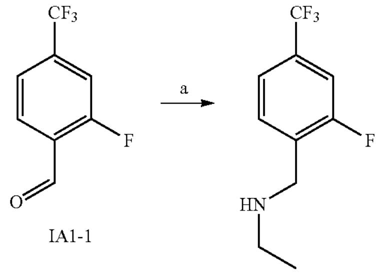

IA1-1

A1-18 a) $EtNH_2$, $MgSO_4$, $NaBH_4$, DCM

Dry $MgSO_4$ (375 mg, 3.12 mmol) was added to a solution of compound 2-fluoro-4-(trifluoromethyl)benzaldehyde iA1-1 (200 mg, 1.04 mmol) and $EtNH_2$ (0.52 mL, 1.04 mmol) in DCM (8 mL). The mixture was stirred at rt for 2 h and then $NaBH_4$ (119 mg, 3.12 mmol) was added to the mixture, and the reaction stirred on. The reaction was filtered, and the filtrate was concentrated in vacuo to give crude A1-18 (267 mg, 1.04 mmol) as a colorless oil. The crude A1-18 was the used without further purification.

LCMS: MS Calcd.: 221; MS Found: 222 ($[M+H]^+$).

A1-34 and A1-65 were prepared by reductive amination from the corresponding alkylamine and 4-(1,1,1,3,3,3-hexafluoro-2-hydroxypropan-2-yl)benzaldehyde. This aldehyde was prepared as described in Michael et al PCT Int. Appl., 2013011033, January 2013.

Synthesis of 2-(4-((ethylamino)methyl)phenyl)-2,2-difluoroethan-1-ol, A1-39

Scheme A1-39

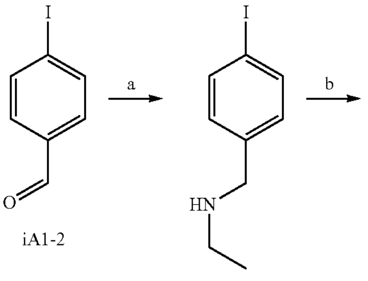

iA1-2 iA1-3

-continued

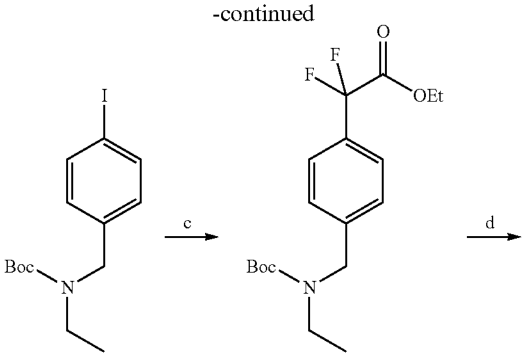

iA1-4 iA1-5

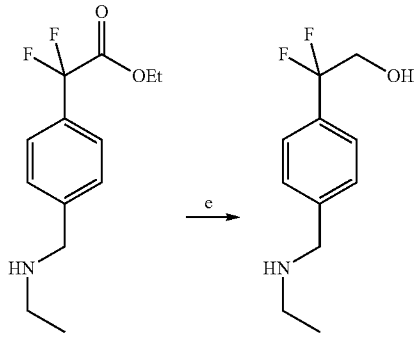

iA1-6 A1-39 a) $EtNH_2$, $NaBH_3CN$, AcOH, MeOH. b) $Boc_2O$, TEA, MeOH. c) Ethyl 2-bromo-2,2-difluoroacetate, Cu, DMSO. d) TFA, DCM. e) $LiAlH_4$, THF.

N-(4-Iodobenzyl)ethanamine, iA1-3 iA1-3

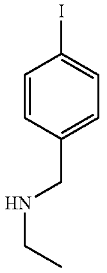

4-Iodobenzaldehyde iA1-2 (2 g, 8.6 mmol) was dissolved in MeOH (90 mL) and $EtNH_2$ (4.8 mL, 2M in MeOH), AcOH (0.5 mL, 8.7 mmol) and $NaBH_3CN$ (650 mg, 10.3 mmol) were added. The reaction mixture was stirred at rt on. Thereafter HCl (10 ml, 2M) was added dropwise and when the bubbling had ceased, $H_2O$ was added and the MeOH was evaporated under reduced pressure. The aq residue was extracted with DCM (×2). The pH of the aq phase was made basic with 2N NaOH and extracted with DCM (3×). The organic phase from the basic extraction was dried ($MgSO_4$) filtered and concentrated to afford iA1-3 (980 mg, 3.75 mmol).

LCMS: MS Calcd.: 261; MS Found: 262 ($[M+H]^+$).

tert-Butyl ethyl(4-iodobenzyl)carbamate, iA1-4 iA1-4

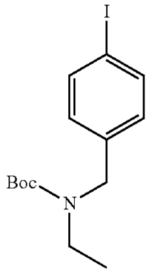

iA1-3 (980 mg, 3.75 mmol) was suspended in MeOH (30 mL) and TEA (1.0 mL, 7.2 mmol) was added, followed by $Boc_2O$ (1 g, 4.6 mmol). This mixture was stirred at rt for 18h. Then the solvent was evaporated under reduced pressure. The residue was re-dissolved in DCM and washed with $H_2O$ (×3) and brine (×1), dried ($MgSO_4$) and concentrated in vacuo to afford iA1-4 (1.16 g, 3.2 mmol).

LCMS: MS Calcd.: 361; MS Found: 362 ($[M+H]^+$).

Ethyl 2-(4-(((tert-butoxycarbonyl)(ethyl)amino) methyl)phenyl)-2,2-difluoroacetate, iA1-5 iA1-5

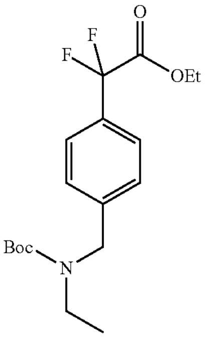

iA1-4 (400 mg, 1.1 mmol), ethyl 2-bromo-2,2-difluoroacetate (0.3 mL, 2.3 mmol) and Cu (250 mg, 3.9 mmol) were suspended in DMSO (8 mL) in a sealed tube and heated on to 60° C. The reaction was poured onto a saturated solution of $NH_4Cl$ (100 mL) and $H_2O$ (50 mL) was added. This aq phase was extracted with EA (×3) and the combined EA phase was dried ($MgSO_4$) and concentrated in vacuo. The residue (650 mg) was purified by Flash CC (Hex:EA=100:0 to 90:10) to afford iA1-5 (365 mg, 1.0 mmol).

LCMS: MS Calcd.: 357; MS Found: 358 ($[M+H]^+$).

Ethyl 2-(4-((ethylamino)methyl)phenyl)-2,2-difluoroacetate, iA1-6 iA1-6

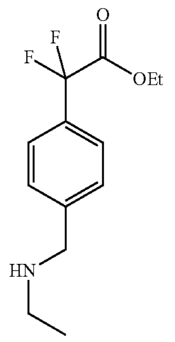

iA1-5 (365 mg, 1.0 mmol) was dissolved in DCM (10 mL) and then TFA (2 mL, 26.1 mmol) was added. The reaction mixture was stirred at rt for a couple of hours and then concentrated in vacuo. The residue was suspended in $H_2O$ and made basic by adding $Na_2CO_3$ in portions and then the aq phase was extracted with $Et_2O$ (×2). This combined organic phase was washed with $H_2O$ (×1), dried with $MgSO_4$ and concentrated in vacuo to afford iA1-6 (136 mg, 0.53 mmol).

LCMS: MS Calcd.: 257; MS Found: 258 ($[M+H]^+$).

2-(4-((Ethylamino)methyl)phenyl)-2,2-difluoroethan-1-ol, A1-39

A1-39

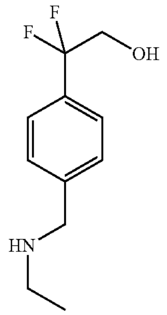

A suspensión of $LiAlH_4$ (80 mg, 2.1 mmol) in THF (4 ml) was cooled with an ice bath and then a solution of iA-6 (136 mg, 0.53 mmol) in THE (2 mL) was added dropwise. The reaction mixture was allowed to reach rt and was stirred for another 2h. To this mixture the following were dropwise and in turn added; $H_2O$ (0.2 mL), NaOH (2N, 0.2 mL) and finally, $H_2O$ (0.6 mL). After filtration through Celite®, the filtrate was dried ($MgSO_4$), filtered and concentrated in vacuo to afford A1-39 (92 mg, 0.43 mmol).

LCMS: MS Calcd.: 215; MS Found: 216 ($[M+H]^+$).

Synthesis of N-(2-fluoro-4-(1-methyl-1H-pyrazol-4-yl)benzyl)cyclopropanamine, A1-67

Scheme A1-67

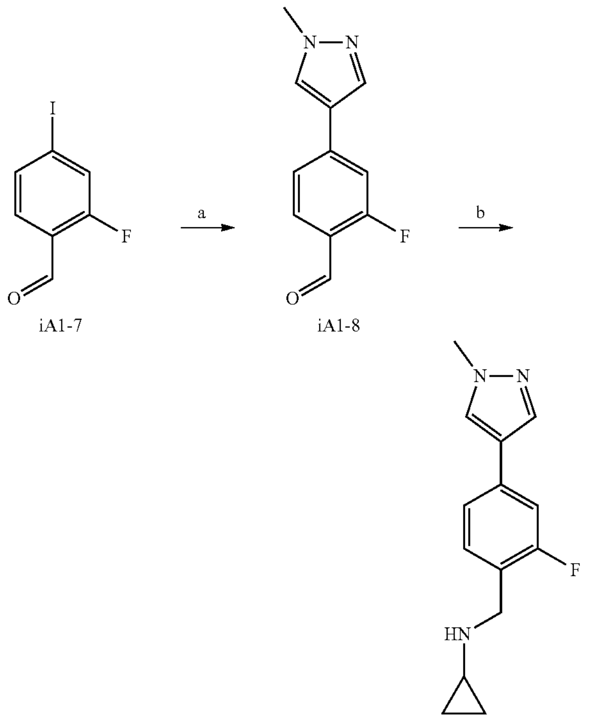

A1-67 a) 1-Methyl-4-(4,4,5,5-tetramethyl-1,3,2-dioxaborolan-2-yl)-1H-pyrazole, $PdCl_2dppf$, DCM, $NaHCO_3$, dioxane. b) Cyclopropanamine, $NaBH_4$, MeOH.

2-Fluoro-4-(1-methyl-1H-pyrazol-4-yl)benzaldehyde, iA1-8 iA1-8

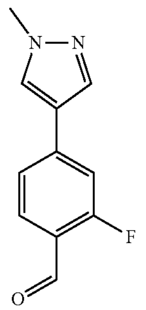

2-Fluoro-4-iodobenzaldehyde iA1-7 (1.05 g, 4.20 mmol) and 1-methyl-4-(4,4,5,5-tetramethyl-1,3,2-dioxaborolan-2-yl)-1H-pyrazole (1.75 g, 8.41 mmol) were dissolved in 1,4-dioxane (12 mL) and $NaHCO_3$ (6.3 mL, 13 mmol, 2M) was added. $N_2$ was bubbled through the solution and then PdCl2dppf·DCM was added. The reaction mixture was heated at 80° C. in a sealed tube on. The reaction mixture cooled was filtered through Celite®, washed with EA and the solvent was removed in vacuo. The residue was purified by Fash CC (Hex:$Et_2O$) to afford iA1-8 (826 mg, 4.05 mmol).

LCMS: MS Calcd.: 204; MS Found: 205 ($[M+H]^+$).

N-(2-Fluoro-4-(1-methyl-1H-pyrazol-4-yl)benzyl) cyclopropanamine, A1-67

A1-67

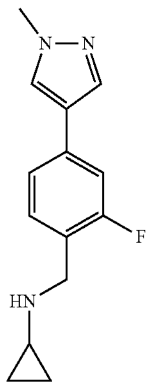

Cyclopropanamine (310 μL, 4.47 mmol) was added to solution of iA1-8 (826 mg, 4.05 mmol) in MeOH (30 mL). The reaction mixture was heated to reflux on, cooled to 0° C. and then $NaBH_4$ (306 mg, 8.09 mmol) was added and then stirred at rt for 4h. The solvent was removed in vacuo, $H_2O$ was added, and the product was extracted with DCM. The combined organic phase was washed with $H_2O$, brine, dried through a phase separator cartridge and concentrated to afford A1-67 (806 mg, 3.29 mmol).

LCMS: MS Calcd.: 245; MS Found: 256 ($[M+H]^+$).

Synthesis of Boc-Protected Piperidines, A4

The A4 building blocks were either commercially available or synthesized as outlined below.

Synthesis of tert-butyl 4-(aminomethyl)-3-(trifluoromethyl)piperidine-1-carboxylate, A4-5

Scheme A4-5

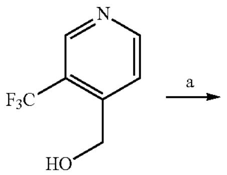

iA4-1

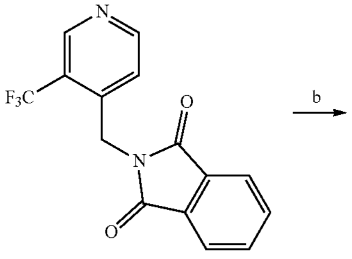

iA4-2

-continued

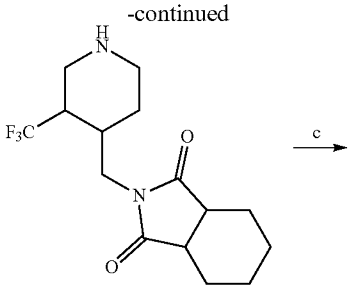

iA4-3

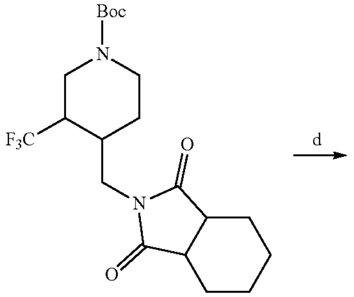

iA4-4

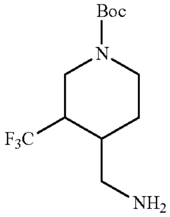

A4-5 a) Phtalimide, DCM, $Ph_3P$, DIAD. b) $PtO_2$, $H_2$, AcOH. c) TEA, DCM, $Boc_2O$. d) Hydrzine, EtOH.

2-((3-(Trifluoromethyl)pyridin-4-yl)methyl)isoindoline-1,3-dione, iA4-2 iA4-2

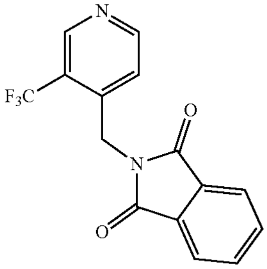

Under stirring and at 0° C. DIAD (1.20 g, 5.97 mmol) was added to a solution of (3-(trifluoromethyl)pyridin-4-yl) MeOH (iA4-1) (0.70 g, 3.98 mmol), phthalimide (0.70 g, 4.77 mmol) and $Ph_3P$ (1.56 g, 5.97 mmol) in DCM (50 mL). Thereafter the reaction was stirred at rt for 4h before quenching with $H_2O$. The resulting mixture was extracted with DCM (2×50 mL), and the combined and organic phases were dried ($Na_2SO_4$), concentrated, and the residue was purified by Flash CC (EA:PE=1:5) to yield crude iA4-2 (1.2 g) as a white solid, that contained Phthalimide. This crude material was used without further purification.

LCMS: MS Calcd.: 306; MS Found: 307 ($[M+1]^+$).

2-((3-(Trifluoromethyl)piperidin-4-yl)methyl)hexahydro-1H-isoindole-1,3(2H)-dione, iA4-3 iA4-3

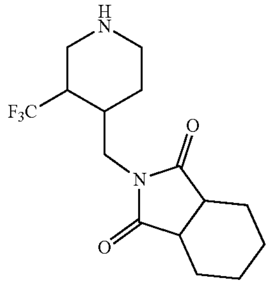

At rt $PtO_2$ (0.2 g) was added to a solution of iA4-2 (1.2 g, 3.9 mmol) in AcOH (5 mL) and the reaction was stirred at 50° C. for 2 days under $H_2$ (60 psi). Thereafter the pH was adjusted to 8-9 with $NH_4OH$ at 0° C. The resulting mixture was extracted with EA (2×100 mL), and the combined organic phases were washed with brine (10 mL), dried ($Na_2SO_4$), and finally concentrated to yield iA4-3 (1.4 g) as a yellow oil, that was used without further purification.

LCMS: MS Calcd.: 318; MS Found: 319 ($[M+1]^+$).

tert-Butyl 4-((1,3-dioxooctahydro-2H-isoindol-2-yl)methyl)-3-(trifluoromethyl)piperidine-1-carboxylate (iA4-4)

iA4-4

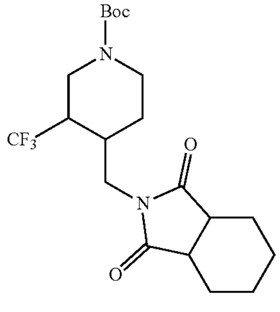

At rt $Boc_2O$ (1.02 g, 4.68 mmol) was added to a solution of iA4-3 (1.4 g, 3.9 mmol) and TEA (0.78 g, 7.8 mmol) in DCM (20 mL). The reaction was stirred at rt for 2 and then $H_2O$ was added. The resulting mixture was extracted with DCM (2×50 mL), and the combined organic phases were dried ($Na_2SO_4$) and concentrated to yield iA4-4 (1.7 g) as a yellow oil. This material was used without further purification.

LCMS: MS Calcd.: 418; MS Found: 363 ($[M+1-56]^+$).

tert-Butyl 4-(aminomethyl)-3-(trifluoromethyl)piperidine-1-carboxylate (A4-5)

A4-5

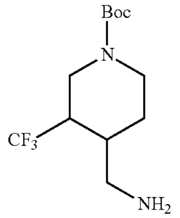

At rt hydrazine hydrate (85%, 6 mL) was added to a solution of iA4-4 (crude 1.4 g, 3.9 mmol) in EtOH (10 mL). The reaction was heated to 80° C. for 3 h and then $H_2O$ (10 mL) was added. The EtOH was evaporated, and the resulting mixture was extracted with EA (2×50 mL). The combined organic phases were dried ($Na_2SO_4$) and concentrated to afford A4-5 (0.9 g) as a brown oil, that was used without further purification.

LCMS: MS Calcd.: 282; MS Found: 227 ($[M+1-56]^+$).

Synthesis of enantiomerically enriched rel-tert-butyl (3R,4R)-4-(aminomethyl)-3-hydroxypiperidine-1-carboxylate, A4-1"

Scheme A4-1″

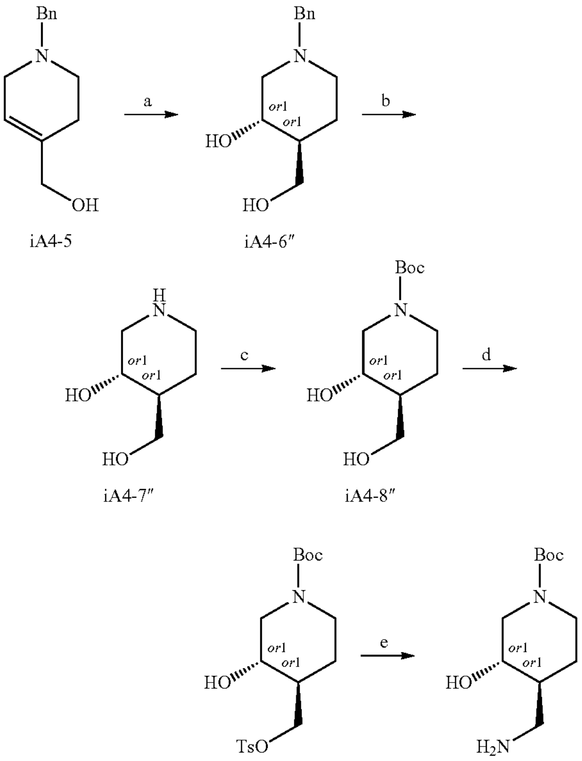

iA4-5 iA4-6″ iA4-7″ iA4-8″ iA4-9″ A4-1″ a) (+)-alpine boramine TMEDA complex, $BF_3{\cdot}Et_2O$, $Et_2O$/THF then $H_2O_2$, NaOH. b) Pd/C, $HCO_2NH_4$, MeOH. c) $Boc_2O$, DCM/MeOH. d) TsCl, pyridine. e) $NH_3$.

rel-(3R,4R)-1-Benzyl-4-(hydroxymethyl)piperidin-3-ol, iA4-6"

iA4-6"

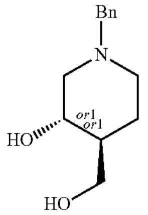

Under an inert atmosphere (Ar) and at rt $BF_3 \cdot Et_2O$ (12 mL, 97.2 mmol) was added dropwise to a stirred solution of (+)-alpine boramine TMEDA complex (20.28 g, 48.7 mmol) in a mix of dry $Et_2O$ (150 mL) and dry THF (32 mL). After 2h and 15 min a solution of iA4-5 (7.6 g, 37.0 mmol) in THF (32 mL) was added dropwise to the white suspension over ca. 15 min and the reaction was stirred at rt for 2.5 h and then to 55° C. on. The reaction was cooled on an ice bath and then $H_2O$ (7.6 mL) was added dropwise, followed by NaOH (5M, 12 mL) and aq $H_2O_2$ solution (35%, 19.2 mL) and finally aq NaOH (50%, 48 mL). The mixture was then heated to reflux (oil bath 60° C.) for 4h and then cooled to rt. An aq solution of $K_2CO_3$ (sat, 80 mL) was added and the mixture was extracted with EA (3×400 mL). The combined organic phase was dried and concentrated in vacuo to give an oil (26 g). The crude material was dissolved in EA (220 mL) and extracted with HCl (5M, 2×110 mL). The combined acidic aq layer was washed with EA (200 mL), cooled on an ice bath and then solid $K_2CO_3$ (ca. 101 g) was added in portions until the pH of the aq phase remained strongly basic. The basic aq phase was thereafter extracted with EA (4×200 mL) and the combined EA phase was dried and concentrated in vacuo to give iA4-6" (8.08 g, 36 mmol).

MS Calcd.: 221; MS Found: 222 ($[M+H]^+$).

$^1$H NMR (400 MHz, Chloroform-d) δ 1.16-1.31 (m, 1H), 1.42-1.61 (m, 2H), 1.79-1.88 (m, 1H), 1.90-1.99 (m, 1H), 2.79 (dd, J=9.4, 1.8 Hz, 1H), 2.91-3.00 (m, 1H), 3.46 (d, J=13.0 Hz, 1H), 3.52 (d, J=13.0 Hz, 1H), 3.59-3.74 (m, 3H), 7.17-7.34 (m, 5H).

HPLC analysis (Chiralpak ID, gradient: 1-45% iIPA (+0.2% DEA) in $CO_2$ over 17 min) showed an 88:12 mixture of enantiomers (76% ee)

rel-(3R,4R)-4-(Hydroxymethyl)piperidin-3-ol, iA4-7"

iA4-7"

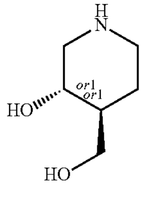

Ammonium formate (6.91 g, 109.6 mmol) and Pd/C (10%, 0.711 g, 0.67 mmol) were added to a solution of the iA4-6" (8.08 g, 36.5 mmol) in MeOH (110 mL) and the reaction was stirred and heated to reflux (oil bath temp 80° C.). Further portions of Pd/C (10%, 0.711 g, 0.67 mmol) were added after 30 min and again after 60 min. After 3.5 h the reaction mixture was cooled and filtered through Celite®. The filtercake was washed with MeOH and the filtrate and washings were combined and concentrated under reduced pressure to give iA4-7" (4.70 g, 35.8 mmol).

MS Calcd.: 131; MS Found: 132 ($[M+H]^+$).

$^1$H NMR (400 MHz, DMSO-d6) δ 0.98-1.13 (m, 1H), 1.20-1.33 (m, 1H), 1.59-1.69 (m, 1H), 2.07-2.18 (m, 1H), 2.24-2.36 (m, 1H), 2.80 (d, J=12.0 Hz, 1H), 2.90 (dd, J=11.5, 4.5 Hz, 1H), 3.11 (d, J=4.1 Hz, 1H), 3.25-3.36 (m, 1H), 3.59 (dd, J=10.2, 4.1 Hz, 1H), 4.32 (br s, 1H), 4.49 (br s, 1H).

rel-tert-Butyl (3R,4R)-3-hydroxy-4-(hydroxymethyl) piperidine-1-carboxylate, iA4-8"

iA4-8"

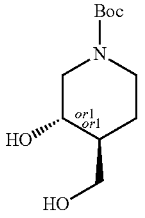

A solution of $Boc_2O$ (7.82 g, 35.8 mmol) in DCM (20 mL) was added dropwise to a stirred, cooled (ice bath) solution of iA4-7" (4.70 g, 35.8 mmol) in a mix of DCM (30 mL) and MeOH (12 mL). After stirring on, the mixture was concentrated and the residue was purified by Flash CC (MeOH: DCM=0:100-5:95) to yield iA4-8" (7.96 g) as a colorless oil.

MS Calcd.: 231; MS Found: 232 ($[M+H]^+$).

$^1$H NMR (400 MHz, Chloroform-d) δ 1.07-1.21 (m, 1H), 1.45 (s, 9H), 1.53-1.62 (m, 2H), 1.64-1.75 (m, 1H), 2.47-2.58 (m, 1H), 2.59-2.73 (m, 1H), 3.49-3.60 (m, 1H), 3.65-3.74 (m, 1H), 3.74-3.83 (m, 1H), 3.98-4.31 (m, 2H).

rel-tert-Butyl (3R,4R)-3-hydroxy-4-((tosyloxy) methyl)piperidine-1-carboxylate, iA4-9"

iA4-9"

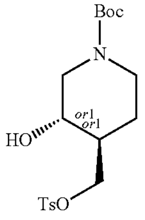

TsCl (7.22 g, 37.9 mmol) was added portionwise (over 10 min) to a stirred solution of iA4-8" (7.96 g, 34.4 mmol) in dry pyridine (17 mL on an ice bath. The mixture was allowed to reach rt over 3h. Subsequently, the mixture was diluted with DCM, washed with aq HCl (1M), aq $NaHCO_3$ (4%), brine, dried and concentrated to give a thick yellow oil. This residue was purified by flash CC (EA:Hex=0:100-40:60) to yield iA4-9" (8.49 g, 22 mmol) as a white solid.

MS Calcd.: 385; MS Found: 386 ($[M+H]^+$).

$^1$H NMR (400 MHz, Chloroform-d) δ 1.36-1.42 (m, 1H), 1.45 (s, 9H), 1.62-1.73 (m, 2H), 2.42-2.54 (m, 4H), 2.55-

2.71 (m, 1H), 3.40-3.52 (m, 1H), 3.93-4.14 (m, 2H), 4.15-4.32 (m, 2H), 7.35 (d, J=8.0 Hz, 2H), 7.76-7.81 (d, J=8.0 Hz, 2H).

rel-tert-Butyl (3R,4R)-4-(aminomethyl)-3-hydroxypiperidine-1-carboxylate, A4-1"

A4-1"

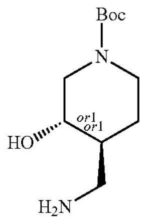

iA4-9" (52 mg, 0.14 mmol) was dissolved in $NH_3$ (32 wt %, 0.82 mL, 14 mmol) in a pressure tube and the reaction was heated on at 80° C. After cooling to rt $H_2O$ was added and the product was extracted with DCM. The combined organic layer was washed with $H_2O$, dried through a phase separator cartridge and concentrated in vacuo to yield A4-1" (27 mg, 0.12 mmol) as a white solid.

MS Calcd.: 230; MS Found: 231 ($[M+H]^+$).

This enantiomerically enriched intermediate was then used for the synthesis of the corresponding A6 intermediates, that subsequently gave the corresponding A7 final compounds following the experimental procedures described above.

Synthesis of tert-butyl 4-(aminomethyl)-4-carbamoylpiperidine-1-carboxylate, A4-9

Scheme A4-9

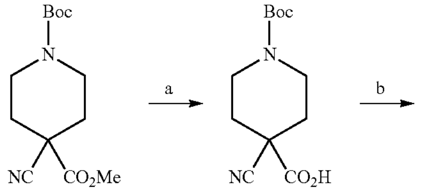

iA4-10 iA4-11

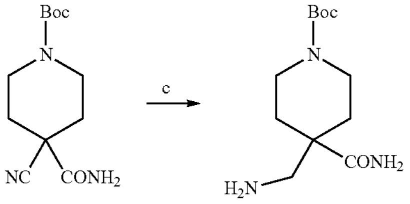

iA4-12 A4-9 a) LiOH, THF. b) $NH_3$, HATU, DMF. c) $PtO_2$, AcOH.

1-(tert-Butoxycarbonyl)-4-cyanopiperidine-4-carboxylic acid, iA4-11 iA4-11

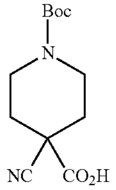

1-(tert-Butyl) 4-methyl 4-cyanopiperidine-1,4-dicarboxylate, iA4-10, (500 mg, 1.9 mmol) was dissolved in THF (7 mL) and a solution of LiOH (180 mg, 7.2 mmol) in $H_2O$ (1 mL) was added. The reaction mixture was stirred at rt on. The reaction mixture was diluted with $Et_2O$ (20 mL) and then washed with $H_2O$ (3×10 mL). The aq phase was acidified with citric acid (1N, 10 mL) and extracted with DCM (3×20 ml). The combined organic phase was dried ($MgSO_4$), filtered, and concentrated to afford iA4-11 (503 mg, 1.98 mmol).

LCMS: MS Calcd.: 254; MS Found: 253 ($[M-H]^-$).

tert-Butyl 4-carbamoyl-4-cyanopiperidine-1-carboxylate, iA4-12 iA4-12

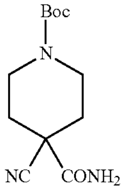

iA4-11 (500 mg, 1.9 mmol) was dissolved in DMF (10 mL) and DIEA (1.0 mL, 5.7 mmol) was added, followed by addition of $NH_3$ (6 ml, 0.5M solution) and HATU (900 mg, 2.4 mmol). This mixture was stirred at rt for 18h, then diluted with EA (100 mL) and washed with $H_2O$ (2×25 mL). The organic phase was dried ($MgSO_4$) and concentrated in vacuo to afford iA4-12 (700 mg, 2.76 mmol).

$^1H$ NMR (400 MHz, Chloroform-d) δ 1.46 (s, 9H), 1.95 (d, J=12.7 Hz, 2H), 2.07 (td, J=13.2, 12.6, 4.4 Hz, 2H), 3.11-3.25 (m, 2H), 3.72 (dtd, J=13.3, 6.7, 4.2 Hz, 2H), 4.21 (s, 2H).

tert-Butyl 4-(aminomethyl)-4-carbamoylpiperidine-1-carboxylate, A4-9

A4-9

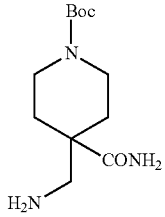

$PtO_2$ (45 mg, 0.2 mmol) was added to a solution of iA4-12 (480 mg, 1.9 mmol) in AcOH (10 ml). This mixture was hydrogenated at 15 Psi in a Parr apparatus for 18h. The reaction mixture was filtered and concentrated in vacuo to yield A4-9 (390 mg, 1.5 mmol) as an oil.

LCMS: MS Calcd.: 257; MS Found: 258 ([M+H]$^+$).

Synthesis of tert-butyl 4-(aminomethyl)-4-cyanopiperidine-1-carboxylate, A4-13

Scheme A4-13

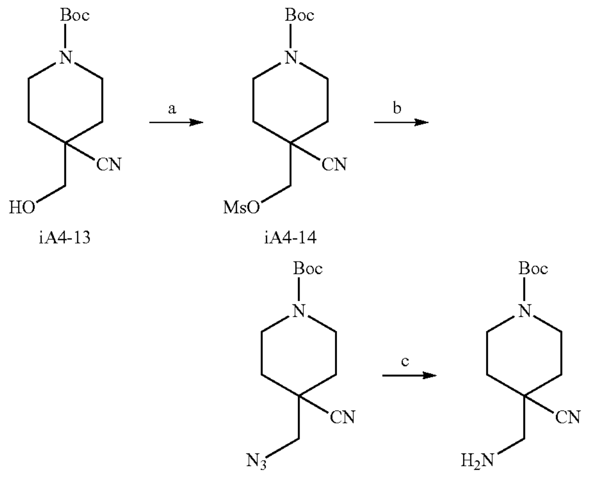

iA4-13 iA4-14 iA4-15 A4-13 a) MsCl, TEA, DCM. b) $NaN_3$, DMF. c) H2, Pd/C, EtOH.

tert-Butyl 4-cyano-4-(((methylsulfonyl)oxy)methyl) piperidine-1-carboxylate, iA4-14 iA4-14

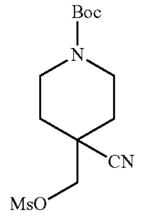

TEA (726 μL, 5 mmol) and methanesulfonyl chloride (193 μL, 2.5 mmol) were added to a solution of tert-butyl 4-cyano-4-(hydroxymethyl)piperidine-1-carboxylate iA4-13 (500 mg, 2 mmol) in 20 mL of anhydrous DCM and the reaction was stirred at rt for 2 h. Thereafter, DCM (20 mL) was added. The organic phase was washed with $H_2O$ (30 mL), brine (30 mL), dried ($MgSO_4$) and concentrated in vacuo to afford iA4-14 (642 mg, 2.02 mmol) as a white solid.

LCMS: MS Calcd.: 318.4; MS Found: 319 ([M+H]$^+$).

tert-Butyl 4-(azidomethyl)-4-cyanopiperidine-1-carboxylate, iA4-15 iA4-15

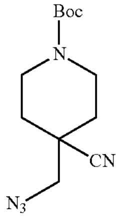

$NaN_3$ (840 mg, 13 mmol) was added to a solution of iA4-14 (0.42 g, 1.3 mmol) in DMF (0.5 mL) and the reaction mixture was stirred at 100° C. for 2 days. More $NaN_3$ (420 mg) was added and the reaction was stirred at 100° C. for an additional 15 h. Then, the reaction mixture was treated with $Et_2O$ (30 mL) and $H_2O$ (30 mL), the organic phase was washed with brine (30 mL), dried ($Na_2SO_4$) and concentrated in vacuo to give iA4-15 (0.34 g, 1.28 mmol).

LCMS: MS Calcd.: 265.3; MS Found: 266 ([M+H]$^+$).

tert-Butyl 4-(aminomethyl)-4-cyanopiperidine-1-carboxylate, A4-13

A4-13

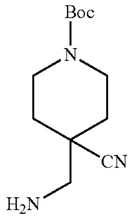

A solution of iA4-15 (26 mg, 0.097 mmol) in EtOH (3 ml) was added to Pd/C (10%, 3 mg) and placed under a $H_2$ (1 atm) and the reaction mixture was stirred on. Then the mixture was filtered through a pad of Celite® and concentrated in vacuo to afford A4-13 (20 mg, 0.08 mmol).

LCMS: MS Calcd.: 239.3; MS Found: 240 ([M+H]$^+$).

General Method B—Synthesis from Cbz-Protected Piperidines.

General Scheme B

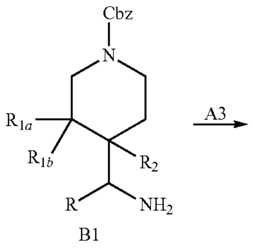

B1

-continued

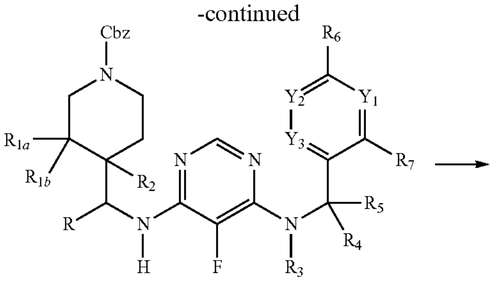

B2

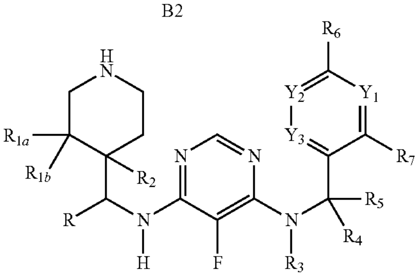

B3

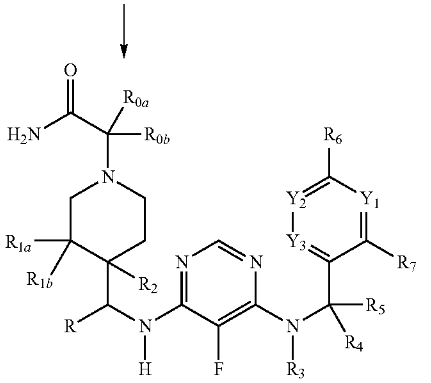

B4

Intermediate A3, a base (such as; DIEA, TEA or $K_2CO_3$) and the primary amine B1 were dissolved in a solvent (such as DMSO or DMSO-$H_2O$, $H_2O$, $H_2O$-EtOH mixtures) and the temperature was then increased to 70-100° C. on, or until the reaction was considered complete. Thereafter, workup and purification gave Intermediate B2. The following Cbz-deprotection then gave B3 that was often used without further purification, in the alkylation with 2-bromoacetamide and a suitable base, such as $K_2CO_3$, DIEA, TEA, to yield B4.

In the cases when the B4 products were mixture of stereoisomers they were often (but not always) subjected to chiral resolution (chromatography) to obtain single stereoisomers as end products.

Example B4-1

Synthesis of 2-(4-(((6-(cyclopropyl(4-(trifluoromethyl)benzyl)amino)-5-fluoropyrimidin-4-yl)amino)methyl)-3-hydroxy-3-methylpiperidin-1-yl)acetamide (B4-1) and following purification of the stereo isomers B4-1-1 and B4-1-2

Scheme B4-1

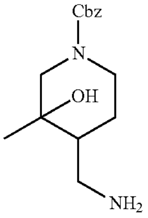

B1-1

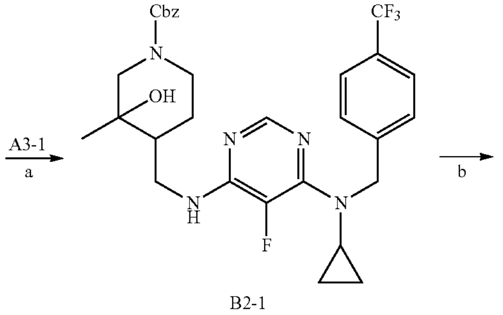

B2-1

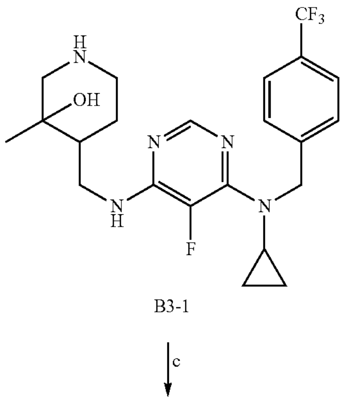

B3-1

-continued

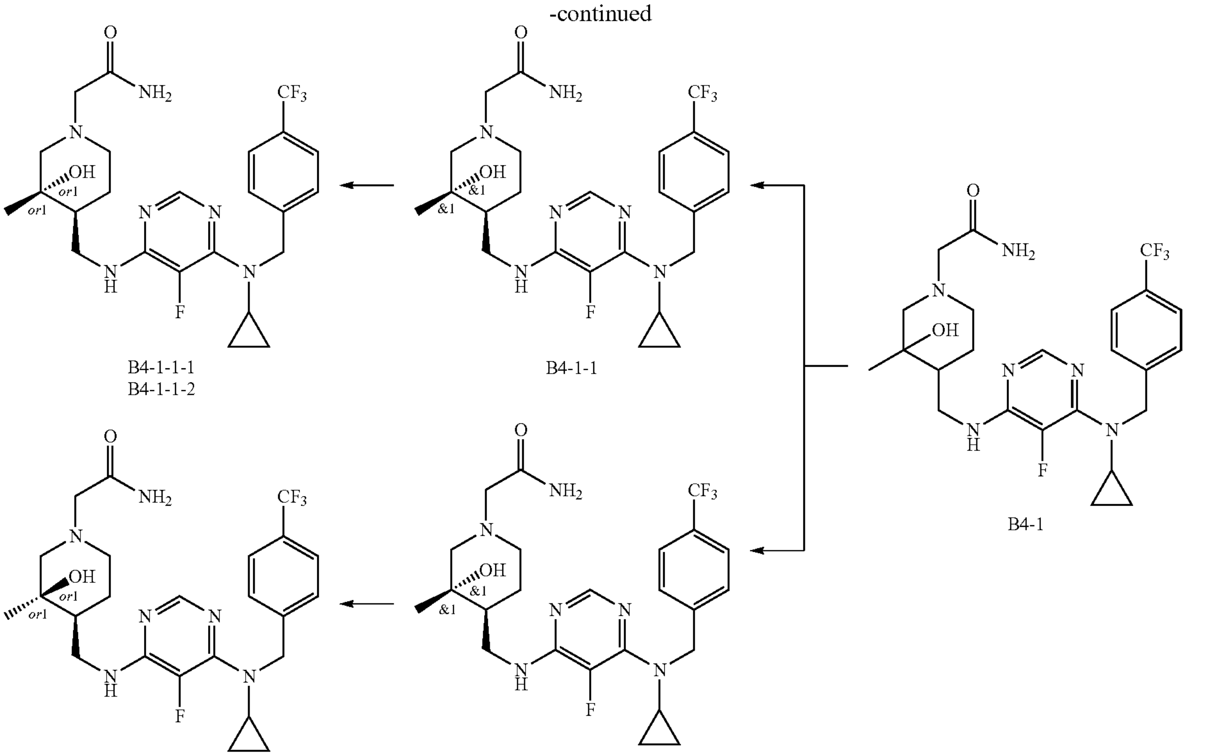

B4-1-1-1
B4-1-1-2

B4-1-1

B4-1

B4-1-2-1
B4-1-2-2

B4-1-2 a) DIEA, DMSO. b) $Pd(OH)_2$, $H_2$, MeOH. c) 2-Bromoacetamide, $K_2CO_3$, DMF.

Benzyl 4-(((6-(cyclopropyl(4-(trifluoromethyl)benzyl)amino)-5-fluoropyrimidin-4-yl)amino)methyl)-3-hydroxy-3-methylpiperidine-1-carboxylate (B2-1)

B2-1

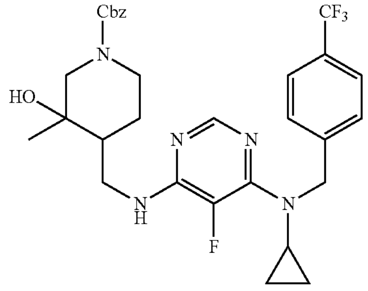

To a solution of benzyl 4-(aminomethyl)-3-hydroxy-3-methylpiperidine-1-carboxylate (173 mg, 0.62 mmol) and A3-1 (205 mg, 0.62 mmol) in DMSO (6 mL) DIEA (241 mg, 1.87 mmol) was added and the reaction was stirred at 90° C. for 2 h under microwave irradiation. After cooling to rt, $H_2O$ (60 mL) was added and the mixture was extracted with EA (3×). The combined organic layer was washed with brine (2×20 mL), dried ($Na_2SO_4$), filtered and concentrated in vacuo. The remaining residue was purified by Prep TLC (MeOH:DCM=1:20) to afford B2-1 (267 mg, 0.45 mmol) as a white solid, that was used without further purification.

LCMS: Observed MS 588 ($[M+1]^+$).

4-(((6-(Cyclopropyl(4-(trifluoromethyl)benzyl)amino)-5-fluoropyrimidin-4-yl)amino)methyl)-3-methylpiperidin-3-ol (B3-1)

B3-1

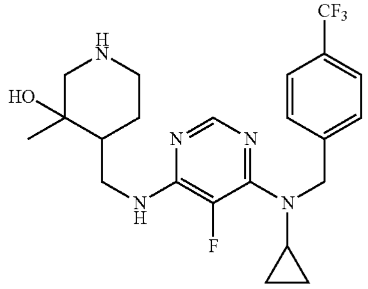

$Pd(OH)_2$ (90 mg, 20%) was added to a solution of B2-1 (267 mg, 0.46 mmol) in MeOH (10 mL) and the reaction was stirred at rt under $H_2$ (1 atm) on. The mixture was filtered, and the filtrate was concentrated in vacuo to yield B3-1 (366 mg) as a white solid, that was used without further purification.

LCMS: MS Calcd.: 453; MS Found: 454 ($[M+1]^+$).

2-(4-(((6-(Cyclopropyl(4-(trifluoromethyl)benzyl)amino)-5-fluoropyrimidin-4-yl)amino)methyl)-3-hydroxy-3-methylpiperidin-1-yl)acetamide (B4-1)

B4-1

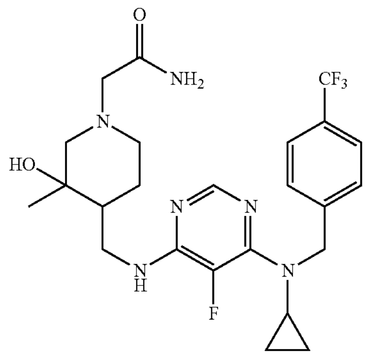

At rt $K_2CO_3$ (1.12 g, 8.10 mmol) and 2-bromoacetamide (233 mg, 1.62 mmol) were added to a solution of B3-1 (366 mg, 0.81 mmol) in DMF (10 mL). The reaction was stirred at 35° C. for 4 h and then quenched by the addition of $H_2O$ (80 mL). The resulting mixture was extracted with EA (3×30 mL) and the combined organic layer was washed with brine (3×20 mL) and concentrated in vacuo. The remains (540 mg) were purified by Prep HPLC to afford two diastereomeric products B4-1-1 (140 mg) and B4-1-2 (130 mg) as white solids.

B4-1-1 was then subjected to chiral chromatography to yield B4-1-1-1 ($1^{st}$ eluting isomer) and B4-1-1-2 ($2^{nd}$ eluting isomer). NUE020138 and NUE020139

B4-1-2 was then subjected to chiral chromatography to yield B4-1-2-1 ($1^{st}$ eluting isomer) and B4-1-2-2 ($2^{nd}$ eluting isomer). NUE020698 and NUE020699

MS Calcd.: 510; MS Found: 511 ($[M+1]^+$).

The following cmpds were synthesized according to General Method B using the shown starting materials (Table B).

TABLE B

| B1 | B4 |
|---|---|
| B1-2<br>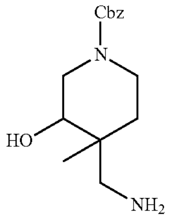<br>benzyl 4-(aminomethyl)-3-hydroxy-4-methylpiperidine-1-carboxylate | B4-2-1-1<br>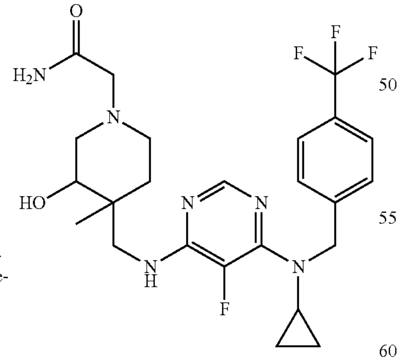<br>2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide<br>$1^{st}$ eluting isomer |

TABLE B-continued

| B1 | B4 |
|---|---|
| B1-2 | B4-2-1-2<br>2-(4-(((6-(cyclopropyl(4-(trifluoromethyl)benzyl)amino)-5-fluoropyrimidin-4-yl)amino)methyl)-3-hydroxy-4-methylpiperidin-1-yl)acetamide<br>$2^{nd}$ eluting isomer |

For the B4-2 compounds only 2 compounds (enantiomers) were isolated.

General Method C:

General scheme C

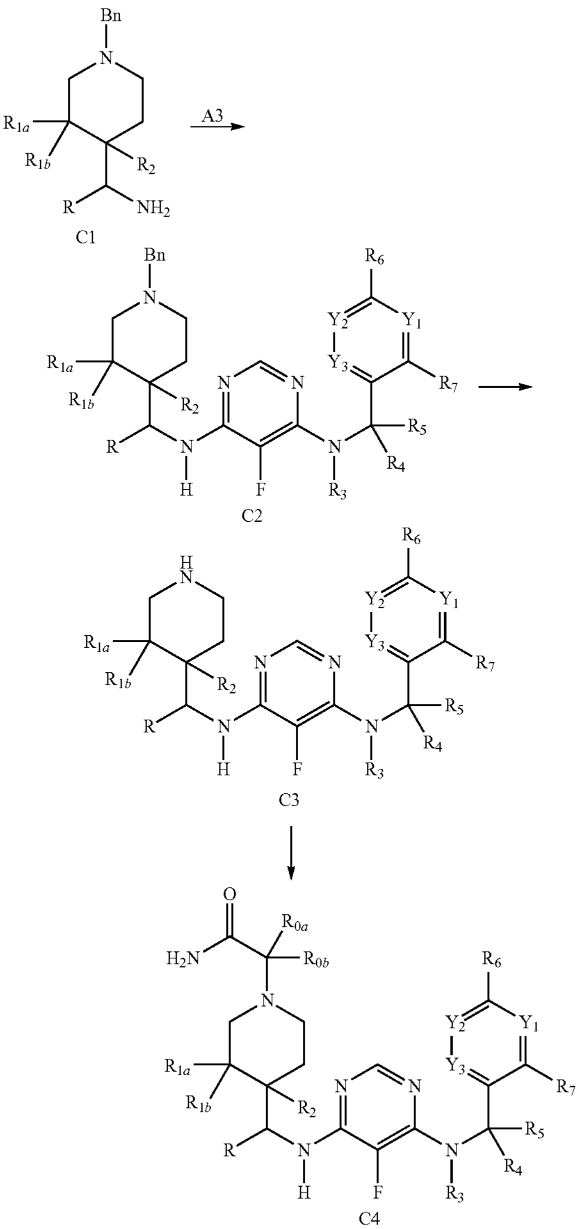

Intermediate A3, a base (such as; DIEA, TEA or $K_2CO_3$) and the primary amine C1 were dissolved in a solvent (such as DMSO or DMSO-$H_2O$, $H_2O$, $H_2O$-EtOH mixtures) and the temperature was then increased to 70-100° C. on, or until the reaction was considered complete. Thereafter, workup and purification gave Intermediate C2. The following Bn-deprotection under $H_2$ atmosphere and using Pd as a catalyst, gave C3 that was often used without further purification, in the alkylation with 2-bromoacetamide and a suitable base, such as $K_2CO_3$, DIEA, TEA, to yield $C_4$.

In the cases when the C4 products were mixture of stereoisomers they were often (but not always) subjected to chiral resolution (chromatography) to obtain single stereoisomers as end products.

Examples C4-1

Synthesis of 2-(4-(((6-(cyclopropyl(4-(trifluoromethyl)benzyl)amino)-5-fluoropyrimidin-4-yl)amino)methyl)-3-hydroxy-4-(hydroxymethyl)piperidin-1-yl)acetamide (C4-1) and isolation of two isomers (C4-1-1 and C4-1-2)

Scheme C4-1

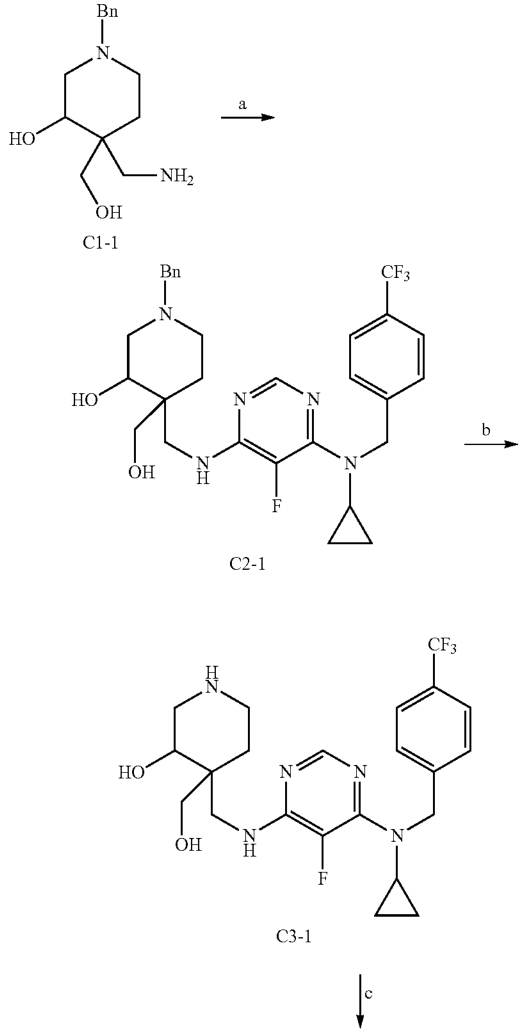

C1-1
C2-1
C3-1

-continued

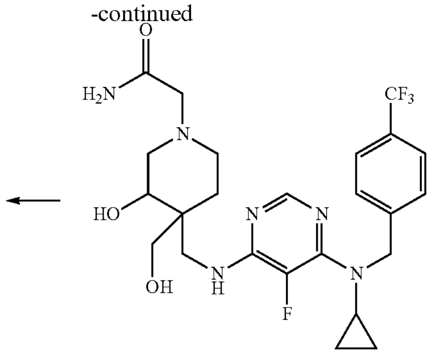
C4-1-1
C4-1-2
C4-1 a) DIEA, A2-1, DMSO. b) Pd/C, $H_2$, EA. c) 2-Bromoacetamide, $K_2CO_3$.

1-Benzyl-4-(((6-(cyclopropyl(4-(trifluoromethyl)benzyl)amino)-5-fluoropyrimidin-4-yl)amino)methyl)-4-(hydroxymethyl)piperidin-3-ol (C2-1)

C2-1

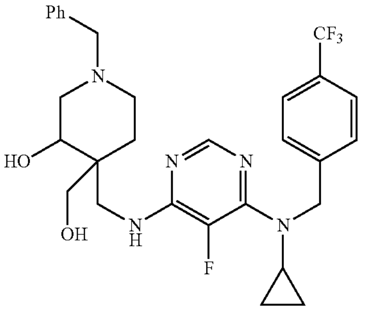

DIEA (465 mg, 3.6 mmol) and A3-1 (434 mg, 1.32 mmol) were added to a solution of C1-1 (300 mg, 1.2 mmol) in DMSO (5 mL). The reaction was heated to 95° C. on under microwave irradiation. Then, the mixture was poured into $H_2O$ (20 mL) and extracted with EA (3×20 mL). The combined organic layers were washed with brine (20 mL), dried ($Na_2SO_4$), filtered, and then concentrated in vacuo. The residue was purified by Flash CC (DCM/MeOH=10:1) to afford C2-1 (432 mg, 64% yield) as a yellow oil.

LCMS: MS Calcd.: 559; MS Found: 560 ($[M+1]^+$).

4-(((6-(Cyclopropyl(4-(trifluoromethyl)benzyl)amino)-5-fluoropyrimidin-4-yl)amino)methyl)-4-(hydroxymethyl)piperidin-3-ol (C3-1)

C3-1

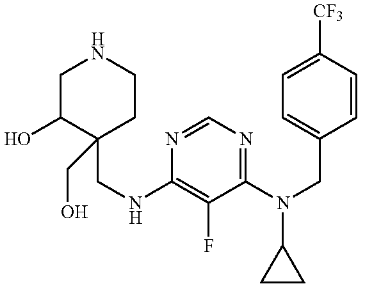

First Pd/C (10%, 90 mg) and thereafter several drops of HOAc were added to a solution of C2-1 (432 mg, 0.77 mmol) in EA (10 mL). The reaction was stirred at ambient temperature under a $H_2$ atmosphere (1 atm) for 2 days. Then the mixture was filtered, washed with EA and pH neutralized with sat $NaHCO_3$. The resulting mixture was extracted with EA, the pooled organic phase was concentrated in vacuo to afford crude C3-1 (247 mg, 68% yield) as brown semi-solid, which was used without further purification.

LCMS: MS Calcd.: 469; MS Found: 470 ($[M+1]^+$).

2-(4-(((6-(Cyclopropyl(4-(trifluoromethyl)benzyl)amino)-5-fluoropyrimidin-4-yl)amino)methyl)-3-hydroxy-4-(hydroxymethyl)piperidin-1-yl)acetamide (C4-1)

C4-1

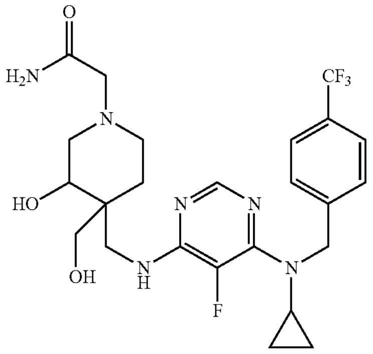

2-Bromoacetamide (87 mg, 0.63 mmol) and $K_2CO_3$ (363 mg, 2.6 mmol) were added to a solution of C3-1 (247 mg, 0.52 mmol) in DMF (10 mL) and the reaction was stirred at rt on. The reaction was poured into $H_2O$ (30 mL), extracted with EA (3×30 mL). The combined organic phase was washed with brine (30 mL), dried ($Na_2SO_4$), filtered and then concentrated in vacuo. The residue was purified by Flash CC (DCM/MeOH=15/1) to yield C4-1 (84 mg, 30% yield) as a white solid.

Isolation of Two Isomers of C4-1—C4-1-1 and C4-1-2

After Prep-Chiral-HPLC, two enantiomers C4-1-1 ($1^{st}$ eluting isomer) and C4-1-2 ($2^{nd}$ eluting isomer) were isolated from the racemic compound C4-1 as white solids.

The following cmpds were synthesized according to General Method C using the shown starting materials (Table C).

TABLE C

| C1 | A3 | C4 |
|---|---|---|
| C1-1 | A3-3<br>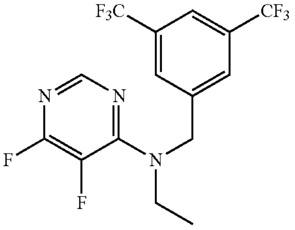<br>N-(3,5-bis(trifluoromethyl)benzyl)-N-ethyl-5,6-difluoropyrimidin-4-amine | C4-2-1<br>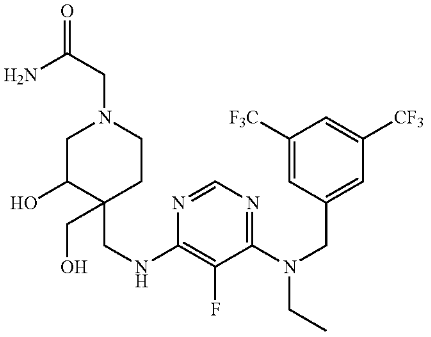<br>2-(4-(((6-((3,5-bis(trifluoromethyl)benzyl)(ethyl)amino)-5-fluoropyrimidin-4-yl)amino)methyl)-3-hydroxy-4-(hydroxymethyl)piperidin-1-yl)acetamide<br>$1^{st}$ eluting isomer |
| C1-1 | A3-3 | C4-2-2<br>2-(4-(((6-((3,5-bis(trifluoromethyl)benzyl)(ethyl)amino)-5-fluoropyrimidin-4-yl)amino)methyl)-3-hydroxy-4-(hydroxymethyl)piperidin-1-yl)acetamide<br>$2^{nd}$ eluting isomer |

Synthesis of 4-(aminomethyl)-1-benzyl-4-(hydroxymethyl)piperidin-3-ol, C1-1

Scheme C1-1

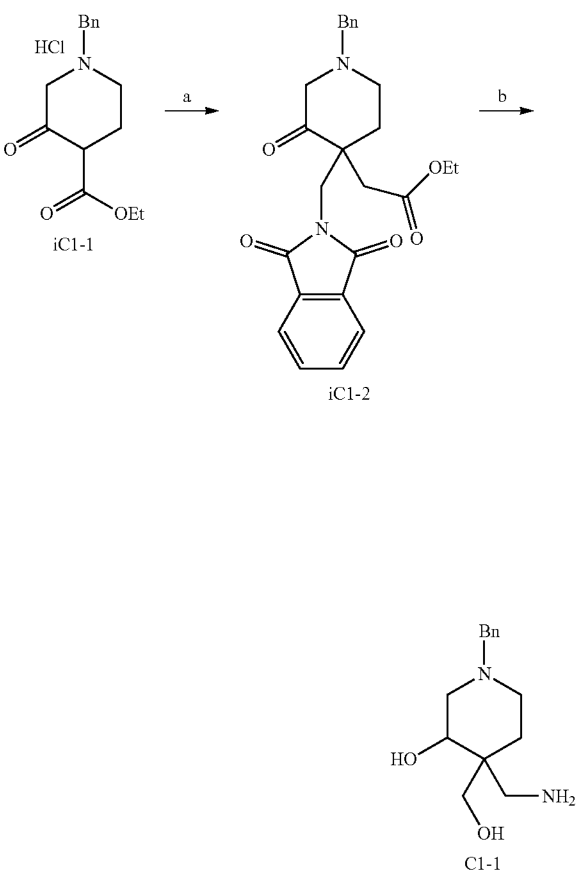

a) 2-(Bromomethyl)phtalimide, tBuOK, THF. b) $NaBH_4$, iPrOH/$H_2O$.

Ethyl 1-benzyl-4-((1,3-dioxoisoindolin-2-yl)methyl)-3-oxopiperidine-4-carboxylate, iC1-2 iC1-2

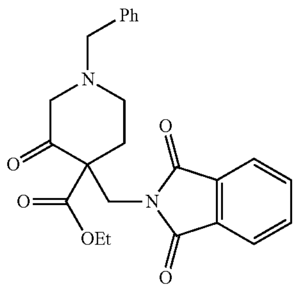

Ethyl 1-benzyl-3-oxopiperidine-4-carboxylate hydrocholide iC1-1 (5.0 g, 16.8 mmol) was added to an ice-cooled suspension of tBuOK (5.6 g, 50 mmol) in THF (50 mL) and the reaction was stirred at 0° C. for 30 min. Then the reaction was warmed to rt, and stirred at this temperature for 60 min. The reaction was again cooled before the addition of 2-(bromomethyl)phtalimide (6.3 g, 25.2 mmol) in THF (30 mL) at 0° C. The reaction mixture was stirred at 0° C. for 60 min, warmed up to ambient temperature and stirred at this temperature on. The reaction was quenched with $NH_4Cl$ (sat, 50 mL), extracted with EA (3×50 mL), the combined organic phase was washed with brine (50 mL), dried ($Na_2SO_4$), filtered, concentrated and the residue was purified by Flash CC, (DCM:MeOH=20:1) to afford crude iC1-2 (2.4 g, 34% yield) as white solid.

LCMS: MS Calcd.: 420; MS Found: 421 ($[M+1]^+$).

4-(Aminomethyl)-1-benzyl-4-(hydroxymethyl)piperidin-3-ol, C1-1

C1-1

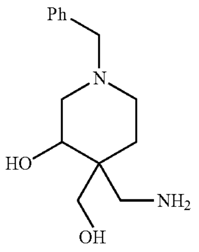

$NaBH_4$ (1.2 g, 31.4 mmol) was added to suspension of crude iC1-2 (2.2 g, 5.2 mmol) in iPrOH/$H_2O$ (7/1, 72 mL) at rt. The reaction was stirred at this temperature for 5 h. The reaction was quenched by the addition of conc HCl until the pH was ca 1. The mixture was warmed to 80° C. and stirred at this temperature on. The mixture was filtered and washed with DCM (10 mL). The aq solution was neutralized with sat. $NaHCO_3$, freeze-dried and dissolved in EA (20 mL), filtered and washed with EA (10 mL). The combined organic layers were concentrated in vacuo to afford C1-1 (600 mg, 45% yield) as a pale-yellow solid, which was used directly in next step without further purification.

LCMS: MS Calcd.: 250; MS Found: 251 ($[M+1]^+$).

General Method 1D—Synthesis of 1,2-Diols

General Scheme 1D

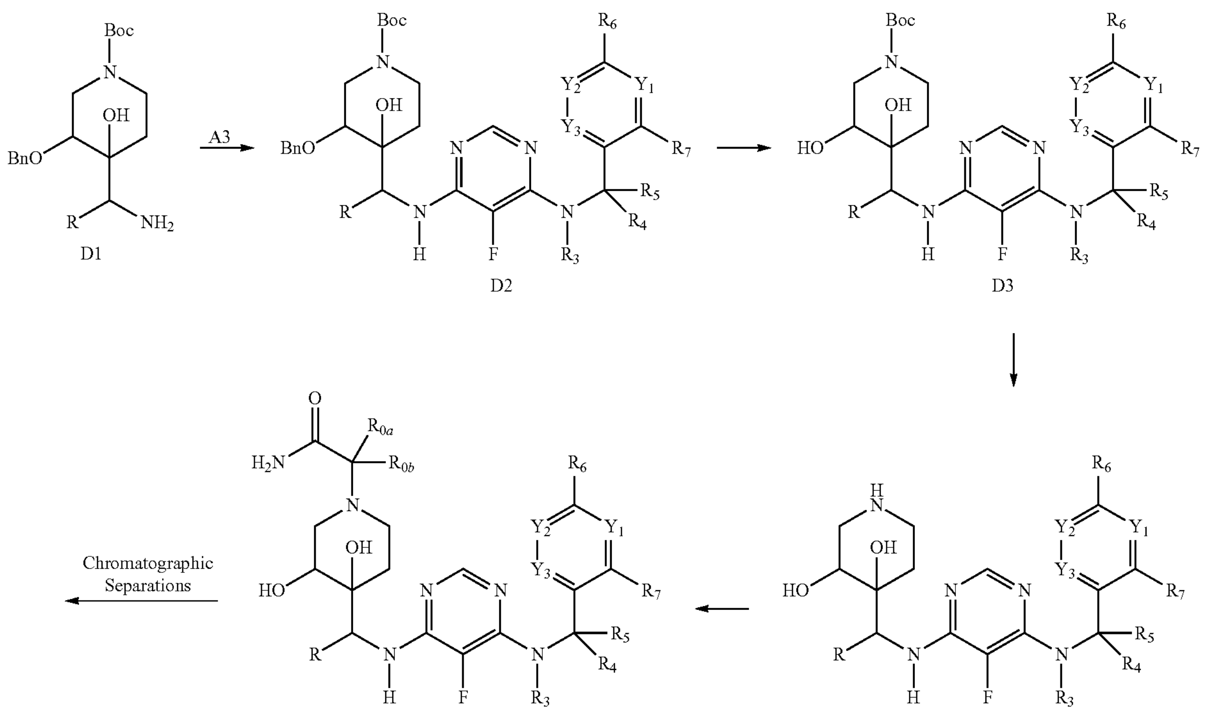

D1 D2 D3 D4 D5

Intermediate A3, a base (such as; DIEA, TEA or $Cs_2CO_3$) and the primary amine D1 were dissolved in a solvent (such as DMSO or DMSO-$H_2O$, $H_2O$, $H_2O$-ethanol mixtures) and the temperature was increased to 70-100° C. on, or until the reaction was considered complete. Workup and purification then gave Intermediate D2, which was subjected to deprotection of the benzyl ether using Pd/C to produce D3. Boc-deprotection of D3 (using TFA in DCM) gave intermediate D4 as the corresponding salt. Intermediate D4 was then used directly in the alkylation with the corresponding 2-bromoacetamide and a suitable base (most often $K_2CO_3$) in DMF to produce D5.

The diastereomers (cis trans diols) were separated using non-chiral chromatographic methods. Finally, the enantiomers were isolated using chiral chromatographic methods to yield the end compounds.

Example D5-1

Synthesis and isolation of the 4 stereoisomers of 2-(4-(((6-(ethyl(4-(trifluoromethyl)benzyl)amino)-5-fluoropyrimidin-4-yl)amino)methyl)-3,4-dihydroxypiperidin-1-yl)acetamide, D5-1-1-1 & D5-1-1-2, and D5-1-2-1 & D5-1-2-2

Scheme D5-1

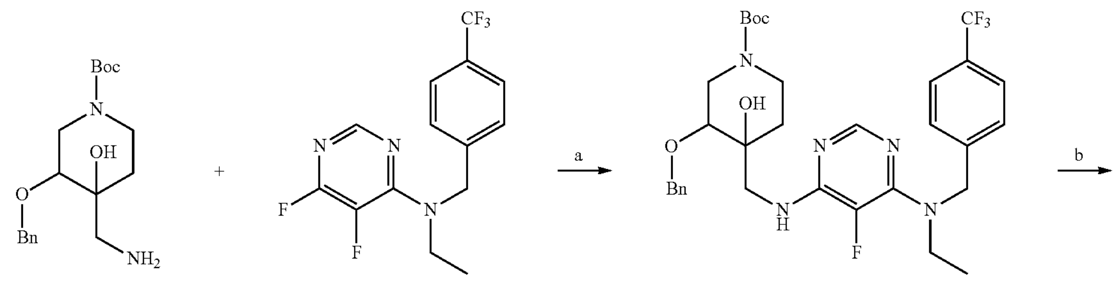

D1 A3-2 D2-1

-continued

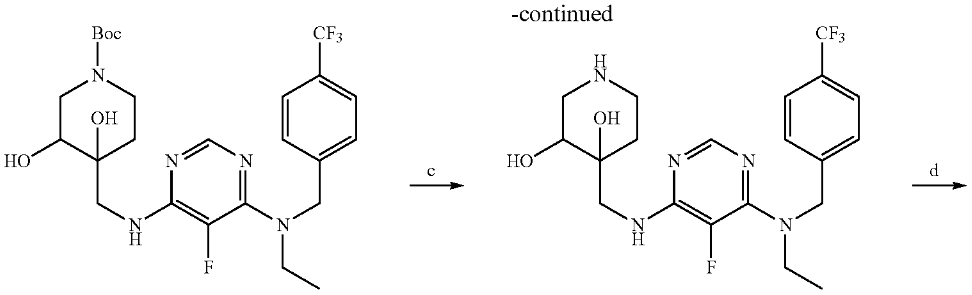

D3-1

D4-1

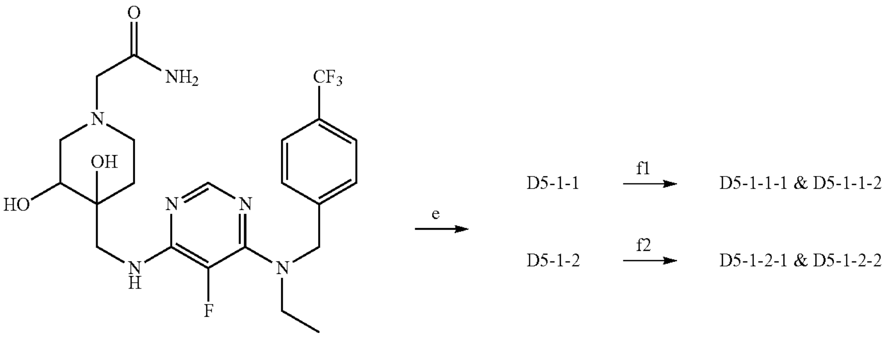

D5-1 a) DIEA, DMSO, rt. b) Pd/C, $NH_4HCO_2$, MeOH. c) TFA, DCM. d) 2-Bromoacetamide, $K_2CO_3$, DMF. e) Prep-TLC. f1) CHIRALPAK IG. f2) CHIRALPAK IE.

tert-Butyl 3-(benzyloxy)-4-(((6-(ethyl(4-(trifluoromethyl)benzyl)amino)-5-fluoropyrimidin-4-yl)amino)methyl)-4-hydroxypiperidine-1-carboxylate, D2-1

D2-1

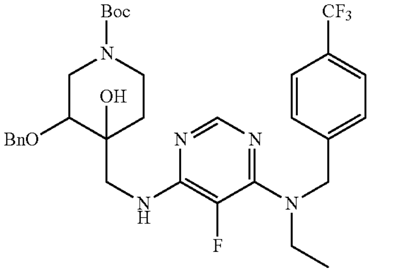

DIEA (743 mg, 5.8 mmol) was added to a solution of crude D1 (1.36 g) and A3-2 (608 mg, 1.9 mmol) in DMSO (12 mL). The reaction was then stirred at 90° C. for 2 h under microwave irradiation. The mixture was then poured into $H_2O$ (80 mL) and extracted with EA (3x30 mL). The combined organic layer was washed with brine (3x20 mL), dried ($Na_2SO_4$), filtered and concentrated in vacuo. The remaining residue was purified by Flash CC (EA:PE=1:5 to 1:2) to give D2-1 (1.3 g, >100%) as a colorless oil.

LCMS: MS Calcd.: 633; MS Found: 634 ($[M+1]^+$).

tert-Butyl 4-(((6-(ethyl(4-(trifluoromethyl)benzyl)amino)-5-fluoropyrimidin-4-yl)amino)methyl)-3,4-dihydroxypiperidine-1-carboxylate, D3-1

D3-1

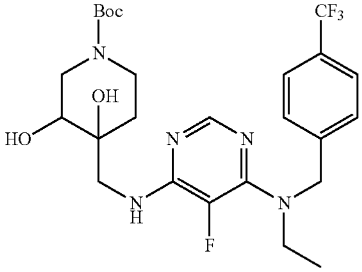

Pd/C (10%, 1.0 g) was added to a mixture of D2-1 (1.3 g, 1.9 mmol) and $NH_4HCO_2$ (2.9 g, 46.1 mmol) in MeOH (40 mL). The reaction was refluxed on, filtered and concentrated in vacuo. The remaining residue was purified by Flash CC (EA:PE=1:2 to 1:1.5) to give D3-1 (360 mg, 34%) as a white solid.

LCMS: MS Calcd.: 543; MS Found: 544 ($[M+1]^+$).

4-(((6-(Ethyl(4-(trifluoromethyl)benzyl)amino)-5-fluoropyrimidin-4-yl)amino)methyl)piperidine-3,4-diol TFA salt, D4-1

D4-1

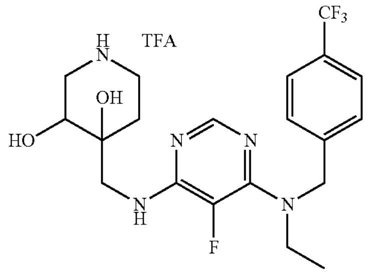

TFA (4 mL) was added to a solution of D3-1 (360 mg, 0.66 mmol) in DCM (10 mL) and the reaction was stirred at rt for 60 min. The reaction mixture was concentrated in vacuo to afford the crude D4-1 (830 mg, >100%) as a yellow oil, which was used without further purification.

LCMS: MS Calcd.: 443; MS Found: 444 ($[M+1]^+$).

2-(4-(((6-(Ethyl(4-(trifluoromethyl)benzyl)amino)-5-fluoropyrimidin-4-yl)amino)methyl)-3,4-dihydroxypiperidin-1-yl)acetamide, D5-1

D5-1

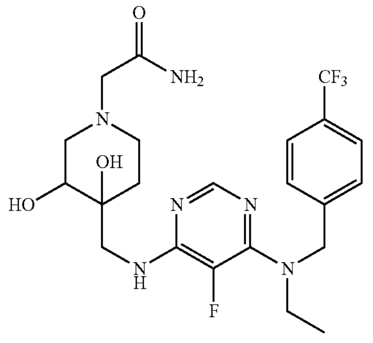

$K_2CO_3$ (911 mg, 6.60 mmol) and 2-bromoacetamide (183 mg, 1.33 mmol) were in turn added to a solution of crude D5-1 (830 mg, 0.66 mmol) in DMF (10 mL) and the reaction was stirred at 25° C. for 2 h. The reaction was quenched with $H_2O$ (60 mL) and then extracted with EA (3×30 mL). The combined organic layers were washed with brine (3×15 mL), dried ($Na_2SO_4$), filtered and concentrated in vacuo. The residue was then purified according to the procedure below to obtain the 4 stereo isomers.

Separation and isolation of the stereoisomers D5-1-1-1, D5-1-1-2, D5-1-2-1 and D5-1-2-2 from D5-1.

Preparative TLC (MeOH:DCM=1:10) to afford two products D5-1-1 (60 mg) and D5-1-2 (90 mg).

D5-1-1 was thereafter subjected to chiral chromatography (CHIRALPAK IG) which gave the enantiomers D5-1-1-1 (1st eluting isomer (19 mg) and D5-1-1-2 (2nd eluting isomer) (19 mg) as white solids.

D5-1-2 was thereafter subjected to chiral chromatography (CHIRALPAK IE) which gave the enantiomers D5-1-2-1 (1st eluting isomer (25 mg) and D5-1-2-2 (2nd eluting isomer) (26 mg) as white solids.

General method 1D was used to prepare the following example numbers using the shown starting materials (Table D).

TABLE 1D

| A1 | D5 |
|---|---|
| A1-13<br>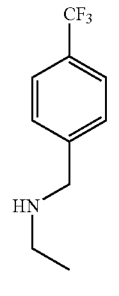<br>N-(4-(trifluoro-methyl)benzyl) ethanamine | D5-1-1-1<br>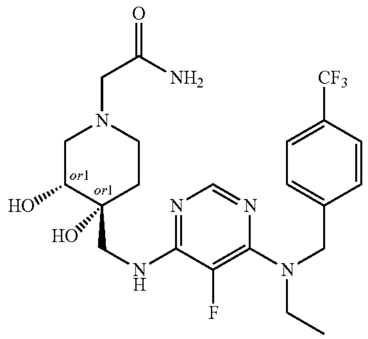<br>rel-2-((3R,4R)-4-(((6-(ethyl(4-(trifluoromethyl) benzyl)amino)-5-fluoropyrimidin-4-yl)amino) methyl)-3,4-dihydroxypiperidin-1-yl)acetamide<br>1st eluting isomer |
| A1-13 | D5-1-1-2<br>rel-2-((3R,4R)-4-(((6-(ethyl(4-(trifluoromethyl) benzyl)amino)-5-fluoropyrimidin-4-yl)amino) methyl)-3,4-dihydroxypiperidin-1-yl)acetamide<br>2nd eluting isomer |
| A1-13 | D5-1-2-1<br>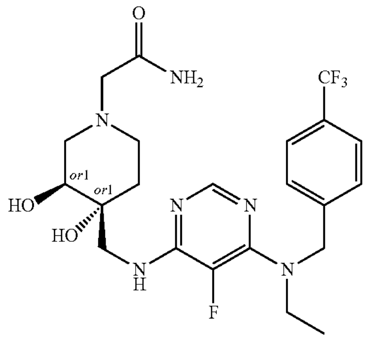<br>rel-2-((3R,4S)-4-(((6-(ethyl(4-(trifluoromethyl) benzyl)amino)-5-fluoropyrimidin-4-yl)amino) methyl)-3,4-dihydroxypiperidin-1-yl)acetamide<br>1st eluting isomer |
| A1-13 | D5-1-2-2<br>rel-2-((3R,4S)-4-(((6-(ethyl(4-(trifluoromethyl) benzyl)amino)-5-fluoropyrimidin-4-yl)amino) methyl)-3,4-dihydroxypiperidin-1-yl)acetamide<br>2nd eluting isomer |

TABLE 1D-continued

| A1 | D5 |
|---|---|
| A1-1<br>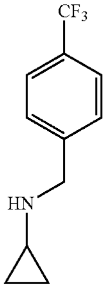<br>(trifluoromethyl)benzyl)cyclopropanamine | D5-2-1-1<br>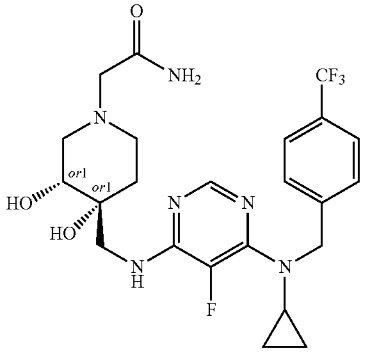<br>rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide<br>1st eluting isomer |
| A1-1 | D5-2-1-2<br>rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)acetamide<br>2nd eluting isomer |
| A1-1 | D5-2-2-1<br>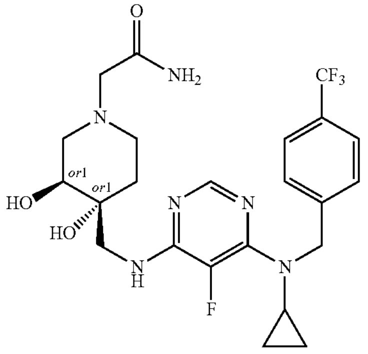<br>rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide-1st eluting isomer |
| A1-1 | D5-2-2-2<br>rel-2-((3R,4S)-4-(((6-(cyclopropyl(4-(trifluoromethyl)benzyl)amino)-5-fluoropyrimidin-4-yl)amino)methyl)-3-hydroxypiperidin-1-yl)acetamide-2nd eluting isomer |
| A1-18<br>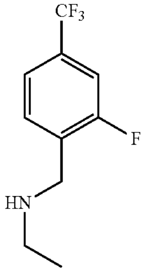<br>N-(2-fluoro-4-(trifluoromethyl)benzyl)ethanamine | D5-3-1-1<br>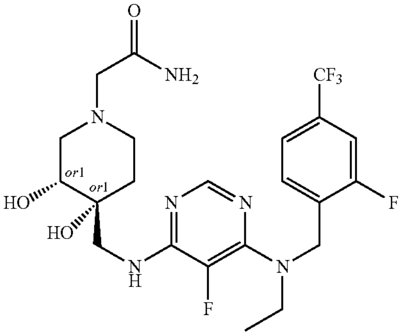<br>rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide<br>1st eluting isomer |
| A1-18 | D5-3-1-2<br>rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide<br>2nd eluting isomer |
| A1-18 | D5-3-2-1<br>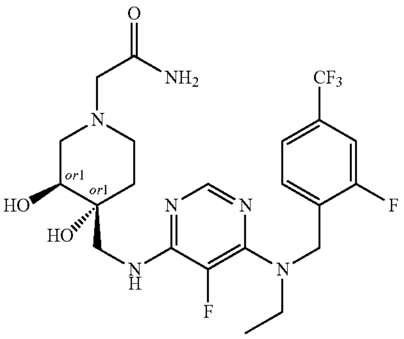<br>rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide<br>1st eluting isomer |
| A1-18 | D5-3-2-2<br>rel-2-((3R,4S)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide<br>2nd eluting isomer |

Synthesis of tert-butyl 4-(aminomethyl)-3-(benzyloxy)-4-hydroxypiperidine-1-carboxylate, D1

Scheme D1

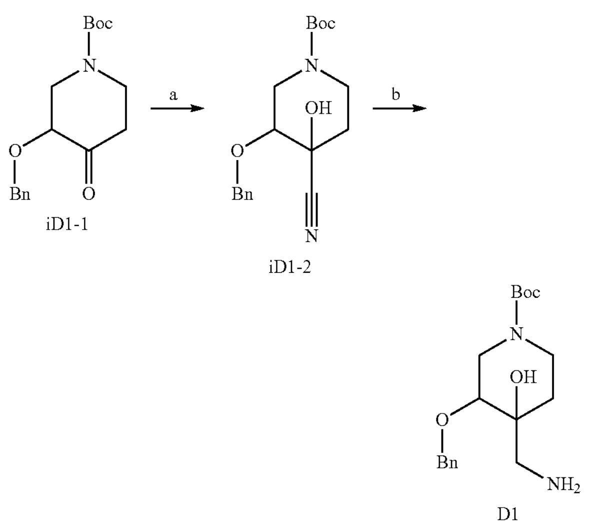

a) KCN, $NaHCO_3$, DCM, $H_2O$. b)$LiAlH_4$, THF.

tert-Butyl 3-(benzyloxy)-4-cyano-4-hydroxypiperidine-1-carboxylate, iD1-2 iD1-2

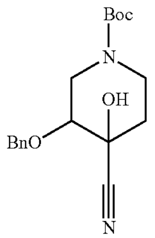

A solution of tert-buty 3-(benzyloxy)-4-oxopiperidine-1-carboxylate (1.9 g, 6.2 mmol) in DCM (20 mL) was added to a solution of KCN (1.0 g, 15.6 mmol) and $NaHCO_3$ (2.1 g, 24.9 mmol) in $H_2O$ (20 mL) and stirred at rt on. $H_2O$ (10 mL), was added and the mixture was extracted with DCM (3×20 mL). The combined organic phase was washed with brine (3×20 mL), dried ($Na_2SO_4$), filtered and concentrated in vacuo to yield iD1-2 (1.7 g, 5.1 mmol) as a colorless oil, which was used without further purification.

LCMS: MS Calcd.: 332; MS Found: 333 ($[M+1]^+$).

tert-Butyl 4-(aminomethyl)-3-(benzyloxy)-4-hydroxypiperidine-1-carboxylate, iD1-3

D1

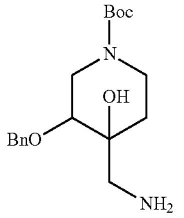

Under a $N_2$ atmosphere $LiAlH_4$ (390 mg, 10.2 mmol) was added to a solution of iD1-2 (1.7 g, 5.1 mmol) in THF (20 mL) at 0° C. The reaction was stirred at rt on and then mixture quenched by the addition of $H_2O$ (0.4 mL), 15% NaOH (0.4 mL), and then $H_2O$ (1.2 mL). The mixture was filtered, and then extracted with DCM (3×15 mL). The combined organic layers were washed with brine (20 mL), dried ($Na_2SO_4$), filtered and concentrated in vacuo to yield crude iD1-3 (1.36 g, 4.0 mmol) as a colorless oil, which was used without further purification.

LCMS: MS Calcd.: 336; MS Found: 337 ($[M+1]^+$).

General Method 2D

Alternatively, the 1,2-diols were synthesized in an enantiomerically enriched fashion by employing the Sharpless Dihydroxylation.

General Scheme 2D

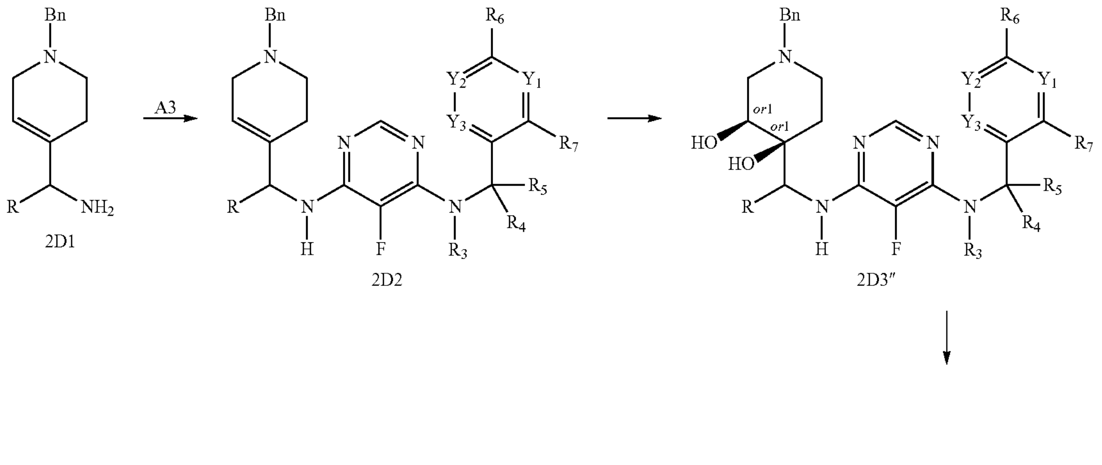

-continued

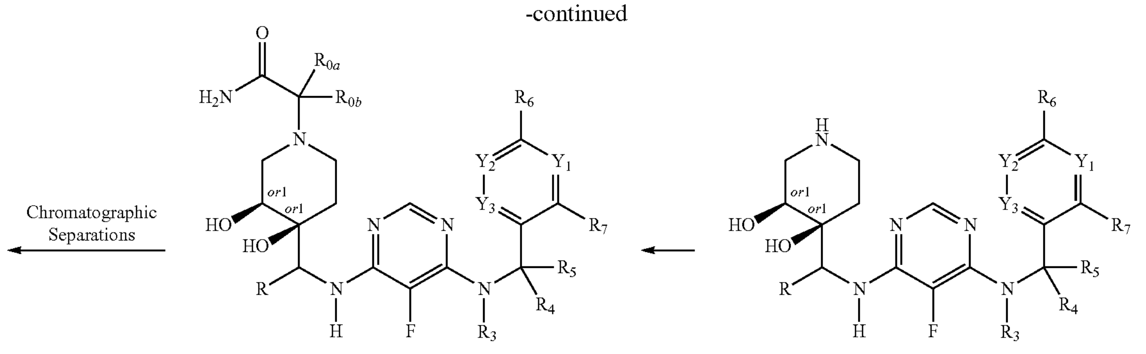

D5″ D4″

Example D5-1-1

Synthesis of enantiomerically enriched rel-((3R, 4R)-4-(((6-(ethyl(4-(trifluoromethyl)benzyl)amino)-5-fluoropyrimidin-4-yl)amino)methyl)-3,4-dihydroxypiperidin-1-yl)acetamide, D5-1-1" and separation of the two isomers D5-1-1-1 and D5-1-1-2

Scheme D5-1-1

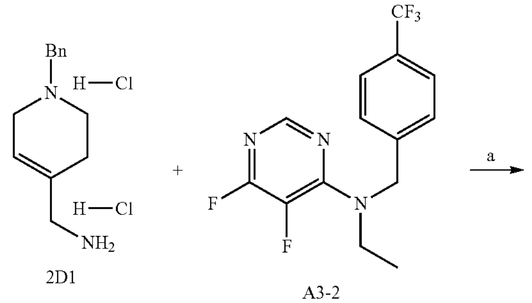

2D1 A3-2

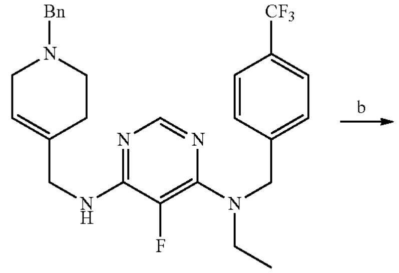

2D2-1

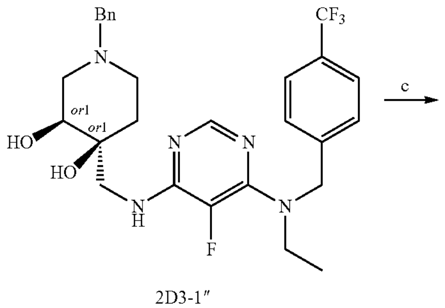

2D3-1″

-continued

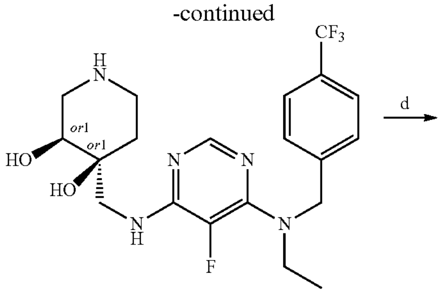

D4-1-1″

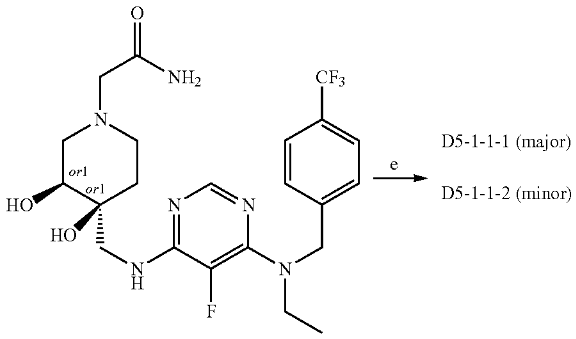

D5-1-1″ a) DIEA, DMSO. b) $K_2FeCN_6$, $K_2CO_3$, $DHQ_2(PHAL)$, $K_2OsO_2(OH)_4$, $MeSO_2NH_2$, $tBuOH/H_2O$. c) Pd/C, MeOH. d) 2-Bromoacteamide, $K_2CO_3$, DMF. e) CHIRALPAK IG.

$N^4$-((1-benzyl-1,2,3,6-tetrahydropyridin-4-yl)methyl)-$N^6$-ethyl-5-fluoro-$N^6$-(4-(trifluoromethyl)benzyl)pyrimidine-4,6-diamine, 2D2-1

2D2-1

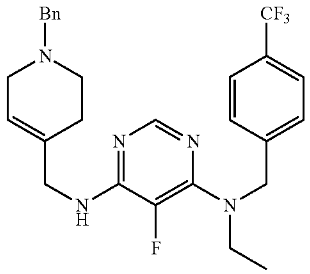

N-ethyl-5,6-difluoro-N-(4-(trifluoromethyl)benzyl)pyrimidin-4-amine (A3-2) (1.3 g, 4.0 mmol) and (1-benzyl-1,2,3,6-tetrahydropyridin-4-yl)methanamine (2D1) (1.1 g, 4.0 mmol), were added to a solution of DIEA (2.6 g, 20.0 mmol) in DMSO (20 mL) and the reaction was stirred at 90° C. on. $H_2O$ (60 mL) was added and the mixture was extracted with EA (3×20 mL). The combined organic layer was washed with brine (3×20 mL), dried ($Na_2SO_4$), filtered and concentrated in vacuo. The remaining residue was purified by Flash CC (MeOH:DCM=1:30) to yield 2D2-1 (1.0 g, 50%) as a yellow oil.

LCMS: MS Calcd.: 499; MS Found: 500 ($[M+H]^+$).

Enantiomerically enriched rel-(3R,4R)-1-benzyl-4-(((6-(ethyl(4-(trifluoromethyl)benzyl)amino)-5-fluoropyrimidin-4-yl)amino)methyl)piperidine-3,4-diol, 2D3-1"

2D3-1″

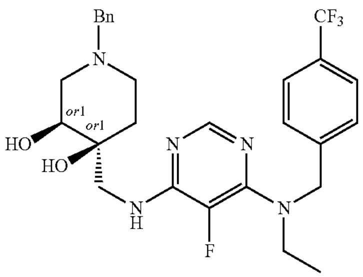

Compound 2D2-1 (1.0 g, 2.0 mmol) was added to a mix of t-BuOH/$H_2O$ (15 mL/15 mL). The mixture was cooled to 0° C. and the following were added; $K_3Fe(CN)_6$ (2.0 g, 6.0 mmol), $K_2CO_3$ (830 mg, 6.0 mmol), $(DHQ)_2PHAL$ (47 mg, 0.06 mmol), $K_2OsO_2(OH)_4$ (22 mg, 0.06 mmol) and $MeSO_2NH_2$ (190 mg, 2.0 mmol). The reaction was stirred at rt on and thereafter quenched by the addition of $NaNO_2$ (12 g) and $H_2O$ (30 mL). After stirring the quenched mixture at rt for 1h it was extracted with DCM (3×20 mL). The combined organic layer was washed with brine and concentrated in vacuo. The remaining residue was purified by Flash CC (EA:PE=1:2 to 1:1) to yield 2D3-1" (900 mg, 84%) as a brown oil.

LCMS: MS Calcd.: 533; MS Found: 534 ($[M+H]^+$).

Enantiomerically enriched rel-(3R,4R)-4-(((6-(ethyl(4-(trifluoromethyl)benzyl)amino)-5-fluoropyrimidin-4-yl)amino)methyl)piperidine-3,4-diol, D4-1-1"

D4-1-1″

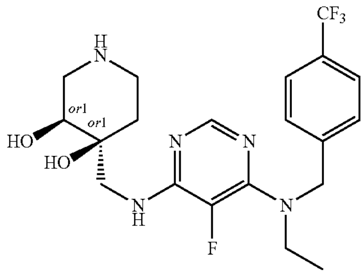

Compound 2D3-1" (900 mg, 1.69 mmol) was dissolved in MeOH (20 mL) and then Pd/C (480 mg, 10%) was added. The reaction was stirred under $H_2$ (1 atm) on. The reaction was filtered and concentrated in vacuo to yield D4-1-1" (526 mg, 70%) as a white solid.

LCMS: MS Calcd.: 443; MS Found: 444 ($[M+H]^+$).

Enantiomerically enriched rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide, D5-1-1" and isolation of the enantiomers D5-1-1-1 (major) and D5-1-1-2 (minor)

D5-1-1″

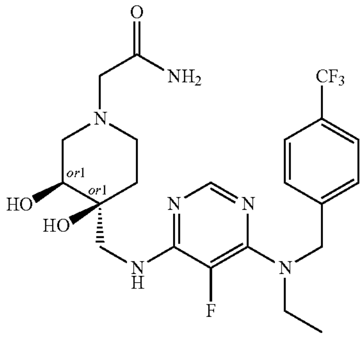

Compound D4-1-1" (526 mg, 1.19 mmol), $K_2CO_3$ (1.6 g, 11.90 mmol) and 2-bromoacetamide (328 mg, 2.37 mmol) were added to DMF (10 mL). The reaction was stirred at 25° C. for 2 h, and then quenched by the addition of $H_2O$ (50 mL). The resulting mixture was extracted with EA (3×20 mL) and the combined organic layer was washed with brine (3×20 mL), dried ($Na_2SO_4$), filtered and concentrated in vacuo. The remaining residue was purified by Prep-TLC (MeOH:DCM=1:10) yield D5-1-1" (325 mg, 54%) as a white solid.

LCMS: MS Calcd.: 500; MS Found: 501 ($[M+H]^+$).

The enantiomers of D5-1-1" (320 mg) were then isolated, as previously described, to yield rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide D5-1-1-1 (250 mg, major isomer) and rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)acetamide D5-1-1-2 (50 mg, minor isomer).

General method 2D was used to prepare the following example numbers using the shown starting materials (Table 2D).

TABLE 2D

| A1 | D5 |
|---|---|
| A1-13<br>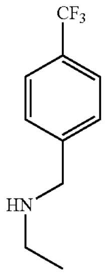<br>N-(4-(trifluoromethyl)benzyl)ethanamine | D5-1-1-1<br>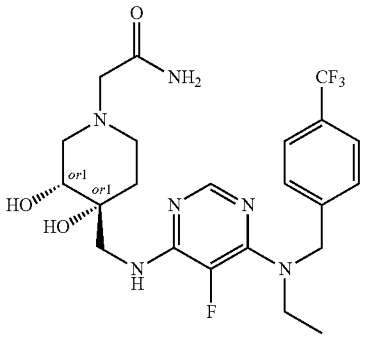<br>rel-2-((3R,4R)-4-(((6-(ethyl(4-(trifluoro-methyl)benzyl)amino)-5-fluoropyrimidin-4-yl)amino)methyl)-3,4-dihydroxypiperidin-1-yl)acetamide<br>Major isomer |
| A1-13 | D5-1-1-2<br>rel-2-((3R,4R)-4-(((6-(ethyl(4-(trifluoro-methyl)benzyl)amino)-5-fluoropyrimidin-4-yl)amino)methyl)-3,4-dihydroxypiperidin-1-yl)acetamide<br>Minor isomer |
| A1-18<br>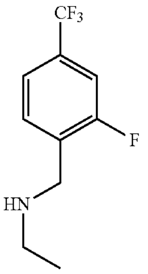<br>N-(2-fluoro-4-(trifluoromethyl)benzyl)ethanamine | D5-3-1-1<br>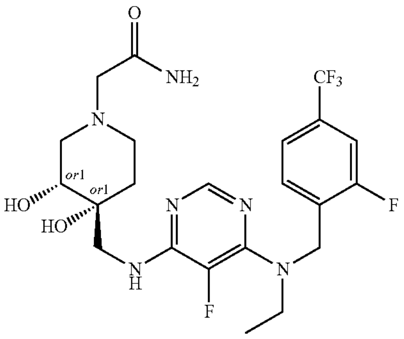<br>rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acetamide<br>Major isomer |
| A1-18 | D5-3-1-2<br>rel-2-((3R,4R)-4-(((6-(ethyl(2-fluoro-4-(trifluoromethyl)benzyl)amino)-5-fluoropyrimidin-4-yl)amino)methyl)-3,4-dihydroxypiperidin-1-yl)acet-amide<br>Minor isomer |

TABLE 2D-continued

| A1 | D5 |
|---|---|
| A1-65<br>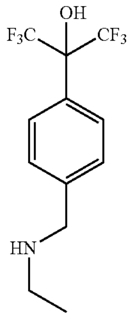<br>2-(4-((ethylamino)methyl)phenyl)-1,1,1,3,3,3-hexafluoropropan-2-ol | D5-4”<br>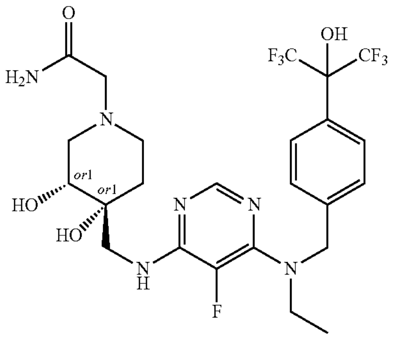<br>rel-2-((3R,4R)-4-(((6-(ethyl(4-(1,1,1,3,3,3-hexafluoro-2-hydroxypropan-2-yl)benzyl)amino)-5-fluoropyrimidin-4-yl)amino)methyl)-3,4-dihydroxypiperidin-1-yl)acetamide<br>Enantiomerically enriched |
| A1-67<br>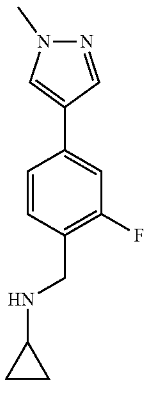<br>N-(2-fluoro-4-(1-methyl-1H-pyrazol-4-yl)benzyl)cyclo-propanamine | D5-5-1<br>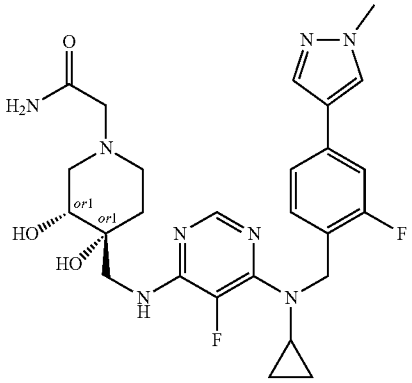<br>rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide<br>Major isomer |
| A1-67 | D5-5-2<br>rel-2-((3R,4R)-4-(((6-(cyclopropyl(2-fluoro-4-(1-methyl-1H-pyrazol-4-yl)benzyl)amino)-5-fluoropyrimidin-4-yl)amino)methyl)-3,4-dihydroxypiperidin-1-yl)acetamide<br>Minor isomer |

TABLE 2D-continued

| A1 | D5 |
| --- | --- |
| A1-34 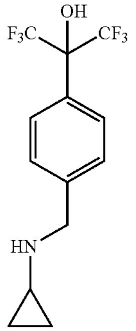 ((cyclopropylamino) methyl)phenyl)-1,1,1,3,3,3-hexafluoropropan-2-ol | D5-6" 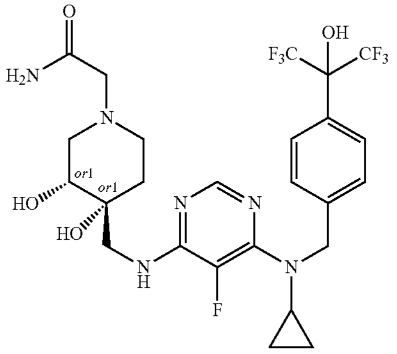 rel-2-((3R,4R)-4-(((6-(cyclopropyl(4-(1,1,1,3,3,3-hexafluoro-2-hydroxypropan-2-yl)benzyl) amino)-5-fluoropyrimidin-4-yl)amino) methyl)-3,4-dihydroxypiperidin-1-yl)acetamide Enantiomerically enriched |

General Method 2D'—Synthesis with Substituted Bromoacetamides

General scheme 2D'

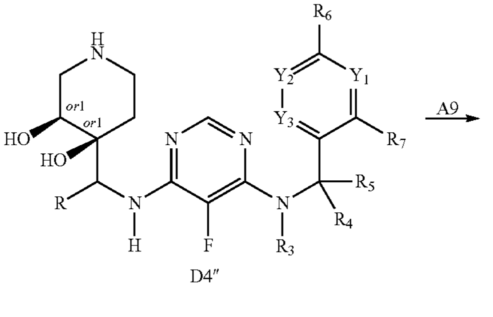

-continued

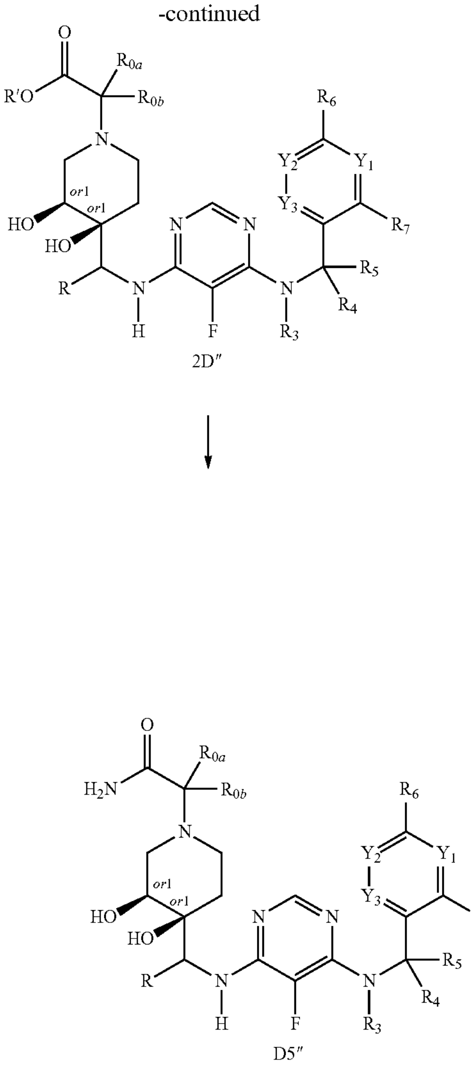

If $R_0$ group differed from H, the alkylation of D4" was performed with the corresponding 2-bromoacetoester A9 and a suitable base (as described in General Method 2A above) to give 2D'. These alkylations often required higher temperatures (up to 100° C.). Thereafter, subsequent aminolysis ($NH_3$ in MeOH) gave D5". Experimental procedures were in accordance to those described under General Method 2A.

The following examples were synthesized according to General Method 2D' using the shown starting materials (Table 2D').

TABLE 2D'

| D4 | A9 | D5 |
|---|---|---|
| D4-1-1"<br>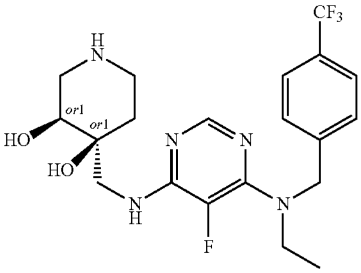<br>rel-(3R,4R)-4-(((6-(ethyl(4-(trifluoromethyl)benzyl)amino)-5-fluoropyrimidin-4-yl)amino)methyl)piperidine-3,4-diol<br>Enantiomerically enriched | A9-1<br>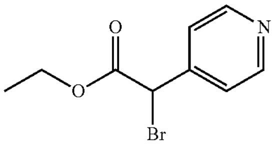<br>ethyl 2-bromo-2-(pyridin-4-yl)acetate | D5-7"<br>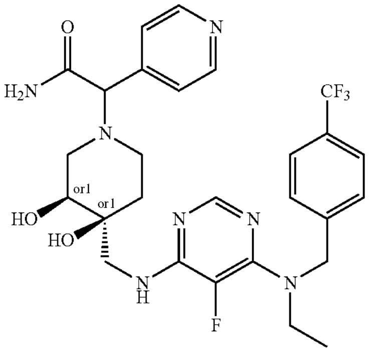<br>rel-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>Enantiomerically enriched |
| D4-1-1" | A9-1 | D5-7-1<br>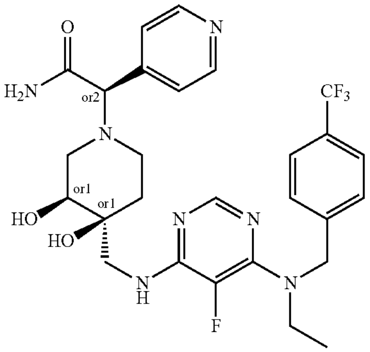<br>rel-(R)-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>OR<br>rel-(R)-2-((3S,4S)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>1st eluting major isomer |
| D4-1-1" | A9-1 | D5-7-2<br>rel-(R)-2-((3R,4R)-4-(((6-(ethyl(4-(trifluoromethyl)benzyl)amino)-5-fluoropyrimidin-4-yl)amino)methyl)-3,4-dihydroxypiperidin-1-yl)-2-(pyridin-4-yl)acetamide<br>OR<br>rel-(R)-2-((3S,4S)-4-(((6-(ethyl(4-(trifluoromethyl)benzyl)amino)-5-fluoropyrimidin-4-yl)amino)methyl)-3,4- |

TABLE 2D'-continued

| D4 | A9 | D5 |
|---|---|---|
| | | dihydroxypiperidin-1-yl)-2-(pyridin-4-yl)acetamide 2nd eluting major isomer |
| D4-2-1" | A9-1 | D5-8" |
| 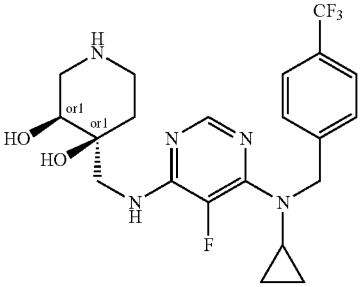 rel-(3R,4R)-4-(((6-(cyclopropyl(4-(trifluoromethyl)benzyl)amino)-5-fluoropyrimidin-4-yl)amino)methyl)piperidine-3,4-diol Enantiomerically enriched | | 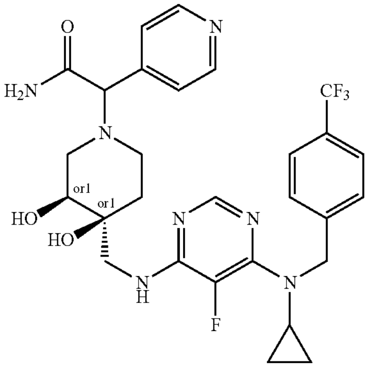 rel-2-((3R,4R)-4-(((6-(cyclopropyl(4-(trifluoromethyl)benzyl)amino)-5-fluoropyrimidin-4-yl)amino)methyl)-3,4-dihydroxypiperidin-1-yl)-2-(pyridin-4-yl)acetamide Enantiomerically enriched |

For the D5-7-1 and D5-7-2 compounds only the 2 major isomers were isolated.

General scheme 3D

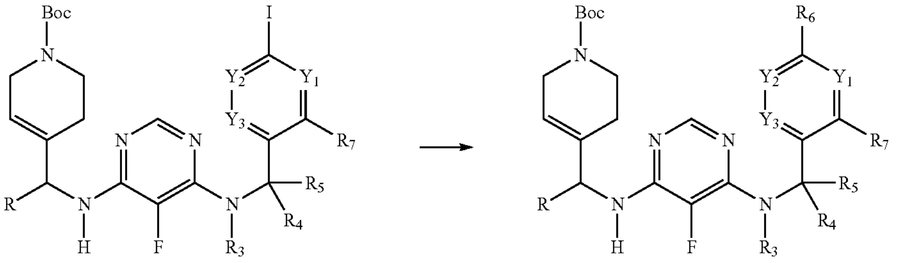

3D1 2D2

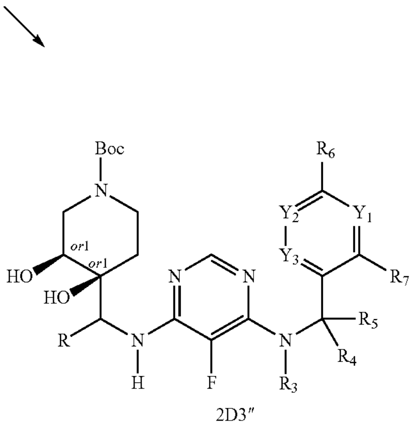

2D3"

-continued

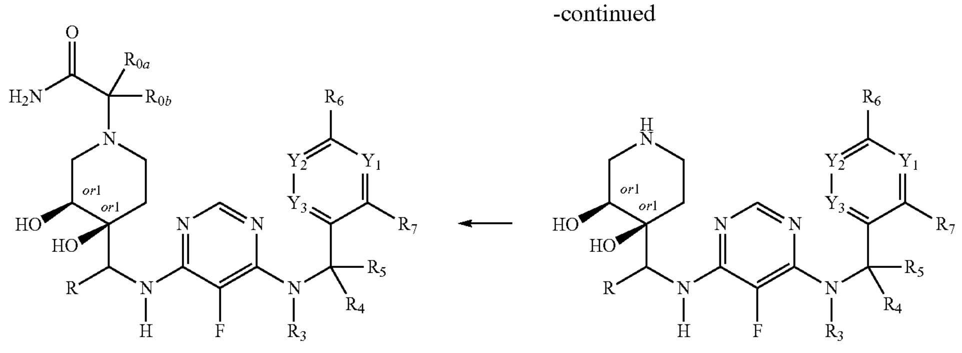

D5″ D4″

In the cases when $R_6$ was a heterocyclic ring the General Method 3D was used. The synthesis of intermediate 3D1 was accomplished as described in General Method 2D using the corresponding iodo-benzylamine. The $R_6$ group was thereafter introduced by either a standard Suzuki coupling (together with the corresponding boronic acid or boronic ester) or a standard Buchwald N-arylation (together with Cu and the corresponding nitrogen containing heterocyclic ring). Finally, D5" derivative was synthesized from 2D2 intermediate according to general method 2D.

Example D5-9"

Synthesis of enantiomerically enriched-rel-2-((3R, 4R)-4-(((6-(cyclopropyl(2-fluoro-4-(1H-pyrazol-1-yl)benzyl)amino)-5-fluoropyrimidin-4-yl)amino) methyl)-3,4-dihydroxypiperidin-1-yl)acetamide, D5-9"

Scheme D5-9″

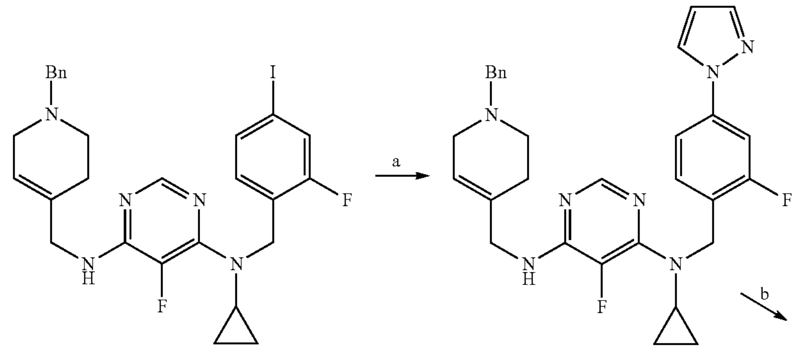

3D1-1 3D2-1

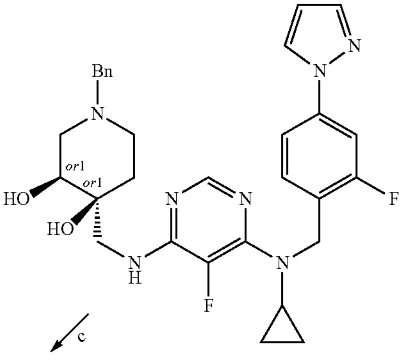

3D3-1″

-continued

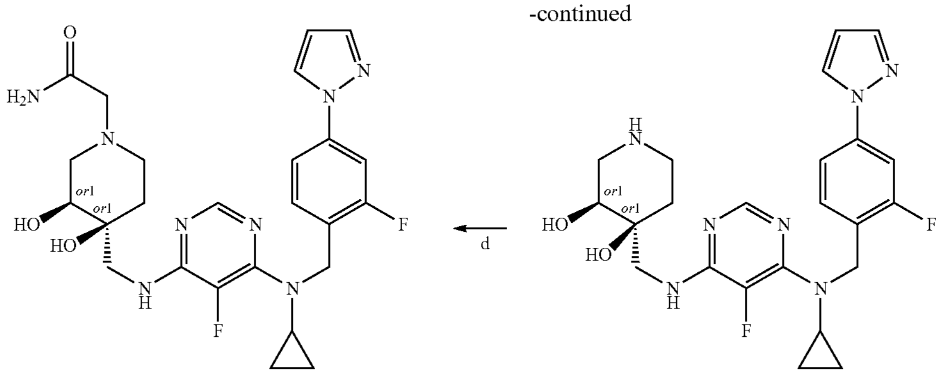

D5-9″ 3D4-1″ a) 1H-pyrazole, $K_2CO_3$, trans-1,2-cyclohexane-1,2-diamine, CuI, NMP. b) $K_3Fe(CN)_6$, $K_2CO_3$, $(DHQ)_2PHAL$, $K_2OsO_2(OH)_4$, $MeSO_2NH_2$. c) Pd/C, $H_2$. d) 2-bromoacetamide, $Na_2CO_3$ N-((1-Benzyl-1,2,3,6-tetrahydropyridin-4-yl)methyl)-$N^6$-cyclopropyl-5-fluoro-$N^6$-(2-fluoro-4-(1H-pyrazol-1-yl)benzyl)pyrimidine-4,6-diamine, 3D2-1

3D2-1

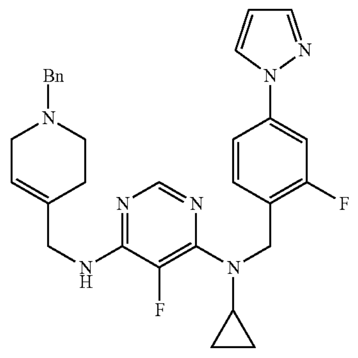

Under an inert atmosphere 1H-pyrazole (77 mg, 1.13 mmol), potassium carbonate (157 mg, 1.13 mmol), trans-1,2-cyclohexane-1,2-diamine (26 mg, 0.23 mmol) and CuI (11 mg, 58 μmol) were added to a solution of 3D1-1 (334 mg, 0.57 mmol) in NMP (6 mL). The reaction mixture was stirred on at 120° C. $H_2O$ was added and the product was extracted with EA (×3). The combined organic layer was washed with $H_2O$, brine, dried ($MgSO_4$), filtered and concentrated in vacuo. The residue was then purified by flash CC (MeOH:DCM=15:85) followed by C18 column ($H_2O$:MeOH=0:100 to 100:0). 3D2-1 was obtained (116 mg, 0.22 mmol) as a white solid.

LCMS: MS Calcd.: 527.6; MS Found: 528 ($[M+H]^+$).

Enantiomerically enriched rel-(3R,4R)-1-benzyl-4-(((6-(cyclopropyl(2-fluoro-4-(1H-pyrazol-1-yl)benzyl)amino)-5-fluoropyrimidin-4-yl)amino)methyl)piperidine-3,4-diol, 3D3-1"

3D3-1″

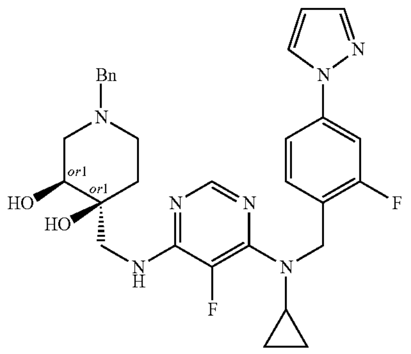

3D2-1 (116 mg, 0.22 mmol) was mixed with tBuOH (2 mL)/$H_2O$ (2 mL) at 0° C. and then the following reagents were added: $K_3Fe(CN)_6$ (217 mg, 0.66 mmol), $K_2CO_3$ (91 mg, 0.66 mmol), $(DHQ)_2PHAL$ (5 mg, 6.4 μmol), $K_2OsO_2(OH)_4$ (2.5 mg, 6.9 μmol) and $MeSO_2NH_2$ (21 mg, 0.22 mmol). The reaction was stirred on at rt. The reaction was thereafter quenched by the addition of $NaNO_2$ (167 mg) and $H_2O$ (1 mL), and the mixture was stirred at rt for 2h. The mixture was diluted with $H_2O$ and extracted with DCM (×3), the combined organic layer was washed with $H_2O$ and brine, dried ($MgSO_4$) and concentrated in vacuo. The residue was then purified by flash CC (MeOH:DCM=1:9) to yield 3D3-1" (58 mg, 0.10 mmol) as a solid.

LCMS: MS Calcd.: 561.6; MS Found: 562 ($[M+H]^+$).

Enantiomerically enriched rel-(3R,4R)-4-(((6-(cyclopropyl(2-fluoro-4-(1H-pyrazol-1-yl)benzyl)amino)-5-fluoropyrimidin-4-yl)amino)methyl)piperidine-3,4-diol, 3D4-1"

3D4-1″

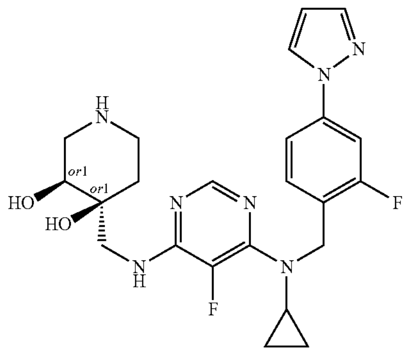

3D3-1"(58 mg, 0.10 mmol) was dissolved in MeOH (10 mL) and 10% Pd/C (15 mg, 13 μmol) was added. The reaction mixture was stirred under 20 psi of $H_2$ for 2 days. The mixture was filtered through Celite© and the solvent was removed in vacuo. The solid thus obtained (27 mg, 57 μmol) was used for next reaction without further purification.

LCMS: MS Calcd.: 471.5; MS Found: 472 ($[M+H]^+$).

Enantiomerically enriched rel-2-((3R,4R)-4-(((6-(cyclopropyl(2-fluoro-4-(1H-pyrazol-1-yl)benzyl)amino)-5-fluoropyrimidin-4-yl)amino)methyl)-3,4-dihydroxypiperidin-1-yl)acetamide, D5-9"

D5-9″

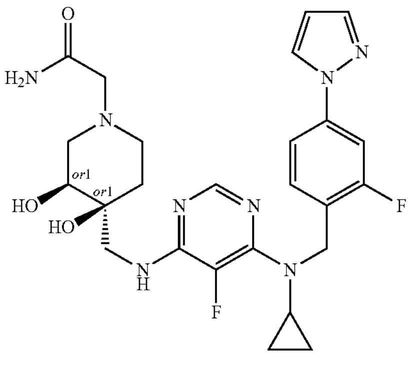

$Na_2CO_3$ (30 mg, 0.28 mmol) and 2-bromoacetamide (9.5 mg, 69 μmol) were added to a solution of 3D4-1 (27 mg, 57 μmol) in dry DMF (1 mL). The reaction mixture was stirred on at rt. $H_2O$ was added and the product was extracted with EA (×3). The combined organic layer was washed with $H_2O$ and brine, dried over $MgSO_4$, filtered and concentrated. The residue was then purified by flash CC (MeOH:DCM=15:85) followed by $C_{18}$ column ($H_2O$:MeOH=0:100 to 100:0). Additional purification by preparative HPLC yielded D5-9" (10 mg, 19 μmol) as a white solid.

LCMS: MS Calcd.: 528.6; MS Found: 529 ($[M+H]^+$).

Example D5-10" (obtained as a side-product during the synthesis of D5-9")

Enantiomerically enriched rel-2-((3R,4R)-4-(((6-(cyclopropyl(2-fluorobenzyl)amino)-5-fluoropyrimidin-4-yl)amino)methyl)-3,4-dihydroxypiperidin-1-yl)acetamide, D5-10"

D5-10″

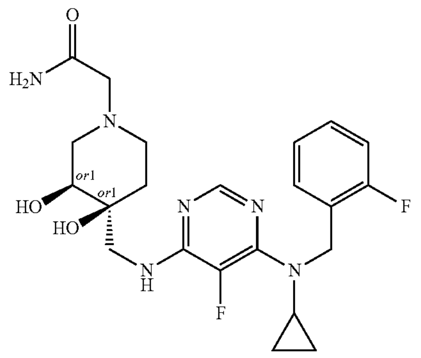

General Method E

Example E6-1

Synthesis of 2-(4-amino-4-(((6-(cyclopropyl(4-(trifluoromethyl)benzyl)amino)-5-fluoropyrimidin-4-yl)amino)methyl)piperidin-1-yl)acetamide, E6-1

Scheme E6-1

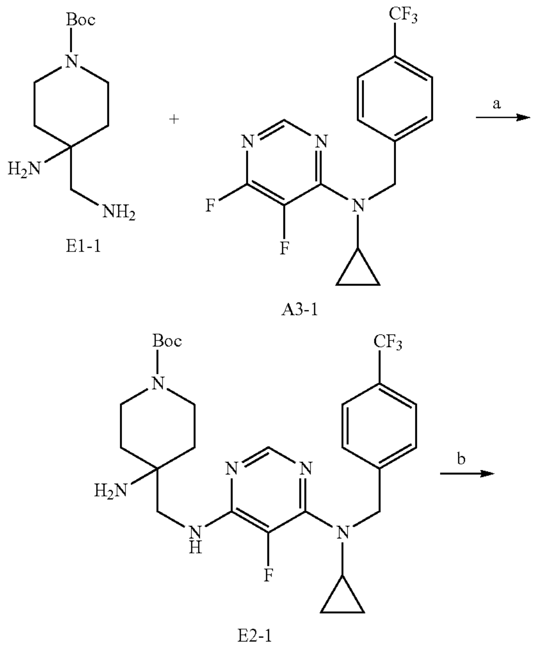

-continued

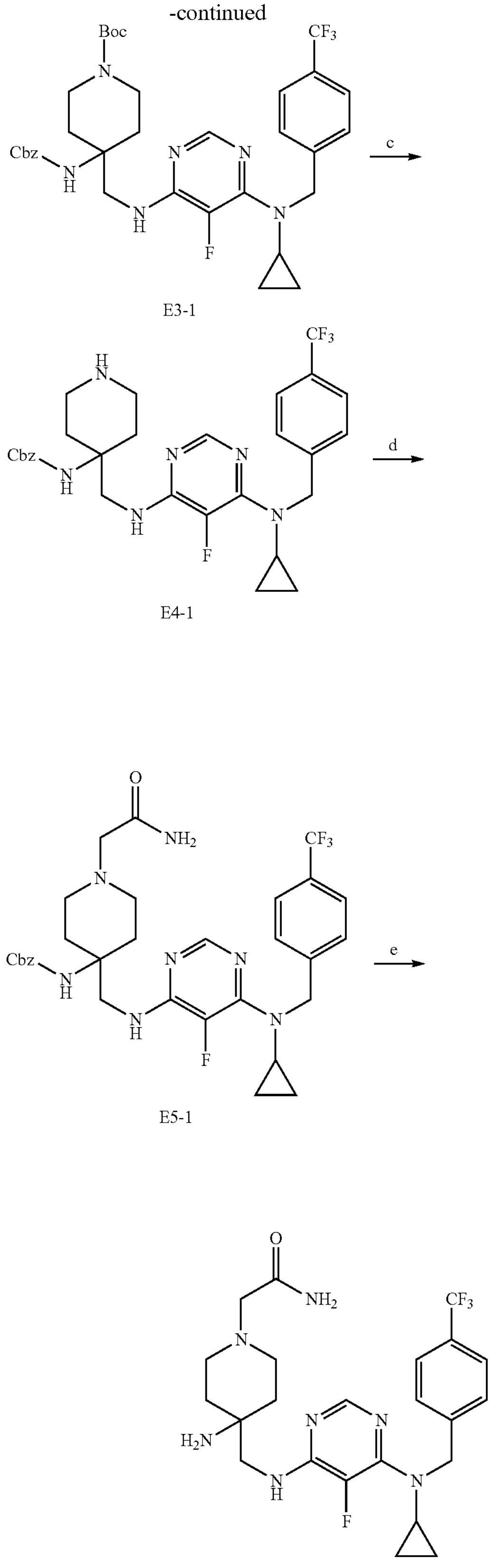

E3-1

E4-1

E5-1

E6-1 a) DMSO, DIEA. b) CbzCl, $K_2CO_3$. c) i) TFA, $H_2O$. d) 2-Bromoacetamide, $K_2CO_3$. e) Pd/C, $H_2$.

tert-Butyl 4-amino-4-(((6-(cyclopropyl(4-(trifluoromethyl)benzyl)amino)-5-fluoropyrimidin-4-yl)amino)methyl)piperidine-1-carboxylate, E2-1

E2-1

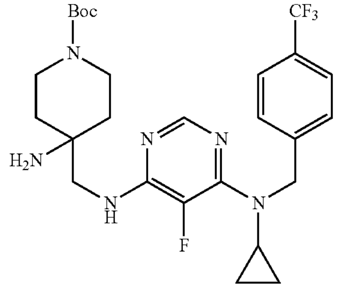

DIEA (251 mg, 1.95 mmol) was added to a stirred solution of tert-butyl 4-amino-4-(aminomethyl)piperidine-1-carboxylate (150 mg, 0.65 mmol) and A3-1 (215 mg, 1.0 mmol) in DMSO (5 mL) at rt. The reaction was then heated to 95° C. for 2.5 h, cooled to rt and extracted with three times with EA. The combined organic phase was dried ($Na_2SO_4$) filtered and concentrated under reduce pressure. The remaining residue was purified using Flash CC (MeOH:DCM) to afford E2-1 (280 mg, 80% yield) as colorless oil.

LCMS: MS Calcd.: 538; MS Found: 539 ($[M+1]^+$).

tert-Butyl 4-(((benzyloxy)carbonyl)amino)-4-(((6-(cyclopropyl(4-(trifluoromethyl)benzyl)amino)-5-fluoropyrimidin-4-yl)amino)methyl)piperidine-1-carboxylate, E3-1

E3-1

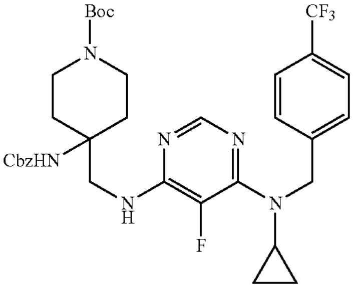

At rt CbzCl (177 mg, 1.04 mmol) was added to a solution of E2-1 (280 mg, 0.52 mmol) and $K_2CO_3$ (287 mg, 2.08 mmol) in THF/$H_2O$ (10 mL/10 mL). The reaction was stirred at rt for 16 h before it was extracted with three times with EA. The organic phase was washed with brine (10 mL), dried ($Na_2SO_4$), filtered and concentrated to afford the title compound E3-1 as colorless oil (320 mg), which was used without further purification.

LCMS: MS Calcd.: 672; MS Found: 673 ($[M+1]^+$).

Benzyl (4-(((6-(cyclopropyl(4-(trifluoromethyl)benzyl)amino)-5-fluoropyrimidin-4-yl)amino)methyl)piperidin-4-yl)carbamate·TFA salt, E4-1

E4-1

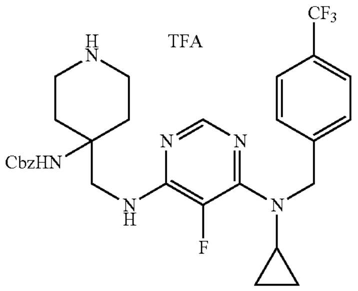

At rt TFA (2 mL) was added to a solution of compound E3-1 (320 mg, 0.47 mmol) in DCM (5 mL) and the reaction was stirred at this temperature for 1 h and concentrated to afford E4-1 as colorless oil (crude 400 mg), which was used without further purification.

LCMS: MS Calcd.: 572; MS Found: 573 ($[M+1]^+$).

Benzyl (1-(2-amino-2-oxoethyl)-4-(((6-(cyclopropyl(4-(trifluoromethyl)benzyl)amino)-5-fluoropyrimidin-4-yl)amino)methyl)piperidin-4-yl)carbamate, E5-1

E5-1

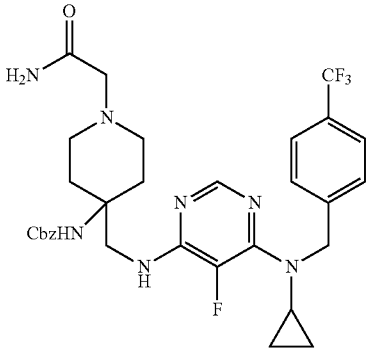

At rt 2-bromoacetamide (131 mg, 0.95 mmol) was added to a solution of E4-1 (crude 400 mg, 0.47 mmol) and $K_2CO_3$ (394 mg, 2.85 mmol) in DMF (5 mL) and the reaction was stirred at 25° C. for 2 h. The reaction mixture was extracted with three times with EA and the organic phase was dried ($Na_2SO_4$), filtered and concentrated in vacuo. The residue was purified by Flash CC (MeOH: DCM) to yield E5-1 (250 mg) as a white solid.

LCMS: MS Calcd.: 529; MS Found: 530 ($[M+1]^+$).

2-(4-Amino-4-(((6-(cyclopropyl(4-(trifluoromethyl)benzyl)amino)-5-fluoropyrimidin-4-yl)amino)methyl)piperidin-1-yl)acetamide, E6-1

E6-1

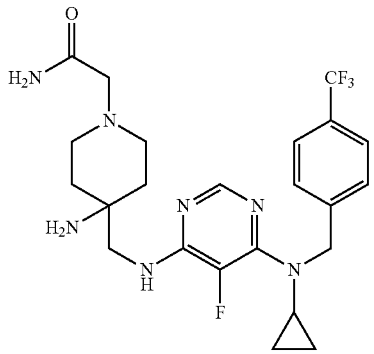

At rt $Pd(OH)_2$ (80 mg, 20%) was added to a solution of compound E5-1 (250 mg, 0.47 mmol) in EtOH (5 mL) and the reaction was stirred under $H_2$ (1 atm) on. The reaction was filtered and concentrated in vacuo to afford a crude product. This crude was thereafter purified by prep HPLC to afford E6-1 (97.5 mg) as a white solid.

LCMS: MS Calcd.: 495; MS Found: 496 ($[M+1]^+$).

General Method F—One-Pot, Two Step Synthesis

General Scheme F

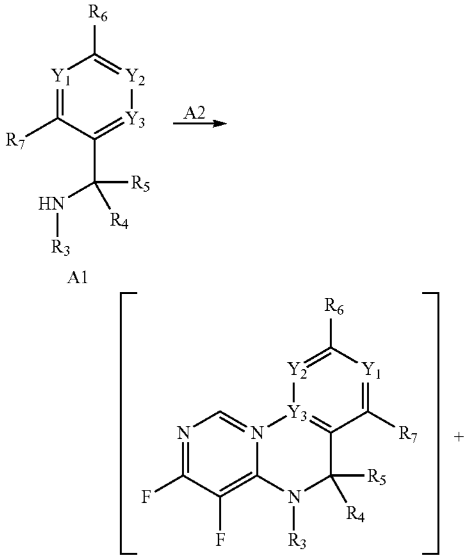

A1

A3

-continued

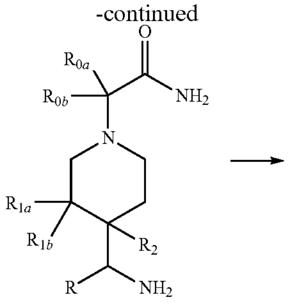

F1

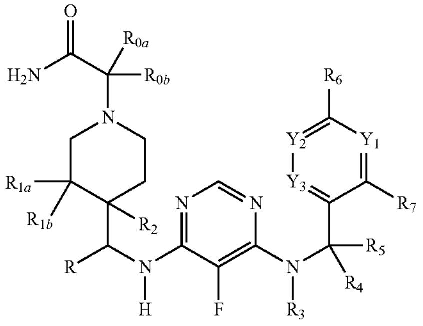

F2

The compounds have also been synthesized using a one-pot, two step synthesis procedure. The secondary amine A1 and 4,5,6-trifluoropyrimidine A2 were added to a solution of DIEA in DMSO and stirred at rt for 3 h to produce A3 in situ. Thereafter, F1 was added together with additional DIEA and the reaction was heated at 80° C. on. The reaction mixture was cooled to rt and concentrated. The remaining residue was thereafter purified by Prep HPLC to yield F2 compounds.

Example F2-1

Synthesis of rac-2-((3R,4R)-4-(((5-fluoro-6-(methyl (2-methylbenzyl)amino)pyrimidin-4-yl)amino) methyl)-3-hydroxypiperidin-1-yl)acetamide (F2-1)

Scheme F2-1

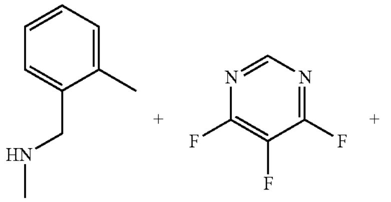

F1-1

-continued

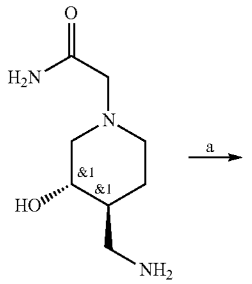

A1-41

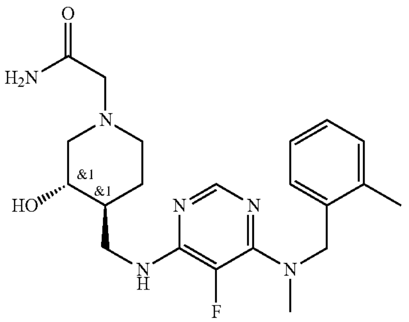

F2-1 a) i) DIEA, DMSO, rt. ii) DIEA, DMSO, 80° C.

A solution of 4,5,6-trifluoropyrimidine (160 mM in DMSO, 1 equivalent) and DIEA (neat, 6 equivalents) were added to a solution of N-methyl-1-(o-tolyl) methanamine·HCl (A1-41), (160 mM in DMSO, 1 equivalent). The reaction was shaken at rt for 3 h. Thereafter, a DMSO solution of rac-2-((3R,4R)-4-(aminomethyl)-3-hydroxypiperidin-1-yl)acetamide hydrochloride (F1-1) (160 mM, 1 equivalent) and DIEA (neat, 4 equivalents) were added and the reaction was shaken at 80° C. on. The reaction was then allowed to cool and then concentrated under reduced pressure. Subsequent analysis and purification by HPLC gave F2-1 (43%).

The following compounds were synthesized according to Method F using the shown starting materials (Table F).

TABLE F

| A1 | F2 |
|---|---|
| A1-42<br>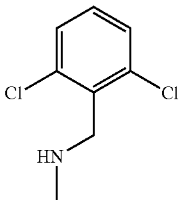<br>1-(2,6-dichlorophenyl)-N-methylmethanamine | F2-2<br>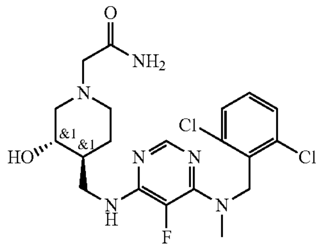<br>rac-2-((3R,4R)-4-(((6-((2,6-dichlorobenzyl) (methyl)amino)-5-fluoropyrimidin-4-yl)amino) methyl)-3-hydroxypiperidin-1-yl)acetamide |

TABLE F-continued

| A1 | F2 |
|---|---|
| A1-43 | F2-3 |
| 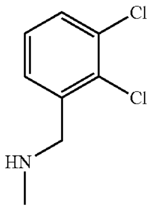 | 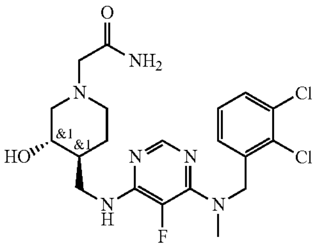 |
| 1-(2,3-dichlorophenyl)-N-methylmethanamine | rac-2-((3R,4R)-4-(((6-((2,3-dichlorobenzyl)(methyl)amino)-5-fluoropyrimidin-4-yl)amino)methyl)-3-hydroxypiperidin-1-yl)acetamide |
| A1-44 | F2-4 |
| 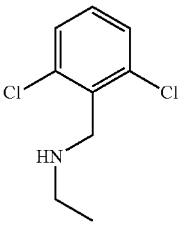 | 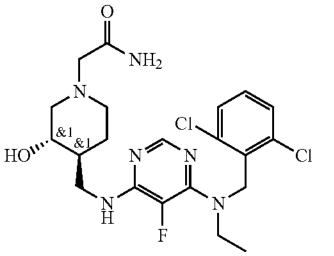 |
| dichlorobenzyl) ethanamine | rac-2-((3R,4R)-4-(((6-((2,6-dichlorobenzyl)(ethyl)amino)-5-fluoropyrimidin-4-yl)amino)methyl)-3-hydroxypiperidin-1-yl)acetamide |
| A1-45 | F2-5 |
| 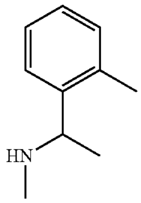 | 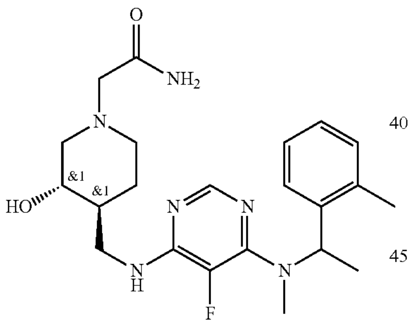 |
| N-methyl-1-(o-tolyl)ethan-1-amine | rac-2-((3R,4R)-4-(((5-fluoro-6-(methyl(1-(o-tolyl)ethyl)amino)pyrimidin-4-yl)amino)methyl)-3-hydroxypiperidin-1-yl)acetamide |
| A1-46 | F2-6 |
| 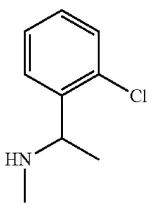 | 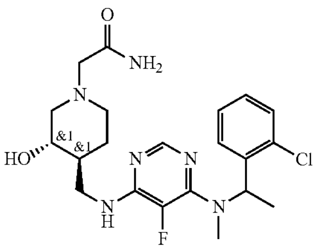 |
| 1-(2-chlorophenyl)-N-methylethan-1-amine | rac-2-((3R,4R)-4-(((6-((1-(2-chlorophenyl)ethyl)(methyl)amino)-5-fluoropyrimidin-4-yl)amino)methyl)-3-hydroxypiperidin-1-yl)acetamide |

TABLE F-continued

| A1 | F2 |
|---|---|
| A1-47 | F2-7 |
| 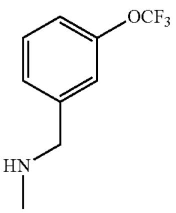 | 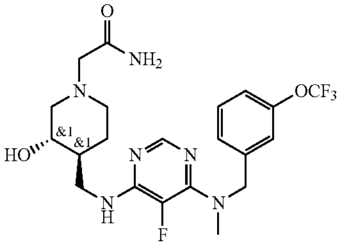 |
| N-methyl-1-(3-(trifluoromethoxy)phenyl) methanamine | rac-2-((3R,4R)-4-(((5-fluoro-6-(methyl(3-(trifluoromethoxy)benzyl)amino)pyrimidin-4-yl)amino)methyl)-3-hydroxypiperidin-1-yl) acetamide |
| A1-48 | F2-8 |
| 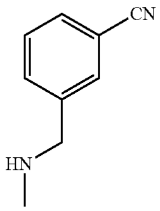 | 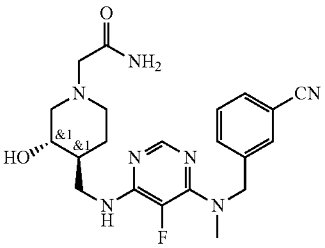 |
| ((methylamino)methyl) benzonitrile | rac-2-((3R,4R)-4-(((6-((3-cyanobenzyl)(methyl)amino)-5-fluoropyrimidin-4-yl)amino)methyl)-3-hydroxypiperidin-1-yl)acetamide |
| A1-49 | F2-9 |
| 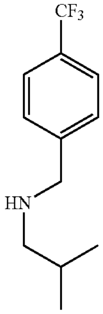 | 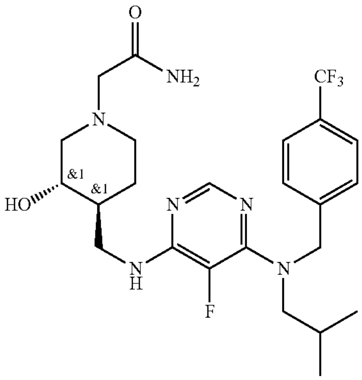 |
| 2-methyl-N-(4-(trifluoromethyl) benzyl) propan-1-amine | rac-2-((3R,4R)-4-(((5-fluoro-6-(isobutyl(4-(trifluoromethyl)benzyl)amino)pyrimidin-4-yl) amino)methyl)-3-hydroxypiperidin-1-yl) acetamide |

TABLE F-continued

| A1 | F2 |
|---|---|
| A1-50 | F2-10 |
| 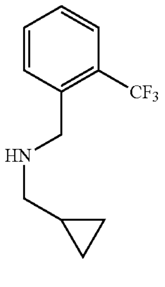 | 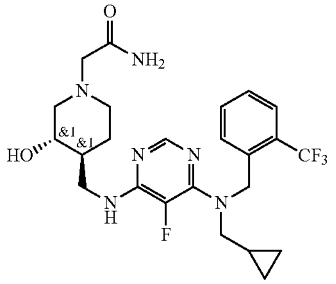 |
| 1-cyclopropyl-N-(2-(trifluoromethyl)benzyl) methanamine | rac-2-((3R,4R)-4-(((6-((cyclopropylmethyl)(2-(trifluoromethyl)benzyl)amino)-5-fluoropyrimidin-4-yl)amino)methyl)-3-hydroxypiperidin-1-yl)acetamide |
| A1-51 | F2-11 |
| 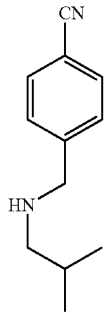 | 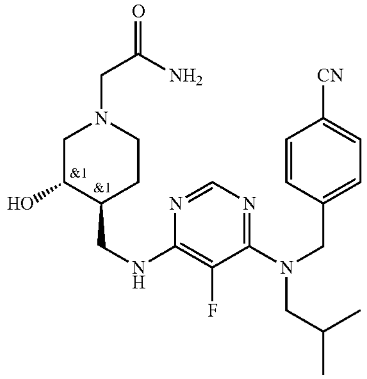 |
| ((isobutylamino)methyl) benzonitrile | rac-2-((3R,4R)-4-(((6-((4-cyanobenzyl)(isobutyl) amino)-5-fluoropyrimidin-4-yl)amino)methyl)-3-hydroxypiperidin-1-yl)acetamide |
| A1-52 | F2-12 |
| 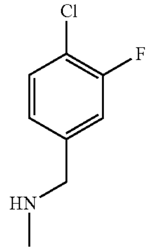 | 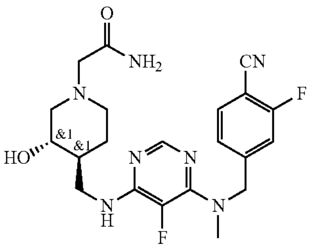 |
| 1-(4-chloro-3-fluorophenyl)-N-methylmethanamine | rac-2-((3R,4R)-4-(((6-((4-chloro-3-fluorobenzyl)(methyl)amino)-5-fluoropyrimidin-4-yl)amino)methyl)-3-hydroxypiperidin-1-yl)acetamide |

TABLE F-continued

| A1 | F2 |
|---|---|
| A1-53 | F2-13 |
| 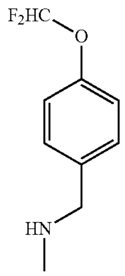 | 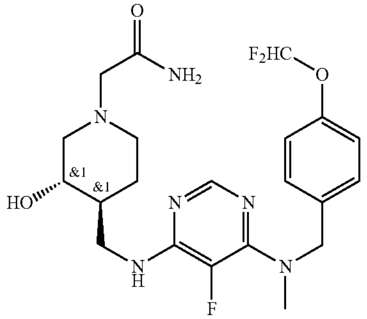 |
| (difluoromethoxy) phenyl)-N-methylmethanamine | rac-2-((3R,4R)-4-(((6-((4-(difluoromethoxy)benzyl)(methyl)amino)-5-fluoropyrimidin-4-yl)amino)methyl)-3-hydroxypiperidin-1-yl)acetamide |
| A1-54 | F2-14 |
| 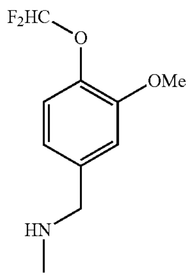 | 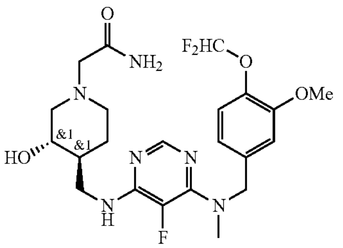 |
| 1-(4-(difluoromethoxy)-3-methoxyphenyl)-N-methylmethanamine | rac-2-((3R,4R)-4-(((6-((4-(difluoromethoxy)-3-methoxybenzyl)(methyl)amino)-5-fluoropyrimidin-4-yl)amino)methyl)-3-hydroxypiperidin-1-yl)acetamide |
| A1-55 | F2-15 |
| 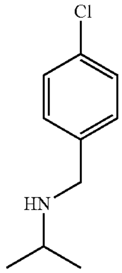 | 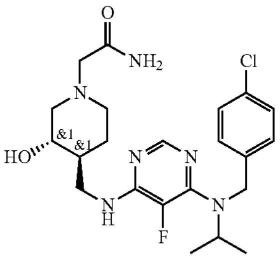 |
| N-(4-chlorobenzyl) propan-2-amine | rac-2-((3R,4R)-4-(((6-((4-chlorobenzyl) (isopropyl)amino)-5-fluoropyrimidin-4-yl)amino)methyl)-3-hydroxypiperidin-1-yl)acetamide |

TABLE F-continued

| A1 | F2 |
| --- | --- |
| A1-56 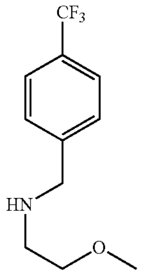 2-methoxy-N-(4-(trifluoromethyl) benzyl)ethan-1-amine | F2-16 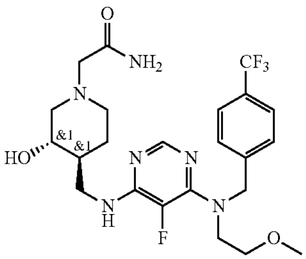 rac-2-((3R,4R)-4-(((5-fluoro-6-((2-methoxyethy])(4-(trifluoromethyl)benzyl) amino)pyrimidin-4-yl)amino)methyl)-3-hydroxypiperidin-1-yl)acetamide |
| A1-57 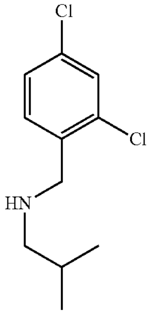 N-(2,4-dichlorobenzyl)-2-methylpropan-1-amine | F2-17 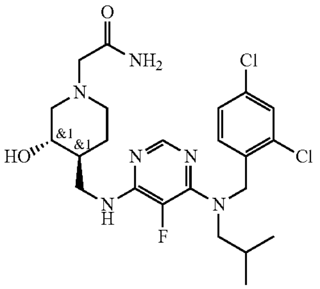 rac-2-((3R,4R)-4-(((6-((2,4-dichlorobenzyl) (isobutyl)amino)-5-fluoropyrimidin-4-yl) amino)methyl)-3-hydroxypiperidin-1-yl)acetamide |
| A1-58 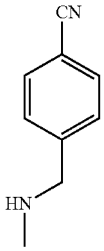 4-((methylamino) methyl) benzonitrile | F2-18 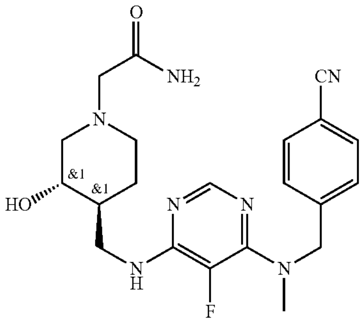 rac-2-((3R,4R)-4-(((6-((4-cyanobenzyl)(methyl) amino)-5-fluoropyrimidin-4-yl)amino)methyl)-3-hydroxypiperidin-1-yl)acetamide |
| A1-59 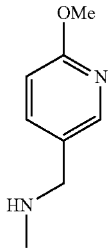 1-(6-methoxy-pyridin-3-yl)-N-methylmethan-amine | F2-19 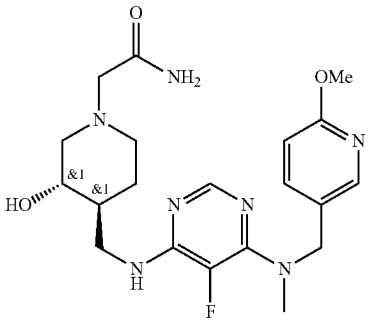 rac-2-((3R,4R)-4-(((5-fluoro-6-(((6-methoxy-pyridin-3-yl)methyl)(methyl)amino)pyrimidin-4-yl)amino)methyl)-3-hydroxypiperidin-1-yl)acetamide |
| A1-60 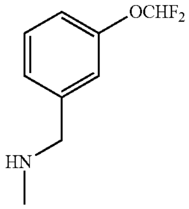 1-(3-(difluoromethoxy) phenyl)-N-methylmethanamine | F2-20 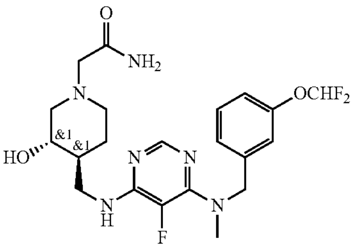 rac-2-((3R,4R)-4-(((6-((3-(difluoromethoxy)benzyl)(methyl)amino)-5-fluoropyrimidin-4-yl)amino)methyl)-3-hydroxypiperidin-1-yl)acetamide |
| A1-61 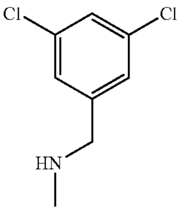 1-(3,5-dichlorophenyl)-N-methylmethanamine | F2-21 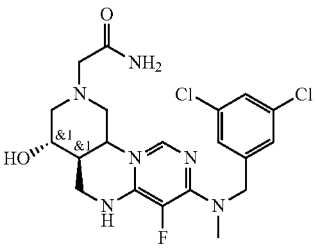 rac-2-((3R,4R)-4-(((6-((3,5-dichlorobenzyl) (methyl)amino)-5-fluoropyrimidin-4-yl) amino)methyl)-3-hydroxypiperidin-1-yl) acetamide |

TABLE F-continued

| A1 | F2 |
|---|---|
| A1-62 | F2-22 |
| 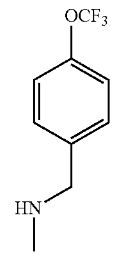 | 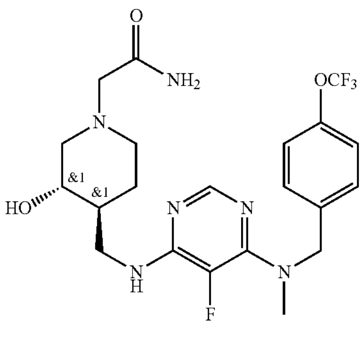 |
| N-methyl-1-(4-(trifluoromethoxy) phenyl) methanamine | rac-2-((3R,4R)-4-(((5-fluoro-6-(methyl(4-(trifluoromethoxy)benzyl)amino)pyrimidin-4-yl)amino)methyl)-3-hydroxypiperidin-1-yl) acetamide |
| A1-63 | F2-23 |
| 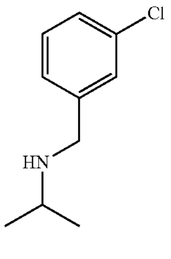 | 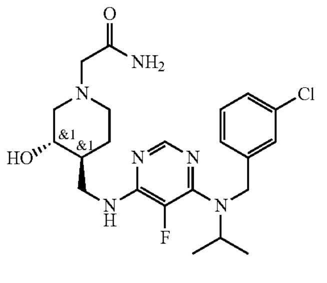 |
| N-(3-chlorobenzyl)propan-2-amine | rac-2-((3R,4R)-4-(((6-((3-chlorobenzyl) (isopropyl)amino)-5-fluoropyrimidin-4-yl)amino)methyl)-3-hydroxypiperidin-1-yl)acetamide |

Synthesis of rac-2-((3R,4R)-4-(aminomethyl)-3-hydroxypiperidin-1-yl)acetamide hydrochloride, F1-1

Scheme F1-1

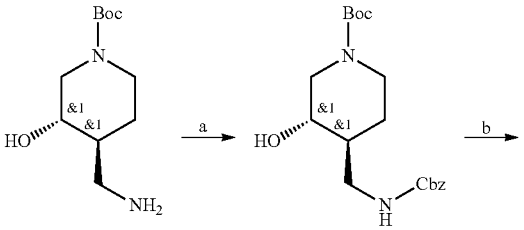

A4-1 iF1-1

-continued

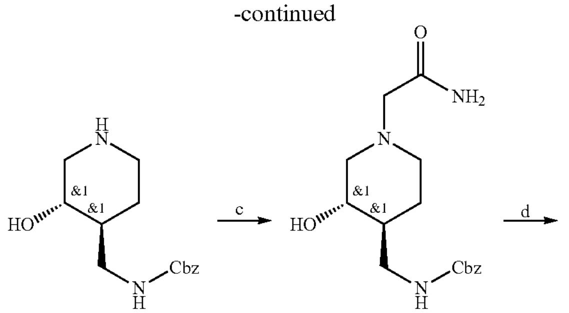

iF1-2 iF1-3

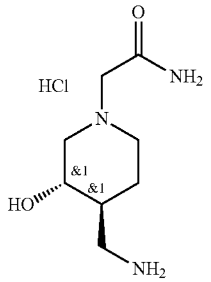

F1-1 a) CbzCl, $NaHCO_3$. b) TFA, DCM. c) 2-bromoacetamide, $K_2CO_3$. d) Pd/C, $H_2$, HCl.

rac-tert-Butyl (3R,4R)-4-((((benzyloxy)carbonyl) amino)methyl)-3-hydroxypiperidine-1-carboxylate, iF1-1 iF1-1

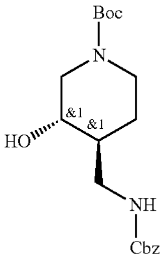

$NaHCO_3$ (3.4 g, 40.5 mmol) and Cbz-Cl (2.7 g, 16.2 mmol) were added to a solution of A4-1 (4.6 g, 13.5 mmol) in THF/$H_2O$ (10 mL/3 mL). The reaction was then stirred at 35° C. for 16 h. $H_2O$ (20 mL) was added in and the mixture was extracted with DCM (3×30 mL). The combined organic layers were dried ($Na_2SO_4$), filtered and concentrated in vacuo to afford iF1-1 as a colorless oil (3.8 g, yield 10.4 mmol), which was used directly in next step without further purification.

LCMS: MS Calcd.: 364; MS Found: 365 ($[M+1]^+$).

rac-Benzyl (((3R,4R)-3-hydroxypiperidin-4-yl) methyl)carbamate, iF1-2 iF1-2

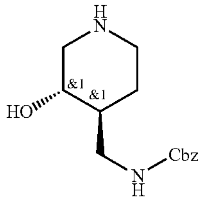

TFA (5 mL) was added to a solution of iF1-1 (3.8 g, 10.7 mmol) in DCM (10 mL) and the reaction was stirred at rt for 5 h. The mixture was concentrated in vacuo to yield iF1-2 as a brown oil (3.2 g). which was used directly in next step without further purification.

LCMS: MS Calcd.: 264; MS Found: 265 ($[M+1]^+$).

rac-Benzyl (((3R,4R)-1-(2-amino-2-oxoethyl)-3-hydroxypiperidin-4-yl)methyl)carbamate, iF1-3 iF1-3

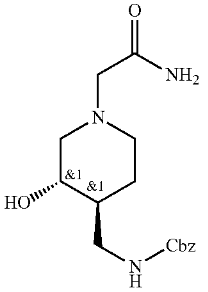

$K_2CO_3$ (4.43 g, 32.1 mmol) and 2-bromoacetamide (1.77 g, 12.8 mmol) were added to a solution of iF-2 (3.21 g, 10.7 mmol) in DMF (10 mL) and the reaction was stirred at 35° C. for 16 h. Then $H_2O$ (120 mL) was added and the mixture was extracted with EA (3x30 mL). The combined organic layers were dried ($Na_2SO_4$), filtered and concentrated. The residue was purified by HPLC to afford trans iF1-3 as a white solid (500 mg, yield 1.6 mmol), which was used directly in next step without further purification.

LCMS: MS Calcd.: 321; MS Found: 322 ($[M+1]^+$).

rac-2-((3R,4R)-4-(Aminomethyl)-3-hydroxypiperidin-1-yl)acetamide hydrochloride, F1-1

F1-1

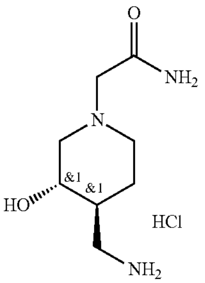

Pd/C (10%, 100 mg) was added to a solution of iF-3 (500 g, 1.56 mmol) in MeOH (30 mL) and the reaction was stirred at 35° C. for 3 h under a $H_2$ atmosphere (50 psi). The mixture was filtered and concentrated under reduced pressure to afford crude F1-1 as a white solid (300 mg). Then the solid was stirred with HCl in 1,4-dioxane (4 M) to afford the title compound (54 mg, 0.24 mmol) as a white solid.

MS Calcd.: 187; MS Found: 188 ($[M+1]^+$).

$^1$H-NMR (400 MHz, MeOH-d4): δ 3.85 (s, 2H), δ3.70-3.76 (m, 1H), δ 3.38-3.49 (m, 2H), δ 3.08-3.13 (m, 1H), δ 2.96-3.13 (m, 1H), δ 2.86-2.91 (m, 1H), δ 2.77-2.83 (m, 1H), δ 1.95-1.99 (m, 1H), δ 1.81-1.82 (m, 1H), δ 1.51-1.62 (m, 1H).

Analytical data

| Patent example | $^1$H-NMR | m/z $(M + H)^+$ | Chiral separation |
|---|---|---|---|
| A7-1 | $^1$H NMR (400 MHZ, $CDCl_3$): δ 0.72-0.76 (m, 2H), 0.78-0.81 (m, 2H), 1.41-1.46 (m, 1H), 1.52-1.57 (m, 1H), 1.61-1.67 (m, 1H), 2.08-2.28 (m, 2H), 2.84-2.95 (m, 2H), 3.01-3.09 (m, 3H), 3.13 (ddd, J = 14.5, 5.7, 2.6 Hz, 1H), 3.33-3.36 (m, 1H), 4.14 (ddd, J = 14.6, 7.7, 3.2 Hz, 1H), 4.87 (s, 2H), 5.04 (s, 1H), 5.35 (s, 1H), 5.62 (d, J = 3.1 Hz, 1H), 6.91 (s, 1H), 7.36 (d, J = 8.0 Hz, 2H), 7.56 (d, J = 8.1 Hz, 2H), 7.95 (d, J = 1.3 Hz, 1H). | 497 | |
| A7-1-1 | $^1$H NMR (400 MHZ, $CDCl_3$): δ 7.95 (d, J = 1.3 Hz, 1H), 7.56 (d, J = 8.1 Hz, 2H), 7.36 (d, J = 8.0 Hz, 2H), 6.91 (s, 1H), 5.62 (d, J = 3.3 Hz, 1H), 5.37 (s, 1H), 5.05 (s, 1H), 4.87 (s, 2H), 4.14 (ddd, J = 14.6, 7.7, 3.2 Hz, 1H), 3.40-3.30 (m, 1H), 3.13 (ddd, J = 14.6, 5.7, 2.6 Hz, 1H), 3.09-3.01 (m, 3H), 2.95-2.82 (m, 2H), 2.26-2.10 (m, 2H), 1.68-1.51 (m, 2H), 1.49-1.38 (m, 1H), 0.83-0.77 (m, 2H), 0.75-0.69 (m, 2H). | 497 | Reprosil AMS ($MeOH:CO2:NH_3$ = 35:65:0.2) |
| A7-1-2 | $^1$H NMR (400 MHZ, $CDCl_3$): δ 7.95 (d, J = 1.3 Hz, 1H), 7.56 (d, J = 8.1 Hz, 2H), 7.36 (d, J = 8.0 Hz, 2H), 6.92 (s, 1H), 5.64 (s, 1H), 5.36 (s, 1H), 5.05 (s, 1H), 4.14 (ddd, J = 14.6, 7.6, 3.2 Hz, 1H), 3.41-3.30 (m, 1H), 3.14 (ddd, J = 14.6, 5.7, 2.5 Hz, 1H), 3.10-3.00 (m, 3H), 2.94-2.84 (m, 2H), 2.27-2.10 (m, 2H), 1.69-1.63 (m, 1H), 1.49-1.39 (m, 1H), 0.84-0.77 (m, 2H), 0.75-0.69 (m, 2H). | 497 | Reprosil AMS ($MeOH:CO2:NH_3$ = 35:65:0.2) |
| A7-2 | $^1$H NMR (400 MHZ, $CDCl_3$): δ 0.68-0.80 (m, 4H), 1.33 (qd, J = 12.2, 3.9 Hz, 3H), 1.80 (d, J = 12.9 Hz, 2H), 2.18 (td, J = 11.7, 2.3 Hz, 2H), 2.34 (s, 3H), 2.85-2.95 (m, 3H), 2.99 (s, | 495 | |

-continued

| Analytical data | | | |
|---|---|---|---|
| Patent example | $^1$H-NMR | m/z (M + H)$^+$ | Chiral separation |
| | 2H), 3.39 (t, J = 6.4 Hz, 2H), 4.80 (s, 3H), 5.37 (s, 1H), 7.06 (s, 1H), 7.24 (d, J = 7.7 Hz, 1H), 7.39 (d, J = 10.5 Hz, 2H), 7.97 (d, J = 1.5 Hz, 1H). | | |
| A7-3-1 | $^1$H NMR (300 MHZ, $CD_3OD$): δ 8.79 (s, 1H), 8.06-8.04 (m, 1H), 7.81 (s, 1H), 7.47 (d, J = 8.4 Hz, 1H), 5.00 (s, 2H), 3.82-3.76 (m, 1H), 3.52-3.45 (m, 1H), 3.13 (s, 2H), 3.11-3.05 (m, 2H), 2.92-2.88 (m, 1H), 2.58-2.45 (m, 1H), 2.36-2.14 (m, 2H), 1.93-1.86 (m, 1H), 1.70-1.57 (m, 1H), 0.85-0.71 (m, 4H). | 512 | IA (Hex:EtOH = 70:30) |
| A7-3-2 | $^1$H NMR (300 MHZ, $CD_3OD$): δ 8.79 (s, 1H), 8.07-8.04 (m, 1H), 7.81 (s, 1H), 7.47 (d, J = 8.4 Hz, 1H), 4.98 (s, 2H), 3.83-3.76 (m, 1H), 3.52-3.32 (m, 1H), 3.11 (s, 2H), 3.08-3.04 (m, 2H), 2.95-2.90 (m, 1H), 2.58-2.45 (m, 1H), 2.37-2.16 (m, 2H), 1.92-1.86 (m, 1H), 1.69-1.61 (m, 1H), 0.85-0.71 (m, 4H). | 512 | IA (Hex:EtOH = 70:30) |
| A7-4-1 | $^1$H NMR (400 MHZ, DMSO-$d_6$): δ 7.84 (s, 1H), 7.68-7.66 (d, J = 8.0 Hz, 2H), 7.44-7.42 (d, J = 8.0 Hz, 2H), 7.18 (s, 1H), 7.10-7.04 (m, 2H), 4.84 (s, 2H), 4.51-4.38 (m, 1H), 3.69-3.64 (m, 1H), 3.07-3.05 (m, 1H), 2.90 (s, 2H), 2.70-2.67 (d, J = 12.4 Hz, 1H), 2.15-2.00 (m, 2H), 1.80-1.74 (m, 2H), 1.30-1.23 (m, 1H), 0.73-0.68 (m, 4H). | 500 | IG ($CO_2$:MeOH = 70:30) |
| A7-4-2 | $^1$H NMR (300 MHZ, DMSO-$d_6$): δ 8.89 (s, 1H), 8.14-8.11 (d, J = 5.1 Hz, 1H), 7.78 (s, 1H), 7.45-7.43 (d, J = 5.1 Hz, 1H), 7.18 (s, 1H), 7.09 (s, 1H), 7.05-7.04 (m, 1H), 4.92 (s, 2H), 4.54-4.38 (m, 1H), 3.68-3.63 (m, 1H), 3.32-3.23 (m, 1H), 3.07-3.03 (m, 2H), 2.90 (s, 2H), 2.72-2.66 (m, 1H), 2.16-2.11 (m, 1H), 2.06-1.97 (m, 1H), 1.80-1.72 (m, 2H), 1.29-1.21 (m, 1H), 0.74-0.72 (s, 4H). | 500 | IG ($CO_2$:MeOH = 70:30) |
| A7-5-1 | $^1$H NMR (400 MHZ, DMSO-$d_6$): δ 7.839-7.835 (d, J = 1.6 Hz, 1H), 7.68-7.66 (d, J = 8.0 Hz, 2H), 7.44-7.42 (d, J = 8.0 Hz, 2H), 7.18 (s, 1H), 7.10-7.04 (m, 2H), 4.84 (s, 2H), 4.51-4.50 (d, J = 4.8 Hz, 1H), 4.39-4.38 (d, J = 4.4 Hz, 1H), 3.09-3.04 (m, 1H), 2.90 (s, 2H), 2.70-2.67 (d, J = 11.2 Hz, 1H), 2.16-2.00 (m, 2H), 1.78-1.74 (m, 2H), 1.30-1.23 (m, 1H), 0.75-0.65 (m, 4H). | 499 | IG ($CO_2$:MeOH = 75:25) |
| A7-5-2 | $^1$H NMR (400 MHZ, DMSO-$d_6$): δ 7.84 (s, 1H), 7.68-7.66 (d, J = 8.0 Hz, 2H), 7.44-7.42 (d, J = 8.0 Hz, 2H), 7.18 (s, 1H), 7.10-7.04 (m, 2H), 4.84 (s, 2H), 4.51-4.38 (m, 1H), 3.69-3.64 (m, 1H), 3.07-3.05 (m, 1H), 2.90 (s, 2H), 2.70-2.67 (d, J = 12.4 Hz, 1H), 2.15-2.00 (m, 2H), 1.80-1.74 (m, 2H), 1.30-1.23 (m, 1H), 0.73-0.68 (m, 4H). | 499 | IG ($CO_2$:MeOH = 75:25) |
| A7-6-1 | $^1$H NMR (400 MHZ, $CD_3OD$): δ 7.85 (d, J = 1.2 Hz, 1H), 7.59 (d, J = 8.4 Hz, 1H), 7.42 (d, J = 8.4 Hz, 1H), 3.76-3.81 (dd, J = 13.6, 4.8 Hz, 1H), 3.45-3.50 (dd, J = 14.0, 8.4 Hz, 1H), 3.07-3.10 (m, 3H), 2.87-2.93 (m, 2H), 2.45-2.56 (m, 1H), 2.32 (t, J = 11.6 Hz, 1H), 2.16-2.25 (m, 1H), 1.85-1.89 (m, 1H), 1.60-1.67 (m, 1H), 0.76-0.79 (m, 2H), 0.66-0.70 (m, 2H). | 517 | IC (Hex:EtOH = 70:30) |
| A7-6-2 | $^1$H NMR (400 MHZ, $CD_3OD$): δ 7.85 (d, J = 1.2 Hz, 1H), 7.59 (d, J = 8.0 Hz, 1H), 7.42 (d, J = 8.4 Hz, 1H), 3.76-3.81 (dd, J = 14.0, 5.2 Hz, 1H), 3.45-3.51 (dd, J = 14.0, 8.8 Hz, 1H), 3.05-3.11 (m, 3H), 2.87-2.93 (m, 2H), 2.46-2.57 (m, 1H), 2.32 (t, J = 11.2 Hz, 1H), 2.16-2.25 (m, 1H), 1.85-1.89 (m, 1H), 1.60-1.65 (m, 1H), 0.77-0.79 (m, 2H), 0.68-0.70 (m, 2H). | 517 | IC (Hex:EtOH = 70:30) |
| A7-7-1 | $^1$H NMR (400 MHZ, $CD_3OD$): δ 7.85 ( d, J = 1.2 Hz, 1H), 7.59 (d, J = 8.4 Hz, 1H), 7.42 (d, J = 7.6 Hz, 1H), 4.85 (s, 2H), 3.81-3.77 (m, 1H), 3.38-3.35 (m, 1H), 3.07-2.98 (m, 3H), 2.91-2.81 (m, 2H), 2.46-2.41 (m, 1H), 2.31-2.19 (m, 2H), 2.03-1.91 (m, 1H), 1.51-1.46 (m, 1H), 0.81-0.76 (m, 2H), 0.69-0.68 (m, 2H). | 549 | IA (Hex:IPA:DEA = 70:30:0.2) |
| A7-7-2 | $^1$H NMR (400 MHZ, $CD_3OD$): δ 7.85 ( d, J = 1.2 Hz, 1H), 7.59 (d, J = 8.4 Hz, 1H), 7.42 (d, J = 8.4 Hz, 1H), 4.85 (s, 2 H), 3.81-3.77 ( m, 1H), 3.38-3.33 (m, 1H), 3.07-2.98 (m, 3H), 2.92-2.81 ( m, 2H), 2.46-2.42 (m, 1H), 2.32-2.19 (m, 2H), 2.03-1.91 (m, 1H), 1.51-1.47 (m, 1H), 0.79-0.76 (m, 2H), 0.71-0.69 (m, 2H). | 549 | IA (Hex:IPA:DEA = 70:30:0.2) |
| A7-7-3 | 1H NMR (400 MHZ, $CD_3OD$): δ 7.85 ( d, J = 1.2 Hz, 1H), 7.59 (d, J = 8.0 Hz, 1H), 7.42 (d, J = 7.6 Hz, 1H), 4.86 (s, 2H), 3.64-3.50 ( m, 1H), 3.03 (dd, J = 11.2, 16.4 Hz, 2H), 2.92-2.82 ( m, 2H), 2.78-2.72 (m, 2H), 2.61-2.58 (m, 1H), 2.43-2.39 (m, 1H), 2.27-2.26 (m, 1H), 1.83-1.70 (m, 2H), 0.81-0.76 (m, 2H), 0.71-0.67 (m, 2H). | 549 | IG (Hex:IPA:DEA = 80:20:0.2) |

-continued

Analytical data

| Patent example | $^1$H-NMR | m/z $(M + H)^+$ | Chiral separation |
|---|---|---|---|
| A7-7-4 | 1H NMR (400 MHZ, $CD_3OD$): δ 7.85 ( d, J = 1.2 Hz, 1H), 7.59 (d, J = 8.0 Hz, 1H), 7.43 (d, J = 8.0 Hz, 1H), 4.86 (s, 2H), 3.61-3.50 ( m, 1H), 3.02 (dd, J = 16.4, 20.8 Hz, 2H), 2.92-2.84 ( m, 2H), 2.77-2.74 (m, 2H), 2.61-2.59 (m, 1H), 2.43-2.40 (m, 1H), 2.28-2.27 (m, 1H), 1.82-1.73 (m, 2H), 0.81-0.77 (m, 2H), 0.71-0.67 (m, 2H). | 549 | IG (Hex:IPA:DEA = 80:20:0.2) |
| A7-8 | $^1$H NMR (600 MHZ, DMSO-$d_6$): δ 7.81 (d, J = 1.5 Hz, 1H), 7.55 (ABq, J = 150.1, 8.1 Hz, 4H), 7.18-7.11 (m, 1H), 7.10-7.01 (m, 2H), 4.83 (s, 2H), 3.55-3.51 (m, 5H), 2.93-2.89 (m, 1H), 2.76 (s, 2H), 2.69-2.64 (m, 2H), 2.01-1.95 (m, 4H), 1.57-1.51 (m, 2H), 0.76-0.70 (m, 2H), 0.70-0.65 (m, 2H). | 540 | |
| A7-9 | $^1$H NMR (400 MHZ, $CDCl_3$): δ 0.72-0.76 (m, 2H), 0.78-0.84 (m, 2H), 1.64-1.74 (m, 4H), 2.51-2.73 (m, 4H), 2.99-3.15 (m, 3H), 3.48-3.52 (m, 3H), 4.98 (s, 2H), 5.16 (d, J = 3.2 Hz, 1H), 5.38 (s, 1H), 7.08 (s, 1H), 7.30 (d, J = 8.2 Hz, 1H), 7.76-7.94 (m, 2H), 8.81 (s, 1H). | 498 | |
| A7-10 | $^1$H NMR (400 MHZ, $CDCl_3$): δ 0.67-0.75 (m, 2H), 0.76-0.83 (m, 2H), 1.60-1.76 (m, 4H), 2.56-2.72 (m, 4H), 2.90 (dq, J = 6.7, 3.1 Hz, 1H), 3.04 (s, 2H), 3.50 (d, J = 6.1 Hz, 2H), 4.70 (s, 1H), 4.86 (s, 2H), 5.11-5.17 (m, 1H), 5.37 (s, 1H), 7.07 (s, 1H), 7.35 (d, J = 8.0 Hz, 2H), 7.56 (d, J = 8.1 Hz, 2H), 7.93 (d, J = 1.4 Hz, 1H). | 497 | |
| A7-11 | $^1$H NMR (400 MHz, $CDCl_3$): δ 0.70-0.76 (m, 2H), 0.80-0.88 (m, 2H), 1.60-1.77 (m, 4H), 2.55-2.74 (m, 4H), 2.91 (tt, J = 6.8, 3.4 Hz, 1H), 3.05 (s, 2H), 3.51 (d, J = 6.1 Hz, 2H), 4.50 (s, 1H), 4.89 (s, 2H), 5.12-5.22 (m, 1H), 5.37 (s, 1H), 7.07 (s, 1H), 7.62 (d, J = 8.0 Hz, 1H), 7.73-7.79 (m, 1H), 7.91 (d, J = 1.4 Hz, 1H), 8.65 (s, 1H). | 498 | |
| A7-12 | $^1$H NMR (300 MHz, DMSO-$d_6$): δ 10.66 (s, 1H), 7.85 (d, J = 1.7 Hz, 1H), 7.30-7.15 (m, 1H), 7.15-6.99 (m, 2H), 6.86-6.73 (m, 3H), 4.65 (s, 2H), 4.53 (s, 2H), 3.60 (dd, J = 20.1, 6.3 Hz, 2H), 2.90-2.76 (m, 3H), 2.69-2.56 (m, 2H), 2.34-2.19 (m, 2H), 1.90-1.61 (m, 4H), 0.80-0.57 (m, 4H). | 502 | |
| A7-13 | $^1$H NMR (300 MHZ, DMSO-$d_6$): δ 7.86 (d, J = 1.7 Hz, 1H), 7.26-7.20 (m, 1H), 7.20-7.14 (m, 2H), 7.14-7.02 (m, 3H), 4.76 (s, 2H), 3.59 (dd, J = 20.1, 6.3 Hz, 2H), 3.31 (s, 3H), 2.90-2.78 (m, 3H), 2.69-2.56 (m, 2H), 2.35-2.16 (m, 2H), 1.90-1.60 (m, 4H), 0.80-0.59 (m, 4H). | 502 | |
| A7-14 | $^1$H NMR (300 MHZ, DMSO-$d_6$) δ 8.92-8.84 (m, 1H), 8.12 (ddd, J = 8.3, 2.4, 0.8 Hz, 1H), 7.77 (d, J = 1.8 Hz, 1H), 7.44 (d, J = 8.2 Hz, 1H), 7.12 (d, J = 21.8 Hz, 2H), 7.01-6.86 (m, 1H), 5.00 (d, J = 4.9 Hz, 1H), 4.92 (s, 2H), 3.52 (dt, J = 13.3, 4.7 Hz, 1H), 3.42-3.35 (m, 1H), 3.31-3.23 (m, 1H), 3.11-2.96 (m, 1H), 2.92-2.75 (m, 3H), 2.70 (d, J = 11.1 Hz, 1H), 2.00-1.88 (m, 1H), 1.84 (t, J = 10.0 Hz, 1H), 1.71-1.57 (m, 1H), 1.49-1.17 (m, 2H), 0.80-0.64 (m, 4H). | 498 | |
| A7-14-1 | 1HNMR (400 MHZ $CDCl_3$): δ 7.95 (d, J = 1.2 Hz, 1H), 7.55 (d, J = 8.0 Hz, 2H), 7.37 (d, J = 8.0 Hz, 2H), 6.93 (s, 1H), 5.67 (d, J = 3.6 Hz, 1H), 5.56 (s, 1H), 5.05-5.15 (m, 1H), 4.87 (s, 2H), 4.09-4.16 (m, 1H), 3.34-3.37 (m, 1H), 3.11-3.17 (m, 1H), 3.02-3.08 (m, 3H), 2.85-2.92 (m, 2H), 2.11-2.24 (m, 2H), 1.44-1.65 (m, 2H), 1.40-1.50 (m, 1H), 0.74-0.82 (m, 2H), 0.72-0.74 (m, 2H) | 497 | ID (Hex:IPA:DEA = 50:50:0.3) |
| A7-14-2 | 1HNMR (400 MHZ $CDCl_3$): δ 7.95 (d, J = 1.2 Hz, 1H), 7.55 (d, J = 8.0 Hz, 2H), 7.37 (d, J = 8.0 Hz, 2H), 6.92 (s, 1H), 5.65 (d, J = 3.2 Hz, 1H), 5.53 (s, 1H), 5.06-5.11 (m, 1H), 4.87 (s, 2H), 4.09-4.16 (m, 1H), 3.30-3.37 (m, 1H), 3.11-3.17 (m, 1H), 3.02-3.08 (m, 3H), 2.85-2.93 (m, 2H), 2.11-2.24 (m, 2H), 1.54-1.66 (m, 2H), 1.43-1.47 (m, 1H), 0.74-0.82 (m, 2H) | 497 | ID (Hex:IPA:DEA = 50:50:0.3) |
| A7-15 | $^1$H NMR (300 MHZ, DMSO-$d_6$): δ 7.82 (d, J = 1.9 Hz, 1H), 7.37 (d, J = 73.8 Hz, 1H), 7.22-7.04 (m, 4H), 6.97 (dd, J 8.5, 2.4 Hz, 1H), 6.90-6.79 (m, 1H), 4.96 (d, J = 4.5 Hz, 1H), 4.80-4.64 (m, 3H), 3.50 (dt, J = 13.2, 4.6 Hz, 1H), 3.32-3.21 (m, 2H), 2.88-2.76 (m, 3H), 2.67 (d, J = 11.2 Hz, 1H), 2.15-1.97 (m, 4H), 1.97-1.77 (m, 2H), 1.69-1.46 (m, 3H), 1.45-1.12 (m, 2H). | 527 | |
| A7-15-1 | $^1$H NMR (400 MHZ, $CD_3OD$): δ 7.80 (d, J = 1.6 Hz, 1H), 7.19-7.15 (t, J = 8.4 Hz, 1H), 6.93-6.87 (m, 2H), 7.00-6.63 (t, J = 74 Hz, 1H), 4.73 (s, 2H), 4.69-4.67 (m, 1H), 3.61-3.58 (m, 1H), 3.44-3.40 (m, 2H), 2.99-2.96 (m, 3H), 2.83-2.80 (m, 2H), 2.19-1.98 (m, 6H), 1.71-1.62 (m, 3H), 1.48-1.44 (m, 2H). | 527 | IG, Hex:EtOH = 70:30 |
| A7-15-2 | $^1$H NMR (400 MHZ, $CD_3OD$): δ 7.80 (d, J = 1.6 Hz, 1H), 7.19-7.15 (t, J = 8.4 Hz, 1H), 6.93-6.87 (m, 2H), 7.00-6.63 (t, J = 74 Hz, 1H), 4.86 (s, 2H), 4.79-4.68 (m, 1H), 3.61-3.58 (m, 1H), | 527 | IG, Hex:EtOH = 70:30 |

-continued

| Analytical data | | | |
|---|---|---|---|
| Patent example | $^1$H-NMR | m/z (M + H)$^+$ | Chiral separation |
| | 3.45-3.40 (m, 2H), 2.99-2.96 (m, 3H), 2.83-2.80 (m, 2H), 2.19-1.98 (m, 6H), 1.73-1.62 (m, 3H), 1.48-1.44 (m, 2H). | | |
| A7-16 | $^1$H NMR (400 MHZ, $CDCl_3$): δ 7.85 (d, J = 16.0 Hz, 1H), 7.49 (d, J = 8.0 Hz, 2H), 7.24 (d, J = 8.0 Hz, 2H), 6.85 (d, J = 3.2 Hz, 1H), 5.61 (s, 1H), 5.38 (d, J = 3.6 Hz, 1H), 4.88 (s, 1H), 4.79 (s, 2H), 4.76-4.71 (m, 1H), 4.07-4.01 (m, 1H), 3.25-3.23 (m, 1H), 3.04-3.02 (m, 1H), 3.00-2.97 (m, 1H), 2.94 (s, 2H), 2.77 (d, J = 12.0 Hz, 1H), 2.14-1.93 (m, 6H), 1.52-1.30 (m, 2H). | 512 | |
| A7-16-1 | $^1$H NMR (400 MHZ, $CDCl_3$): δ 7.92 (d, J = 1.6 Hz, 1H), 7.56 (d, J = 8.4 Hz, 2H), 7.31 (d, J = 8.0 Hz, 2H), 6.93 (d, J = 4.0 Hz, 1H), 5.70 (d, J = 2.8 Hz, 1H), 5.55 (d, J = 4.0 Hz, 1H), 4.98 (s, 1H), 4.86-4.80 (m, 3H), 4.12-4.07 (m, 1H), 3.31-3.30 (m, 1H), 3.10-3.10 (m, 1H), 3.06-3.02 (m, 1H), 3.01 (s, 2H), 2.83 (s, 1H), 2.19-2.03 (m, 6H), 1.66-1.44 (m, 5H). | 512 | ID (Hex:EtOH = 70:30) |
| A7-16-2 | $^1$H NMR (400 MHZ, $CDCl_3$): δ 7.93 (d, J = 1.2 Hz, 1H), 7.56 (d, J = 8.4 Hz, 2H), 7.31 (d, J = 7.6 Hz, 2H), 6.92 (d, J = 3.6 Hz, 1H), 5.69 (s, 1H), 5.50 (d, J = 3.6 Hz, 1H), 4.96 (s, 1H), 4.86-4.83 (m, 3H), 4.12-4.07 (m, 1H), 3.31-3.30 (m, 1H), 3.07-3.06 (m, 1H), 3.06-3.04 (m, 1H), 3.01 (s, 2H), 2.86-2.83 (m, 1H), 2.21-2.03 (m, 6H), 1.69-1.25 (m, 5H). | 512 | ID (Hex:EtOH = 70:30) |
| A7-17 | $^1$H NMR (400 MHZ, $CDCl_3$): δ 8.82 (s, 2H), 7.91 (s, 1H), 6.93 (br s, 1H), 5.50-5.43 (m, 2H), 5.15 (br s, 1H), 4.88 (dd, J = 22.8, 16.0 Hz, 2H), 4.15-4.09 (m, 1H), 3.33-3.31 (m, 1H), 3.17-3.11 (m, 1H), 3.07-3.03 (m, 1H), 3.02 (s, 2H), 2.97-2.93 (m, 1H), 2.88-2.85 (m, 1H), 2.22-2.10 (m, 2H), 1.65-1.52 (m, 2H), 1.46-1.43 (m, 1H), 0.89-0.86 (m, 2H), 0.76 (s, 2H). | 499 | |
| A7-17-1 | $^1$H NMR (400 MHZ, $CDCl_3$): δ 8.83 (s, 2H), 7.92 (s, 1H), 6.93 (br s, 1H), 5.54 (br s, 1H), 5.44 (br s, 1H), 5.17 (br s, 1H), 4.88 (dd, J = 21.2 and 16.0 Hz, 2H), 4.16-4.09 (m, 1H), 3.34-3.31 (m, 1H), 3.18-3.12 (m, 1H), 3.07-3.02 (m, 3H), 2.98-2.93 (m, 1H), 2.89-2.86 (m, 1H), 2.23-2.11 (m, 2H), 1.66-1.44 (m, 3H), 0.90-0.88 (m, 2H), 0.77 (s, 2H). | 499 | IC (CO2:MeOH:DEA = 70:30:0.3) |
| A7-17-2 | $^1$H NMR (400 MHZ, $CDCl_3$): δ 8.83 (s, 2H), 7.92 (s, 1H), 6.94 (br s, 1H), 5.65 (br s, 1H), 5.44 (br s, 1H), 5.19 (br s, 1H), 4.88 (dd, J = 19.6 and 16.0 Hz, 2H), 4.15-4.09 (m, 1H), 3.36-3.30 (m, 1H), 3.18-3.12 (m, 1H), 3.07-3.02 (m, 3H), 2.99-2.93 (m, 1H), 2.88-2.85 (m, 1H), 2.23-2.08 (m, 2H), 1.66-1.44 (m, 3H), 0.90-0.87 (m, 2H), 0.77 (s, 2H). | 499 | IC (CO2:MeOH:DEA = 70:30:0.3) |
| A7-18 | $^1$H NMR (400 MHZ, $CDCl_3$): δ 8.76 (s, 2H), 7.88 (s, 1H), 6.92 (br s, 1H), 5.49-5.41 (m, 2H), 5.07-5.05 (m, 1H), 4.87 (s, 2H), 4.78-4.74 (m, 1H), 4.13-4.07 (m, 1H), 3.30-3.27 (m, 1H), 3.14-3.08 (m, 1H), 3.05-3.01 (m, 3H), 2.87-2.84 (m, 1H), 2.25-2.05 (m, 6H), 1.60-1.54 (m, 2H), 1.51-1.33 (m, 2H). | 513 | |
| A7-18-1 | $^1$H NMR (400 MHZ, $CDCl_3$): δ 8.77 (s, 2H), 7.89 (s, 1H), 6.95 (br s, 1H), 5.54 (br s, 1H), 5.43 (br s, 1H), 5.07 (br s, 1H), 4.88 (s, 2H), 4.79-4.75 (m, 1H), 4.14-4.08 (m, 1H), 3.33-3.28 (m, 1H), 3.15-3.09 (m, 1H), 3.06-3.03 (m, 3H), 2.88-2.85 (m, 1H), 2.26-2.06 (m, 6H), 1.66-1.39 (m, 4H) | 513 | ID (Hex:IPA:DEA = 40:60:0.3) |
| A7-18-2 | $^1$H NMR (400 MHZ, $CDCl_3$): δ 8.77 (s, 2H), 7.89 (s, 1H), 6.93 (br s, 1H), 5.52 (br s, 1H), 5.43 (br s, 1H), 5.08 (br s, 1H), 4.88 (s, 2H), 4.79-4.75 (m, 1H), 4.14-4.08 (m, 1H), 3.33-3.29 (m, 1H), 3.15-3.09 (m, 1H), 3.06-3.02 (m, 3H), 2.88-2.85 (m, 1H), 2.26-2.06 (m, 6H), 1.66-1.39 (m, 4H) | 513 | ID (Hex:IPA:DEA = 40:60:0.3) |
| A7-19 | $^1$H NMR (400 MHZ, $CD_3OD$): δ 7.83 ( d, J = 1.6 Hz, 1H), 7.59 (d, J = 8.4 Hz, 1H), 7.46 (d, J = 8.0 Hz, 1H), 4.84-4.81 (m, 1H), 4.79 (s, 2H), 3.66-3.61 (m, 1H), 3.47-3.41 (m, 2H), 3.02-2.99 ( m, 3H), 2.84 (d, J = 10.4 Hz, 2H), 2.13-2.00 (m, 2H), 1.75-1.73 (m, 2H), 1.49-1.47 (m, 2H), 1.23 (d, J = 6.8 Hz, 6H). | 442 | |
| A7-19-1 | $^1$H NMR (400 MHZ, $CD_3OD$): δ 7.83 (d, J = 2.0 Hz, 1 H), 7.60 (d, J = 8.4 Hz, 1 H), 7.46 (d, J = 8.4 Hz, 1 H), 4.84-4.81 (m, 1 H), 4.79 (s, 2 H), 3.66-3.61 (m, 1 H), 3.47-3.41 (m, 2 H), 3.02-2.99 ( m, 3 H), 2.84 (d, J = 10.4 Hz, 2 H), 2.14-2.00 (m, 2 H), 1.76-1.73 (m, 2 H), 1.51-1.47 (m, 2 H), 1.24 (d, J = 6.4 Hz, 6 H) | 442 | IG (Hex:etOH = 60:40) |
| A7-19-2 | $^1$H NMR (400 MHZ, $CD_3OD$): δ 7.83 (d, J = 2.0 Hz, 1 H), 7.60 (d, J = 8.4 Hz, 1 H), 7.46 (d, J = 8.4 Hz, 1 H), 4.84-4.81 (m, 1 H), 4.79 (s, 2 H), 3.66-3.61 (m, 1 H), 3.47-3.41 (m, 2 H), 3.02-2.99 ( m, 3 H), 2.84 (d, J = 10.4 Hz, 2 H), 2.14-2.00 (m, 2 H), 1.76-1.73 (m, 2 H), 1.51-1.47 (m, 2 H), 1.24 (d, J = 6.4 Hz, 6 H) | 442 | IG (Hex:etOH = 60:40) |
| A7-20 | $^1$H NMR (400 MHZ, $CD_3OD$): δ 7.82 (d, J = 2.0 Hz, 1H), 7.61 (d, J = 8.0 Hz, 2H), 7.43 (d, J = 8.4 Hz, 2H), 4.84 (s, 2H), 3.60 (dd, J = 13.6, 4.8 Hz, 1H), 3.48-3.41 (m, 2H), 3.13 (d, J = 3.6 | 471 | |

-continued

| Analytical data | | | |
|---|---|---|---|
| Patent example | $^1$H-NMR | m/z $(M + H)^+$ | Chiral separation |
| | Hz, 3H), 3.00-2.96 (m, 3H), 2.82 (d, J = 10.0 Hz, 1H), 2.14-2.09 (m, 1H), 1.99 (t, J = 10.0 Hz, 1H), 1.76-1.73 (m, 1H), 1.51-1.48 (m, 2H). | | |
| A7-20-1 | $^1$H NMR (400 MHZ, $CD_3OD$): δ 7.73 (d, J = 1.6 Hz, 1H), 7.51 (d, J = 8.4 Hz, 2H), 7.33 (d, J = 8.0 Hz, 2H), 4.75 (s, 2H), 3.51 (dd, J = 14.0, 5.2 Hz, 1H), 3.39-3.32 (m, 2H), 3.04 (d, J = 3.6 Hz, 3H), 2.91-2.88 (m, 3H), 2.72 (d, J = 10.0 Hz, 1H), 2.05-2.00 (m, 1H), 1.92 (t, J = 10.0 Hz, 1H), 1.65-1.63 (m, 1H), 1.41-1.38 (m, 2H) | 471 | IE (Hex:EtOH = 60:40) |
| A7-20-2 | $^1$H NMR (400 MHZ, $CD_3OD$): δ 7.73 (d, J = 1.6 Hz, 1H), 7.52 (d, J = 8.4 Hz, 2H), 7.33 (d, J = 8.4 Hz, 2H), 4.75 (s, 2H), 3.51 (dd, J = 13.6, 4.8 Hz, 1H), 3.39-3.32 (m, 2H), 3.04 (d, J = 3.6 Hz, 3H), 2.91-2.87 (m, 3H), 2.73 (d, J = 9.6 Hz, 1H), 2.05-2.00 (m, 1H), 1.90 (t, J = 10.4 Hz, 1H), 1.66-1.63 (m, 1H), 1.41-1.37 (m, 2H). | 471 | IE (Hex:EtOH = 60:40) |
| A7-21 | $^1$H NMR (400 MHZ, $CD_3OD$): δ 7.71 (d, J = 1.2 Hz, 1H), 7.50 (d, J = 8.4 Hz, 2H), 7.33 (d, J = 8.4 Hz, 2H), 4.77 (s, 2H), 3.51 (dd, J = 13.2, 4.8 Hz, 1H), 3.49-3.44 (m, 2H), 3.38-3.30 (m, 2H), 2.91-2.85 (m, 3H), 2.72 (d, J = 11.2 Hz, 1H), 2.05-1.99 (m, 1H), 1.89 (t, J = 10.0 Hz, 1H), 1.65-1.63 (m, 1H), 1.41-1.36 (m, 2H). 1.09 (t, J = 6.8 Hz, 3H). | 485 | |
| A7-21-1 | $^1$H NMR (400 MHZ, $CD_3OD$): δ 7.71 (d, J = 1.6 Hz, 1H), 7.50 (d, J = 8.4 Hz, 2H), 7.34 (d, J = 8.4 Hz, 2H), 4.77 (s, 2H), 3.51 (dd, J = 13.6, 5.2 Hz, 1H), 3.49-3.44 (m, 2H), 3.39-3.30 (m, 2H), 2.91-2.88 (m, 3H), 2.72 (d, J = 10.0 Hz, 1H), 2.05-2.02 (m, 1H), 1.89 (t, J = 10.0 Hz, 1H), 1.66-1.63 (m, 1H), 1.41-1.36 (m, 2H), 1.09 (t, J = 6.8 Hz, 3H). | 485 | ID(Hex:IPA:DEA) = 50:50:0.3 |
| A7-21-2 | $^1$H NMR (400 MHZ, $CD_3OD$) δ 7.71 (d, J = 1.6 Hz, 1H), 7.50 (d, J = 8.0 Hz, 2H), 7.33 (d, J = 8.0 Hz, 2H), 4.77 (s, 2H), 3.51 (dd, J = 14.0, 4.8 Hz, 1H), 3.49-3.44 (m, 2H), 3.38-3.30 (m, 2H), 2.91-2.88 (m, 3H), 2.72 (d, J = 11.2 Hz, 1H), 2.05-2.00 (m, 1H), 1.90 (t, J = 10.0 Hz, 1H), 1.66-1.63 (m, 1H), 1.41-1.36 (m, 2H), 1.08 (t, J = 6.8 Hz, 3H) | 485 | ID(Hex:IPA:DEA) = 50:50:0.3 |
| A7-22 | $^1$H NMR (400 MHZ, $CDCl_3$): δ 7.94 (s, 1H), 7.37-7.30 (m, 3H), 6.94 (br s, 1H), 5.66 (br s, 1H), 5.51 (br s, 1H), 5.08 (br s, 1H), 4.90 (s, 2H), 4.16-4.10 (m, 1H), 3.38-3.33 (m, 1H), 3.16-3.11 (m, 1H), 3.08-3.04 (m, 3H), 2.96-2.87 (m, 2H), 2.24-2.12 (m, 2H), 1.65-1.55 (m, 2H), 1.46-1.41 (m, 1H), 0.84-0.74 (m, 4H). | 515 | |
| A7-22-1 | $^1$H NMR (400 MHZ, $CDCl_3$): δ 7.94 (s, 1H), 7.34-7.30 (m, 3H), 6.93 (br s, 1H), 5.67 (br s, 1H), 5.53 (br s, 1H), 5.08 (br s, 1H), 4.91 (s, 2H), 4.17-4.10 (m, 1H), 3.35-3.31 (m, 1H), 3.16-3.03 (m, 4H), 2.94-2.86 (m, 2H), 2.24-2.11 (m, 2H), 1.63-1.55 (m, 2H), 1.46-1.43 (m, 1H), 0.82-0.79 (m, 2H), 0.74-0.73 (m, 2H) | 515 | ID (Hex:EtOH:DEA = 80:20:0.3) |
| A7-22-2 | $^1$H NMR (400 MHZ, $CDCl_3$): δ 7.94 (s, 1H), 7.34-7.30 (m, 3H), 6.93 (br s, 1H), 5.66(br s, 1H), 5.50 (br s, 1H), 5.08 (br s, 1H), 4.91 (s, 2H), 4.17-4.10 (m, 1H), 3.37-3.32 (m, 1H), 3.16-3.03 (m, 4H), 2.95-2.86 (m, 2H), 2.24-2.11 (m, 2H), 1.62-1.55 (m, 2H), 1.46-1.41 (m, 1H), 0.82-0.78 (m, 2H), 0.74-0.73 (m, 2H) | 515 | ID (Hex:EtOH:DEA = 80:20:0.3) |
| A7-23 | $^1$H NMR (400 MHZ, $CDCl_3$): δ 8.61 (s, 1H), 7.91 ( d, J = 1.2 Hz, 1H), 7.70 (d, J = 8.0 Hz, 1H), 7.63 (d, J = 8.4 Hz, 1H), 6.92 (d, J = 1.2 Hz, 1H), 5.56 (d, J = 1.6 Hz, 1H), 5.41 (d, J = 6.4 Hz, 1H), 5.00-4.98 (m, 1H), 4.89 (s, 1H), 4.81-4.77 (m, 1H), 4.16-4.10 ( m, 1H), 3.31-3.29 (m, 1H), 3.13-3.02 (m, 4H), 2.86 (d, J = 11.2 Hz, 1H), 2.22-2.01 (m, 6H), 1.71-1.66 (m, 2H), 1.57-1.49 (m, 1H), 1.44-1.38 (m, 1H). | 512 | ID (Hex:IPA = 50:50) |
| A7-23-1 | $^1$H NMR (400 MHZ, $CDCl_3$): 8.60 (d, J = 1.2 Hz, 1 H), 7.91 ( d, J = 1.2 Hz, 1 H), 7.70 (d, J = 8.0 Hz, 1 H), 7.62 (d, J = 8.0 Hz, 1 H), 6.93 (d, J = 2.8 Hz, 1 H), 5.57 (d, J = 3.6 Hz, 1 H), 5.43 (s, 1 H), 5.11-4.97 (m, 1 H), 4.89 (s, 2 H), 4.81-4.77 (m, 1 H), 4.16-4.10 ( m, 1 H), 3.31-3.29 (m, 1 H), 3.13-3.02 (m, 4 H), 2.86 (d, J = 11.2 Hz, 1 H), 2.22-2.01 (m, 6 H), 1.71-1.66 (m, 2 H), 1.57-1.49 (m, 2 H), 1.44-1.41 (m, 1 H) | 512 | ID (Hex:IPA = 50:50) |
| A7-23-2 | $^1$H NMR (400 MHZ, $CDCl_3$) 8.60 (d, J = 1.2 Hz, 1 H), 7.91 ( d, J = 1.2 Hz, 1 H), 7.70 (d, J = 8.0 Hz, 1 H), 7.62 (d, J = 8.0 Hz, 1 H), 6.93 (d, J = 2.8 Hz, 1 H), 5.57 (d, J = 3.6 Hz, 1 H), 5.43 (s, 1 H), 5.11-4.97 (m, 1 H), 4.89 (s, 2 H), 4.81-4.77 (m, 1 H), 4.16-4.10 ( m, 1 H), 3.31-3.29 (m, 1 H), 3.13-3.02 (m, 4 H), 2.86 (d, J = 11.2 Hz, 1 H), 2.22-2.01 (m, 6 H), 1.71-1.66 (m, 2 H), 1.57-1.49 (m, 2 H), 1.44-1.41 (m, 1 H) | 512 | ID (Hex:IPA = 50:50) |
| A7-24 | $^1$H NMR (400 MHZ, $CDCl_3$): δ 8.81 (s, 1H), 7.91 (d, J = 1.2 Hz, 1H), 7.87-7.85 (m, 1H), 7.32 (d, J = 8.4 Hz, 1H), 6.92 (s, 1H), 5.63 (s, 1H), 5.49 (d, J = 3.2 Hz, 1H), 5.00-4.98 (m, 1H), 4.96 (s, 2H), 4.89-4.84 (m, 1H), 4.15-4.09 (m, 1H), 3.33-3.31 | 512 | |

-continued

| Analytical data | | | |
|---|---|---|---|
| Patent example | $^1$H-NMR | m/z $(M + H)^+$ | Chiral separation |
| | (m, 1H), 3.12-3.10 (m, 1H), 3.08-3.04 (m, 1H), 3.02 (s, 2H), 2.85 (d, J = 12.0 Hz, 1H), 2.22-2.03 (m, 6H), 1.68-1.48 (m, 2H). | | |
| A7-24-1 | $^1$H NMR (400 MHZ, $CDCl_3$): δ 8.81 (d, J = 0.8 Hz, 1H), 7.91 (d, J = 1.6 Hz, 1H), 7.87-7.85 (m, 1H), 7.33 (d, J = 8.4 Hz, 1H), 6.93 (d, J = 0.4 Hz, 1H), 5.64 (d, J = 3.2 Hz, 1H), 5.57 (d, J = 4.0 Hz, 1H), 5.01-4.96 (m, 1H), 4.96 (s, 2H), 4.89-4.84 (m, 1H), 4.12-4.09 (m, 1H), 3.30 (d, J = 3.6 Hz, 1H), 3.12-3.05 (m, 2H), 3.01 (s, 2H), 2.85 (d, J = 11.6 Hz, 1H), 2.21-2.03 (m, 6H), 1.59-1.40 (m, 2H). | 512 | IG (Hex:EtOH = 40:60) |
| A7-24-2 | $^1$H NMR (400 MHZ, $CDCl_3$): δ 8.81 (s, 1H), 7.92 (d, J = 1.2 Hz, 1H), 7.87-7.85 (m, 1H), 7.33 (d, J = 8.0 Hz, 1H), 6.93 (d, J = 4.0 Hz, 1H), 5.65 (s, 1H), 5.54 (d, J = 3.6 Hz, 1H), 5.00-4.96 (m, 1H), 4.96 (s, 2H), 4.89-4.84 (m, 1H), 4.12-4.09 (m, 1H), 3.31 (d, J = 4.4 Hz, 1H), 3.12-3.04 (m, 2H), 3.02 (s, 2H), 2.85 (d, J = 11.6 Hz, 1H), 2.21-2.03 (m, 6H), 1.60-1.40 (m, 2H). | 512 | IG (Hex:EtOH = 40:60) |
| A7-25 | $^1$H NMR (400 MHZ, $CDCl_3$): δ 8.57 (s, 1H), 7.94 ( d, J = 0.8 Hz, 1H), 7.76-7.74 (m, 1H), 7.58 (d, J = 8.0 Hz, 1H), 6.95 (m, 1H), 6.63 (t, J = 55.6 Hz, 1H), 5.55 (d, J = 8.4 Hz, 1H), 5.10 (s, 1H), 4.88 (dd, J = 14.8, 23.2 Hz, 2H), 4.17-4.11 (m, 1H), 3.16-3.11 ( m, 1H), 3.08-3.05 (m, 2H), 3.03 (s, 2H), 2.92-2.87 (m, 2H), 2.23-2.11 (m, 2H), 1.65-1.52 (m, 2H), 1.47-1.41 (m, 1H), 0.85-0.80 (m, 2H), 0.75-0.74 (m, 2H). | 480 | |
| A7-25-1 | $^1$H NMR (400 MHZ, $CD_3OD$): δ 8.44 (s, 1 H), 7.80-7.77 ( m, 1 H), 7.75 (d, J = 1.2 Hz, 1 H), 7.55 (d, J = 8.0 Hz, 1 H), 6.60 (t, J = 55.2 Hz, 1 H), 4.80 (s, 1 H), 3.56-3.51 (m, 1 H), 3.38-3.34 (m, 2 H), 2.91-2.87 (m, 3 H), 2.85-2.81 (m, 1 H), 2.74-2.72 (m, 1 H), 2.04-2.00 (m, 1 H), 1.94-1.89 (m, 1H) 1.66-1.64 (m, 1 H), 1.38-1.36 (m, 2 H), 0.75-0.70 (m, 2 H), 0.62-0.60 (m, 2 H) | 480 | AD (Hex:EtOH:DEA = 60:40:0.3) |
| A7-25-2 | $^1$H NMR (400 MHZ, $CD_3OD$): δ 8.44 (s, 1 H), 7.80-7.77 ( m, 1 H), 7.74 (d, J = 1.6 Hz, 1 H), 7.54 (d, J = 8.4 Hz, 1 H), 6.60 (t, J = 55.2 Hz, 1 H), 4.79 (s, 1 H), 3.52-3.51 (m, 1 H), 3.38-3.35 (m, 2 H), 2.90-2.87 (m, 3 H), 2.83-2.82 (m, 1 H), 2.74-2.72 (m, 1 H), 2.00-1.99 (m, 1 H), 1.94-1.89 (m, 1H) 1.65-1.61 (m, 1 H), 1.38-1.36 (m, 2 H), 0.75-0.70 (m, 2 H), 0.62-0.60 (m, 2 H) | 480 | AD (Hex:EtOH:DEA = 60:40:0.3) |
| A7-26 | $^1$H NMR (400 MHZ, $CDCl_3$): δ 7.92 (s, 1H), 7.52-7.31 (m, 3H), 6.96 (br s, 1H), 5.75 (br s, 1H), 5.48 (br s, 1H), 4.98 (br s, 1H), 4.91-4.81 (m, 2H), 4.16-4.10 (m, 1H), 3.63-3.50 (m, 2H), 3.34-3.33 (m, 1H), 3.13-3.04 (m, 4H), 2.88-2.86 (m, 1H), 2.24-2.12 (m, 2H), 1.77-1.50 (m, 2H), 1.45-1.39 (m, 1H), 1.24 (t, J = 7.2 Hz, 3H). | 503 | |
| A7-26-1 | $^1$H NMR (400 MHZ, $CDCl_3$): 7.92 (s, 1H), 7.40-7.31 (m, 3H), 6.94 (br s, 1H), 5.75(br s, 1H), 5.47(br s, 1H), 4.98(s, 1H), 4.87 (dd, J = 22.0, 16.8 Hz, 2H), 4.17-4.11 (m, 1H), 3.61-3.53 (m, 2H), 3.34-3.31 (m, 1H), 3.13-3.03 (m, 4H), 2.88-2.85 (m, 1H), 2.23-2.11 (m, 2H), 1.61-1.52 (m, 2H), 1.44-1.42 (m, 1H), 1.24 (t, J = 6.8 Hz, 3H) | 503 | ID (Hex:EtOH:DEA = 80:20:0.3) |
| A7-26-2 | $^1$H NMR (400 MHZ, $CDCl_3$): 7.92 (s, 1H), 7.41-7.31 (m, 3H), 6.94 (br s, 1H), 5.75(brs, 1H), 5.49(br s, 1H), 4.98(s, 1H), 4.87 (dd, J = 22.0, 17.2 Hz, 2H), 4.17-4.10 (m, 1H), 3.61-3.53 (m, 2H), 3.35-3.30 (m, 1H), 3.13-3.03 (m, 4H), 2.88-2.85 (m, 1H), 2.23-2.11 (m, 2H), 1.62-1.53 (m, 2H), 1.45-1.42 (m, 1H), 1.24 (t, J = 6.8 Hz, 3H) | 503 | ID (Hex:EtOH:DEA = 80:20:0.3) |
| A7-27 | $^1$H NMR (400 MHZ, $CDCl_3$): δ 8.82 (s, 1H), 7.91 (s, 1H), 7.87 (d, J = 8.4 Hz, 1H), 7.40 (d, J = 8.0 Hz, 1H), 6.93 (br s, 1H), 5.73 (br s, 1H), 5.51 (br s, 1H), 4.99-4.87 (m, 3H), 4.16-4.10 (m, 1H), 3.67-3.59 (m, 2H), 3.35-3.30 (m, 1H), 3.12-3.02 (m, 4H), 2.88-2.85 (m, 1H), 2.23-2.11 (m, 2H), 1.64-1.52 (m, 2H), 1.44-1.39 (m, 1H), 1.25 (t, J = 8.4 Hz, 3H). | 486 | |
| A7-27-1 | $^1$H NMR (400 MHZ, $CDCl_3$): δ 8.82 (s, 1H), 7.91-7.86 (m, 2H), 7.40 (d, J = 8.0 Hz, 1H), 6.97 (br s, 1H), 5.63(br s, 1H), 5.00-4.87(m, 3H), 4.17-4.10 (m, 1H), 3.67-3.59 (m, 2H), 3.36-3.30 (m, 1H), 3.12-3.00 (m, 4H), 2.88-2.86 (m, 1H), 2.24-2.12 (m, 2H), 1.63-1.53 (m, 2H), 1.45-1.32 (m, 1H), 1.25 (t, J = 6.8 Hz, 3H) | 486 | IE (Hex:EtOH:DEA = 60:40:0.3) |
| A7-27-2 | $^1$H NMR (400 MHZ, $CDCl_3$): δ 8.82 (s, 1H), 7.91-7.86 (m, 2H), 7.40 (d, J = 8.4 Hz, 1H), 6.97 (br s, 1H), 5.76(br s, 1H), 5.65(br s, 1H), 5.00-4.87 (m, 3H), 4.17-4.10 (m, 1H), 3.70-3.57 (m, 2H), 3.36-3.30 (m, 1H), 3.12-2.98 (m, 4H), 2.88-2.85 (m, 1H), 2.24-2.11 (m, 2H), 1.63-1.50 (m, 2H), 1.44-1.31 (m, 2H), 1.25 (t, J = 6.8 Hz, 3H) | 486 | IE (Hex:EtOH:DEA = 60:40:0.3) |
| A7-28 | $^1$H NMR (400 MHZ, DMSO-$d_6$): δ 0.62-0.81 (m, 4H), 1.28 (dd, J = 12.4, 8.5 Hz, 1H), 1.40 (m, 1H), 1.64 (d, J = 10.1 Hz, | 498 | |

-continued

| Patent example | $^1$H-NMR | m/z $(M + H)^+$ | Chiral separation |
|---|---|---|---|
| | Analytical data | | |
| | 1H), 1.84 (t, J = 10.0 Hz, 1H), 1.93 (t, J = 10.2 Hz, 1H), 2.69 (d, J = 11.6 Hz, 1H), 2.79-2.89 (m, 3H), 2.90-2.99 (m, 1H), 3.53 (dt, J = 13.4, 4.7 Hz, 1H), 4.87 (s, 2H), 4.99 (d, J = 5.3 Hz, 1H), 6.97 (s, 1H), 7.08 (s, 1H), 7.14 (s, 1H), 7.79-7.87 (m, 2H), 7.90 (d, J = 9.7 Hz, 1H), 8.65 (s, 1H). | | |
| A7-28-1 | $^1$H NMR (400 MHZ, $CDCl_3$): δ 8.65 (d, J = 1.7 Hz, 1H), 7.94 (d, J = 1.3 Hz, 1H), 7.77 (d, J = 8.1 Hz, 1H), 7.63 (d, J = 8.0 Hz, 1H), 6.92 (s, 1H), 5.51 (s, 1H), 5.35 (s, 1H), 5.08 (s, 1H), 4.90 (d, J = 7.8 Hz, 2H), 4.14 (ddd, J = 14.7, 7.8, 3.2 Hz, 1H), 3.34 (dt, J = 10.0, 4.9 Hz, 1H), 3.14 (ddd, J = 14.6, 5.8, 2.8 Hz, 1H), 3.10-3.01 (m, 3H), 2.96-2.84 (m, 2H), 2.25-2.11 (m, 2H), 1.69-1.63 (m, 1H), 1.49-1.38 (m, 2H), 0.88-0.80 (m, 2H), 0.77-0.70 (m, 2H). | 498 | Reprosil AMS (Methanol:CO2:$NH_3$ = 35:65:0.2) |
| A7-28-2 | $^1$H NMR (400 MHZ, $CDCl_3$): δ 8.65 (d, J = 1.6 Hz, 1H), 7.94 (d, J = 1.3 Hz, 1H), 7.78 (dd, J = 8.0, 1.6 Hz, 1H), 7.63 (d, J = 8.0 Hz, 1H), 6.93 (s, 1H), 5.52 (d, J = 3.8 Hz, 1H), 5.38 (s, 1H), 5.09 (s, 1H), 4.90 (d, J = 7.8 Hz, 2H), 4.14 (ddd, J = 14.6, 7.7, 3.2 Hz, 1H), 3.34 (tt, J = 9.8, 4.0 Hz, 1H), 3.14 (ddd, J = 14.6, 5.7, 2.7 Hz, 1H), 3.10-3.01 (m, 3H), 2.96-2.84 (m, 2H), 2.25-2.09 (m, 2H), 1.68-1.63 (m, 1H), 1.49-1.39 (m, 2H), 0.89-0.81 (m, 2H), 0.78-0.71 (m, 2H). | 498 | Reprosil AMS (Methanol:CO2:$NH_3$ = 35:65:0.2) |
| A7-29 | $^1$H NMR (400 MHZ, $CDCl_3$): δ8.56 (s, 1H), 7.94 (m, 1H), 7.72-7.70 (m, 1H), 7.60 (d, J = 8.4 Hz, 1H), 6.95 (brs, 1H), 5.65 (s, 1H), 5.44 (s, 1H), 5.08 (s, 1H), 4.87 (dd, J = 16.0, 31.2 Hz, 2H), 4.18-4.11 (m, 1H), 3.36-3.31 ( m, 1H), 3.15-3.06 (m, 2H), 3.02 (s, 2H), 2.92-2.87 (m, 2H), 2.24-2.14 (m, 2H), 2.01 (t, J = 18.8 Hz, 3H), 1.63-1.55 (m, 2H), 1.46-1.41 (m, 1H), 0.86-0.81 (m, 2H), 0.75-0.74 (m, 2H). | 494 | |
| A7-29-1 | $^1$H NMR (400 MHZ, $CDCl_3$): δ 8.56 (s, 1 H), 7.95-7.94 (m, 1 H), 7.72-7.70 (m, 1 H), 7.60 (d, J = 8.4 Hz, 1 H), 6.95 (br, 1 H), 5.65 (s, 1 H), 5.44 (s, 1 H), 5.08 (s, 1H), 4.87 (dd, J1 = 15.6 Hz, J2 = 30.4 Hz, 2 H), 4.18-4.11 (m, 1 H), 3.36-3.31 ( m, 1 H), 3.16-3.06 (m, 2 H), 3.03 (s, 2 H), 2.92-2.86 (m, 2 H), 2.24-2.11 (m, 2 H), 2.01 (t, J = 18.4 Hz), 1.63-1.55 (m, 2 H), 1.46-1.41 (m, 1 H), 0.84-0.81 (m, 2 H), 0.75-0.74 (m, 2 H) | 494 | ID (Hex:EtOH:DEA = 70:30:0.3) |
| A7-29-2 | $^1$H NMR (400 MHZ, $CDCl_3$): δ 8.56 (s, 1 H), 7.95-7.94 (m, 1 H), 7.72-7.70 (m, 1 H), 7.60 (d, J = 8.4 Hz, 1 H), 6.95 (br, 1 H), 5.65 (s, 1 H), 5.44 (s, 1 H), 5.08 (s, 1H), 4.87 (dd, J1 = 15.6 Hz, J2 = 30.4 Hz, 2 H), 4.18-4.11 (m, 1 H), 3.36-3.31 ( m, 1 H), 3.16-3.06 (m, 2 H), 3.03 (s, 2 H), 2.92-2.86 (m, 2 H), 2.24-2.11 (m, 2 H), 2.01 (t, J = 18.4 Hz 1.63-1.55 (m, 2 H), 1.46-1.41 (m, 1 H), 0.84-0.81 (m, 2 H), 0.75-0.74 (m, 2 H) | 494 | ID (Hex:EtOH:DEA = 70:30:0.3) |
| A7-30 | $^1$H NMR (400 MHZ, $CDCl_3$): δ 1.42 (m, 1H), 1.53 (ddd, J = 24.6, 12.2, 4.0 Hz, 2H), 2.13 (t, J = 10.4 Hz, 1H), 2.20 (td, J = 11.4, 3.0 Hz, 1H), 2.86 (d, J = 11.2 Hz, 1H), 3.02 (s, 2H), 3.03-3.08 (m, 1H), 3.11 (ddd, J = 14.7, 5.7, 2.7 Hz, 1H), 3.33 (m, 1H), 3.67-3.97 (m, 2H), 4.13 (ddd, J = 14.6, 7.8, 3.2 Hz, 1H), 4.61 (t, J = 4.8 Hz, 1H), 4.73 (t, J = 4.8 Hz, 1H), 4.85-5.10 (m, 3H), 5.43 (brs, 1H), 5.55 (brs, 1H), 6.92 (brs, 1H), 7.36 (d, J = 8.0 Hz, 2H), 7.59 (d, J = 8.0 Hz, 2H), 7.94 (d, J = 1.6 Hz, 1H). | 503 | |
| A7-31 | $^1$H NMR (400 MHZ, $CDCl_3$): δ 1.34-1.67 (m, 3H), 2.12 (t, J = 10.4 Hz, 1H), 2.18 (td, J = 11.5, 2.9 Hz, 1H), 2.33-2.63 (m, 4H), 2.85 (m, 1H), 3.01 (s, 2H), 3.02-3.07 (m, 1H), 3.11 (ddd, J = 14.6, 5.5, 2.8 Hz, 1H), 3.32 (tt, J = 9.8, 3.8 Hz, 1H), 4.10 (ddd, J = 14.3, 7.6, 3.3 Hz, 1H), 4.78 (s, 2H), 4.95-5.22 (m, 3H), 5.48 (d, J = 3.6 Hz, 1H), 5.65 (brd, J = 4.0 Hz, 1H), 6.90 (brd, J = 4.0 Hz, 1H), 7.31 (d, J = 8.0 Hz, 2H), 7.57 (d, J = 8.0 Hz, 2H), 7.94 (d, J = 1.4 Hz, 1H). | 529 | |
| A7-32 | $^1$H NMR (400 MHZ, $CDCl_3$): δ 1.35-1.65 (m, 4H), 2.08-2.37 (m, 4H), 2.73 (dq, J = 12.8, 6.6 Hz, 2H), 2.85 (d, J = 11.3 Hz, 1H), 3.02 (s, 2H), 3.03-3.07 (m, 1H), 3.10 (ddd, J = 14.6, 5.6, 2.7 Hz, 1H), 3.32 (td, J = 9.9, 4.4 Hz, 1H), 4.11 (dtd, J = 13.3, 7.6, 6.3, 3.1 Hz, 1H), 4.37 (ddd, J = 16.7, 9.4, 7.3 Hz, 1H), 4.71 (p, J = 6.6 Hz, 1H), 4.85 (s, 2H), 5.01 (brs, 1H), 5.37-5.63 (m, 2H), 6.90 (brs, 1H), 7.31 (d, J = 8.0 Hz, 2H), 7.58 (d, J = 8.0 Hz, 2H), 7.95 (d, J = 1.4 Hz, 1H). | 529 | |
| A7-33 | ND | 496 | |
| A7-34 | ND | 495 | |
| A7-35 | ND | 482 | |
| A7-36 | ND | 438 | |
| A7-37 | ND | 484 | |
| A7-38 | ND | 480 | |
| A7-39 | ND | 481 | |

-continued

| Analytical data | | | |
|---|---|---|---|
| Patent example | $^1$H-NMR | m/z $(M + H)^+$ | Chiral separation |
| A7-40 | $^1$H NMR (400 MHZ, $CDCl_3$): δ 0.69-0.75 (m, 2H), 0.76-0.84 (m, 2H), 1.40-1.45 (m, 2H), 1.58-1.63 (m, 1H), 1.91 (t, J = 18.1 Hz, 3H), 2.08-2.26 (m, 2H), 2.89 (dt, J = 10.0, 5.1 Hz, 2H), 3.00-3.17 (m, 4H), 3.34 (dt, J = 10.3, 5.0 Hz, 1H), 4.15 (ddd, J = 14.4, 7.6, 3.1 Hz, 1H), 4.84 (s, 2H), 5.02 (s, 1H), 5.33 (s, 1H), 5.68 (s, 1H), 6.93 (s, 1H), 7.30 (d, J = 8.1 Hz, 2H), 7.44 (d, J = 8.3 Hz, 2H), 7.96 (d, J = 1.3 Hz, 1H). | 493 | |
| A7-41 | $^1$H NMR (400 MHZ, $CDCl_3$): δ 0.69 (s, 2H), 0.92 (s, 2H), 1.39 (s, 3H), 1.41-1.48 (m, 1H), 1.50-1.64 (m, 2H), 2.14 (t, J = 10.4 Hz, 1H), 2.21 (td, J = 11.3, 3.4 Hz, 1H), 2.88 (d, J = 11.3 Hz, 1H), 3.03 (s, 2H), 3.03-3.07 (m, 1H), 3.13 (ddd, J = 14.6, 5.7, 2.6 Hz, 1H), 3.36 (td, J = 9.8, 4.2 Hz, 1H), 4.13 (ddd, J = 14.6, 7.6, 3.2 Hz, 1H), 4.88 (s, 2H), 5.07 (brt, J = 8.2 Hz, 1H), 5.52 (m, 1H), 5.70 (brs, 1H), 6.92 (brs, 1H), 7.30 (d, J = 8.0 Hz, 2H), 7.53 (d, J = 8.0 Hz, 2H), 7.88 (d, J = 1.5 Hz, 1H). | 511 | |
| A7-42 | $^1$H NMR (400 MHZ, $CDCl_3$): δ 0.70-0.76 (m, 2H), 0.78 0.86 (m, 2H), 1.38-1.46 (m, 2H), 2.14-2.21 (m, 2H), 2.82-2.92 (m, 2H), 3.04-3.21 (m, 4H), 3.31-3.37 (m, 1H), 4.11-4.18 (s, 1H), 4.84 (s, 2H), 5.01 (s, 1H), 5.34 (s, 1H), 5.65 (s, 1H), 6.49 (t, J = 73.4 Hz, 1H), 6.86 (d, J = 9.0 Hz, 2H), 7.23 (d, J = 8.4 Hz, 1H), 7.95 (s, 1H). | 513 | |
| A7-43 | $^1$H NMR (400 MHZ, $CDCl_3$): δ 0.69-0.75 (m, 2H), 0.76-0.81 (m, 2H), 1.42-2.45 (m, 2H), 1.59-1.63 (m, 1H), 2.07-2.27 (m, 2H), 2.87 (dt, J = 6.7, 3.3 Hz, 2H), 2.99-3.19 (m, 4H), 3.32-3.36 (m, 1H), 4.10-4.19 (m, 1H), 5.02 (s, 2H), 5.34 (s, 1H), 5.67 (s, 1H), 6.49 (t, J = 74.0 Hz, 1H), 6.92 (s, 1H), 7.06 (d, J = 8.6 Hz, 2H), 7.25 (d, J = 8.2 Hz, 2H), 7.96 (d, J = 1.3 Hz, 1H). | 495 | |
| A7-44 | $^1$H NMR (400 MHZ, DMSO-$d_6$): δ 0.62-0.79 (m, 4H), 1.44-1.61 (m, 2H), 2.02 (d, J = 13.9 Hz, 2H), 2.07-2.20 (m, 2H), 2.59 (d, J = 7.8 Hz, 2H), 2.77 (s, 2H), 2.90 (dq, J = 6.4, 3.2 Hz, 1H), 3.46 (d, J = 5.9 Hz, 2H), 4.84 (s, 2H), 6.40 (s, 1H), 7.06 (s, 2H), 7.15 (s, 1H), 7.29 (s, 1H), 7.43 (d, J = 8.0 Hz, 2H), 7.68 (d, J = 8.1 Hz, 2H), 7.84 (d, J = 1.6 Hz, 1H). | 524 | |
| A7-45 | $^1$H NMR (400 MHZ, $CDCl_3$): δ 0.70-0.76 (m, 2H), 0.81-0.88 (m, 2H), 1.47-1.69 (m, 4H), 2.48-2.61 (m, 4H), 2.92 (ddt, J = 10.5, 6.9, 3.7 Hz, 1H), 3.03 (s, 2H), 3.33 (d, J = 7.1 Hz, 2H), 3.41 (d, J = 6.9 Hz, 2H), 4.89 (s, 2H), 4.97-5.03 (m, 1H), 5.15 (t, J = 7.5 Hz, 1H), 5.37 (s, 1H), 7.04(s, 1H), 7.63 (d, J = 8.0 Hz, 1H), 7.77 (dd, J = 8.0, 1.6 Hz, 1H), 7.92 (d, J = 1.3 Hz, 1H), 8.65 (d, J = 1.7 Hz, 1H). | 512 | |
| A7-46 | $^1$H NMR (600 MHZ, $CDCl_3$): δ 0.60-0.80 (m, 4H), 1.31 (m, 2H), 1.62 (m, 1H), 1.79 (brd, J = 13.4 Hz, 2H), 2.16 (td, J = 11.8, 2.3 Hz, 2H), 2.20 (s, 3H), 2.28 (s, 3H), 2.80 (m, 1H), 2.90 (brd, J = 11.6 Hz, 2H), 2.98 (s, 2H), 3.38 (t, J = 6.5 Hz, 2H), 4.68 (s, 2H), 4.80 (m, 1H), 5.68 (s, 1H), 6.98 (s, 1H), 7.06 (s, 1H), 7.11 (s, 1H), 7.98 (d, J = 1.4 Hz, 1H). | 475 | |
| A7-47 | $^1$H NMR (400 MHZ, DMSO-$d_6$): δ 0.67 (m, 4H), 1.17-1.31 (m, 2H), 1.50-1.66 (m, 4H), 1.98 (d, J = 9.5 Hz, 3H), 2.17 (s, 3H), 2.20 (s, 3H), 2.78 (d, J = 11.3 Hz, 3H), 3.21 (t, J = 6.2 Hz, 2H), 4.66 (s, 2H), 6.87-6.97 (m, 2H), 7.02 (t, J = 6.4 Hz, 2H), 7.09 (d, J = 12.1 Hz, 2H), 7.81 (d, J = 1.7 Hz, 1H). | 441 | |
| A7-48 | $^1$H NMR (400 MHZ, DMSO-$d_6$): δ 0.60-0.80 (m, 4H), 0.92 (d, J = 6.6 Hz, 3H), 1.25 (d, J = 13.1 Hz, 2H), 1.46 (d, J = 4.4 Hz, 2H), 1.59 (d, J = 9.5 Hz, 1H), 1.86 (m, 1H), 2.39-2.48 (m, 2H), 2.82 (d, J = 16.1 Hz, 1H), 2.85-2.97 (m, 2H), 3.23 (t, J = 6.4 Hz, 2H), 4.83 (s, 2H), 7.06 (t, J = 5.7 Hz, 1H), 7.10 (d, J = 2.6 Hz, 1H), 7.15 (d, J = 2.9 Hz, 1H), 7.43 (d, J = 8.0 Hz, 2H), 7.67 (d, J = 8.1 Hz, 2H), 7.82 (d, J = 1.6 Hz, 1H). | 495 | |
| A7-49 | $^1$H NMR (400 MHZ, $CDCl_3$): δ 0.71-0.78 (m, 2H), 0.77-0.81 (m, 2H), 1.34-1.46 (m, 2H), 1.52-1.57 (m, 1H), 1.78 (tt, J = 12.6, 6.4 Hz, 1H), 2.28 (t, J = 10.2 Hz, 2H), 2.82-3.20 (m, 6H), 3.67-3.82 (m, 2H), 4.88 (s, 2H), 5.02 (s, 1H), 5.40 (s, 2H), 7.35 (d, J = 8.0 Hz, 2H), 7.49 (s, 1H), 7.55 (d, J = 8.1 Hz, 2H), 7.93 (d, J = 1.3 Hz, 1H). | 497 | |
| A7-50 | $^1$H NMR (400 MHZ, $CDCl_3$): δ 0.68-0.75 (m, 2H), 0.75-0.84 (m, 2H), 1.75 (td, J = 13.5, 3.9 Hz, 2H), 2.00 (d, J = 11.5 Hz, 2H), 2.52 (td, J = 12.2, 2.2 Hz, 2H), 2.89-2.94 (M, 3H), 3.08 (s, 2H), 3.79 (d, J = 6.8 Hz, 2H), 4.87 (s, 2H), 5.11 (d, J = 3.3 Hz, 1H), 5.41 (s, 1H), 6.88 (s, 1H), 7.35 (d, J = 8.0 Hz, 2H), 7.56 (d, J = 8.1 Hz, 2H), 7.96 (d, J = 1.4 Hz, 1H). | 506 | |
| A7-51 | $^1$H NMR (400 MHZ, $CDCl_3$) δ 0.72-0.76 (m, 2H), 0.78-0.82 (m, 2H), 1.61-1.66 (m, 4H), 2.53-2.57 (m, 4H), 2.85-2.95 (m, 1H), 3.03 (s, 2H), 3.34 (s, 2H), 3.41 (d, J = 7.0 Hz, | 511 | |

-continued

| Patent example | $^1$H-NMR | m/z $(M+H)^+$ | Chiral separation |
|---|---|---|---|
| | 2H), 4.87 (s, 2H), 4.95 (s, 1H), 5.30 (s, 1H), 5.36 (s, 1H), 7.04 (s, 1H), 7.35 (d, J = 8.0 Hz, 2H), 7.56 (d, J = 8.1 Hz, 2H), 7.93 (d, J = 1.2 Hz, 1H). | | |
| A7-52 | $^1$H NMR (400 MHZ, DMSO-$d_6$): δ 0.73 (d, J = 5.4 Hz, 4H), 1.42 (t, J = 5.4 Hz, 4H), 2.39 (ddt, J = 18.6, 12.7, 6.3 Hz, 4H), 2.82 (s, 2H), 3.06 (m, 1H), 3.25 (d, J = 5.2 Hz, 2H), 4.93 (bs, 3H), 6.88 (t, J = 4.7 Hz, 1H), 7.09 (d, J = 20.3 Hz, 2H), 7.45 (d, J = 8.3 Hz, 1H), 7.78 (d, J = 1.5 Hz, 1H), 8.13(dd, J = 8.3, 2.1 Hz, 1H), 8.89 (s, 1H). | 512 | |
| A7-53 | $^1$H NMR (600 MHZ, $CDCl_3$): δ 0.68 (m, 2H), 0.75 (m, 2H), 1.32 (m, 2H), 1.62 (m, 1H), 1.79 (brd, J = 10.2 Hz, 2H), 2.16 (td, J = 11.7, 2.3 Hz, 2H), 2.33 (s, 6H), 2.85 (m, 1H), 2.90 (brd, J = 11.6 Hz, 2H), 2.98 (s, 2H), 3.38 (t, J = 6.5 Hz, 2H), 4.69 (s, 2H), 4.80 (m, 1H), 5.61 (s, 1H), 6.94 (s, 2H), 7.06 (s, 1H), 8.00 (d, J = 1.5 Hz, 1H). | 475 | |
| A7-54 | $^1$H NMR (400 MHZ, $CDCl_3$): δ 0.73 (d, J = 3.7 Hz, 2H), 0.80 (q, J = 5.6 Hz, 2H), 1.43 (dd, J = 22.5, 6.8 Hz, 3H), 2.17 (t, J = 10.4 Hz, 1H), 2.20-2.29 (m, 1H), 2.85-2.96 (m, 2H), 3.05 (s, 2H), 3.07-3.19 (m, 2H), 3.34 (td, J = 10.1, 4.4 Hz, 1H), 4.15 (ddd, J = 14.5, 7.5, 3.2 Hz, 2H), 4.78-4.93 (m, 2H), 5.04 (s, 1H), 5.44 (s, 1H), 6.99 (d, J = 8.4 Hz, 1H), 7.32 (d, J = 8.6 Hz, 2H), 7.65 (d, J = 8.2 Hz, 2H), 7.94 (d, J = 1.3 Hz, 1H). | 595 | |
| A7-54-1 | $^1$H NMR (400 MHZ, DMSO-$d_6$): δ 8.64 (bs, 1H), 7.83 (d, J = 1.6 Hz, 1H), 7.62 (d, J = 8.2 Hz, 2H), 7.34 (d, J = 8.2 Hz, 2H), 7.15 (s, 1H), 7.08 (s, 1H), 6.93 (s, 1H), 5.76 (s, 1H), 5.00 (d, J = 4.8 Hz, 2H), 4.80 (s, 2H), 3.52 (dt, J = 13.3, 4.7 Hz, 2H), 2.95-2.78 (m, 4H), 2.74-2.64 (m, 1H), 2.00-1.88 (m, 1H), 1.84 (t, J = 10.1 Hz, 1H), 1.65 (d, J = 9.9 Hz, 1H), 1.40 (s, 1H), 1.35-1.19 (m, 1H), 0.78-0.61 (m, 4H). | 595 | Reprosil AMS ($MeOH:CO_2:NH_3$ = 30:70:0.2) |
| A7-54-2 | $^1$H NMR (400 MHZ, DMSO-$d_6$): δ 8.63 (s, 1H), 7.83 (d, J = 1.6 Hz, 1H), 7.62 (d, J = 8.2 Hz, 2H), 7.35 (d, J = 8.5 Hz, 2H), 7.15 (s, 1H), 7.08 (s, 1H), 6.93 (s, 1H), 5.00 (d, J = 5.2 Hz, 1H), 4.80 (s, 2H), 3.52 (dt, J = 13.1, 4.6 Hz, 1H), 2.95-2.79 (m, 4H), 2.75-2.64 (m, 2H), 2.00-1.88 (m, 1H), 1.84 (t, J = 10.1 Hz, 1H), 1.65 (d, J = 10.4 Hz, 1H), 1.40 (s, 1H), 1.34-1.19 (m, 2H), 0.78-0.62 (m, 4H). | 595 | Reprosil AMS ($MeOH:CO_2:NH_3$ = 30:70:0.2) |
| A7-55" | $^1$H NMR (400 MHZ, $CDCl_3$): δ 0.70-0.76 (m, 2H), 0.77-0.83 (m, 2H), 1.18-1.24 (m, 6H), 1.40-1.48 (m, 2H), 1.62-1.69 (m, 1H), 2.08 (t, J = 10.2 Hz, 1H), 2.14-2.24 (m, 1H), 2.80 (d, J = 11.1 Hz, 1H), 2.90 (dd, J = 6.9, 3.8 Hz, 1H), 3.03-3.18 (m, 2H), 3.27-3.33 (m, 1H), 4.12 (dd, J = 14.4, 7.7 Hz, 1H), 4.87 (s, 2H), 5.05 (s, 1H), 5.12 (s, 1H), 5.53 (d, J = 3.6 Hz, 1H), 7.00 (s, 1H), 7.36 (d, J = 8.0 Hz, 2H), 7.56 (d, J = 8.0 Hz, 2H), 7.96 (d, J = 1.3 Hz, 1H). | 525 | |
| A7-56 | $^1$H NMR (400 MHZ, DMSO-$d_6$): δ 0.61-0.78 (m, 4H), 1.26 (qd, J = 12.2, 4.0 Hz, 1H), 1.40 (s, 1H), 1.64 (d, J = 9.8 Hz, 1H), 1.84 (t, J = 10.1 Hz, 1H), 1.93 (t, J = 10.3 Hz, 1H), 2.64-2.74 (m, 1H), 2.84 (dd, J = 19.2, 3.5 Hz, 3H), 3.17 (d, J = 4.2 Hz, 1H), 3.40 (m, 2H), 3.53 (dt, J = 13.2, 4.6 Hz, 1H), 4.79 (s, 2H), 4.99 (s, 1H), 6.94 (t, J = 5.7 Hz, 1H), 7.08 (s, 1H), 7.16 (d, J = 9.7 Hz, 2H), 7.19-7.30 (m, 2H), 7.45 (t, J = 7.9 Hz, 1H), 7.84 (d, J = 1.6 Hz, 1H). | 513 | |
| A7-57" | $^1$H NMR (400 MHZ, $CDCl_3$): δ 1.18-1.27 (m, 9H), 1.40-1.46 (m, 2H), 1.62-1.67 (m, 1H), 2.07 (t, J = 10.2 Hz, 1H), 2.14-2.23 (m, 1H), 2.79 (d, J = 10.8 Hz, 1H), 3.01-3.17 (m, 2H), 3.26-3.34 (m, 1H), 3.46-3.64 (m, 2H), 4.12 (ddd, J = 14.5, 7.6, 2.5 Hz, 1H), 4.84 (d, J = 6.4 Hz, 2H), 4.96 (s, 1H), 5.16 (d, J = 4.5 Hz, 1H), 5.65 (s, 1H), 6.99 (d, J = 5.7 Hz, 1H), 7.37 (d, J = 8.0 Hz, 2H), 7.58 (d, J = 8.1 Hz, 2H), 7.94 (d, J = 1.6 Hz, 1H). | 513 | |
| A7-58 | $^1$H NMR (400 MHZ, $CDCl_3$): δ 7.96 (d, J = 1.2 Hz, 1H), 7.49 (d, J = 7.9 Hz, 1H), 6.96 (s, 1H), 6.91-6.85 (m, 2H), 5.38(s, 1H), 5.05 (s, 1H), 4.91-4.75 (m, 2H), 4.19-4.08 (m, 1H), 3.86 (s, 3H), 3.42-3.32 (m, 1H), 3.18-3.02 (m, 2H), 2.97-2.87 (m, 2H), 2.33-2.08 (m, 3H), 1.51-1.40 (m, 3H), 0.84-0.77 (m, ), 0.76-0.69 (m, 2H). | 527 | |
| A7-59 | $^1$H NMR (400 MHZ, $CDCl_3$): δ 7.91 (d, J = 3.4 Hz, 1H), 7.56 (d, J = 8.0 Hz, 2H), 7.36 (d, J = 8.0 Hz, 2H), 6.74 (brd, J = 8.5 Hz, 0.5H), 6.17 (m, 1.5H), 5.52 (dd, J = 34.4, 11.0 Hz, 0.5H), 5.05 (brs, 1H), 4.93-4.63 (m, 2H), 4.30 (d, J = 8.2 Hz, 0.5H), 4.11 (m, 1H), 3.65-3.27 (m, 3H), 3.24-2.70 (m, 2.5H), 2.65-2.23 (m, 1.5H), 1.90-1.39 (m, 4H), 1.20 (t, J = 6.9 Hz, 3H). | 510 | |

-continued

| Patent example | $^1$H-NMR | m/z $(M + H)^+$ | Chiral separation |
|---|---|---|---|
| | Analytical data | | |
| A7-60 | $^1$H NMR (400 MHz, $CDCl_3$): δ 1.41 (m, 1H), 1.47-1.66 (m, 2H), 2.13 (t, J = 10.4 Hz, 1H), 2.19 (td, J = 11.4, 3.1 Hz, 1H), 2.86 (m, 1H), 3.02 (s, 2H), 3.02-3.07 (m, 1H), 3.11 (ddd, J = 14.6, 5.7, 2.6 Hz, 1H), 3.32 (brt, J = 8.6 Hz, 1H), 4.13 (ddd, J = 14.6, 7.7, 3.2 Hz, 1H), 4.72-4.93 (m, 2H), 5.01 (brt, J = 8.1 Hz, 1H), 5.61 (m, 1H), 5.68 (m, 1H), 6.92 (m, 1H), 7.36 (d, J = 8.0 Hz, 2H), 7.58 (d, J = 8.0 Hz, 2H), 7.94 (d, J = 1.6 Hz, 1H). | 474 | |
| A7-61 | $^1$H NMR (400 MHZ, $CDCl_3$): δ 7.93 (d, J = 1.3 Hz, 1H), 7.21-7.12 (m, 2H), 7.05 (s, 1H), 6.93 (s, 1H), 5.68 (s, 1H), 5.35 (s, 1H), 5.01 (s, 1H), 4.83 (d, J = 10.4 Hz, 2H), 4.14 (ddd, J = 14.6, 7.7, 3.3 Hz, 1H), 3.87 (s, 3H), 3.40-3.30 (m, 1H), 3.17-3.09 (m, 1H), 3.05 (d, J = 14.3 Hz, 3H), 2.95 (dq, J = 6.3, 3.0 Hz, 1H), 2.88 (d, J = 9.1 Hz, 1H), 2.26-2.09 (m, 2H), 1.66-1.61 (m, 1H), 1.48-1.38 (m, 2H), 0.81-0.74 (m, 2H), 0.74-0.69 (m, 2H). | 527 | |
| A7-62 | $^1$H NMR (400 MHZ, $CDCl_3$): δ 8.58 (m, 2H), 7.93 (d, J = 1.6 Hz, 0.5H), 7.90 (d, J = 1.6 Hz, 0.5H), 7.58 (d, J = 8.1 Hz, 2H), 7.37 (d, J = 8.1 Hz, 2H), 7.21 (m, 2H), 6.93 (d, J = 4.1 Hz, 1H), 5.78 (d, J = 4.0 Hz, 2H), 4.98 (brs, 1H), 4.92-4.72 (m, 2H), 4.08 (ddt, J = 14.4, 7.1, 3.4 Hz, 1H), 3.98 (d, J = 5.6 Hz, 1H), 3.54 (m, 2H), 3.40 (m, 0.5H), 3.31 (m, 0.5H), 3.21 (m, 0.5H), 3.14-2.97 (m, 1.5H), 2.88 (m, 0.5H), 2.69(m, 0.5H), 2.20 (td, J = 11.1, 3.7 Hz, 0.5H), 2.12 (t, J = 10.3 Hz, 0.5H), 1.87-1.28 (m, 4H), 1.21 (t, J = 7.0 Hz, 3H). | 562 | |
| A7-63 | $^1$H NMR (400 MHZ, $CDCl_3$): δ 8.62 (m, 2H), 7.94 (dd, J = 11.6, 1.3 Hz, 1H), 7.56 (d, J = 8.1 Hz, 2H), 7.36 (d, J = 8.1 Hz, 2H), 7.22 (m, 2H), 6.91 (d, J = 4.1 Hz, 1H), 5.82-5.50 (m, 2H), 5.06 (s, 1H), 4.87 (d, J = 4.0 Hz, 2H), 4.09 (ddd, J = 14.8, 7.5, 3.7 Hz, 1H), 3.99 (d, J = 6.7 Hz, 1H), 3.41 (m, 0.5H), 3.32 (m, 0.5H), 3.22 (m, 0.5H), 3.16-2.99 (m, 2H), 2.91 (m, 1.5H), 2.70 (m, 0.5H), 2.21 (td, J = 11.1, 3.8 Hz, 0.5H), 2.13 (t, J = 10.3 Hz, 0.5H), 1.84-1.44 (m, 3.5H), 0.88-0.65 (m, 4H). | 574 | |
| A7-64 | $^1$H NMR (400 MHZ, $CDCl_3$): δ 0.71-0.78 (m, 2H), 0.77-0.81 (m, 2H), 1.34-1.46 (m, 2H), 1.52-1.57 (m, 1H), 1.78 (tt, J = 12.6, 6.4 Hz, 1H), 2.28 (t, J = 10.2 Hz, 2H), 2.82-3.20 (m, 6H), 3.67-3.82 (m, 2H), 4.88 (s, 2H), 5.02 (s, 1H), 5.40 (s, 2H), 7.35 (d, J = 8.0 Hz, 2H), 7.49 (s, 1H), 7.55 (d, J = 8.1 Hz, 2H), 7.93 (d, J = 1.3 Hz, 1H). | 511 | |
| A7-65 | $^1$H NMR (400 MHZ, $CDCl_3$): δ 0.68-0.76 (m, 2H), 0.77-0.84 (m, 2H), 1.37-1.57 (m, 3H), 2.18-2.38 (m, 1H), 2.51-2.74 (m, 1H), 2.82-288 (m, 2H), 2.99-3.29 (m, 5H), 3.36 (d, J = 4.3 Hz, 1H), 3.78-3.94 (m, 1H), 3.99 (ddd, J = 11.5, 7.4, 4.1 Hz, 1H), 4.13 (dd, J = 14.7, 7.6 Hz, 1H), 4.87 (s, 2H), 5.03 (s, 1H), 5.43 (s, 1H), 5.66 (s, 1H), 7.06 (d, J = 16.6 Hz, 1H), 7.36 (d, J = 7.9 Hz, 2H), 7.56 (d, J = 8.2 Hz, 2H), 7.95 (dd, J = 2.6, 1.4 Hz, 1H). | 527 | |
| A7-66-1 | $^1$H NMR (400 MHZ, $CDCl_3$): δ 1.21 (t, J = 7.0 Hz, 3H), 1.36-1.46 (m, 2H), 1.59-1.69 (m, 1H), 2.22 (t, J = 10.3 Hz, 1H), 2.65 (td, J = 11.4, 2.9 Hz, 1H), 2.87 (d, J = 11.3 Hz, 1H), 3.00-3.15 (m, 3H), 3.22 (dd, J = 7.9, 4.0 Hz, 3H), 3.54 (td, J = 14.5, 7.3 Hz, 2H), 3.80-3.87 (m, 2H), 3.95-4.03 (m, 1H), 4.13 (ddd, J = 14.7, 7.7, 3.2 Hz, 1H), 4.84 (d, J = 8.6 Hz, 2H), 4.93 (s, 1H), 5.42 (s, 1H), 5.77 (s, 1H), 7.04 (s, 1H), 7.37 (d, J = 8.0 Hz, 2H), 7.58 (d, J = 8.1 Hz, 2H), 7.93 (d, J = 1.7 Hz, 1H). | 515 | Lux C2 ($MeOH:CO_2:NH_3$ = 35:65:0.2) |
| A7-66-2 | $^1$H NMR (400 MHZ, $CDCl_3$): δ 1.21 (t, J = 7.0 Hz, 3H), 1.37-1.46 (m, 2H), 1.60-1.66 (m, 1H), 2.29-2.40 (m, 1H), 2.56 (t, J = 10.2 Hz, 1H), 2.85 (d, J = 10.1 Hz, 1H), 3.01-3.25 (m, 5H), 3.34 (d, J = 4.6 Hz, 1H), 3.46-3.63 (m, 2H), 3.89 (s, 1H), 3.94-4.04 (m, 1H), 4.14 (dd, J = 12.5, 7.7 Hz, 1H), 4.83 (d, J = 8.3 Hz, 2H), 4.92 (s, 1H), 5.41 (s, 1H), 5.75 (s, 1H), 7.08 (s, 1H), 7.37 (d, J = 8.0 Hz, 2H), 7.58 (d, J = 8.1 Hz, 2H), 7.93 (d, J = 1.6 Hz, 1H). | 515 | Lux C2 ($MeOH:CO_2:NH_3$ = 35:65:0.2) |
| A7-67" | $^1$H NMR (400 MHZ, $CDCl_3$): δ 1.21 (t, J = 7.0 Hz, 3H), 1.35-1.65 (m, 2H), 1.82-2.05 (m, 2H), 2.11-2.55 (m, 2H), 2.67-3.06 (m, 3H), 3.10 (dd, J = 14.5, 5.8 Hz, 1H), 3.25-3.47 (m, 2H), 3.48-3.74 (m, 3H), 3.84 (dt, J = 10.1, 5.0 Hz, 1H), 4.14 (dd, J = 14.7, 7.5 Hz, 1H), 4.75-4.98 (m, 3H), 5.46 (s, 1H), 5.85 (s, 1H), 7.37 (d, J = 8.1 Hz, 2H), 7.58 (d, J = 8.2 Hz, 2H), 7.93 (t, J = 1.5 Hz, 1H). | 529 | |
| A7-68 | $^1$H NMR (400 MHZ, $CDCl_3$): δ 0.68-0.74 (m, 2H), 0.75-0.83 (m, 2H), 1.50-1.69 (m, 2H), 1.70-1.76 (m, 2H), 2.63-2.77 (m, 3H), 2.90 (dq, J = 6.7, 3.0 Hz, 1H), 2.98 (t, J = 9.7 | 527 | |

-continued

| Patent example | Analytical data $^1$H-NMR | m/z $(M + H)^+$ | Chiral separation |
|---|---|---|---|
| | Hz, 1H), 3.24 (dd, J = 7.6, 3.9 Hz, 2H), 3.49 (dd, J = 6.0, 2.4 Hz, 2H), 3.89 (d, J = 8.0 Hz, 1H), 4.02 (dd, J = 11.2, 7.7 Hz, 1H), 4.80 (s, 1H), 4.86 (s, 2H), 5.13 (d, J = 2.9 Hz, 1H), 5.46 (s, 1H), 7.35 (d, J = 8.0 Hz, 2H), 7.56 (d, J = 8.1 Hz, 2H), 7.92 (d, J = 1.4 Hz, 1H). | | |
| A7-69" | $^1$H NMR (400 MHZ, $CDCl_3$): δ 0.70-0.76 (m, 2H), 0.78-0.86 (m, 2H), 1.41-1.65 (m, 3H), 2.07-2.29 (m, 2H), 2.91 (dq, J = 6.5, 3.0 Hz, 2H), 2.98-3.22 (m, 2H), 3.35 (s, 1H), 4.15 (ddd, J = 14.6, 7.5, 3.1 Hz, 1H), 4.87 (s, 2H), 5.04 (s, 1H), 5.33 (s, 1H), 5.62 (s, 1H), 6.92 (s, 1H), 7.36 (d, J = 8.0 Hz, 2H), 7.56 (d, J = 8.1 Hz, 2H), 7.95 (d, J = 1.2 Hz, 1H). | 499 | |
| A7-70 | $^1$H NMR (400 MHZ, $CDCl_3$): δ 0.69-0.75 (m, 2H), 0.77-0.82 (m, 2H), 1.49 (m, 4H), 2.57-2.68 (m, 2H), 2.77 (m, 2H), 2.90 (m, 1H), 3.23 (m, 1H), 3.32 (s, 2H), 3.41 (dd, J = 6.9, 3.7 Hz, 2H), 3.90 (dd, J = 11.3, 4.1 Hz, 1H), 4.01 (dd, J = 11.3, 7.1 Hz, 1H), 4.87 (s, 2H), 4.96 (m, 1H), 5.30 (s, 1H), 5.49 (d, J = 4.5 Hz, 1H), 7.23 (s, 1H), 7.35 (d, J = 8.0 Hz, 2H), 7.56 (d, J = 8.1 Hz, 2H), 7.93 (d, J = 1.3 Hz, 1H). | \|541 | |
| A7-71 | $^1$H NMR (400 MHZ, $CDCl_3$): δ 7.95 (m, 1H), 7.56 (d, J = 7.9 Hz, 2H), 7.36 (d, J = 7.9 Hz, 2H), 5.78 (m, 1H), 5.39 (m, 2H), 5.05 (m, 1H), 4.85 (m, 2H), 4.10 (m, 1H), 3.96 (m, 2H), 3.36 (m, 2H), 3.30-2.97 (m, 3H), 2.89 (m, 1.5H), 2.81 (m, 0.5H), 2.71 (d, J = 8.3 Hz, 0.5H), 2.64 (d, J = 8.3 Hz, 0.5H), 2.38 (m, 0.5H), 2.24 (m, 1.5H), 2.07 (m, 1H), 1.68 (m, 1H), 1.50-1.35 (m, 4H), 0.92-0.64 (m, 5H). | 581 | |
| A7-72 | ND | 497 | |
| A7-73 | $^1$H NMR (400 MHZ, $CDCl_3$): δ 1.21 (t, J = 7.0 Hz, 3H), 1.24-1.45 (m, 3H), 2.07-2.27 (m, 2H), 2.86 (d, J = 10.8 Hz, 1H), 2.96-3.15 (m, 5H), 3.32 (td, J = 9.9, 4.2 Hz, 1H), 3.56 (q, J = 7.2, 6.5 Hz, 2H), 3.99-4.08 (m, 2H), 4.16 (ddd, J = 14.5, 7.8, 3.0 Hz, 1H), 4.23-4.34 (m, 2H), 4.78 (d, J = 10.1 Hz, 2H), 4.90 (s, 1H), 5.32 (s, 1H), 6.94 (s, 1H), 7.26 (d, J = 8.3 Hz, 2H), 7.43 (d, J = 8.3 Hz, 2H), 7.68 (s, 1H), 7.79 (d, J = 0.6 Hz, 1H), 7.95 (d, J = 1.6 Hz, 1H). | 527 | |
| A7-74 | $^1$H NMR (400 MHZ, $CDCl_3$): δ 0.70-0.76 (m, 2H), 0.77-0.83 (m, 2H), 1.36-1.80 (m, 3H), 2.10-2.26 (m, 2H), 2.84-2.92 (m, 2H), 3.01-3.16 (m, 4H), 3.35 (td, J = 10.0, 4.6 Hz, 1H), 3.94 (s, 3H), 4.14 (ddd, J = 14.4, 7.5, 3.1 Hz, 1H), 4.79-4.84 (m, 2H), 5.01 (s, 1H), 5.37 (s, 1H), 5.75 (s, 1H), 6.94 (s, 1H), 7.26 (d, J = 8.3 Hz, 2H), 7.40 (d, J = 8.3 Hz, 2H), 7.58 (s, 1H), 7.73 (d, J = 0.7 Hz, 1H), 7.97 (d, J = 1.3 Hz, 1H). | 509 | |
| A7-75 | $^1$H NMR (400 MHZ, $CDCl_3$): δ 0.70-0.76 (m, 2H), 0.77-0.83 (m, 2H), 1.52-1.65 (m, 3H), 2.10-2.27 (m, 2H), 2.82-2.94 (m, 2H), 3.00-3.17 (m, 4H), 3.34 (dt, J = 10.1, 5.0 Hz, 1H), 3.94 (s, 3H), 4.14 (ddd, J = 14.6, 7.6, 3.2 Hz, 1H), 4.86 (s, 2H), 5.01 (s, 1H), 5.34 (s, 1H), 5.73 (s, 1H), 6.94 (s, 1H), 7.09-7.25 (m, 3H), 7.58 (s, 1H), 7.72 (d, J = 0.7 Hz, 1H), 7.97 (d, J = 1.3 Hz, 1H). | 527 | |
| A7-76 | $^1$H NMR (400 MHZ, $CDCl_3$): δ 0.71-0.77 (m, 2H), 0.77-0.84 (m, 2H), 1.40-1.52 (m, 3H), 2.10-2.24 (m, 2H), 2.91 (dd, J = 6.8, 3.5 Hz, 2H), 3.00-3.22 (m, 4H), 3.36 (br s, 1H), 4.09-4.21 (m, 1H), 4.88 (s, 2H), 5.02 (s, 1H), 5.37 (s, 1H), 5.69 (s, 1H), 6.47 (dd, J = 2.5, 1.8 Hz, 1H), 7.00 (s, 1H), 7.28-7.54 (m, 3H), 7.72 (d, J = 1.4 Hz, 1H), 7.89 (d, J = 2.1 Hz, 1H), 7.97 (d, J = 1.2 Hz, 1H). | 513 | |
| A7-77 | $^1$H NMR (400 MHz, $CDCl_3$): δ 1.20 (t, J = 7.0 Hz, 3H), 1.41 (m, 1H), 1.56 (m, 2H), 2.13 (t, J = 10.4 Hz, 1H), 2.20 (m, 1H), 2.71 (q, J = 7.1 Hz, 1H), 2.85 (d, J = 11.2 Hz, 1H), 3.01 (d, J = 0.9 Hz, 2H), 3.02-3.15 (m, 2H), 3.34 (td, J = 10.0, 4.4 Hz, 1H), 3.46-3.63 (m, 2H), 4.13 (m, 1H), 4.73-4.88 (m, 2H), 4.98 (brt, J = 8.1 Hz, 1H), 5.53 (brd, J = 3.8 Hz, 1H), 6.43-6.49 (m, 1H), 6.94 (m, 1H), 7.35 (d, J = 8.6 Hz, 2H), 7.64 (d, J = 8.6 Hz, 3H), 7.71 (d, J = 1.5 Hz, 1H), 7.94 (d, J = 1.5 Hz, 1H). | 483 | |
| A7-78 | $^1$H NMR (400 MHZ, $CDCl_3$): δ 1.21 (t, J = 7.0 Hz, 3H), 1.42 (m, 1H), 1.48-1.66 (m, 2H), 2.13 (t, J = 10.4 Hz, 1H), 2.20 (td, J = 11.4, 3.1 Hz, 1H), 2.86 (d, J = 11.3 Hz, 1H), 3.00-3.03 (s, 2H), 3.03-3.08 (m, 1H), 3.11 (ddd, J = 14.6, 5.7, 2.6 Hz, 1H), 3.34 (td, J = 9.8, 4.2 Hz, 1H), 3.53 (dtd, J = 16.4, 7.3, 1.9 Hz, 2H), 4.12 (ddd, J = 14.6, 7.7, 3.2 Hz, 1H), 4.72-4.93 (m, 2H), 5.00 (brt, J = 8.2 Hz, 1H), 5.55 (brs, 1H), 5.66 (brs, 1H), 6.91 (brs, 1H), 7.36 (d, J = 8.4 Hz, 2H), 7.61 (d, J = 8.4 Hz, 2H), 7.91 (d, J = 1.6 Hz, 1H). | 442 | |
| A7-79 | $^1$H NMR (400 MHZ, $CDCl_3$): δ 1.21 (t, J = 7.0 Hz, 3H), 2.04 -2.28 (m, 2H), 2.87 (d, J = 11.3 Hz, 2H), 2.98-3.17 (m, 4H), | 497 | |

-continued

| Analytical data | | | |
|---|---|---|---|
| Patent example | $^1$H-NMR | m/z $(M + H)^+$ | Chiral separation |
| | 3.34 (td, J = 9.9, 4.3 Hz, 2H), 3.48-3.62 (m, 3H), 3.97 (t, J = 13.3 Hz, 2H), 4.15 (ddd, J = 14.6, 7.6, 3.1 Hz, 2H), 4.74-4.88 (m, 2H), 4.93 (s, 1H), 5.36 (s, 2H), 6.94 (s, 1H), 7.34 (d, J = 8.3 Hz, 2H), 7.48 (d, J = 8.3 Hz, 2H), 7.93 (d, J = 1.6 Hz, 1H). | | |
| A7-80 | $^1$H NMR (400 MHZ, $CDCl_3$): δ 0.67 (m, 2H), 0.75 (m, 2H), 1.86 (dt, J = 13.9, 7.2 Hz, 2H), 2.42 (m, 4H), 2.75 (m, 2H), 2.85 (tt, J = 6.6, 3.3 Hz, 1H), 2.99 (s, 2H), 3.76 (d, J = 5.8 Hz, 2H), 4.83 (s, 2H), 5.50 (m, 1H), 5.97 (d, J = 4.7 Hz, 1H), 7.18 (d, J = 4.6 Hz, 1H), 7.33 (d, J = 8.0 Hz, 2H), 7.53 (d, J = 8.0 Hz, 2H), 7.96 (d, J = 1.3 Hz, 1H), 8.13 (s, 1H). | 548 | |
| A7-81 | $^1$H NMR (400 MHZ, $CDCl_3$): δ 0.69 (m, 2H), 0.76 (m, 2H), 1.88 (ddd, J = 13.3, 9.9, 3.7 Hz, 2H), 2.39 (m, 4H), 2.71-2.92 (m, 3H), 2.99 (s, 2H), 3.83 (d, J = 6.3 Hz, 2H), 4.84 (s, 2H), 5.13 (m, 1H), 5.46 (brs, 1H), 7.05 (brs, 1H), 7.34 (d, J = 8.0 Hz, 2H), 7.54 (d, J = 8.0 Hz, 2H), 7.94 (d, J = 1.4 Hz, 1H), 8.72 (s, 1H). | 549 | |
| A7-82 | $^1$H NMR (400 MHZ, $CDCl_3$): δ 0.68 (m, 2H), 0.76 (m, 2H), 1.90 (td, J = 10.6, 5.3 Hz, 3H), 2.39 (m, 4H), 2.86 (m, 3H), 3.01 (s, 2H), 3.87 (d, J = 6.6 Hz, 2H), 4.83 (s, 2H), 5.13 (brm, 1H), 5.54 (brs, 1H), 7.00 (brs, 1H), 7.33 (d, J = 8.0 Hz, 2H), 7.54 (d, J = 8.0 Hz, 2H), 7.87 (d, J = 1.4 Hz, 1H), 8.40 (s, 1H). | 549 | |
| A7-83 | $^1$H NMR (400 MHZ, $CDCl_3$): δ 0.62-0.70 (m, 2H), 0.72-0.79 (m, 2H), 1.84-1.96 (m, 2H), 2.48-2.61 (m, 4H), 2.76-2.87 (m, 3H), 3.01 (s, 2H), 3.86 (s, 3H), 3.90 (d, J = 6.2 Hz, 2H), 4.82 (s, 2H), 5.13 (s, 1H), 5.42 (s, 1H), 7.00 (s, 1H), 7.32 (d, J = 8.0 Hz, 2H), 7.55 (d, J = 8.1 Hz, 2H), 7.88 (d, J = 1.3 Hz, 1H), 7.99 (s, 1H). | 562 | |
| A7-84 | $^1$H NMR (400 MHZ, $CDCl_3$): δ 0.65-0.71 (m, 2H), 0.74-0.80 (m, 2H), 1.76-1.91 (m, 3H), 2.33 (dd, J = 13.3, 3.5 Hz, 2H), 2.42-2.55 (m, 2H), 2.74 (ddd, J = 10.8, 6.5, 3.5 Hz, 1H), 2.87 (tt, J = 6.8, 3.4 Hz, 1H), 3.00 (s, 2H), 3.76 (d, J = 6.1 Hz, 2H), 4.84 (s, 2H), 5.32-5.41 (m, 1H), 5.50 (d, J = 4.4 Hz, 1H), 7.01-7.05 (m, 2H), 7.34 (d, J = 8.0 Hz, 2H), 7.55 (d, J = 8.1 Hz, 2H), 7.96 (d, J = 1.3 Hz, 1H). | 547 | |
| A7-85 | $^1$H NMR (400 MHZ, $CDCl_3$): δ 0.64-0.71 (m, 2H), 0.72-0.80 (m, 2H), 1.94 (ddd, J = 13.6, 9.9, 3.7 Hz, 2H), 2.19 2.40 (m, 4H), 2.77 (dt, J = 10.1, 4.4 Hz, 2H), 2.86 (dq, J = 6.7, 3.0 Hz, 1H), 2.97 (s, 2H), 3.71 (d, J = 6.1 Hz, 2H), 4.84 (s, 2H), 4.97 (s, 1H), 5.39 (s, 1H), 7.05 (s, 1H), 7.34 (d, J = 8.0 Hz, 2H), 7.55 (d, J = 8.1 Hz, 2H), 7.60 (s, 1H), 7.96 (d, J = 1.4 Hz, 1H). | 548 | |
| A7-86 | $^1$H NMR (400 MHZ, $CDCl_3$): δ 0.70-0.76 (m, 2H), 0.77-0.83 (m, 2H), 1.38-1.68 (m, 3H), 2.07-2.28 (m, 2H), 2.82-2.94 (m, 2H), 3.01-3.18 (m, 4H), 3.34 (dt, J = 10.0, 5.0 Hz, 1H), 4.10-4.21 (m, 1H), 4.84 (d, J = 2.7 Hz, 2H), 5.02 (s, 1H), 5.36 (s, 1H), 5.70 (s, 1H), 6.46 (dd, J = 2.4, 1.8 Hz, 1H), 6.93 (s, 1H), 7.35 (d, J = 8.6 Hz, 2H), 7.63 (d, J = 8.6 Hz, 2H), 7.71 (d, J = 1.4 Hz, 1H), 7.87-7.93 (m, 1H), 7.98 (d, J = 1.3 Hz, 1H). | 495 | |
| A7-87 | $^1$H NMR (400 MHZ, $CDCl_3$): δ 0.68-0.75 (m, 2H), 0.77-0.81 (m, 2H), 1.35-1.46 (m, 4H), 1.88 (m, 4H), 2.90 (m, 1H), 3.07 (m, 4H), 3.74-3.96 (m, 3H), 4.86 (d, J = 2.3 Hz, 2H), 5.01 (s, 1H), 5.43 (s, 1H), 7.36 (d, J = 8.0 Hz, 2H), 7.56 (d, J = 8.1 Hz, 2H), 7.93 (d, J = 1.3 Hz, 1H). | 511 | |
| B4-1-1-1 | $^1$H NMR (400 MHZ, $CDCl_3$): δ 7.97 (s, 1H), 7.54 (d, J = 8.0 Hz, 2H), 7.34 (d, J = 7.6 Hz, 2H), 6.89 (br s, 1H), 5.67-5.63 (m, 2H), 4.84 (s, 2H), 3.62-3.56 (m, 1H), 3.37-3.30 (m, 1H), 3.23 (br s, 1H), 3.01 (dd, J = 28.8, 16.4 Hz, 2H), 2.90-2.85 (m, 2H), 2.69 (d, J = 10.8 Hz, 1H), 2.23-2.13 (m, 2H), 1.81-1.69 (m, 4H), 1.50-1.44 (m, 1H), 1.34 (s, 3H), 0.79-0.69 (m, 4H). | 511 | IF ($CO_2$:EtOH:DEA = 60:40:0.3) |
| B4-1-1-2 | $^1$H NMR (400 MHZ, $CDCl_3$): δ 7.97 (s, 1H), 7.54 (d, J = 7.6 Hz, 2H), 7.34 (d, J = 7.6 Hz, 2H), 6.87 (br s, 1H), 5.62 (br s, 2H), 4.85 (s, 2H), 3.62-3.56 (m, 1H), 3.37-3.30 (m, 1H), 3.16 (br s, 1H), 3.00 (dd, J = 28.4, 16.4 Hz, 2H), 2.98-2.86 (m, 2H), 2.68 (d, J = 10.4 Hz, 1H), 2.21-2.11 (m, 2H), 1.81-1.71 (m, 4H), 1.48-1.44 (m, 1H), 1.34 (s, 3H), 0.79-0.69 (m, 4H). | 511 | IF ($CO_2$:EtOH:DEA = 60:40:0.3) |
| B4-1-2-1 | $^1$H NMR (400 MHZ, $CDCl_3$): δ 7.97 (s, 1H), 7.54 (d, J = 8.4 Hz, 2H), 7.35 (d, J = 8.0 Hz, 2H), 6.73 (br s, 1H), 5.62-5.55 (m, 2H), 4.85 (s, 2H), 3.83-3.78 (m, 1H), 3.51-3.45 (m, 1H), 3.19 (s, 1H), 3.05 (s, 2H), 2.97-2.95 (m, 1H), 2.88-2.85 (m, 1H), 2.68-2.65 (m, 1H), 2.20-2.14 (m, 2H), 1.84-1.79 (m, 1H), 1.66-1.54 (m, 5H), 1.29-1.25 (m, 4H), 0.77-0.69 (m, 4H). | 511 | ID ($CO_2$:EtOH = 60:40) |

-continued

| Analytical data | | | |
|---|---|---|---|
| Patent example | $^1$H-NMR | m/z $(M + H)^+$ | Chiral separation |
| B4-1-2-2 | $^1$H NMR (400 MHZ, $CDCl_3$): δ7.97 (s, 1H), 7.54 (d, J = 8.4 Hz, 2H), 7.35 (d, J = 8.0 Hz, 2H), 6.75 (br s, 1H), 5.62-5.59 (m, 2H), 4.84 (s, 2H), 3.84-3.78 (m, 1H), 3.51-3.45 (m, 1H), 3.22 (s, 1H), 3.05 (s, 2H), 2.97-2.94 (m, 1H), 2.88-2.84 (m, 1H), 2.68-2.65 (m, 1H), 2.20-2.14 (m, 2H), 1.84-1.76 (m, 1H), 1.69-1.54 (m, 5H), 1.29-1.25 (m, 4H), 0.77-0.69 (m, 4H). | 511 | ID ($CO_2$:EtOH = 60:40) |
| B4-2-1-1 | $^1$H NMR (400 MHZ, $CD_3OD$): δ7.83 (d, J = 0.8 Hz, 1 H), 7.60 (d, J = 8.4 Hz, 1 H), 7.43 (d, J = 8.0 Hz, 1 H), 4.86 (s, 2 H), 3.66-3.57 (m, 2 H), 3.06-3.03 (m, 2 H), 2.93-2.90 (m, 1 H), 2.79-2.76 (m, 1 H), 2.69-2.66(m, 1 H), 2.41-2.32 (m, 2 H), 1.77-1.72 (m, 1 H) 1.38-1.29 (m, 2 H), 0.94 (s, 3 H), 0.80-0.79 (m, 2 H), 0.71-0.70 (m, 2 H). | 511 | IA (Hex:EtOH:DEA = 60:40:0.3) |
| B4-2-1-2 | $^1$H NMR (400 MHZ, $CD_3OD$): δ 7.85 (d, J = 0.8 Hz, 1 H), 7.61 (d, J = 8.4 Hz, 1 H), 7.44 (d, J = 8.0 Hz, 1 H), 4.89 (s, 2 H), 3.67-3.58 (m, 2 H), 3.07-3.03 (m, 2 H), 2.94-2.91 (m, 1 H), 2.79-2.75 (m, 1 H), 2.68-2.65(m, 1 H), 2.40-2.28 (m, 2 H), 1.77-1.76 (m, 1 H) 1.38-1.30 (m, 2 H), 095 (s, 3 H), 0.82-0.79 (m, 2 H), 0.74-0.72 (m, 2 H). | 511 | IA (Hex:EtOH:DEA = 60:40:0.3) |
| C4-1-1 | $^1$H NMR (400 MHZ, $CDCl_3$): δ 7.93 (s, 1H), 7.57 (d, J = 8 Hz, 2H), 7.36 (d, J = 7.6 Hz, 2H), 6.93 (s, 1H), 5.50-5.55 (m, 2H), 5.04-5.06 (m, 1H), 4.88 (s, 2H), 4.17 (d, J = 11.6 Hz, 1H), 3.99-4.05 (m, 1H), 3.67-3.69 (m, 1H), 3.36-3.47 (m, 2H), 3.02-3.13 (dd, J = 26.8, 16.4 Hz, 2H), 2.90-2.97 (m, 2H), 2.56-2.64 (m, 2H), 2.29-2.33 (m, 1H), 1.49-1.52 (m, 2H), 0.77-0.82 (m, 2H), 0.73-0.75 (m, 2H). | 527 | (Hex:EtOH:DEA = 60:40:0.3) |
| C4-1-2 | 1HNMR (400MHZ, $CDCl_3$): δ 7.97 (s, 1H), 7.61 (d, J = 8.4 Hz, 2H), 7.40 (d, J = 8 Hz, 2H), 6.97 (s, 1H), 5.52 (s, 1), 5.08 (s, 1H), 4.92 (s, 2H), 4.22 (d, J = 12.6 Hz, 1H), 4.03-4.07 (m, 1H), 3.70-3.73 (m, 1H), 3.39-3.51 (m, 2H), 3.06-3.17 (m, 2H), 2.94-3.01 (m, 2H), 2.59-2.68 (m, 2H), 2.32-2.36 (m, 1H), 1.49-1.57 (m, 2H), 0.81-0.92 (m, 2H), 0.71-0.81 (m, 2H). | 527 | IF (Hex:EtOH:DEA = 60:40:0.3) |
| C4-2-1 | $^1$H NMR (400 MHZ, $CDCl_3$): δ 7.92 (s, 1H), 7.79 (s, 1H), 7.72 (s, 2H), 6.94 (s, 1H), 5.53-5.56 (m, 2H), 5.20 (br, 1H), 5.00-5.04 (m, 1H), 4.84-4.93 (dd, J = 20.0, 16.8 Hz, 2H), 4.15-4.20 (m, 1H), 3.98-4.04 (dd, J = 14.8, 7.2 Hz, 1H), 3.67-3.70 (m, 1H), 3.53-3.58 (m, 2H), 3.36-3.48 (m, 2H), 3.02-3.13 (dd, J = 27.2, 16.4 Hz, 2H), 2.93-2.97 (m, 1H), 2.56-2.64 (dd, J = 20.4, 12.4 Hz, 2H), 2.28-2.35 (m, 1H), 1.49-1.52 (m, 2H), 1.23-1.27 (t, J = 6.8 Hz, 3H). | 583 | IG (Hex:EtOH = 60:40) |
| C4-2-2 | $^1$H NMR (400 MHZ, $CDCl_3$): δ 7.92 (d, J = 1.6 Hz, 1H), 7.79 (s, 1H), 7.72 (s, 2H), 6.94 (s, 1H), 5.53-5.57 (m, 2H), 5.21 (br, 1H), 5.00-5.05 (m, 1H), 4.83-4.93 (dd, J = 20.0, 16.4 Hz, 2H), 4.15-4.20 (m, 1H), 3.98-4.04 (dd, J = 14.8, 7.2 Hz, 1H), 3.67-3.70 (m, 1H), 3.53-3.58 (dd, J = 13.6, 6.8 Hz, 2H), 3.36-3.48 (m, 2H), 3.02-3.13 (dd, J = 26.8, 16.4 Hz, 2H), 2.93-2.97 (m, 1H), 2.56-2.64 (dd, J = 20.0, 10.4 Hz, 2H), 2.28-2.35 (m, 1H), 1.49-1.54 (m, 2H), 1.23-1.34 (t, J = 7.2 Hz, 3H). | 583 | IG (Hex:EtOH = 60:40) |
| D5-1-1-1 | $^1$H NMR (400 MHZ, $CDCl_3$): δ 7.91 (s, 1H), 7.58 (d, J = 8.0 Hz, 2H), 7.36 (d, J = 8.0 Hz, 2H), 6.98 (br s, 1H), 5.60 (br s, 1H), 5.33 (br s, 1H), 5.03 (br s, 1H), 4.84 (dd, J = 22.0, 16.0 Hz, 2H), 3.74 (q, J = 7.2 Hz, 1H), 3.60-3.49 (m, 3H), 3.35 (brs, 1H), 3.15 (dd, J = 14.8, 6.0 Hz, 1H), 3.05 (s, 2H), 2.80-2.76 (m, 1H), 2.60-2.54 (m, 2H), 2.45 (t, J = 10.8 Hz, 1H), 1.78-1.62 (m, 2H), 1.22 (t, J = 7.2 Hz, 3H). | 501 | G (Hex:EtOH = 50:50) |
| D5-1-1-2 | $^1$H NMR (400 MHZ, $CDCl_3$): δ 7.91 (s, 1H), 7.58 (d, J = 8.4 Hz, 2H), 7.36 (d, J = 8.4 Hz, 2H), 6.98 (br s, 1H), 5.48 (br s, 1H), 5.32 (br s, 1H), 5.01 (br s, 1H), 4.84 (dd, J = 22.0, 16.8 Hz, 2H), 3.74 (q, J = 7.2 Hz, 1H), 3.58-3.52 (m, 3H), 3.32 (brs, 1H), 3.15 (dd, J = 14.4, 6.0 Hz, 1H), 3.04 (s, 2H), 2.79-2.75 (m, 1H), 2.63-2.53 (m, 2H), 2.44 (t, J = 10.8 Hz, 1H), 1.77-1.64 (m, 2H), 1.22 (t, J = 7.2 Hz, 3H). | 501 | IG (Hex:EtOH = 50:50) |
| D5-1-2-1 | $^1$H NMR (400 MHZ, $CDCl_3$): δ 7.88 (s, 1H), 7.57 (d, J = 8.0 Hz, 2H), 7.35 (d, J = 8.0 Hz, 3H), 5.63 (br s, 1H), 5.26 (br s, 2H), 4.83 (s, 2H), 3.85-3.79 (m, 2H), 3.56-3.51 (m, 2H), 3.44 (s, 1H), 3.22 (dd, J = 14.8, 5.6 Hz, 1H), 3.11-3.00 (m, 2H), 2.82-2.70 (m, 3H), 2.61-2.56 (m, 1H), 2.01-1.96 (m, 1H), 1.48-1.44 (m, 1H), 1.20 (t, J = 7.2 Hz, 3H). | 501 | IE (Hex:EtOH = 50:50) |
| D5-1-2-2 | $^1$H NMR (400 MHZ, $CDCl_3$): δ 7.89 (s, 1H), 7.57 (d, J = 8.0 Hz, 2H), 7.35 (d, J = 8.0 Hz, 2H), 7.30 (br s, 1H), 5.54 (br s, 1H), 5.21 (br s, 2H), 4.83(s, 2H), 3.86-3.81(m, 1H), 3.73 (br s, 1H), 3.54 (q, J = 5.6 Hz, 2H), 3.43 (s, 1H), 3.20 (dd, J = 14.8 snd 6.0 Hz, 1H), 3.05 (dd, J = 26.4, 16.4 Hz, 2H), 2.82-2.79 (m, 1H), 2.74-2.69 (m, 2H), 2.61-2.54 (m, 1H), 2.02-1.94 (m, 1H), 1.47-1.44 (m, 1H), 1.20 (t, J = 6.8 Hz, 3H). | 501 | IE (Hex:EtOH = 50:50) |

-continued

| Analytical data | | | |
|---|---|---|---|
| Patent example | $^1$H-NMR | m/z $(M + H)^+$ | Chiral separation |
| D5-2-1-1 | $^1$H NMR (400 MHZ, $CDCl_3$): δ 7.92 (s, 1H), 7.56 (d, J = 8.4 Hz, 2H), 7.35 (d, J = 7.6 Hz, 2H), 6.93 (br s, 1H), 5.53 (br s, 1H), 5.23 (br s, 1H), 5.11 (br s, 1H), 4.87 (s, 2H), 3.73 (q, J = 7.2 Hz, 1H), 3.56-3.53 (m, 1H), 3.33 (s, 1H), 3.17 (dd, J = 14.4, 6.4 Hz, 1H), 3.04 (s, 2H), 2.92-2.90 (m, 1H), 2.79-2.75 (m, 1H), 2.60-2.55 (m, 2H), 2.44 (t, J = 10.4 Hz, 1H), 1.75-1.68 (m, 2H), 0.79-0.72 (m, 4H). | 513 | IG (Hex:EtOH:DEA = 60:40:0.3) |
| D5-2-1-2 | $^1$H NMR (400 MHZ, $CDCl_3$): δ 7.91 (s, 1H), 7.55 (d, J = 8.0 Hz, 2H), 7.34 (d, J = 8.0 Hz, 3H), 5.59 (br s, 1H), 5.33 (br s, 1H), 5.31 (br s, 1H), 4.86 (dd, J = 24.0, 16.0 Hz, 2H), 3.84 (q, J = 7.2 Hz, 1H), 3.78-3.75 (m, 1H), 3.44 (s, 1H), 3.23(dd, J = 14.8, 6.0 Hz, 1H), 3.05 (dd, J = 25.2, 16.8 Hz, 2H), 2.93-2.88 (m, 1H), 2.82-2.69 (m, 3H), 2.61-2.55 (m, 1H), 2.03-1.95 (m, 1H), 1.46 (d, J = 12.4 Hz, 1H), 0.80-0.71 (m, 4H). | 513 | IG (Hex:EtOH:DEA = 60:40:0.3) |
| D5-2-2-1 | $^1$H NMR (400 MHZ, $CDCl_3$): δ 7.92 (s, 1H), 7.56 (d, J = 8.0 Hz, 2H), 7.35 (d, J = 8.4 Hz, 2H), 6.92 (br s, 1H), 5.47 (br s, 1H), 5.22 (br s, 1H), 5.09 (br s, 1H), 4.87 (s, 2H), 3.74 (q, J = 7.2 Hz, 1H), 3.56-3.53 (m, 1H), 3.31 (s, 1H), 3.17 (dd, J = 14.8, 6.0 Hz, 1H), 3.04 (s, 2H), 2.92-2.90 (m, 1H), 2.79-2.75 (m, 1H), 2.61-2.55 (m, 2H), 2.44 (t, J = 10.4 Hz, 1H), 1.75-1.66 (m, 2H), 0.79-0.72 (m, 4H). | 513 | IG (Hex:EtOH:DEA = 70:30:0.3) |
| D5-2-2-2 | $^1$H NMR (400 MHZ, $CDCl_3$): δ 7.91 (s, 1H), 7.55 (d, J = 8.4 Hz, 2H), 7.34 (d, J = 8.4 Hz, 2H), 7.30 (br s, 1H), 5.55 (br s, 1H), 5.31 (br s, 1H), 5.18 (br s, 1H), 4.86 (dd, J = 24.0, 16.0 Hz, 2H), 3.84 (q, J = 6.8 Hz, 1H), 3.72 (br s, 1H), 3.44 (s, 1H), 3.23(dd, J = 14.8, 6.0 Hz, 1H), 3.05 (dd, J = 25.2, 16.4 Hz, 2H), 2.93-2.89(m, 1H), 2.82-2.70 (m, 3H), 2.61-2.55 (m, 1H), 2.03-1.95 (m, 1H), 1.46 (d, J = 13.2 Hz, 1H), 0.79-0.71 (m, 4H). | 513 | IG (Hex:EtOH:DEA = 70:30:0.3) |
| D5-3-1-1 | $^1$H NMR (400 MHZ, $CDCl_3$): δ 7.91 (s, 1H), 7.40-7.31 (m, 3H), 6.94 (br s, 1H), 5.59 (br s, 1H), 5.22 (br s, 1H), 5.04 (br s, 1H), 4.87 (s, 2H), 3.76-3.71 (m, 1H), 3.59-3.56 (m, 3H), 3.34 (s, 1H), 3.19-3.14 (m, 1H), 3.04 (s, 2H), 2.78-2.76 (m, 1H), 2.60-2.54 (m, 2H), 2.44 (t, J = 10.4 Hz, 1H), 1.72-1.66 (m, 2H), 1.24 (t, J = 6.8 Hz, 3H). | 519 | IF (Hex:EtOH:DEA = 60:40:0.3) |
| D5-3-1-2 | $^1$H NMR (400 MHZ, $CDCl_3$): δ 7.91 (s, 1H), 7.38-7.31 (m, 3H), 6.94 (br s, 1H), 5.56 (br s, 1H), 5.22 (br s, 1H), 5.03 (br s, 1H), 4.87 (s, 2H), 3.76-3.71 (m, 1H), 3.61-3.56 (m, 3H), 3.34 (s, 1H), 3.19-3.14 (m, 1H), 3.04 (s, 2H), 2.78-2.76 (m, 1H), 2.60-2.57 (m, 2H), 2.44 (t, J = 10.4 Hz, 1H), 1.76-1.69 (m, 2H), 1.24 (t, J = 6.4 Hz, 3H). | 519 | IF (Hex:EtOH:DEA = 60:40:0.3) |
| D5-3-2-1 | $^1$H NMR (400 MHZ, $CDCl_3$): δ 7.88 (s, 1H), 7.38-7.31 (m, 4H), 5.60 (br s, 1H), 5.26 (br s, 1H), 5.15 (br s, 1H), 4.86 (s, 2H), 3.86-3.80 (m, 2H), 3.57-3.55 (m, 2H), 3.44 (s, 1H), 3.25-3.20 (m, 1H), 3.11-3.00 (m, 2H), 2.82-2.70 (m, 3H), 2.62-2.56 (m, 1H), 2.02-1.95 (m, 1H), 1.48-1.45 (m, 1H), 1.23 (t, J = 6.8 Hz, 3H). | 519 | IF (Hex:EtOH:DEA = 70:30:0.3) |
| D5-3-2-2 | $^1$H NMR (400 MHZ, $CDCl_3$): δ 7.88 (s, 1H), 7.36-7.31 (m, 4H), 5.67 (br s, 1H), 5.30-5.23 (m, 2H), 4.86 (s, 2H), 3.96 (br s, 1H), 3.84-3.79 (m, 1H), 3.57-3.55 (m, 2H), 3.44 (s, 1H), 3.26-3.21 (m, 1H), 3.12-3.01 (m, 2H), 2.83-2.71 (m, 3H), 2.63-2.57 (m, 1H), 2.02-1.95 (m, 1H), 1.48-1.45 (m, 1H), 1.23 (t, J = 6.8 Hz, 3H). | 519 | IF (Hex:EtOH:DEA = 70:30:0.3) |
| D5-4" | $^1$H NMR (400 MHZ, DMSO-$d_6$): δ 8.65 (s, 1H), 7.83 (s, 1H), 7.64 (d, J = 8.0 Hz, 2H), 7.39 (d, J = 8.3 Hz, 2H), 7.17 (s, 1H), 7.05 (s, 1H), 6.74 (s, 1H), 4.89 (d, J = 6.0 Hz, 1H), 4.79 (s, 2H), 4.21 (s, 1H), 3.58-3.40 (m, 4H), 2.81 (bs, 2H), 2.50 (m, 2H), 2.44 (d, J = 9.8 Hz, 1H), 2.32-2.14 (m, 2H), 1.62-1.50 (m, 1H), 1.45 (d, J = 13.6 Hz, 1H), 1.14 (t, J = 6.9 Hz, 3H). | 599 | |
| D5-5-1 | $^1$H NMR (400 MHZ, $CDCl_3$): δ 7.95 (d, J = 1.2 Hz, 1H), 7.72 (d, J = 0.7 Hz, 1H), 7.58 (s, 1H), 7.25-7.10 (m, 3H), 6.93 (b.s, 1H), 5.35 (s, 1H), 5.24 (s, 1H), 5.05 (d, J = 3.2 Hz, 1H), 4.86 (s, 2H), 3.94 (s, 3H), 3.74 (dd, J = 14.6, 7.2 Hz, 1H), 3.55 (b.s, 1H), 3.31 (b.s, 1H), 3.17 (dd, J = 14.4, 5.8 Hz, 1H), 3.05 (s, 2H), 2.91 (dq, J = 6.4, 3.0 Hz, 1H), 2.78 (b.s, 1H), 2.67-2.52 (m, 2H), 2.45 (t, J = 10.6 Hz, 1H), 1.77-1.65 (m, 2H), 0.86-0.78 (m, 2H), 0.77-0.72 (m, 2H). | 543 | Lux A2 (EtOH:$CO_2$ = 45:55) |
| D5-5-2 | $^1$H NMR (400 MHZ, DMSO-$d_6$): δ 8.15 (s, 1H), 7.87 (d, J = 0.7 Hz, 1H), 7.86 (d, J = 1.5 Hz, 1H), 7.43-7.29 (m, 2H), 7.26-7.14 (m, 2H), 7.05 (s, 1H), 6.82 (s, 1H), 4.89 (s, 1H), 4.77 (s, 2H), 3.85 (s, 3H), 3.55-3.40 (m, 3H), 3.40-3.26 (m, 2H), 2.60-2.40 (m, 3H), 2.32-2.16 (m, 2H), 1.64-1.42 (m, 2H), 0.80-0.63 (m, 4H). | 543 | Lux A2 (EtOH:$CO_2$ = 45:55) |

-continued

| Analytical data | | | |
|---|---|---|---|
| Patent example | $^1$H-NMR | m/z $(M + H)^+$ | Chiral separation |
| D5-6" | $^1$H NMR (400 MHZ, DMSO-$d_6$): δ 8.63 (s, 1H), 7.84 (d, J = 1.5 Hz, 1H), 7.62 (d, J = 8.2 Hz, 2H), 7.36 (d, J = 8.5 Hz, 2H), 7.17 (s, 1H), 7.05 (s, 1H), 6.84 (s, 1H), 4.88 (d, J = 6.1 Hz, 1H), 4.81 (s, 2H), 3.47 (ddt, J = 16.8, 10.7, 6.0 Hz, 2H), 3.38-3.27 (m, 1H), 2.96-2.87 (m, 1H), 2.81 (d, J = 1.5 Hz, 2H), 2.61-2.50 (m, 2H), 2.31-2.15 (m, 2H), 1.62-1.41 (m, 3H), 0.78-0.65 (m, 4H). | 611 | |
| D5-7" | $^1$H NMR (400 MHZ, $CDCl_3$): δ 8.51 (dt, J = 4.1, 2.2 Hz, 2H), 7.85 (dd, J = 8.7, 1.5 Hz, 1H), 7.55 (d, J = 8.3 Hz, 2H), 7.34 (d, J = 8.1 Hz, 2H), 7.21 (d, J = 6.0 Hz, 2H), 7.05 (brs, 1H), 6.51 (brs, 1H), 5.34 (brd, J = 6.7 Hz, 1H), 4.81 (s, 2H), 3.92 (d, J = 7.0 Hz, 1H), 3.73-3.45 (m, 4.5H), 3.41 (s, 2H), 3.13 (dd, J = 14.5, 5.8 Hz, 1H), 2.83 (m, 0.5H), 2.70 (d, J = 10.6 Hz, 0.5H), 2.53-2.35 (m, 2H), 2.15 (dt, J = 10.6, 5.2 Hz, 0.5H), 2.02 (t, J = 10.5 Hz, 0.5H), 1.82-1.49 (m, 2H), 1.19 (t, J = 7.0 Hz, 3H). | 578 | |
| D5-7-1 | $^1$H NMR (400 MHZ, $CDCl_3$): δ 8.51 (dt, J = 4.1, 2.2 Hz, 2H), 7.85 (dd, J = 8.7, 1.5 Hz, 1H), 7.55 (d, J = 8.3 Hz, 2H), 7.34 (d, J = 8.1 Hz, 2H), 7.21 (d, J = 6.0 Hz, 2H), 7.05 (brs, 1H), 6.51 (brs, 1H), 5.34 (brd, J = 6.7 Hz, 1H), 4.81 (s, 2H), 3.92 (d, J = 7.0 Hz, 1H), 3.73-3.45 (m, 4.5H), 3.41 (s, 2H), 3.13 (dd, J = 14.5, 5.8 Hz, 1H), 2.83 (m, 0.5H), 2.70 (d, J = 10.6 Hz, 0.5H), 2.53-2.35 (m, 2H), 2.15 (dt, J = 10.6, 5.2 Hz, 0.5H), 2.02 (t, J = 10.5 Hz, 0.5H), 1.82-1.49 (m, 2H), 1.19 (t, J = 7.0 Hz, 3H). | 578 | IC ($CO_2$:EtOH = 60:40) |
| D5-7-2 | $^1$H NMR (400 MHZ, $CDCl_3$): δ 8.51 (dt, J = 4.1, 2.2 Hz, 2H), 7.85 (dd, J = 8.7, 1.5 Hz, 1H), 7.55 (d, J = 8.3 Hz, 2H), 7.34 (d, J = 8.1 Hz, 2H), 7.21 (d, J = 6.0 Hz, 2H), 7.05 (brs, 1H), 6.51 (brs, 1H), 5.34 (brd, J = 6.7 Hz, 1H), 4.81 (s, 2H), 3.92 (d, J = 7.0 Hz, 1H), 3.73-3.45 (m, 4.5H), 3.41 (s, 2H), 3.13 (dd, J = 14.5, 5.8 Hz, 1H), 2.83 (m, 0.5H), 2.70 (d, J = 10.6 Hz, 0.5H), 2.53-2.35 (m, 2H), 2.15 (dt, J = 10.6, 5.2 Hz, 0.5H), 2.02 (t, J = 10.5 Hz, 0.5H), 1.82-1.49 (m, 2H), 1.19 (t, J = 7.0 Hz, 3H). | 578 | IC ($CO_2$:EtOH = 60:40) |
| D5-8" | $^1$H NMR (400 MHZ, $CDCl_3$): δ 8.52 (dt, J = 4.0, 2.3 Hz, 2H), 7.88 (dd, J = 8.7, 1.0 Hz, 1H), 7.54 (d, J = 8.2 Hz, 2H), 7.33 (d, J = 8.0 Hz, 2H), 7.22 (d, J = 6.0 Hz, 2H), 7.05(m, 1H), 6.49 (brs, 1H), 5.43 (m, 1H), 4.84 (d, J = 5.2 Hz, 2H), 3.92 (d, J = 7.5 Hz, 1H), 3.63 (m, 2H), 3.50 (m, 0.5H), 3.42 (s, 2H), 3.17 (dd, J = 14.4, 5.6 Hz, 1H), 2.96-2.77 (m, 1.5H), 2.71 (m, 1H), 2.51 (m, 1H), 2.39 (m, 1H), 2.17 (t, J = 9.0 Hz, 0.5H), 2.03 (t, J = 10.4 Hz, 0.5H), 1.81-1.51 (m, 2H), 0.88-0.63 (m, 4H). | 590 | |
| D5-9" | $^1$H NMR (400 MHZ, $CDCl_3$): δ 7.95 (d, J = 1.1 Hz, 1H), 7.89 (d, J = 2.4 Hz, 1H), 7.72 (d, J = 1.6 Hz, 1H), 7.47 (dd, J = 11.0, 2.0 Hz, 1H), 7.39 (dd, J = 8.3, 2.1 Hz, 1H), 7.32 (t, J = 8.1 Hz, 1H), 6.93 (s, 1H), 6.50-6.44 (m, 1H), 5.40 (s, 1H), 5.06 (s, 1H), 4.89 (s, 2H), 3.75 (dd, J = 14.6, 7.2 Hz, 1H), 3.55 (dd, J = 10.5, 4.9 Hz, 1H), 3.17 (dd, J = 14.5, 6.1 Hz, 1H), 3.05 (s, 2H), 2.97-2.86 (m, 1H), 2.78 (dd, J = 10.2, 4.5 Hz, 1H), 2.57 (td, J = 11.4, 3.4 Hz, 2H), 2.45 (t, J = 10.6 Hz, 1H), 2.26-2.18 (m, 1H), 1.77-1.68 (m, 2H), 0.84-0.79 (m, 2H), 0.77-0.70 (m, 2H). | 529 | |
| D5-10" | $^1$H NMR (400 MHZ, $CDCl_3$): δ 7.94 (s, 1H), 7.22 (d, J = 7.5 Hz, 2H), 7.10-7.03 (m, 3H), 5.35 (s, 1H), 5.03 (s, 1H), 4.88 (s, 1H), 3.74 (dd, J = 14.6, 7.2 Hz, 1H), 3.59-3.52 (m, 1H), 3.16 (dd, J = 14.4, 6.0 Hz, 1H), 3.05 (s, 2H), 2.89 (d, J = 7.1 Hz, 1H), 2.78 (s, 1H), 2.68-2.53 (m, 2H), 2.48-2.41 (m, 1H), 1.79-1.64 (m, 2H), 0.82-0.77 (m, 2H), 0.76-0.71 (m, 2H). | 463 | |
| E6-1 | $^1$H NMR (400 MHZ, $CD_3OD$): δ7.85 ( d, J = 1.2 Hz, 1H), 7.59 (d, J = 8.0 Hz, 1H), 7.43 (d, J = 8.4 Hz, 1H), 4.87 (s, 2H), 3.49 (s, 2H), 3.02 (s, 2H), 2.92-2.88 ( m, 1H), 2.65-2.51 (m, 4H), 1.77-1.70 (m, 2H), 1.56-1.53 (m, 2H), 0.81-0.77 (m, 2H), 0.70-0.67 (m, 2H). | 496 | |
| F2-1 | ND | 417 | |
| F2-2 | ND | 471 | |
| F2-3 | ND | 471 | |
| F2-4 | ND | 485 | |
| F2-5 | ND | 431 | |
| F2-6 | ND | 451 | |
| F2-7 | ND | 487 | |
| F2-8 | ND | 428 | |
| F2-9 | ND | 513 | |
| F2-10 | ND | 511 | |

-continued

| Analytical data | | | |
|---|---|---|---|
| Patent example | $^1$H-NMR | m/z $(M + H)^+$ | Chiral separation |
| F2-11 | ND | 456 | |
| F2-12 | ND | 455 | |
| F2-13 | ND | 469 | |
| F2-14 | ND | 499 | |
| F2-15 | ND | 465 | |
| F2-16 | ND | 515 | |
| F2-17 | ND | 499 | |
| F2-18 | ND | 428 | |
| F2-19 | ND | 434 | |
| F2-20 | ND | 469 | |
| F2-21 | ND | 471 | |
| F2-22 | ND | 487 | |
| F2-23 | ND | 465 | |

Biological Evaluation

The activity of the compounds was evaluated using a RORγ Reporter assay (also referred to as Gal4 assay). The Gal4 and the Th17 assays (another suitable assay) are both cell-based assays monitoring functional activity of the compound assayed.

The activity of the compounds disclosed was also evaluated using the IL-17A secretion in activated PBMCs assay.

Compounds disclosed herein have also been evaluated in a mouse in vivo pharmacodynamic model (anti-CD3-induced plasma IL-17A).

In addition, the compounds disclosed herein may be evaluated in various mouse disease models, e.g. Collagen-induced Arthritis (CIA) model (an animal model for rheumatoid arthritis) and Experimental Autoimmune Encephalomyelitis (EAE) model (an animal model for multiple sclerosis).

RORγ Reporter Assay (Gal4)

The HEK293 cell line is co-transfected transiently with two plasmids, one with the RORγ ligand-binding domain fused to galactose-responsive transcription factor (Gal4), and the other with the luciferase reporter gene and Gal binding sites (UAS). This construction allows to determine the RORγ activity in a cellular system through the measurement of luminescence.

A suspension of RORγ reporter cells was dispensed into plates and cultured 2 h at 37° C. and 5% CO2. Media formulation consisted in DMEM/F-12 medium (Gibco) supplemented with 10% heat inactivated FBS (Sigma-Aldrich), non-essential aminoacids (Sigma-Aldrich), 2 mM Glutamax (Gibco) and 100 U/mL penicillin (Sigma-Aldrich). Dose-response curves with compounds were prepared in 100% DMSO and further diluted 100-fold in culture medium. Compound solutions were added to the plate containing cells (final DMSO concentration of 0.1%) and incubated for 24 h at 37° C. and 5% CO2. Luciferase detection reagent was added to each well, and relative light units (RLUs) were quantified from each assay well using a plate reading luminometer.

Values of average RLU±S.D. were computed for all treatment sets, followed by the calculations of percent-reduction of RORγ activity in response to respective test compound. The following formula was used: activity=100*[1−[x test compound/average vehicle] where the theoretical minimum reduction (0% reduction). For all experiments, the activity values were plotted versus compound concentrations in one single plot and adjusted to a four-parameter logistic curve to obtain the absolute $EC_{50}$ value along with the 95% confidence interval. These calculations were performed in excel-fit software using X-204 model curve.

The results of RORγ Reporter (Gal4) Assay are shown in the Table 2 below.

TABLE 2

| RORγ Reporter Assay (Gal4) | |
|---|---|
| Patent example | $EC_{50}$ (nM) |
| A7-01 | 0.9 |
| A7-01-1 | 1.3 |
| A7-01-2 | 1.5 |
| A7-02 | 76 |
| A7-03-1 | 44 |
| A7-03-2 | ND |
| A7-04-1 | 28 |
| A7-04-2 | 89 |
| A7-05-1 | 4 |
| A7-05-2 | 14 |
| A7-06-1 | 44 |
| A7-06-2 | 4 |
| A7-07-1 | 49 |
| A7-07-2 | 93 |
| A7-07-3 | 21 |
| A7-07-4 | 170 |
| A7-08 | 15 |
| A7-09 | 44 |
| A7-10 | 3.3 |
| A7-11 | 72 |
| A7-12 | 150 |
| A7-13 | 230 |
| A7-14 | 15 |
| A7-14-1 | 8.3 |
| A7-14-2 | 21 |
| A7-15 | 160 |
| A7-15-1 | 51 |
| A7-15-2 | 310 |
| A7-16 | 19 |
| A7-16-1 | 25 |
| A7-16-2 | 22 |
| A7-17 | ND |
| A7-17-1 | 40 |
| A7-17-2 | 95 |
| A7-18 | 130 |
| A7-18-1 | 140 |
| A7-18-2 | 82 |
| A7-19 | 42 |
| A7-19-1 | 40 |
| A7-19-2 | 27 |
| A7-20 | 26 |
| A7-20-1 | 35 |
| A7-20-2 | 32 |
| A7-21 | 12 |
| A7-21-1 | 9.3 |
| A7-21-2 | 13 |

TABLE 2-continued

RORγ Reporter Assay (Gal4)

| Patent example | $EC_{50}$ (nM) |
|---|---|
| A7-22 | 4 |
| A7-22-1 | 4.9 |
| A7-22-2 | 3.4 |
| A7-23 | 81 |
| A7-23-1 | 81 |
| A7-23-2 | 100 |
| A7-24 | 120 |
| A7-24-1 | ND |
| A7-24-2 | ND |
| A7-25 | 330 |
| A7-25-1 | 630 |
| A7-25-2 | 320 |
| A7-26 | 17 |
| A7-26-1 | 27 |
| A7-26-2 | 8.5 |
| A7-27 | 540 |
| A7-27-1 | ND |
| A7-27-2 | ND |
| A7-28 | 20.5 |
| A7-28-1 | 42 |
| A7-28-2 | 75 |
| A7-29 | ND |
| A7-29-1 | 35 |
| A7-29-2 | 70 |
| A7-30 | >1000 |
| A7-31 | 29 |
| A7-32 | 34 |
| A7-33 | ND |
| A7-34 | 90 |
| A7-35 | 310 |
| A7-36 | 860 |
| A7-37 | 670 |
| A7-38 | 590 |
| A7-39 | 37 |
| A7-40 | 5.5 |
| A7-41 | 27 |
| A7-42 | 18 |
| A7-43 | 11 |
| A7-44 | 24 |
| A7-45 | 46 |
| A7-46 | >1000 |
| A7-47 | >1000 |
| A7-48 | 17 |
| A7-49 | 168 |
| A7-50 | 8.1 |
| A7-51 | 2.4 |
| A7-52 | 42 |
| A7-53 | >1000 |
| A7-54 | 0.6 |
| A7-54-1 | 3.8 |
| A7-54-2 | 2.5 |
| A7-55 | 4.7 |
| A7-56 | 5.3 |
| A7-57 | 7.9 |
| A7-58 | 13 |
| A7-59 | 14 |
| A7-60 | 19 |
| A7-61 | >1000 |
| A7-62 | 1.8 |
| A7-63 | 3.4 |
| A7-64 | 73 |
| A7-65 | 5.8 |
| A7-66-1 | 26 |
| A7-66-2 | 88 |
| A7-67 | 43 |
| A7-68 | 20 |
| A7-69 | 2.7 |
| A7-70 | 8.8 |
| A7-71 | 3.9 |
| A7-72 | 52 |
| A7-73 | 99 |
| A7-74 | 12 |
| A7-75 | 13 |
| A7-76 | 6.6 |
| A7-77 | 73 |
| A7-78 | 65 |
| A7-79 | 164 |
| A7-80 | 53 |
| A7-81 | 5.3 |
| A7-82 | 8.1 |
| A7-83 | >1000 |
| A7-84 | 301 |
| A7-85 | 7.9 |
| A7-86 | 9.4 |
| A7-87 | 181 |
| B4-1-1-1 | 55 |
| B4-1-1-2 | 5.1 |
| B4-1-2-1 | 42 |
| B4-1-2-2 | 170 |
| B4-2-1-1 | 7.5 |
| B4-2-1-2 | 8.6 |
| C4-1-1 | 5.3 |
| C4-1-2 | 4.3 |
| C4-2-1 | ND |
| C4-2-2 | ND |
| D5-01-1-1 | 0.9 |
| D5-01-1-2 | 9.6 |
| D5-01-2-1 | ND |
| D5-01-2-2 | ND |
| D5-02-1-1 | 1.2 |
| D5-02-1-2 | 61 |
| D5-02-2-1 | 1.9 |
| D5-02-2-2 | 180 |
| D5-03-1-1 | 1.6 |
| D5-03-1-2 | 9.3 |
| D5-03-2-1 | ND |
| D5-03-2-2 | ND |
| D5-04 | 5.5 |
| D5-05-1 | 5.8 |
| D5-05-2 | 29 |
| D5-06 | 16 |
| D5-07 | 4.5 |
| D5-07-1 | 2.9 |
| D5-07-2 | 71 |
| D5-08 | 6.1 |
| D5-09 | 18 |
| D5-10 | >1000 |
| E6-1 | 150 |
| F2-01 | ND |
| F2-02 | ND |
| F2-03 | 99 |
| F2-04 | ND |
| F2-05 | ND |
| F2-06 | 350 |
| F2-07 | 30 |
| F2-08 | 700 |
| F2-09 | ND |
| F2-10 | ND |
| F2-11 | ND |
| F2-12 | ND |
| F2-13 | ND |
| F2-14 | ND |
| F2-15 | ND |
| F2-16 | ND |
| F2-17 | ND |
| F2-18 | ND |
| F2-19 | ND |
| F2-20 | ND |
| F2-21 | ND |
| F2-22 | ND |
| F2-23 | ND |

As can be seen from the Table 2 above, the fluoropyrimidine derivatives of the present disclosure were found to show beneficial activity across the RORγ Reporter (Gal4) Assay.

According to an embodiment, compounds having $EC_{50}$<1000 nM values in the RORγ Reporter Assay (Gal4) are disclosed herein.

According to another preferred embodiment compounds having $EC_{50}$<500 nM values in the RORγ Reporter Assay (Gal4) are disclosed herein.

According to another more preferred embodiment compounds having $EC_{50}$<100 nM values in the RORγ Reporter Assay (Gal4) are disclosed herein.

Th17 Assay (Another Suitable Assay)

Human peripheral blood mononuclear cells (PBMCs) were isolated from buffy coats of healthy human volunteers using the Ficoll paque PLUS kit (GE Healthcare, cat no 17-1440-02), as instructed by the manufacturer. Naive CD4+ T cells were isolated with Naive CD4+ T cell kit, human (Milteny Biotec, cat no 130-094-131). The following modifications were made to the manufacturer's protocol: 1) Incubation with Biotin-Antibody Cocktail and Anti-Biotin MicroBeads was prolonged to 30 minutes, and 2) Cells were washed with 40 mL of Miltenyi buffer. Differentiation of Th17 cells in anti-CD3 (BD Pharmingen, 5 μg/ml) coated 96-well plates (400,000 cells/well, 160 μl RPMI 1640+10% Fetal Bovine Serum) containing 5 μg/ml anti-CD28 (BD Pharmingen), 10 ng/ml IL-2 (R&D Systems), 2.5 ng/ml TGFP-1 (R&D Systems), 20 ng/ml IL-1β (R&D Systems), 20 ng/ml IL-6 (R&D Systems), 30 ng/ml IL-23 (R&D Systems), 2.5 μg/ml anti-IL-4 (R&D Systems) and 1 μg/ml anti-IFNγ (R&D Systems) and with test compound during the entire differentiation (or vehicle, 0.1% DMSO for control). Test compounds were tested in triplicates, diluted 1000-fold in medium (final DMSO concentration is 0.1%). Incubated for seven days at 37° C., 5% $CO_2$, 95% humidity, and 2-fluoro-4'-[[4-(4-pyridinylmethyl)-1-piperazinyl]methyl]-α,α-bis(trifluoromethyl)-[1,1'-biphenyl]-4-methanol (SR2211 Calbiochem, Cat. No. 557353) was used as positive control. As negative control, cells were differentiated into Th0 using 5 μg/ml anti-CD28 (BD Pharmingen), 10 ng/ml IL-2 (R&D Systems), 2 μg/ml anti-ILA (R&D Systems) and 2 μg/ml anti-IFNγ (R&D Systems) are negative control. IL-17 levels in supernatants were measured with ELISA (R&D Systems). See Table 3 below.

TABLE 3

| Example | $EC_{50}$ (nM) |
|---|---|
| A7-3-1 | 83 |

IL-17A Secretion in Activated PBMCs

Heparin-treated whole blood from healthy human volunteers was supplied from Hospital de Sant Pau (Barcelona) under the approval of the local ethical review board for human studies (Hospital de Sant Pau, Barcelona, Spain). Human peripheral blood mononuclear cells (PBMCs) were isolated from healthy human volunteers by density gradient centrifugation using the Ficoll-Paque (GE Healthcare). PBMCs were suspended in cell culture medium which consisted on RPMI 1640 medium (Sigma-Aldrich) containing 10% heat inactivated fetal bovine serum (Sigma-Aldrich), 2 mM L-Glutamine (Gibco), 20 mM Hepes (Gibco) and 100 U/mL penicillin (Sigma-Aldrich). Cells were seeded in 384-well plate (DiscoverX), at 40,000 cells per well and cultured 2 h at 37° C. and 5% CO2.

Dose-response curves with compounds were prepared using a 5-fold serial dilution (10 concentrations) in 100% DMSO and further diluted 100-fold in culture medium. Compound solutions (5 μL) were added to the plate containing cells (final DMSO concentration of 0.1%) and incubated for 30 min. Then, cells were stimulated with CD3/CD28 Dynabeads (ThermoFisher, at a bead-to-cell ratio of 1:1) for 48 h at 37° C. and 5% CO2.

IL-17A levels in supernatant were determined by immunoassay using hIL17A QBeads (Intellicyt) and by fluorescence analysis in iQue flow cytometer following the manufacturer's instructions. Inhibition of IL-17A secretion was calculated using the following formula: inhibition=100*[1−[(x−mean basal condition)/(mean top condition−mean basal condition)]]. Activated DMSO-treated cells were used as top condition and activated GNE09461 (10 μM)-treated cells as basal condition. Inhibition values were plotted versus compound concentrations and adjusted to a four-parameter logistic curve to obtain the absolute IC50 value along with the 95% confidence interval.

TABLE 4

IL-17A secretion in activated PBMCs

| Patent example | $IC_{50}$ (nM) |
|---|---|
| A7-01 | 8.7 |
| A7-01-1 | 6.3 |
| A7-01-2 | 2.7 |
| A7-02 | 58 |
| A7-09 | 190 |
| A7-10 | 17 |
| A7-11 | 200 |
| A7-14 | 28 |
| A7-14-1 | 38 |
| A7-14-2 | 110 |
| A7-21 | 80 |
| A7-26-2 | 29 |
| A7-28 | 120 |
| A7-28-1 | 62 |
| A7-28-2 | 81 |
| A7-31 | 180 |
| A7-32 | 220 |
| A7-40 | 7.7 |
| A7-42 | 200 |
| A7-43 | 35 |
| A7-44 | 74 |
| A7-45 | 80 |
| A7-50 | 40 |
| A7-51 | 7.3 |
| A7-52 | 130 |
| A7-54 | 5.6 |
| A7-54-1 | 9.8 |
| A7-54-2 | 6.2 |
| A7-55 | 4.9 |
| A7-56 | 66%@10 uM |
| A7-57 | 39 |
| A7-60 | 87 |
| A7-62 | 7.2 |
| A7-63 | 2.3 |
| A7-65 | 12 |
| A7-66-1 | 18 |
| A7-66-2 | 210 |
| A7-68 | 21 |
| A7-69 | 3.1 |
| A7-70 | 12 |
| A7-74 | 23 |
| A7-75 | 18 |
| A7-76 | 92 |
| A7-77 | 440 |
| A7-78 | 70%@10 uM |
| A7-81 | 120 |
| A7-82 | 150 |
| A7-85 | 120 |
| A7-86 | 55 |
| D5-01-1-1 | 1.9 |
| D5-01-1-2 | 24 |
| D5-03-1-1 | 3 |
| D5-04 | 1 |

TABLE 4-continued

| IL-17A secretion in activated PBMCs | |
|---|---|
| Patent example | $IC_{50}$ (nM) |
| D5-05-1 | 23 |
| D5-05-2 | 200 |
| D5-07 | 2.5 |
| D5-08 | 2.7 |

As can be seen from the Table 4 above, the fluoropyrimidine derivatives of the present disclosure were found to show beneficial activity across the IL-17A secretion in activated PBMCs Assay.

According to an embodiment, compounds having $IC_{50}$<500 nM values in the IL-17A secretion in activated PBMCs Assay are disclosed herein.

According to another preferred embodiment, compounds having $IC_{50}$<200 nM values in the IL-17A secretion in activated PBMCs Assay are disclosed herein.

According to another more preferred embodiment, compounds having $IC_{50}$<100 nM values in the IL-17A secretion in activated PBMCs Assay are disclosed herein.

According to another still more preferred embodiment, compounds having $IC_{50}$<50 nM values in the IL-17A secretion in activated PBMCs Assay are disclosed herein.

In Vivo IL-17A Induction in Anti-CD3 Model in Mice

Male C57BL/6JRj mice (7 week old) were purchased from Janvier Labs and housed at the animal facilities of Almirall throughout the study. Animals were allowed to condition for 5 days in their new environment at 22° C.±2° C., 55%±10% relative humidity and 12 h: 12 h light:dark cycles. Animals were housed in polycarbonate cages, with free access to water and non-purified stock diet (2014 Teklad Global 14% Protein Rodent Maintenance Diet, Envigo) during the full course of the studies. Care of animals was undertaken in compliance with the European Committee Directive 2010/63/EU, and the Catalan and Spanish law. All procedures were performed according to the ARRIVE guidelines (Animal Research: Reporting of In Vivo Experiments) and with approval from the Animal Experimentation Ethical Committee of Almirall (Barcelona, Spain).

Mice were injected intraperitoneally with 7.5 μg of anti-CD3e (Clone 145-2C11 from Pharmingen BD) at 0 h (day 0) and 48 h (day 3) time-points. The non-induced-group were injected with PBS instead of anti-CD3e. At study completion (4 h after anti-CD3e injection), animals were anaesthetized with isofluorane (Baxter) and 0.5-1 mL blood samples were drawn by intracardiac puncture in heparinized tubes. Plasma samples were stored at −80° C. for subsequent analysis.

Test compounds were freshly suspended in sterile 0.5% methylcellulose 0.1% tween-80 solution (10 mL/kg body weight). Compounds administered by oral gavage according to the selected dosing and body weight; control animals received an equivalent volume of vehicle. Treatments were given twice daily from day 0 to day 3, last administration was done 1 h before anti-CD3e injection.

Plasma levels of IL-17A were measured by ELISA (R&D Systems) according to the manufacturer's instruction. Results were calculated as the percentage of reduction of plasma IL-17A versus the difference between non-induced and anti-CD3e induced groups through the formula: inhibition=100*[1−[(x−mean non-induced)/(mean control vehicle−mean non-induced)]]. The IL-17A inhibition for each treatment can be expressed as the mean for each treatment group±S.E.M. Statistical analysis of data were conducted with one-way ANOVA followed by Dunnett's multiple comparisons test when appropriate. Differences were considered significant when p≤0.05.

Results:

| Compound | Inhibition of IL-17A (%) at 3 mg/kg |
|---|---|
| A7-1-1 | 80% |
| D5-1-1-1 | 92% |
| D5-3-1-1 | 93% |

Collagen-Induced Arthritis (CIA) Study

Collagen-induced arthritis is an animal model of rheumatoid arthritis used to evaluate the efficacy of test compounds. CIA was induced at Washington Biotechnology Inc. (Baltimore) in male DBA/1J mice (Jackson Laboratories) by subcutaneous injection at the base of the tail with 50 μl of a bovine collagen/complete Freund's adjuvant emulsion. After 21 days, the mice were further boosted by a further subcutaneous injection of 50 μl of a collagen/incomplete Freund's adjuvant emulsion. For treatment, compound or vehicle (2% DMSO, 10% HP-β-CD in MilliQ water) was given orally twice daily at various doses selected from 3, 10, 30 mg/kg, beginning at the day of CIA induction (Prophylactic setting), or after disease initiation (at day 27, therapeutic setting). Treatment lasted until day 41, and the animals were scored three times weekly. Each paw was scored and the sum of all four scores was recorded as the Arthritic Index (AI). The maximum possible AI was 16. 0=no visible effects of arthritis; 1=edema and/or erythema of one digit; 2=edema and/or erythema of 2 joints; 3=edema and/or erythema of more than 2 joints; 4=severe arthritis of the entire paw and digits including limb deformation and ankylosis of the joint. The Arthritis Index for each treatment can be expressed as the mean score for each treatment group+/−S.E.M.

For example, dosing of compound A7-1-1 @ 3 mpk p.o. b.i.d. resulted in 74% reduction in AI as compared to the anti-IL-17A antibody and dosing of compound A7-14-1 @ 10 mpk p.o. b.i.d. resulted in 80% reduction in AI as compared to the anti-IL-17A antibody.

In summary, compounds disclosed herein have been found to at least modulate the activity of RORγ. Compounds disclosed herein are active, e.g. having a Gal4<1000 nM, such as <500 nM, such as <100 nM and. Additionally, in a property comparison study they have shown an improved lipophilicity manifested by a decrease in Log P and/or Log D compared to previously described high potent compounds, see e.g. Tables 5 a-c. Overall, compounds show an improved LipE (a parameter linking potency and lipophilicity of a given compound, used in medicinal chemistry and drug design to assess druglikeness), LiPE=−log ($EC_{50}$)−c Log P. In these tables, all numbers (except Gal4 activity) are calculated; methods are indicated in column titles.

TABLE 5 a

| Examples | RORγ Gal4 assay | Number of compounds | ALogP Canvas[1] | LipE Canvas[1] |
|---|---|---|---|---|
| Compounds disclosed herein | $EC_{50}$ < 100 nM | 121 | 2.72 | 5.09 |
| Compounds disclosed in WO2016020288 | $EC_{50}$ < 100 nM[1] | 35[2] | 4.62 | 3.02 |

TABLE 5 b

| Examples | RORγ Gal4 assay | Number of compounds | ALogP Canvas[1] | LipE Canvas[1] |
|---|---|---|---|---|
| Compounds disclosed herein | $EC_{50}$ < 500 nM | 137 | 2.66 | 4.96 |
| Compounds disclosed in WO2016020288 | $EC_{50}$ < 500 nM[1] | 59[3] | 4.6 | 2.61 |

TABLE 5 c

| Examples | RORγ Gal4 assay (based on % inhibition at 0.1 and/or 1 uM) | Number of compounds | ALogP Canvas[1] |
|---|---|---|---|
| Compounds disclosed in WO2016020288 | $EC_{50}$ < 100 nM | 61[4] | 4.63 |
| Compounds disclosed in WO2016020288 | $EC_{50}$ < 500 nM[1] | 105[5] | 4.66 |

[1] average value based on "number of compounds"

[2]Gal4 of Examples A2; A3; A6; A7; A49; A53; A59; A61; A62; A63; A64; A69; A73; A75; A76; A78; A81; A83; A85; A89; A91; A97; A98; A101; A102; A104; A110; A167; A168; A169; A171; A165; A174; A175; T1; disclosed in WO2016020288.

[3]Gal4 of Examples, in addition to [(2)], A9; A58; A60; A65; A66; A67; A74; A77; A80; A82; A88; A103; A107; A108; A109; A11; A112; A114; A115; A170; A172; A176; A179; X; disclosed in WO2016020288.

[4]Gal4 of Examples in <100 range: A2; A3; A6; A7; A49; A53; A59; A61; A62; A63; A64; A69; A73; A75; A76; A78; A81; A83; A85; A89; A91; A97; A98; A101; A102; A104; A110; A167; A168; A169; A171; A165; A174; A175; T1; A8; All; A14; A18; A22; A24; A25; A26; A28; A29; A30; A31; A35; A36; A37; A39; A41; A44; A54; A57; A128; A147; A158; A160; A161; A163 disclosed in WO2016020288. [5]Gal4 of Examples in <500 range: A2; A3; A6; A7; A49; A53; A59; A61; A62; A63; A64; A69; A73; A75; A76; A78; A81; A83; A85; A89; A91; A97; A98; A101; A102; A104; A110; A167; A168; A169; A171; A165; A174; A175; T1; A9; A58; A60; A65; A66; A67; A74; A77; A80; A82; A88; A103; A107; A108; A109; A111; A112; A114; A115; A170; A172; A176; A179; X; A8; A11; A14; A18; A22; A24; A25; A26; A28; A29; A30; A31; A35; A36; A37; A39; A41; A44; A54; A57; A128; A147; A158; A160; A161; A163; A1; A5; A12; A13; A15; A19; A23; A 27; A32; A33; A34; A38; A95; A105; A106; A120; A143; A159; A162; A181 disclosed in WO2016020288.

The RORγ Gal4 data used to generate the comparisons in Tables 5 a and b are based on generated Gal4 data for the listed compounds (data not available in WO2016020288). LipE has not been reported in Table 5 c as Gal4 data existed as % inhibition only, except for the compounds used in Tables 5 a and b. In connection with the above Tables 5 a-c, Tables 6 to 11 show a comparison between compounds of the present disclosure and known compounds of structural similarity, and considered relevant.

TABLE 6

ALogP numbers are calculated by Canvas. ([(1)]WO2016020288, [(2)]Table 2 herein).

| Structure | OR Enantiomer 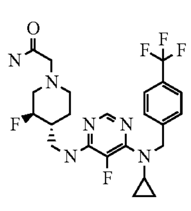 [SMILES: NC(=O)CN1CC[C@H](CNc2ncnc(N(Cc3ccc(C(F)(F)F)cc3)C3CC3)c2F)[C@@H](F)C1] | OR Enantiomer 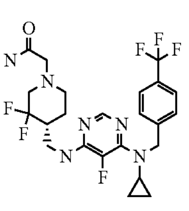 [SMILES: NC(=O)CN1CC[C@H](CNc2ncnc(N(Cc3ccc(C(F)(F)F)cc3)C3CC3)c2F)C(F)(F)C1] | OR Enantiomer 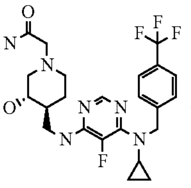 [SMILES: NC(=O)CN1CC[C@@H](CNc2ncnc(N(Cc3ccc(C(F)(F)F)cc3)C3CC3)c2F)[C@H](O)C1] | OR Enantiomer 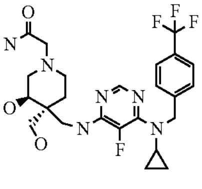 | OR Enantomer 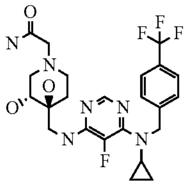 |
|---|---|---|---|---|---|
| Ex. No | A7-5-1 | A7-6-2 | A7-1-1 | C4-1-2 | D5-2-2-1 |
| Gal4 assay | $EC_{50}$ < 100 nM[(2)] | $EC_{50}$ < 100 nM[(2)] | $EC_{50}$ < 100 nM[(2)] | $EC_{50}$ < 100 nM[(2)] | $EC_{50}$ < 100 nM[(2)] |
| ALogP Canvas | 3.82 | 3.98 | 2.88 | 2.19 | 2.00 |
| Structure | 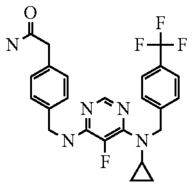 [SMILES: NC(=O)Cc1ccc(CNc2ncnc(N(Cc3ccc(C(F)(F)F)cc3)C3CC3)c2F)cc1] | 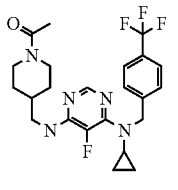 [SMILES: CC(=O)N1CCC(CNc2ncnc(N(Cc3ccc(C(F)(F)F)cc3)C3CC3)c2F)CC1] | 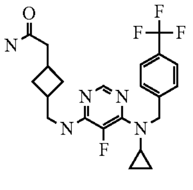 [SMILES: NC(=O)CC1CC(CNc2ncnc(N(Cc3ccc(C(F)(F)F)cc3)C3CC3)c2F)C1] | 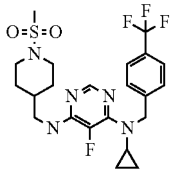 [SMILES: CS(=O)(=O)N1CCC(CNc2ncnc(N(Cc3ccc(C(F)(F)F)cc3)C3CC3)c2F)CC1] | 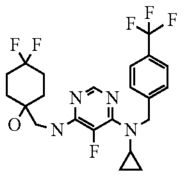 [SMILES: OC1(CNc2ncnc(N(Cc3ccc(C(F)(F)F)cc3)C3CC3)c2F)CCC(F)(F)CC1] |
| Ex. No | Example A2[(1)] | Example A11[(1)] | Example A95[(1)] | Example A7[(1)] | Example A44[(1)] |
| Gal4 assay | $EC_{50}$ <100 nM[(1)] | $EC_{50}$ < 100 nM[(1)] | $EC_{50}$ < 500 nM[(1)] | $EC_{50}$ <100 nM[(1)] | $EC_{50}$ < 100 nM[(1)] |
| ALogP Canvas | 4.92 | 4.28 | 4.37 | 4.07 | 4.75 |

TABLE 7

ALogP numbers are calculated by Canvas. . ([1]WO2016020288, [2]Table 2 herein).

| Structure | AND Enar 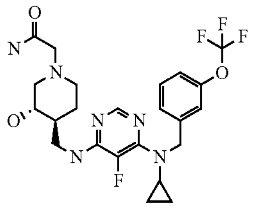 [SMILES: NC(=O)CN1CC[C@@H](CNc2ncnc(N(Cc3cccc(OC(F)(F)F)c3)C3CC3)c2F)[C@H](O)C1] | AND Enantiome 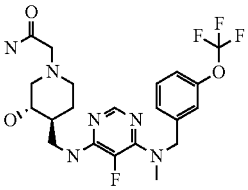 [SMILES: CN(Cc1cccc(OC(F)(F)F)c1)c1ncnc(NC[C@@H]2CCN(CC(N)=O)C[C@H]2O)c1F] | 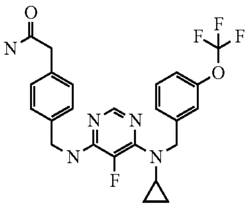 [SMILES: NC(=O)Cc1ccc(CNc2ncnc(N(Cc3cccc(OC(F)(F)F)c3)C3CC3)c2F)cc1] | 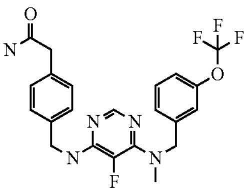 [SMILES: CN(Cc1cccc(OC(F)(F)F)c1)c1ncnc(NCc2ccc(CC(N)=O)cc2)c1F] |
|---|---|---|---|---|
| Ex. No | A7-56 | F2-7 | Example A102[1] | Example A128[1] |
| Gal4 assay | $EC_{50}$ < 100 nM[2] | $EC_{50}$ < 100 nM[2] | $EC_{50}$ <100 nM[1] | $EC_{50}$ < 100 nM[1] |
| ALogP Canvas | 4.05 | 3.57 | 6.09 | 5.60 |

TABLE 8

ALogP numbers are calculated by Canvas. ([1]WO2016020288, [2]Table 2 herein).

| Structure | 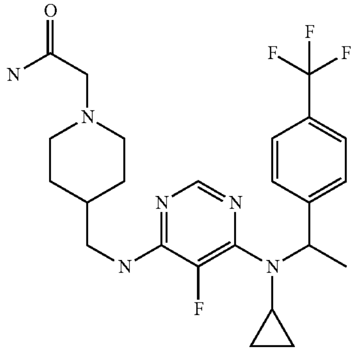 [SMILES: CC(c1ccc(C(F)(F)F)cc1)N(c1ncnc(NCC2CCN(CC(N)=O)CC2)c1F)C1CC1] | 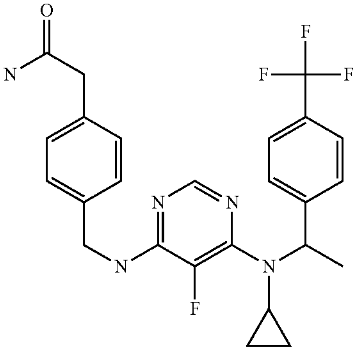 [SMILES: CC(c1ccc(C(F)(F)F)cc1)N(c1ncnc(NCc2ccc(CC(N)=O)cc2)c1F)C1CC1] |
|---|---|---|
| Ex. No | A7-34 | Example A3[1] |
| Gal4 assay | $EC_{50}$ < 100 nM[2] | $EC_{50}$ < 100 nM[1] |
| ALogP Canvas | 4.22 | 5.29 |

TABLE 9

ALogP numbers are calculated by Canvas. ([1]WO2016020288, [2]Table 2 herein).

| Structure | OR Ena 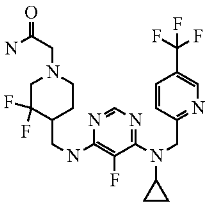 [SMILES: NC(=O)CN1CCC(CNc2ncnc(N(Cc3ccc(C(F)(F)F)cn3)C3CC3)c2F)C(F)(F)C1] | 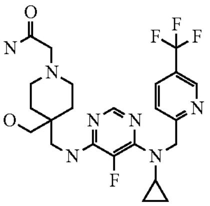 [SMILES: NC(=O)CN1CCC(CO)(CNc2ncnc(N(Cc3ccc(C(F)(F)F)cn3)C3CC3)c2F)CC1] | OR Enantiome 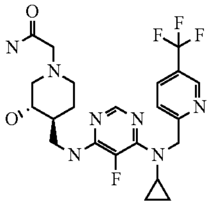 [SMILES: NC(=O)CN1CC[C@@H](CNc2ncnc(N(Cc3ccc(C(F)(F)F)cn3)C3CC3)c2F)[C@H](O)C1] | 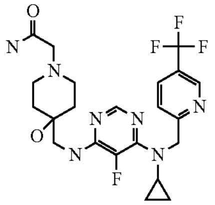 [SMILES: NC(=O)CN1CCC(O)(CNc2ncnc(N(Cc3ccc(C(F)(F)F)cn3)C3CC3)c2F)CC1] | 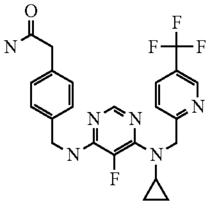 [SMILES: NC(=O)Cc1ccc(CNc2ncnc(N(Cc3ccc(C(F)(F)F)cn3)C3CC3)c2F)cc1] |
|---|---|---|---|---|---|
| Ex. No | A7-3-1 | A7-52 | A7-14-1 | A7-9 | Example A85[1] |
| Gal4 assay | $EC_{50}$ < 100 nM[2] | $EC_{50}$ <100 nM[2] | $EC_{50}$ < 100 nM[2] | $EC_{50}$ < 100 nM[2] | $EC_{50}$ < 100 nM[1] |
| ALogP Canvas | 3.04 | 2.09 | 1.94 | 1.64 | 3.98 |

TABLE 10

ALogP numbers are calculated by Canvas. ([1]WO2016020288, [2]Table 2 herein).

| | | | | |
|---|---|---|---|---|
| | | OR Enantiomer | | |
| Structure | 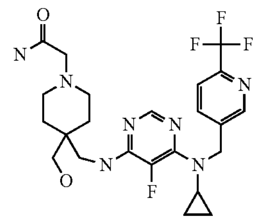 [SMILES: NC(=O)CN1CCC(CO)(CNc2ncnc(N(Cc3ccc(C(F)(F)F)nc3)C3CC3)c2F)CC1] | 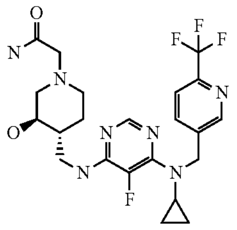 [SMILES: NC(=O)CN1CC[C@H](CNc2ncnc(N(Cc3ccc(C(F)(F)F)nc3)C3CC3)c2F)[C@@H](O)C1] | 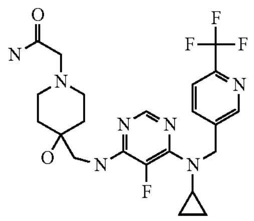 [SMILES: NC(=O)CN1CCC(O)(CNc2ncnc(N(Cc3ccc(C(F)(F)F)nc3)C3CC3)c2F)CC1] | 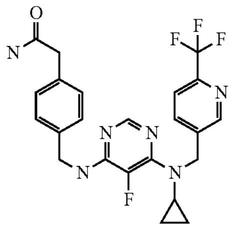 [SMILES: NC(=O)Cc1ccc(CNc2ncnc(N(Cc3ccc(C(F)(F)F)nc3)C3CC3)c2F)cc1] |
| Ex. No | A7-45 | A7-28-2 | A7-11 | Example A83[1] |
| Gal4 assay | $EC_{50}$ < 100 nM[2] | $EC_{50}$ < 100 nM[2] | $EC_{50}$ < 100 nM[2] | $EC_{50}$ < 100 nM[1] |
| ALogP Canvas | 2.3 | 2.16 | 1.86 | 4.19 |

TABLE 11

ALogP numbers are calculated by Canvas. [1]WO2016020288, [2]Table 2 herein

| | | |
|---|---|---|
| | OR Enantiomer | |
| Structure | 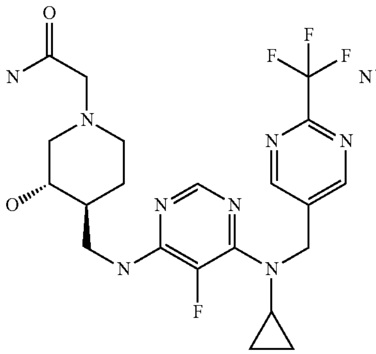 | 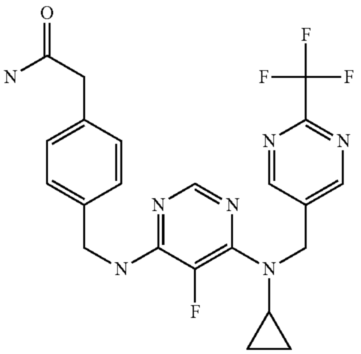 [SMILES: NC(=O)Cc1ccc(CNc2ncnc(N(Cc3cnc(C(F)(F)F)nc3)C3CC3)c2F)cc1] |
| Ex. No | A7-17-1 | Example A98[1] |
| Gal4 assay | $EC_{50}$ < 100 nM[2] | $EC_{50}$ < 100 nM[1] |
| ALogP Canvas | 1.20 | 3.24 |

The A Log P and LipE are calculated using Canvas, a part of the Schrödinger software suite, Release 2019-1.

As mentioned, the compounds disclosed herein may thus be improved modulators of RORγ, e.g. having an attractive interaction (e.g. high binding ability) to the hydrophobic binding sites of the ligand binding domain (LBD) of the RORγ receptor and improved physical chemical properties as discussed above.

Additionally it has been found that compounds disclosed herein have in vivo usefulness, and could consequently be useful in treating inflammatory, metabolic and autoimmune diseases or symptoms thereof.

The invention claimed is:

1. A method of treating a disease selected from acne, atopic dermatitis, lichen planus, multiple sclerosis, rheumatoid arthritis, juvenile idiopathic arthritis, osteoarthritis, ankylosing spondylitis, psoriasis, psoriatic arthritis, ichthyoses, bullous diseases, hidradenitis suppurativa, ulcerative colitis, colitis, Crohn's disease, inflammatory bowel disease (IBD) and lupus erythematosus in a subject suffering therefrom, the method comprising: administering to the subject a compound, stereoisomer, or salt having a structure selected from the group consisting of:

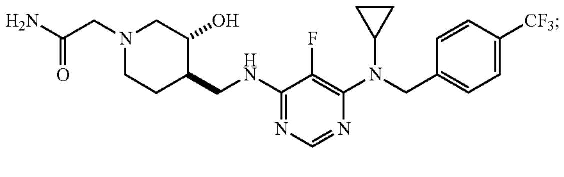

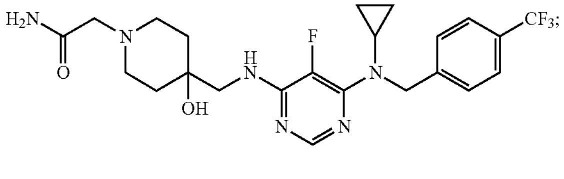

-continued
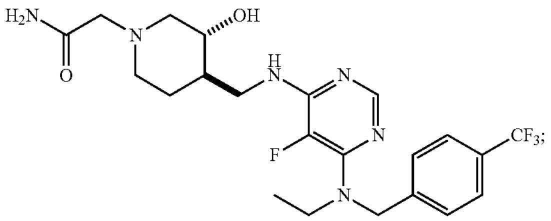
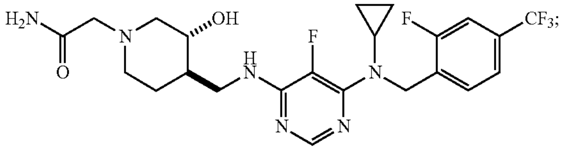
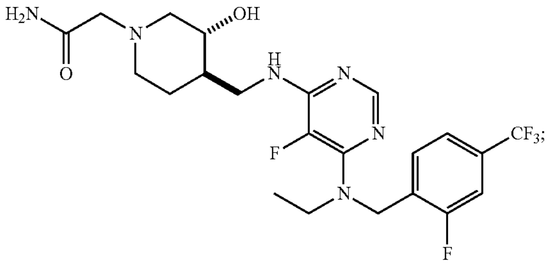
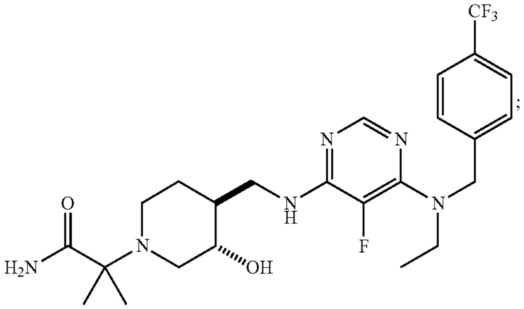
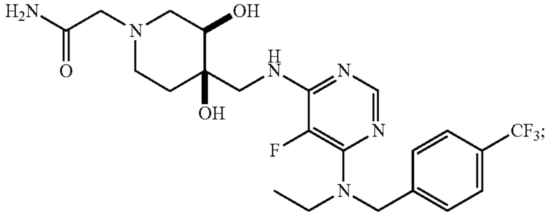
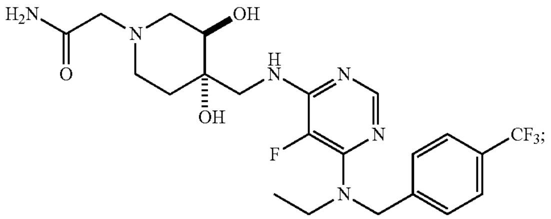
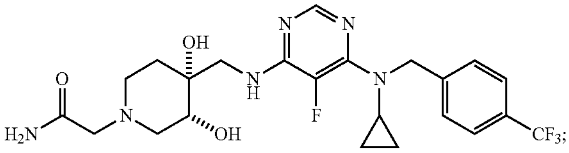
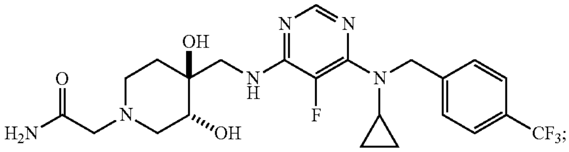
-continued
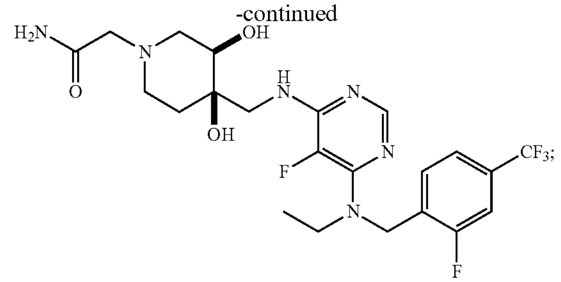
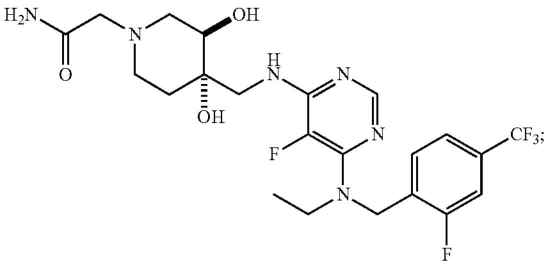
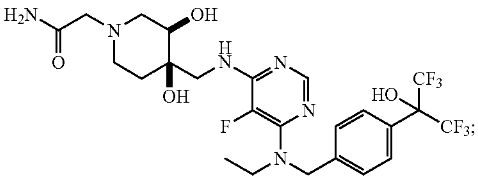
and
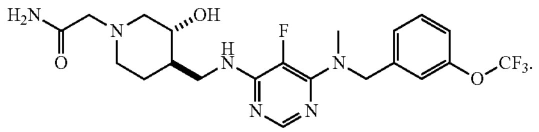
2. The method of claim 1, wherein the compound, stereoisomer, or salt has a structure of:
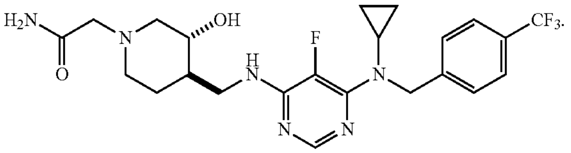 [SMILES: NC(=O)CN1CC[C@H](CNc2ncnc(N(Cc3ccc(C(F)(F)F)cc3)C3CC3)c2F)[C@@H](O)C1]
3. The method of claim 1, wherein the compound, stereoisomer, or salt has a structure of:
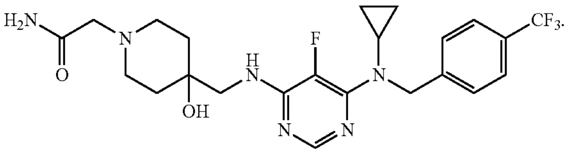 [SMILES: NC(=O)CN1CCC(O)(CNc2ncnc(N(Cc3ccc(C(F)(F)F)cc3)C3CC3)c2F)CC1]

4. The method of claim 1, wherein the compound, stereoisomer, or salt has a structure of:

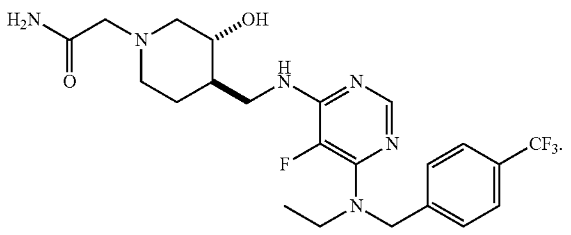 [SMILES: CCN(Cc1ccc(C(F)(F)F)cc1)c1ncnc(NC[C@H]2CCN(CC(N)=O)C[C@@H]2O)c1F]

5. The method of claim 1, wherein the compound, stereoisomer, or salt has a structure of:

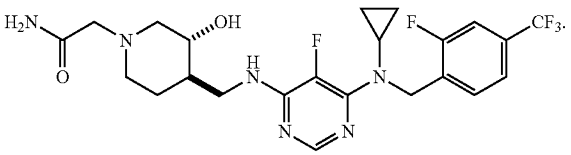 [SMILES: NC(=O)CN1CC[C@H](CNc2ncnc(N(Cc3ccc(C(F)(F)F)cc3F)C3CC3)c2F)[C@@H](O)C1]

6. The method of claim 1, wherein the compound, stereoisomer, or salt has a structure of:

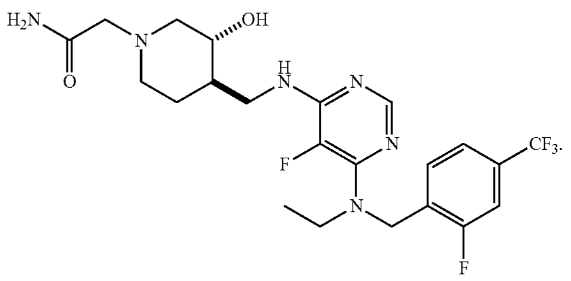 [SMILES: CCN(Cc1ccc(C(F)(F)F)cc1F)c1ncnc(NC[C@H]2CCN(CC(N)=O)C[C@@H]2O)c1F]

7. The method of claim 1, wherein the compound, stereoisomer, or salt has a structure of:

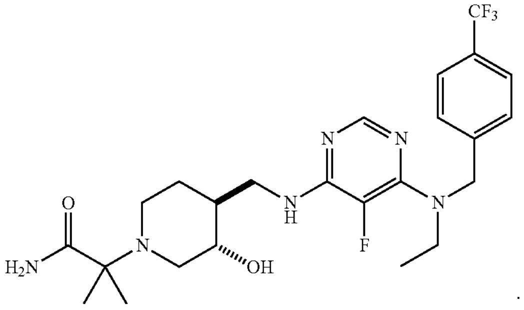

8. The method of claim 1, wherein the compound, stereoisomer, or salt has a structure of:

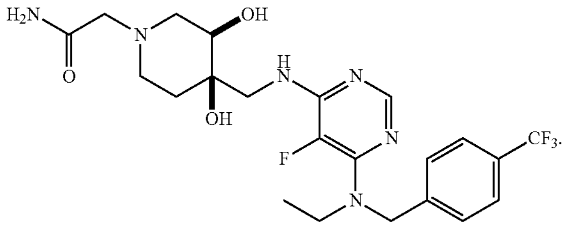 [SMILES: CCN(Cc1ccc(C(F)(F)F)cc1)c1ncnc(NC[C@]2(O)CCN(CC(N)=O)C[C@H]2O)c1F]

9. The method of claim 1, wherein the compound, stereoisomer, or salt has a structure of:

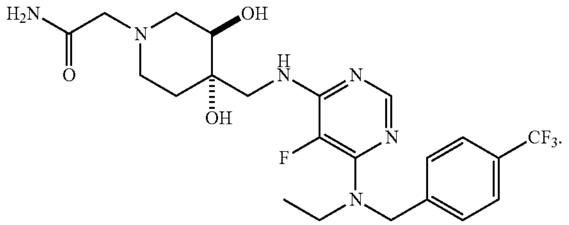 [SMILES: CCN(Cc1ccc(C(F)(F)F)cc1)c1ncnc(NC[C@@]2(O)CCN(CC(N)=O)C[C@H]2O)c1F]

10. The method of claim 1, wherein the compound, stereoisomer, or salt has a structure of:

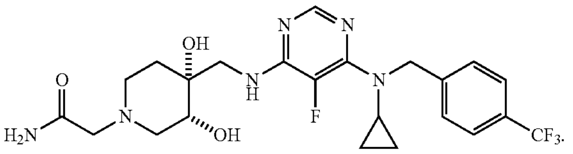 [SMILES: NC(=O)CN1CC[C@@](O)(CNc2ncnc(N(Cc3ccc(C(F)(F)F)cc3)C3CC3)c2F)[C@H](O)C1]

11. The method of claim 1, wherein the compound, stereoisomer, or salt has a structure of:

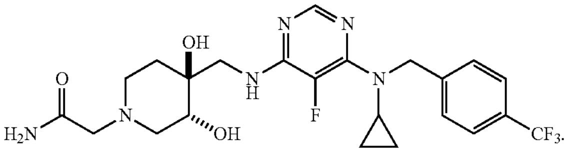 [SMILES: NC(=O)CN1CC[C@](O)(CNc2ncnc(N(Cc3ccc(C(F)(F)F)cc3)C3CC3)c2F)[C@H](O)C1]

12. The method of claim 1, wherein the compound, stereoisomer, or salt has a structure of:

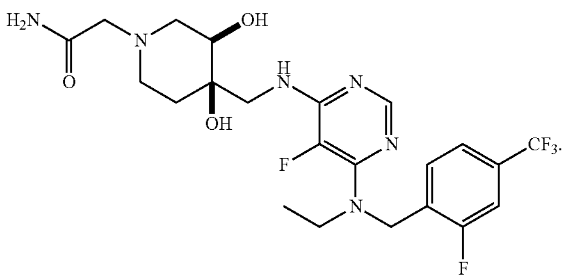 [SMILES: CCN(Cc1ccc(C(F)(F)F)cc1F)c1ncnc(NC[C@]2(O)CCN(CC(N)=O)C[C@H]2O)c1F]

13. The method of claim 1, wherein the compound, stereoisomer, or salt has a structure of:

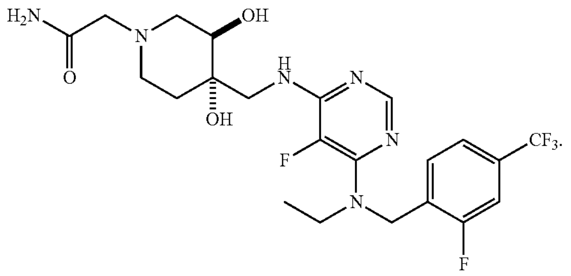 [SMILES: CCN(Cc1ccc(C(F)(F)F)cc1F)c1ncnc(NC[C@@]2(O)CCN(CC(N)=O)C[C@H]2O)c1F]

14. The method of claim 1, wherein the compound, stereoisomer, or salt has a structure of:

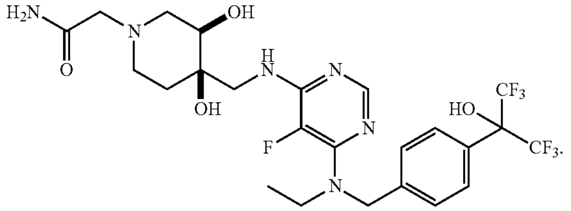 [SMILES: CCN(Cc1ccc(C(O)(C(F)(F)F)C(F)(F)F)cc1)c1ncnc(NC[C@]2(O)CCN(CC(N)=O)C[C@H]2O)c1F]

15. The method of claim 1, wherein the compound, stereoisomer, or salt has a structure of:

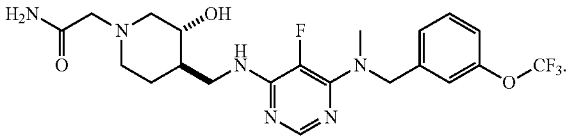 [SMILES: CN(Cc1cccc(OC(F)(F)F)c1)c1ncnc(NC[C@H]2CCN(CC(N)=O)C[C@@H]2O)c1F]

16. The method of claim 1, wherein the disease is psoriasis.

17. The method of claim 1, wherein the disease is psoriatic arthritis.

18. The method of claim 1, wherein the disease is rheumatoid arthritis.

* * * * *